United States Patent
Foley et al.

(10) Patent No.: US 10,266,526 B2
(45) Date of Patent: Apr. 23, 2019

(54) SUBSTITUTED 1,2,3-TRIAZOLES AS SMYD INHIBITORS FOR TREATING CANCER

(71) Applicant: EPIZYME, INC., Cambridge, MA (US)

(72) Inventors: Megan Alene Cloonan Foley, Somerville, MA (US); Kevin Wayne Kuntz, Woburn, MA (US); James Edward John Mills, Kent (GB); Lorna Helen Mitchell, Cambridge, MA (US); Michael John Munchhof, Salem, CT (US); Darren Martin Harvey, Acton, MA (US)

(73) Assignee: EPIZYME, INC., Cambridge, MA (US)

( * ) Notice: Subject to any disclaimer, the term of this patent is extended or adjusted under 35 U.S.C. 154(b) by 0 days.

(21) Appl. No.: 15/510,586

(22) PCT Filed: Sep. 9, 2015

(86) PCT No.: PCT/US2015/049221
§ 371 (c)(1),
(2) Date: Mar. 10, 2017

(87) PCT Pub. No.: WO2016/040505
PCT Pub. Date: Mar. 17, 2016

(65) Prior Publication Data
US 2017/0355695 A1  Dec. 14, 2017

Related U.S. Application Data

(60) Provisional application No. 62/048,773, filed on Sep. 10, 2014, provisional application No. 62/146,799, filed on Apr. 13, 2015.

(51) Int. Cl.
| | |
|---|---|
| *A61K 31/4192* | (2006.01) |
| *C07D 249/04* | (2006.01) |
| *C07D 451/04* | (2006.01) |
| *C07D 213/81* | (2006.01) |
| *C07D 213/82* | (2006.01) |
| *C07D 231/14* | (2006.01) |
| *C07D 233/90* | (2006.01) |
| *C07D 401/12* | (2006.01) |
| *C07D 241/26* | (2006.01) |
| *C07D 261/10* | (2006.01) |
| *C07D 263/34* | (2006.01) |
| *C07D 275/03* | (2006.01) |
| *C07D 209/08* | (2006.01) |
| *C07D 277/56* | (2006.01) |
| *C07C 271/18* | (2006.01) |
| *C07D 205/04* | (2006.01) |
| *C07D 211/34* | (2006.01) |
| *C07D 237/24* | (2006.01) |
| *C07D 401/14* | (2006.01) |
| *C07D 403/12* | (2006.01) |

(Continued)

(52) U.S. Cl.
CPC .......... *C07D 451/04* (2013.01); *C07C 271/18* (2013.01); *C07D 205/04* (2013.01); *C07D 209/08* (2013.01); *C07D 211/34* (2013.01); *C07D 213/81* (2013.01); *C07D 213/82* (2013.01); *C07D 231/14* (2013.01); *C07D 233/90* (2013.01); *C07D 237/24* (2013.01); *C07D 241/26* (2013.01); *C07D 249/04* (2013.01); *C07D 261/10* (2013.01); *C07D 263/34* (2013.01); *C07D 275/03* (2013.01); *C07D 277/56* (2013.01); *C07D 401/12* (2013.01); *C07D 401/14* (2013.01); *C07D 403/12* (2013.01); *C07D 403/14* (2013.01); *C07D 413/12* (2013.01); *C07D 417/14* (2013.01)

(58) Field of Classification Search
CPC .......................... A61K 31/4192; C07D 249/04
USPC ............................................ 514/359; 548/255
See application file for complete search history.

(56) References Cited

U.S. PATENT DOCUMENTS

| 6,743,924 B2 | 6/2004 | Ikemoto et al. |
| 2005/0032838 A1 | 2/2005 | Bailey et al. |

(Continued)

FOREIGN PATENT DOCUMENTS

| EP | 2532661 A1 | 12/2012 |
| WO | WO 2006/092608 A1 | 9/2006 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Sterne, Kessler, Goldstein & Fox P.L.L.C.

(57) ABSTRACT

The present disclosure provides carboxamides and sulfonamides having Formula (I): and the pharmaceutically acceptable salts and solvates thereof, wherein A, Y, B, X, and Z are defined as set forth in the specification. The present disclosure is also directed to the use of compounds of Formula (I) to treat a disorder responsive to the blockade of SMYD proteins such as SMYD3 or SMYD2. Compounds of the present disclosure are especially useful for treating cancer.

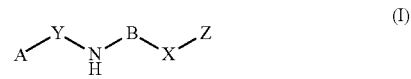

(I)

17 Claims, No Drawings
Specification includes a Sequence Listing.

(51) Int. Cl.
  *C07D 403/14* (2006.01)
  *C07D 413/12* (2006.01)
  *C07D 417/14* (2006.01)

(56) References Cited

U.S. PATENT DOCUMENTS

2008/0146569 A1  6/2008  Blake et al.
2009/0191181 A1  7/2009  Nakamura et al.
2010/0173888 A1  7/2010  Thoroarnsen et al.

FOREIGN PATENT DOCUMENTS

WO  WO 2016/040498 A1  3/2016
WO  WO 2016/040502 A1  3/2016
WO  WO 2016/040504 A1  3/2016
WO  WO 2016/040508 A1  3/2016
WO  WO 2016/040511 A1  3/2016
WO  WO 2016/040515 A1  3/2016

OTHER PUBLICATIONS

Vippagunta, et al. Advanced Drug Delivery Reviews, 48, 2001, 18.*
Riebsomer, et al. Journal of Organic Chemistry, 16, 1951, 1643-1647.*
L.H. Mitchell et al. "Novel Oxindole Sulfonamides and Sulfamides: EPZ031686, the First Orally Bioavailable Small Molecule SMYD3 Inhibitor" *ACS Medicinal Chemistry Letters* 7:134-138, American Chemical Society, United States (2015).
Supplemental European Search Report, Appl. No. EP 15 84 0789; European Patent Office; dated Apr. 20, 2018.
Abu-Farha, M. et al., "Proteomic analyses of the SMYD family interactomes identify HSP90 as a novel target for SMYD2," *J. Mol. Cell Biol.* 3:301-308, Oxford University Press, United States (2011).
Bingham, A.L. et al., "Over one hundred solvates of sulfathiazole," *Chem. Commun.* 7:603-604, Royal Society of Chemistry, United Kingdom (2001).
Caira, M.R. et al., "Preparation and Crystal Characterization of a Polymorph, a Monohydrate, and an Ethyl Acetate Solvate of the Antifungal Fluconazole," *J. Pharm. Sci.* 93:601-611, Wiley-Liss, Inc. and American Pharmaceutical Association, United States (2004).
Cho, H.-S. et al., "RB1 Methylation by SMYD2 Enhances Cell Cycle Progression through an Increase of RB1 Phosphorylation," *Neoplasia* 14:476-486, Neoplasia Press, Inc., United States (2012).
Fujii, T. et al., "Smyd3 Is Required for the Development of Cardiac and Skeletal Muscle in Zebrafish," *PLoS One* 6:e23491, Public Library of Science, United States (2011).
GenBank, "*Homo sapiens* mitogen-activated protein kinase kinase kinase 2 (MAP3K2), mRNA," Accession No. NM_006609.3, accessed at https://www.ncbi.nlm.nih.gov/nuccore/NM_006609.3, Mar. 27, 2011.
GenBank, "N-lysine Methyltransferase SMYD2 [*Homo sapiens*]," Accession No. NP_064582.2, accessed at https://www.ncbi.nlm.nih.gov/protein/NP_064582.2, Jun. 25, 2017.
GenPept, "histone-lysine N-methyltransferase SMYD3 isoform 1 [*Homo sapiens*]," Sequence NP_001161212.1, accessed at https://www.ncbi.nlm.nih.gov/protein/267844824/, Jun. 26, 2017.
Hamamoto, R. et al., "Enhanced SMYD3 expression is essential for the growth of breast cancer cells," *Cancer Sci.* 97:113-118, Japanese Cancer Association, Wiley Publishing, United Kingdom (2006).
Hamamoto, R. et al., "SMYD3 encodes a histone methyltransferase involved in the proliferation of cancer cells," *Nat. Cell Biol.* 6:731-740, Nature Publishing Group, Macmillan Magazines Ltd., United Kingdom (2004).
Hu, L. et al., "Identification of Smyd4 as a Potential Tumor Suppressor Gene Involved in Breast Cancer Development," *Cancer Res.* 69:4067-4072, American Association for Cancer Research, United States (2009).

International Preliminary Report on Patentability for International Patent Application No. PCT/US2015/049221, The International Bureau of WIPO, Switzerland, dated Mar. 14, 2017.
International Search Report for International Patent Application No. PCT/US2015/049221, United States Patent and Trademark Office, Alexandria, Virginia, dated Feb. 9, 2016.
Komatsu, S. et al., "Overexpression of SMYD2 contributes to malignant outcome in gastric cancer," *Br. J. Cancer* 112:357-364, Nature Publishing Group, United Kingdom (2015).
Komatsu, S. et al., "Overexpression of SMYD2 relates to tumor cell proliferation and malignant outcome of esophageal squamous cell carcinoma," *Carcinogenesis* 30:1139-1146, Oxford University Press, United Kingdom (2009).
Liu, C. et al., "SMYD3 as an Oncogenic Driver in Prostate Cancer by Stimulation of Androgen Receptor Transcription," *J. Nat. Cancer Inst.* 105:1719-1728, Oxford University Press, United States (2013).
Mazur, P.K. etal., "SMYD3 links lysine methylation of MAP3K2 to Ras-driven cancer," *Nature* 510: 283-287, Nature Publishing Group, United Kingdom (2014).
Moss, G.P., "Basic Terminology of Stereochemistry," *Pure Appl. Chem.* 68:2193-2222, IUPAC, Blackwell Scientific Publications, United Kingdom (1996).
De Almeida Nagata, D.E. et al., "Epigenetic control of Foxp3 by SMYD3 H3K4 histone methyltransferase controls iTreg development and regulates pathogenic T cell responses during pulmonary viral infection," *Mucosal Immunol.* 8:1131-1143, Nature Publishing Group, United States (2015).
Nguyen, H. et al., "LLY-507, a Cell-active, Potent, and Selective Inhibitor of Protein-lysine Methyltransferase SMYD2," *J. Biol. Chem.* 290:13641-13653, American Society for Biochemistry and Molecular Biology, Inc., United States (2015).
Peserico, A. et al., "A SMYD3 Small-Molecule Inhibitor Impairing Cancer Cell Growth," *J. Cell. Physiol.* 230:2447-2460, Wiley-Liss, United States (2015).
Proserpio, V. et al., "The methyltransferase SMYD3 mediates the recruitment of transcriptional cofactors at the myostatin and c-Met genes and regulates skeletal muscle atrophy," *Genes Dev.* 27:1299-1312, Cold Spring Harbor Laboratory Press, United States (2013).
PubChem-16787823 Create Date: Nov. 13, 2007.
PubChem-21882591 Create Date: Dec. 5, 2007.
PubChem-29103931 Create Date: May 28, 2009.
PubChem-31143316 Create Date: May 28, 2009.
PubChem-62318333 Create Date: Oct. 22, 2012.
PubChem-63283375 Create Date: Oct. 22, 2012.
PubChem-66185604 Create Date: Oct. 24, 2012.
PubChem-766053 Create Date: Jul. 8, 2005.
Sakamoto, L.H. et al., "SMYD2 is highly expressed in pediatric acute lymphoblastic leukemia and constitutes a bad prognostic factor," *Leuk. Res.* 38:496-502, Elsevier Ltd., United Kingdom (2014).
UniProtKB/Swiss-Prot, "SMYD3_HUMAN," accession No. Q9H7B4. 4, accessed at https://www.ncbi.nlm.nih.gov/protein/Q9H7B4, accessed on Jun. 7, 2017.
Van Aller, G.S. et al., "Smyd3 regulates cancer cell phenotypes and catalyzes histone H4 lysine 5 methylation," *Epigenetics* 7:340-343, Landes Bioscience, United States (2012).
Van Tonder, E.C. et al., "Preparation and Physicochemical Characterization of 5 Niclosamide Solvates and 1 Hemisolvate," *AAPS PharmSciTech* 5:E12, American Association of Pharmaceutical Scientists, United States (2004).
Wuts, P.G.M. and Greene, T.W., Greene's Protective Groups in Organic Synthesis, 4th Ed., John Wiley & Sons, Inc., United States (2007).
Xu, G. et al., "The Histone Methyltransferase Smyd2 is a Negative Regulator of Macrophage Activation by Suppressing Interleukin 6 (IL-6) and Tumor Necrosis Factor α (TNF-α) Production," *J. Biol. Chem.* 290:5414-5423, American Society for Biochemistry and Molecular Biology, United States (2015).

* cited by examiner

SEQUENCE LISTING

<160> NUMBER OF SEQ ID NOS: 3

<210> SEQ ID NO 1
<211> LENGTH: 855
<212> TYPE: PRT
<213> ORGANISM: Artificial Sequence
<220> FEATURE:
<223> OTHER INFORMATION: synthesized protein

<400> SEQUENCE: 1

Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

```
Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

His Asn Gln Thr Ser Leu Tyr Lys Lys Ala Gly Thr Met Asp Asp Gln
225                 230                 235                 240

Gln Ala Leu Asn Ser Ile Met Gln Asp Leu Ala Val Leu His Lys Ala
                245                 250                 255

Ser Arg Pro Ala Leu Ser Leu Gln Glu Thr Arg Lys Ala Lys Ser Ser
            260                 265                 270

Ser Pro Lys Lys Gln Asn Asp Val Arg Val Lys Phe Glu His Arg Gly
        275                 280                 285

Glu Lys Arg Ile Leu Gln Phe Pro Arg Pro Val Lys Leu Glu Asp Leu
    290                 295                 300

Arg Ser Lys Ala Lys Ile Ala Phe Gly Gln Ser Met Asp Leu His Tyr
305                 310                 315                 320

Thr Asn Asn Glu Leu Val Ile Pro Leu Thr Thr Gln Asp Asp Leu Asp
                325                 330                 335

Lys Ala Leu Glu Leu Leu Asp Arg Ser Ile His Met Lys Ser Leu Lys
            340                 345                 350

Ile Leu Leu Val Ile Asn Gly Ser Thr Gln Ala Thr Asn Leu Glu Pro
        355                 360                 365

Leu Pro Ser Leu Glu Asp Leu Asp Asn Thr Val Phe Gly Ala Glu Arg
    370                 375                 380

Lys Lys Arg Leu Ser Ile Ile Gly Pro Thr Ser Arg Asp Arg Ser Ser
385                 390                 395                 400

Pro Pro Pro Gly Tyr Ile Pro Asp Glu Leu His Gln Val Ala Arg Asn
                405                 410                 415

Gly Ser Phe Thr Ser Ile Asn Ser Glu Gly Glu Phe Ile Pro Glu Ser
            420                 425                 430

Met Glu Gln Met Leu Asp Pro Leu Ser Leu Ser Ser Pro Glu Asn Ser
        435                 440                 445
```

```
Gly Ser Gly Ser Cys Pro Ser Leu Asp Ser Pro Leu Asp Gly Glu Ser
            450                 455                 460
Tyr Pro Lys Ser Arg Met Pro Arg Ala Gln Ser Tyr Pro Asp Asn His
465                 470                 475                 480
Gln Glu Phe Ser Asp Tyr Asp Asn Pro Ile Phe Glu Lys Phe Gly Lys
                485                 490                 495
Gly Gly Thr Tyr Pro Arg Arg Tyr His Val Ser Tyr His His Gln Glu
            500                 505                 510
Tyr Asn Asp Gly Arg Lys Thr Phe Pro Arg Ala Arg Thr Gln Gly
                515                 520                 525
Asn Gln Leu Thr Ser Pro Val Ser Phe Ser Pro Thr Asp His Ser Leu
530                 535                 540
Ser Thr Ser Ser Gly Ser Ser Ile Phe Thr Pro Glu Tyr Asp Asp Ser
545                 550                 555                 560
Arg Ile Arg Arg Arg Gly Ser Asp Ile Asp Asn Pro Thr Leu Thr Val
                565                 570                 575
Met Asp Ile Ser Pro Pro Ser Arg Ser Pro Arg Ala Pro Thr Asn Trp
            580                 585                 590
Arg Leu Gly Lys Leu Leu Gly Gln Gly Ala Phe Gly Arg Val Tyr Leu
            595                 600                 605
Cys Tyr Asp Val Asp Thr Gly Arg Glu Leu Ala Val Lys Gln Val Gln
            610                 615                 620
Phe Asp Pro Asp Ser Pro Glu Thr Ser Lys Glu Val Asn Ala Leu Glu
625                 630                 635                 640
Cys Glu Ile Gln Leu Leu Lys Asn Leu Leu His Glu Arg Ile Val Gln
                645                 650                 655
Tyr Tyr Gly Cys Leu Arg Asp Pro Gln Glu Lys Thr Leu Ser Ile Phe
            660                 665                 670
Met Glu Tyr Met Pro Gly Gly Ser Ile Lys Asp Gln Leu Lys Ala Tyr
            675                 680                 685
Gly Ala Leu Thr Glu Asn Val Thr Arg Lys Tyr Thr Arg Gln Ile Leu
            690                 695                 700
Glu Gly Val His Tyr Leu His Ser Asn Met Ile Val His Arg Asp Ile
705                 710                 715                 720
Lys Gly Ala Asn Ile Leu Arg Asp Ser Thr Gly Asn Val Lys Leu Gly
                725                 730                 735
Asp Phe Gly Ala Ser Lys Arg Leu Gln Thr Ile Cys Leu Ser Gly Thr
            740                 745                 750
Gly Met Lys Ser Val Thr Gly Thr Pro Tyr Trp Met Ser Pro Glu Val
            755                 760                 765
Ile Ser Gly Gln Gly Tyr Gly Arg Lys Ala Asp Ile Trp Ser Val Ala
            770                 775                 780
Cys Thr Val Val Glu Met Leu Thr Glu Lys Pro Pro Trp Ala Glu Phe
785                 790                 795                 800
Glu Ala Met Ala Ala Ile Phe Lys Ile Ala Thr Gln Pro Thr Asn Pro
                805                 810                 815
Lys Leu Pro Pro His Val Ser Asp Tyr Thr Arg Asp Phe Leu Lys Arg
            820                 825                 830
Ile Phe Val Glu Ala Lys Leu Arg Pro Ser Ala Asp Glu Leu Leu Arg
            835                 840                 845
His Met Phe Val His Tyr His
850                 855
```

-continued

```
<210> SEQ ID NO 2
<211> LENGTH: 428
<212> TYPE: PRT
<213> ORGANISM: Artificial Sequence
<220> FEATURE:
<223> OTHER INFORMATION: synthesized protein

<400> SEQUENCE: 2
```

Met Glu Pro Leu Lys Val Glu Lys Phe Ala Thr Ala Lys Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
    130                 135                 140

Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Ile Ser Leu Leu Asn His Ser Cys
        195                 200                 205

Asp Pro Asn Cys Ser Ile Val Phe Asn Gly Pro His Leu Leu Leu Arg
    210                 215                 220

Ala Val Arg Asp Ile Glu Val Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gln Asp Lys Asp
            260                 265                 270

Ala Asp Met Leu Thr Gly Asp Glu Gln Val Trp Lys Glu Val Gln Glu
        275                 280                 285

Ser Leu Lys Lys Ile Glu Glu Leu Lys Ala His Trp Lys Trp Glu Gln
    290                 295                 300

Val Leu Ala Met Cys Gln Ala Ile Ile Ser Ser Asn Ser Glu Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Leu Leu Glu Glu Ala Leu Phe Tyr Gly Thr
            340                 345                 350

Arg Thr Met Glu Pro Tyr Arg Ile Phe Phe Pro Gly Ser His Pro Val
        355                 360                 365

-continued

```
Arg Gly Val Gln Val Met Lys Val Gly Lys Leu Gln Leu His Gln Gly
        370             375             380

Met Phe Pro Gln Ala Met Lys Asn Leu Arg Leu Ala Phe Asp Ile Met
385             390             395             400

Arg Val Thr His Gly Arg Glu His Ser Leu Ile Glu Asp Leu Ile Leu
                405             410             415

Leu Leu Glu Glu Cys Asp Ala Asn Ile Arg Ala Ser
            420             425

<210> SEQ ID NO 3
<211> LENGTH: 29
<212> TYPE: PRT
<213> ORGANISM: Artificial Sequence
<220> FEATURE:
<223> OTHER INFORMATION: synthesized protein
<220> FEATURE:
<221> NAME/KEY: MISC_FEATURE
<223> OTHER INFORMATION: C-terminal amide cap

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala
            20                  25
```

SUBSTITUTED 1,2,3-TRIAZOLES AS SMYD INHIBITORS FOR TREATING CANCER

BACKGROUND OF THE INVENTION

Field of the Invention

The present disclosure provides carboxamides and sulfonamides as SMYD protein inhibitors, such as SMYD3 and SMYD2 inhibitors, and therapeutic methods of treating conditions and diseases wherein inhibition of SMYD proteins such as SMYD3 and SMYD2 provides a benefit.

Background

Epigenetic regulation of gene expression is an important biological determinant of protein production and cellular differentiation and plays a significant pathogenic role in a number of human diseases. Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., SMYD proteins such as SMYD3 and SMYD2), many of which are associated with genetic alterations that can cause human disease, such as proliferative disorders. Thus, there is a need for the development of small molecules that are capable of inhibiting the activity of SMYD proteins such as SMYD3 and SMYD2.

BRIEF SUMMARY OF THE INVENTION

In one aspect, the present disclosure provides carboxamido and sulfonamide compounds represented by Formulae I-XVIII below, and the pharmaceutically acceptable salts and solvates thereof, collectively referred to herein as "Compounds of the Disclosure."

In another aspect, the present disclosure provides a Compound of the Disclosure and one or more pharmaceutically acceptable carriers.

In another aspect, the present disclosure provides a method of inhibiting SMYD proteins, such as SMYD3 or SMYD2, or both, in a mammal, comprising administering to the mammal an effective amount of at least one Compound of the Disclosure.

In another aspect, the present disclosure provides methods for treating a disease, disorder, or condition, e.g., cancer, responsive to inhibition of SMYD proteins, such as SMYD3 or SMYD2, or both, comprising administering a therapeutically effective amount of a Compound of the Disclosure.

In another aspect, the present disclosure provides the use of Compounds of the Disclosure as inhibitors of SMYD3.

In another aspect, the present disclosure provides the use of Compounds of the Disclosure as inhibitors of SMYD2.

In another aspect, the present disclosure provides the use of Compounds of the Disclosure as inhibitors of SMYD proteins.

In another aspect, the present disclosure provides a pharmaceutical composition for treating a disease, disorder, or condition responsive to inhibition of SMYD proteins, such as SMYD3 or SMYD2, or both, wherein the pharmaceutical composition comprises a therapeutically effective amount of a Compound of the Disclosure in a mixture with one or more pharmaceutically acceptable carriers.

In another aspect, the present disclosure provides Compounds of the Disclosure for use in treating cancer in a mammal, e.g., breast, cervical, colon, kidney, liver, head and neck, skin, pancreatic, ovary, esophageal, lung, and prostate cancer.

In another aspect, the present disclosure provides a Compound of the Disclosure for use in the manufacture of a medicament for treating cancer in a mammal.

In another aspect, the present disclosure provides kit comprising a Compound of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

One aspect of the present disclosure is based on the use of Compounds of the Disclosure as inhibitors of SMYD proteins. In view of this property, the Compounds of the Disclosure are useful for treating diseases, disorders, or conditions, e.g., cancer, responsive to inhibition of SMYD proteins.

One aspect of the present disclosure is based on the use of Compounds of the Disclosure as inhibitors of SMYD3. In view of this property, the Compounds of the Disclosure are useful for treating diseases, disorders, or conditions, e.g., cancer, responsive to inhibition of SMYD3.

One aspect of the present disclosure is based on the use of Compounds of the Disclosure as inhibitors of SMYD2. In view of this property, the Compounds of the Disclosure are useful for treating diseases, disorders, or conditions, e.g., cancer, responsive to inhibition of SMYD2.

In one embodiment, Compounds of the Disclosure are compounds having Formula I:

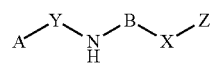

and the pharmaceutically acceptable salts or solvates, e.g., hydrates, thereof, wherein:

A is selected from the group consisting of 1,2,3-triazolyl, 1,2,4-triazolyl, 1-imidazolyl, 1-isoquinolinyl, 1-pyrazolyl, 2-(1,2,3,4-tetrahydroquinolinyl), 2-benzo[d]imidazolyl, 2-benzo[d]thiazolyl, 2-chromenyl-4-one, 2-furanyl, 2-imidazo[1,2-b]pyridazinyl, 2-imidazolyl, 2-indolyl, 2-naphthalenyl, 2-pyrazinyl, 2-pyridyl, 2-pyrimidinyl, 2-pyrrolidinyl, 2-pyrrolyl, 2-quinolinyl, 2-quinoxalinyl, 2-thiazolo[5,4-c]pyridinyl, 2-thiazolyl, 2-thiophenyl, 3-(1,2,3,4-tetrahydroisoquinoline), 3-(1,2,4-oxadiazolyl), 3-imidazo[1,2-a]pyrimidinyl, 3-indazolyl, 3-indolyl, 3-isothiazolyl, 3-pyrazolyl, 3-pyridazinyl, 3-pyridinyl-2-one, 3-pyridyl, 3-pyrrolo[3,2-b]pyridinyl, 3-quinolinyl, 4-(2,2-difluorobenzo[d][1,3]dioxolyl), 4-cyclohexanyl-1-amine, 4-imidazolyl, 4-indolinyl-2-one, 4-indolyl, 4-isothiazolyl, 4-oxazolyl, 4-piperidinyl, 4-pyrazolyl, 4-pyridyl, 4-quinolinyl, 5-(1,3-dihydro-2H-benzo[d]imidazolyl-2-one), 5-(1,3-dihydro-2H-pyrrolo[2,3-b]pyridinyl-2-one), 5-(1,3-dihydro-2H-pyrrolo[2,3-c]pyridinyl-2-one), 5-(2,2-difluorobenzo[d][1,3]dioxolyl), 5-(2,4-dihydro-3H-1,2,4-triazolyl-3-one), 5-4H-furo[3,2-b]pyrrolyl, 5-benzo[c][1,2,5]oxadiazolyl, 5-benzo[d][1,3]dioxolyl, 5-benzo[d]oxazolyl-2(3H)-one, 5-bicyclo[2.2.1]heptyl-2-ene, 5-indolinyl-2,3-dione, 5-indolinyl-2-one, 5-indolyl, 5-isoindolinyl-1-one, 5-isoxazolyl, 5-pyrazolo[3,4-c]pyridinyl, 5-pyrazolyl, 5-pyrimidinyl, 5-thiazolyl, 6-(1,2,3,4-tetrahydronaphthalenyl), 6-(3,4-dihydroquinolinyl-2(1H)-one), 6-(3,4-dihydroquinoxalinyl-2(1H)-one), 6-(4,5-dihydropyridazinyl-3 (2H)-one), 6-benzo[b][1,4]oxazinyl-3-one, 6-benzo[d]imidazolyl, 6-benzo[d]oxazolyl-2(3H)-one, 6-benzo[d]thiazolyl, 6-chromenyl-2-one, 6-imidazo[2,1-b]thiazole, 6-indazolyl, 6-indolinyl-2-one, 6-indolyl, 6-isoquinolinyl, 6-quinolinyl, 6-quinoxalinyl, 6-quinoxalinyl-2(1H)-one, 7-(3,4-dihydroquinolinyl-2(1H)-one), 7-(3,4-dihydroquinoxalin-2(1H)-one), 7-benzo[b][1,4]oxazinyl-3-one, 7-indolinyl-2-one, 7-quinolinyl, 8-benzo[b][1,4]oxazinyl-3-one, cyclopropanyl, phenyl, 4-(prop-1-en-1-yl)-imidazole, 1-butanyl-imidazole, sec-butylcyclopropane, 2-(ethylsulfonyl)propanyl, 1-isobutylpyrrolidine, 4-pyridyl 1-oxide, and 5-benzo[c][1,2,5]oxadiazolyl 1-oxide, each of which is optionally substituted with one, two, or three substituents independently selected from the group consisting of halo, hydroxy, alkoxy, amino, alkylamino, dialkylamino, (amino)alkyl, (alkylamino)alkyl, (dialkylamino)alkyl, $C_{1-6}$ alkyl, haloalkyl, hydroxyalkyl, (carboxamido)alkyl, (cycloalkyl)alkyl, optionally substituted $C_{3-12}$ cycloalkyl, optionally substituted $C_{6-14}$ aryl, optionally substituted 5- to 14-membered heteroaryl, optionally substituted 4- to 14-membered heterocyclo, aralkyl, —N(H)C(=O)R$^6$, —C(=O)R$^7$, and —S(=O)$_2$R$^8$;

Y is selected from the group consisting of —C(R$^{5a}$)(R$^{5b}$)C(=O)—, —C(=O)—, and —S(=O)$_2$—;

B is selected from the group consisting of $C_{1-10}$ alkylenyl, optionally substituted $C_{3-12}$ cycloalkylenyl, optionally substituted $C_{6-14}$ arylenyl, optionally substituted 4- to 14-membered heterocyclenyl, and —C(H)R$^1$R$^2$, with the proviso that B is not optionally substituted pyrrolidinenyl;

X is selected from the group consisting of —N(R$^3$)—, —S(=O)$_2$—, —S(=O)$_2$N(R$^3$)—, —N(R$^3$)S(=O)$_2$—, —S(=O)$_2$C(R$^4$)(H)—, —C(=O)—, —C(=O)N(R$^3$)—, —N(R$^3$)C(=O)—, —C(=O)O—, —OC(=O)—, —C(=O)C(R$^4$)(H)N(R$^3$)—, —N(R$^3$)C(=O)C(R$^4$)(H)—, and —C(=O)C(R$^4$)(H)—; or X is absent, i.e., Z forms a bond with B;

Z is selected from the group consisting of hydrogen, optionally substituted $C_{1-6}$ alkyl, fluoroalkyl, hydroxyalkyl, (amino)alkyl, (alkylamino)alkyl, (dialkylamino)alkyl, (cycloalkylamino)alkyl, (heterocyclo)alkyl, (cycloalkyl)alkyl, (amino)(hydroxy)alkyl, (amino)(aryl)alkyl, (hydroxy)(aryl)alkyl, (aralkylamino)alkyl, (hydroxyalkylamino)alkyl, alkoxyalkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl; or Z is —CH(R$^{9a}$)(R$^{9b}$);

R$^{9a}$ is selected from the group consisting of hydrogen, $C_{1-6}$ alkyl, fluoroalkyl, hydroxyalkyl, (amino)alkyl, (alkylamino)alkyl, (dialkylamino)alkyl, alkoxyalkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl;

R$^{9b}$ is selected from the group consisting of optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl;

R$^1$ is selected from the group consisting of hydrogen, $C_{1-6}$ alkyl, (amino)alkyl, (alkylamino)alkyl, (dialkylamino)alkyl, hydroxyalkyl, alkoxyalkyl, aryloxyalkyl, optionally substituted $C_{3-12}$ cycloalkyl, optionally substituted 4- to 14-membered heterocyclo, optionally substituted $C_{6-14}$ aryl, aralkyl, and alkoxycarbonyl;

R$^2$ is selected from the group consisting of $C_{1-6}$ alkyl, optionally substituted $C_{3-12}$ cycloalkyl, optionally substituted $C_{6-14}$ aryl, optionally substituted 5- to 14-membered heteroaryl, optionally substituted 4- to 14-membered heterocyclo, and (heteroaryl)alkyl;

R$^3$ is selected from the group consisting of hydrogen and $C_{1-4}$ alkyl; and R$^4$ is selected from the group consisting of hydrogen, $C_{1-4}$ alkyl, hydroxy, amino, alkylamino, dialkylamino, cycloalkylamino, (amino)alkyl, (alkylamino)alkyl, (dialkylamino)alkyl, and hydroxyalkyl.

R$^{5a}$ is selected from the group consisting of hydrogen and $C_{1-4}$ alkyl;

R$^{5b}$ is selected from the group consisting of hydrogen, $C_{1-4}$ alkyl, and 4- to 14-membered heterocyclo;

R$^6$ is $C_{1-4}$ alkyl,

R$^7$ is $C_{1-4}$ alkyl; and

R$^8$ is selected from the group consisting of $C_{1-4}$ alkyl, amino, alkylamino, and dialkylamino, wherein —X—Z is attached to any available carbon or nitrogen atom of B, R$^1$, or R$^2$, e.g., when R$^2$ is $C_{1-6}$ alkyl, e.g., ethyl, a hydrogen atom of that ethyl group is replaced with —X—Z to give —CH$_2$CH$_2$—X—Z or

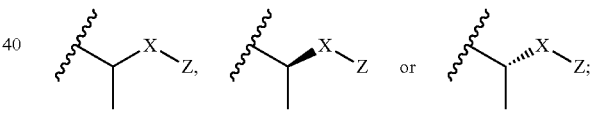

or when R$^2$ is optionally substituted $C_{3-12}$ cycloalkyl, e.g., cyclohexyl, a hydrogen atom of the cyclohexyl group is replaced with —X—Z to give:

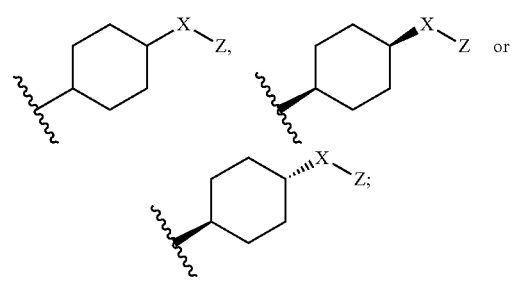

or when R$^2$ is optionally substituted 4- to 14-membered heterocyclo, e.g., piperidinyl, the hydrogen atom attached to the piperidinyl nitrogen atom is replaced with —X—Z to give:

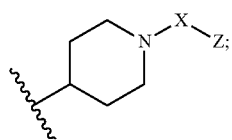

or when $R^2$ is optionally substituted $C_{6-14}$ aryl, e.g., phenyl, a hydrogen atom on that phenyl group is replaced with —X—Z to give:

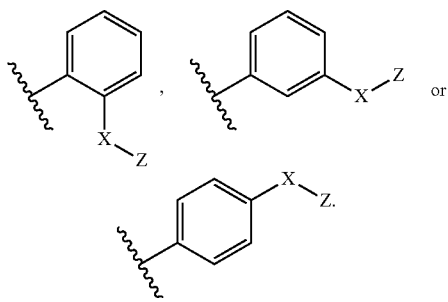

In another embodiment, Compounds of the Disclosure are compounds having Formula I, and the pharmaceutically acceptable salts or solvates, e.g., hydrates, thereof, wherein Z is selected from the group consisting of hydrogen, optionally substituted $C_{1-6}$ alkyl, fluoroalkyl, hydroxyalkyl, (amino)alkyl, (alkylamino)alkyl, (dialkylamino)alkyl, (cycloalkylamino)alkyl, (heterocyclo)alkyl, (cycloalkyl)alkyl, (amino)(hydroxy)alkyl, (amino)(aryl)alkyl, (hydroxy)(aryl) alkyl, (aralkylamino)alkyl, (hydroxyalkylamino)alkyl, alkoxyalkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl.

In another embodiment, Compounds of the Disclosure are compounds having Formula I, and the pharmaceutically acceptable salts or solvates, e.g., hydrates, thereof, wherein X is absent.

In another embodiment, Compounds of the Disclosure are compounds having Formula I, and the pharmaceutically acceptable salts or solvates, e.g., hydrates, thereof, wherein X is absent; B is optionally substituted 4- or 6- to 14-membered heterocyclenyl; and Z is selected from the group consisting of hydrogen, optionally substituted $C_{1-6}$ alkyl, fluoroalkyl, hydroxyalkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl) alkyl.

In another embodiment, Compounds of the Disclosure are compounds having Formula I, and the pharmaceutically acceptable salts or solvates, e.g., hydrates, thereof, wherein B is optionally substituted 4- or 6- to 14-membered heterocyclenyl; X is absent; and Z is —CH($R^{9a}$)($R^{9b}$).

In another embodiment, Compounds of the Disclosure are compounds having Formula I, and the pharmaceutically acceptable salts or solvates, e.g., hydrates, thereof, wherein B is optionally substituted 4- or 6- to 14-membered heterocyclenyl; X is absent; and Z is —CH($R^{9a}$)($R^{9b}$), wherein:

$R^{9a}$ is selected from the group consisting of hydrogen, $C_{1-6}$ alkyl, and optionally substituted $C_{3-12}$ cycloalkyl; and $R^{9b}$ is selected from the group consisting of optionally substituted $C_{6-14}$ aryl, optionally substituted 5- to 14-membered heteroaryl, optionally substituted $C_{3-12}$ cycloalkyl, aralkyl, and (heteroaryl)alkyl.

In another embodiment, Compounds of the Disclosure are compounds having Formula I, and the pharmaceutically acceptable salts or solvates, e.g., hydrates, thereof, wherein B is $C_{1-10}$ alkylenyl. In another embodiment, X is selected from the group consisting of —N($R^3$)C(=O)C($R^4$)(H)— and —N($R^3$)C(=O)—. In another embodiment, Z is selected from the group consisting of $C_{1-6}$ alkyl and (amino) alkyl.

In another embodiment, Compounds of the Disclosure are compounds having Formula I, and the pharmaceutically acceptable salts or solvates, e.g., hydrates, thereof, wherein B is optionally substituted $C_{6-14}$ arylenyl. In another embodiment, B is divalent form of optionally substituted phenyl.

In another embodiment, Compounds of the Disclosure are compounds having Formula II:

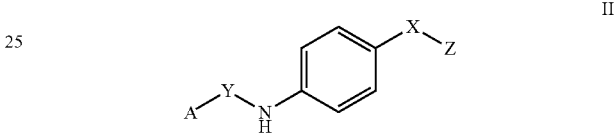

II and the pharmaceutically acceptable salts or solvates, e.g., hydrates, thereof, wherein X is absent and Z is (amino)alkyl; and A and Y are as defined above in connection with Formula I.

In another embodiment, Compounds of the Disclosure are compounds having Formula I, and the pharmaceutically acceptable salts or solvates, e.g., hydrates, thereof, wherein B is optionally substituted $C_{3-12}$ cycloalkylenyl.

In another embodiment, Compounds of the Disclosure are compounds having Formula III, Formula IV, or Formula V:

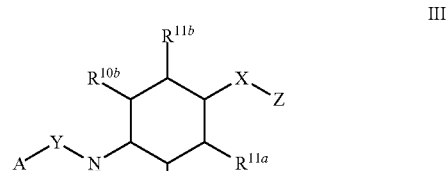

III

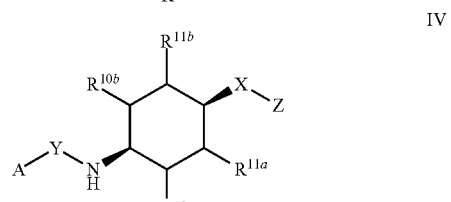

IV

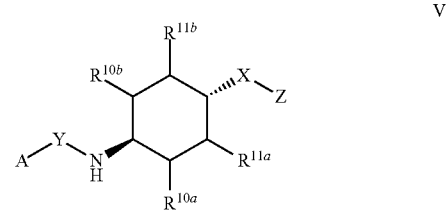

V and the pharmaceutically acceptable salts or solvates, e.g., hydrates, thereof, wherein $R^{10a}$, $R^{10b}$, $R^{11a}$, and $R^{11b}$ are each independently selected from the group consisting of hydrogen and $C_{1-4}$ alkyl; and A, Y, X, and Z are as defined above in connection with Formula I. In another embodiment, X is —N($R^3$)C(=O)— and Z is (amino)alkyl. In another embodiment, X is —N($R^3$)— and Z is hydrogen.

In another embodiment, Compounds of the Disclosure are compounds having Formula I, and the pharmaceutically acceptable salts or solvates, e.g., hydrates, thereof, wherein B is optionally substituted 4- to 14-membered heterocyclenyl.

In another embodiment, Compounds of the Disclosure are compounds having Formula VI, Formula VII, or Formula VIII:

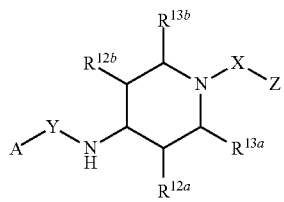

VI

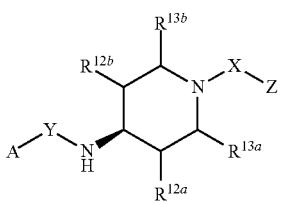

VII

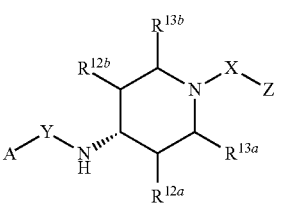

VIII and the pharmaceutically acceptable salts or solvates, e.g., hydrates, thereof, wherein $R^{12a}$, $R^{12b}$, $R^{13a}$, and $R^{13b}$ are each independently selected from the group consisting of hydrogen and $C_{1-4}$ alkyl; and A, Y, X, and Z are as defined above in connection with Formula I. In another embodiment, X is selected from the group consisting of —C(=O)C($R^4$)(H)—, —C(=O)—, and —S(=O)$_2$—; and $R^4$ is selected from the group consisting of hydrogen and amino. In another embodiment, Z is selected from the group consisting of (amino)alkyl, (alkylamino)alkyl, (dialkylamino)alkyl, (heterocyclo)alkyl, optionally substituted $C_{3-12}$ cycloalkyl, optionally substituted $C_{6-14}$ aryl, aralkyl, and (hetaroaryl)alkyl.

In another embodiment, Compounds of the Disclosure are compounds having Formula VI, Formula VII, or Formula VIII, and the pharmaceutically acceptable salts or solvates, e.g., hydrates, thereof, wherein $R^{12a}$, $R^{12b}$, $R^{13a}$, and $R^{13b}$ are each independently selected from the group consisting of hydrogen and $C_{1-4}$ alkyl; A is 5-indolinyl-2-one that is optionally substituted with one or two substituents selected from the group consisting of halo, hydroxy, alkoxy, amino, alkylamino, dialkylamino, (amino)alkyl, (alkylamino)alkyl, (dialkylamino)alkyl, $C_{1-6}$ alkyl, haloalkyl, and hydroxyalkyl; Y is —C(=O)—; X is —S(=O)$_2$—; and Z is as defined above in connection with Formula I. In another embodiment, A is 6-chloro-5-indolinyl-2-one, i.e.,

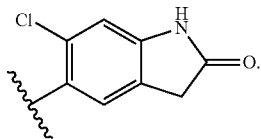 [SMILES: *c1cc2c(cc1Cl)NC(=O)C2]

In another embodiment, Z is selected from the group consisting of (amino)alkyl, (alkylamino)alkyl, (dialkylamino)alkyl, (heterocyclo)alkyl, optionally substituted $C_{3-12}$ cycloalkyl, optionally substituted $C_{6-14}$ aryl, aralkyl, and (hetaroaryl)alkyl.

In another embodiment, Compounds of the Disclosure are compounds having Formula I, and the pharmaceutically acceptable salts or solvates, e.g., hydrates, thereof, wherein B is —C(H)$R^1R^2$. In this embodiment, a hydrogen atom of $R^1$ and $R^2$ is replaced with —X—Z.

In another embodiment, Compounds of the Disclosure are compounds having Formula IX, Formula X, or Formula XI:

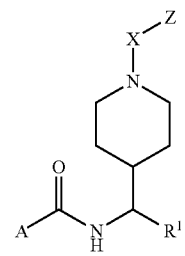

IX

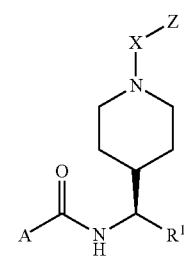

X

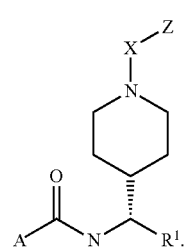

XI and the pharmaceutically acceptable salts or solvates, e.g., hydrates, thereof. In another embodiment, $R^1$ is selected from the group consisting of hydrogen, $C_{1-6}$ alkyl, alkoxycarbonyl, and optionally substituted $C_{6-14}$ aryl. In another embodiment, $R^1$ is selected from the group consisting of hydrogen and methyl. In another embodiment, X is —C(=O)C($R^4$)(H)— and $R^4$ is amino. In another embodiment, X is selected from the group consisting of:

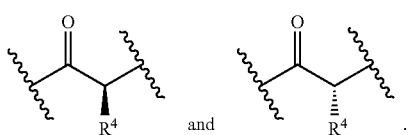
and

In another embodiment, Z is $C_{1-6}$ alkyl. In another embodiment, Z is methyl.

In another embodiment, Compounds of the Disclosure are compounds having any one of Formula I-XI, and the pharmaceutically acceptable salts or solvates, e.g., hydrates, thereof, wherein Y is —C($R^{5a}$)($R^{5b}$)C(=O)—. In another embodiment, $R^{5a}$ and $R^{5b}$ are each independently selected from the group consisting of hydrogen and methyl.

In another embodiment, Compounds of the Disclosure are compounds having any one of Formula I-XI, and the pharmaceutically acceptable salts or solvates, e.g., hydrates, thereof, wherein Y is —S(=O)$_2$—.

In another embodiment, Compounds of the Disclosure are compounds having any one of Formula I-XI, and the pharmaceutically acceptable salts or solvates, e.g., hydrates, thereof, wherein Y is —C(=O)—.

In another embodiment, Compounds of the Disclosure are compounds having any one of Formula I-XI, and the pharmaceutically acceptable salts or solvates, e.g., hydrates, thereof, wherein A is selected from the group consisting of 1,2,3-triazolyl, 1,2,4-triazolyl, 2-(1,2,3,4-tetrahydroquinolinyl), 2-indolyl, 2-thiazolyl, 3-(1,2,4-oxadiazolyl), 3-isothiazolyl, 5-(1,3-dihydro-2H-benzo[d]imidazolyl-2-one), 5-(1,3-dihydro-2H-pyrrolo[2,3-b]pyridinyl-2-one), 5-(1,3-dihydro-2H-pyrrolo[2,3-c]pyridinyl-2-one), 5-(2,2-difluorobenzo[d][1,3]dioxolyl), 5-benzo[d]oxazolyl-2(3H)-one, 5-indolinyl-2-one, 6-benzo[b][1,4]oxazinyl-3-one, and 6-isoquinolinyl.

In another embodiment, Compounds of the Disclosure are compounds having any one of Formula I-XI, and the pharmaceutically acceptable salts or solvates, e.g., hydrates, thereof, wherein A is 5-indolinyl-2-one.

In another embodiment, Compounds of the Disclosure are compounds having Formula XII:

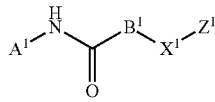

and the pharmaceutically acceptable salts or solvates, e.g., hydrates, thereof, wherein:

$A^1$ is selected from the group consisting of 1,2,3-triazolyl, 1,2,4-triazolyl, 1-imidazolyl, 1-isoquinolinyl, 1-pyrazolyl, 2-(1,2,3,4-tetrahydroquinolinyl), 2-benzo[d]imidazolyl, 2-benzo[d]thiazolyl, 2-chromenyl-4-one, 2-furanyl, 2-imidazo[1,2-b]pyridazinyl, 2-imidazolyl, 2-indolyl, 2-naphthalenyl, 2-pyrazinyl, 2-pyridyl, 2-pyrimidinyl, 2-pyrrolidinyl, 2-pyrrolyl, 2-quinolinyl, 2-quinoxalinyl, 2-thiazolo[5,4-c]pyridinyl, 2-thiazolyl, 2-thiophenyl, 3-(1,2,3,4-tetrahydroisoquinoline), 3-(1,2,4-oxadiazolyl), 3-imidazo[1,2-a]pyrimidinyl, 3-indazolyl, 3-indolyl, 3-isothiazolyl, 3-pyrazolyl, 3-pyridazinyl, 3-pyridinyl-2-one, 3-pyridyl, 3-pyrrolo[3,2-b]pyridinyl, 3-quinolinyl, 4-(2,2-difluorobenzo[d][1,3]dioxolyl), 4-cyclohexanyl-1-amine, 4-imidazolyl, 4-indolinyl-2-one, 4-indolyl, 4-isothiazolyl, 4-oxazolyl, 4-piperidinyl, 4-pyrazolyl, 4-pyridyl, 4-quinolinyl, 5-(1,3-dihydro-2H-benzo[d]imidazolyl-2-one), 5-(1,3-dihydro-2H-pyrrolo[2,3-b]pyridinyl-2-one), 5-(1,3-dihydro-2H-pyrrolo[2,3-c]pyridinyl-2-one), 5-(2,2-difluorobenzo[d][1,3]dioxolyl), 5-(2,4-dihydro-3H-1,2,4-triazolyl-3-one), 5-4H-furo[3,2-b]pyrrolyl, 5-benzo[c][1,2,5]oxadiazolyl, 5-benzo[d][1,3]dioxolyl, 5-benzo[d]oxazolyl-2(3H)-one, 5-bicyclo[2.2.1]heptyl-2-ene, 5-indolinyl-2,3-dione, 5-indolinyl-2-one, 5-indolyl, 5-isoindolinyl-1-one, 5-isoxazolyl, 5-pyrazolo[3,4-c]pyridinyl, 5-pyrazolyl, 5-pyrimidinyl, 5-thiazolyl, 6-(1,2,3,4-tetrahydronaphthalenyl), 6-(3,4-dihydroquinolinyl-2(1H)-one), 6-(3,4-dihydroquinoxalinyl-2(1H)-one), 6-(4,5-dihydropyridazinyl-3 (2H)-one), 6-benzo[b][1,4]oxazinyl-3-one, 6-benzo[d]imidazolyl, 6-benzo[d]oxazolyl-2(3H)-one, 6-benzo[d]thiazolyl, 6-chromenyl-2-one, 6-imidazo[2,1-b]thiazole, 6-indazolyl, 6-indolinyl-2-one, 6-indolyl, 6-isoquinolinyl, 6-quinolinyl, 6-quinoxalinyl, 6-quinoxalinyl-2(1H)-one, 7-(3,4-dihydroquinolinyl-2(1H)-one), 7-(3,4-dihydroquinoxalin-2(1H)-one), 7-benzo[b][1,4]oxazinyl-3-one, 7-indolinyl-2-one, 7-quinolinyl, 8-benzo[b][1,4]oxazinyl-3-one, cyclopropanyl, phenyl, 4-(prop-1-en-1-yl)-imidazole, 1-butanyl-imidazole, sec-butylcyclopropane, 2-(ethylsulfonyl)propanyl, 1-isobutylpyrrolidine, 4-pyridyl 1-oxide, and 5-benzo[c][1,2,5]oxadiazolyl 1-oxide, each of which is optionally substituted with one, two, or three substituents independently selected from the group consisting of halo, hydroxy, alkoxy, amino, alkylamino, dialkylamino, (amino)alkyl, (alkylamino)alkyl, (dialkylamino)alkyl, $C_{1-6}$ alkyl, haloalkyl, hydroxyalkyl, (carboxamido)alkyl, (cycloalkyl)alkyl, optionally substituted $C_{3-12}$ cycloalkyl, optionally substituted $C_{6-14}$ aryl, optionally substituted 5- to 14-membered heteroaryl, optionally substituted 4- to 14-membered heterocyclo, and aralkyl;

$B^1$ is selected from the group consisting of optionally substituted $C_{3-12}$ cycloalkylenyl and optionally substituted 4- to 14-membered heterocyclenyl;

$X^1$ is selected from the group consisting of —N($R^{3a}$)—, —S(=O)$_2$—, —S(=O)$_2$N($R^{3a}$)—, —N($R^{3a}$)S(=O)$_2$—, —S(=O)$_2$C($R^{4a}$)(H)—, —C(=O)—, —C(=O)N($R^{3a}$)—, —N($R^{3a}$)C(=O)—, —C(=O)O—, —OC(=O)—, —C(=O)C($R^{4a}$)(H)N($R^{3a}$)—, —N($R^{3a}$)C(=O)C($R^{4a}$)(H)—, and —C(=O)C($R^{4a}$)(H)—; or $X^1$ is absent, i.e., $Z^1$ forms a bond with $B^1$;

$Z^1$ is selected from the group consisting of hydrogen, optionally substituted $C_{1-6}$ alkyl, fluoroalkyl, hydroxyalkyl, (amino)alkyl, (alkylamino)alkyl, (dialkylamino)alkyl, (cycloalkylamino)alkyl, (heterocyclo)alkyl, (cycloalkyl)alkyl, (amino)(hydroxy)alkyl, (amino)(aryl)alkyl, (hydroxy)(aryl)alkyl, (aralkylamino)alkyl, (hydroxyalkylamino)alkyl, alkoxyalkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl;

$R^{3a}$ is selected from the group consisting of hydrogen and $C_{1-4}$ alkyl; and $R^{4a}$ is selected from the group consisting of hydrogen, $C_{1-4}$ alkyl, hydroxy, amino, alkylamino, and dialkylamino.

In another embodiment, Compounds of the Disclosure are compounds having Formula XII, or a pharmaceutically acceptable salt or hydrate thereof, wherein $A^1$ is 5-indolinyl-2-one. In another embodiment, $B^1$ is optionally substituted $C_{3-12}$ cycloalkylenyl. In another embodiment, $X^1$ is selected from the group consisting of —S(=O)$_2$— and —C(=O)—. In another embodiment, $Z^1$ is selected from the group consisting of (amino)alkyl, (alkylamino)alkyl, and (dialkylamino)alkyl.

In another embodiment, Compounds of the Disclosure are compounds having Formula XIII:

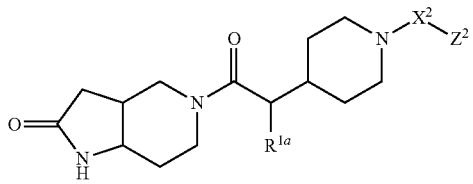

or a pharmaceutically acceptable salt or hydrate thereof, wherein $X^2$ is selected from the group consisting of —N($R^{3b}$)—, —S(=O)$_2$—, —S(=O)$_2$N($R^{3b}$)—, —N($R^{3b}$)S(=O)$_2$—, —S(=O)$_2$C($R^{4b}$)(H)—, —C(=O)—, —C(=O)N($R^{3b}$)—, —N($R^{3b}$)C(=O)—, —C(=O)O—, —OC(=O)—, —C(=O)C($R^{4b}$)(H)N($R^{3b}$)—, —N($R^{3b}$)C(=O)C($R^{4b}$)(H)—, and —C(=O)C($R^{4b}$)(H)—; or X is absent, i.e., $Z^2$ forms a bond with the nitrogen atom;

$Z^2$ is selected from the group consisting of hydrogen, optionally substituted $C_{1-6}$ alkyl, fluoroalkyl, hydroxyalkyl, (amino)alkyl, (alkylamino)alkyl, (dialkylamino)alkyl, (cycloalkylamino)alkyl, (heterocyclo)alkyl, (cycloalkyl)alkyl, (amino)(hydroxy)alkyl, (amino)(aryl)alkyl, (hydroxy)(aryl)alkyl, (aralkylamino)alkyl, (hydroxyalkylamino)alkyl, alkoxyalkyl, optionally substituted $C_{6-14}$ aryl, optionally substituted 4- to 14-membered heterocyclo, optionally substituted 5- to 14-membered heteroaryl optionally substituted $C_{3-12}$ cycloalkyl, aralkyl, and (heteroaryl)alkyl;

$R^{1a}$ is selected from the group consisting of hydrogen, $C_{1-6}$ alkyl, and optionally substituted $C_{6-14}$ aryl;

$R^{3b}$ is selected from the group consisting of hydrogen and $C_{1-4}$ alkyl; and $R^{4b}$ is selected from the group consisting of hydrogen, $C_{1-4}$ alkyl, hydroxy, amino, alkylamino, and dialkylamino.

In another embodiment, Compounds of the Disclosure are compounds having Formula XIII, or a pharmaceutically acceptable salt or hydrate thereof, wherein $X^2$ is selected from the group consisting of —S(=O)$_2$— and —C(=O)—. In another embodiment, $Z^2$ is selected from the group consisting of (amino)alkyl, (alkylamino)alkyl, and (dialkylamino)alkyl. In another embodiment, $X^2$ is absent; and $Z^2$ is hydrogen. In another embodiment, $R^{1a}$ is selected from the group consisting of hydrogen and methyl.

In another embodiment, Compounds of the Disclosure are compounds having Formula I, and the pharmaceutically acceptable salts or solvates, e.g., hydrates, thereof, wherein Y is —C(=O)— and A is selected from the group consisting of 5-indolinyl-2-one and 1,2,3-triazolyl.

In another embodiment, Compounds of the Disclosure are compounds having Formula XIV:

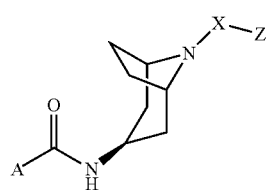

XIV and the pharmaceutically acceptable salts or solvates, e.g., hydrates, thereof, wherein A, X, and Z are as defined above in connection with Formula I. In another embodiment, X is selected from the group consisting of S(=O)$_2$— and —S(=O)$_2$C($R^4$)(H)—. In another embodiment, X is —S(=O)$_2$—. In another embodiment, X is —S(=O)$_2$CH$_2$—. In another embodiment, Z is selected from the group consisting of optionally substituted $C_{6-14}$ aryl, optionally substituted 4- to 14-membered heterocyclo, and optionally substituted $C_{3-12}$ cycloalkyl. In another embodiment, Z is optionally substituted 4- to 14-membered heterocyclo. In another embodiment, Z is an optionally substituted piperidinyl, wherein the nitrogen atom is attached to X or the 4-carbon atom is attached to X. In another embodiment, A is 5-indolinyl-2-one that is optionally substituted with one or two substituents selected from the group consisting of halo, hydroxy, alkoxy, amino, alkylamino, dialkylamino, (amino)alkyl, (alkylamino)alkyl, (dialkylamino)alkyl, $C_{1-6}$ alkyl, haloalkyl, and hydroxyalkyl. In another embodiment, A is 6-chloro-5-indolinyl-2-one, i.e.,

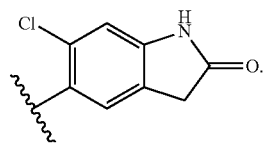 [SMILES: *c1cc2c(cc1Cl)NC(=O)C2]

In another embodiment, a Compound of the Disclosure is N-((1R,3r,5S)-8-((4-(benzylamino)piperidin-1-yl)sulfonyl)-8-azabicyclo[3.2.1]octan-3-yl)-6-chloro-2-oxoindoline-5-carboxamide or 6-chloro-2-oxo-N-((1R,3r,5S)-8-(((1-(4,4,4-trifluorobutyl)piperidin-4-yl)methyl)sulfonyl)-8-azabicyclo[3.2.1]octan-3-yl)indoline-5-carboxamide, and the pharmaceutically acceptable salts or solvates, e.g., hydrates, thereof.

It will be understood by those of ordinary skill in the art that compounds having Formula XIV can be drawn in various ways, e.g.,

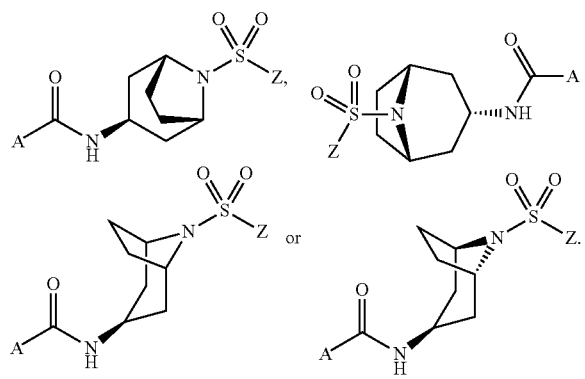

In another embodiment, Compounds of the Disclosure are compounds having Formula I, and the pharmaceutically acceptable salts or solvates, e.g., hydrates, thereof, wherein A is 1,2,3-triazolyl which may be optionally substituted with one substituent, and Y is —C(=O)—.

In another embodiment, Compounds of the Disclosure are compounds having having Formula XV:

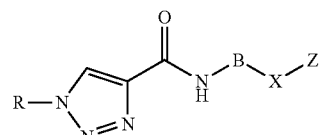

XV and the pharmaceutically acceptable salts or solvates, e.g., hydrates, thereof, wherein:

R is selected from the group consisting of $C_{1-6}$ alkyl and $C_{3-12}$ cycloalkyl;

B is optionally substituted 4- or 6- to 14-membered heterocyclenyl, e.g., B is:

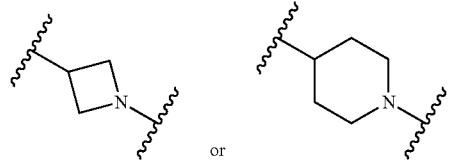 [SMILES: *C1CN(*)C1 ; *C1CCN(*)CC1]

or (wherein the nitrogen atom is attached to —X—Z); and

X and Z are as defined above in connection with Formula I. In another embodiment, X is absent. In another embodiment, Z is selected from the group consisting of hydrogen, $C_{1-6}$ alkyl, $C_{3-12}$ cycloalkyl, aralkyl, and (heteroaryl)alkyl, or Z is —CH($R^{9a}$)($R^{9b}$). In another embodiment, Z is selected from the group consisting of aralkyl and (heteroaryl)alkyl. In another embodiment, Z is (heteroaryl)alkyl that is substituted with an aralkyl, e.g.,

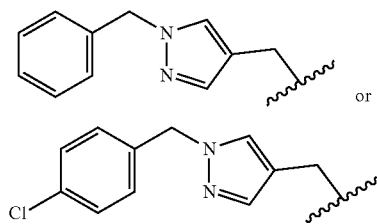

or or (heteroaryl)alkyl, e.g.,

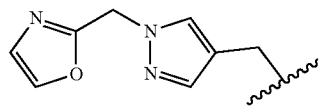

In another embodiment, Compounds of the Disclosure are compounds having having Formula XVI:

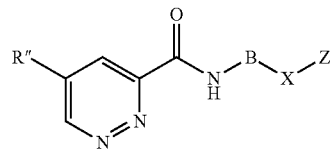

XVI and the pharmaceutically acceptable salts or solvates, e.g., hydrates, thereof, wherein:

R'' is selected from the group consisting of $C_{1-6}$ alkyl and $C_{3-12}$ cycloalkyl;

B is optionally substituted 4- or 6- to 14-membered heterocyclenyl, e.g., B is:

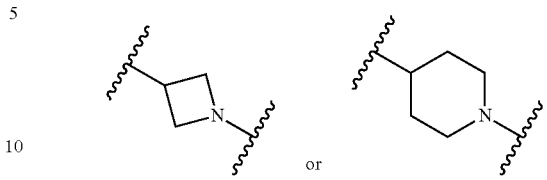

or (wherein the nitrogen atom is attached to —X—Z); and

X and Z are as defined above in connection with Formula I. In another embodiment, X is absent. In another embodiment, Z is selected from the group consisting of hydrogen, $C_{1-6}$ alkyl, $C_{3-12}$ cycloalkyl, aralkyl, and (heteroaryl)alkyl, or Z is —CH($R^{9a}$)($R^{9b}$). In another embodiment, Z is selected from the group consisting of aralkyl and (heteroaryl)alkyl. In another embodiment, Z is (heteroaryl)alkyl that is substituted with an aralkyl, e.g.,

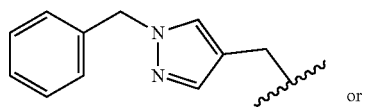

or

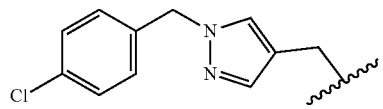

or (heteroaryl)alkyl, e.g.,

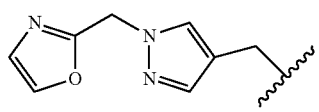

In another embodiment, Compounds of the Disclosure are compounds having having Formula XVII:

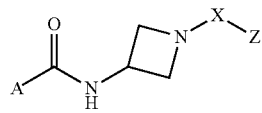

XVII and the pharmaceutically acceptable salts or solvates, e.g., hydrates, thereof, wherein A, X, and Z are as defined above in connection with Formula I. In another embodiment, X is absent. In another embodiment, Z is selected from the group consisting of hydrogen, $C_{1-6}$ alkyl, $C_{3-12}$ cycloalkyl, aralkyl, and (heteroaryl)alkyl, or Z is —CH($R^{9a}$)($R^{9b}$). In another embodiment, Z is selected from the group consisting of aralkyl and (heteroaryl)alkyl. In another embodiment, Z is aralkyl. In another embodiment, Z is (heteroaryl)alkyl. In another embodiment, Z is (heteroaryl)alkyl that is substituted with an aralkyl, e.g.,

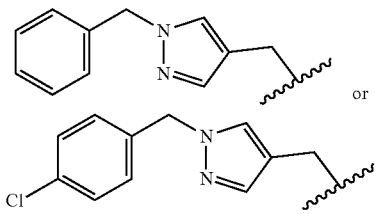

or (heteroaryl)alkyl, e.g.,

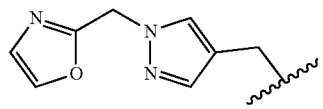

In another embodiment, Compounds of the Disclosure are compounds having having Formula XVIII:

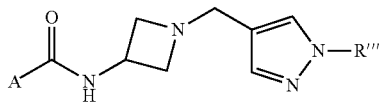

and the pharmaceutically acceptable salts or solvates, e.g., hydrates, thereof, wherein:

R''' is selected from the group consisting of aralkyl and (heteroaryl)alkyl; and A is as defined above in connection with Formula I. In another embodiment, A is selected from the group consisting of 1,2,3-triazolyl, 3-pyridazinyl, 2-pyridyl, and 2-imidazolyl, each of which is optionally substituted with one substituent selected from the group consisting of $C_{1-6}$ alkyl and $C_{3-6}$ cycloalkyl. In another embodiment, A is selected from the group consisting of:

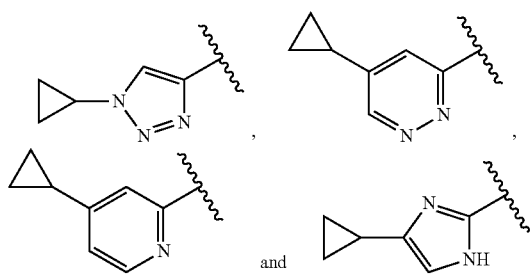

In another embodiment, R''' is aralkyl. In another embodiment, R''' is (heteroaryl)alkyl. In another embodiment, R''' is benzyl wherein the phenyl group is optionally substituted with one or two substituents, e.g., —CH$_2$(4-Cl-Ph), —CH$_2$(3-Cl-Ph), and —CH$_2$(4-CF$_3$-Ph).

In another embodiment, Compounds of the Disclosure are compounds of Table 1, and the pharmaceutically acceptable salts or solvates, e.g., hydrates, thereof, or different pharmaceutically acceptable salt thereof. The chemical names of the compounds of Table 1 are provided in Table 1A.

In another embodiment, Compounds of the Disclosure are compounds of Table 3, and the pharmaceutically acceptable salts or solvates, e.g., hydrates, thereof, or different pharmaceutically acceptable salt thereof. The chemical names of the compounds of Table 3 are provided in Table 3A.

In another embodiment, Compounds of the Disclosure are compounds of Table 4, and the pharmaceutically acceptable salts or solvates, e.g., hydrates, thereof, or different pharmaceutically acceptable salt thereof. The chemical names of the compounds of Table 4 are provided in Table 4A.

In another embodiment, Compounds of the Disclosure are compounds of Table 5, and the pharmaceutically acceptable salts or solvates, e.g., hydrates, thereof, or different pharmaceutically acceptable salt thereof.

In another embodiment, Compounds of the Disclosure are compounds of Table 6, and the pharmaceutically acceptable salts or solvates, e.g., hydrates, thereof, or different pharmaceutically acceptable salt thereof. The chemical names of the compounds of Table 6 are provided in Table 6A.

In another embodiment, Compounds of the Disclosure are compounds of Tables 1, 1A, 3, 3A, 4, 4A, 5, 6 and 6A, and the pharmaceutically acceptable salts or solvates, e.g., hydrates, thereof, or different pharmaceutically acceptable salt thereof.

In another embodiment, Compounds of the Disclosure are compounds selected from the group consisting of:

rel-N-{1-[(1S)-1-[2-chloro-3-(2-hydroxyethoxy)phenyl]ethyl]azetidin-3-yl}-1-cyclopropyl-1H-1,2,3-triazole-4-carboxamide;

N-(1-((1-(4-chlorobenzyl)-1H-pyrazol-4-yl)methyl)azetidin-3-yl)-5-cyclopropylpyridazine-3-carboxamide;

N-(1-((1-(4-chlorobenzyl)-1H-pyrazol-4-yl)methyl)azetidin-3-yl)-4-cyclopropylpicolinamide;

N-(1-((1-(4-chlorobenzyl)-1H-pyrazol-4-yl)methyl)azetidin-3-yl)-1-cyclopropyl-1H-1,2,3-triazole-4-carboxamide;

N-(1-((1-(4-chlorobenzyl)-1H-pyrazol-4-yl)methyl)azetidin-3-yl)-4-cyclopropyl-1H-imidazole-2-carboxamide; and 1-cyclopropyl-N-(1-((1-(4-methoxybenzyl)-1H-pyrazol-4-yl)methyl)azetidin-3-yl)-1H-1,2,3-triazole-4-carboxamide, and the pharmaceutically acceptable salts or solvates, e.g., hydrates, thereof.

It should be appreciated that the Compounds of the Disclosure in certain embodiments are the free base, various salts, and hydrate forms, and are not limited to the particular salt listed in Tables 1 and 3-6.

TABLE 1
| Cpd. No. | Structure | Salt Form |
|---|---|---|
| 3 | 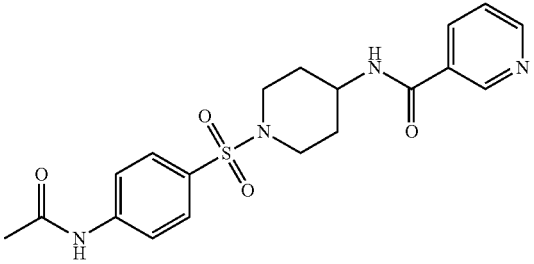 [SMILES: CC(=O)Nc1ccc(S(=O)(=O)N2CCC(NC(=O)c3cccnc3)CC2)cc1] | None |
| 4 | 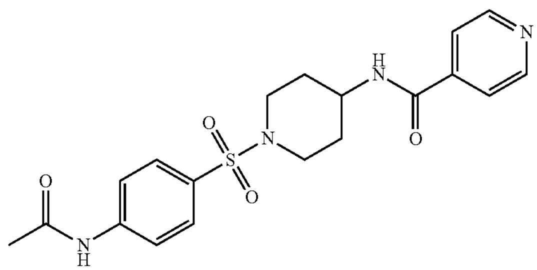 [SMILES: CC(=O)Nc1ccc(S(=O)(=O)N2CCC(NC(=O)c3ccncc3)CC2)cc1] | None |
| 5 | 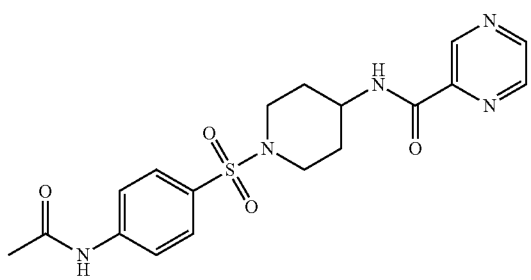 [SMILES: CC(=O)Nc1ccc(S(=O)(=O)N2CCC(NC(=O)c3cnccn3)CC2)cc1] | None |
| 6 | 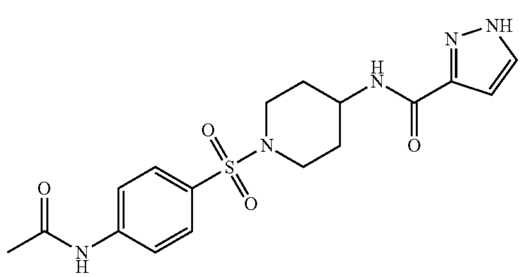 [SMILES: CC(=O)Nc1ccc(S(=O)(=O)N2CCC(NC(=O)c3cc[nH]n3)CC2)cc1] | None |
| 7 | 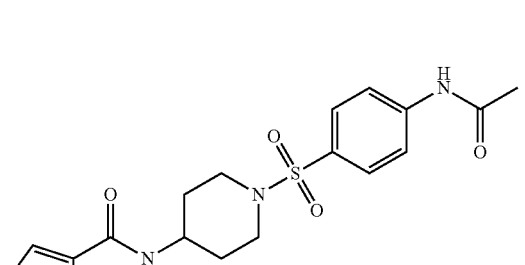 | |

TABLE 1-continued

| Cpd. No. | Structure | Salt Form |
|---|---|---|
| 8 | 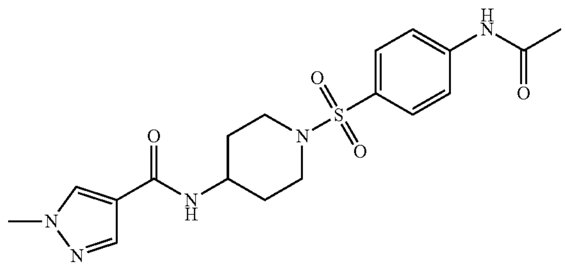 [SMILES: CC(=O)Nc1ccc(S(=O)(=O)N2CCC(NC(=O)c3cnn(C)c3)CC2)cc1] | None |
| 9 | 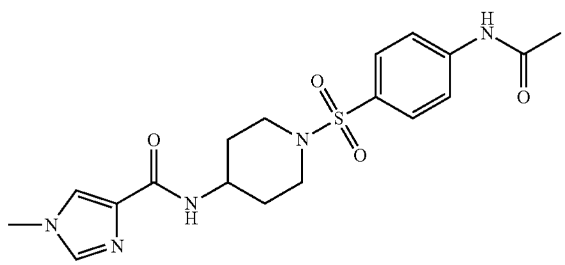 [SMILES: CC(=O)Nc1ccc(S(=O)(=O)N2CCC(NC(=O)c3cn(C)cn3)CC2)cc1] | None |
| 10 | 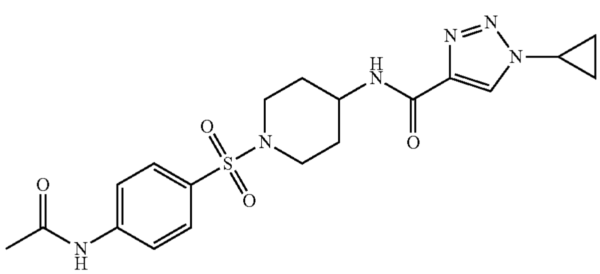 [SMILES: CC(=O)Nc1ccc(S(=O)(=O)N2CCC(NC(=O)c3cn(C4CC4)nn3)CC2)cc1] | None |
| 11 | 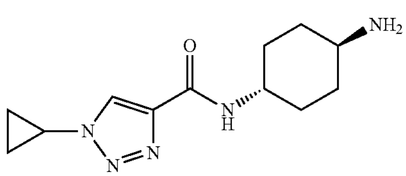 [SMILES: N[C@H]1CC[C@H](NC(=O)c2cn(C3CC3)nn2)CC1] | HCl |
| 12 | 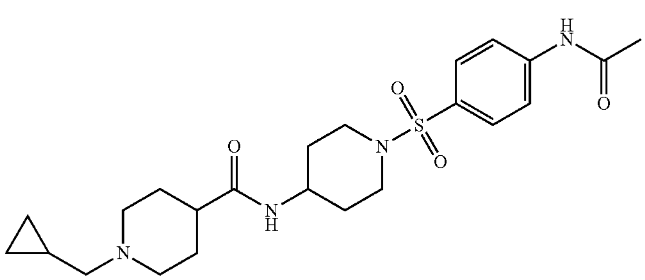 [SMILES: CC(=O)Nc1ccc(S(=O)(=O)N2CCC(NC(=O)C3CCN(CC4CC4)CC3)CC2)cc1] | None |
| 13 | 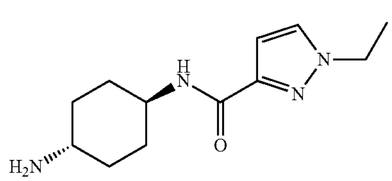 [SMILES: CCn1ccc(C(=O)N[C@H]2CC[C@H](N)CC2)n1] | HCl |

TABLE 1-continued

| Cpd. No. | Structure | Salt Form |
|---|---|---|
| 14 | 3-ethyl-N-(trans-4-aminocyclohexyl)isoxazole-5-carboxamide | HCl |
| 15 | 1-ethyl-N-(trans-4-aminocyclohexyl)-1H-imidazole-4-carboxamide | HCl |
| 16 | 2-ethyl-N-(trans-4-aminocyclohexyl)oxazole-4-carboxamide | HCl |
| 17 | 5-ethyl-N-(trans-4-aminocyclohexyl)isothiazole-3-carboxamide | HCl |
| 18 | N-(trans-4-aminocyclohexyl)-4-ethylbenzamide | TFA |
| 19 | N-(trans-4-aminocyclohexyl)-3-oxo-3,4-dihydro-2H-benzo[b][1,4]oxazine-7-carboxamide | TFA |
| 20 | N-(trans-4-aminocyclohexyl)-3-oxo-3,4-dihydro-2H-benzo[b][1,4]oxazine-6-carboxamide | TFA |
| 21 | N-(trans-4-aminocyclohexyl)-3-ethylbenzamide | TFA |

TABLE 1-continued

| Cpd. No. | Structure | Salt Form |
|---|---|---|
| 22 | 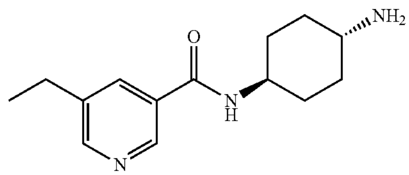 [SMILES: CCc1cncc(C(=O)N[C@H]2CC[C@H](N)CC2)c1] | TFA |
| 23 | 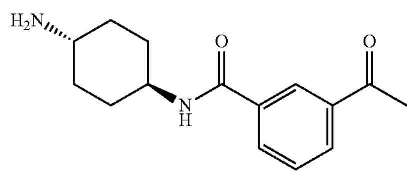 [SMILES: CC(=O)c1cccc(C(=O)N[C@H]2CC[C@H](N)CC2)c1] | HCl |
| 24 | 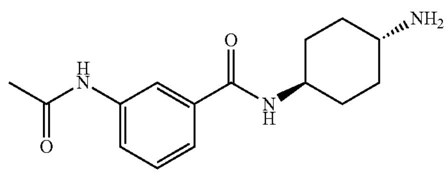 [SMILES: CC(=O)Nc1cccc(C(=O)N[C@H]2CC[C@H](N)CC2)c1] | HCl |
| 25 | 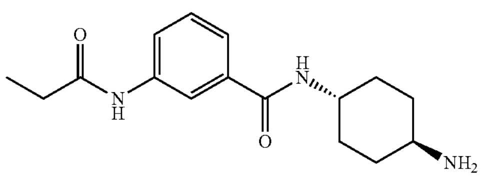 [SMILES: CCC(=O)Nc1cccc(C(=O)N[C@H]2CC[C@H](N)CC2)c1] | HCl |
| 26 | 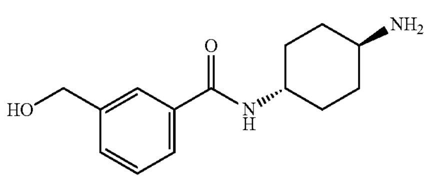 [SMILES: N[C@H]1CC[C@H](NC(=O)c2cccc(CO)c2)CC1] | HCl |
| 27 | 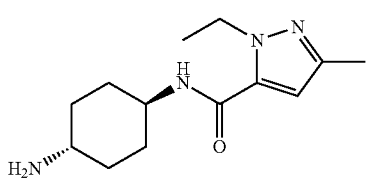 [SMILES: CCn1nc(C)cc1C(=O)N[C@H]1CC[C@H](N)CC1] | HCl |
| 28 | 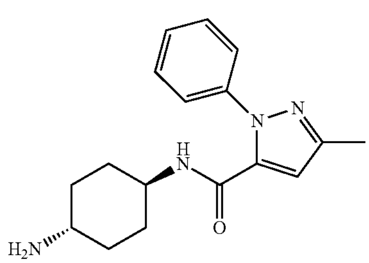 [SMILES: Cc1cc(C(=O)N[C@H]2CC[C@H](N)CC2)n(-c2ccccc2)n1] | HCl |

TABLE 1-continued
| Cpd. No. | Structure | Salt Form |
|---|---|---|
| 29 | 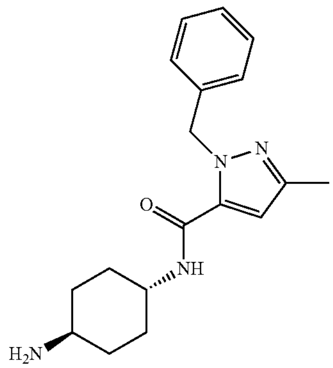 [SMILES: Cc1cc(C(=O)N[C@H]2CC[C@H](N)CC2)n(Cc2ccccc2)n1] | HCl |
| 30 | 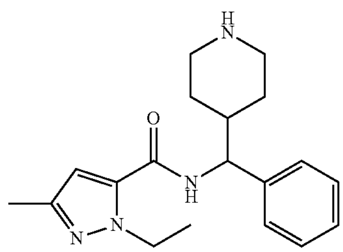 [SMILES: CCn1nc(C)cc1C(=O)NC(c1ccccc1)C1CCNCC1] | HCl |
| 31 | 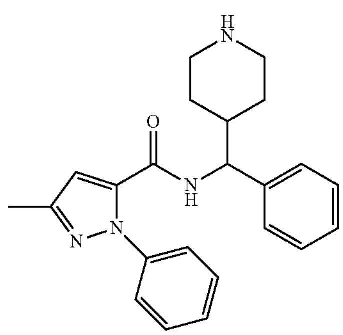 [SMILES: Cc1cc(C(=O)NC(c2ccccc2)C2CCNCC2)n(-c2ccccc2)n1] | HCl |
| 32 | 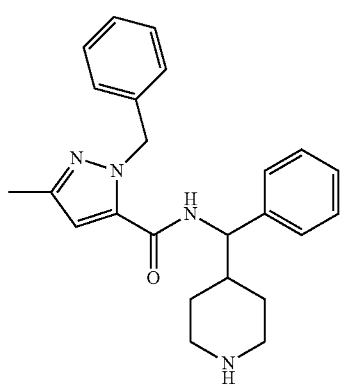 [SMILES: Cc1cc(C(=O)NC(c2ccccc2)C2CCNCC2)n(Cc2ccccc2)n1] | HCl |
| 33 | 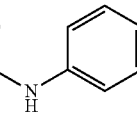 | HCl |

TABLE 1-continued

| Cpd. No. | Structure | Salt Form |
|---|---|---|
| 34 | 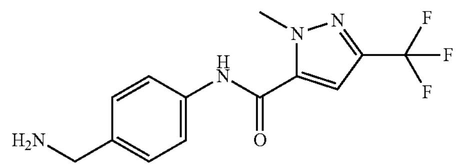 [SMILES: Cn1nc(C(F)(F)F)cc1C(=O)Nc1ccc(CN)cc1] | HCl |
| 35 | 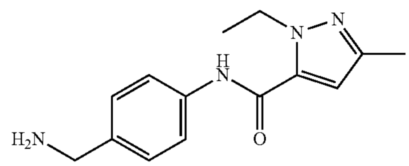 [SMILES: CCn1nc(C)cc1C(=O)Nc1ccc(CN)cc1] | HCl |
| 36 | 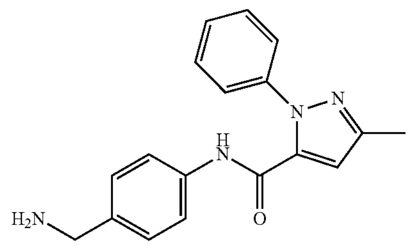 [SMILES: Cc1cc(C(=O)Nc2ccc(CN)cc2)n(-c2ccccc2)n1] | HCl |
| 37 | 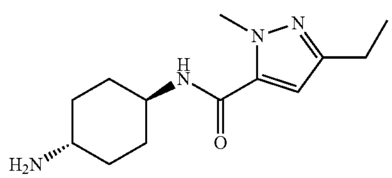 [SMILES: CCc1cc(C(=O)N[C@H]2CC[C@H](N)CC2)n(C)n1] | HCl |
| 38 | 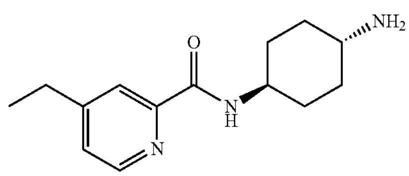 | None |
| 39 | 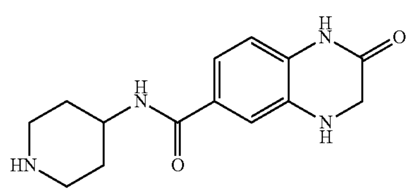 [SMILES: O=C1CNc2cc(C(=O)NC3CCNCC3)ccc2N1] | None |
| 40 | 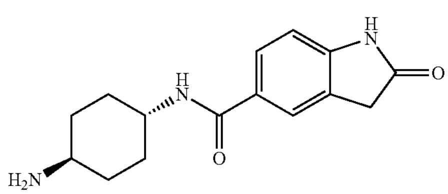 [SMILES: N[C@H]1CC[C@H](NC(=O)c2ccc3c(c2)CC(=O)N3)CC1] | HCl |
| 42 | 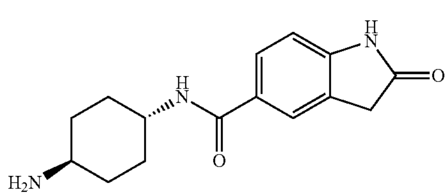 [SMILES: N[C@H]1CC[C@H](NC(=O)c2ccc3c(c2)CC(=O)N3)CC1] | HCl |

TABLE 1-continued

| Cpd. No. | Structure | Salt Form |
|---|---|---|
| 43 | 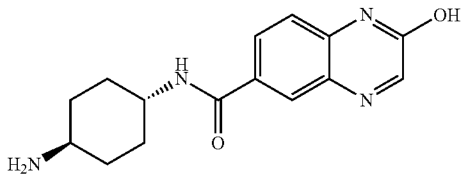 [SMILES: N[C@H]1CC[C@H](NC(=O)c2ccc3nc(O)cnc3c2)CC1] | HCl |
| 44 | 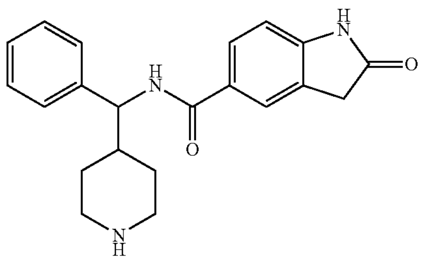 [SMILES: O=C1Cc2cc(C(=O)NC(c3ccccc3)C3CCNCC3)ccc2N1] | TFA |
| 45 | 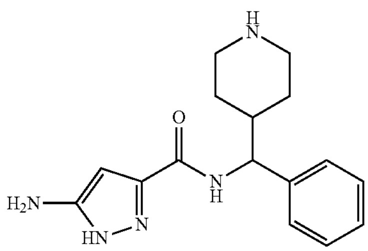 [SMILES: Nc1cc(C(=O)NC(c2ccccc2)C2CCNCC2)n[nH]1] | TFA |
| 46 | 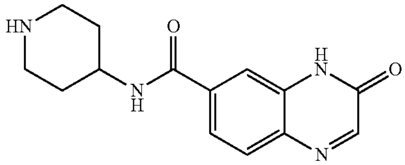 [SMILES: O=C(NC1CCNCC1)c1ccc2ncc(=O)[nH]c2c1] | TFA |
| 47 | 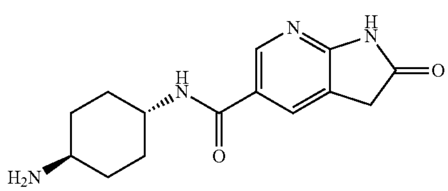 [SMILES: N[C@H]1CC[C@H](NC(=O)c2cnc3c(c2)CC(=O)N3)CC1] | HCl |
| 48 | 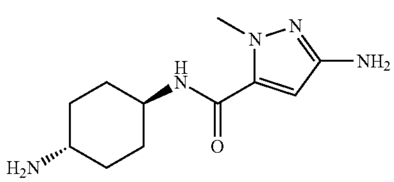 [SMILES: Cn1nc(N)cc1C(=O)N[C@H]1CC[C@H](N)CC1] | HCl |
| 49 | 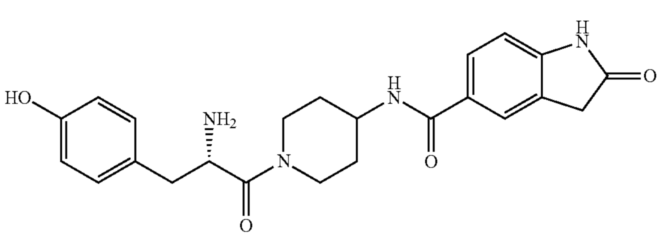 [SMILES: N[C@@H](Cc1ccc(O)cc1)C(=O)N1CCC(NC(=O)c2ccc3c(c2)CC(=O)N3)CC1] | HCl |

TABLE 1-continued

| Cpd. No. | Structure | Salt Form |
|---|---|---|
| 50 | 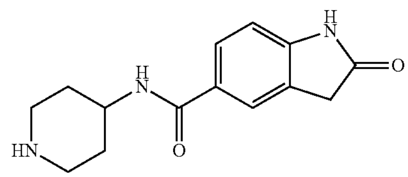 [SMILES: O=C1Cc2cc(C(=O)NC3CCNCC3)ccc2N1] | HCl |
| 51 | 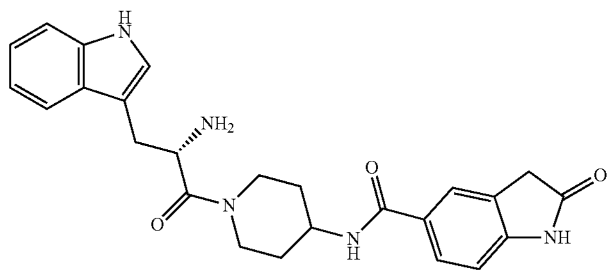 [SMILES: N[C@@H](Cc1c[nH]c2ccccc12)C(=O)N1CCC(NC(=O)c2ccc3c(c2)CC(=O)N3)CC1] | TFA |
| 52 | 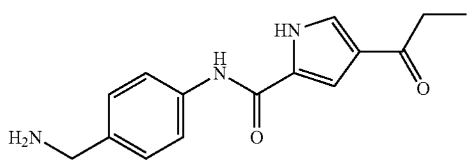 [SMILES: CCC(=O)c1c[nH]c(C(=O)Nc2ccc(CN)cc2)c1] | HCl |
| 53 | 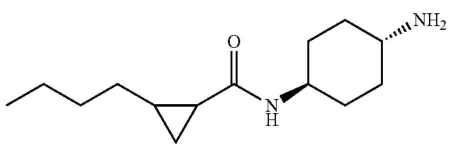 [SMILES: CCCCC1CC1C(=O)N[C@H]1CC[C@H](N)CC1] | HCl |
| 54 | 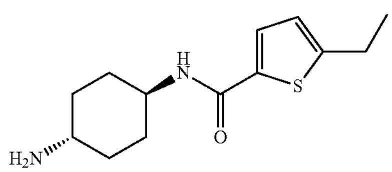 [SMILES: CCc1ccc(C(=O)N[C@H]2CC[C@H](N)CC2)s1] | HCl |
| 55 | 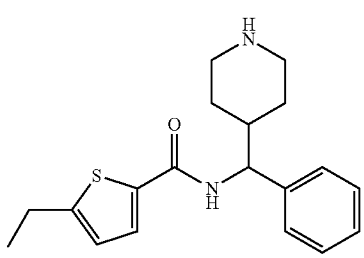 [SMILES: CCc1ccc(C(=O)NC(c2ccccc2)C2CCNCC2)s1] | HCl |
| 56 | 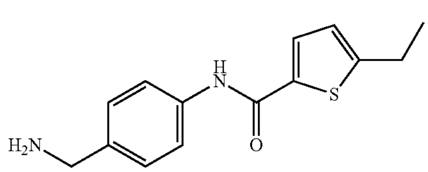 [SMILES: CCc1ccc(C(=O)Nc2ccc(CN)cc2)s1] | HCl |
| 57 | 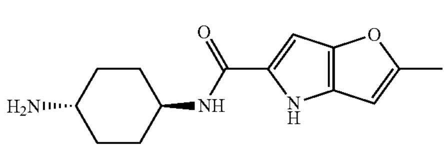 [SMILES: Cc1cc2[nH]c(C(=O)N[C@H]3CC[C@H](N)CC3)cc2o1] | HCl |

TABLE 1-continued

| Cpd. No. | Structure | Salt Form |
|---|---|---|
| 58 | 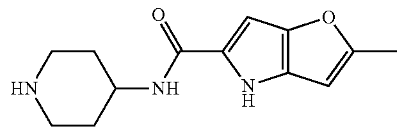 [SMILES: Cc1cc2[nH]c(C(=O)NC3CCNCC3)cc2o1] | HCl |
| 59 | 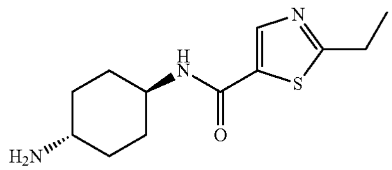 [SMILES: CCc1ncc(C(=O)N[C@H]2CC[C@H](N)CC2)s1] | HCl |
| 60 | 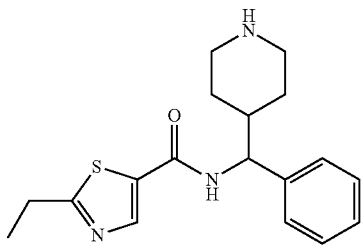 [SMILES: CCc1ncc(C(=O)NC(c2ccccc2)C2CCNCC2)s1] | HCl |
| 61 | 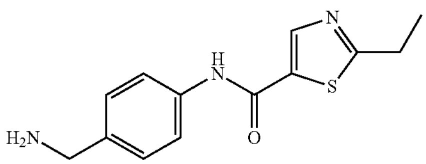 [SMILES: CCc1ncc(C(=O)Nc2ccc(CN)cc2)s1] | HCl |
| 62 | 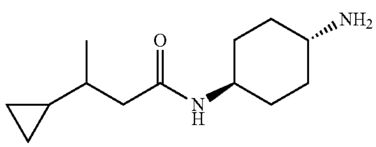 [SMILES: CC(CC(=O)N[C@H]1CC[C@H](N)CC1)C1CC1] | HCl |
| 63 | 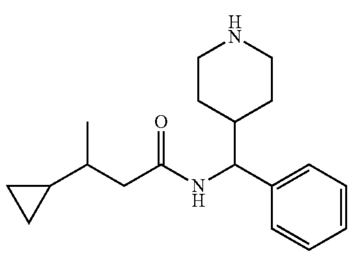 [SMILES: CC(CC(=O)NC(c1ccccc1)C1CCNCC1)C1CC1] | HCl |
| 64 | 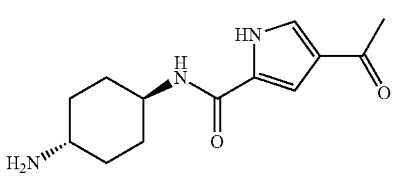 [SMILES: CC(=O)c1c[nH]c(C(=O)N[C@H]2CC[C@H](N)CC2)c1] | HCl |
| 65 | 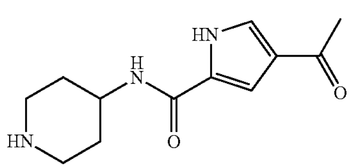 [SMILES: CC(=O)c1c[nH]c(C(=O)NC2CCNCC2)c1] | HCl |

TABLE 1-continued

| Cpd. No. | Structure | Salt Form |
|---|---|---|
| 66 | 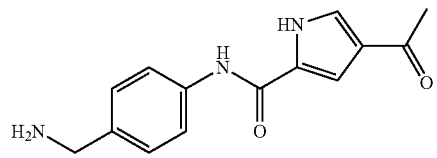 [SMILES: CC(=O)c1c[nH]c(C(=O)Nc2ccc(CN)cc2)c1] | HCl |
| 67 | 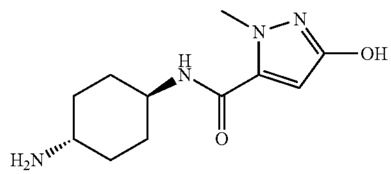 [SMILES: Cn1nc(O)cc1C(=O)N[C@H]1CC[C@H](N)CC1] | HCl |
| 68 | 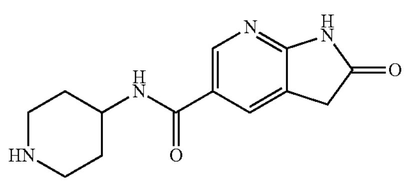 [SMILES: O=C1Cc2cc(C(=O)NC3CCNCC3)cnc2N1] | HCl |
| 69 | 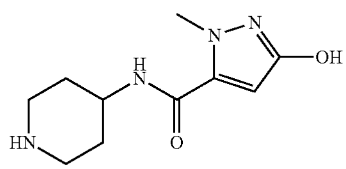 [SMILES: Cn1nc(O)cc1C(=O)NC1CCNCC1] | TFA |
| 70 | 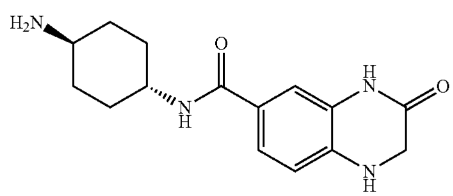 [SMILES: N[C@H]1CC[C@H](NC(=O)c2ccc3c(c2)NC(=O)CN3)CC1] | TFA |
| 71 | 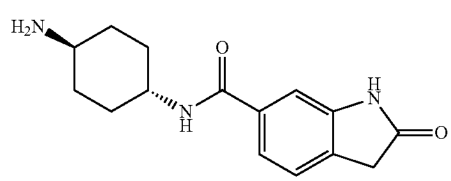 [SMILES: N[C@H]1CC[C@H](NC(=O)c2ccc3c(c2)NC(=O)C3)CC1] | TFA |
| 72 | 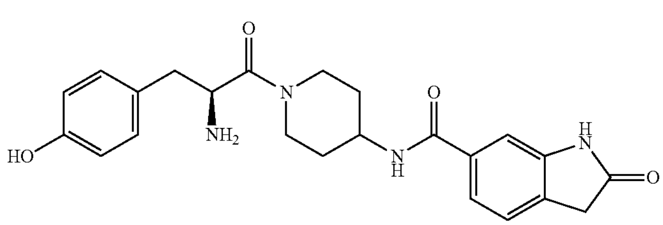 [SMILES: N[C@@H](Cc1ccc(O)cc1)C(=O)N1CCC(NC(=O)c2ccc3c(c2)NC(=O)C3)CC1] | TFA |
| 73 | 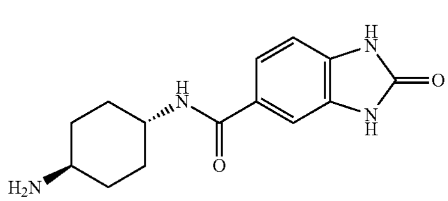 [SMILES: N[C@H]1CC[C@H](NC(=O)c2ccc3[nH]c(=O)[nH]c3c2)CC1] | HCl |

TABLE 1-continued

| Cpd. No. | Structure | Salt Form |
|---|---|---|
| 74 | (1,4-trans-diaminocyclohexyl)-N-carboxamide linked to 2-oxo-1,2,3,4-tetrahydroquinoline-6-yl | HCl |
| 75 | (1,4-trans-diaminocyclohexyl)-N-carboxamide linked to 6-aminonaphthalen-2-yl | HCl |
| 76 | (1,4-trans-diaminocyclohexyl)-N-carboxamide linked to 2-hydroxyquinolin-6-yl | HCl |
| 77 | 4-propanoyl-1H-pyrrole-2-carboxamide, N-[phenyl(piperidin-4-yl)methyl] | HCl |
| 78 | 2-(ethylsulfonyl)-N-(4-aminocyclohexyl)propanamide | HCl |
| 79 | 5-[(dimethylamino)methyl]-N-(4-aminocyclohexyl)furan-2-carboxamide | HCl |
| 80 | 2-amino-N-[phenyl(piperidin-4-yl)methyl]-1,3-oxazole-4-carboxamide | HCl |

TABLE 1-continued

| Cpd. No. | Structure | Salt Form |
|---|---|---|
| 81 | 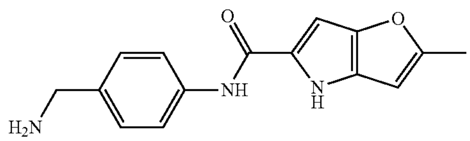 [SMILES: Cc1cc2[nH]c(C(=O)Nc3ccc(CN)cc3)cc2o1] | TFA |
| 82 | 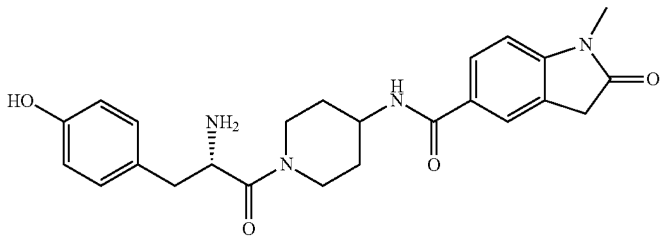 [SMILES: CN1C(=O)Cc2cc(C(=O)NC3CCN(C(=O)[C@@H](N)Cc4ccc(O)cc4)CC3)ccc21] | TFA |
| 83 | 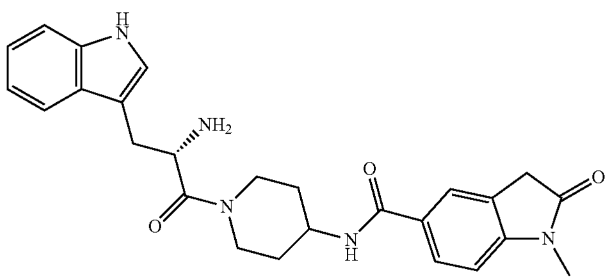 [SMILES: CN1C(=O)Cc2cc(C(=O)NC3CCN(C(=O)[C@@H](N)Cc4c[nH]c5ccccc45)CC3)ccc21] | TFA |
| 84 | 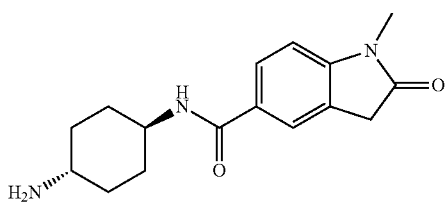 [SMILES: CN1C(=O)Cc2cc(C(=O)N[C@H]3CC[C@H](N)CC3)ccc21] | TFA |
| 85 | 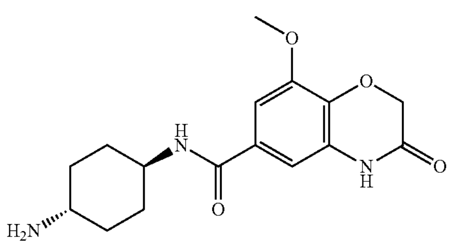 [SMILES: COc1cc(C(=O)N[C@H]2CC[C@H](N)CC2)cc2c1OCC(=O)N2] | HCl |
| 86 | 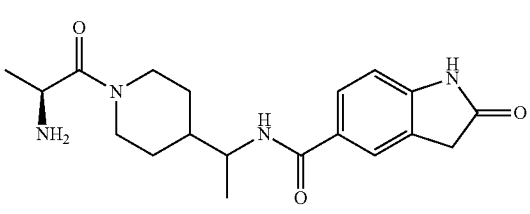 [SMILES: CC(NC(=O)c1ccc2c(c1)CC(=O)N2)C1CCN(C(=O)[C@H](C)N)CC1] | HCl |
| 87 | 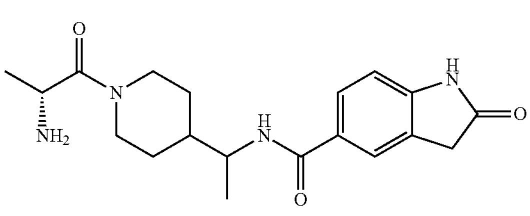 [SMILES: CC(NC(=O)c1ccc2c(c1)CC(=O)N2)C1CCN(C(=O)[C@@H](C)N)CC1] | HCl |

TABLE 1-continued

| Cpd. No. | Structure | Salt Form |
|---|---|---|
| 88 | 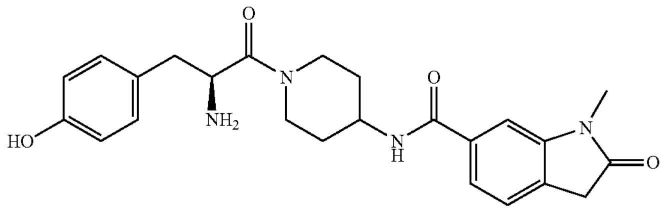 [SMILES: CN1C(=O)Cc2ccc(C(=O)NC3CCN(C(=O)[C@@H](N)Cc4ccc(O)cc4)CC3)cc21] | TFA |
| 89 | 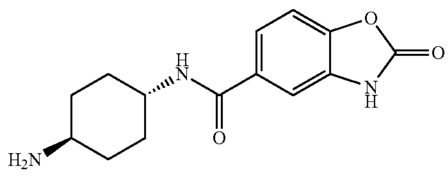 [SMILES: N[C@H]1CC[C@H](NC(=O)c2ccc3oc(=O)[nH]c3c2)CC1] | TFA |
| 90 | 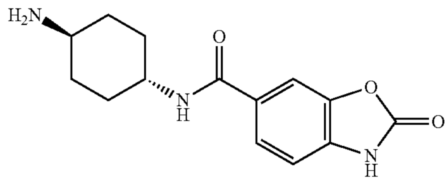 [SMILES: N[C@H]1CC[C@H](NC(=O)c2ccc3[nH]c(=O)oc3c2)CC1] | TFA |
| 91 | 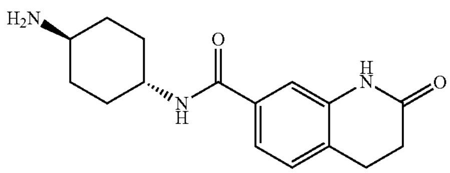 [SMILES: N[C@H]1CC[C@H](NC(=O)c2ccc3c(c2)NC(=O)CC3)CC1] | TFA |
| 92 | 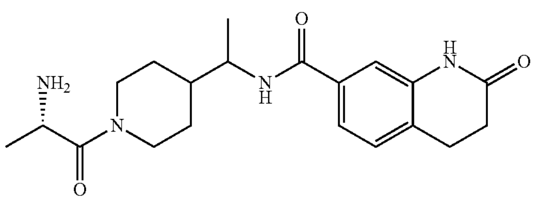 [SMILES: CC(NC(=O)c1ccc2c(c1)NC(=O)CC2)C1CCN(C(=O)[C@H](C)N)CC1] | TFA |
| 93 | 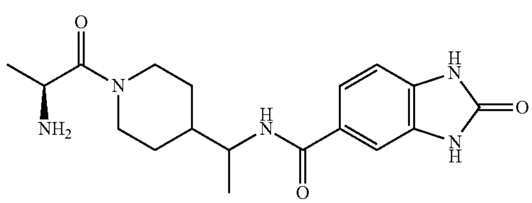 [SMILES: CC(NC(=O)c1ccc2[nH]c(=O)[nH]c2c1)C1CCN(C(=O)[C@H](C)N)CC1] | HCl |
| 94 | 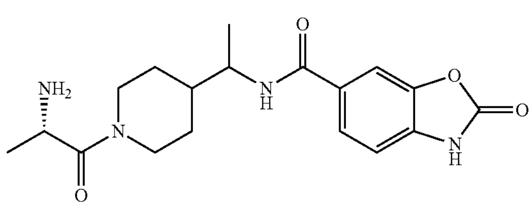 [SMILES: CC(NC(=O)c1ccc2[nH]c(=O)oc2c1)C1CCN(C(=O)[C@H](C)N)CC1] | HCl |
| 95 | 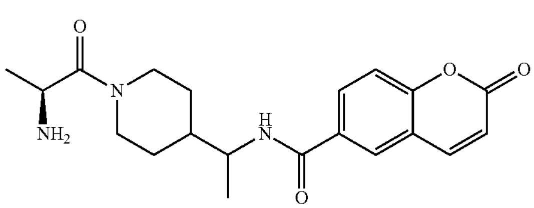 [SMILES: CC(NC(=O)c1ccc2oc(=O)ccc2c1)C1CCN(C(=O)[C@H](C)N)CC1] | HCl |

TABLE 1-continued

| Cpd. No. | Structure | Salt Form |
|---|---|---|
| 96 | 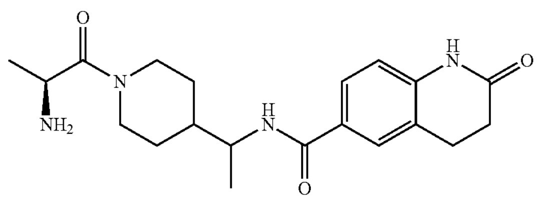 [SMILES: CC(NC(=O)c1ccc2c(c1)CCC(=O)N2)C1CCN(C(=O)[C@H](C)N)CC1] | HCl |
| 97 | 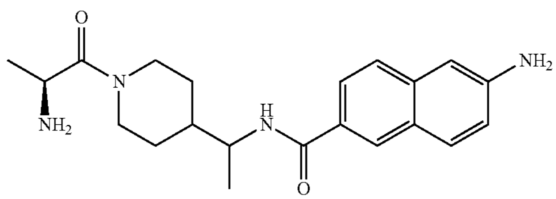 [SMILES: CC(NC(=O)c1ccc2cc(N)ccc2c1)C1CCN(C(=O)[C@H](C)N)CC1] | HCl |
| 98 | 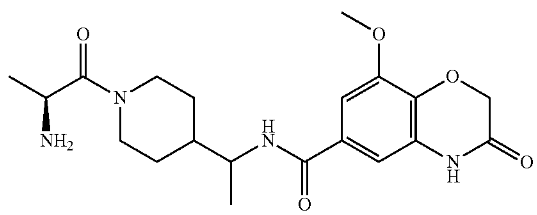 [SMILES: COc1cc(C(=O)NC(C)C2CCN(C(=O)[C@H](C)N)CC2)cc2c1OCC(=O)N2] | HCl |
| 99 | 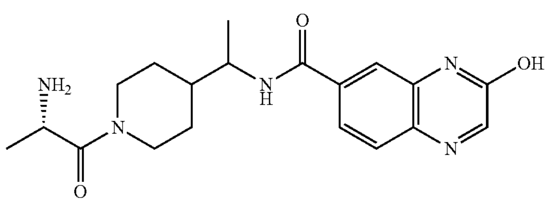 [SMILES: CC(NC(=O)c1ccc2ncc(O)nc2c1)C1CCN(C(=O)[C@H](C)N)CC1] | TFA |
| 100 | 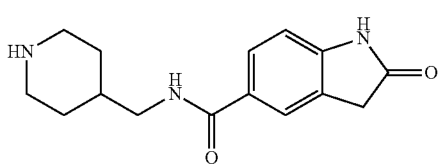 [SMILES: O=C1Cc2cc(C(=O)NCC3CCNCC3)ccc2N1] | HCl |
| 101 | 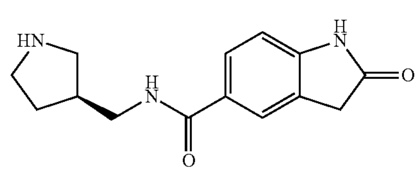 [SMILES: O=C1Cc2cc(C(=O)NC[C@H]3CCNC3)ccc2N1] | HCl |
| 102 | 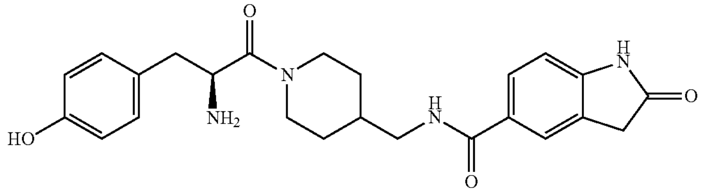 [SMILES: N[C@@H](Cc1ccc(O)cc1)C(=O)N1CCC(CNC(=O)c2ccc3c(c2)CC(=O)N3)CC1] | HCl |

TABLE 1-continued

| Cpd. No. | Structure | Salt Form |
|---|---|---|
| 103 | 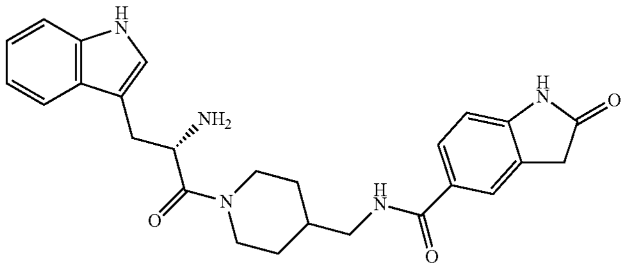 [SMILES: N[C@@H](Cc1c[nH]c2ccccc12)C(=O)N1CCC(CNC(=O)c2ccc3c(c2)CC(=O)N3)CC1] | TFA |
| 104 | 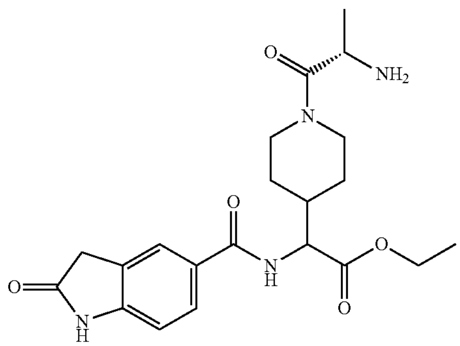 [SMILES: CCOC(=O)C(NC(=O)c1ccc2c(c1)CC(=O)N2)C1CCN(C(=O)[C@H](C)N)CC1] | TFA |
| 105 | 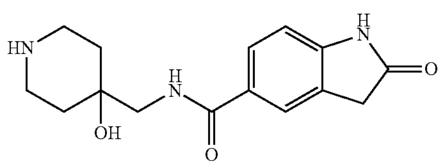 [SMILES: O=C1Cc2cc(C(=O)NCC3(O)CCNCC3)ccc2N1] | TFA |
| 106 | 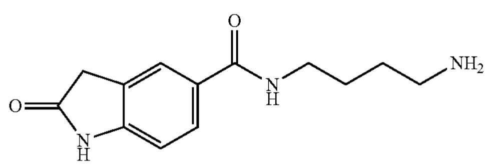 [SMILES: NCCCCNC(=O)c1ccc2c(c1)CC(=O)N2] | TFA |
| 107 | 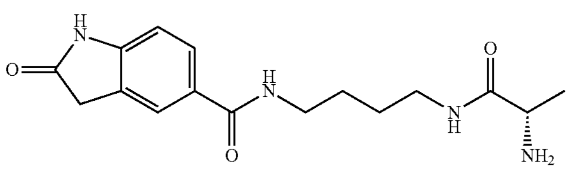 [SMILES: C[C@H](N)C(=O)NCCCCNC(=O)c1ccc2c(c1)CC(=O)N2] | TFA |
| 108 | 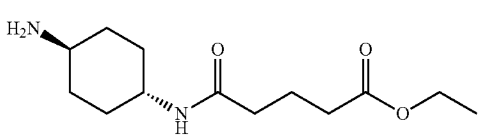 [SMILES: CCOC(=O)CCCC(=O)N[C@H]1CC[C@H](N)CC1] | HCl |
| 109 | 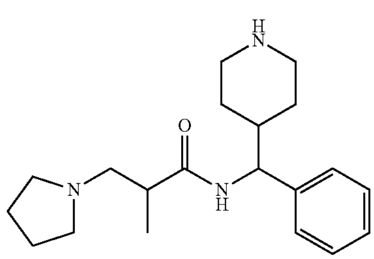 [SMILES: CC(CN1CCCC1)C(=O)NC(c1ccccc1)C1CCNCC1] | HCl |

TABLE 1-continued

| Cpd. No. | Structure | Salt Form |
|---|---|---|
| 110 | 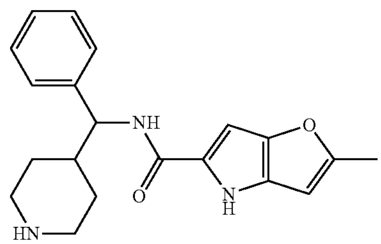 [SMILES: Cc1cc2[nH]c(C(=O)NC(c3ccccc3)C3CCNCC3)cc2o1] | HCl |
| 111 | 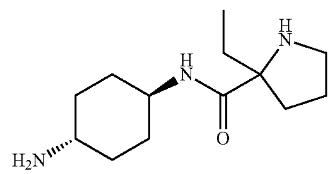 [SMILES: CCC1(C(=O)N[C@H]2CC[C@H](N)CC2)CCCN1] | HCl |
| 112 | 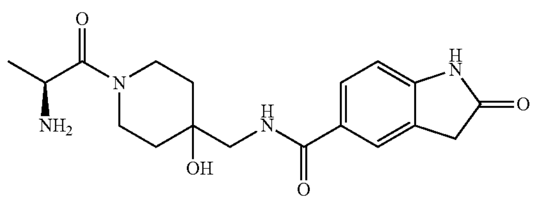 [SMILES: C[C@H](N)C(=O)N1CCC(O)(CNC(=O)c2ccc3c(c2)CC(=O)N3)CC1] | TFA |
| 113 | 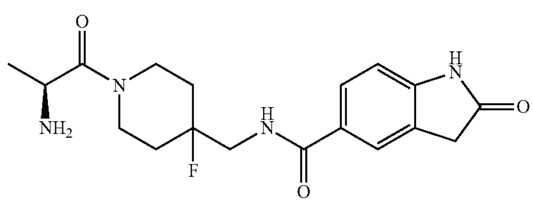 | HCl |
| 114 | 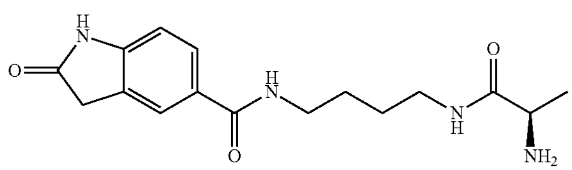 [SMILES: C[C@@H](N)C(=O)NCCCCNC(=O)c1ccc2c(c1)CC(=O)N2] | TFA |
| 115 | 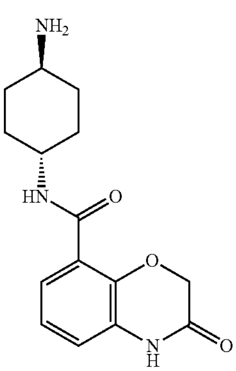 [SMILES: N[C@H]1CC[C@H](NC(=O)c2cccc3c2OCC(=O)N3)CC1] | TFA |
| 116 | 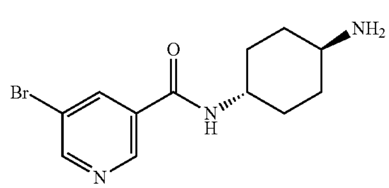 [SMILES: N[C@H]1CC[C@H](NC(=O)c2cncc(Br)c2)CC1] | TFA |

TABLE 1-continued

| Cpd. No. | Structure | Salt Form |
|---|---|---|
| 117 | 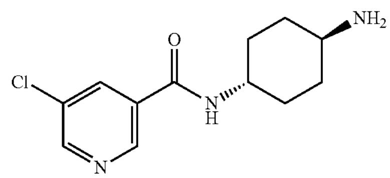 [SMILES: N[C@H]1CC[C@H](NC(=O)c2cncc(Cl)c2)CC1] | TFA |
| 118 | 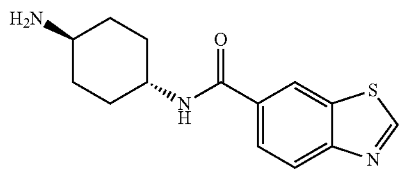 [SMILES: N[C@H]1CC[C@H](NC(=O)c2ccc3ncsc3c2)CC1] | TFA |
| 119 | 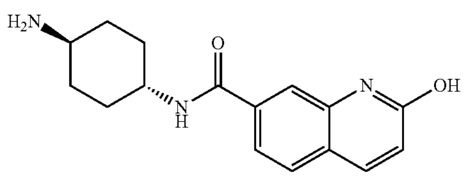 [SMILES: N[C@H]1CC[C@H](NC(=O)c2ccc3ccc(O)nc3c2)CC1] | HCl |
| 120 | 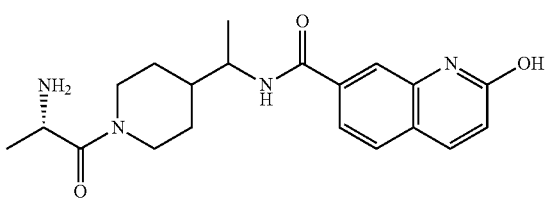 [SMILES: CC(NC(=O)c1ccc2ccc(O)nc2c1)C1CCN(C(=O)[C@H](C)N)CC1] | TFA |
| 121 | 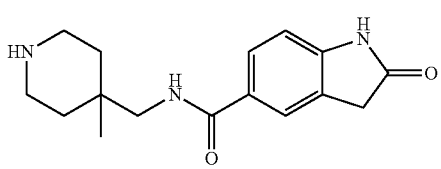 [SMILES: CC1(CNC(=O)c2ccc3c(c2)CC(=O)N3)CCNCC1] | HCOOH |
| 122 | 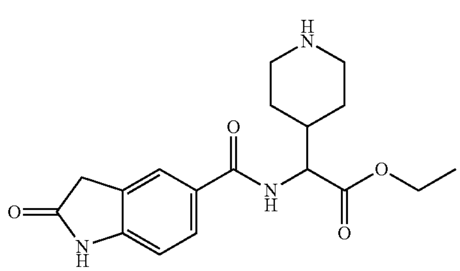 [SMILES: CCOC(=O)C(NC(=O)c1ccc2c(c1)CC(=O)N2)C1CCNCC1] | TFA |
| 123 | 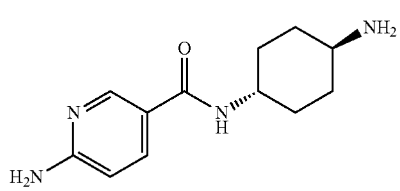 [SMILES: Nc1ccc(C(=O)N[C@H]2CC[C@H](N)CC2)cn1] | TFA |

| Cpd. No. | Structure | Salt Form |
|---|---|---|
| 125 | 7-fluoro-2-hydroxyquinoline-4-carboxamide linked to trans-4-aminocyclohexyl | TFA |
| 126 | 2-chloro-5-(4H-1,2,4-triazol-4-yl)benzamide linked to trans-4-aminocyclohexyl | TFA |
| 127 | 4H-1,2,4-triazole-3-carboxamide linked to trans-4-aminocyclohexyl | TFA |
| 129 | 2-(pyridin-3-yl)acetamide linked to trans-4-aminocyclohexyl | TFA |
| 130 | 3-aminopropanamide-N-(trans-4-{[(2-oxo-2,3-dihydro-1H-indol-5-yl)carbonyl]amino}cyclohexyl) | TFA |
| 131 | ethyl 4-({[(2-oxo-2,3-dihydro-1H-indol-5-yl)carbonyl]amino}methyl)piperidine-4-carboxylate | HCOOH |
| 132 | ethyl 1-(L-alanyl)-4-({[(2-oxo-2,3-dihydro-1H-indol-5-yl)carbonyl]amino}methyl)piperidine-4-carboxylate | TFA |

TABLE 1-continued

| Cpd. No. | Structure | Salt Form |
|---|---|---|
| 133 | 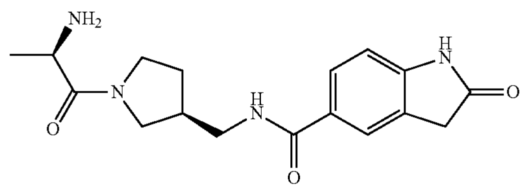 [SMILES: C[C@@H](N)C(=O)N1CC[C@@H](CNC(=O)c2ccc3c(c2)CC(=O)N3)C1] | TFA |
| 134 | 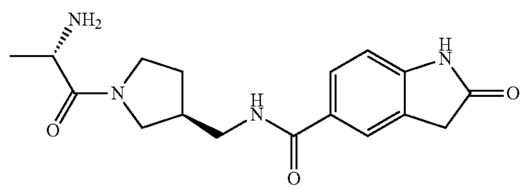 [SMILES: C[C@H](N)C(=O)N1CC[C@@H](CNC(=O)c2ccc3c(c2)CC(=O)N3)C1] | TFA |
| 135 | 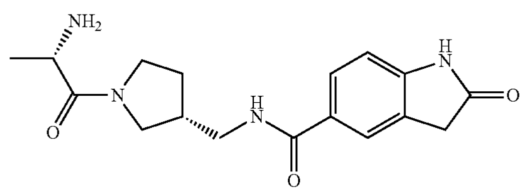 [SMILES: C[C@H](N)C(=O)N1CC[C@H](CNC(=O)c2ccc3c(c2)CC(=O)N3)C1] | TFA |
| 136 | 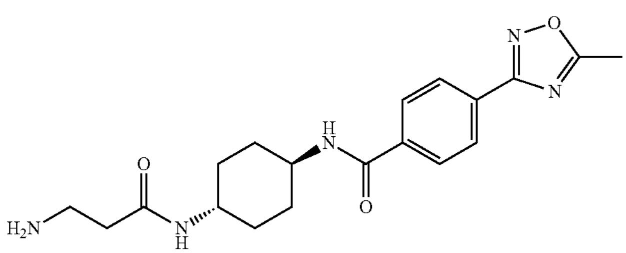 [SMILES: Cc1nc(-c2ccc(C(=O)N[C@H]3CC[C@H](NC(=O)CCN)CC3)cc2)no1] | HCl |
| 137 | 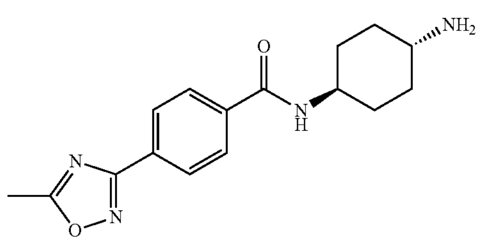 [SMILES: Cc1nc(-c2ccc(C(=O)N[C@H]3CC[C@H](N)CC3)cc2)no1] | HCl |
| 138 | 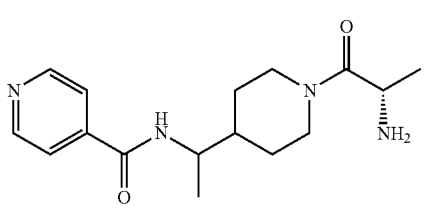 [SMILES: CC(NC(=O)c1ccncc1)C1CCN(C(=O)[C@H](C)N)CC1] | HCl |
| 139 | 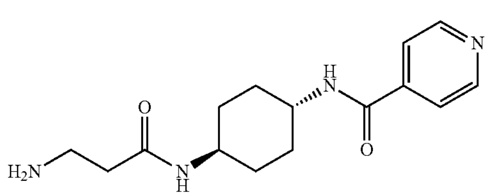 [SMILES: NCCC(=O)N[C@H]1CC[C@H](NC(=O)c2ccncc2)CC1] | HCl |

TABLE 1-continued

| Cpd. No. | Structure | Salt Form |
|---|---|---|
| 140 | 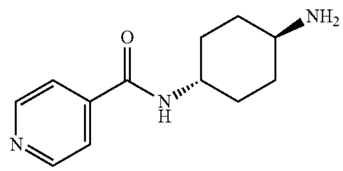 [SMILES: N[C@H]1CC[C@H](NC(=O)c2ccncc2)CC1] | HCl |
| 141 | 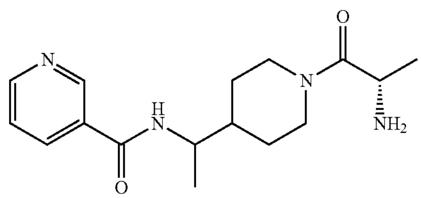 [SMILES: CC(NC(=O)c1cccnc1)C1CCN(C(=O)[C@H](C)N)CC1] | HCl |
| 142 | 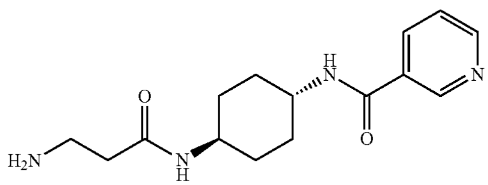 [SMILES: NCCC(=O)N[C@H]1CC[C@H](NC(=O)c2cccnc2)CC1] | HCl |
| 143 | 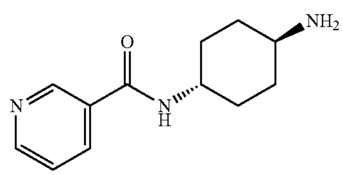 [SMILES: N[C@H]1CC[C@H](NC(=O)c2cccnc2)CC1] | HCl |
| 144 | 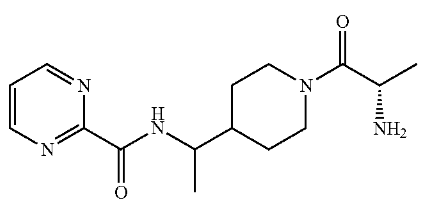 [SMILES: CC(NC(=O)c1ncccn1)C1CCN(C(=O)[C@H](C)N)CC1] | HCl |
| 145 | 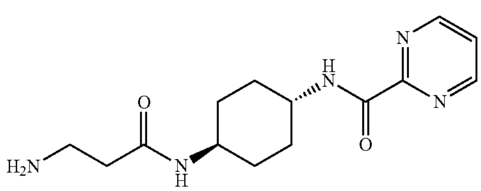 [SMILES: NCCC(=O)N[C@H]1CC[C@H](NC(=O)c2ncccn2)CC1] | HCl |
| 146 | 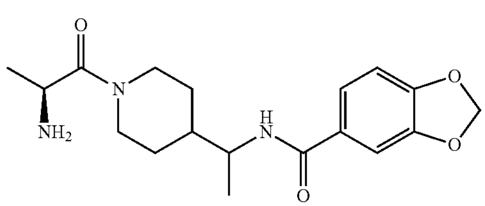 [SMILES: CC(NC(=O)c1ccc2c(c1)OCO2)C1CCN(C(=O)[C@H](C)N)CC1] | HCl |
| 147 | 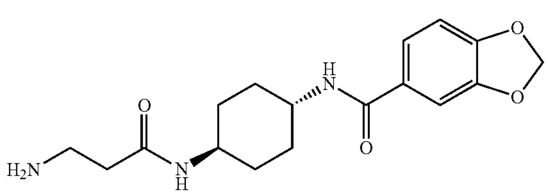 [SMILES: NCCC(=O)N[C@H]1CC[C@H](NC(=O)c2ccc3c(c2)OCO3)CC1] | HCl |

TABLE 1-continued
| Cpd. No. | Structure | Salt Form |
|---|---|---|
| 148 | 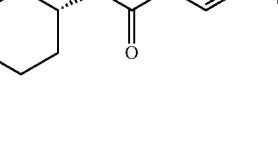 | HCl |
| 149 | 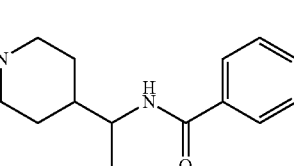 | HCl |
| 150 | 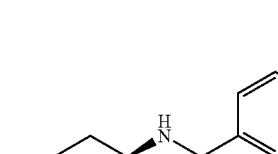 | HCl |
| 151 | 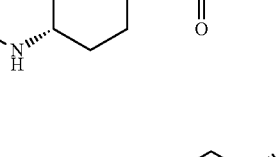 | HCl |
| 152 | 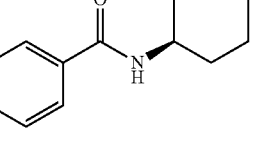 | HCl |
| 153 | 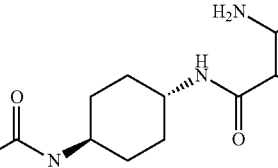 | HCl |
| 154 | 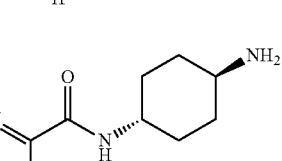 | HCl |

TABLE 1-continued

| Cpd. No. | Structure | Salt Form |
|---|---|---|
| 155 | 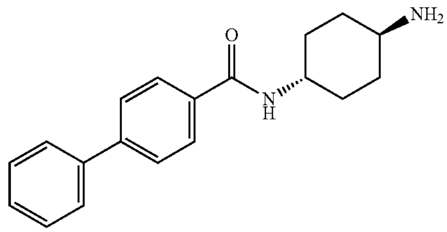 [SMILES: N[C@H]1CC[C@H](NC(=O)c2ccc(-c3ccccc3)cc2)CC1] | HCl |
| 156 | 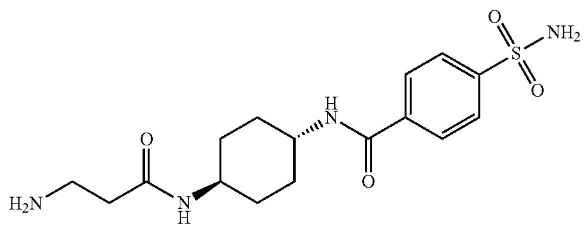 [SMILES: NCCC(=O)N[C@H]1CC[C@H](NC(=O)c2ccc(S(N)(=O)=O)cc2)CC1] | HCl |
| 157 | 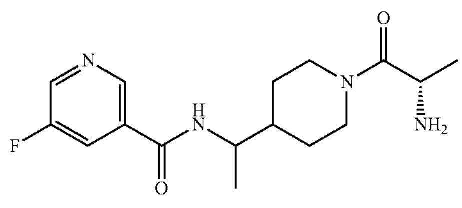 [SMILES: CC(NC(=O)c1cncc(F)c1)C1CCN(C(=O)[C@H](C)N)CC1] | HCl |
| 158 | 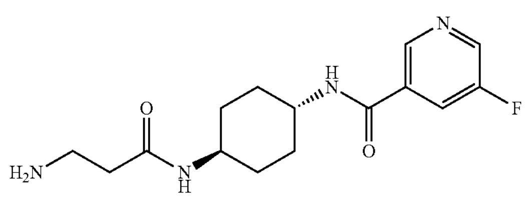 [SMILES: NCCC(=O)N[C@H]1CC[C@H](NC(=O)c2cncc(F)c2)CC1] | HCl |
| 159 | 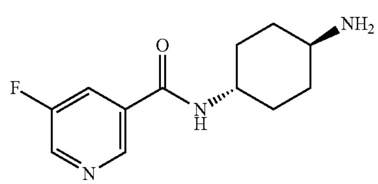 [SMILES: N[C@H]1CC[C@H](NC(=O)c2cncc(F)c2)CC1] | HCl |
| 160 | 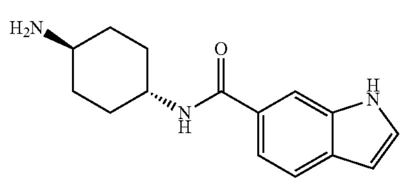 [SMILES: N[C@H]1CC[C@H](NC(=O)c2ccc3cc[nH]c3c2)CC1] | HCl |
| 161 | 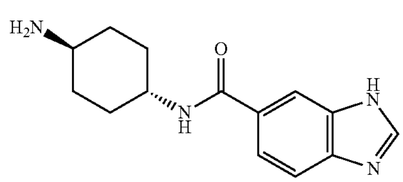 [SMILES: N[C@H]1CC[C@H](NC(=O)c2ccc3nc[nH]c3c2)CC1] | HCl |

TABLE 1-continued

| Cpd. No. | Structure | Salt Form |
|---|---|---|
| 162 | 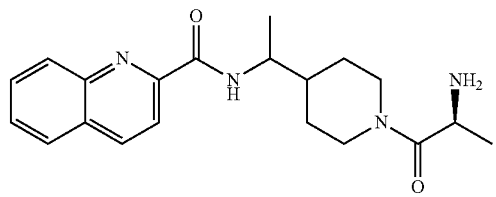 [SMILES: CC(NC(=O)c1ccc2ccccc2n1)C1CCN(C(=O)[C@H](C)N)CC1] | HCl |
| 163 | 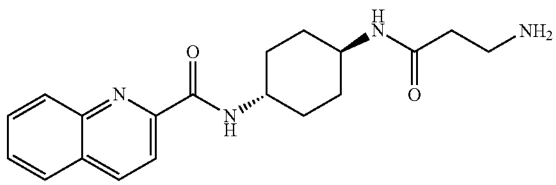 [SMILES: NCCC(=O)N[C@H]1CC[C@H](NC(=O)c2ccc3ccccc3n2)CC1] | HCl |
| 164 | 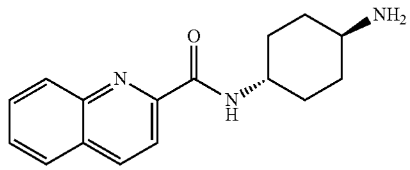 [SMILES: N[C@H]1CC[C@H](NC(=O)c2ccc3ccccc3n2)CC1] | HCl |
| 165 | 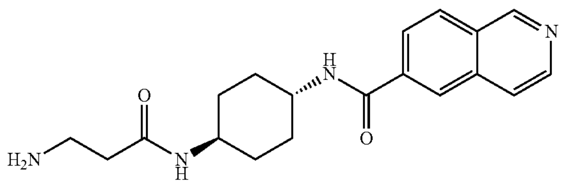 [SMILES: NCCC(=O)N[C@H]1CC[C@H](NC(=O)c2ccc3cnccc3c2)CC1] | HCl |
| 166 | 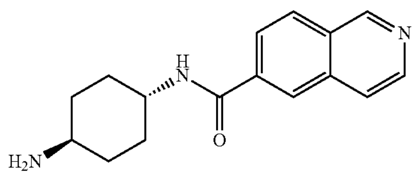 [SMILES: N[C@H]1CC[C@H](NC(=O)c2ccc3cnccc3c2)CC1] | HCl |
| 167 | 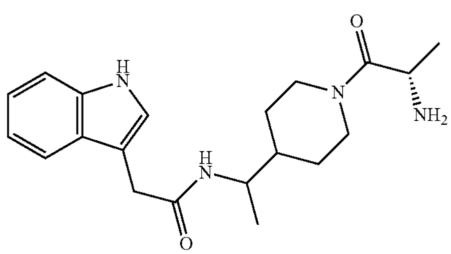 [SMILES: CC(NC(=O)Cc1c[nH]c2ccccc12)C1CCN(C(=O)[C@H](C)N)CC1] | HCl |
| 168 | 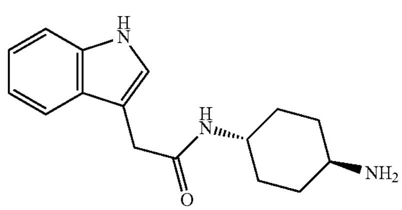 [SMILES: N[C@H]1CC[C@H](NC(=O)Cc2c[nH]c3ccccc23)CC1] | HCl |
| 169 | 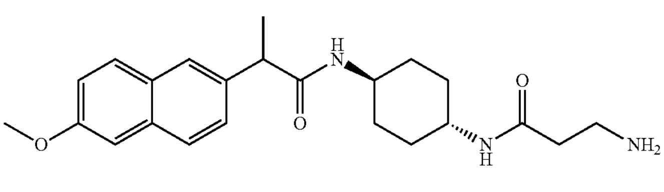 [SMILES: COc1ccc2cc(C(C)C(=O)N[C@H]3CC[C@H](NC(=O)CCN)CC3)ccc2c1] | TFA |

TABLE 1-continued

| Cpd. No. | Structure | Salt Form |
|---|---|---|
| 170 | 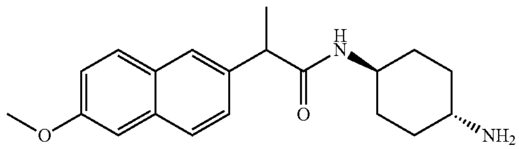 [SMILES: COc1ccc2cc(C(C)C(=O)N[C@H]3CC[C@H](N)CC3)ccc2c1] | TFA |
| 171 | 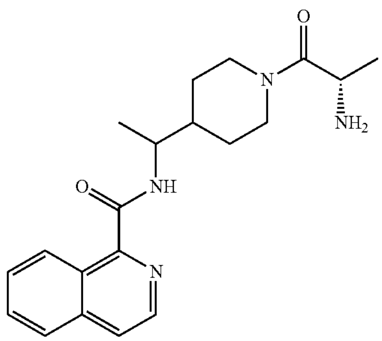 [SMILES: CC(NC(=O)c1nccc2ccccc12)C1CCN(C(=O)[C@H](C)N)CC1] | TFA |
| 172 | 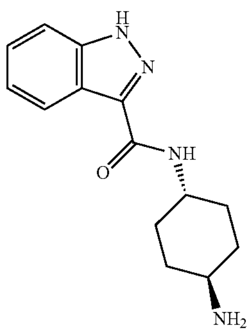 [SMILES: N[C@H]1CC[C@H](NC(=O)c2n[nH]c3ccccc23)CC1] | TFA |
| 173 | 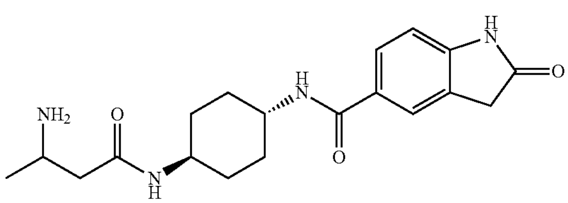 [SMILES: CC(N)CC(=O)N[C@H]1CC[C@H](NC(=O)c2ccc3c(c2)CC(=O)N3)CC1] | TFA |
| 174 | 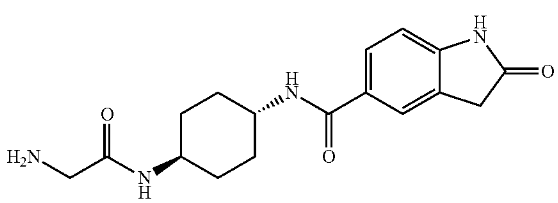 [SMILES: NCC(=O)N[C@H]1CC[C@H](NC(=O)c2ccc3c(c2)CC(=O)N3)CC1] | TFA |
| 175 | 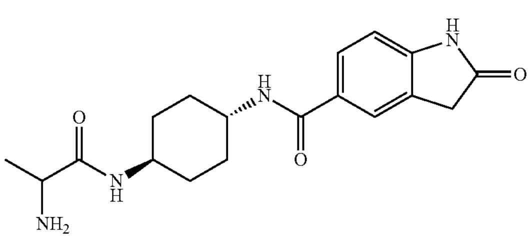 [SMILES: CC(N)C(=O)N[C@H]1CC[C@H](NC(=O)c2ccc3c(c2)CC(=O)N3)CC1] | TFA |

TABLE 1-continued

| Cpd. No. | Structure | Salt Form |
|---|---|---|
| 176 | 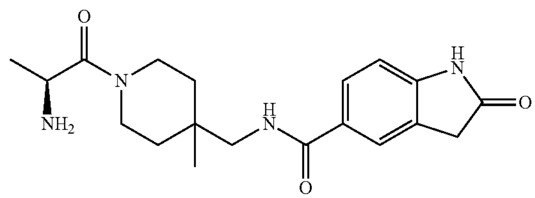 [SMILES: C[C@H](N)C(=O)N1CCC(C)(CNC(=O)c2ccc3c(c2)CC(=O)N3)CC1] | HCOOH |
| 177 | 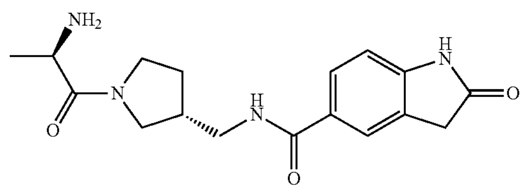 [SMILES: C[C@@H](N)C(=O)N1CC[C@H](CNC(=O)c2ccc3c(c2)CC(=O)N3)C1] | TFA |
| 178 | 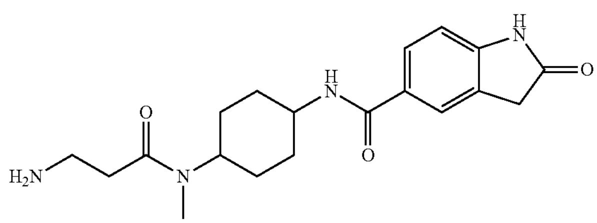 [SMILES: CN(C(=O)CCN)C1CCC(NC(=O)c2ccc3c(c2)CC(=O)N3)CC1] | TFA |
| 179 | 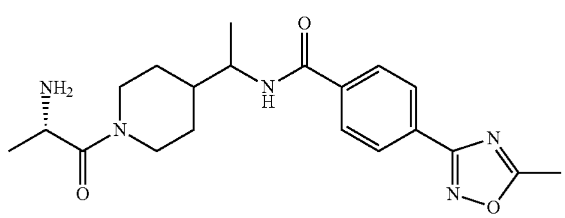 [SMILES: Cc1nc(-c2ccc(C(=O)NC(C)C3CCN(C(=O)[C@H](C)N)CC3)cc2)no1] | HCl |
| 180 | 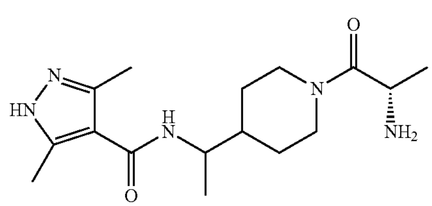 [SMILES: Cc1n[nH]c(C)c1C(=O)NC(C)C1CCN(C(=O)[C@H](C)N)CC1] | HCl |
| 181 | 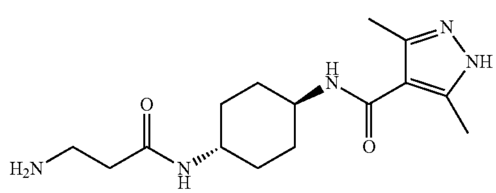 [SMILES: Cc1n[nH]c(C)c1C(=O)N[C@H]1CC[C@H](NC(=O)CCN)CC1] | None |
| 182 | 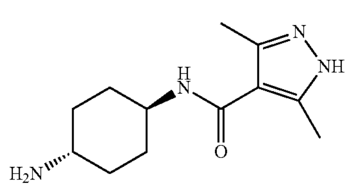 [SMILES: Cc1n[nH]c(C)c1C(=O)N[C@H]1CC[C@H](N)CC1] | None |

TABLE 1-continued

| Cpd. No. | Structure | Salt Form |
|---|---|---|
| 183 | 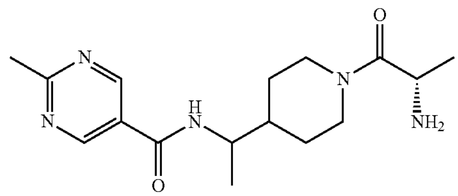 [SMILES: Cc1ncc(C(=O)NC(C)C2CCN(C(=O)[C@H](C)N)CC2)cn1] | None |
| 184 | 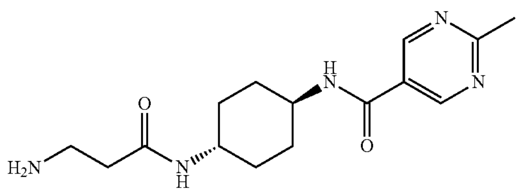 [SMILES: Cc1ncc(C(=O)N[C@H]2CC[C@H](NC(=O)CCN)CC2)cn1] | HCl |
| 185 | 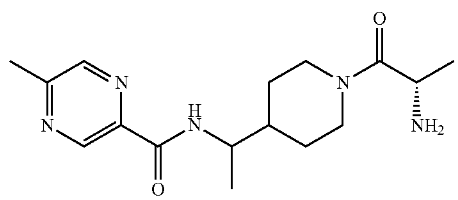 [SMILES: Cc1cnc(C(=O)NC(C)C2CCN(C(=O)[C@H](C)N)CC2)cn1] | TFA |
| 186 | 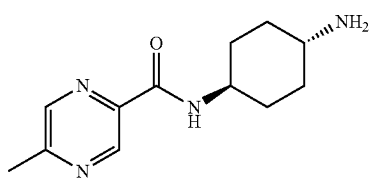 [SMILES: Cc1cnc(C(=O)N[C@H]2CC[C@H](N)CC2)cn1] | TFA |
| 187 | 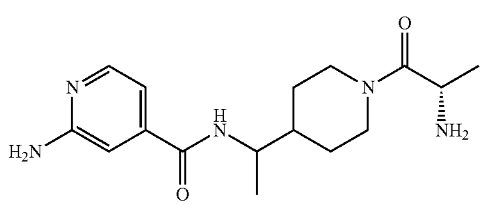 [SMILES: CC(NC(=O)c1ccnc(N)c1)C1CCN(C(=O)[C@H](C)N)CC1] | HCl |
| 188 | 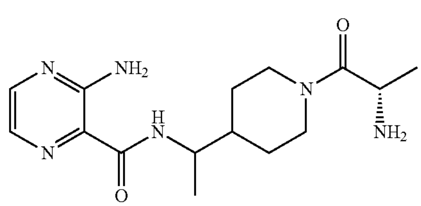 [SMILES: CC(NC(=O)c1nccnc1N)C1CCN(C(=O)[C@H](C)N)CC1] | HCl |
| 189 | 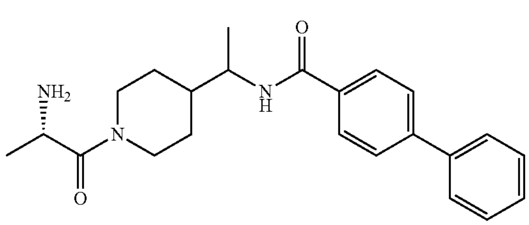 [SMILES: CC(NC(=O)c1ccc(-c2ccccc2)cc1)C1CCN(C(=O)[C@H](C)N)CC1] | HCl |

TABLE 1-continued

| Cpd. No. | Structure | Salt Form |
|---|---|---|
| 190 | 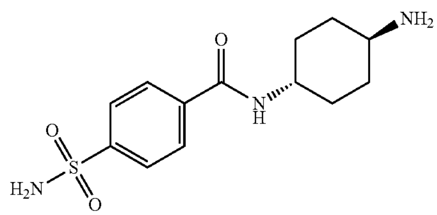 [SMILES: NS(=O)(=O)c1ccc(C(=O)N[C@H]2CC[C@H](N)CC2)cc1] | HCl |
| 191 | 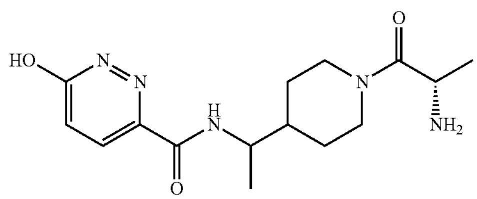 [SMILES: CC(NC(=O)c1ccc(O)nn1)C1CCN(C(=O)[C@H](C)N)CC1] | HCl |
| 192 | 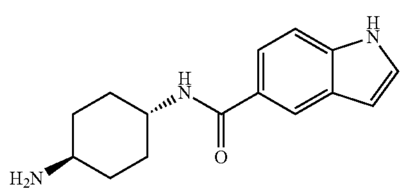 [SMILES: N[C@H]1CC[C@H](NC(=O)c2ccc3[nH]ccc3c2)CC1] | HCl |
| 193 | 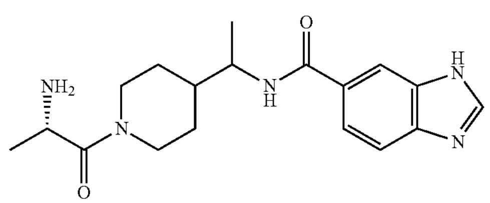 [SMILES: CC(NC(=O)c1ccc2nc[nH]c2c1)C1CCN(C(=O)[C@H](C)N)CC1] | HCl |
| 194 | 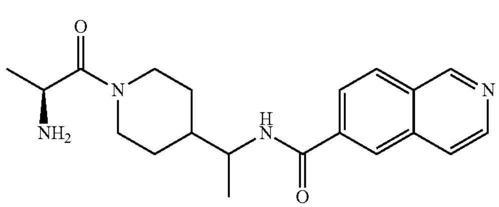 [SMILES: CC(NC(=O)c1ccc2cnccc2c1)C1CCN(C(=O)[C@H](C)N)CC1] | HCl |
| 195 | 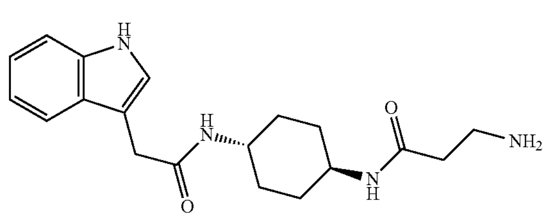 [SMILES: NCCC(=O)N[C@H]1CC[C@H](NC(=O)Cc2c[nH]c3ccccc23)CC1] | HCl |

TABLE 1-continued
| Cpd. No. | Structure | Salt Form |
|---|---|---|
| 196 | 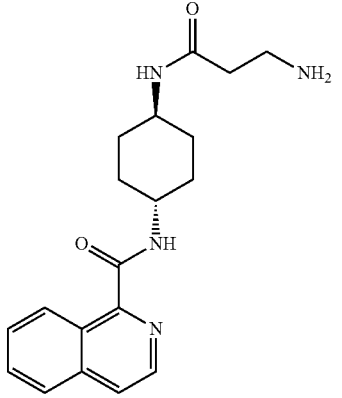 [SMILES: NCCC(=O)N[C@H]1CC[C@H](NC(=O)c2nccc3ccccc23)CC1] | TFA |
| 197 | 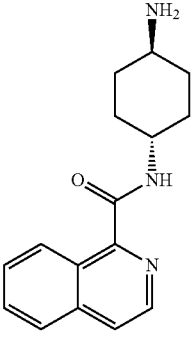 [SMILES: N[C@H]1CC[C@H](NC(=O)c2nccc3ccccc23)CC1] | TFA |
| 198 | 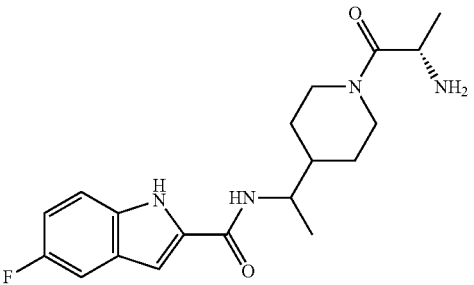 [SMILES: CC(NC(=O)c1cc2cc(F)ccc2[nH]1)C1CCN(C(=O)[C@H](C)N)CC1] | TFA |
| 199 | 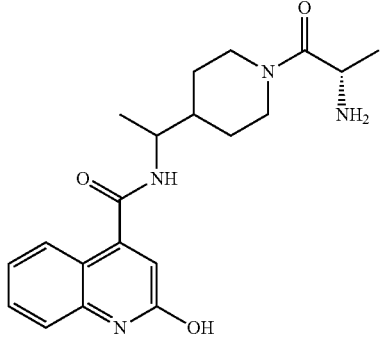 [SMILES: CC(NC(=O)c1cc(O)nc2ccccc12)C1CCN(C(=O)[C@H](C)N)CC1] | HCl |

TABLE 1-continued

| Cpd. No. | Structure | Salt Form |
|---|---|---|
| 200 | 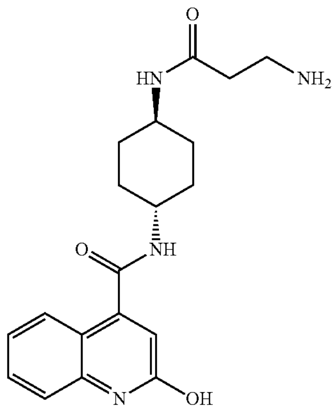 [SMILES: NCCC(=O)N[C@H]1CC[C@H](NC(=O)c2cc(O)nc3ccccc23)CC1] | TFA |
| 201 | 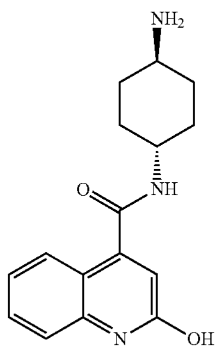 [SMILES: N[C@H]1CC[C@H](NC(=O)c2cc(O)nc3ccccc23)CC1] | TFA |
| 202 | 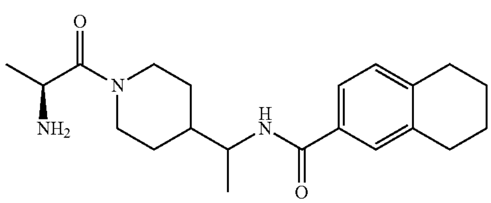 [SMILES: CC(NC(=O)c1ccc2c(c1)CCCC2)C1CCN(C(=O)[C@H](C)N)CC1] | HCl |
| 203 | 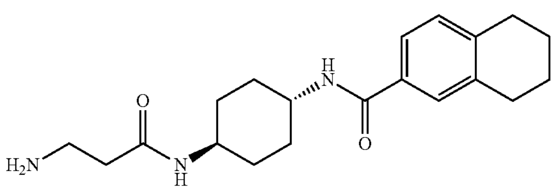 [SMILES: NCCC(=O)N[C@H]1CC[C@H](NC(=O)c2ccc3c(c2)CCCC3)CC1] | HCl |
| 204 | 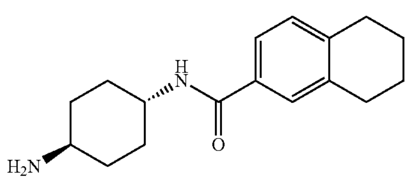 [SMILES: N[C@H]1CC[C@H](NC(=O)c2ccc3c(c2)CCCC3)CC1] | HCl |
| 205 | 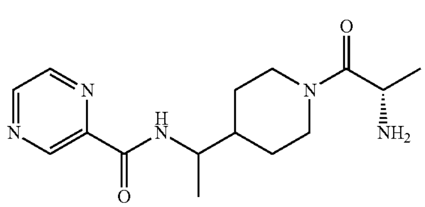 [SMILES: CC(NC(=O)c1cnccn1)C1CCN(C(=O)[C@H](C)N)CC1] | HCl |

TABLE 1-continued

| Cpd. No. | Structure | Salt Form |
|---|---|---|
| 206 | 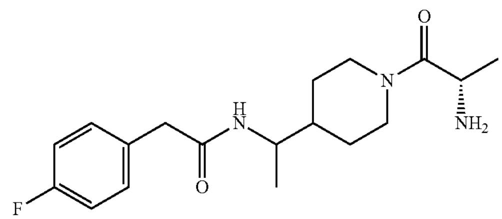 [SMILES: CC(NC(=O)Cc1ccc(F)cc1)C1CCN(C(=O)[C@H](C)N)CC1] | HCl |
| 207 | 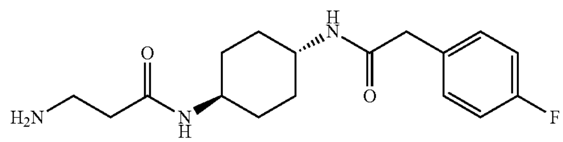 [SMILES: NCCC(=O)N[C@H]1CC[C@H](NC(=O)Cc2ccc(F)cc2)CC1] | HCl |
| 208 | 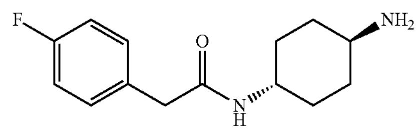 [SMILES: N[C@H]1CC[C@H](NC(=O)Cc2ccc(F)cc2)CC1] | TFA |
| 209 | 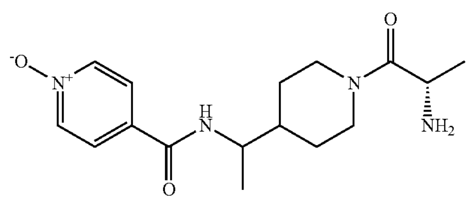 | HCl |
| 210 | 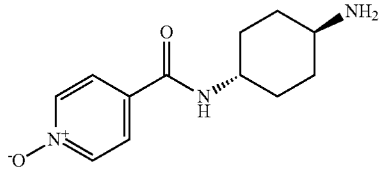 | HCl |
| 211 | 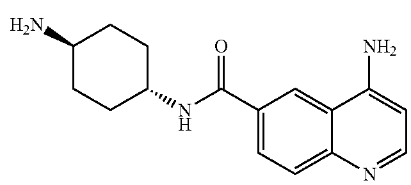 [SMILES: Nc1ccnc2ccc(C(=O)N[C@H]3CC[C@H](N)CC3)cc12] | TFA |
| 212 | 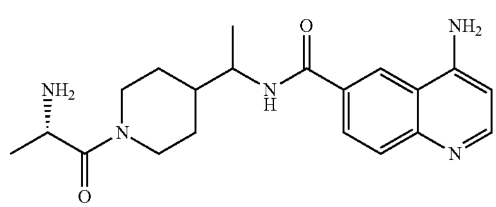 [SMILES: CC(NC(=O)c1ccc2nccc(N)c2c1)C1CCN(C(=O)[C@H](C)N)CC1] | TFA |
| 213 | 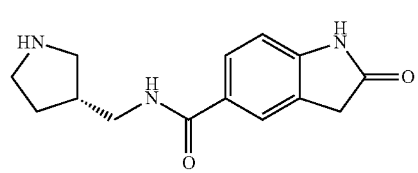 [SMILES: O=C1Cc2cc(C(=O)NC[C@@H]3CCNC3)ccc2N1] | TFA |

TABLE 1-continued

| Cpd. No. | Structure | Salt Form |
|---|---|---|
| 214 | 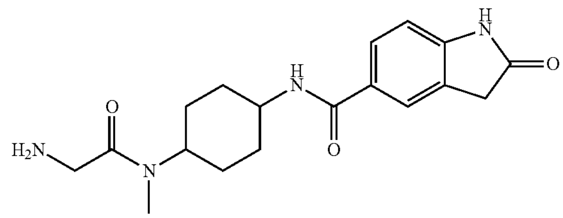 [SMILES: CN(C(=O)CN)C1CCC(NC(=O)c2ccc3c(c2)CC(=O)N3)CC1] | TFA |
| 215 | 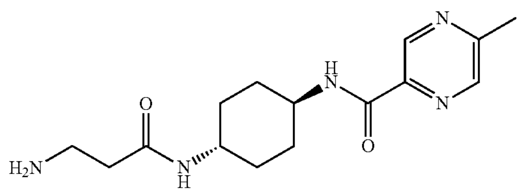 [SMILES: Cc1cnc(C(=O)N[C@H]2CC[C@H](NC(=O)CCN)CC2)cn1] | HCl |
| 216 | 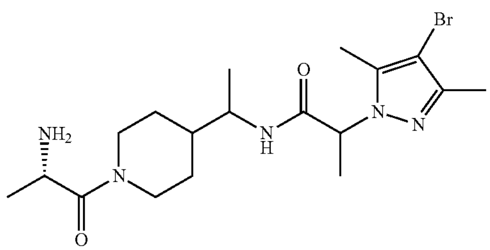 [SMILES: Cc1nn(C(C)C(=O)NC(C)C2CCN(C(=O)[C@H](C)N)CC2)c(C)c1Br] | TFA |
| 217 | 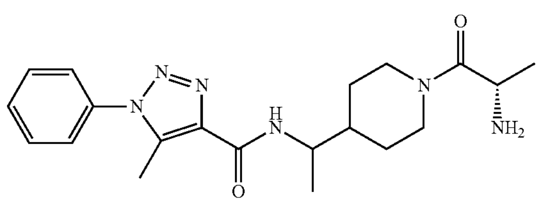 [SMILES: Cc1c(C(=O)NC(C)C2CCN(C(=O)[C@H](C)N)CC2)nnn1-c1ccccc1] | TFA |
| 218 | 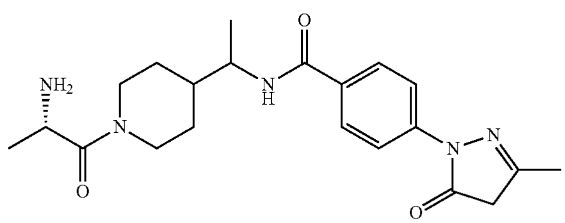 [SMILES: CC1=NN(c2ccc(C(=O)NC(C)C3CCN(C(=O)[C@H](C)N)CC3)cc2)C(=O)C1] | TFA |
| 219 | 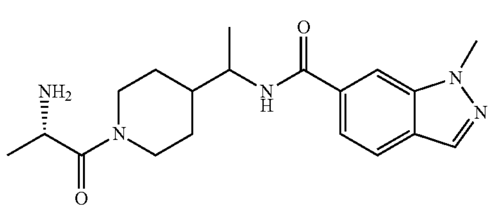 [SMILES: CC(NC(=O)c1ccc2cnn(C)c2c1)C1CCN(C(=O)[C@H](C)N)CC1] | TFA |
| 220 | 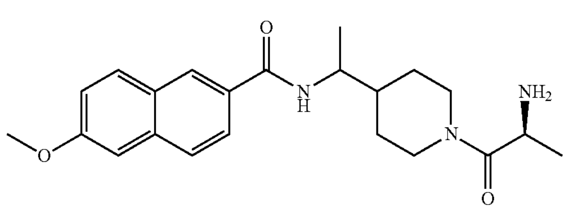 [SMILES: COc1ccc2cc(C(=O)NC(C)C3CCN(C(=O)[C@H](C)N)CC3)ccc2c1] | TFA |

TABLE 1-continued

| Cpd. No. | Structure | Salt Form |
|---|---|---|
| 221 | 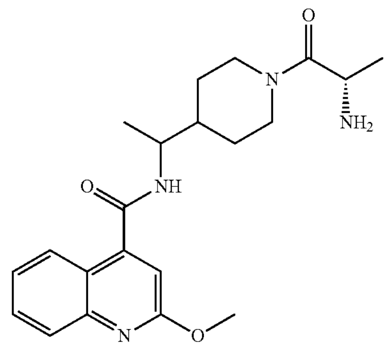 [SMILES: COc1cc(C(=O)NC(C)C2CCN(C(=O)[C@H](C)N)CC2)c2ccccc2n1] | TFA |
| 222 | 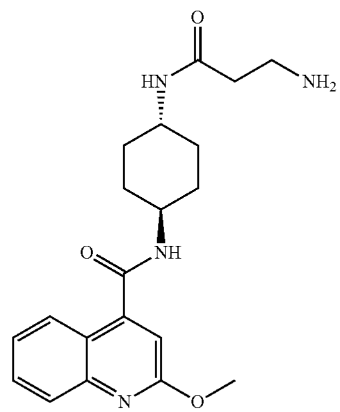 [SMILES: COc1cc(C(=O)N[C@H]2CC[C@H](NC(=O)CCN)CC2)c2ccccc2n1] | TFA |
| 223 | 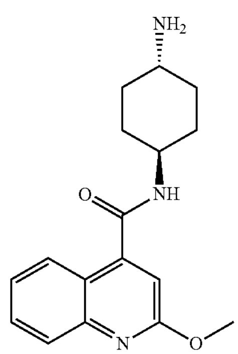 [SMILES: COc1cc(C(=O)N[C@H]2CC[C@H](N)CC2)c2ccccc2n1] | TFA |
| 224 | 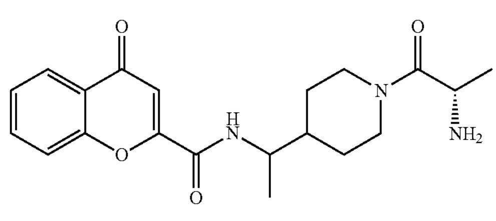 [SMILES: CC(NC(=O)c1cc(=O)c2ccccc2o1)C1CCN(C(=O)[C@H](C)N)CC1] | TFA |
| 225 | 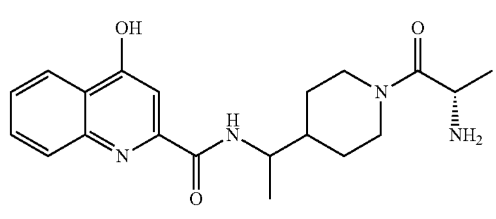 [SMILES: CC(NC(=O)c1cc(O)c2ccccc2n1)C1CCN(C(=O)[C@H](C)N)CC1] | TFA |

TABLE 1-continued

| Cpd. No. | Structure | Salt Form |
|---|---|---|
| 226 | 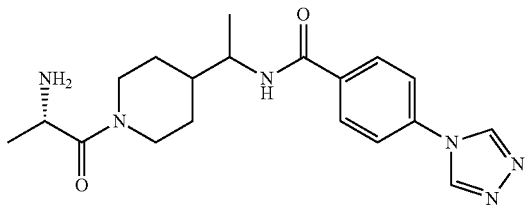 [SMILES: CC(NC(=O)c1ccc(-n2cnnc2)cc1)C1CCN(C(=O)[C@H](C)N)CC1] | TFA |
| 227 | 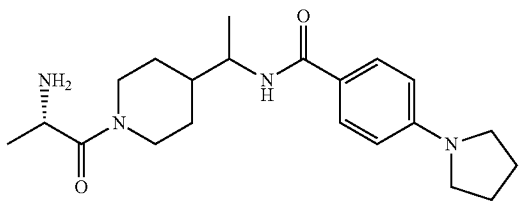 [SMILES: CC(NC(=O)c1ccc(N2CCCC2)cc1)C1CCN(C(=O)[C@H](C)N)CC1] | TFA |
| 228 | 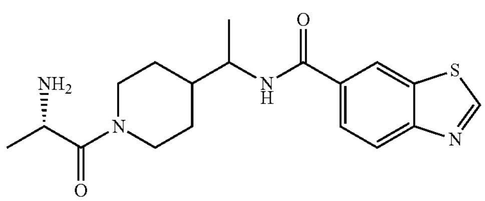 [SMILES: CC(NC(=O)c1ccc2ncsc2c1)C1CCN(C(=O)[C@H](C)N)CC1] | TFA |
| 229 | 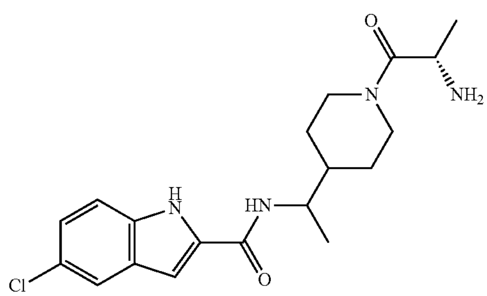 [SMILES: CC(NC(=O)c1cc2cc(Cl)ccc2[nH]1)C1CCN(C(=O)[C@H](C)N)CC1] | HCl |
| 230 | 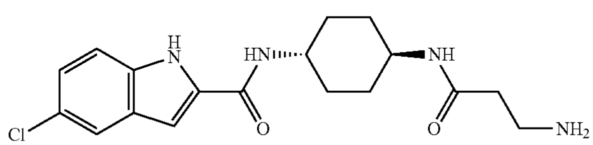 [SMILES: NCCC(=O)N[C@H]1CC[C@H](NC(=O)c2cc3cc(Cl)ccc3[nH]2)CC1] | HCl |
| 231 | 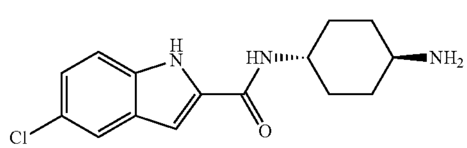 [SMILES: N[C@H]1CC[C@H](NC(=O)c2cc3cc(Cl)ccc3[nH]2)CC1] | HCl |
| 232 | 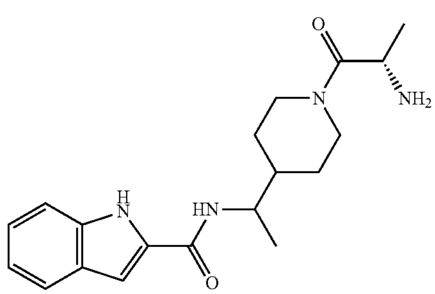 [SMILES: CC(NC(=O)c1cc2ccccc2[nH]1)C1CCN(C(=O)[C@H](C)N)CC1] | HCl |

TABLE 1-continued

| Cpd. No. | Structure | Salt Form |
|---|---|---|
| 233 | 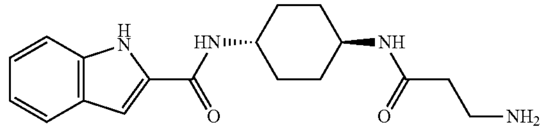 | HCl |
| 234 | 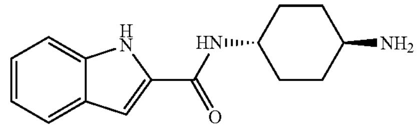 [SMILES: N[C@H]1CC[C@H](NC(=O)c2cc3ccccc3[nH]2)CC1] | HCl |
| 235 | 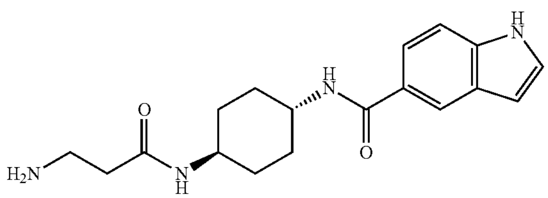 [SMILES: NCCC(=O)N[C@H]1CC[C@H](NC(=O)c2ccc3[nH]ccc3c2)CC1] | HCl |
| 236 | 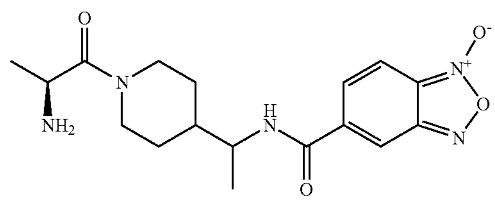 [SMILES: CC(NC(=O)c1ccc2c(c1)no[n+]2[O-])C1CCN(C(=O)[C@H](C)N)CC1] | TFA |
| 237 | 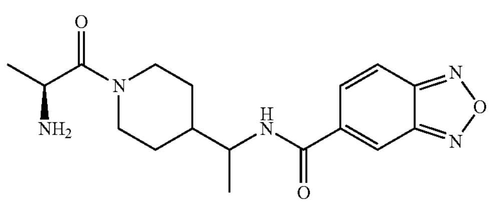 [SMILES: CC(NC(=O)c1ccc2nonc2c1)C1CCN(C(=O)[C@H](C)N)CC1] | TFA |
| 238 | 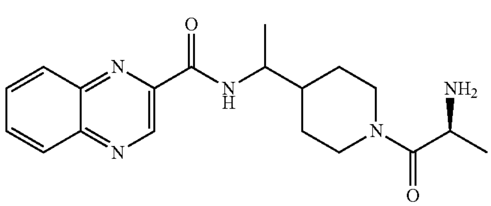 [SMILES: CC(NC(=O)c1cnc2ccccc2n1)C1CCN(C(=O)[C@H](C)N)CC1] | TFA |
| 239 | 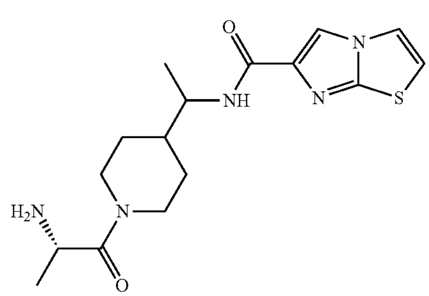 [SMILES: CC(NC(=O)c1cn2ccsc2n1)C1CCN(C(=O)[C@H](C)N)CC1] | TFA |

TABLE 1-continued

| Cpd. No. | Structure | Salt Form |
|---|---|---|
| 241 | 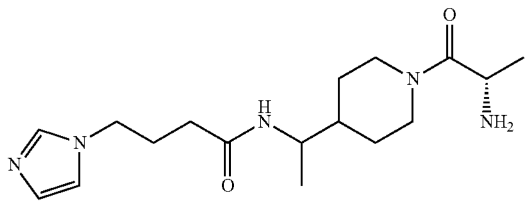 [SMILES: CC(NC(=O)CCCn1ccnc1)C1CCN(C(=O)[C@H](C)N)CC1] | TFA |
| 242 | 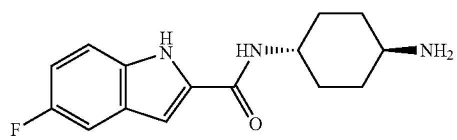 [SMILES: N[C@H]1CC[C@H](NC(=O)c2cc3cc(F)ccc3[nH]2)CC1] | None |
| 243 | 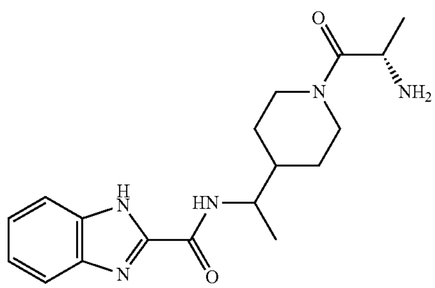 [SMILES: CC(NC(=O)c1nc2ccccc2[nH]1)C1CCN(C(=O)[C@H](C)N)CC1] | TFA |
| 244 | 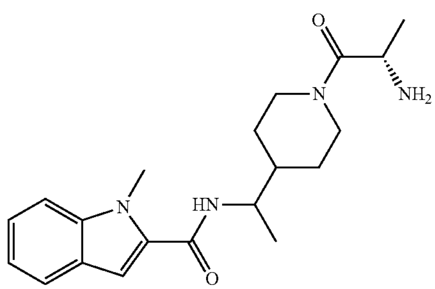 [SMILES: CC(NC(=O)c1cc2ccccc2n1C)C1CCN(C(=O)[C@H](C)N)CC1] | HCl |
| 245 | 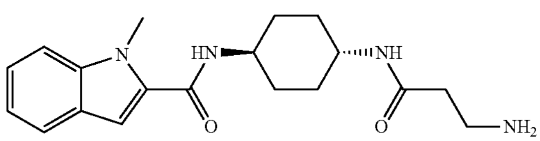 [SMILES: Cn1c(C(=O)N[C@H]2CC[C@H](NC(=O)CCN)CC2)cc2ccccc21] | HCl |
| 246 | 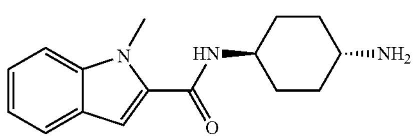 [SMILES: Cn1c(C(=O)N[C@H]2CC[C@H](N)CC2)cc2ccccc21] | HCl |
| 247 | 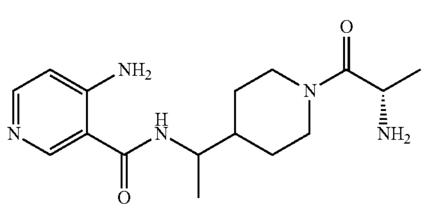 [SMILES: CC(NC(=O)c1cnccc1N)C1CCN(C(=O)[C@H](C)N)CC1] | TFA |

TABLE 1-continued

| Cpd. No. | Structure | Salt Form |
|---|---|---|
| 248 | 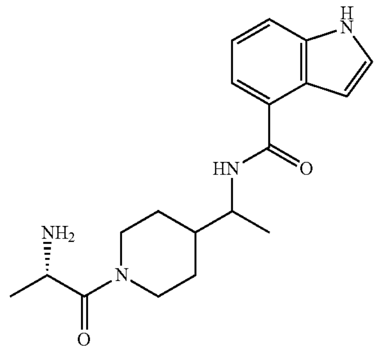 [SMILES: CC(NC(=O)c1cccc2[nH]ccc12)C1CCN(C(=O)[C@H](C)N)CC1] | None |
| 249 | 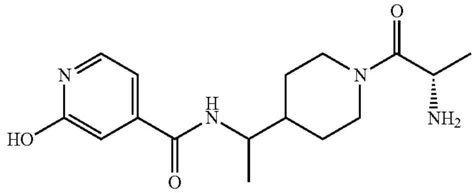 [SMILES: CC(NC(=O)c1ccnc(O)c1)C1CCN(C(=O)[C@H](C)N)CC1] | TFA |
| 250 | 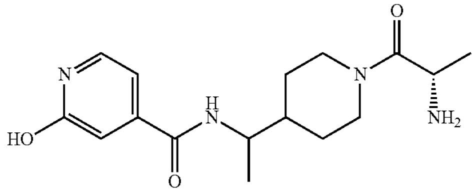 [SMILES: CC(NC(=O)c1ccnc(O)c1)C1CCN(C(=O)[C@H](C)N)CC1] | TFA |
| 251 | 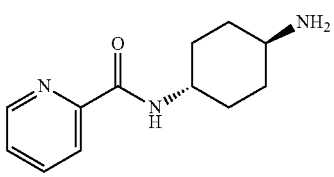 [SMILES: N[C@H]1CC[C@H](NC(=O)c2ccccn2)CC1] | HCl |
| 252 | 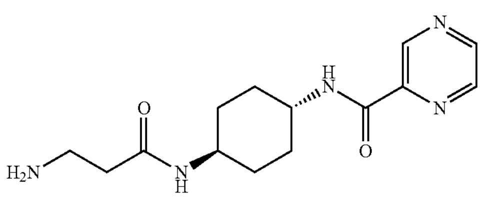 [SMILES: NCCC(=O)N[C@H]1CC[C@H](NC(=O)c2cnccn2)CC1] | HCl |
| 253 | 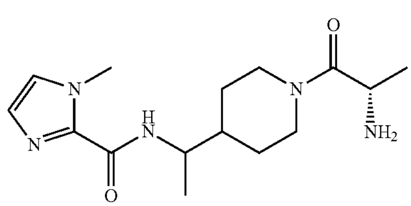 [SMILES: CC(NC(=O)c1nccn1C)C1CCN(C(=O)[C@H](C)N)CC1] | TFA |
| 254 | 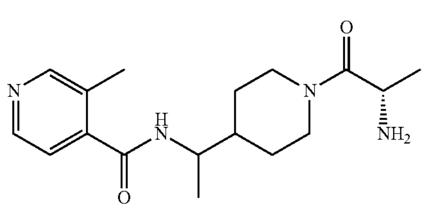 [SMILES: Cc1cnccc1C(=O)NC(C)C1CCN(C(=O)[C@H](C)N)CC1] | TFA |

TABLE 1-continued

| Cpd. No. | Structure | Salt Form |
|---|---|---|
| 255 | 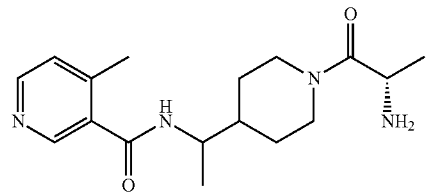 [SMILES: Cc1ccncc1C(=O)NC(C)C1CCN(C(=O)[C@H](C)N)CC1] | TFA |
| 256 | 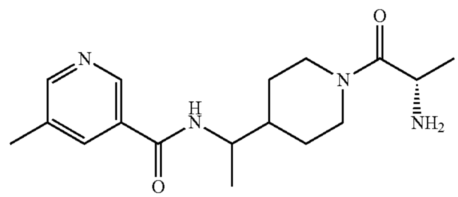 [SMILES: Cc1cncc(C(=O)NC(C)C2CCN(C(=O)[C@H](C)N)CC2)c1] | TFA |
| 257 | 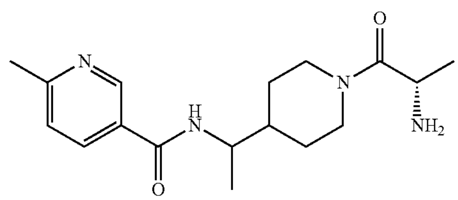 | TFA |
| 258 | 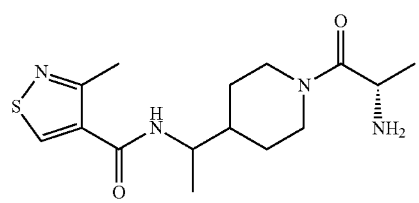 [SMILES: Cc1nscc1C(=O)NC(C)C1CCN(C(=O)[C@H](C)N)CC1] | TFA |
| 259 | 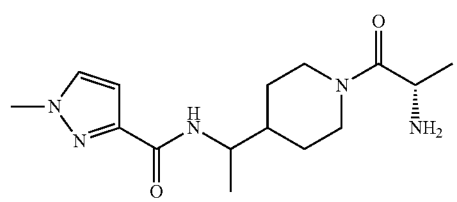 [SMILES: CC(NC(=O)c1ccn(C)n1)C1CCN(C(=O)[C@H](C)N)CC1] | TFA |
| 260 | 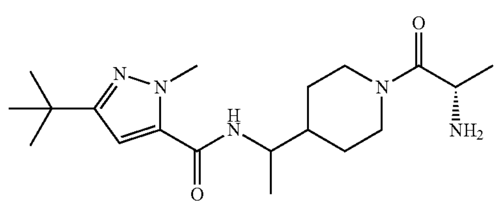 [SMILES: CC(NC(=O)c1cc(C(C)(C)C)nn1C)C1CCN(C(=O)[C@H](C)N)CC1] | TFA |
| 261 | 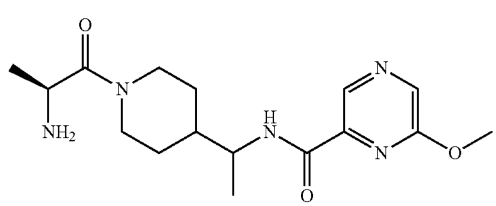 [SMILES: COc1cncc(C(=O)NC(C)C2CCN(C(=O)[C@H](C)N)CC2)n1] | TFA |

TABLE 1-continued

| Cpd. No. | Structure | Salt Form |
|---|---|---|
| 262 | 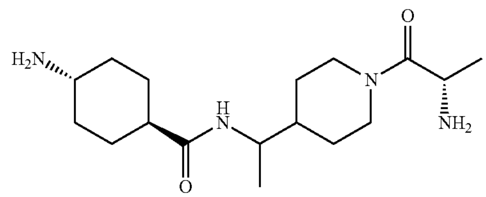 [SMILES: CC(NC(=O)[C@H]1CC[C@H](N)CC1)C1CCN(C(=O)[C@H](C)N)CC1] | HCl |
| 263 | 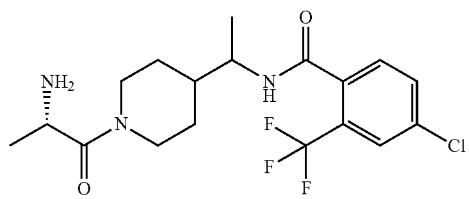 [SMILES: CC(NC(=O)c1ccc(Cl)cc1C(F)(F)F)C1CCN(C(=O)[C@H](C)N)CC1] | TFA |
| 264 | 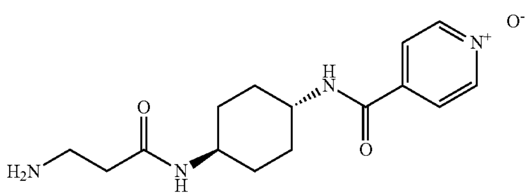 | HCl |
| 265 | 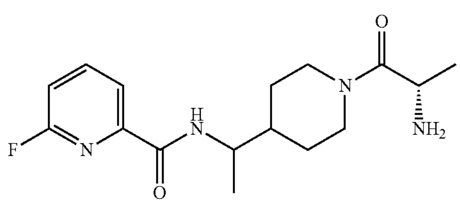 [SMILES: CC(NC(=O)c1cccc(F)n1)C1CCN(C(=O)[C@H](C)N)CC1] | TFA |
| 266 | 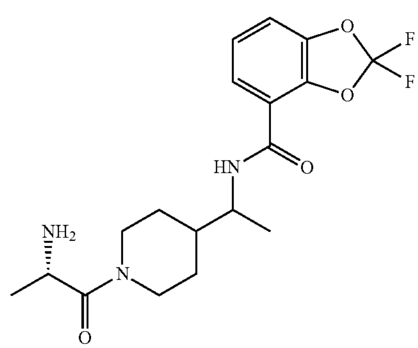 [SMILES: CC(NC(=O)c1cccc2c1OC(F)(F)O2)C1CCN(C(=O)[C@H](C)N)CC1] | TFA |
| 267 | 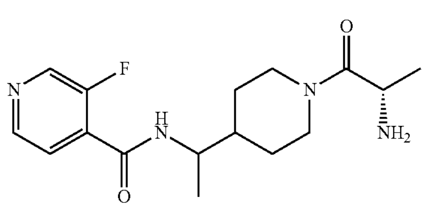 | TFA |

TABLE 1-continued

| Cpd. No. | Structure | Salt Form |
|---|---|---|
| 268 | 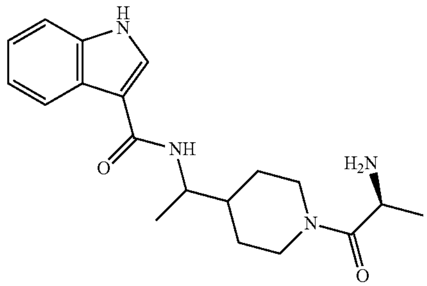 [SMILES: CC(NC(=O)c1c[nH]c2ccccc12)C1CCN(C(=O)[C@H](C)N)CC1] | TFA |
| 269 | 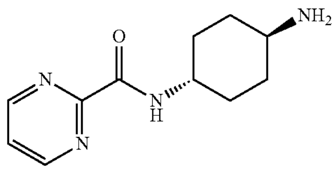 [SMILES: N[C@H]1CC[C@H](NC(=O)c2ncccn2)CC1] | HCl |
| 270 | 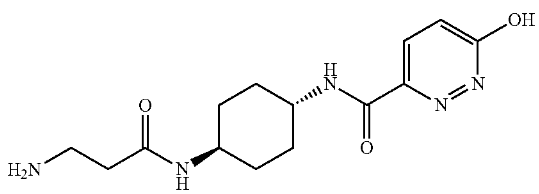 [SMILES: NCCC(=O)N[C@H]1CC[C@H](NC(=O)c2ccc(O)nn2)CC1] | HCl |
| 271 | 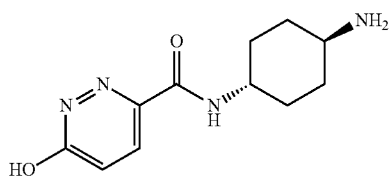 [SMILES: N[C@H]1CC[C@H](NC(=O)c2ccc(O)nn2)CC1] | HCl |
| 272 | 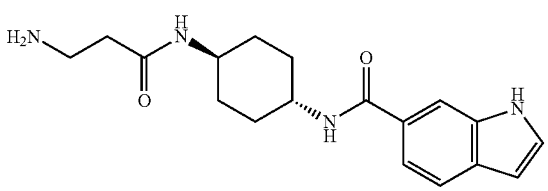 [SMILES: NCCC(=O)N[C@H]1CC[C@H](NC(=O)c2ccc3cc[nH]c3c2)CC1] | HCl |
| 273 | 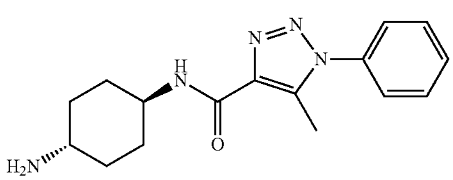 [SMILES: Cc1c(C(=O)N[C@H]2CC[C@H](N)CC2)nnn1-c1ccccc1] | TFA |
| 274 | 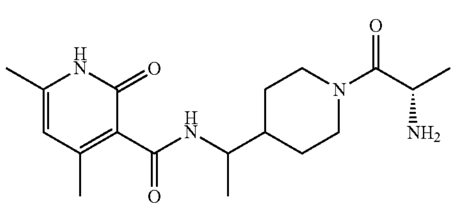 [SMILES: Cc1cc(C)c(C(=O)NC(C)C2CCN(C(=O)[C@H](C)N)CC2)c(=O)[nH]1] | TFA |

TABLE 1-continued

| Cpd. No. | Structure | Salt Form |
|---|---|---|
| 275 | 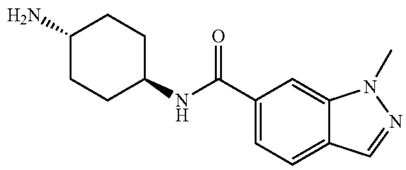 [SMILES: Cn1ncc2ccc(C(=O)N[C@H]3CC[C@H](N)CC3)cc21] | TFA |
| 276 | 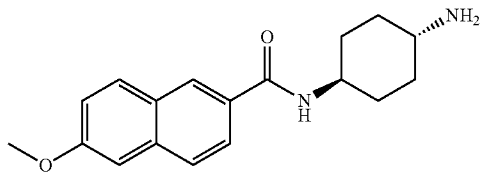 [SMILES: COc1ccc2cc(C(=O)N[C@H]3CC[C@H](N)CC3)ccc2c1] | TFA |
| 277 | 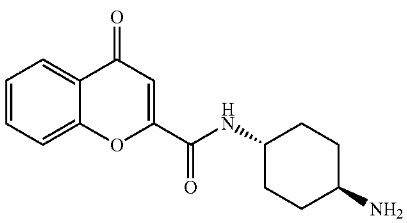 [SMILES: N[C@H]1CC[C@H](NC(=O)c2cc(=O)c3ccccc3o2)CC1] | TFA |
| 278 | 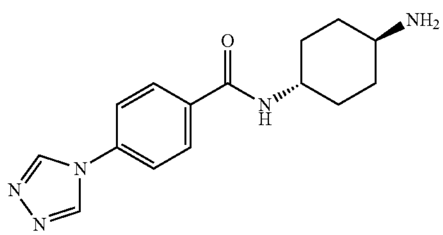 [SMILES: N[C@H]1CC[C@H](NC(=O)c2ccc(-n3cnnc3)cc2)CC1] | TFA |
| 279 | 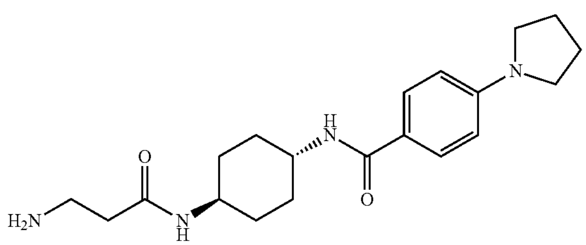 [SMILES: NCCC(=O)N[C@H]1CC[C@H](NC(=O)c2ccc(N3CCCC3)cc2)CC1] | TFA |
| 280 | 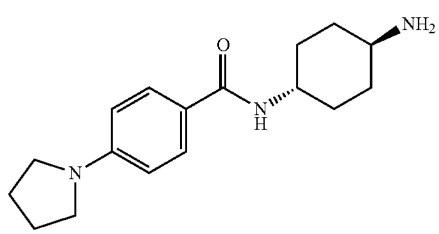 [SMILES: N[C@H]1CC[C@H](NC(=O)c2ccc(N3CCCC3)cc2)CC1] | TFA |
| 281 | 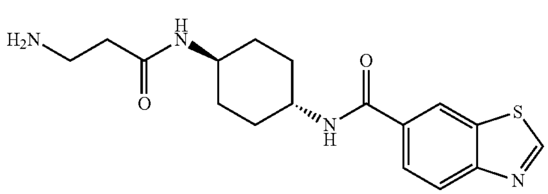 [SMILES: NCCC(=O)N[C@H]1CC[C@H](NC(=O)c2ccc3ncsc3c2)CC1] | HCl |

TABLE 1-continued

| Cpd. No. | Structure | Salt Form |
|---|---|---|
| 283 | 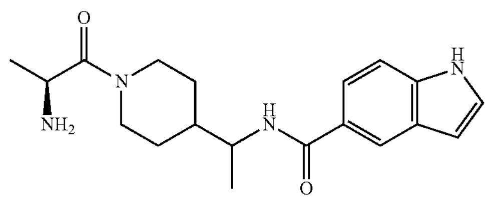 [SMILES: CC(NC(=O)c1ccc2[nH]ccc2c1)C1CCN(C(=O)[C@H](C)N)CC1] | HCl |
| 284 | 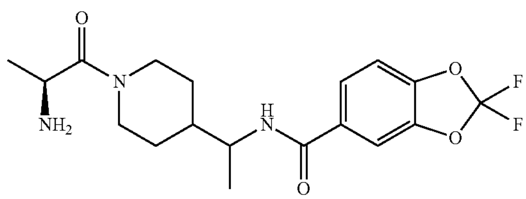 [SMILES: CC(NC(=O)c1ccc2c(c1)OC(F)(F)O2)C1CCN(C(=O)[C@H](C)N)CC1] | TFA |
| 285 | 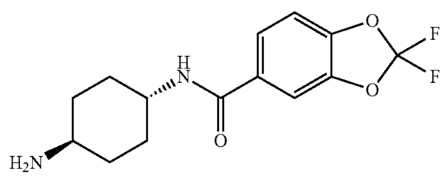 [SMILES: N[C@H]1CC[C@H](NC(=O)c2ccc3c(c2)OC(F)(F)O3)CC1] | HCl |
| 286 | 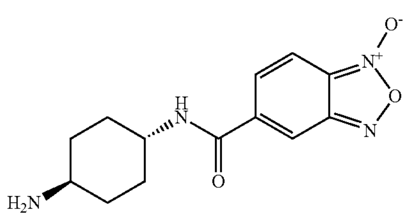 [SMILES: N[C@H]1CC[C@H](NC(=O)c2ccc3c(c2)no[n+]3[O-])CC1] | TFA |
| 287 | 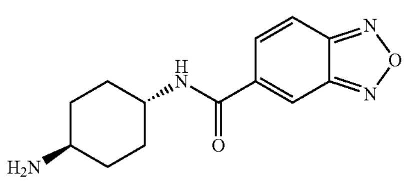 [SMILES: N[C@H]1CC[C@H](NC(=O)c2ccc3nonc3c2)CC1] | TFA |
| 288 | 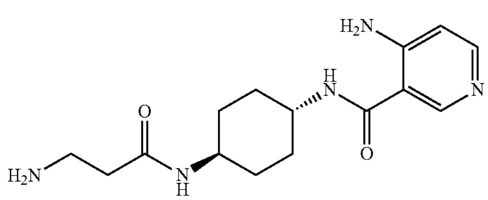 [SMILES: NCCC(=O)N[C@H]1CC[C@H](NC(=O)c2cnccc2N)CC1] | None |
| 289 | 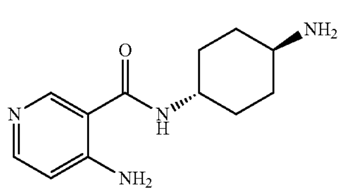 [SMILES: Nc1ccncc1C(=O)N[C@H]1CC[C@H](N)CC1] | None |

TABLE 1-continued

| Cpd. No. | Structure | Salt Form |
|---|---|---|
| 290 | 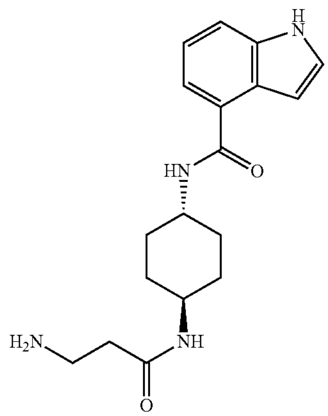 [SMILES: NCCC(=O)N[C@H]1CC[C@H](NC(=O)c2cccc3[nH]ccc23)CC1] | None |
| 291 | 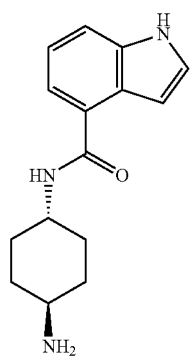 [SMILES: N[C@H]1CC[C@H](NC(=O)c2cccc3[nH]ccc23)CC1] | None |
| 292 | 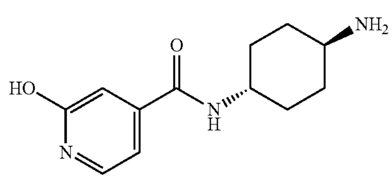 [SMILES: N[C@H]1CC[C@H](NC(=O)c2ccnc(O)c2)CC1] | None |
| 293 | 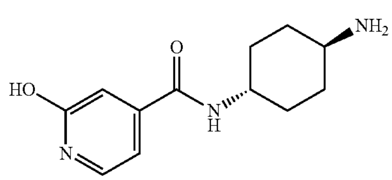 [SMILES: N[C@H]1CC[C@H](NC(=O)c2ccnc(O)c2)CC1] | None |
| 294 | 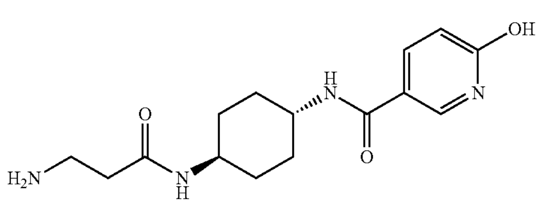 [SMILES: NCCC(=O)N[C@H]1CC[C@H](NC(=O)c2ccc(O)nc2)CC1] | HCl |
| 295 | 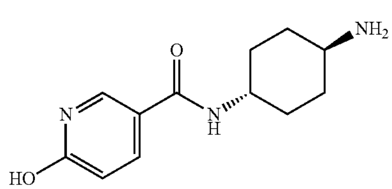 [SMILES: N[C@H]1CC[C@H](NC(=O)c2ccc(O)nc2)CC1] | TFA |

TABLE 1-continued

| Cpd. No. | Structure | Salt Form |
|---|---|---|
| 296 | 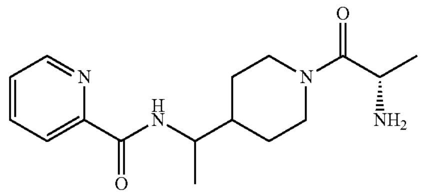 [SMILES: CC(NC(=O)c1ccccn1)C1CCN(C(=O)[C@H](C)N)CC1] | HCl |
| 297 | 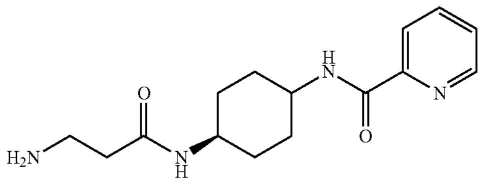 | HCl |
| 298 | 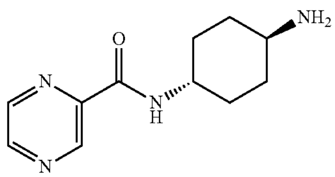 [SMILES: N[C@H]1CC[C@H](NC(=O)c2cnccn2)CC1] | HCl |
| 299 | 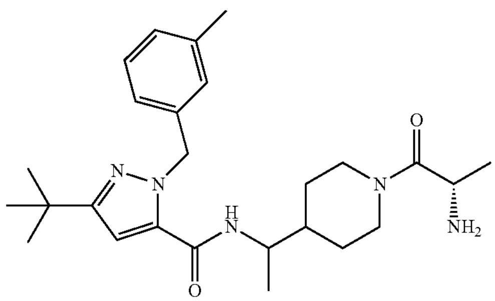 [SMILES: Cc1cccc(Cn2nc(C(C)(C)C)cc2C(=O)NC(C)C2CCN(C(=O)[C@H](C)N)CC2)c1] | TFA |
| 300 | 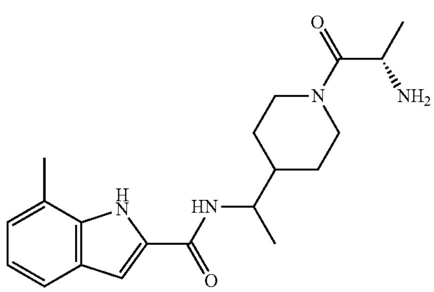 [SMILES: Cc1cccc2cc(C(=O)NC(C)C3CCN(C(=O)[C@H](C)N)CC3)[nH]c12] | TFA |
| 301 | 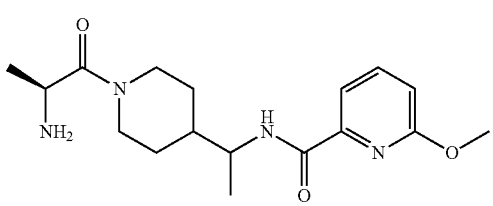 [SMILES: COc1cccc(C(=O)NC(C)C2CCN(C(=O)[C@H](C)N)CC2)n1] | TFA |
| 302 | 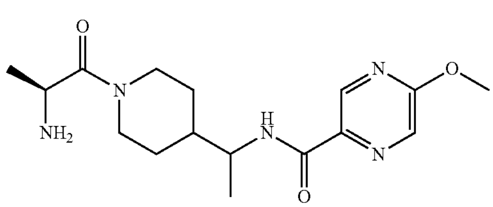 [SMILES: COc1cnc(C(=O)NC(C)C2CCN(C(=O)[C@H](C)N)CC2)cn1] | TFA |

TABLE 1-continued

| Cpd. No. | Structure | Salt Form |
|---|---|---|
| 303 | 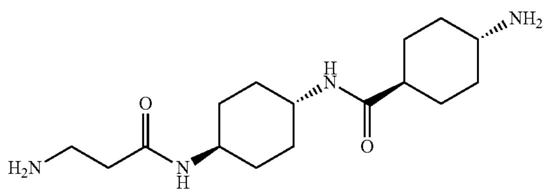 [SMILES: NCCC(=O)N[C@H]1CC[C@H](NC(=O)[C@H]2CC[C@H](N)CC2)CC1] | HCl |
| 304 | 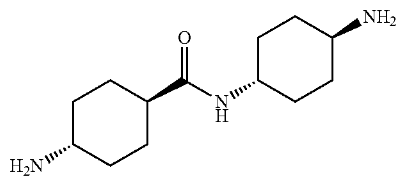 [SMILES: N[C@H]1CC[C@H](NC(=O)[C@H]2CC[C@H](N)CC2)CC1] | HCl |
| 305 | 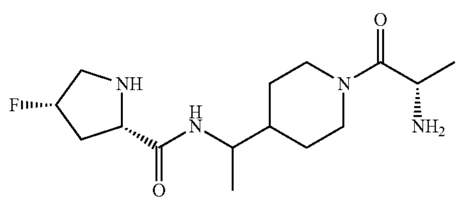 [SMILES: CC(NC(=O)[C@@H]1C[C@H](F)CN1)C1CCN(C(=O)[C@H](C)N)CC1] | TFA |
| 306 | 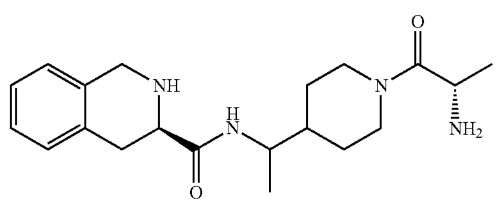 [SMILES: CC(NC(=O)[C@H]1Cc2ccccc2CN1)C1CCN(C(=O)[C@H](C)N)CC1] | TFA |
| 307 | 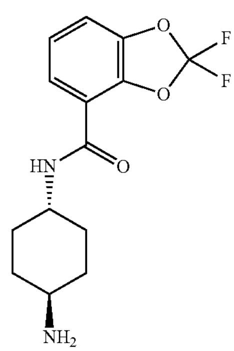 [SMILES: N[C@H]1CC[C@H](NC(=O)c2cccc3c2OC(F)(F)O3)CC1] | TFA |
| 308 | 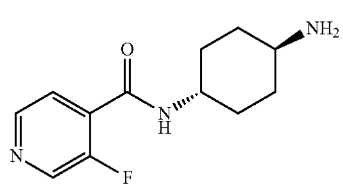 [SMILES: N[C@H]1CC[C@H](NC(=O)c2ccncc2F)CC1] | HCl |
| 309 | 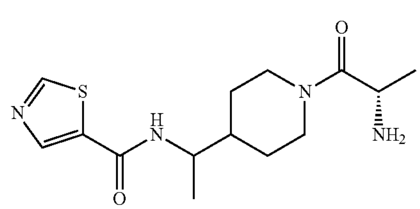 [SMILES: CC(NC(=O)c1cncs1)C1CCN(C(=O)[C@H](C)N)CC1] | TFA |

TABLE 1-continued

| Cpd. No. | Structure | Salt Form |
|---|---|---|
| 310 | 5-hydroxy-N-(1-(1-(L-alanyl)piperidin-4-yl)ethyl)picolinamide | TFA |
| 311 | 6-oxo-1,4,5,6-tetrahydropyridazine-3-carboxamide derivative | TFA |
| 312 | 1H-indazole-3-carboxamide derivative | TFA |
| 313 | 2-(3,5-difluorophenyl)-N-(1-(1-(L-alanyl)piperidin-4-yl)ethyl)acetamide | TFA |
| 314 | 2-(pyridin-3-yl)-N-(1-(1-(L-alanyl)piperidin-4-yl)ethyl)acetamide | TFA |
| 315 | 2-(pyrimidin-5-yl)-N-(1-(1-(L-alanyl)piperidin-4-yl)ethyl)acetamide | TFA |

TABLE 1-continued

| Cpd. No. | Structure | Salt Form |
|---|---|---|
| 316 | 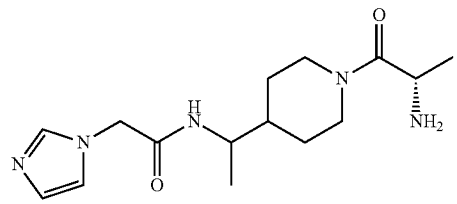 [SMILES: CC(NC(=O)Cn1ccnc1)C1CCN(C(=O)[C@H](C)N)CC1] | TFA |
| 317 | 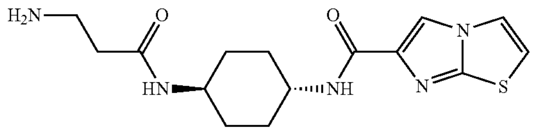 [SMILES: NCCC(=O)N[C@H]1CC[C@H](NC(=O)c2cn3ccsc3n2)CC1] | HCl |
| 318 | 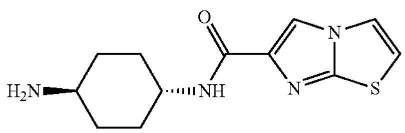 [SMILES: N[C@H]1CC[C@H](NC(=O)c2cn3ccsc3n2)CC1] | HCl |
| 319 | 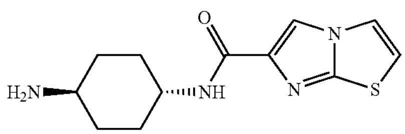 [SMILES: N[C@H]1CC[C@H](NC(=O)c2cn3ccsc3n2)CC1] | TFA |
| 320 | 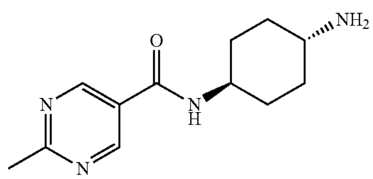 [SMILES: Cc1ncc(C(=O)N[C@H]2CC[C@H](N)CC2)cn1] | None |
| 321 | 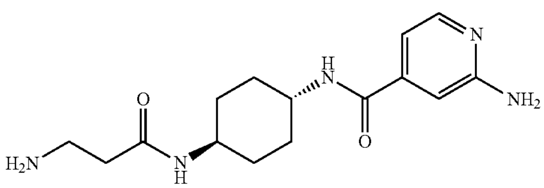 [SMILES: NCCC(=O)N[C@H]1CC[C@H](NC(=O)c2ccnc(N)c2)CC1] | HCl |
| 322 | 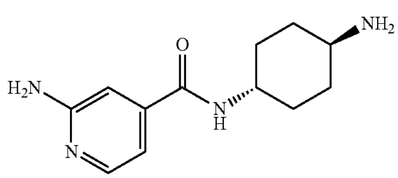 [SMILES: Nc1cc(C(=O)N[C@H]2CC[C@H](N)CC2)ccn1] | None |
| 323 | 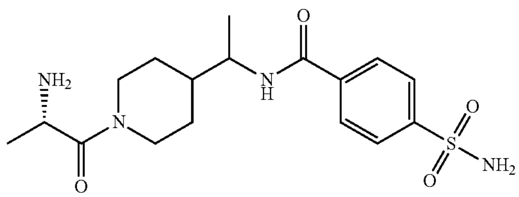 [SMILES: CC(NC(=O)c1ccc(S(N)(=O)=O)cc1)C1CCN(C(=O)[C@H](C)N)CC1] | TFA |
| 324 | 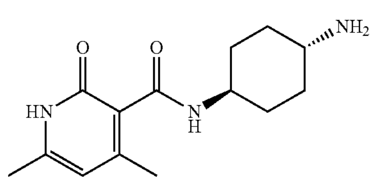 [SMILES: Cc1cc(C)c(C(=O)N[C@H]2CC[C@H](N)CC2)c(=O)[nH]1] | TFA |

TABLE 1-continued

| Cpd. No. | Structure | Salt Form |
|---|---|---|
| 325 | 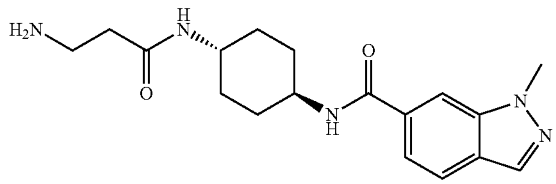 [SMILES: Cn1ncc2ccc(C(=O)N[C@H]3CC[C@H](NC(=O)CCN)CC3)cc21] | HCl |
| 326 | 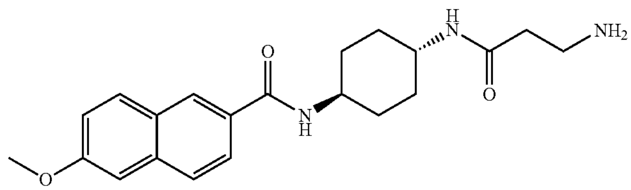 [SMILES: COc1ccc2cc(C(=O)N[C@H]3CC[C@H](NC(=O)CCN)CC3)ccc2c1] | HCl |
| 327 | 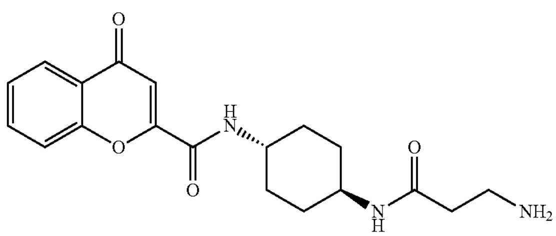 [SMILES: NCCC(=O)N[C@H]1CC[C@H](NC(=O)c2cc(=O)c3ccccc3o2)CC1] | HCl |
| 328 | 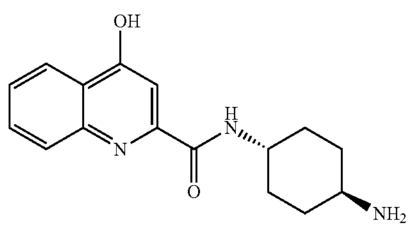 [SMILES: N[C@H]1CC[C@H](NC(=O)c2cc(O)c3ccccc3n2)CC1] | None |
| 329 | 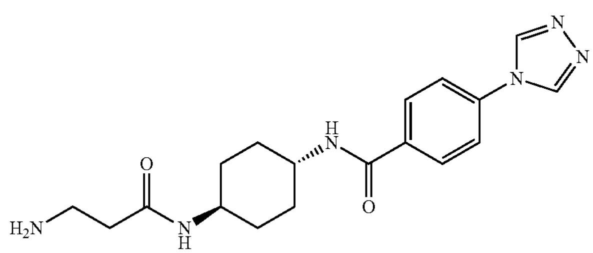 [SMILES: NCCC(=O)N[C@H]1CC[C@H](NC(=O)c2ccc(-n3cnnc3)cc2)CC1] | HCl |
| 330 | 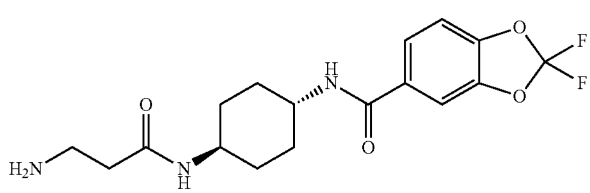 [SMILES: NCCC(=O)N[C@H]1CC[C@H](NC(=O)c2ccc3c(c2)OC(F)(F)O3)CC1] | HCl |
| 331 | 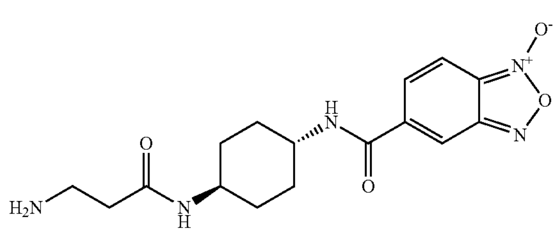 [SMILES: NCCC(=O)N[C@H]1CC[C@H](NC(=O)c2ccc3c(c2)no[n+]3[O-])CC1] | HCl |

TABLE 1-continued

| Cpd. No. | Structure | Salt Form |
|---|---|---|
| 332 | 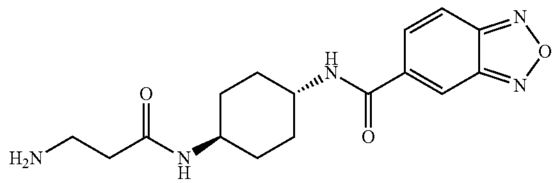 [SMILES: NCCC(=O)N[C@H]1CC[C@H](NC(=O)c2ccc3nonc3c2)CC1] | HCl |
| 333 | 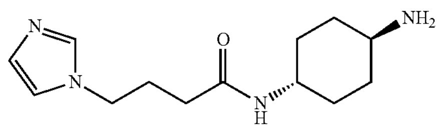 [SMILES: N[C@H]1CC[C@H](NC(=O)CCCn2ccnc2)CC1] | None |
| 334 | 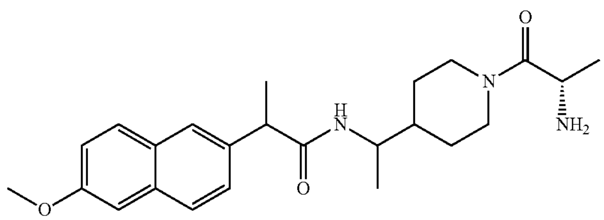 [SMILES: COc1ccc2cc(C(C)C(=O)NC(C)C3CCN(C(=O)[C@H](C)N)CC3)ccc2c1] | None |
| 335 | 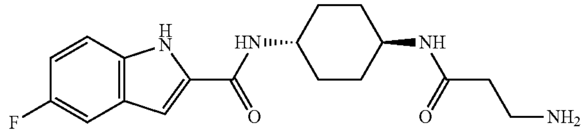 [SMILES: NCCC(=O)N[C@H]1CC[C@H](NC(=O)c2cc3cc(F)ccc3[nH]2)CC1] | None |
| 336 | 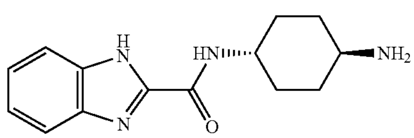 [SMILES: N[C@H]1CC[C@H](NC(=O)c2nc3ccccc3[nH]2)CC1] | None |
| 337 | 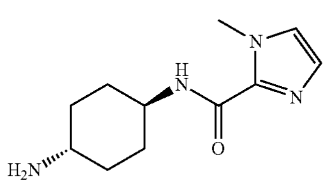 [SMILES: Cn1ccnc1C(=O)N[C@H]1CC[C@H](N)CC1] | None |
| 338 | 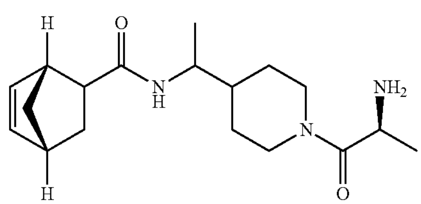 [SMILES: CC(NC(=O)C1C[C@@H]2C=C[C@H]1C2)C1CCN(C(=O)[C@H](C)N)CC1] | TFA |
| 339 | 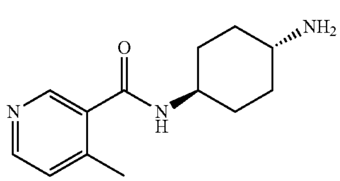 [SMILES: Cc1ccncc1C(=O)N[C@H]1CC[C@H](N)CC1] | None |

TABLE 1-continued

| Cpd. No. | Structure | Salt Form |
|---|---|---|
| 340 | 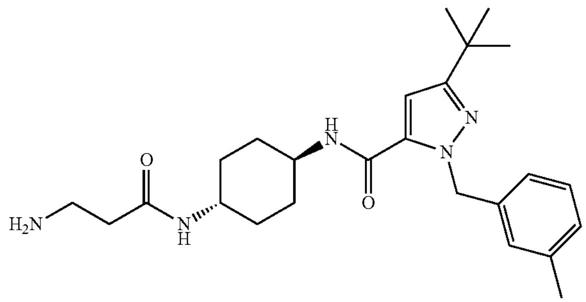 [SMILES: Cc1cccc(Cn2nc(C(C)(C)C)cc2C(=O)N[C@H]2CC[C@H](NC(=O)CCN)CC2)c1] | HCl |
| 341 | 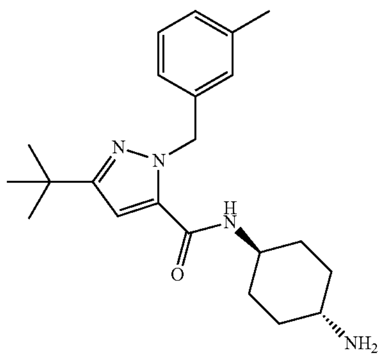 [SMILES: Cc1cccc(Cn2nc(C(C)(C)C)cc2C(=O)N[C@H]2CC[C@H](N)CC2)c1] | TFA |
| 342 | 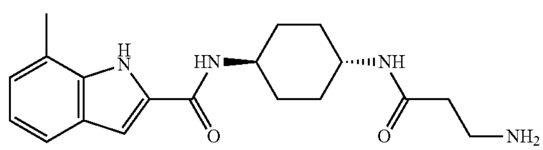 [SMILES: Cc1cccc2cc(C(=O)N[C@H]3CC[C@H](NC(=O)CCN)CC3)[nH]c12] | TFA |
| 343 | 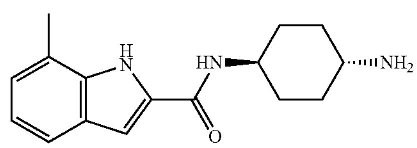 [SMILES: Cc1cccc2cc(C(=O)N[C@H]3CC[C@H](N)CC3)[nH]c12] | TFA |
| 344 | 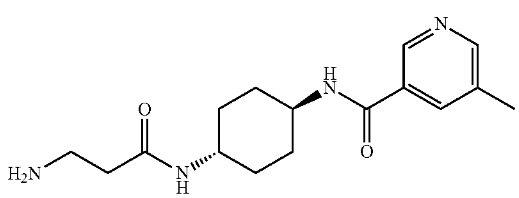 [SMILES: Cc1cncc(C(=O)N[C@H]2CC[C@H](NC(=O)CCN)CC2)c1] | HCl |
| 345 | 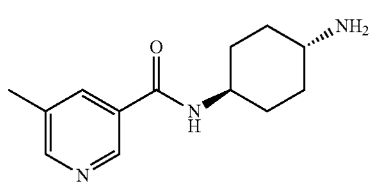 [SMILES: Cc1cncc(C(=O)N[C@H]2CC[C@H](N)CC2)c1] | HCl |
| 346 | 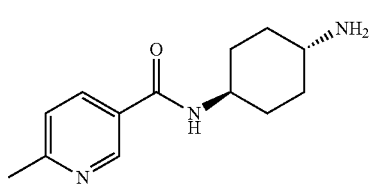 [SMILES: Cc1ccc(C(=O)N[C@H]2CC[C@H](N)CC2)cn1] | HCl |

TABLE 1-continued

| Cpd. No. | Structure | Salt Form |
|---|---|---|
| 347 | 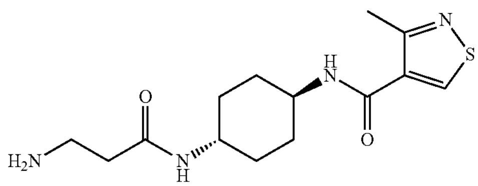 [SMILES: Cc1nscc1C(=O)N[C@H]1CC[C@H](NC(=O)CCN)CC1] | HCl |
| 348 | 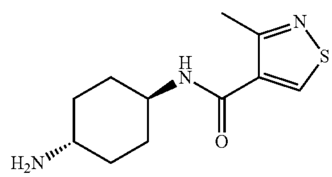 [SMILES: Cc1nscc1C(=O)N[C@H]1CC[C@H](N)CC1] | TFA |
| 349 | 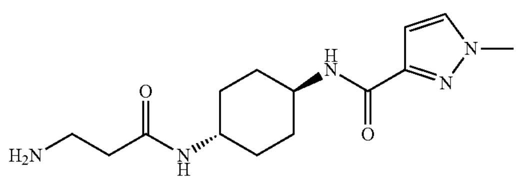 [SMILES: Cn1ccc(C(=O)N[C@H]2CC[C@H](NC(=O)CCN)CC2)n1] | TFA |
| 350 | 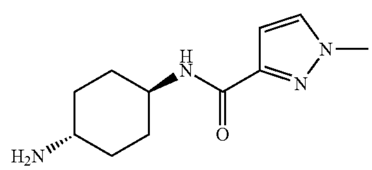 [SMILES: Cn1ccc(C(=O)N[C@H]2CC[C@H](N)CC2)n1] | TFA |
| 351 | 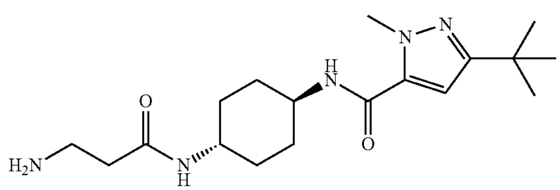 [SMILES: Cn1nc(C(C)(C)C)cc1C(=O)N[C@H]1CC[C@H](NC(=O)CCN)CC1] | HCl |
| 352 | 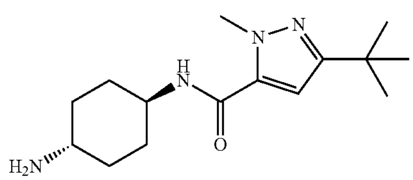 [SMILES: Cn1nc(C(C)(C)C)cc1C(=O)N[C@H]1CC[C@H](N)CC1] | HCl |
| 353 | 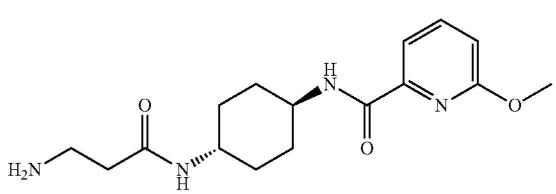 [SMILES: COc1cccc(C(=O)N[C@H]2CC[C@H](NC(=O)CCN)CC2)n1] | HCl |
| 354 | 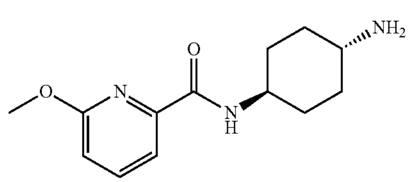 [SMILES: COc1cccc(C(=O)N[C@H]2CC[C@H](N)CC2)n1] | HCl |

TABLE 1-continued

| Cpd. No. | Structure | Salt Form |
|---|---|---|
| 355 | 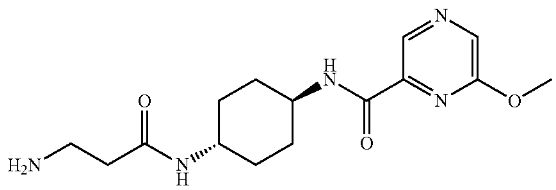 [SMILES: COc1cncc(C(=O)N[C@H]2CC[C@H](NC(=O)CCN)CC2)n1] | HCl |
| 356 | 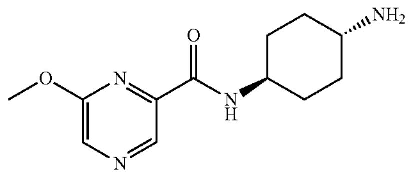 [SMILES: COc1cncc(C(=O)N[C@H]2CC[C@H](N)CC2)n1] | HCl |
| 357 | 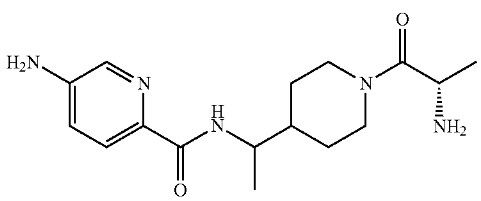 [SMILES: CC(NC(=O)c1ccc(N)cn1)C1CCN(C(=O)[C@H](C)N)CC1] | None |
| 358 | 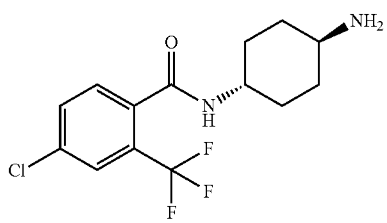 [SMILES: N[C@H]1CC[C@H](NC(=O)c2ccc(Cl)cc2C(F)(F)F)CC1] | TFA |
| 359 | 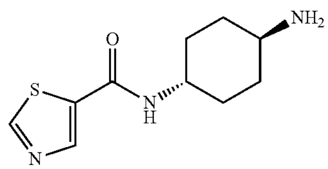 [SMILES: N[C@H]1CC[C@H](NC(=O)c2cncs2)CC1] | TFA |
| 360 | 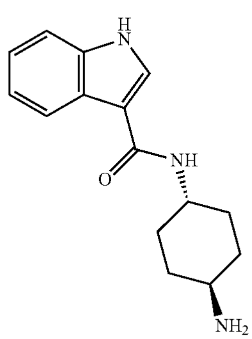 [SMILES: N[C@H]1CC[C@H](NC(=O)c2c[nH]c3ccccc23)CC1] | None |
| 361 | 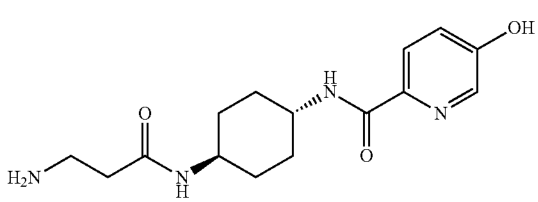 [SMILES: NCCC(=O)N[C@H]1CC[C@H](NC(=O)c2ccc(O)cn2)CC1] | TFA |

TABLE 1-continued

| Cpd. No. | Structure | Salt Form |
|---|---|---|
| 362 | 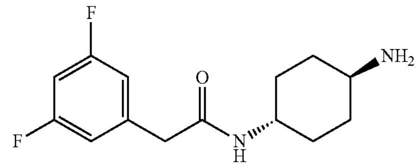 [SMILES: N[C@H]1CC[C@H](NC(=O)Cc2cc(F)cc(F)c2)CC1] | TFA |
| 363 | 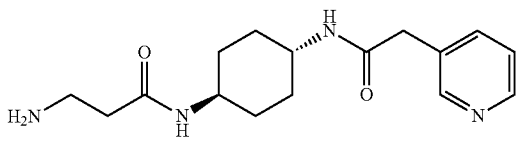 [SMILES: NCCC(=O)N[C@H]1CC[C@H](NC(=O)Cc2cccnc2)CC1] | TFA |
| 364 | 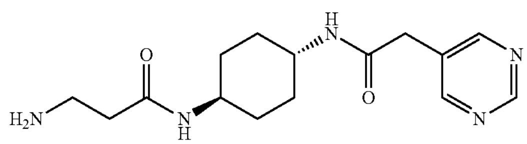 [SMILES: NCCC(=O)N[C@H]1CC[C@H](NC(=O)Cc2cncnc2)CC1] | TFA |
| 365 | 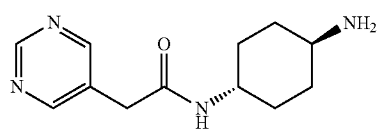 [SMILES: N[C@H]1CC[C@H](NC(=O)Cc2cncnc2)CC1] | TFA |
| 366 | 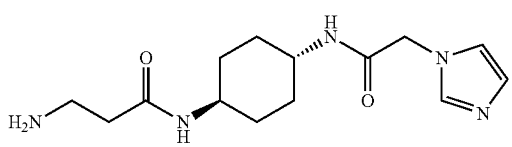 [SMILES: NCCC(=O)N[C@H]1CC[C@H](NC(=O)Cn2ccnc2)CC1] | TFA |
| 367 | 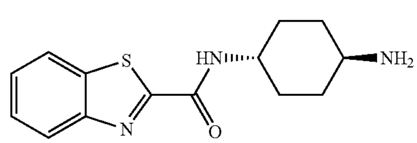 [SMILES: N[C@H]1CC[C@H](NC(=O)c2nc3ccccc3s2)CC1] | TFA |
| 368 | 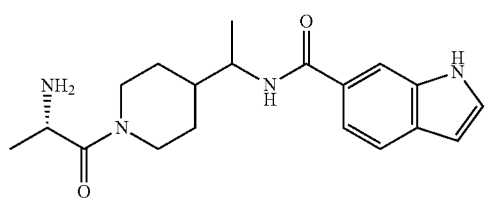 | HCl |
| 369 | 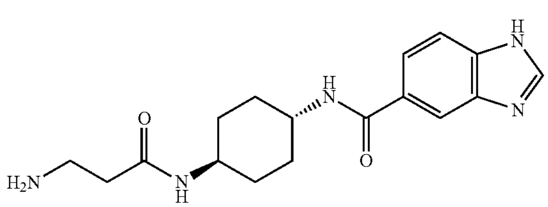 [SMILES: NCCC(=O)N[C@H]1CC[C@H](NC(=O)c2ccc3[nH]cnc3c2)CC1] | HCl |

TABLE 1-continued

| Cpd. No. | Structure | Salt Form |
|---|---|---|
| 370 | 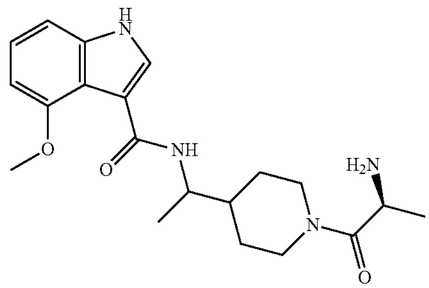 [SMILES: COc1cccc2[nH]cc(C(=O)NC(C)C3CCN(C(=O)[C@H](C)N)CC3)c12] | TFA |
| 371 | 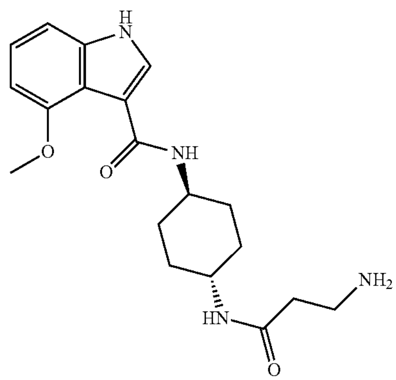 [SMILES: COc1cccc2[nH]cc(C(=O)N[C@H]3CC[C@H](NC(=O)CCN)CC3)c12] | TFA |
| 372 | 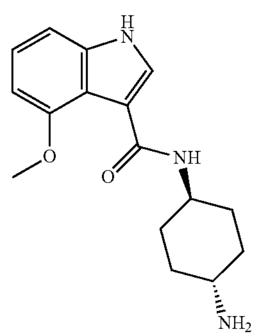 [SMILES: COc1cccc2[nH]cc(C(=O)N[C@H]3CC[C@H](N)CC3)c12] | TFA |
| 373 | 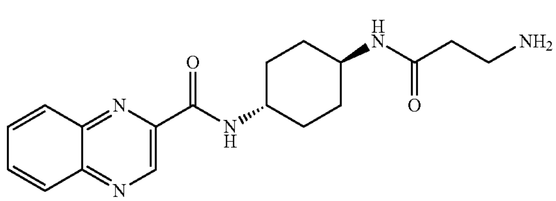 [SMILES: NCCC(=O)N[C@H]1CC[C@H](NC(=O)c2cnc3ccccc3n2)CC1] | TFA |
| 374 | 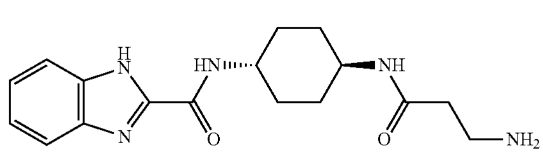 | TFA |
| 375 | 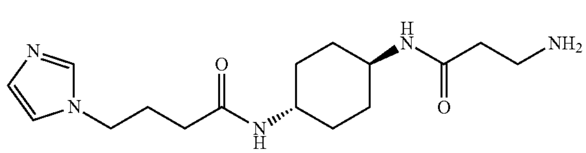 [SMILES: NCCC(=O)N[C@H]1CC[C@H](NC(=O)CCCn2ccnc2)CC1] | TFA |

TABLE 1-continued

| Cpd. No. | Structure | Salt Form |
|---|---|---|
| 376 | 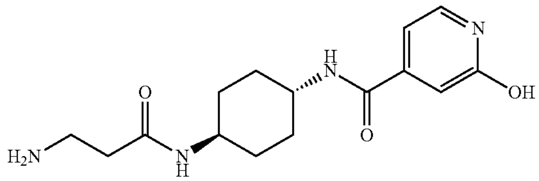 [SMILES: NCCC(=O)N[C@H]1CC[C@H](NC(=O)c2ccnc(O)c2)CC1] | TFA |
| 378 | 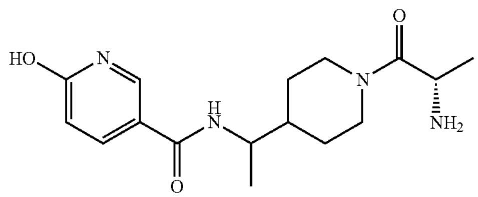 [SMILES: CC(NC(=O)c1ccc(O)nc1)C1CCN(C(=O)[C@H](C)N)CC1] | HCl |
| 379 | 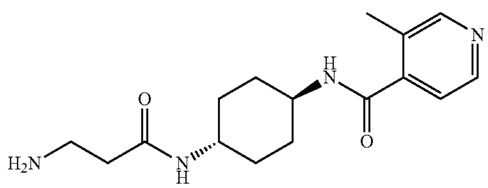 [SMILES: Cc1cnccc1C(=O)N[C@H]1CC[C@H](NC(=O)CCN)CC1] | TFA |
| 380 | 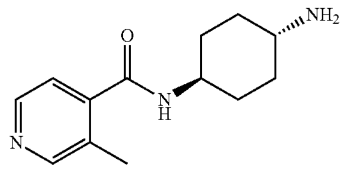 [SMILES: Cc1cnccc1C(=O)N[C@H]1CC[C@H](N)CC1] | None |
| 381 | 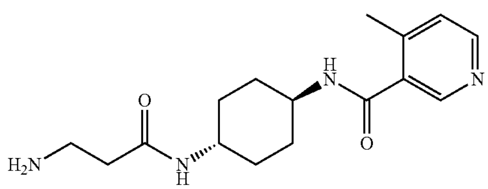 [SMILES: Cc1ccncc1C(=O)N[C@H]1CC[C@H](NC(=O)CCN)CC1] | TFA |
| 382 | 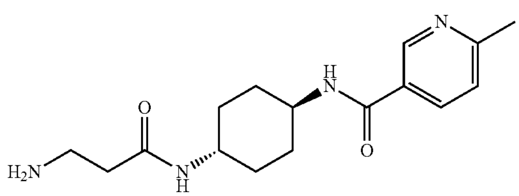 [SMILES: Cc1ccc(C(=O)N[C@H]2CC[C@H](NC(=O)CCN)CC2)cn1] | TFA |
| 383 | 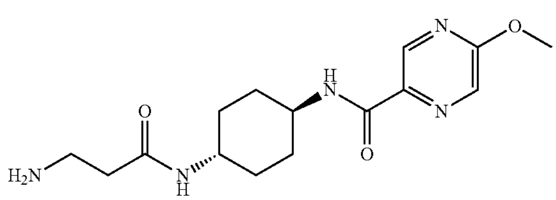 [SMILES: COc1cnc(C(=O)N[C@H]2CC[C@H](NC(=O)CCN)CC2)cn1] | TFA |
| 384 | 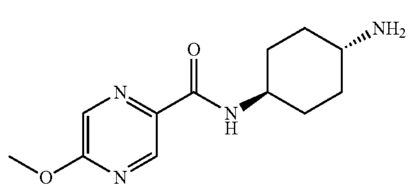 [SMILES: COc1cnc(C(=O)N[C@H]2CC[C@H](N)CC2)cn1] | TFA |

TABLE 1-continued

| Cpd. No. | Structure | Salt Form |
|---|---|---|
| 385 | 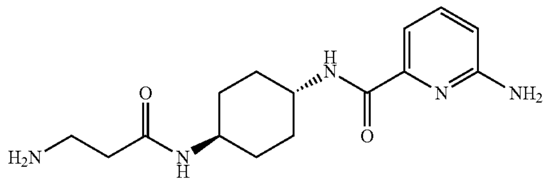 [SMILES: NCCC(=O)N[C@H]1CC[C@H](NC(=O)c2cccc(N)n2)CC1] | TFA |
| 386 | 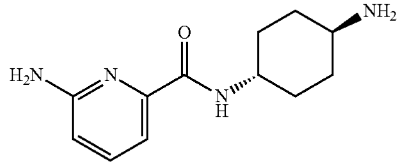 [SMILES: Nc1cccc(C(=O)N[C@H]2CC[C@H](N)CC2)n1] | TFA |
| 387 | 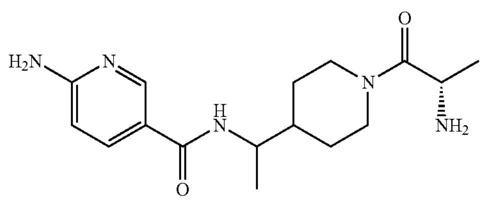 [SMILES: CC(NC(=O)c1ccc(N)nc1)C1CCN(C(=O)[C@H](C)N)CC1] | TFA |
| 388 | 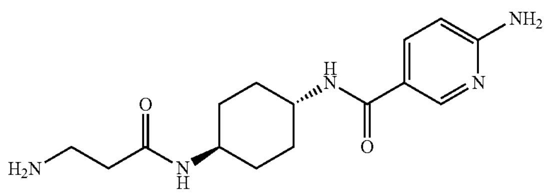 [SMILES: NCCC(=O)N[C@H]1CC[C@H](NC(=O)c2ccc(N)nc2)CC1] | None |
| 389 | 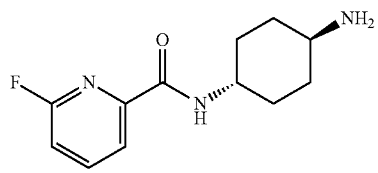 [SMILES: N[C@H]1CC[C@H](NC(=O)c2cccc(F)n2)CC1] | TFA |
| 390 | 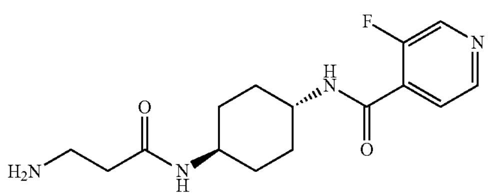 [SMILES: NCCC(=O)N[C@H]1CC[C@H](NC(=O)c2ccncc2F)CC1] | HCl |
| 391 | 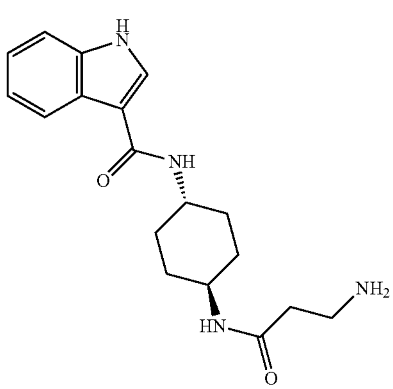 [SMILES: NCCC(=O)N[C@H]1CC[C@H](NC(=O)c2c[nH]c3ccccc23)CC1] | TFA |

TABLE 1-continued

| Cpd. No. | Structure | Salt Form |
|---|---|---|
| 392 | 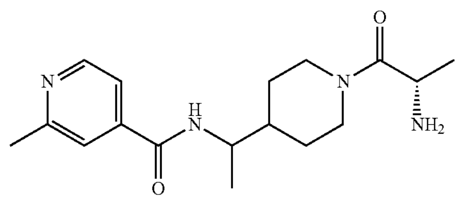 [SMILES: Cc1cc(C(=O)NC(C)C2CCN(C(=O)[C@H](C)N)CC2)ccn1] | TFA |
| 393 | 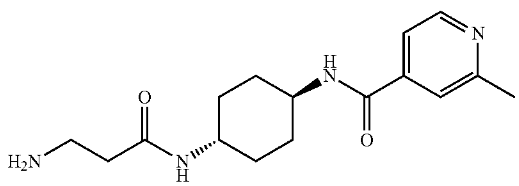 [SMILES: Cc1cc(C(=O)N[C@H]2CC[C@H](NC(=O)CCN)CC2)ccn1] | TFA |
| 394 | 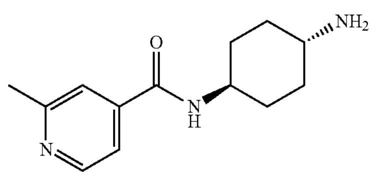 [SMILES: Cc1cc(C(=O)N[C@H]2CC[C@H](N)CC2)ccn1] | None |
| 395 | 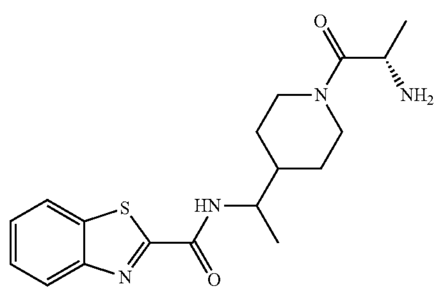 [SMILES: CC(NC(=O)c1nc2ccccc2s1)C1CCN(C(=O)[C@H](C)N)CC1] | HCl |
| 396 | 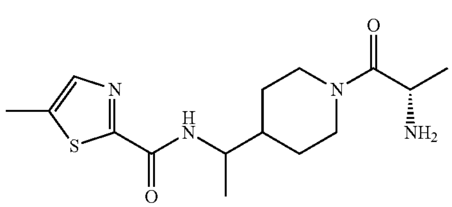 [SMILES: Cc1cnc(C(=O)NC(C)C2CCN(C(=O)[C@H](C)N)CC2)s1] | TFA |
| 397 | 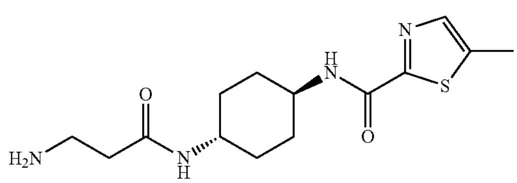 [SMILES: Cc1cnc(C(=O)N[C@H]2CC[C@H](NC(=O)CCN)CC2)s1] | TFA |
| 398 | 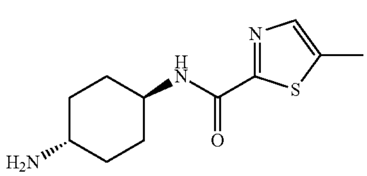 [SMILES: Cc1cnc(C(=O)N[C@H]2CC[C@H](N)CC2)s1] | TFA |

TABLE 1-continued

| Cpd. No. | Structure | Salt Form |
|---|---|---|
| 399 | 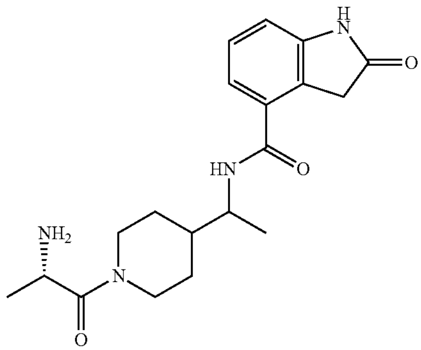 [SMILES: CC(NC(=O)c1cccc2c1CC(=O)N2)C1CCN(C(=O)[C@H](C)N)CC1] | HCl |
| 400 | 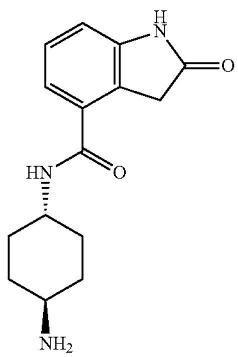 [SMILES: N[C@H]1CC[C@H](NC(=O)c2cccc3c2CC(=O)N3)CC1] | HCl |
| 401 | 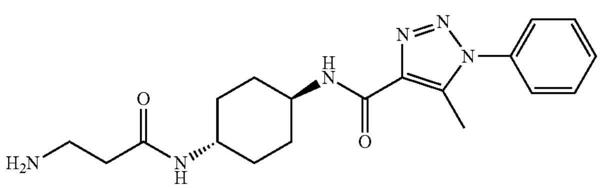 [SMILES: Cc1c(C(=O)N[C@H]2CC[C@H](NC(=O)CCN)CC2)nnn1-c1ccccc1] | TFA |
| 402 | 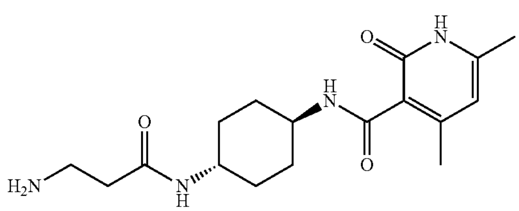 [SMILES: Cc1cc(C)c(C(=O)N[C@H]2CC[C@H](NC(=O)CCN)CC2)c(=O)[nH]1] | TFA |
| 403 | 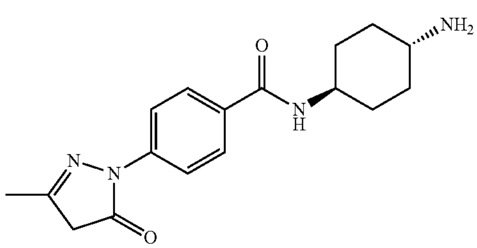 [SMILES: CC1=NN(c2ccc(C(=O)N[C@H]3CC[C@H](N)CC3)cc2)C(=O)C1] | TFA |
| 404 | 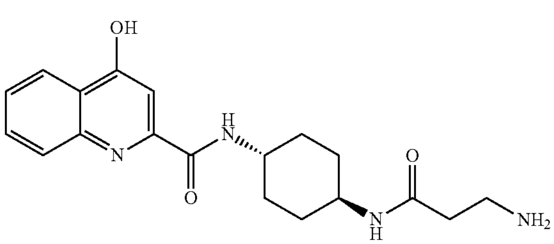 [SMILES: NCCC(=O)N[C@H]1CC[C@H](NC(=O)c2cc(O)c3ccccc3n2)CC1] | None |

TABLE 1-continued

| Cpd. No. | Structure | Salt Form |
|---|---|---|
| 405 | (quinoxaline-2-carboxamide linked to trans-4-aminocyclohexyl) | None |
| 406 | (1H-pyrrolo[3,2-b]pyridin-3-yl-acetamide linked to 1-(piperidin-4-yl)ethyl, piperidine N-acylated with alaninyl) | TFA |
| 407 | (1H-pyrrolo[3,2-b]pyridin-3-yl-acetamide linked to trans-1,4-diaminocyclohexyl, with β-alanyl amide) | TFA |
| 408 | (1H-pyrrolo[3,2-b]pyridin-3-yl-acetamide linked to trans-4-aminocyclohexyl) | TFA |
| 409 | (2-hydroxynicotinamide linked to 1-(piperidin-4-yl)ethyl, piperidine N-acylated with alaninyl) | HCl |
| 410 | (2-hydroxynicotinamide linked to trans-1,4-diaminocyclohexyl, with β-alanyl amide) | HCl |
| 411 | (2-hydroxynicotinamide linked to trans-4-aminocyclohexyl) | HCl |

TABLE 1-continued

| Cpd. No. | Structure | Salt Form |
|---|---|---|
| 412 | 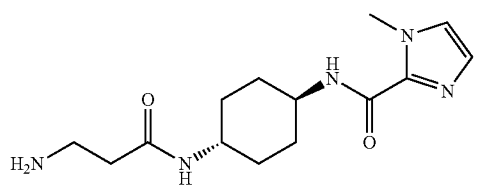 [SMILES: Cn1ccnc1C(=O)N[C@H]1CC[C@H](NC(=O)CCN)CC1] | TFA |
| 413 | 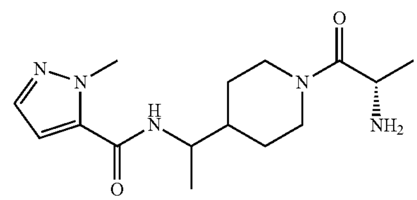 [SMILES: CC(NC(=O)c1ccnn1C)C1CCN(C(=O)[C@H](C)N)CC1] | TFA |
| 414 | 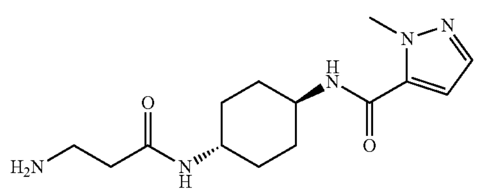 [SMILES: Cn1nccc1C(=O)N[C@H]1CC[C@H](NC(=O)CCN)CC1] | TFA |
| 415 | 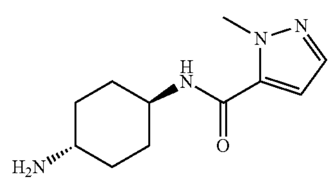 [SMILES: Cn1nccc1C(=O)N[C@H]1CC[C@H](N)CC1] | TFA |
| 416 | 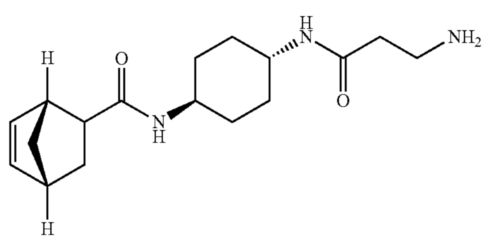 [SMILES: NCCC(=O)N[C@H]1CC[C@H](NC(=O)C2C[C@@H]3C=C[C@H]2C3)CC1] | TFA |
| 417 | 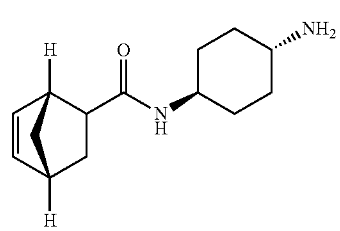 [SMILES: N[C@H]1CC[C@H](NC(=O)C2C[C@@H]3C=C[C@H]2C3)CC1] | TFA |
| 418 | 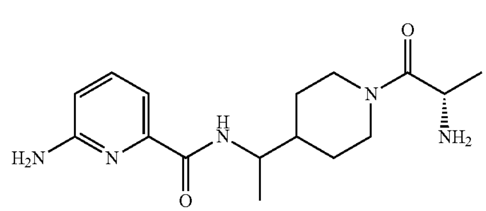 [SMILES: CC(NC(=O)c1cccc(N)n1)C1CCN(C(=O)[C@H](C)N)CC1] | TFA |

TABLE 1-continued

| Cpd. No. | Structure | Salt Form |
|---|---|---|
| 419 | 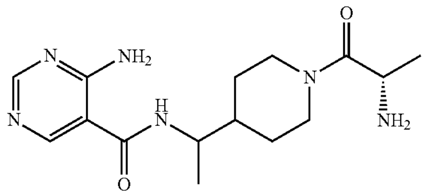 [SMILES: CC(NC(=O)c1cncnc1N)C1CCN(C(=O)[C@H](C)N)CC1] | TFA |
| 420 | 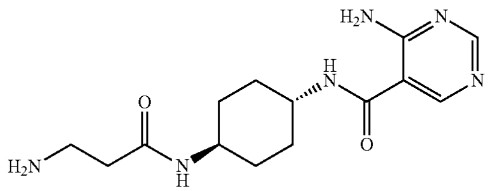 [SMILES: NCCC(=O)N[C@H]1CC[C@H](NC(=O)c2cncnc2N)CC1] | TFA |
| 421 | 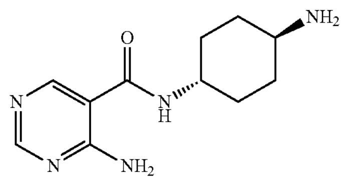 | TFA |
| 422 | 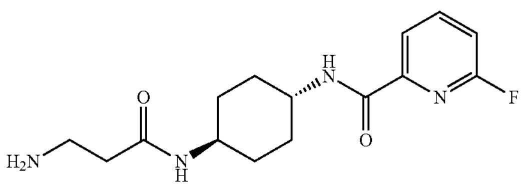 [SMILES: NCCC(=O)N[C@H]1CC[C@H](NC(=O)c2cccc(F)n2)CC1] | TFA |
| 423 | 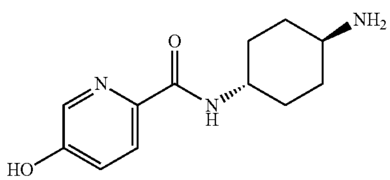 [SMILES: N[C@H]1CC[C@H](NC(=O)c2ccc(O)cn2)CC1] | TFA |
| 424 | 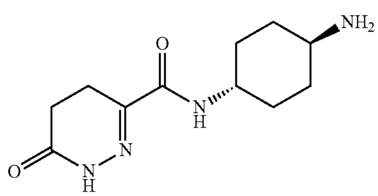 [SMILES: N[C@H]1CC[C@H](NC(=O)C2=NNC(=O)CC2)CC1] | TFA |
| 425 | 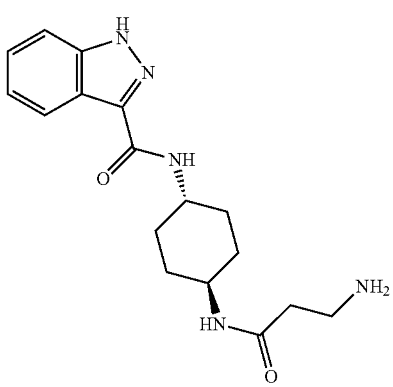 [SMILES: NCCC(=O)N[C@H]1CC[C@H](NC(=O)c2n[nH]c3ccccc23)CC1] | TFA |

TABLE 1-continued
| Cpd. No. | Structure | Salt Form |
|---|---|---|
| 426 | 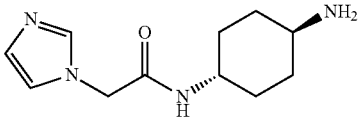 [SMILES: N[C@H]1CC[C@H](NC(=O)Cn2ccnc2)CC1] | TFA |
| 427 | 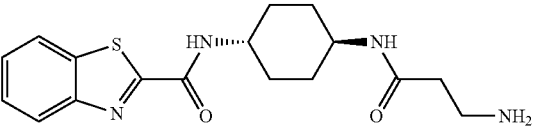 [SMILES: NCCC(=O)N[C@H]1CC[C@H](NC(=O)c2nc3ccccc3s2)CC1] | TFA |
| 428 | 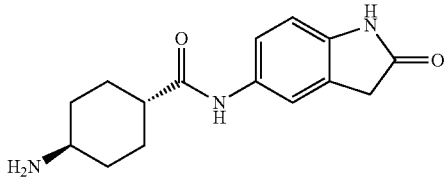 [SMILES: N[C@H]1CC[C@H](C(=O)Nc2ccc3c(c2)CC(=O)N3)CC1] | TFA |
| 429 | 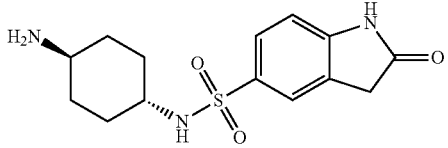 [SMILES: N[C@H]1CC[C@H](NS(=O)(=O)c2ccc3c(c2)CC(=O)N3)CC1] | TFA |
| 430 | 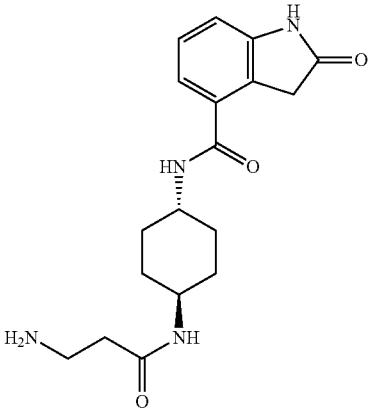 [SMILES: NCCC(=O)N[C@H]1CC[C@H](NC(=O)c2cccc3c2CC(=O)N3)CC1] | HCl |
| 431 | 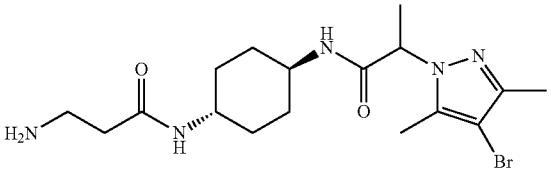 [SMILES: Cc1nn(C(C)C(=O)N[C@H]2CC[C@H](NC(=O)CCN)CC2)c(C)c1Br] | TFA |
| 432 | 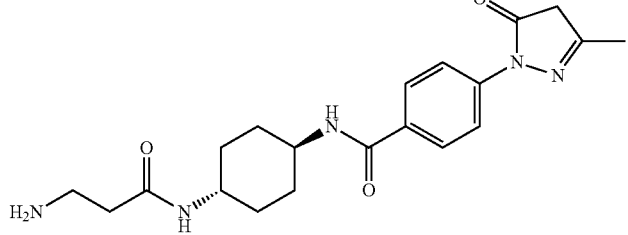 | TFA |

TABLE 1-continued

| Cpd. No. | Structure | Salt Form |
|---|---|---|
| 433 | 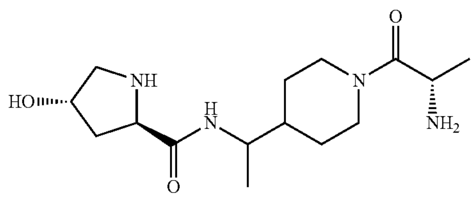 [SMILES: CC(NC(=O)[C@H]1C[C@H](O)CN1)C1CCN(C(=O)[C@H](C)N)CC1] | HCl |
| 434 | 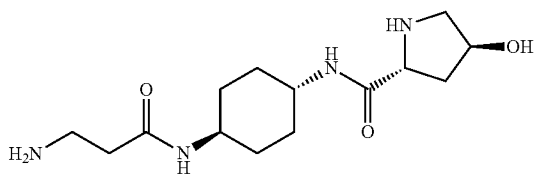 [SMILES: NCCC(=O)N[C@H]1CC[C@H](NC(=O)[C@H]2C[C@H](O)CN2)CC1] | HCl |
| 435 | 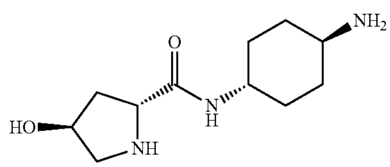 [SMILES: N[C@H]1CC[C@H](NC(=O)[C@H]2C[C@H](O)CN2)CC1] | HCl |
| 436 | 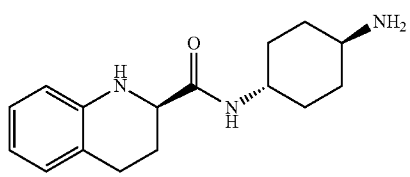 [SMILES: N[C@H]1CC[C@H](NC(=O)[C@H]2CCc3ccccc3N2)CC1] | TFA |
| 437 | 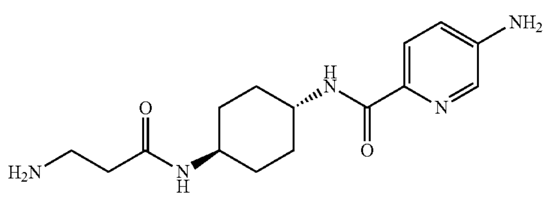 [SMILES: NCCC(=O)N[C@H]1CC[C@H](NC(=O)c2ccc(N)cn2)CC1] | None |
| 438 | 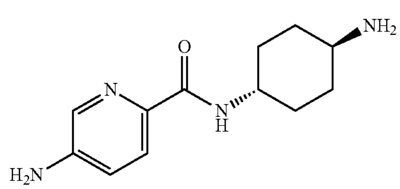 [SMILES: Nc1ccc(C(=O)N[C@H]2CC[C@H](N)CC2)nc1] | TFA |
| 439 | 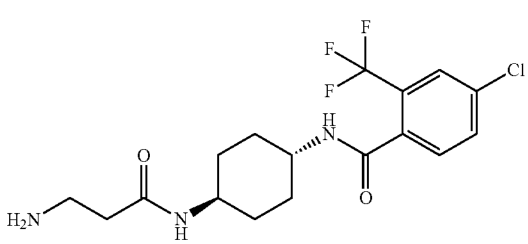 [SMILES: NCCC(=O)N[C@H]1CC[C@H](NC(=O)c2ccc(Cl)cc2C(F)(F)F)CC1] | HCl |

TABLE 1-continued

| Cpd. No. | Structure | Salt Form |
|---|---|---|
| 440 | 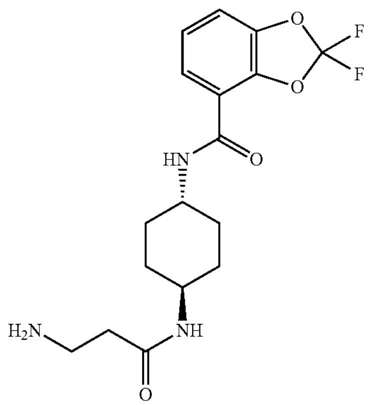 [SMILES: NCCC(=O)N[C@H]1CC[C@H](NC(=O)c2cccc3c2OC(F)(F)O3)CC1] | HCl |
| 441 | 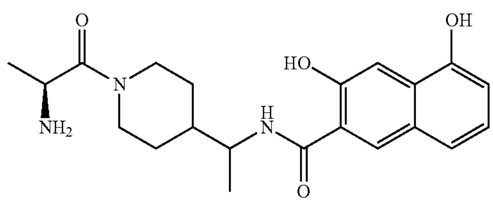 [SMILES: CC(NC(=O)c1cc2cccc(O)c2cc1O)C1CCN(C(=O)[C@H](C)N)CC1] | TFA |
| 442 | 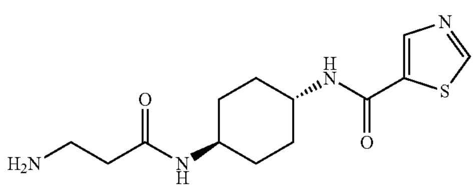 [SMILES: NCCC(=O)N[C@H]1CC[C@H](NC(=O)c2cncs2)CC1] | HCl |
| 443 | 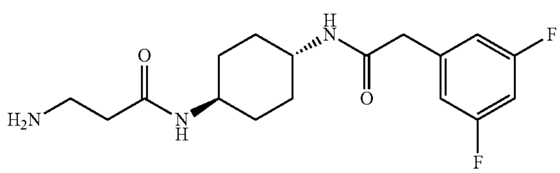 [SMILES: NCCC(=O)N[C@H]1CC[C@H](NC(=O)Cc2cc(F)cc(F)c2)CC1] | HCl |
| 444 | 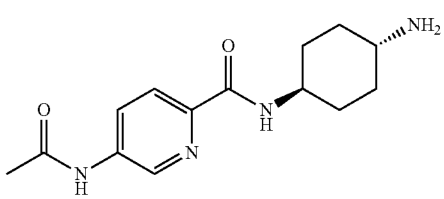 [SMILES: CC(=O)Nc1ccc(C(=O)N[C@H]2CC[C@H](N)CC2)nc1] | TFA |
| 445 | 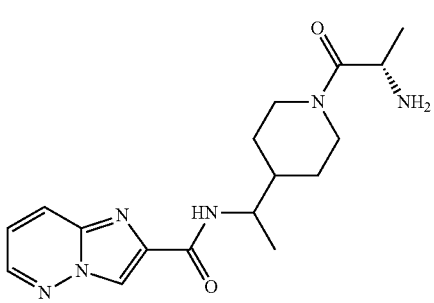 [SMILES: CC(NC(=O)c1cn2ncccc2n1)C1CCN(C(=O)[C@H](C)N)CC1] | TFA |

TABLE 1-continued

| Cpd. No. | Structure | Salt Form |
|---|---|---|
| 446 | 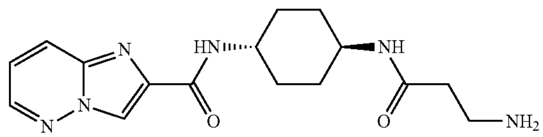 [SMILES: NCCC(=O)N[C@H]1CC[C@H](NC(=O)c2cn3ncccc3n2)CC1] | TFA |
| 447 | 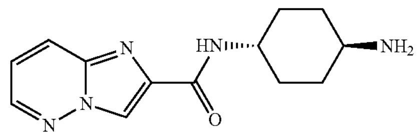 [SMILES: N[C@H]1CC[C@H](NC(=O)c2cn3ncccc3n2)CC1] | TFA |
| 448 | 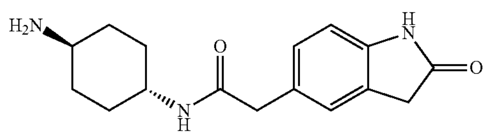 [SMILES: N[C@H]1CC[C@H](NC(=O)Cc2ccc3c(c2)CC(=O)N3)CC1] | TFA |
| 449 | 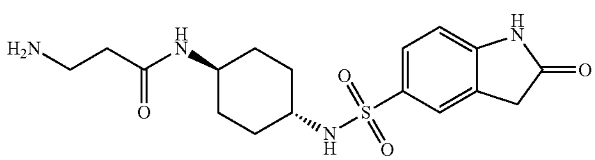 [SMILES: NCCC(=O)N[C@H]1CC[C@H](NS(=O)(=O)c2ccc3c(c2)CC(=O)N3)CC1] | TFA |
| 450 | 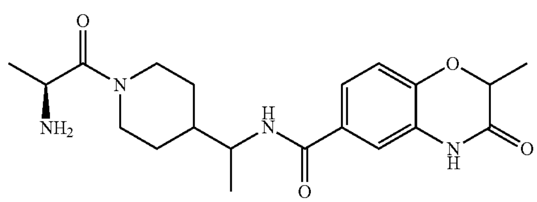 [SMILES: CC1Oc2ccc(C(=O)NC(C)C3CCN(C(=O)[C@H](C)N)CC3)cc2NC1=O] | None |
| 451 | 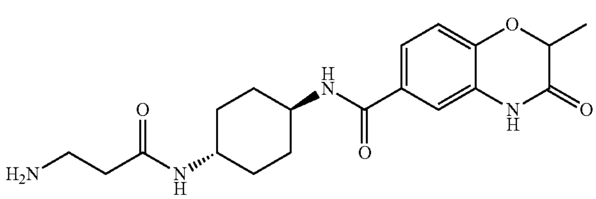 [SMILES: CC1Oc2ccc(C(=O)N[C@H]3CC[C@H](NC(=O)CCN)CC3)cc2NC1=O] | TFA |
| 452 | 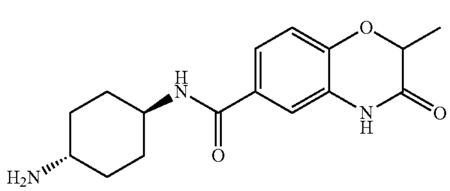 [SMILES: CC1Oc2ccc(C(=O)N[C@H]3CC[C@H](N)CC3)cc2NC1=O] | TFA |
| 453 | 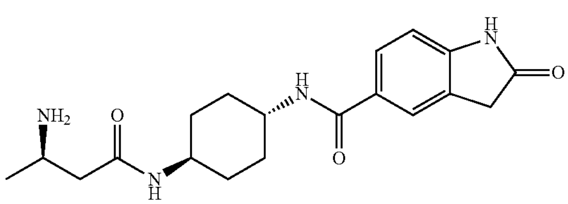 [SMILES: C[C@@H](N)CC(=O)N[C@H]1CC[C@H](NC(=O)c2ccc3c(c2)CC(=O)N3)CC1] | TFA |
| 454 | 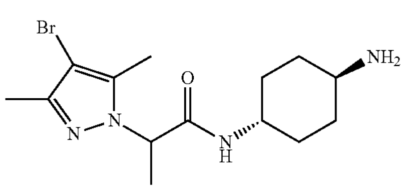 [SMILES: Cc1nn(C(C)C(=O)N[C@H]2CC[C@H](N)CC2)c(C)c1Br] | TFA |

TABLE 1-continued
| Cpd. No. | Structure | Salt Form |
|---|---|---|
| 455 | 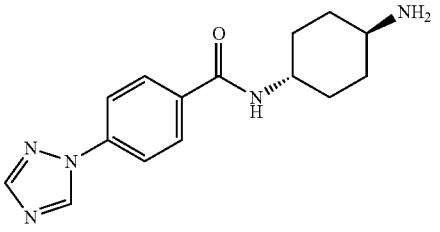 [SMILES: N[C@H]1CC[C@H](NC(=O)c2ccc(-n3cncn3)cc2)CC1] | None |
| 456 | 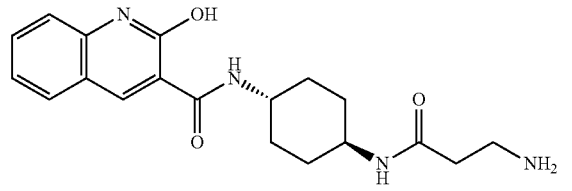 [SMILES: NCCC(=O)N[C@H]1CC[C@H](NC(=O)c2cc3ccccc3nc2O)CC1] | TFA |
| 457 | 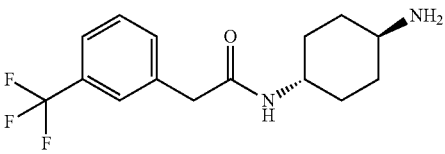 [SMILES: N[C@H]1CC[C@H](NC(=O)Cc2cccc(C(F)(F)F)c2)CC1] | TFA |
| 458 | 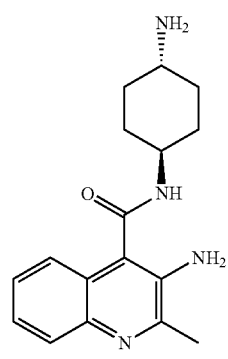 [SMILES: Cc1nc2ccccc2c(C(=O)N[C@H]2CC[C@H](N)CC2)c1N] | None |
| 459 | 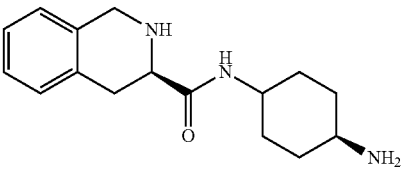 | TFA |
| 460 | 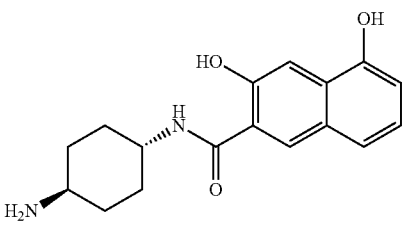 [SMILES: N[C@H]1CC[C@H](NC(=O)c2cc3cccc(O)c3cc2O)CC1] | TFA |
| 461 | 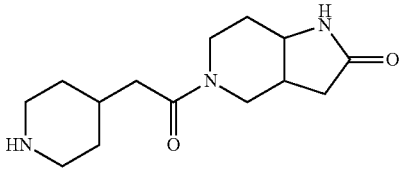 [SMILES: O=C1CC2CN(C(=O)CC3CCNCC3)CCC2N1] | TFA |

TABLE 1-continued

| Cpd. No. | Structure | Salt Form |
|---|---|---|
| 462 | 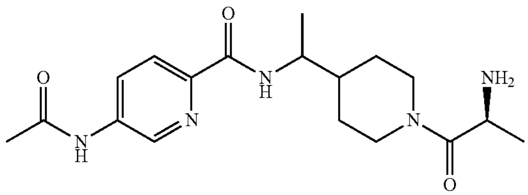 [SMILES: CC(=O)Nc1ccc(C(=O)NC(C)C2CCN(C(=O)[C@H](C)N)CC2)nc1] | TFA |
| 463 | 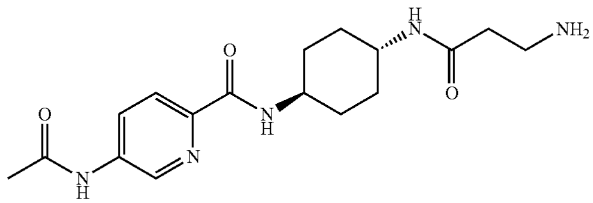 [SMILES: CC(=O)Nc1ccc(C(=O)N[C@H]2CC[C@H](NC(=O)CCN)CC2)nc1] | TFA |
| 464 | 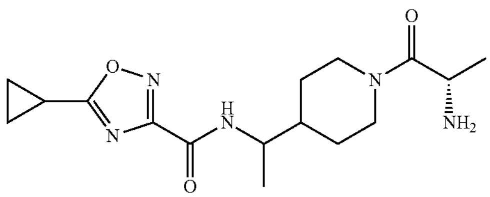 [SMILES: CC(NC(=O)c1noc(C2CC2)n1)C1CCN(C(=O)[C@H](C)N)CC1] | HCl |
| 465 | 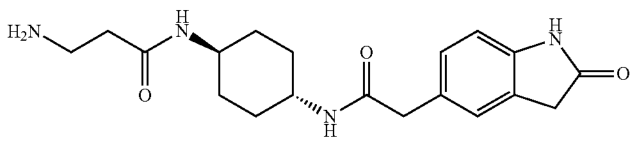 [SMILES: NCCC(=O)N[C@H]1CC[C@H](NC(=O)Cc2ccc3c(c2)CC(=O)N3)CC1] | TFA |
| 466 | 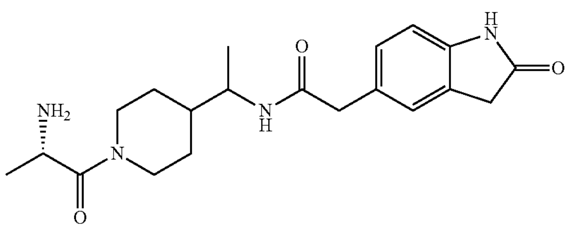 [SMILES: CC(NC(=O)Cc1ccc2c(c1)CC(=O)N2)C1CCN(C(=O)[C@H](C)N)CC1] | TFA |
| 467 | 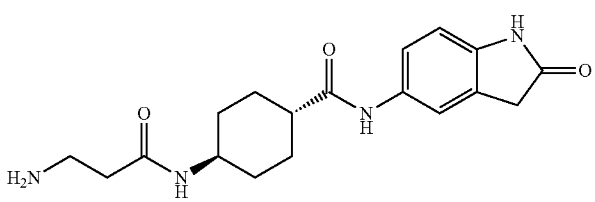 [SMILES: NCCC(=O)N[C@H]1CC[C@H](C(=O)Nc2ccc3c(c2)CC(=O)N3)CC1] | TFA |
| 468 | 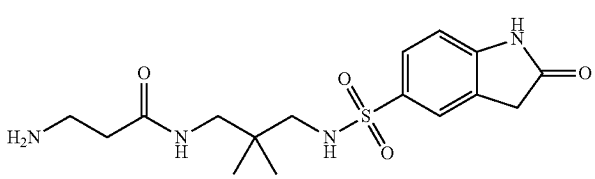 [SMILES: CC(C)(CNC(=O)CCN)CNS(=O)(=O)c1ccc2c(c1)CC(=O)N2] | TFA |
| 469 | 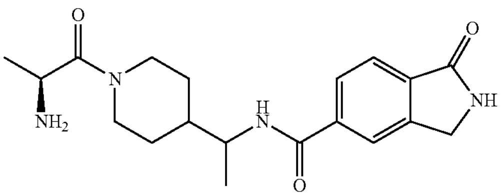 [SMILES: CC(NC(=O)c1ccc2c(c1)CNC2=O)C1CCN(C(=O)[C@H](C)N)CC1] | TFA |

TABLE 1-continued

| Cpd. No. | Structure | Salt Form |
|---|---|---|
| 470 | 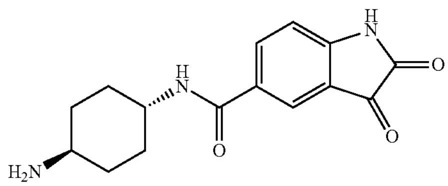 [SMILES: N[C@H]1CC[C@H](NC(=O)c2ccc3c(c2)C(=O)C(=O)N3)CC1] | TFA |
| 471 | 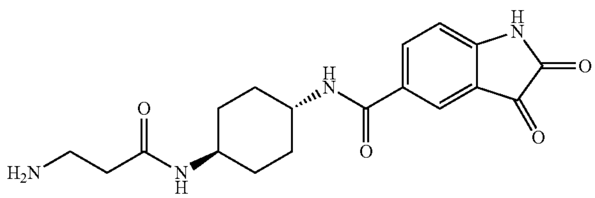 [SMILES: NCCC(=O)N[C@H]1CC[C@H](NC(=O)c2ccc3c(c2)C(=O)C(=O)N3)CC1] | HCl |
| 472 | 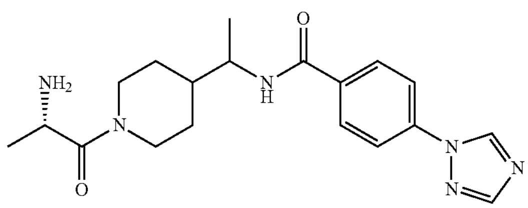 [SMILES: CC(NC(=O)c1ccc(-n2cncn2)cc1)C1CCN(C(=O)[C@H](C)N)CC1] | None |
| 473 | 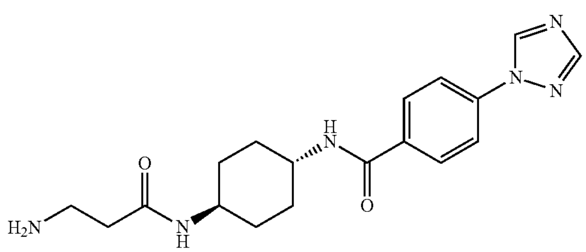 [SMILES: NCCC(=O)N[C@H]1CC[C@H](NC(=O)c2ccc(-n3cncn3)cc2)CC1] | TFA |
| 474 | 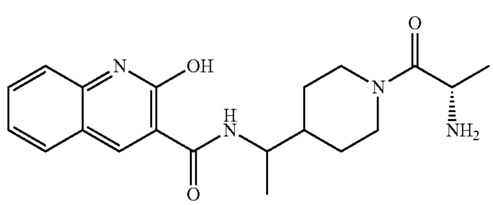 [SMILES: CC(NC(=O)c1cc2ccccc2nc1O)C1CCN(C(=O)[C@H](C)N)CC1] | TFA |
| 475 | 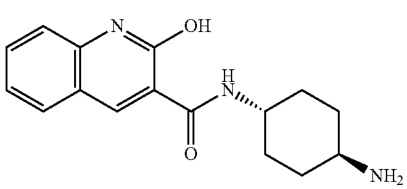 [SMILES: N[C@H]1CC[C@H](NC(=O)c2cc3ccccc3nc2O)CC1] | TFA |
| 476 | 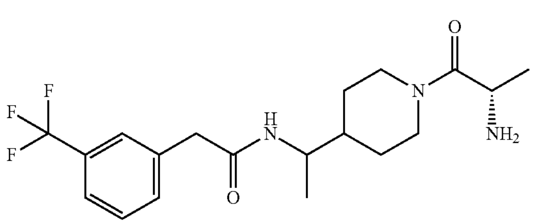 [SMILES: CC(NC(=O)Cc1cccc(C(F)(F)F)c1)C1CCN(C(=O)[C@H](C)N)CC1] | TFA |

TABLE 1-continued

| Cpd. No. | Structure | Salt Form |
|---|---|---|
| 477 | 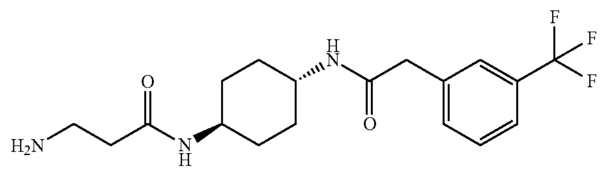 [SMILES: NCCC(=O)N[C@H]1CC[C@H](NC(=O)Cc2cccc(C(F)(F)F)c2)CC1] | TFA |
| 478 | 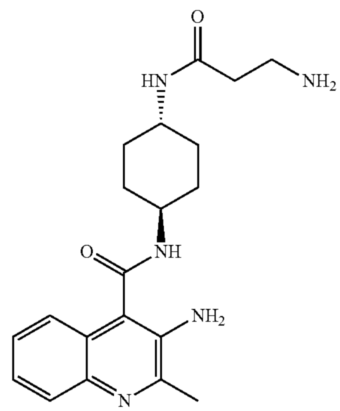 [SMILES: Cc1nc2ccccc2c(C(=O)N[C@H]2CC[C@H](NC(=O)CCN)CC2)c1N] | TFA |
| 479 | 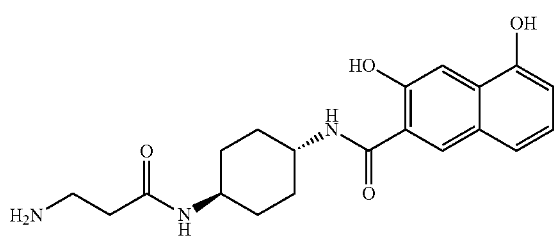 [SMILES: NCCC(=O)N[C@H]1CC[C@H](NC(=O)c2cc3cccc(O)c3cc2O)CC1] | TFA |
| 480 | 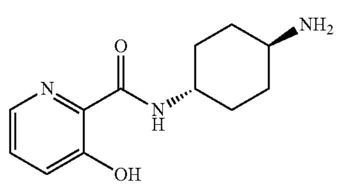 [SMILES: N[C@H]1CC[C@H](NC(=O)c2ncccc2O)CC1] | TFA |
| 481 | 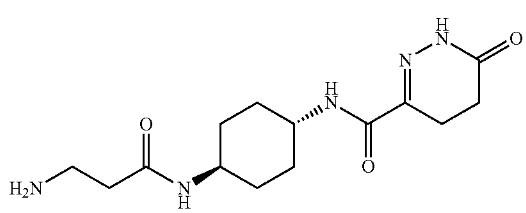 [SMILES: NCCC(=O)N[C@H]1CC[C@H](NC(=O)C2=NNC(=O)CC2)CC1] | TFA |
| 482 | 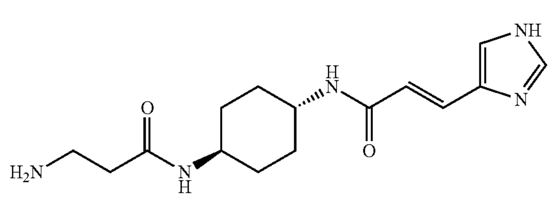 [SMILES: NCCC(=O)N[C@H]1CC[C@H](NC(=O)/C=C/c2c[nH]cn2)CC1] | TFA |

TABLE 1-continued

| Cpd. No. | Structure | Salt Form |
|---|---|---|
| 483 | 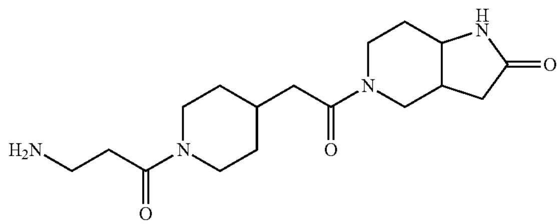 [SMILES: NCCC(=O)N1CCC(CC(=O)N2CCC3NC(=O)CC3C2)CC1] | TFA |
| 484 | 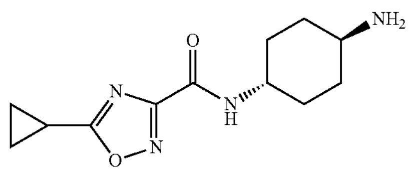 [SMILES: N[C@H]1CC[C@H](NC(=O)c2noc(C3CC3)n2)CC1] | None |
| 485 | 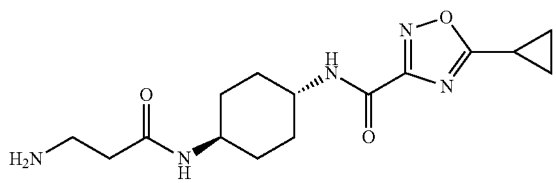 [SMILES: NCCC(=O)N[C@H]1CC[C@H](NC(=O)c2noc(C3CC3)n2)CC1] | None |
| 486 | 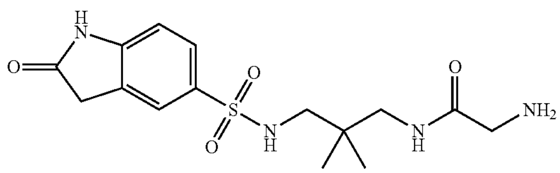 [SMILES: CC(C)(CNC(=O)CN)CNS(=O)(=O)c1ccc2c(c1)CC(=O)N2] | TFA |
| 487 | 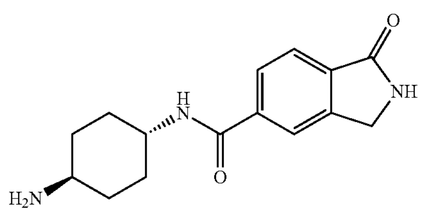 [SMILES: N[C@H]1CC[C@H](NC(=O)c2ccc3c(c2)CNC3=O)CC1] | TFA |
| 488 | 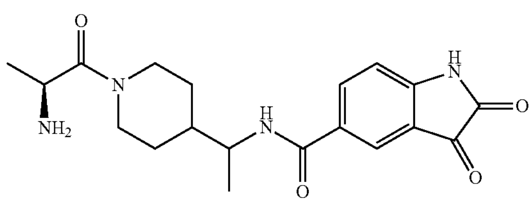 [SMILES: CC(NC(=O)c1ccc2c(c1)C(=O)C(=O)N2)C1CCN(C(=O)[C@H](C)N)CC1] | TFA |
| 489 | 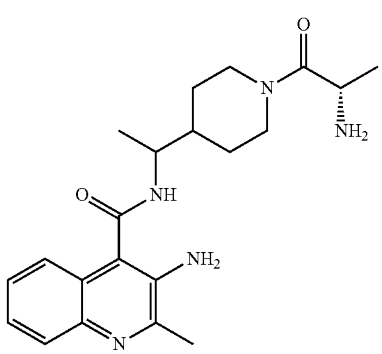 [SMILES: Cc1nc2ccccc2c(C(=O)NC(C)C2CCN(C(=O)[C@H](C)N)CC2)c1N] | TFA |

TABLE 1-continued

| Cpd. No. | Structure | Salt Form |
|---|---|---|
| 490 | 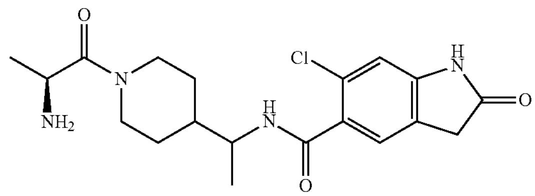 [SMILES: CC(NC(=O)c1cc2c(cc1Cl)NC(=O)C2)C1CCN(C(=O)[C@H](C)N)CC1] | TFA |
| 491 | 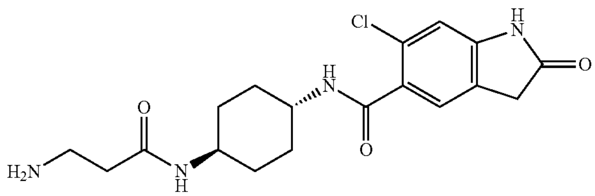 [SMILES: NCCC(=O)N[C@H]1CC[C@H](NC(=O)c2cc3c(cc2Cl)NC(=O)C3)CC1] | TFA |
| 492 | 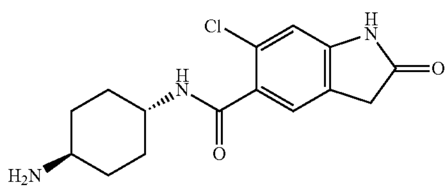 [SMILES: N[C@H]1CC[C@H](NC(=O)c2cc3c(cc2Cl)NC(=O)C3)CC1] | None |
| 493 | 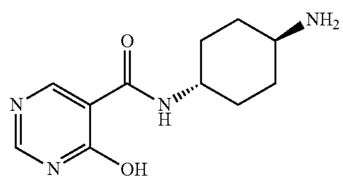 [SMILES: N[C@H]1CC[C@H](NC(=O)c2cncnc2O)CC1] | TFA |
| 494 | 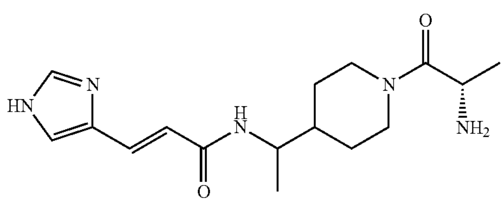 [SMILES: CC(NC(=O)/C=C/c1c[nH]cn1)C1CCN(C(=O)[C@H](C)N)CC1] | None |
| 495 | 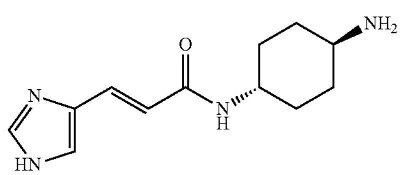 [SMILES: N[C@H]1CC[C@H](NC(=O)/C=C/c2c[nH]cn2)CC1] | None |
| 496 | 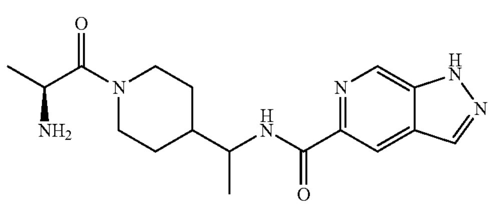 [SMILES: CC(NC(=O)c1cc2cn[nH]c2cn1)C1CCN(C(=O)[C@H](C)N)CC1] | TFA |
| 497 | 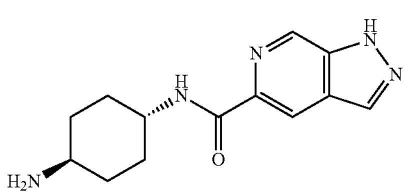 [SMILES: N[C@H]1CC[C@H](NC(=O)c2cc3cn[nH]c3cn2)CC1] | TFA |

TABLE 1-continued

| Cpd. No. | Structure | Salt Form |
|---|---|---|
| 498 | 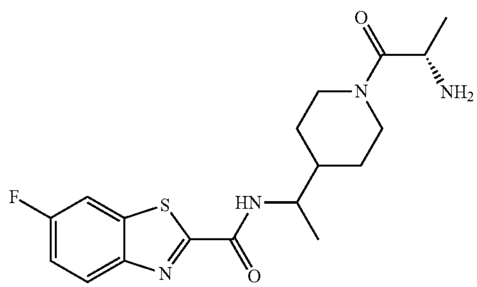 [SMILES: CC(NC(=O)c1nc2ccc(F)cc2s1)C1CCN(C(=O)[C@H](C)N)CC1] | TFA |
| 499 | 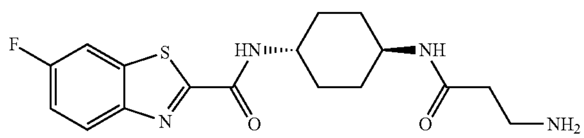 [SMILES: NCCC(=O)N[C@H]1CC[C@H](NC(=O)c2nc3ccc(F)cc3s2)CC1] | TFA |
| 500 | 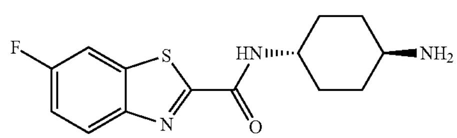 [SMILES: N[C@H]1CC[C@H](NC(=O)c2nc3ccc(F)cc3s2)CC1] | TFA |
| 501 | 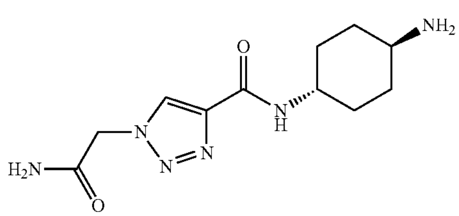 [SMILES: NC(=O)Cn1cc(C(=O)N[C@H]2CC[C@H](N)CC2)nn1] | TFA |
| 502 | 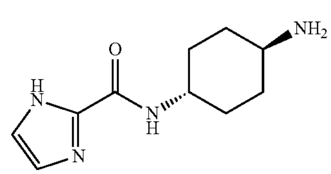 [SMILES: N[C@H]1CC[C@H](NC(=O)c2ncc[nH]2)CC1] | TFA |
| 503 | 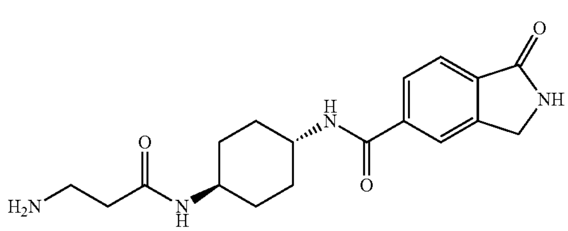 [SMILES: NCCC(=O)N[C@H]1CC[C@H](NC(=O)c2ccc3c(c2)CNC3=O)CC1] | TFA |
| 504 | 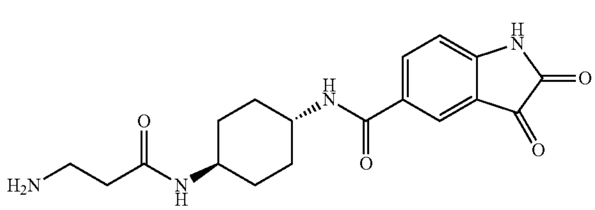 [SMILES: NCCC(=O)N[C@H]1CC[C@H](NC(=O)c2ccc3c(c2)C(=O)C(=O)N3)CC1] | TFA |

TABLE 1-continued

| Cpd. No. | Structure | Salt Form |
|---|---|---|
| 505 | 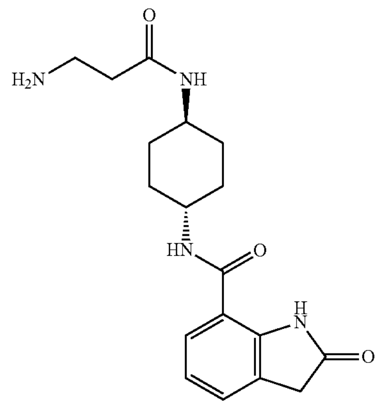 [SMILES: NCCC(=O)N[C@H]1CC[C@H](NC(=O)c2cccc3c2NC(=O)C3)CC1] | TFA |
| 506 | 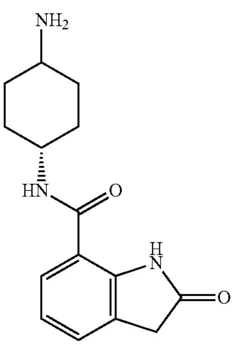 | TFA |
| 507 | 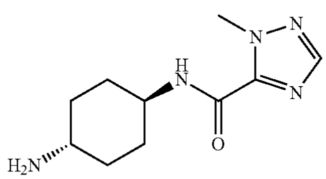 | TFA |
| 508 | 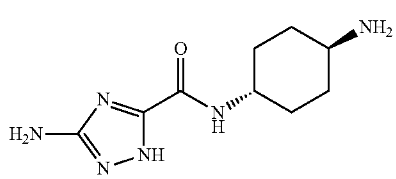 [SMILES: Nc1n[nH]c(C(=O)N[C@H]2CC[C@H](N)CC2)n1] | TFA |
| 509 | 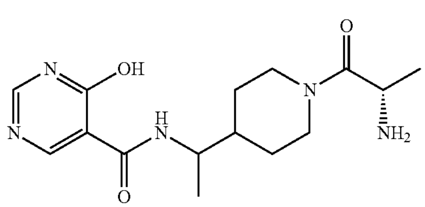 [SMILES: CC(NC(=O)c1cncnc1O)C1CCN(C(=O)[C@H](C)N)CC1] | TFA |
| 510 | 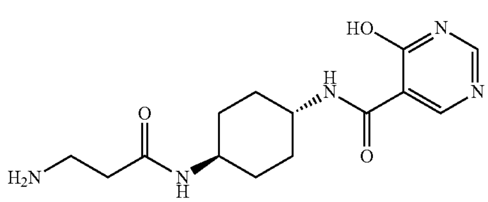 [SMILES: NCCC(=O)N[C@H]1CC[C@H](NC(=O)c2cncnc2O)CC1] | TFA |

TABLE 1-continued

| Cpd. No. | Structure | Salt Form |
|---|---|---|
| 511 | 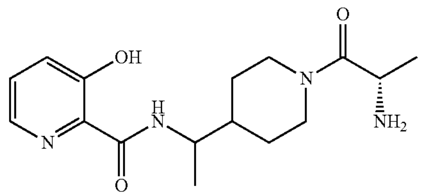 [SMILES: CC(NC(=O)c1ncccc1O)C1CCN(C(=O)[C@H](C)N)CC1] | HCl |
| 512 | 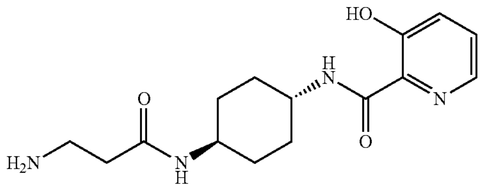 [SMILES: NCCC(=O)N[C@H]1CC[C@H](NC(=O)c2ncccc2O)CC1] | TFA |
| 513 | 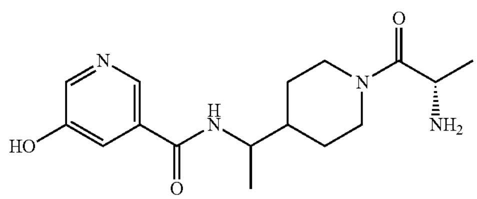 [SMILES: CC(NC(=O)c1cncc(O)c1)C1CCN(C(=O)[C@H](C)N)CC1] | None |
| 514 | 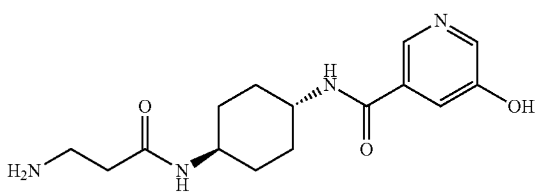 [SMILES: NCCC(=O)N[C@H]1CC[C@H](NC(=O)c2cncc(O)c2)CC1] | None |
| 515 | 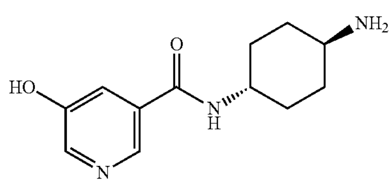 [SMILES: N[C@H]1CC[C@H](NC(=O)c2cncc(O)c2)CC1] | TFA |
| 516 | 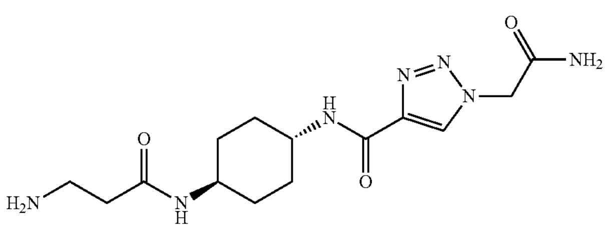 [SMILES: NCCC(=O)N[C@H]1CC[C@H](NC(=O)c2cn(CC(N)=O)nn2)CC1] | None |
| 517 | 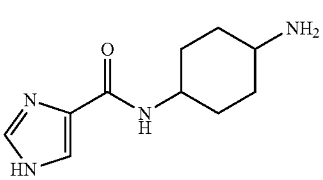 [SMILES: NC1CCC(NC(=O)c2c[nH]cn2)CC1] | None |
| 518 | 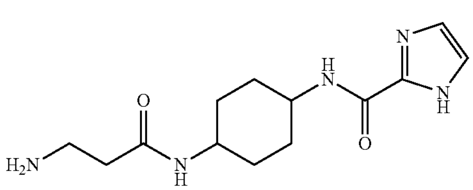 [SMILES: NCCC(=O)NC1CCC(NC(=O)c2ncc[nH]2)CC1] | None |

TABLE 1-continued

| Cpd. No. | Structure | Salt Form |
|---|---|---|
| 519 | 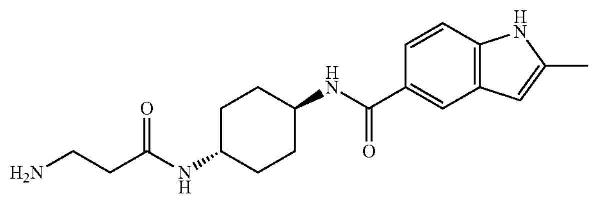 [SMILES: Cc1cc2cc(C(=O)N[C@H]3CC[C@H](NC(=O)CCN)CC3)ccc2[nH]1] | TFA |
| 520 | 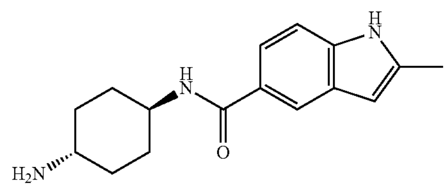 [SMILES: Cc1cc2cc(C(=O)N[C@H]3CC[C@H](N)CC3)ccc2[nH]1] | TFA |
| 521 | 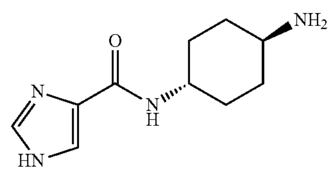 [SMILES: N[C@H]1CC[C@H](NC(=O)c2c[nH]cn2)CC1] | None |
| 522 | 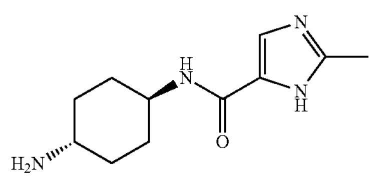 [SMILES: Cc1ncc(C(=O)N[C@H]2CC[C@H](N)CC2)[nH]1] | None |
| 523 | 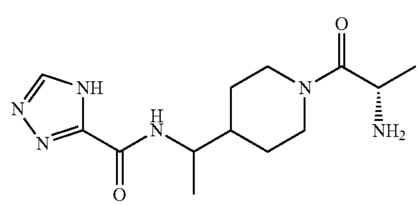 [SMILES: CC(NC(=O)c1nnc[nH]1)C1CCN(C(=O)[C@H](C)N)CC1] | HCl |
| 525 | 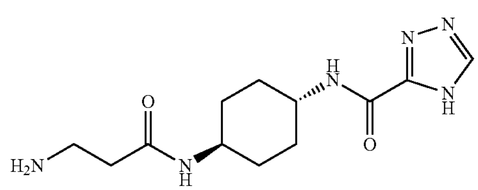 [SMILES: NCCC(=O)N[C@H]1CC[C@H](NC(=O)c2nnc[nH]2)CC1] | HCl |
| 527 | 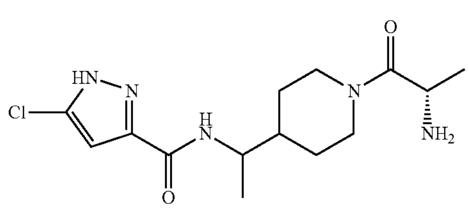 [SMILES: CC(NC(=O)c1cc(Cl)[nH]n1)C1CCN(C(=O)[C@H](C)N)CC1] | TFA |
| 528 | 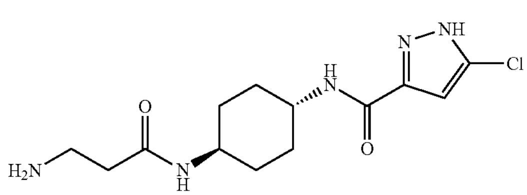 [SMILES: NCCC(=O)N[C@H]1CC[C@H](NC(=O)c2cc(Cl)[nH]n2)CC1] | TFA |

TABLE 1-continued

| Cpd. No. | Structure | Salt Form |
|---|---|---|
| 529 | 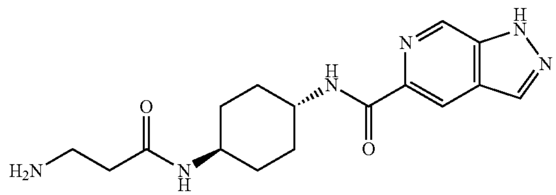 [SMILES: NCCC(=O)N[C@H]1CC[C@H](NC(=O)c2cc3cn[nH]c3cn2)CC1] | TFA |
| 530 | 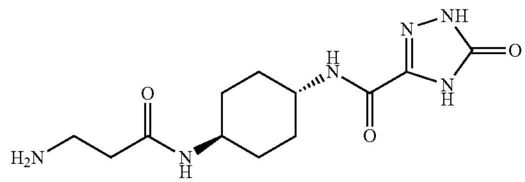 [SMILES: NCCC(=O)N[C@H]1CC[C@H](NC(=O)c2n[nH]c(=O)[nH]2)CC1] | TFA |
| 531 | 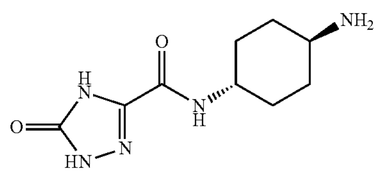 [SMILES: N[C@H]1CC[C@H](NC(=O)c2n[nH]c(=O)[nH]2)CC1] | TFA |
| 532 | 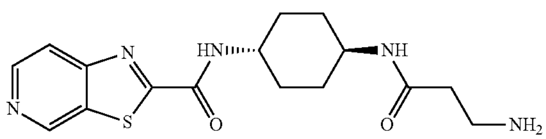 [SMILES: NCCC(=O)N[C@H]1CC[C@H](NC(=O)c2nc3ccncc3s2)CC1] | TFA |
| 533 | 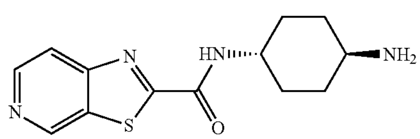 [SMILES: N[C@H]1CC[C@H](NC(=O)c2nc3ccncc3s2)CC1] | TFA |
| 534 | 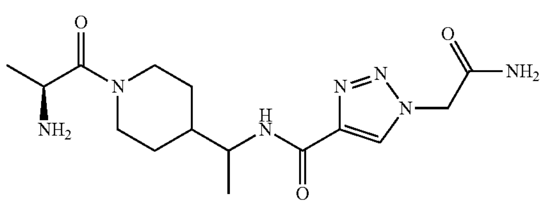 [SMILES: CC(NC(=O)c1cn(CC(N)=O)nn1)C1CCN(C(=O)[C@H](C)N)CC1] | None |
| 535 | 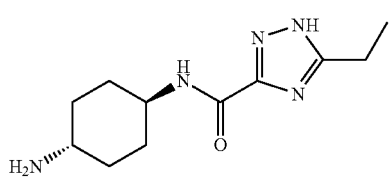 | None |
| 536 | 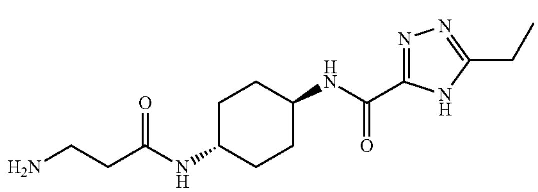 [SMILES: CCc1nnc(C(=O)N[C@H]2CC[C@H](NC(=O)CCN)CC2)[nH]1] | None |

TABLE 1-continued

| Cpd. No. | Structure | Salt Form |
|---|---|---|
| 537 | 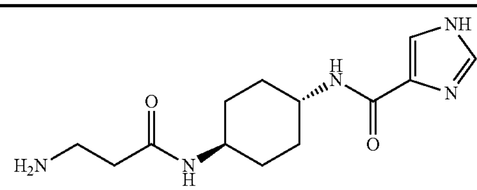 | None |
| 538 | 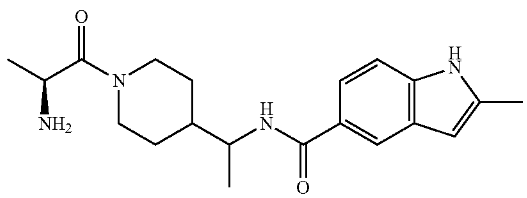 [SMILES: Cc1cc2cc(C(=O)NC(C)C3CCN(C(=O)[C@H](C)N)CC3)ccc2[nH]1] | TFA |
| 539 | 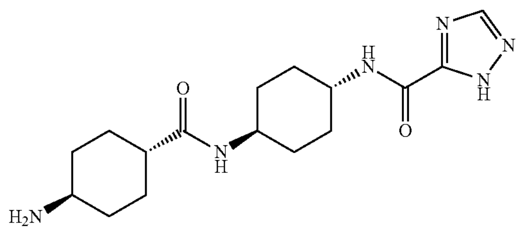 [SMILES: N[C@H]1CC[C@H](C(=O)N[C@H]2CC[C@H](NC(=O)c3ncn[nH]3)CC2)CC1] | None |
| 540 | 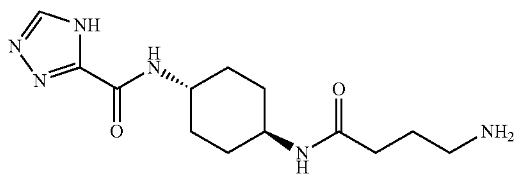 [SMILES: NCCCC(=O)N[C@H]1CC[C@H](NC(=O)c2nnc[nH]2)CC1] | TFA |
| 541 | | TFA |
| 541 | | None |
| 543 | 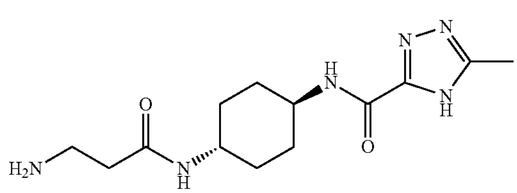 [SMILES: Cc1nnc(C(=O)N[C@H]2CC[C@H](NC(=O)CCN)CC2)[nH]1] | TFA |
| 544 | 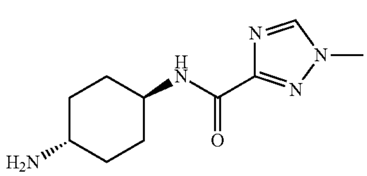 [SMILES: Cn1cnc(C(=O)N[C@H]2CC[C@H](N)CC2)n1] | TFA |

TABLE 1-continued

| Cpd. No. | Structure | Salt Form |
|---|---|---|
| 545 | 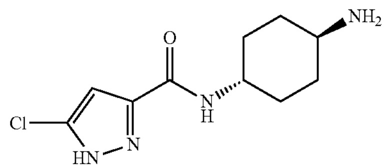 [SMILES: N[C@H]1CC[C@H](NC(=O)c2cc(Cl)[nH]n2)CC1] | TFA |
| 546 | 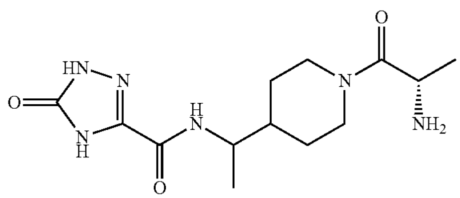 [SMILES: CC(NC(=O)c1n[nH]c(=O)[nH]1)C1CCN(C(=O)[C@H](C)N)CC1] | TFA |
| 547 | 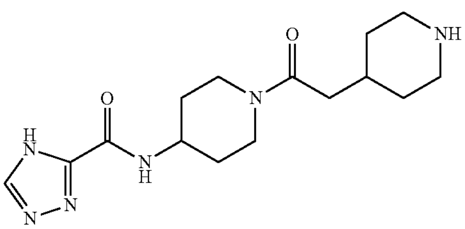 [SMILES: O=C(NC1CCN(C(=O)CC2CCNCC2)CC1)c1nnc[nH]1] | None |
| 548 | 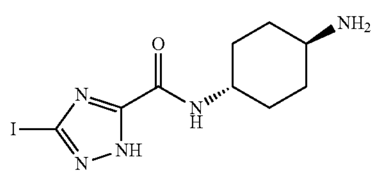 [SMILES: N[C@H]1CC[C@H](NC(=O)c2nc(I)n[nH]2)CC1] | TFA |
| 549 | 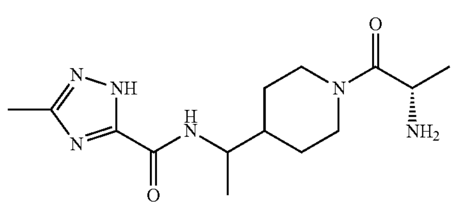 [SMILES: Cc1n[nH]c(C(=O)NC(C)C2CCN(C(=O)[C@H](C)N)CC2)n1] | TFA |
| 550 | 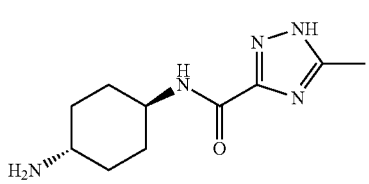 [SMILES: Cc1nc(C(=O)N[C@H]2CC[C@H](N)CC2)n[nH]1] | TFA |
| 551 | 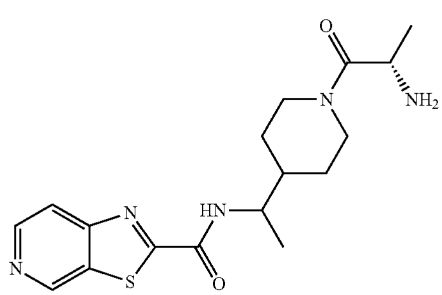 [SMILES: CC(NC(=O)c1nc2ccncc2s1)C1CCN(C(=O)[C@H](C)N)CC1] | TFA |

TABLE 1-continued

| Cpd. No. | Structure | Salt Form |
|---|---|---|
| 552 | 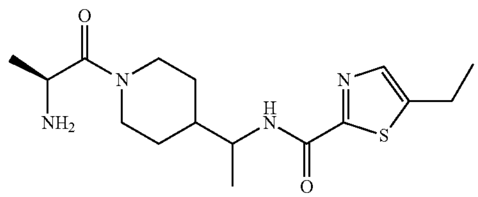 [SMILES: CCc1cnc(C(=O)NC(C)C2CCN(C(=O)[C@H](C)N)CC2)s1] | TFA |
| 553 | 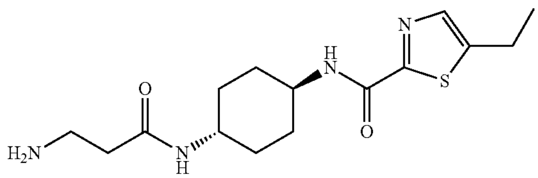 [SMILES: CCc1cnc(C(=O)N[C@H]2CC[C@H](NC(=O)CCN)CC2)s1] | TFA |
| 554 | 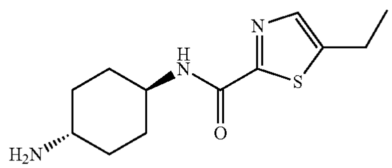 [SMILES: CCc1cnc(C(=O)N[C@H]2CC[C@H](N)CC2)s1] | TFA |
| 555 | 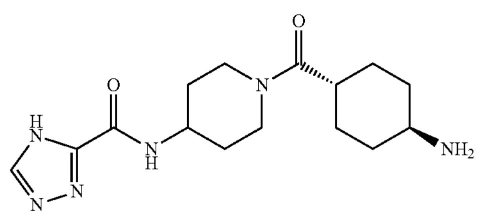 [SMILES: N[C@H]1CC[C@H](C(=O)N2CCC(NC(=O)c3nnc[nH]3)CC2)CC1] | TFA |
| 556 | 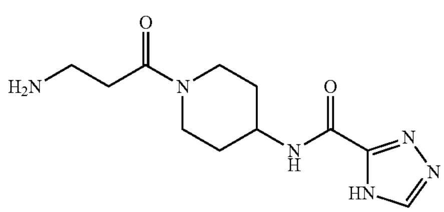 [SMILES: NCCC(=O)N1CCC(NC(=O)c2nnc[nH]2)CC1] | TFA |
| 557 | 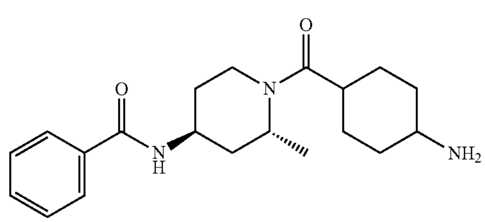 [SMILES: C[C@@H]1C[C@@H](NC(=O)c2ccccc2)CCN1C(=O)C1CCC(N)CC1] | HCl |
| 558 | 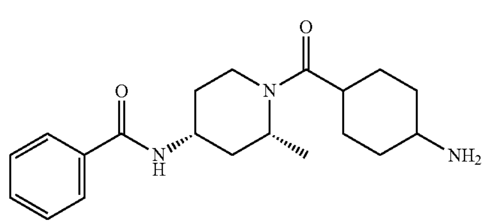 [SMILES: C[C@@H]1C[C@H](NC(=O)c2ccccc2)CCN1C(=O)C1CCC(N)CC1] | HCl |

TABLE 1-continued

| Cpd. No. | Structure | Salt Form |
|---|---|---|
| 559 | 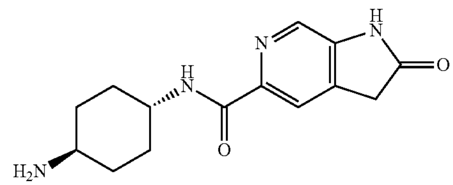 [SMILES: N[C@H]1CC[C@H](NC(=O)c2cc3c(cn2)NC(=O)C3)CC1] | HCl |
| 560 | 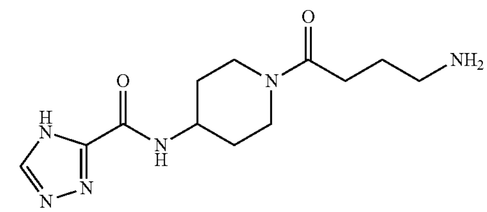 [SMILES: NCCCC(=O)N1CCC(NC(=O)c2nnc[nH]2)CC1] | TFA |
| 561 | 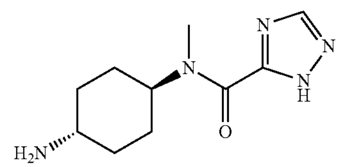 [SMILES: CN(C(=O)c1ncn[nH]1)[C@H]1CC[C@H](N)CC1] | TFA |
| 562 | 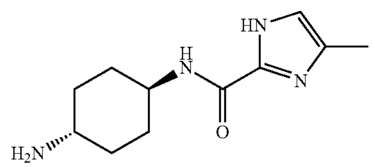 [SMILES: Cc1c[nH]c(C(=O)N[C@H]2CC[C@H](N)CC2)n1] | TFA |
| 563 | 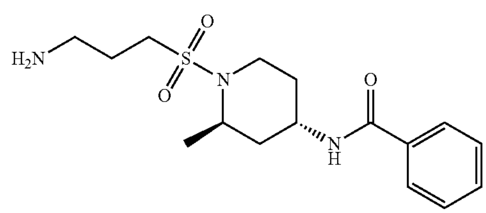 [SMILES: C[C@@H]1C[C@@H](NC(=O)c2ccccc2)CCN1S(=O)(=O)CCCN] | HCl |
| 564 | 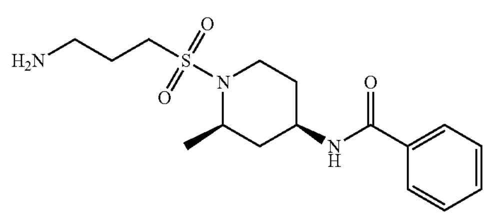 [SMILES: C[C@@H]1C[C@H](NC(=O)c2ccccc2)CCN1S(=O)(=O)CCCN] | HCl |
| 565 | 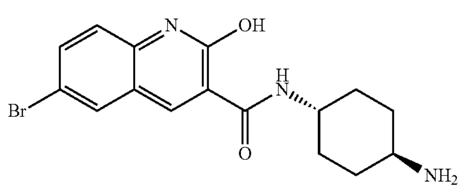 [SMILES: N[C@H]1CC[C@H](NC(=O)c2cc3cc(Br)ccc3nc2O)CC1] | TFA |
| 566 | 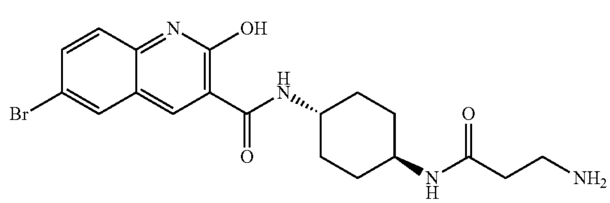 [SMILES: NCCC(=O)N[C@H]1CC[C@H](NC(=O)c2cc3cc(Br)ccc3nc2O)CC1] | TFA |

TABLE 1-continued

| Cpd. No. | Structure | Salt Form |
|---|---|---|
| 567 | 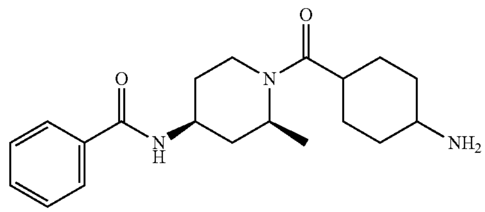 [SMILES: C[C@H]1C[C@@H](NC(=O)c2ccccc2)CCN1C(=O)C1CCC(N)CC1] | HCl |
| 568 | 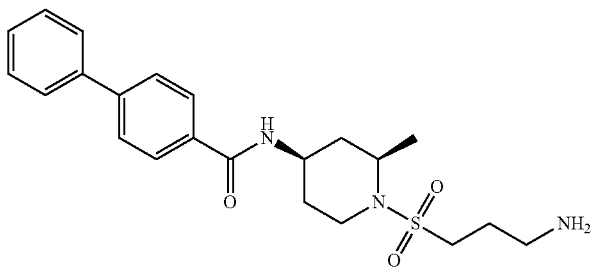 [SMILES: C[C@@H]1C[C@H](NC(=O)c2ccc(-c3ccccc3)cc2)CCN1S(=O)(=O)CCCN] | HCl |
| 569 | 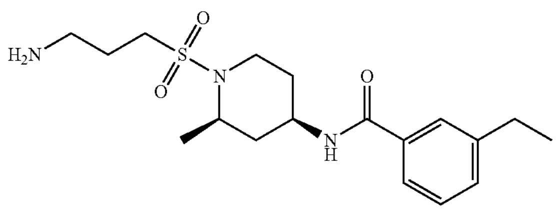 [SMILES: CCc1cccc(C(=O)N[C@@H]2CCN(S(=O)(=O)CCCN)[C@H](C)C2)c1] | HCl |
| 570 | 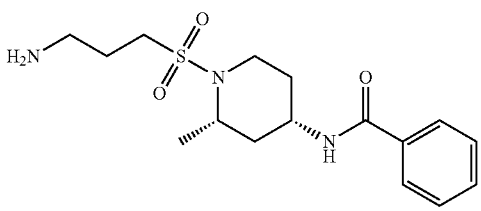 [SMILES: C[C@H]1C[C@@H](NC(=O)c2ccccc2)CCN1S(=O)(=O)CCCN] | HCl |
| 571 | 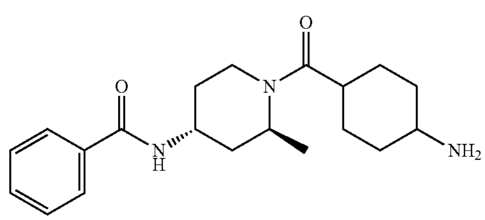 [SMILES: C[C@H]1C[C@H](NC(=O)c2ccccc2)CCN1C(=O)C1CCC(N)CC1] | HCl |
| 572 | 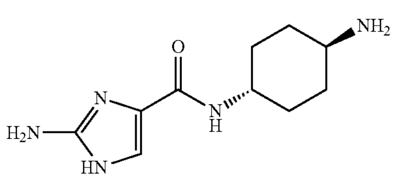 [SMILES: Nc1nc(C(=O)N[C@H]2CC[C@H](N)CC2)c[nH]1] | TFA |
| 573 | 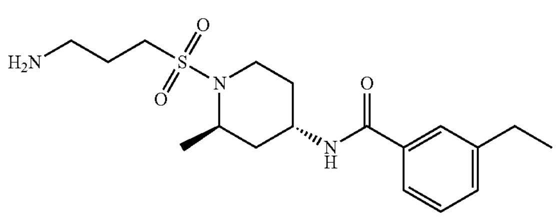 [SMILES: CCc1cccc(C(=O)N[C@H]2CCN(S(=O)(=O)CCCN)[C@H](C)C2)c1] | HCl |

TABLE 1-continued

| Cpd. No. | Structure | Salt Form |
|---|---|---|
| 574 | imidazo[1,2-a]pyrimidine-3-carboxamide linked to trans-4-aminocyclohexyl | TFA |

TABLE 3

| Cpd. No. | Structure | Salt Form |
|---|---|---|
| 575 | 4-aminocyclohexyl-sulfonyl-azabicyclic-NH-C(O)-(2-oxoindoline-5-yl) | TFA |
| 576 | 4-aminopiperidinyl-sulfonyl-azabicyclic-NH-C(O)-(6-fluoro-2-oxoindoline-5-yl) | None |
| 577 | (1-methylpiperidin-4-yl)methyl-sulfonyl-azabicyclic-NH-C(O)-(2-oxoindoline-5-yl) | TFA |
| 578 | 4-aminopiperidinyl-sulfonyl-azabicyclic-NH-C(O)-(2-oxoindoline-5-yl) | TFA |
| 579 | 4-aminopiperidinyl-sulfonyl-azabicyclic-NH-C(O)-(6-chloro-2-oxoindoline-5-yl) | HCl |

TABLE 3-continued

| Cpd. No. | Structure | Salt Form |
|---|---|---|
| 580 | 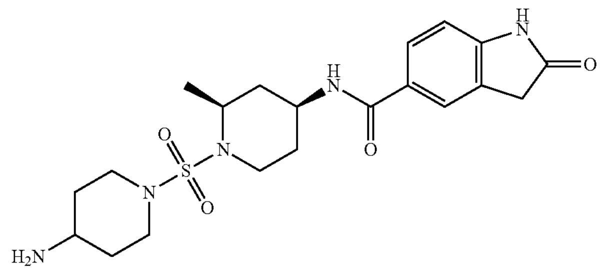 [SMILES: C[C@H]1C[C@@H](NC(=O)c2ccc3c(c2)CC(=O)N3)CCN1S(=O)(=O)N1CCC(N)CC1] | None |
| 581 | 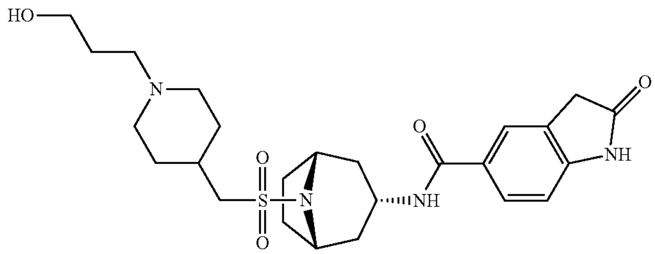 [SMILES: O=C1Cc2cc(C(=O)N[C@H]3C[C@H]4CC[C@@H](C3)N4S(=O)(=O)CC3CCN(CCCO)CC3)ccc2N1] | None |
| 582 | 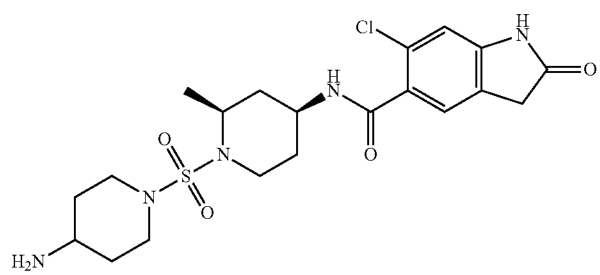 [SMILES: C[C@H]1C[C@@H](NC(=O)c2cc3c(cc2Cl)NC(=O)C3)CCN1S(=O)(=O)N1CCC(N)CC1] | HCl |
| 583 | 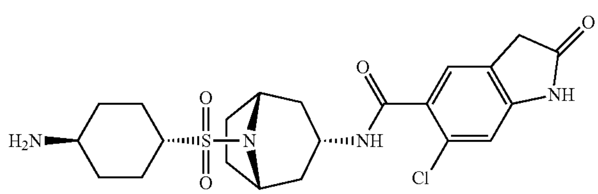 [SMILES: N[C@H]1CC[C@H](S(=O)(=O)N2[C@@H]3CC[C@H]2C[C@@H](NC(=O)c2cc4c(cc2Cl)NC(=O)C4)C3)CC1] | TFA |
| 584 | 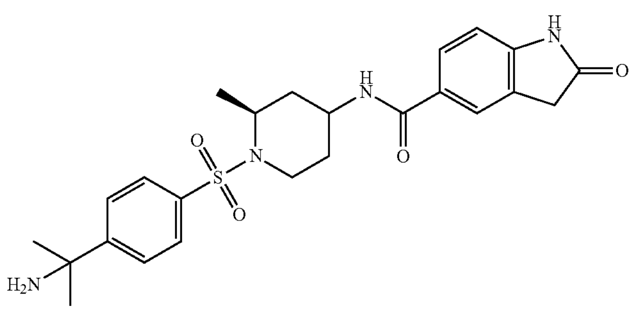 [SMILES: C[C@H]1CC(NC(=O)c2ccc3c(c2)CC(=O)N3)CCN1S(=O)(=O)c1ccc(C(C)(C)N)cc1] | TFA |
| 585 | 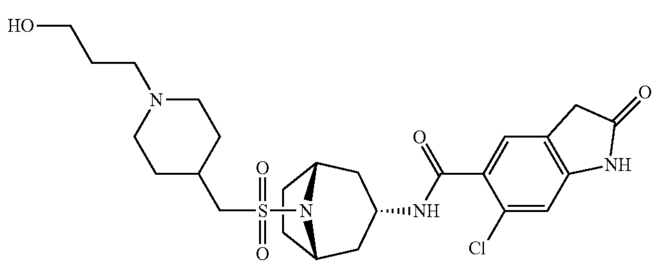 [SMILES: O=C1Cc2cc(C(=O)N[C@H]3C[C@H]4CC[C@@H](C3)N4S(=O)(=O)CC3CCN(CCCO)CC3)c(Cl)cc2N1] | TFA |

TABLE 3-continued

| Cpd. No. | Structure | Salt Form |
|---|---|---|
| 586 | 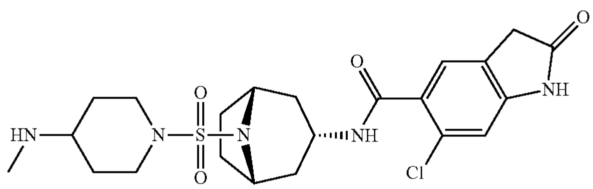 [SMILES: CNC1CCN(S(=O)(=O)N2[C@@H]3CC[C@H]2C[C@@H](NC(=O)c2cc4c(cc2Cl)NC(=O)C4)C3)CC1] | HCl |
| 587 | 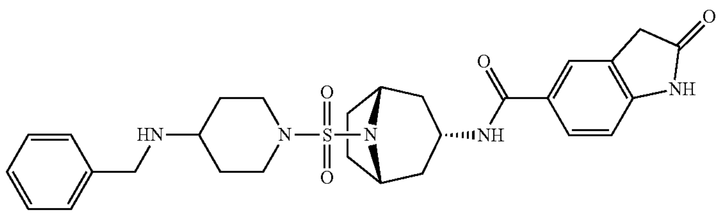 [SMILES: O=C1Cc2cc(C(=O)N[C@H]3C[C@H]4CC[C@@H](C3)N4S(=O)(=O)N3CCC(NCc4ccccc4)CC3)ccc2N1] | TFA |
| 588 | 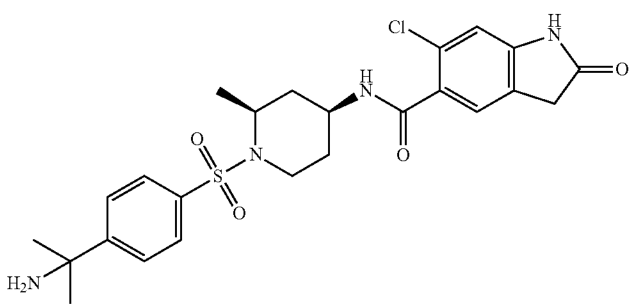 [SMILES: C[C@H]1C[C@@H](NC(=O)c2cc3c(cc2Cl)NC(=O)C3)CCN1S(=O)(=O)c1ccc(C(C)(C)N)cc1] | TFA |
| 589 | 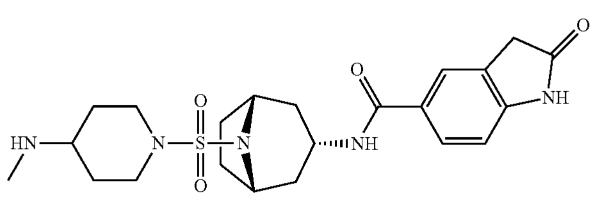 [SMILES: CNC1CCN(S(=O)(=O)N2[C@@H]3CC[C@H]2C[C@@H](NC(=O)c2ccc4c(c2)CC(=O)N4)C3)CC1] | HCl |
| 590 | 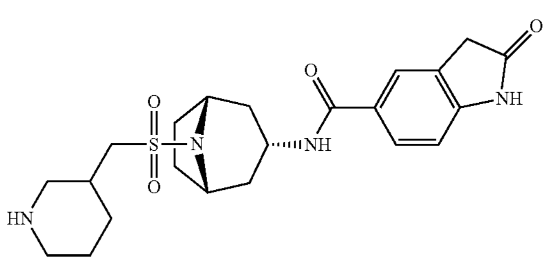 [SMILES: O=C1Cc2cc(C(=O)N[C@H]3C[C@H]4CC[C@@H](C3)N4S(=O)(=O)CC3CCCNC3)ccc2N1] | None |
| 591 | 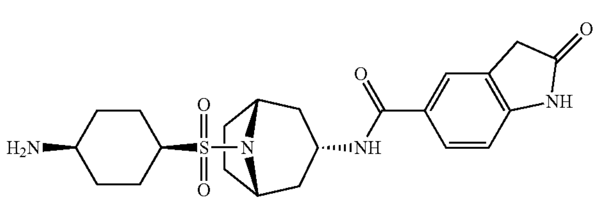 [SMILES: N[C@H]1CC[C@@H](S(=O)(=O)N2[C@@H]3CC[C@H]2C[C@@H](NC(=O)c2ccc4c(c2)CC(=O)N4)C3)CC1] | TFA |

| Cpd. No. | Structure | Salt Form |
|---|---|---|
| 592 | 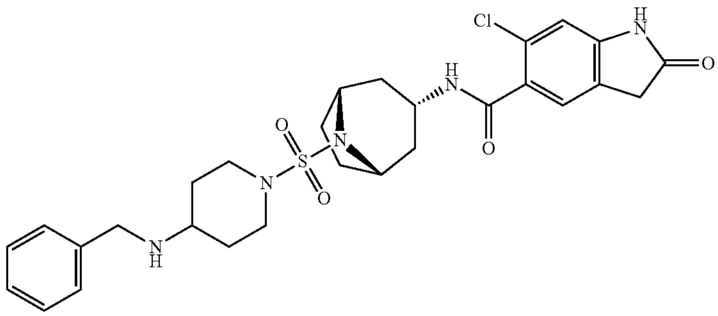 [SMILES: O=C1Cc2cc(C(=O)N[C@H]3C[C@H]4CC[C@@H](C3)N4S(=O)(=O)N3CCC(NCc4ccccc4)CC3)c(Cl)cc2N1] | TFA |
| 593 | 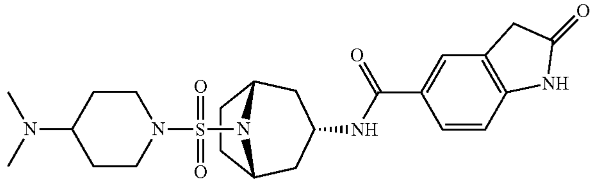 | None |
| 594 | 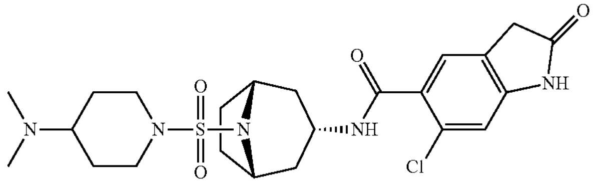 [SMILES: CN(C)C1CCN(S(=O)(=O)N2[C@@H]3CC[C@H]2C[C@@H](NC(=O)c2cc4c(cc2Cl)NC(=O)C4)C3)CC1] | None |
| 595 | 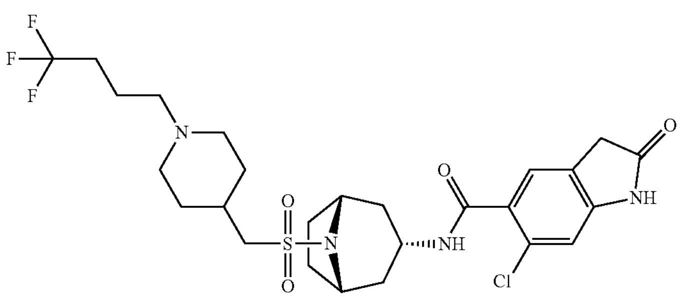 [SMILES: O=C1Cc2cc(C(=O)N[C@H]3C[C@H]4CC[C@@H](C3)N4S(=O)(=O)CC3CCN(CCCC(F)(F)F)CC3)c(Cl)cc2N1] | None |
| 596 | 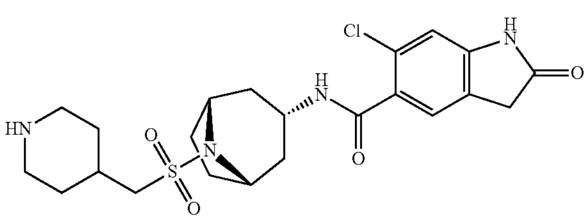 [SMILES: O=C1Cc2cc(C(=O)N[C@H]3C[C@H]4CC[C@@H](C3)N4S(=O)(=O)CC3CCNCC3)c(Cl)cc2N1] | TFA |
| 597 | 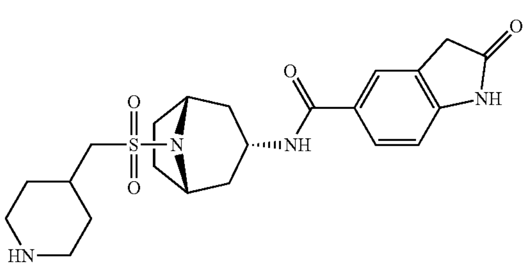 [SMILES: O=C1Cc2cc(C(=O)N[C@H]3C[C@H]4CC[C@@H](C3)N4S(=O)(=O)CC3CCNCC3)ccc2N1] | HCl |

TABLE 3-continued

| Cpd. No. | Structure | Salt Form |
|---|---|---|
| 598 | 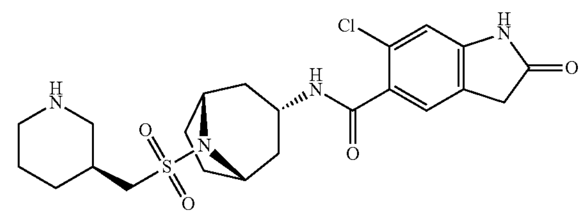 [SMILES: O=C1Cc2cc(C(=O)N[C@H]3C[C@H]4CC[C@@H](C3)N4S(=O)(=O)C[C@H]3CCCNC3)c(Cl)cc2N1] | TFA |
| 599 | 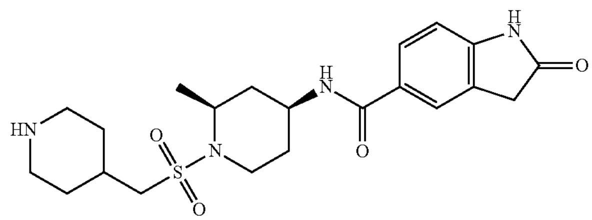 [SMILES: C[C@H]1C[C@@H](NC(=O)c2ccc3c(c2)CC(=O)N3)CCN1S(=O)(=O)CC1CCNCC1] | TFA |
| 600 | 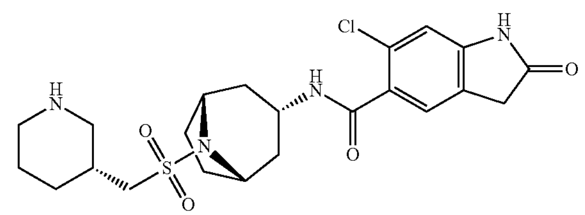 [SMILES: O=C1Cc2cc(C(=O)N[C@H]3C[C@H]4CC[C@@H](C3)N4S(=O)(=O)C[C@@H]3CCCNC3)c(Cl)cc2N1] | TFA |
| 601 | 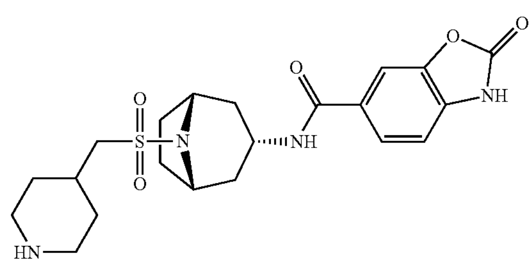 [SMILES: O=C(N[C@H]1C[C@H]2CC[C@@H](C1)N2S(=O)(=O)CC1CCNCC1)c1ccc2[nH]c(=O)oc2c1] | HCl |
| 602 | 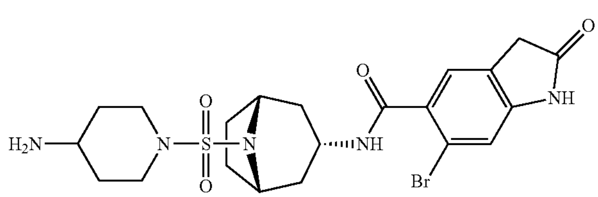 [SMILES: NC1CCN(S(=O)(=O)N2[C@@H]3CC[C@H]2C[C@@H](NC(=O)c2cc4c(cc2Br)NC(=O)C4)C3)CC1] | None |
| 603 | 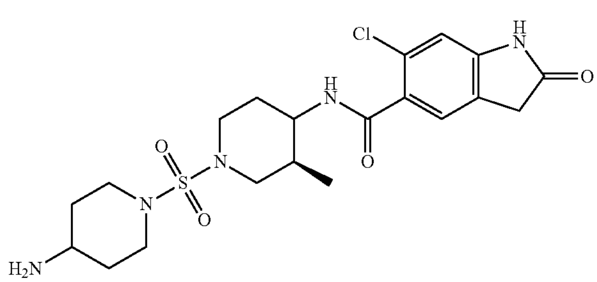 [SMILES: C[C@H]1CN(S(=O)(=O)N2CCC(N)CC2)CCC1NC(=O)c1cc2c(cc1Cl)NC(=O)C2] | TFA |

TABLE 3-continued

| Cpd. No. | Structure | Salt Form |
|---|---|---|
| 604 | 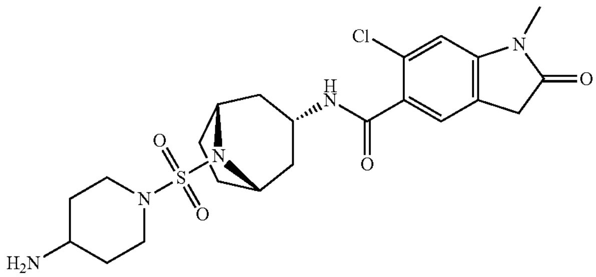 [SMILES: CN1C(=O)Cc2cc(C(=O)N[C@H]3C[C@H]4CC[C@@H](C3)N4S(=O)(=O)N3CCC(N)CC3)c(Cl)cc21] | TFA |
| 605 | 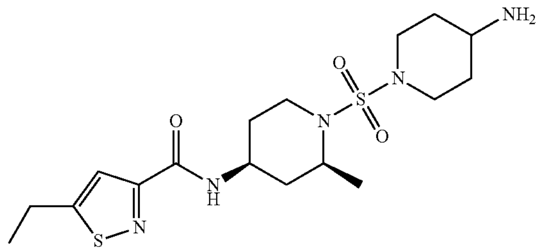 [SMILES: CCc1cc(C(=O)N[C@H]2CCN(S(=O)(=O)N3CCC(N)CC3)[C@@H](C)C2)ns1] | HCl |
| 606 | 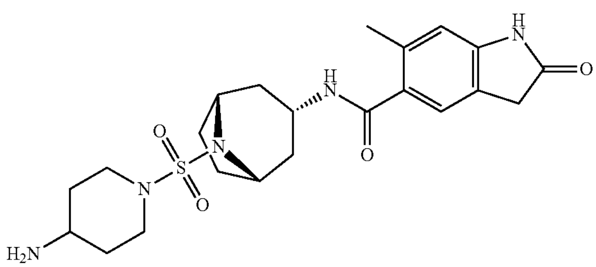 [SMILES: Cc1cc2c(cc1C(=O)N[C@H]1C[C@H]3CC[C@@H](C1)N3S(=O)(=O)N1CCC(N)CC1)CC(=O)N2] | None |
| 607 | 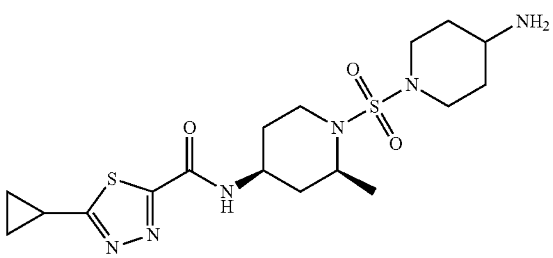 [SMILES: C[C@H]1C[C@@H](NC(=O)c2nnc(C3CC3)s2)CCN1S(=O)(=O)N1CCC(N)CC1] | HCl |
| 608 | 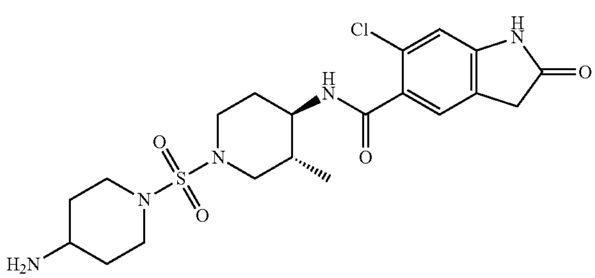 [SMILES: C[C@@H]1CN(S(=O)(=O)N2CCC(N)CC2)CC[C@H]1NC(=O)c1cc2c(cc1Cl)NC(=O)C2] | TFA |
| 609 | 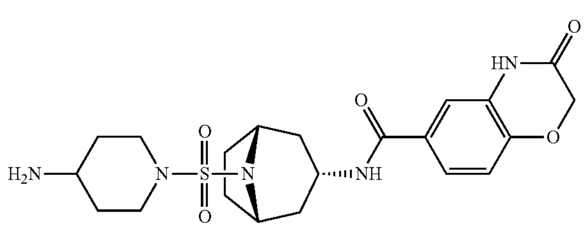 [SMILES: NC1CCN(S(=O)(=O)N2[C@@H]3CC[C@H]2C[C@@H](NC(=O)c2ccc4c(c2)NC(=O)CO4)C3)CC1] | HCl |

TABLE 3-continued

| Cpd. No. | Structure | Salt Form |
|---|---|---|
| 610 | 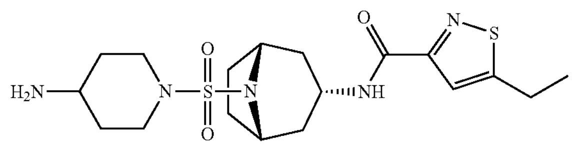 [SMILES: CCc1cc(C(=O)N[C@H]2C[C@H]3CC[C@@H](C2)N3S(=O)(=O)N2CCC(N)CC2)ns1] | HCl |
| 611 | 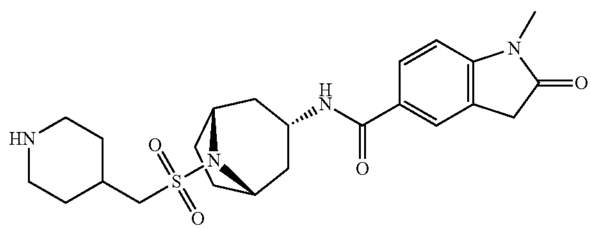 [SMILES: CN1C(=O)Cc2cc(C(=O)N[C@H]3C[C@H]4CC[C@@H](C3)N4S(=O)(=O)CC3CCNCC3)ccc21] | TFA |
| 612 | 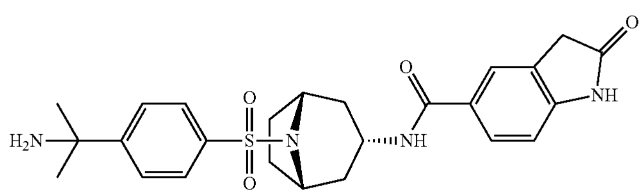 [SMILES: CC(C)(N)c1ccc(S(=O)(=O)N2[C@@H]3CC[C@H]2C[C@@H](NC(=O)c2ccc4c(c2)CC(=O)N4)C3)cc1] | TFA |
| 613 | 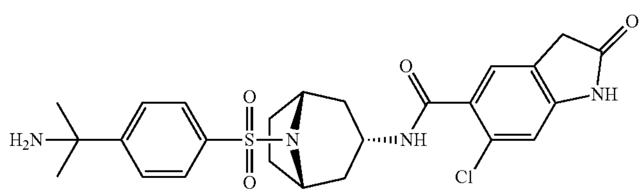 [SMILES: CC(C)(N)c1ccc(S(=O)(=O)N2[C@@H]3CC[C@H]2C[C@@H](NC(=O)c2cc4c(cc2Cl)NC(=O)C4)C3)cc1] | TFA |
| 614 | 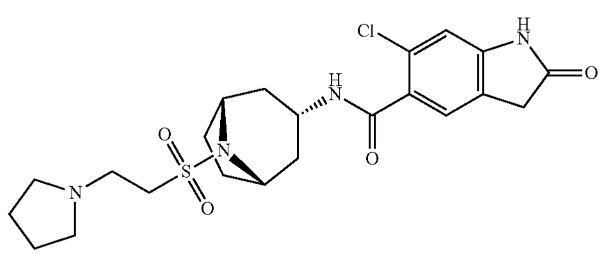 [SMILES: O=C1Cc2cc(C(=O)N[C@H]3C[C@H]4CC[C@@H](C3)N4S(=O)(=O)CCN3CCCC3)c(Cl)cc2N1] | None |
| 615 | 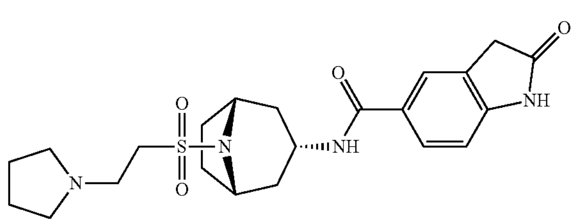 [SMILES: O=C1Cc2cc(C(=O)N[C@H]3C[C@H]4CC[C@@H](C3)N4S(=O)(=O)CCN3CCCC3)ccc2N1] | None |
| 616 | 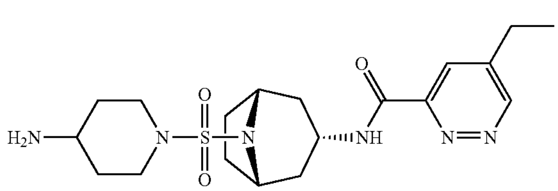 [SMILES: CCc1cnnc(C(=O)N[C@H]2C[C@H]3CC[C@@H](C2)N3S(=O)(=O)N2CCC(N)CC2)c1] | TFA |

TABLE 3-continued

| Cpd. No. | Structure | Salt Form |
|---|---|---|
| 617 | 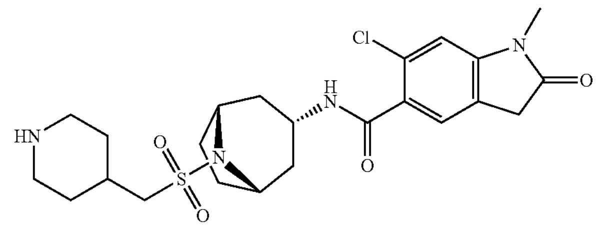 [SMILES: CN1C(=O)Cc2cc(C(=O)N[C@H]3C[C@H]4CC[C@@H](C3)N4S(=O)(=O)CC3CCNCC3)c(Cl)cc21] | TFA |
| 618 | 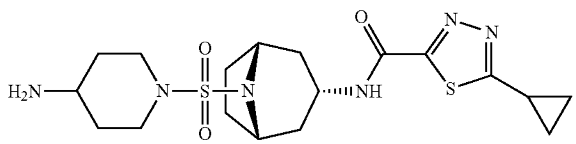 [SMILES: NC1CCN(S(=O)(=O)N2[C@@H]3CC[C@H]2C[C@@H](NC(=O)c2nnc(C4CC4)s2)C3)CC1] | HCl |
| 619 | 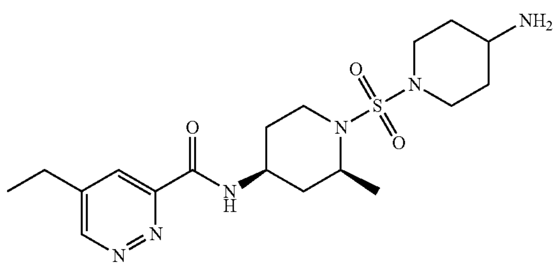 [SMILES: CCc1cnnc(C(=O)N[C@H]2CCN(S(=O)(=O)N3CCC(N)CC3)[C@@H](C)C2)c1] | TFA |
| 620 | 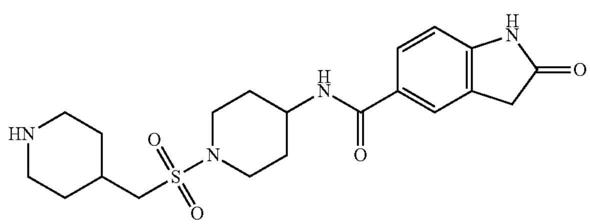 [SMILES: O=C1Cc2cc(C(=O)NC3CCN(S(=O)(=O)CC4CCNCC4)CC3)ccc2N1] | TFA |
| 621 | 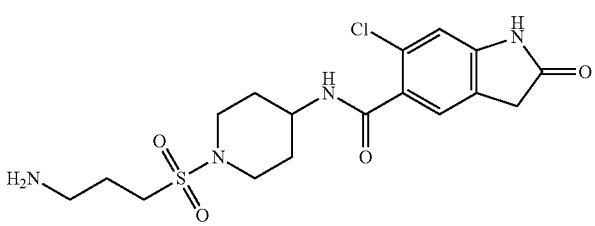 [SMILES: NCCCS(=O)(=O)N1CCC(NC(=O)c2cc3c(cc2Cl)NC(=O)C3)CC1] | TFA |
| 622 | 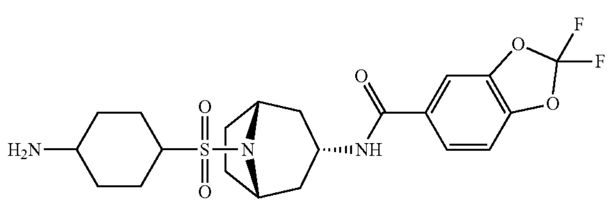 [SMILES: NC1CCC(S(=O)(=O)N2[C@@H]3CC[C@H]2C[C@@H](NC(=O)c2ccc4c(c2)OC(F)(F)O4)C3)CC1] | TFA |
| 623 | 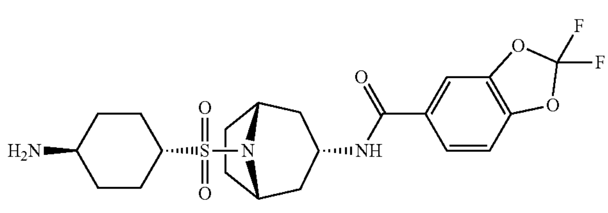 [SMILES: N[C@H]1CC[C@H](S(=O)(=O)N2[C@@H]3CC[C@H]2C[C@@H](NC(=O)c2ccc4c(c2)OC(F)(F)O4)C3)CC1] | None |

TABLE 3-continued

| Cpd. No. | Structure | Salt Form |
|---|---|---|
| 624 | 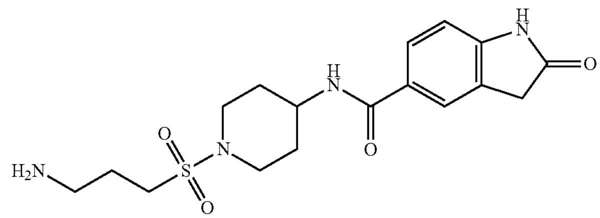 [SMILES: NCCCS(=O)(=O)N1CCC(NC(=O)c2ccc3c(c2)CC(=O)N3)CC1] | None |
| 625 | 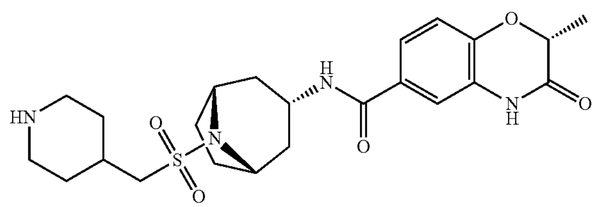 [SMILES: C[C@H]1Oc2ccc(C(=O)N[C@H]3C[C@H]4CC[C@@H](C3)N4S(=O)(=O)CC3CCNCC3)cc2NC1=O] | HCl |
| 626 | 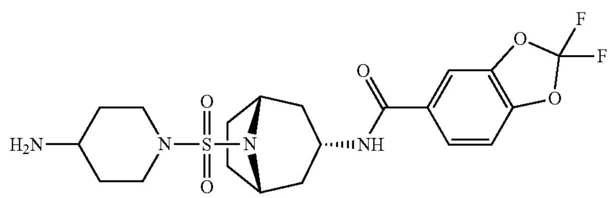 | HCl |
| 627 | 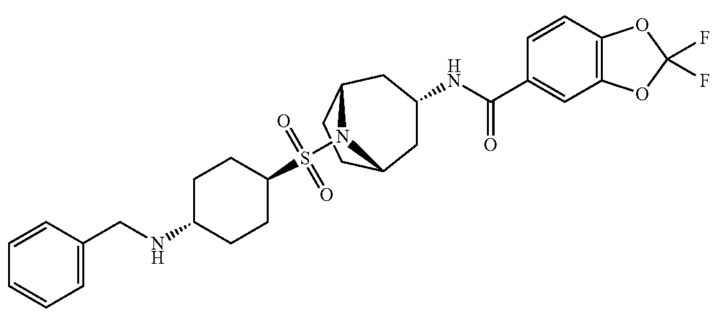 [SMILES: O=C(N[C@H]1C[C@H]2CC[C@@H](C1)N2S(=O)(=O)[C@H]1CC[C@H](NCc2ccccc2)CC1)c1ccc2c(c1)OC(F)(F)O2] | HCl |
| 628 | 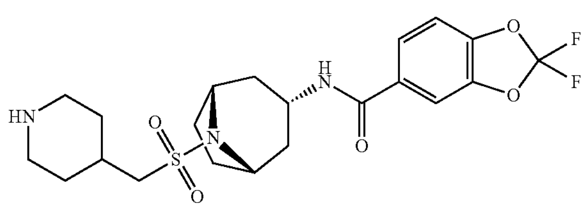 [SMILES: O=C(N[C@H]1C[C@H]2CC[C@@H](C1)N2S(=O)(=O)CC1CCNCC1)c1ccc2c(c1)OC(F)(F)O2] | HCl |
| 629 | 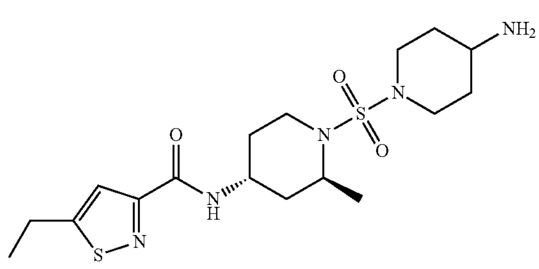 [SMILES: CCc1cc(C(=O)N[C@@H]2CCN(S(=O)(=O)N3CCC(N)CC3)[C@@H](C)C2)ns1] | None |

TABLE 3-continued

| Cpd. No. | Structure | Salt Form |
|---|---|---|
| 630 | 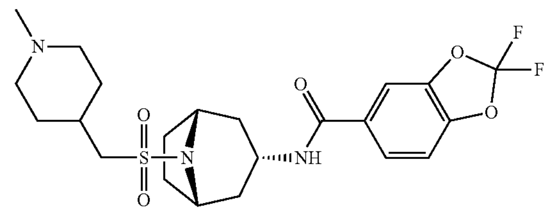 [SMILES: CN1CCC(CS(=O)(=O)N2[C@@H]3CC[C@H]2C[C@@H](NC(=O)c2ccc4c(c2)OC(F)(F)O4)C3)CC1] | None |
| 631 | 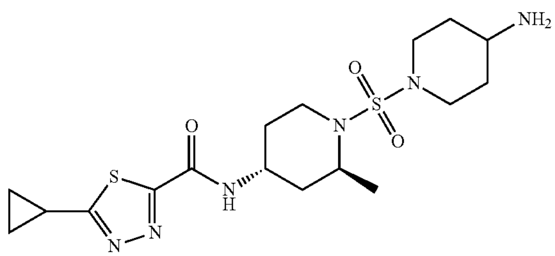 [SMILES: C[C@H]1C[C@H](NC(=O)c2nnc(C3CC3)s2)CCN1S(=O)(=O)N1CCC(N)CC1] | HCl |
| 632 | 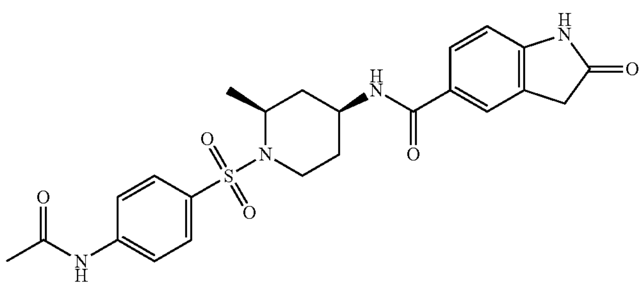 [SMILES: CC(=O)Nc1ccc(S(=O)(=O)N2CC[C@H](NC(=O)c3ccc4c(c3)CC(=O)N4)C[C@@H]2C)cc1] | None |
| 633 | 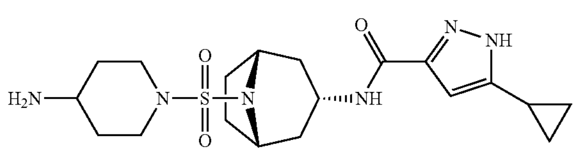 [SMILES: NC1CCN(S(=O)(=O)N2[C@@H]3CC[C@H]2C[C@@H](NC(=O)c2cc(C4CC4)[nH]n2)C3)CC1] | None |
| 634 | 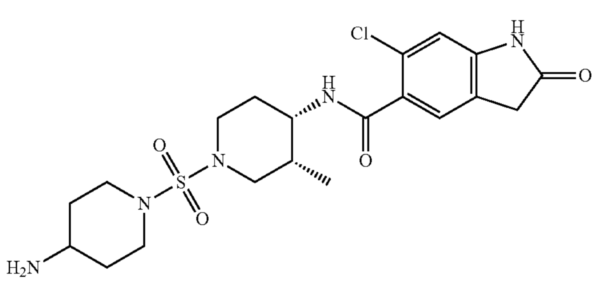 [SMILES: C[C@@H]1CN(S(=O)(=O)N2CCC(N)CC2)CC[C@@H]1NC(=O)c1cc2c(cc1Cl)NC(=O)C2] | None |
| 635 | 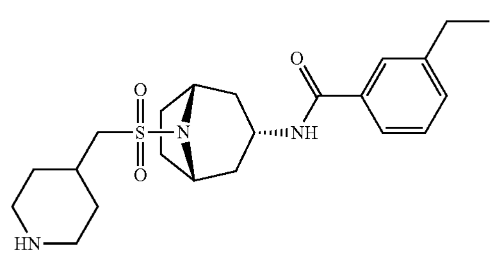 [SMILES: CCc1cccc(C(=O)N[C@H]2C[C@H]3CC[C@@H](C2)N3S(=O)(=O)CC2CCNCC2)c1] | HCl |

TABLE 3-continued

| Cpd. No. | Structure | Salt Form |
|---|---|---|
| 636 | 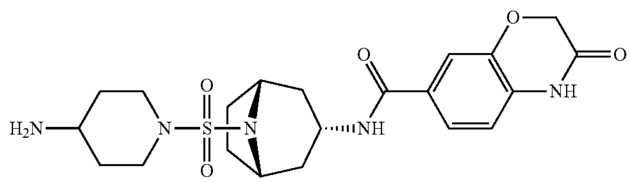 [SMILES: NC1CCN(S(=O)(=O)N2[C@@H]3CC[C@H]2C[C@@H](NC(=O)c2ccc4c(c2)OCC(=O)N4)C3)CC1] | HCl |
| 637 | 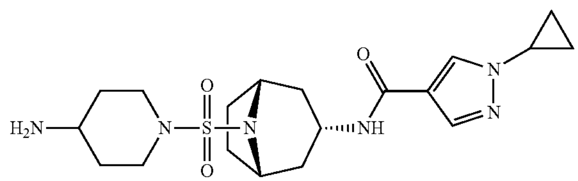 [SMILES: NC1CCN(S(=O)(=O)N2[C@@H]3CC[C@H]2C[C@@H](NC(=O)c2cnn(C4CC4)c2)C3)CC1] | None |
| 638 | 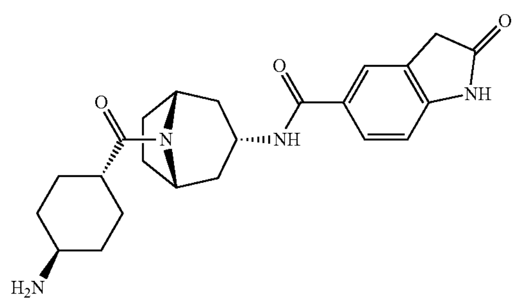 [SMILES: N[C@H]1CC[C@H](C(=O)N2[C@@H]3CC[C@H]2C[C@@H](NC(=O)c2ccc4c(c2)CC(=O)N4)C3)CC1] | TFA |
| 639 | 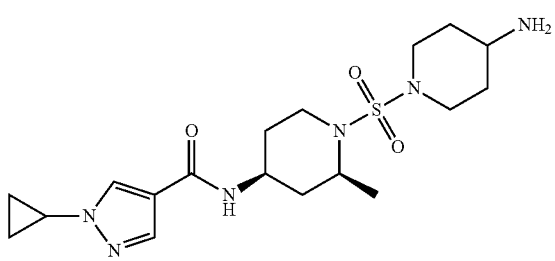 [SMILES: C[C@H]1C[C@@H](NC(=O)c2cnn(C3CC3)c2)CCN1S(=O)(=O)N1CCC(N)CC1] | None |
| 640 | 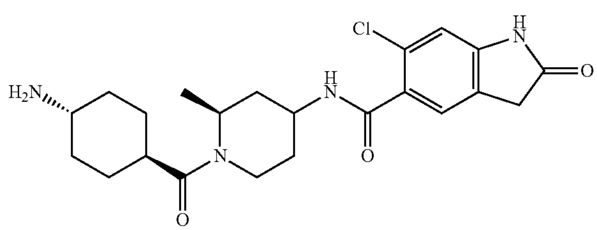 [SMILES: C[C@H]1CC(NC(=O)c2cc3c(cc2Cl)NC(=O)C3)CCN1C(=O)[C@H]1CC[C@H](N)CC1] | TFA |
| 641 | 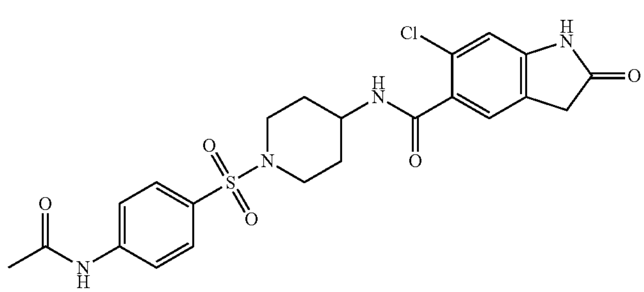 [SMILES: CC(=O)Nc1ccc(S(=O)(=O)N2CCC(NC(=O)c3cc4c(cc3Cl)NC(=O)C4)CC2)cc1] | None |

TABLE 3-continued

| Cpd. No. | Structure | Salt Form |
|---|---|---|
| 642 | 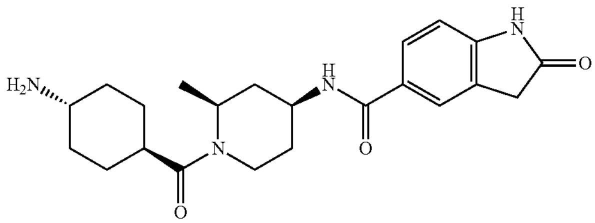 [SMILES: C[C@H]1C[C@@H](NC(=O)c2ccc3c(c2)CC(=O)N3)CCN1C(=O)[C@H]1CC[C@H](N)CC1] | HCl |
| 643 | 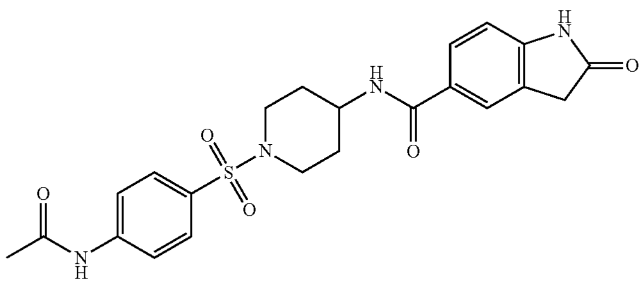 [SMILES: CC(=O)Nc1ccc(S(=O)(=O)N2CCC(NC(=O)c3ccc4c(c3)CC(=O)N4)CC2)cc1] | None |
| 644 | 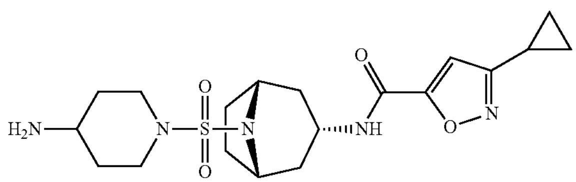 [SMILES: NC1CCN(S(=O)(=O)N2[C@@H]3CC[C@H]2C[C@@H](NC(=O)c2cc(C4CC4)no2)C3)CC1] | HCl |

TABLE 4

| Cpd. No. | Structure | Salt Form |
|---|---|---|
| 645 | 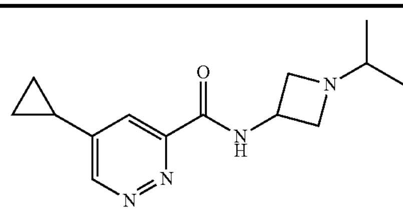 | None |
| 646 | 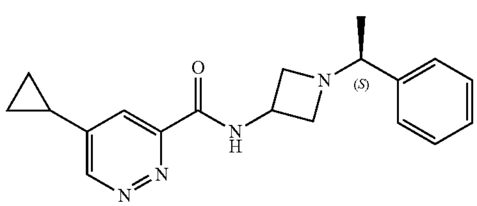 | None |
| 647 | 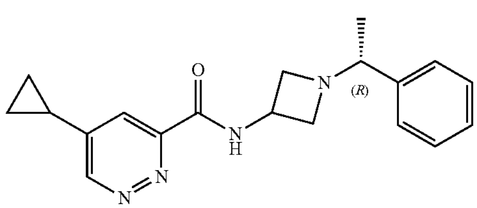 | None |

TABLE 4-continued

| Cpd. No. | Structure | Salt Form |
|---|---|---|
| 648 | (structure) | None |
| 649 | (structure) | None |
| 650 | (structure) | None |
| 651 | (structure) | None |
| 652 | (structure) | None |
| 657 | (structure) | None |
| 659 | (structure) | None |
| 660 | (structure) | None |

TABLE 4-continued

| Cpd. No. | Structure | Salt Form |
|---|---|---|
| 661 | 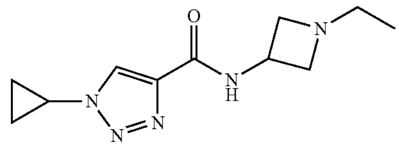 [SMILES: CCN1CC(NC(=O)c2cn(C3CC3)nn2)C1] | None |
| 662 | 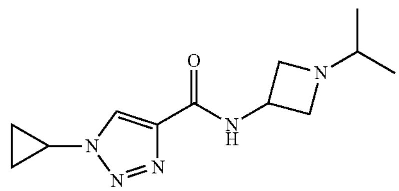 [SMILES: CC(C)N1CC(NC(=O)c2cn(C3CC3)nn2)C1] | None |
| 663 | 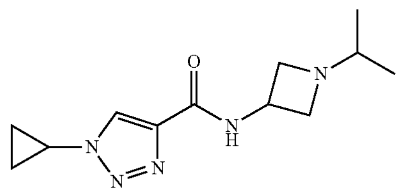 [SMILES: CC(C)N1CC(NC(=O)c2cn(C3CC3)nn2)C1] | None |
| 664 | 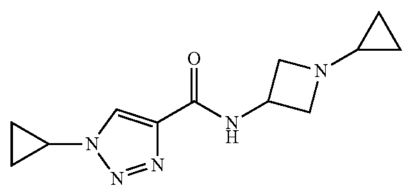 [SMILES: O=C(NC1CN(C2CC2)C1)c1cn(C2CC2)nn1] | None |
| 665 | 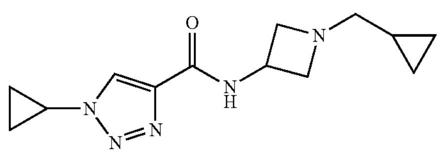 [SMILES: O=C(NC1CN(CC2CC2)C1)c1cn(C2CC2)nn1] | None |
| 666 | 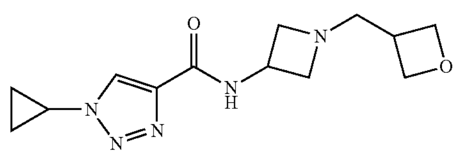 [SMILES: O=C(NC1CN(CC2COC2)C1)c1cn(C2CC2)nn1] | None |
| 667 | 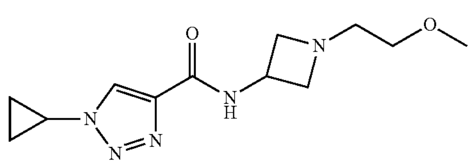 [SMILES: COCCN1CC(NC(=O)c2cn(C3CC3)nn2)C1] | None |
| 668 | 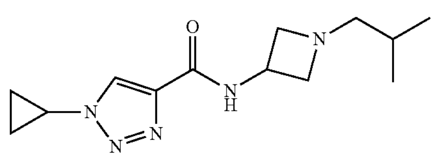 [SMILES: CC(C)CN1CC(NC(=O)c2cn(C3CC3)nn2)C1] | None |
| 669 | 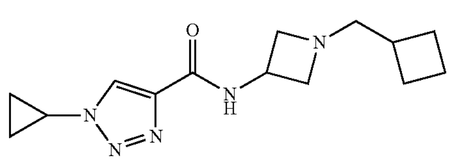 [SMILES: O=C(NC1CN(CC2CCC2)C1)c1cn(C2CC2)nn1] | None |

TABLE 4-continued

| Cpd. No. | Structure | Salt Form |
|---|---|---|
| 670 | 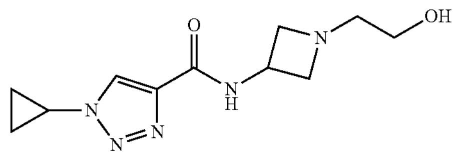 [SMILES: O=C(NC1CN(CCO)C1)c1cn(C2CC2)nn1] | None |
| 671 | 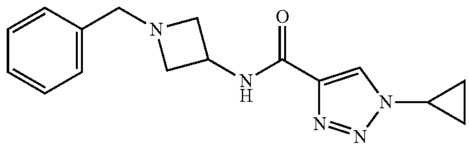 [SMILES: O=C(NC1CN(Cc2ccccc2)C1)c1cn(C2CC2)nn1] | None |
| 672 | 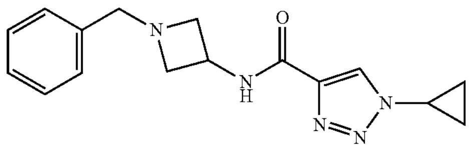 [SMILES: O=C(NC1CN(Cc2ccccc2)C1)c1cn(C2CC2)nn1] | None |
| 673 | 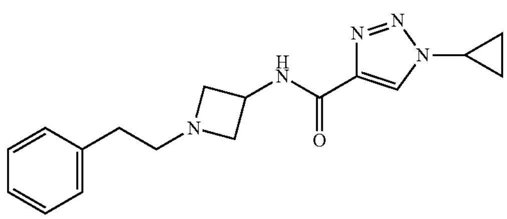 [SMILES: O=C(NC1CN(CCc2ccccc2)C1)c1cn(C2CC2)nn1] | None |
| 674 | 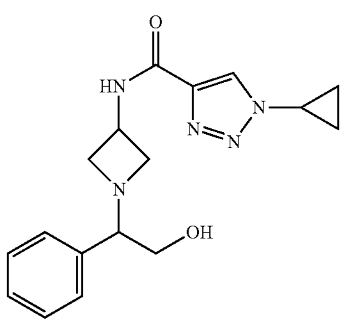 [SMILES: O=C(NC1CN(C(CO)c2ccccc2)C1)c1cn(C2CC2)nn1] | None |
| 675 | 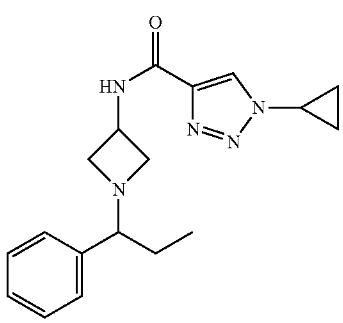 [SMILES: CCC(c1ccccc1)N1CC(NC(=O)c2cn(C3CC3)nn2)C1] | None |
| 676 | 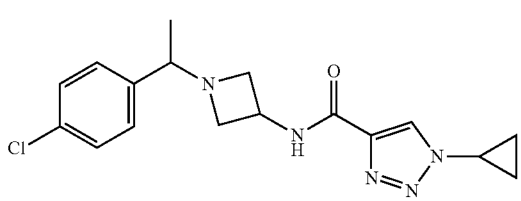 [SMILES: CC(c1ccc(Cl)cc1)N1CC(NC(=O)c2cn(C3CC3)nn2)C1] | None |

TABLE 4-continued

| Cpd. No. | Structure | Salt Form |
|---|---|---|
| 677 | 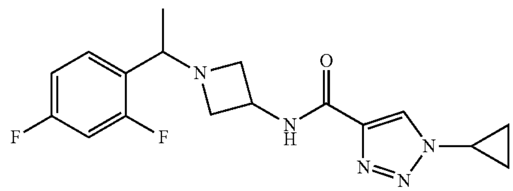 [SMILES: CC(c1ccc(F)cc1F)N1CC(NC(=O)c2cn(C3CC3)nn2)C1] | None |
| 678 | 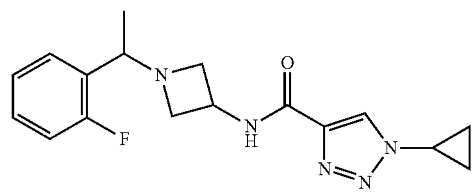 [SMILES: CC(c1ccccc1F)N1CC(NC(=O)c2cn(C3CC3)nn2)C1] | None |
| 679 | 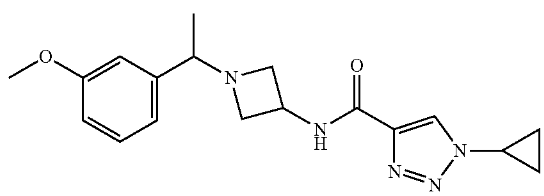 [SMILES: COc1cccc(C(C)N2CC(NC(=O)c3cn(C4CC4)nn3)C2)c1] | None |
| 680 | 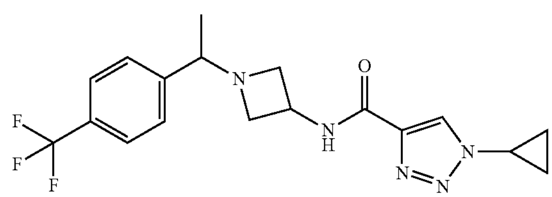 [SMILES: CC(c1ccc(C(F)(F)F)cc1)N1CC(NC(=O)c2cn(C3CC3)nn2)C1] | None |
| 681 | 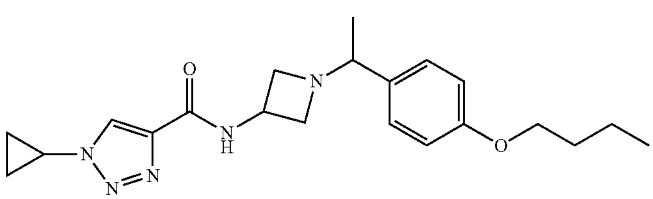 [SMILES: CCCCOc1ccc(C(C)N2CC(NC(=O)c3cn(C4CC4)nn3)C2)cc1] | None |
| 682 | 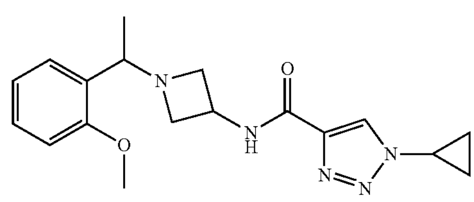 [SMILES: COc1ccccc1C(C)N1CC(NC(=O)c2cn(C3CC3)nn2)C1] | None |
| 683 | 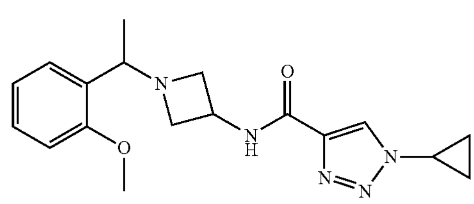 [SMILES: COc1ccccc1C(C)N1CC(NC(=O)c2cn(C3CC3)nn2)C1] | None |

TABLE 4-continued

| Cpd. No. | Structure | Salt Form |
|---|---|---|
| 684 | 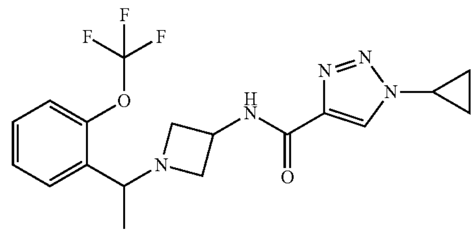 [SMILES: CC(c1ccccc1OC(F)(F)F)N1CC(NC(=O)c2cn(C3CC3)nn2)C1] | None |
| 685 | 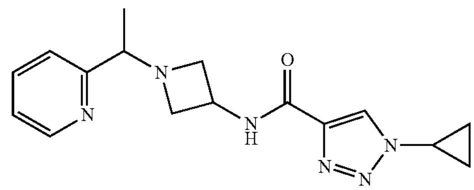 [SMILES: CC(c1ccccn1)N1CC(NC(=O)c2cn(C3CC3)nn2)C1] | None |
| 686 | 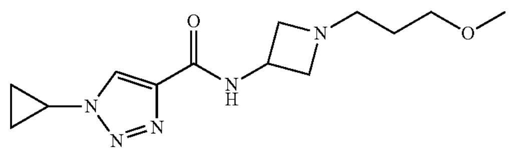 [SMILES: COCCCN1CC(NC(=O)c2cn(C3CC3)nn2)C1] | None |
| 687 | 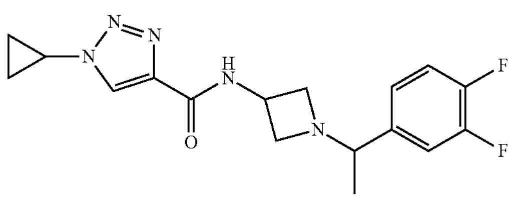 [SMILES: CC(c1ccc(F)c(F)c1)N1CC(NC(=O)c2cn(C3CC3)nn2)C1] | None |
| 688 | 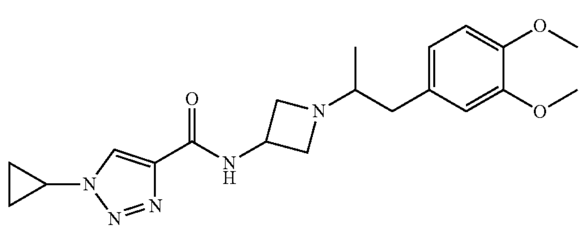 [SMILES: COc1ccc(CC(C)N2CC(NC(=O)c3cn(C4CC4)nn3)C2)cc1OC] | None |
| 689 | 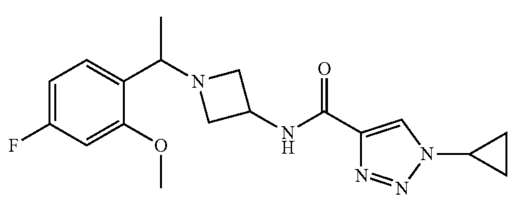 [SMILES: COc1cc(F)ccc1C(C)N1CC(NC(=O)c2cn(C3CC3)nn2)C1] | None |
| 690 | 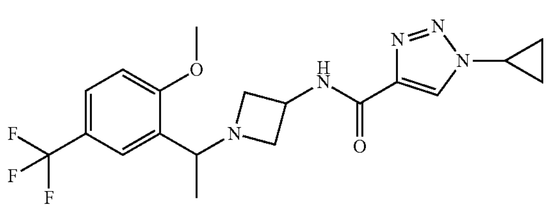 [SMILES: COc1ccc(C(F)(F)F)cc1C(C)N1CC(NC(=O)c2cn(C3CC3)nn2)C1] | None |

TABLE 4-continued

| Cpd. No. | Structure | Salt Form |
|---|---|---|
| 691 | 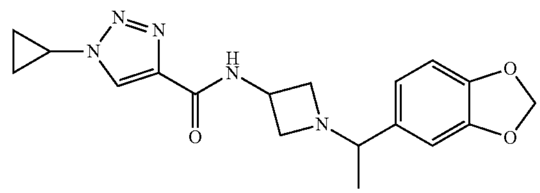 [SMILES: CC(c1ccc2c(c1)OCO2)N1CC(NC(=O)c2cn(C3CC3)nn2)C1] | None |
| 692 | 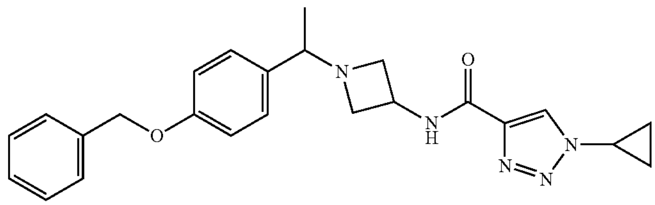 | None |
| 693 | 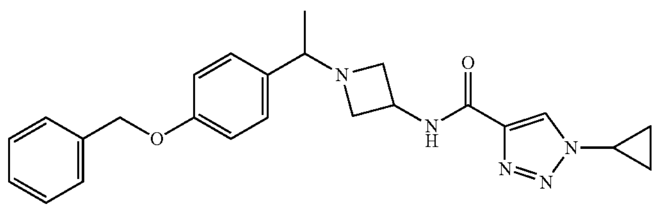 | None |
| 694 | 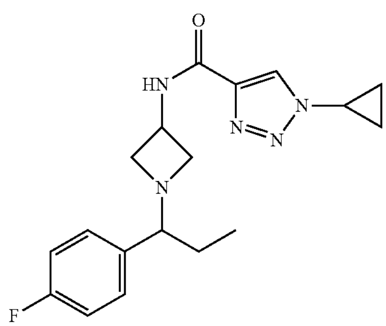 [SMILES: CCC(c1ccc(F)cc1)N1CC(NC(=O)c2cn(C3CC3)nn2)C1] | None |
| 695 | 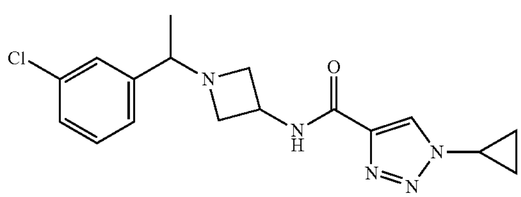 [SMILES: CC(c1cccc(Cl)c1)N1CC(NC(=O)c2cn(C3CC3)nn2)C1] | None |
| 696 | 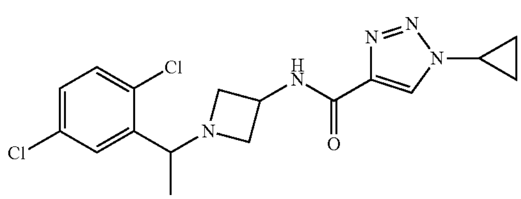 [SMILES: CC(c1cc(Cl)ccc1Cl)N1CC(NC(=O)c2cn(C3CC3)nn2)C1] | None |
| 697 | 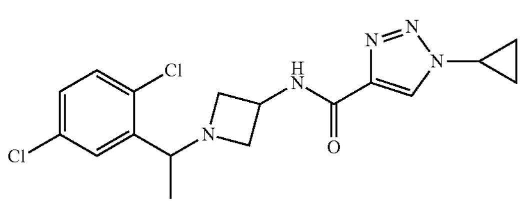 [SMILES: CC(c1cc(Cl)ccc1Cl)N1CC(NC(=O)c2cn(C3CC3)nn2)C1] | None |

TABLE 4-continued

| Cpd. No. | Structure | Salt Form |
|---|---|---|
| 698 | 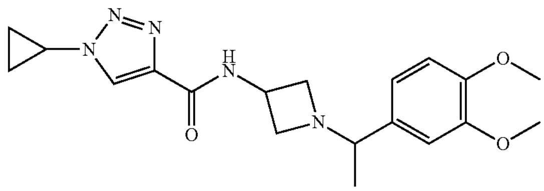 [SMILES: COc1ccc(C(C)N2CC(NC(=O)c3cn(C4CC4)nn3)C2)cc1OC] | None |
| 699 | 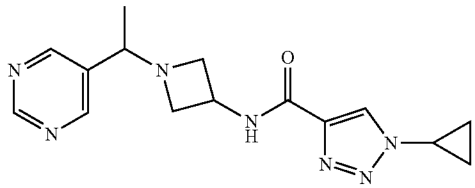 [SMILES: CC(c1cncnc1)N1CC(NC(=O)c2cn(C3CC3)nn2)C1] | None |
| 700 | 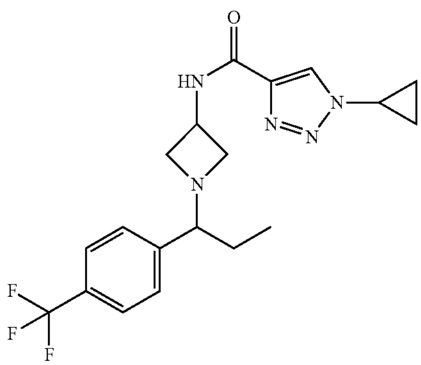 [SMILES: CCC(c1ccc(C(F)(F)F)cc1)N1CC(NC(=O)c2cn(C3CC3)nn2)C1] | None |
| 701 | 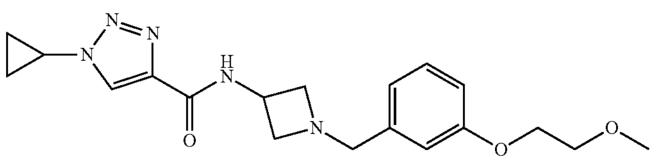 [SMILES: COCCOc1cccc(CN2CC(NC(=O)c3cn(C4CC4)nn3)C2)c1] | None |
| 702 | 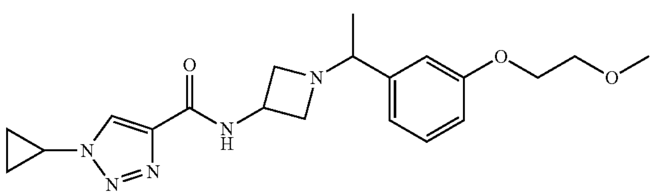 [SMILES: COCCOc1cccc(C(C)N2CC(NC(=O)c3cn(C4CC4)nn3)C2)c1] | None |
| 703 | 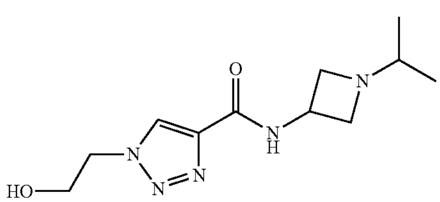 [SMILES: CC(C)N1CC(NC(=O)c2cn(CCO)nn2)C1] | None |
| 704 | 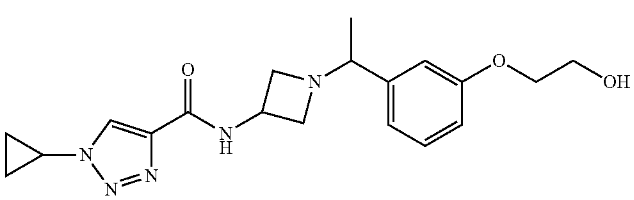 [SMILES: CC(c1cccc(OCCO)c1)N1CC(NC(=O)c2cn(C3CC3)nn2)C1] | None |

TABLE 4-continued

| Cpd. No. | Structure | Salt Form |
|---|---|---|
| 705 | 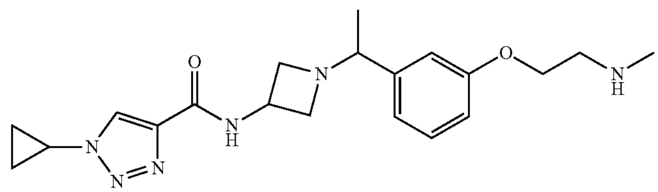 [SMILES: CNCCOc1cccc(C(C)N2CC(NC(=O)c3cn(C4CC4)nn3)C2)c1] | None |
| 706 | 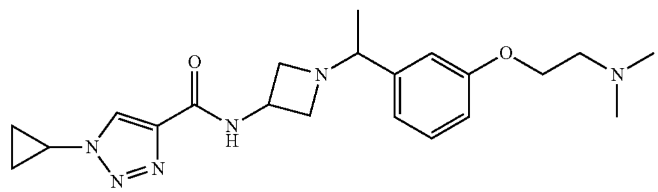 [SMILES: CC(c1cccc(OCCN(C)C)c1)N1CC(NC(=O)c2cn(C3CC3)nn2)C1] | None |
| 707 | 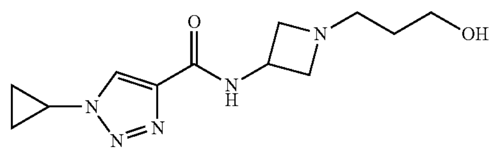 [SMILES: O=C(NC1CN(CCCO)C1)c1cn(C2CC2)nn1] | None |
| 708 | 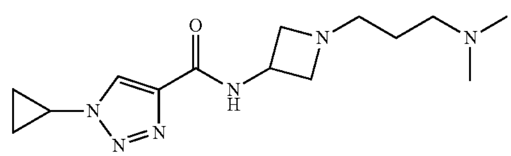 [SMILES: CN(C)CCCN1CC(NC(=O)c2cn(C3CC3)nn2)C1] | None |
| 709 | 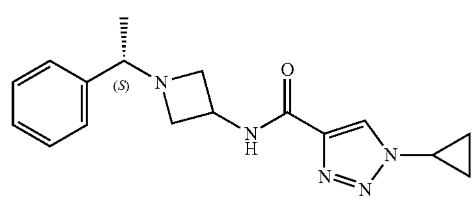 | None |
| 710 | 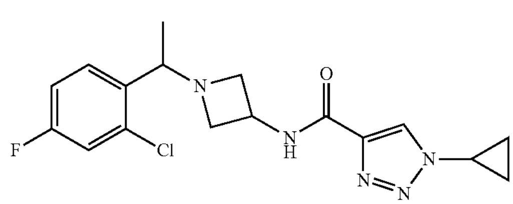 [SMILES: CC(c1ccc(F)cc1Cl)N1CC(NC(=O)c2cn(C3CC3)nn2)C1] | None |
| 711 | 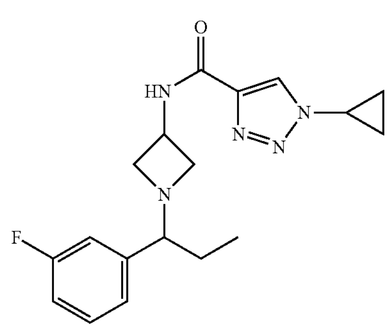 [SMILES: CCC(c1cccc(F)c1)N1CC(NC(=O)c2cn(C3CC3)nn2)C1] | None |

TABLE 4-continued
| Cpd. No. | Structure | Salt Form |
|---|---|---|
| 712 | 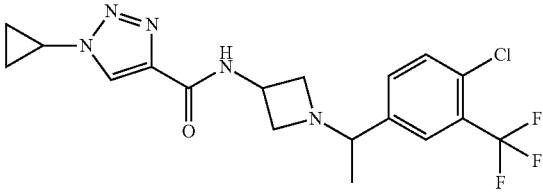 [SMILES: CC(c1ccc(Cl)c(C(F)(F)F)c1)N1CC(NC(=O)c2cn(C3CC3)nn2)C1] | None |
| 713 | 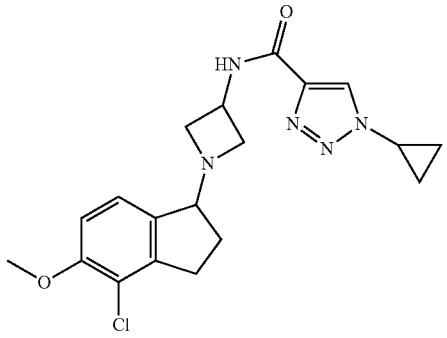 [SMILES: COc1ccc2c(c1Cl)CCC2N1CC(NC(=O)c2cn(C3CC3)nn2)C1] | None |
| 714 | 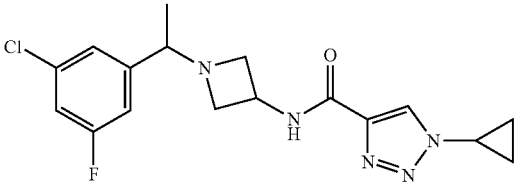 [SMILES: CC(c1cc(F)cc(Cl)c1)N1CC(NC(=O)c2cn(C3CC3)nn2)C1] | None |
| 715 | 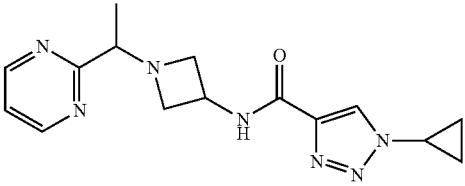 [SMILES: CC(c1ncccn1)N1CC(NC(=O)c2cn(C3CC3)nn2)C1] | None |
| 716 | 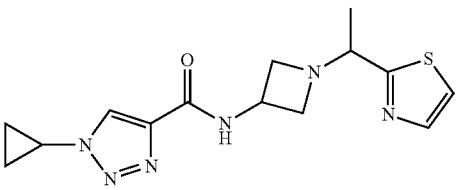 [SMILES: CC(c1nccs1)N1CC(NC(=O)c2cn(C3CC3)nn2)C1] | None |
| 717 | 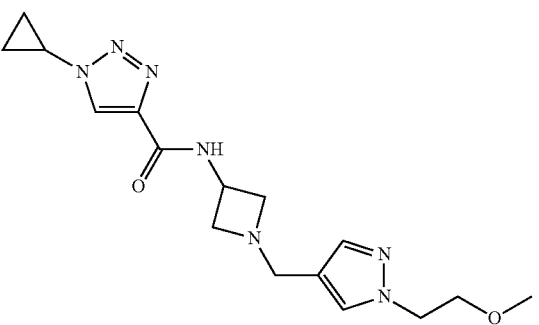 [SMILES: COCCn1cc(CN2CC(NC(=O)c3cn(C4CC4)nn3)C2)cn1] | None |

TABLE 4-continued

| Cpd. No. | Structure | Salt Form |
|---|---|---|
| 718 | 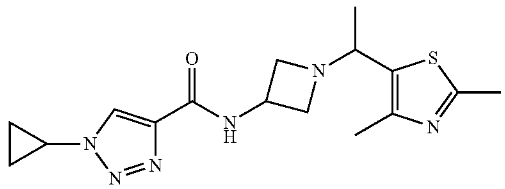 [SMILES: Cc1nc(C)c(C(C)N2CC(NC(=O)c3cn(C4CC4)nn3)C2)s1] | None |
| 719 | 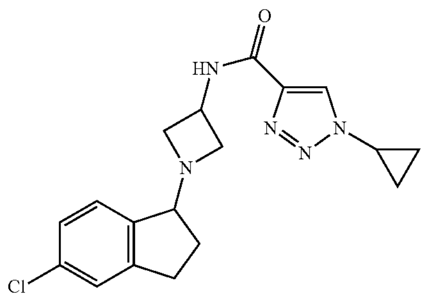 [SMILES: O=C(NC1CN(C2CCc3cc(Cl)ccc32)C1)c1cn(C2CC2)nn1] | None |
| 720 | 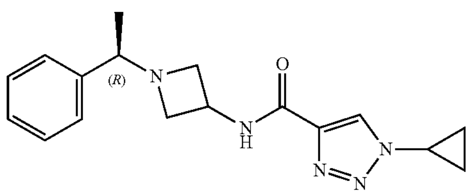 | None |
| 721 | 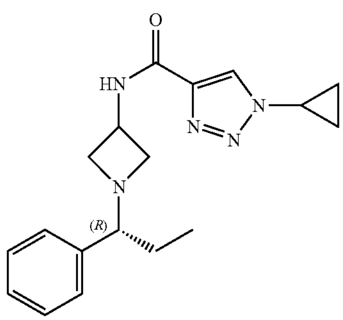 | None |
| 722 | 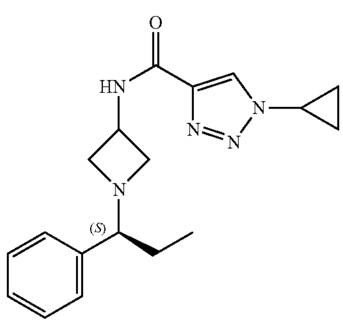 | None |
| 723 | 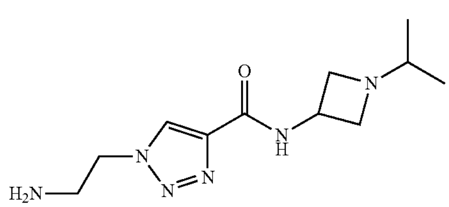 [SMILES: CC(C)N1CC(NC(=O)c2cn(CCN)nn2)C1] | None |

TABLE 4-continued

| Cpd. No. | Structure | Salt Form |
|---|---|---|
| 724 | 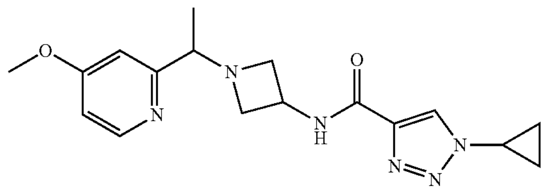 [SMILES: COc1ccnc(C(C)N2CC(NC(=O)c3cn(C4CC4)nn3)C2)c1] | None |
| 725 | 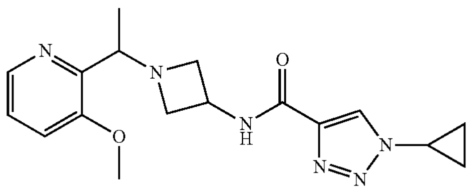 | None |
| 726 | 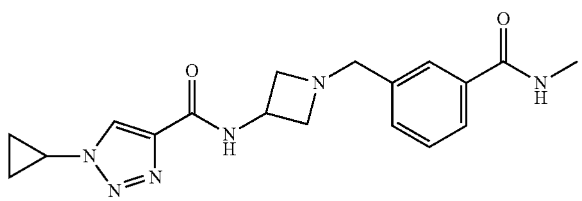 [SMILES: CNC(=O)c1cccc(CN2CC(NC(=O)c3cn(C4CC4)nn3)C2)c1] | None |
| 727 | 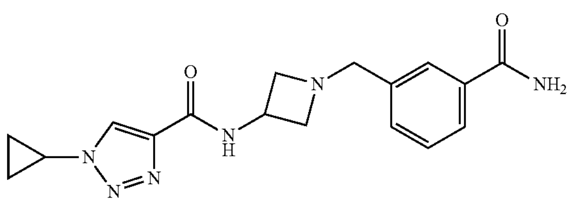 [SMILES: NC(=O)c1cccc(CN2CC(NC(=O)c3cn(C4CC4)nn3)C2)c1] | None |
| 728 | 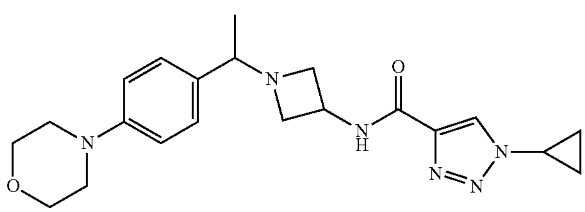 [SMILES: CC(c1ccc(N2CCOCC2)cc1)N1CC(NC(=O)c2cn(C3CC3)nn2)C1] | None |
| 729 | 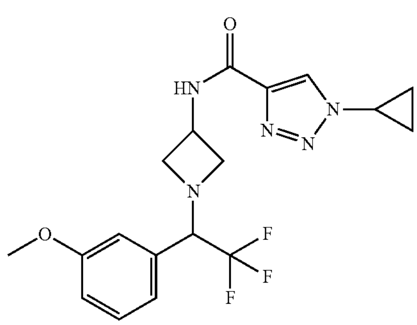 [SMILES: COc1cccc(C(N2CC(NC(=O)c3cn(C4CC4)nn3)C2)C(F)(F)F)c1] | None |
| 730 | 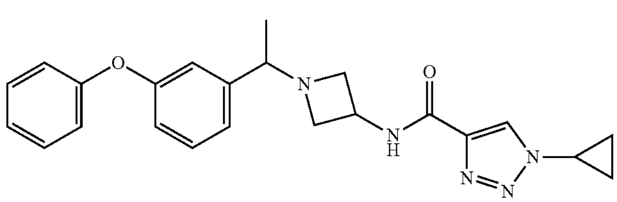 [SMILES: CC(c1cccc(Oc2ccccc2)c1)N1CC(NC(=O)c2cn(C3CC3)nn2)C1] | None |

TABLE 4-continued

| Cpd. No. | Structure | Salt Form |
|---|---|---|
| 731 | 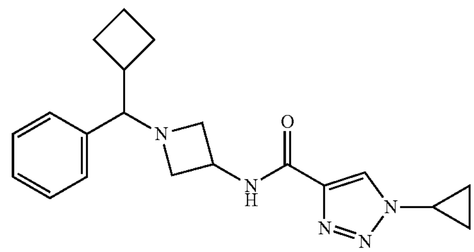 [SMILES: O=C(NC1CN(C(c2ccccc2)C2CCC2)C1)c1cn(C2CC2)nn1] | None |
| 732 | 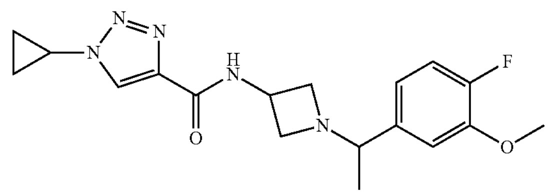 [SMILES: COc1cc(C(C)N2CC(NC(=O)c3cn(C4CC4)nn3)C2)ccc1F] | None |
| 733 | 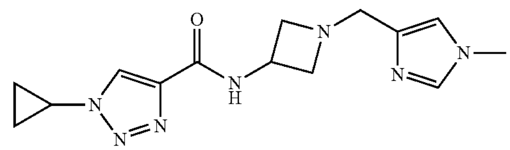 [SMILES: Cn1cnc(CN2CC(NC(=O)c3cn(C4CC4)nn3)C2)c1] | None |
| 734 | 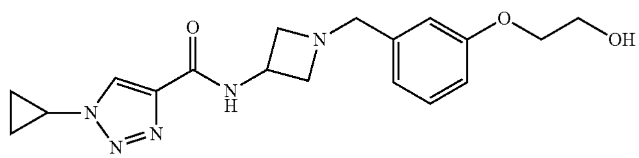 [SMILES: O=C(NC1CN(Cc2cccc(OCCO)c2)C1)c1cn(C2CC2)nn1] | None |
| 735 | 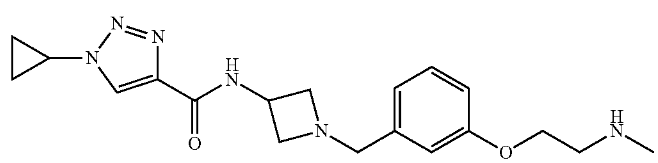 [SMILES: CNCCOc1cccc(CN2CC(NC(=O)c3cn(C4CC4)nn3)C2)c1] | None |
| 736 | 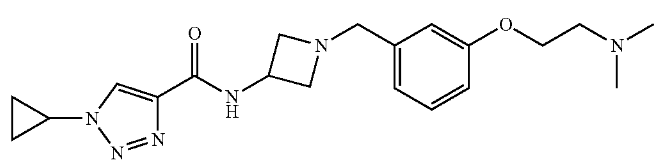 [SMILES: CN(C)CCOc1cccc(CN2CC(NC(=O)c3cn(C4CC4)nn3)C2)c1] | None |
| 737 | 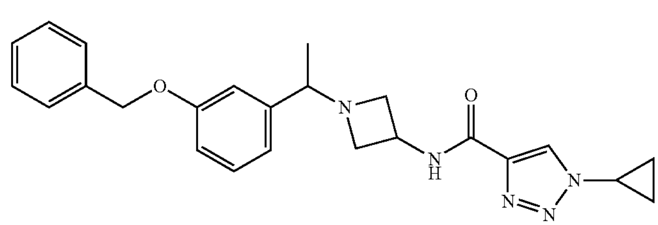 [SMILES: CC(c1cccc(OCc2ccccc2)c1)N1CC(NC(=O)c2cn(C3CC3)nn2)C1] | None |

TABLE 4-continued
| Cpd. No. | Structure | Salt Form |
|---|---|---|
| 738 | 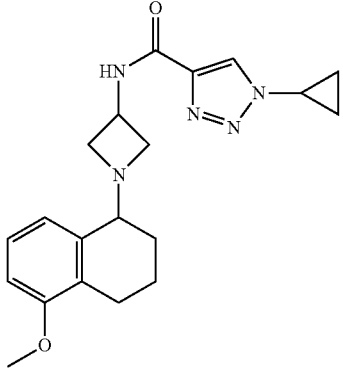 [SMILES: COc1cccc2c1CCCC2N1CC(NC(=O)c2cn(C3CC3)nn2)C1] | None |
| 739 | 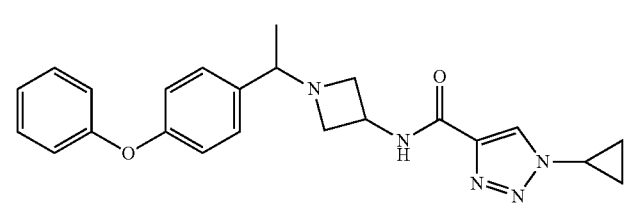 [SMILES: CC(c1ccc(Oc2ccccc2)cc1)N1CC(NC(=O)c2cn(C3CC3)nn2)C1] | None |
| 740 | 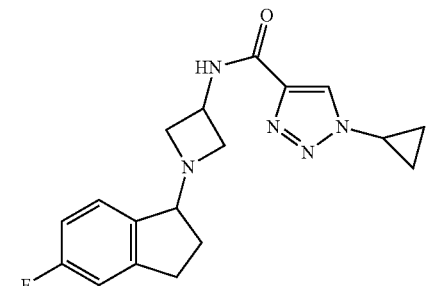 | None |
| 741 | 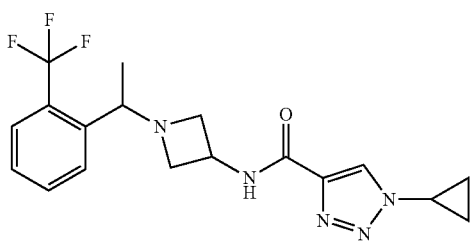 [SMILES: CC(c1ccccc1C(F)(F)F)N1CC(NC(=O)c2cn(C3CC3)nn2)C1] | None |
| 742 | 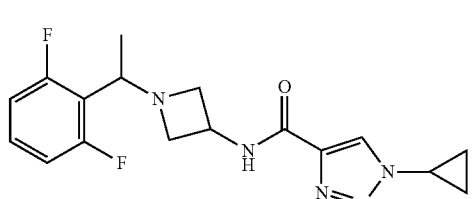 | None |
| 743 | 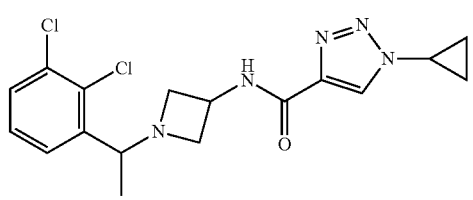 [SMILES: CC(c1cccc(Cl)c1Cl)N1CC(NC(=O)c2cn(C3CC3)nn2)C1] | None |

TABLE 4-continued

| Cpd. No. | Structure | Salt Form |
|---|---|---|
| 744 | 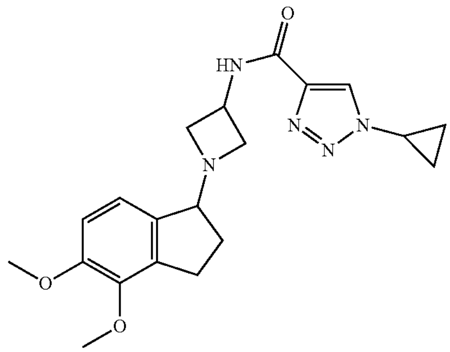 [SMILES: COc1ccc2c(c1OC)CCC2N1CC(NC(=O)c2cn(C3CC3)nn2)C1] | None |
| 745 | 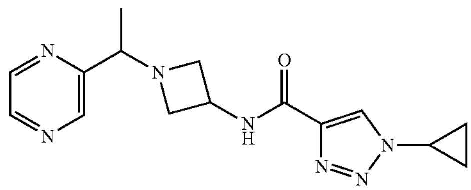 [SMILES: CC(c1cnccn1)N1CC(NC(=O)c2cn(C3CC3)nn2)C1] | None |
| 746 | 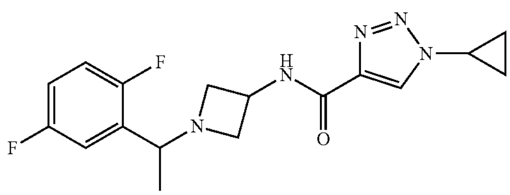 [SMILES: CC(c1cc(F)ccc1F)N1CC(NC(=O)c2cn(C3CC3)nn2)C1] | None |
| 747 | 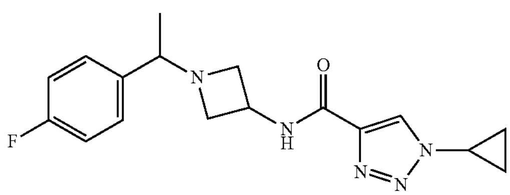 [SMILES: CC(c1ccc(F)cc1)N1CC(NC(=O)c2cn(C3CC3)nn2)C1] | None |
| 748 | 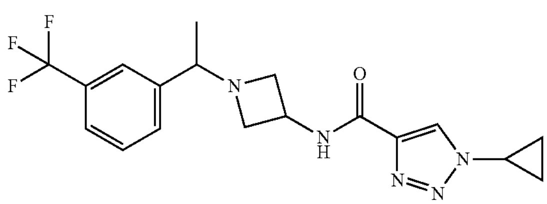 [SMILES: CC(c1cccc(C(F)(F)F)c1)N1CC(NC(=O)c2cn(C3CC3)nn2)C1] | None |
| 749 | 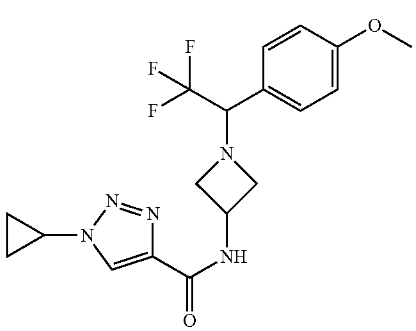 [SMILES: COc1ccc(C(N2CC(NC(=O)c3cn(C4CC4)nn3)C2)C(F)(F)F)cc1] | None |

TABLE 4-continued

| Cpd. No. | Structure | Salt Form |
|---|---|---|
| 750 | 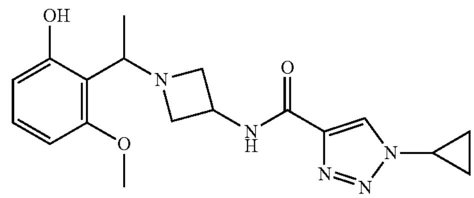 [SMILES: COc1cccc(O)c1C(C)N1CC(NC(=O)c2cn(C3CC3)nn2)C1] | None |
| 751 | 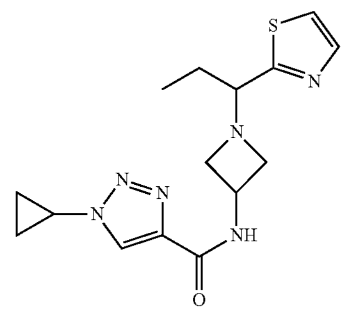 [SMILES: CCC(c1nccs1)N1CC(NC(=O)c2cn(C3CC3)nn2)C1] | None |
| 752 | 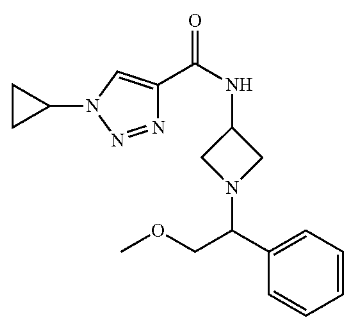 [SMILES: COCC(c1ccccc1)N1CC(NC(=O)c2cn(C3CC3)nn2)C1] | None |
| 753 | 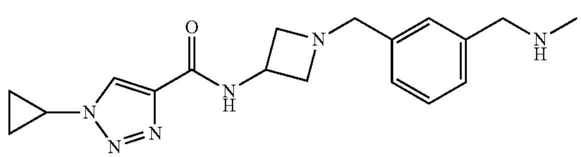 [SMILES: CNCc1cccc(CN2CC(NC(=O)c3cn(C4CC4)nn3)C2)c1] | None |
| 754 | 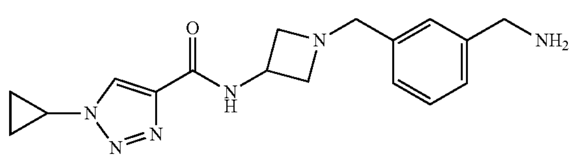 [SMILES: NCc1cccc(CN2CC(NC(=O)c3cn(C4CC4)nn3)C2)c1] | None |
| 755 | 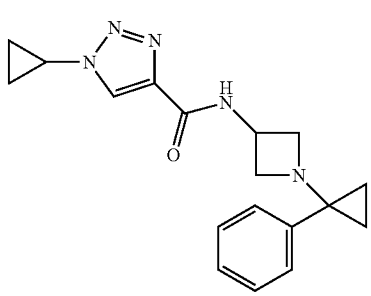 [SMILES: O=C(NC1CN(C2(c3ccccc3)CC2)C1)c1cn(C2CC2)nn1] | None |

TABLE 4-continued

| Cpd. No. | Structure | Salt Form |
|---|---|---|
| 756 | 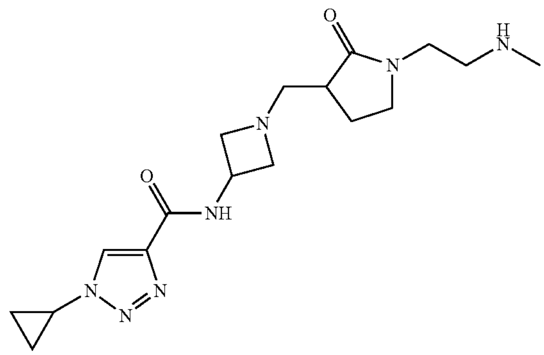 [SMILES: CNCCN1CCC(CN2CC(NC(=O)c3cn(C4CC4)nn3)C2)C1=O] | None |
| 757 | 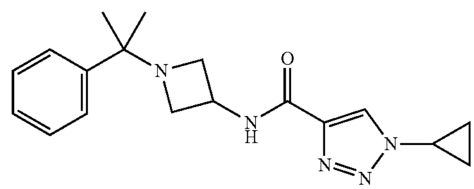 [SMILES: CC(C)(c1ccccc1)N1CC(NC(=O)c2cn(C3CC3)nn2)C1] | None |
| 758 | 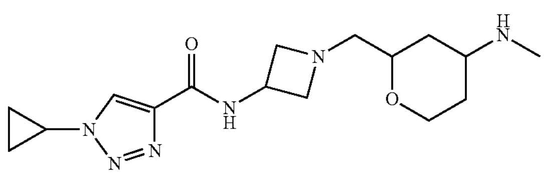 [SMILES: CNC1CCOC(CN2CC(NC(=O)c3cn(C4CC4)nn3)C2)C1] | None |
| 759 | 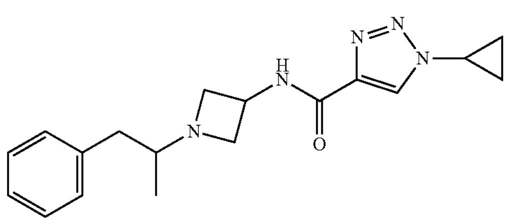 [SMILES: CC(Cc1ccccc1)N1CC(NC(=O)c2cn(C3CC3)nn2)C1] | None |
| 760 | 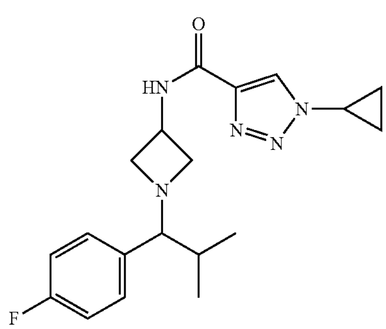 [SMILES: CC(C)C(c1ccc(F)cc1)N1CC(NC(=O)c2cn(C3CC3)nn2)C1] | None |
| 761 | 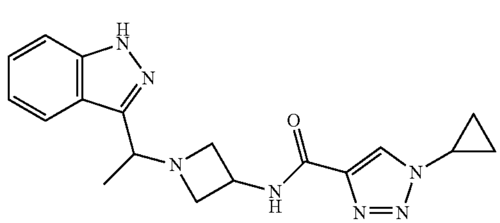 [SMILES: CC(c1n[nH]c2ccccc12)N1CC(NC(=O)c2cn(C3CC3)nn2)C1] | None |

TABLE 4-continued

| Cpd. No. | Structure | Salt Form |
|---|---|---|
| 762 | 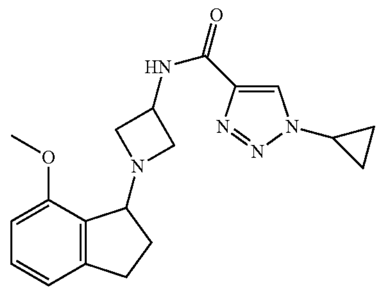 [SMILES: COc1cccc2c1C(N1CC(NC(=O)c3cn(C4CC4)nn3)C1)CC2] | None |
| 763 | 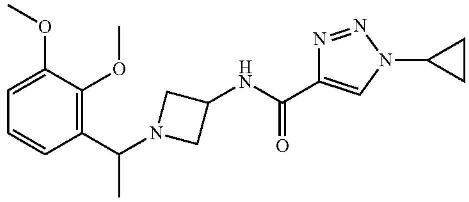 [SMILES: COc1cccc(C(C)N2CC(NC(=O)c3cn(C4CC4)nn3)C2)c1OC] | None |
| 764 | 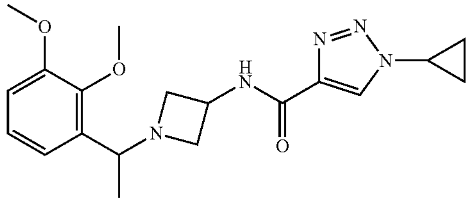 [SMILES: COc1cccc(C(C)N2CC(NC(=O)c3cn(C4CC4)nn3)C2)c1OC] | None |
| 765 | 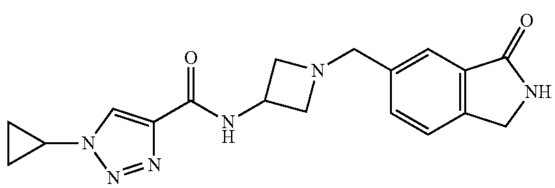 [SMILES: O=C(NC1CN(Cc2ccc3c(c2)C(=O)NC3)C1)c1cn(C2CC2)nn1] | None |
| 766 | 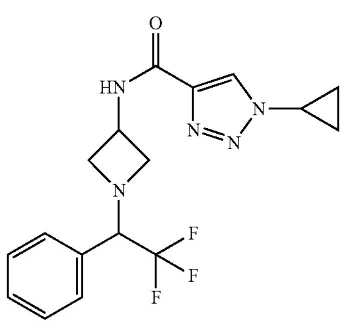 [SMILES: O=C(NC1CN(C(c2ccccc2)C(F)(F)F)C1)c1cn(C2CC2)nn1] | None |
| 767 | 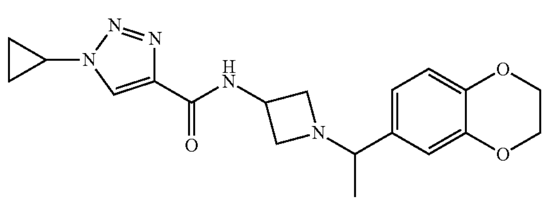 [SMILES: CC(c1ccc2c(c1)OCCO2)N1CC(NC(=O)c2cn(C3CC3)nn2)C1] | None |

TABLE 4-continued

| Cpd. No. | Structure | Salt Form |
|---|---|---|
| 768 | 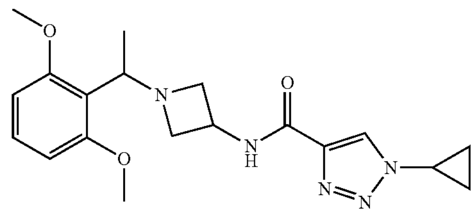 [SMILES: COc1cccc(OC)c1C(C)N1CC(NC(=O)c2cn(C3CC3)nn2)C1] | None |
| 769 | 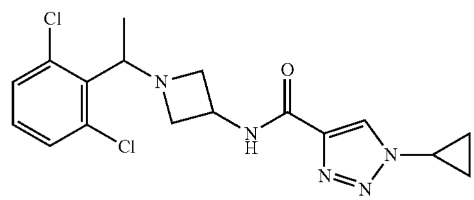 | None |
| 770 | 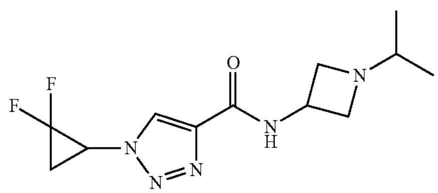 [SMILES: CC(C)N1CC(NC(=O)c2cn(C3CC3(F)F)nn2)C1] | None |
| 771 | 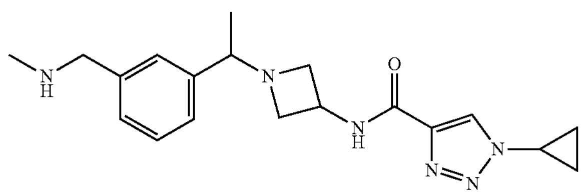 [SMILES: CNCc1cccc(C(C)N2CC(NC(=O)c3cn(C4CC4)nn3)C2)c1] | None |
| 772 | 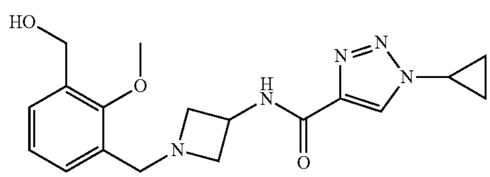 [SMILES: COc1c(CO)cccc1CN1CC(NC(=O)c2cn(C3CC3)nn2)C1] | None |
| 773 | 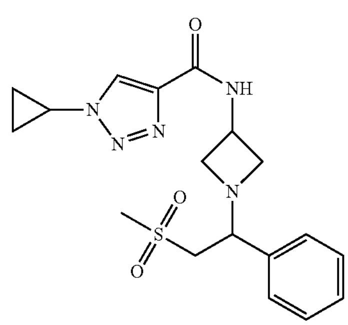 [SMILES: CS(=O)(=O)CC(c1ccccc1)N1CC(NC(=O)c2cn(C3CC3)nn2)C1] | None |
| 774 | 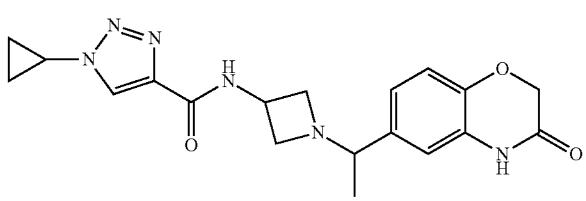 [SMILES: CC(c1ccc2c(c1)NC(=O)CO2)N1CC(NC(=O)c2cn(C3CC3)nn2)C1] | None |

TABLE 4-continued

| Cpd. No. | Structure | Salt Form |
|---|---|---|
| 775 | 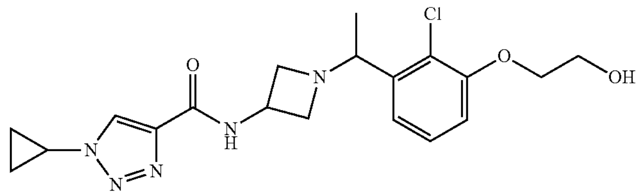 [SMILES: CC(c1cccc(OCCO)c1Cl)N1CC(NC(=O)c2cn(C3CC3)nn2)C1] | None |
| 776 | 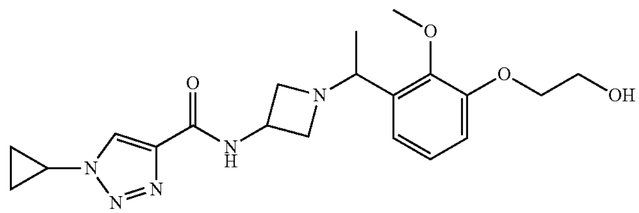 [SMILES: COc1c(OCCO)cccc1C(C)N1CC(NC(=O)c2cn(C3CC3)nn2)C1] | None |
| 777 | 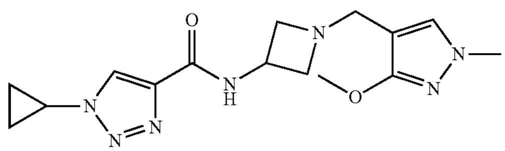 [SMILES: COc1nn(C)cc1CN1CC(NC(=O)c2cn(C3CC3)nn2)C1] | None |
| 778 | 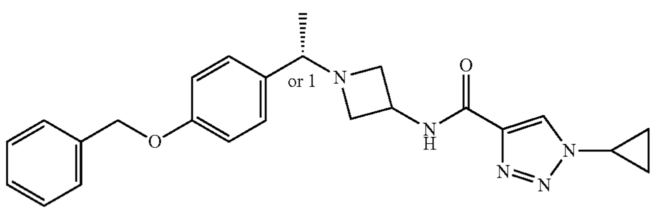 [SMILES: C[C@@H](c1ccc(OCc2ccccc2)cc1)N1CC(NC(=O)c2cn(C3CC3)nn2)C1] | None |
| 779 | 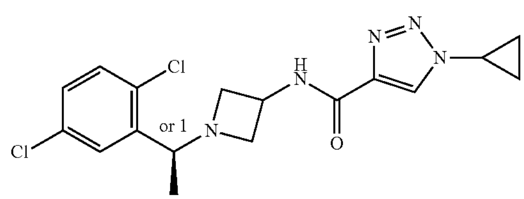 [SMILES: C[C@@H](c1cc(Cl)ccc1Cl)N1CC(NC(=O)c2cn(C3CC3)nn2)C1] | None |
| 780 | 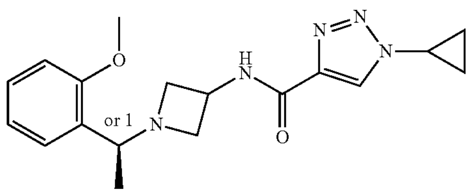 [SMILES: COc1ccccc1[C@H](C)N1CC(NC(=O)c2cn(C3CC3)nn2)C1] | None |
| 781 | 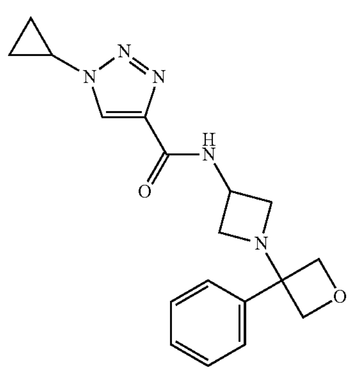 [SMILES: O=C(NC1CN(C2(c3ccccc3)COC2)C1)c1cn(C2CC2)nn1] | None |

TABLE 4-continued

| Cpd. No. | Structure | Salt Form |
|---|---|---|
| 782 | 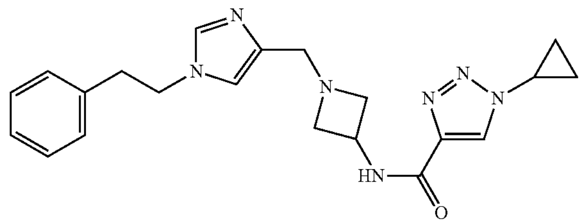 [SMILES: O=C(NC1CN(Cc2cn(CCc3ccccc3)cn2)C1)c1cn(C2CC2)nn1] | None |
| 783 | 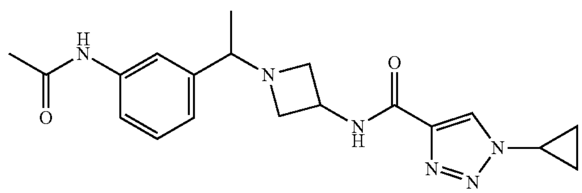 [SMILES: CC(=O)Nc1cccc(C(C)N2CC(NC(=O)c3cn(C4CC4)nn3)C2)c1] | None |
| 784 | 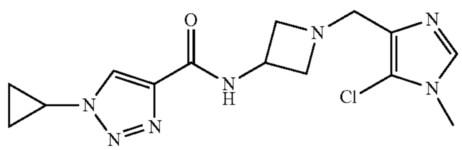 [SMILES: Cn1cnc(CN2CC(NC(=O)c3cn(C4CC4)nn3)C2)c1Cl] | None |
| 785 | 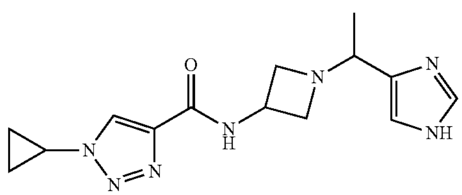 [SMILES: CC(c1c[nH]cn1)N1CC(NC(=O)c2cn(C3CC3)nn2)C1] | None |
| 786 | 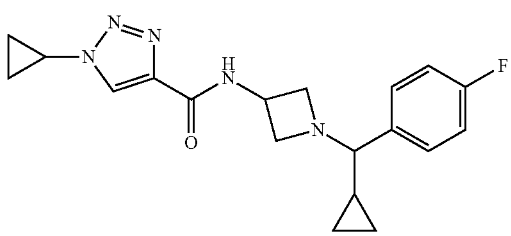 [SMILES: O=C(NC1CN(C(c2ccc(F)cc2)C2CC2)C1)c1cn(C2CC2)nn1] | None |
| 787 | 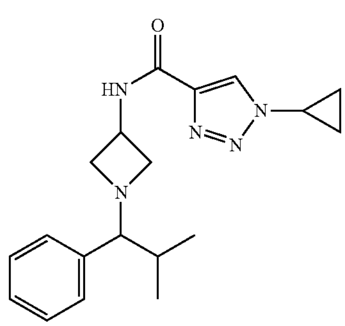 [SMILES: CC(C)C(c1ccccc1)N1CC(NC(=O)c2cn(C3CC3)nn2)C1] | None |
| 788 | 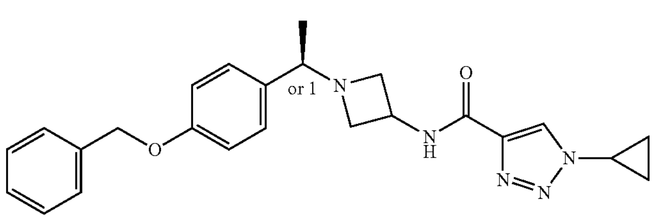 [SMILES: C[C@H](c1ccc(OCc2ccccc2)cc1)N1CC(NC(=O)c2cn(C3CC3)nn2)C1] | None |

TABLE 4-continued
| Cpd. No. | Structure | Salt Form |
|---|---|---|
| 789 | 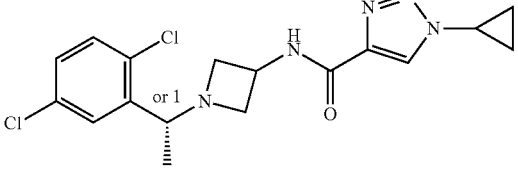 | None |
| 790 | 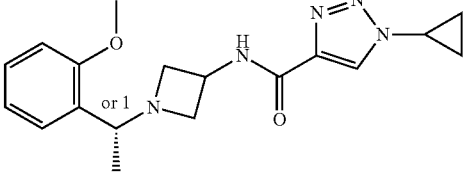 | None |
| 791 | 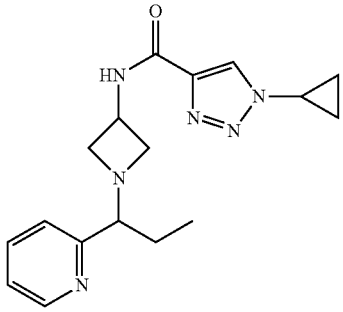 [SMILES: CCC(c1ccccn1)N1CC(NC(=O)c2cn(C3CC3)nn2)C1] | None |
| 792 | 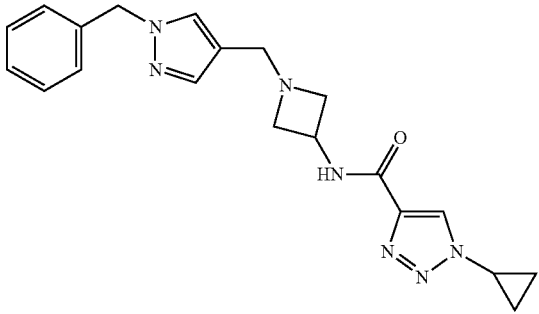 [SMILES: O=C(NC1CN(Cc2cnn(Cc3ccccc3)c2)C1)c1cn(C2CC2)nn1] | None |
| 793 | 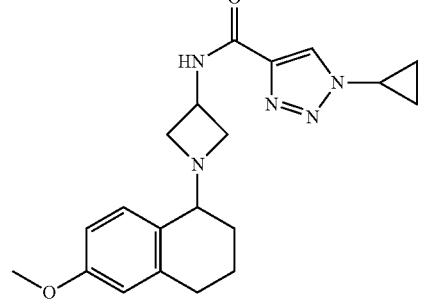 | None |
| 794 | 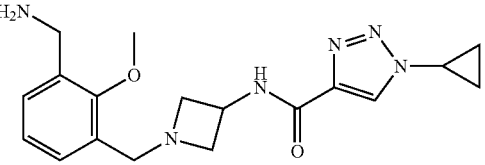 [SMILES: COc1c(CN)cccc1CN1CC(NC(=O)c2cn(C3CC3)nn2)C1] | None |

US 10,266,526 B2
243                                                                     244
TABLE 4-continued
| Cpd. No. | Structure | Salt Form |
|---|---|---|
| 795 | 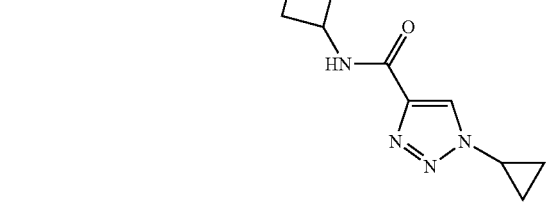 | None |
| 796 | 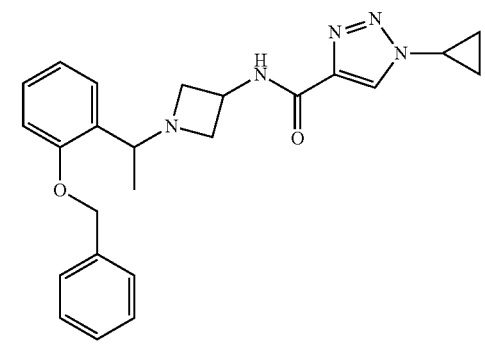 [SMILES: CC(c1ccccc1OCc1ccccc1)N1CC(NC(=O)c2cn(C3CC3)nn2)C1] | None |
| 797 | 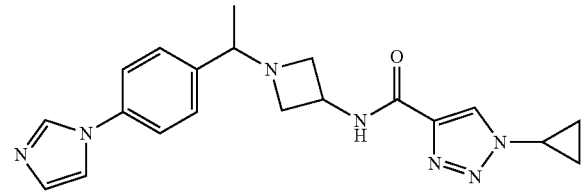 [SMILES: CC(c1ccc(-n2ccnc2)cc1)N1CC(NC(=O)c2cn(C3CC3)nn2)C1] | None |
| 798 | 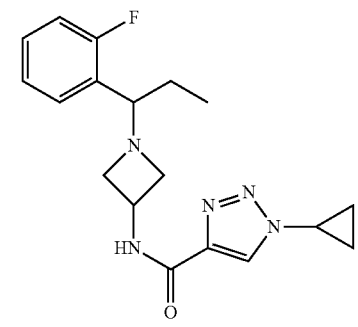 [SMILES: CCC(c1ccccc1F)N1CC(NC(=O)c2cn(C3CC3)nn2)C1] | None |
| 799 | 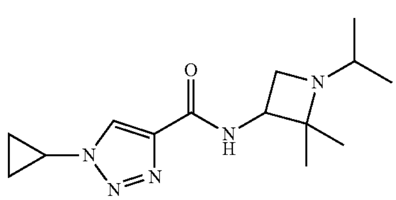 [SMILES: CC(C)N1CC(NC(=O)c2cn(C3CC3)nn2)C1(C)C] | None |
| 800 | 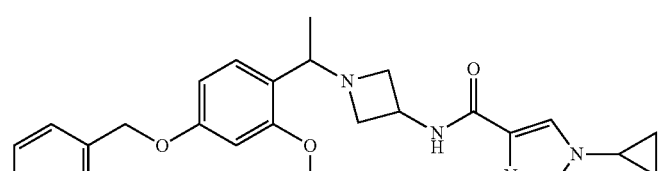 | None |

TABLE 4-continued

| Cpd. No. | Structure | Salt Form |
|---|---|---|
| 801 | 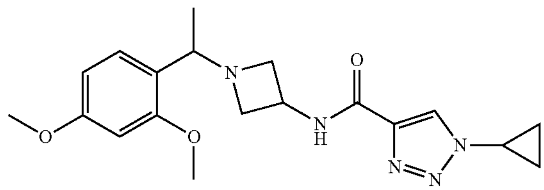 [SMILES: COc1ccc(C(C)N2CC(NC(=O)c3cn(C4CC4)nn3)C2)c(OC)c1] | None |
| 802 | 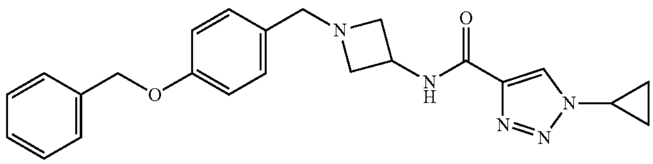 [SMILES: O=C(NC1CN(Cc2ccc(OCc3ccccc3)cc2)C1)c1cn(C2CC2)nn1] | None |
| 803 | 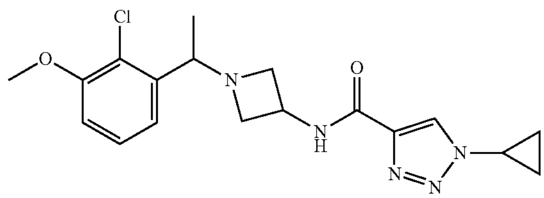 [SMILES: COc1cccc(C(C)N2CC(NC(=O)c3cn(C4CC4)nn3)C2)c1Cl] | None |
| 804 | 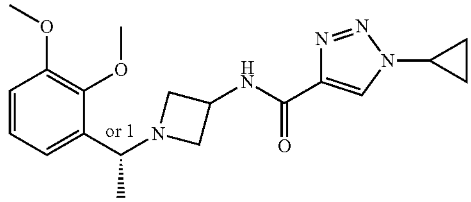 [SMILES: COc1cccc([C@@H](C)N2CC(NC(=O)c3cn(C4CC4)nn3)C2)c1OC] | None |
| 805 | 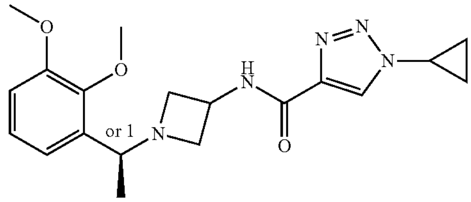 [SMILES: COc1cccc([C@H](C)N2CC(NC(=O)c3cn(C4CC4)nn3)C2)c1OC] | None |
| 806 | 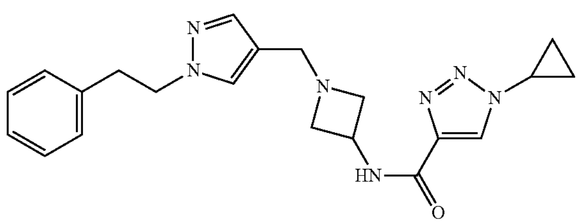 [SMILES: O=C(NC1CN(Cc2cnn(CCc3ccccc3)c2)C1)c1cn(C2CC2)nn1] | None |
| 807 | 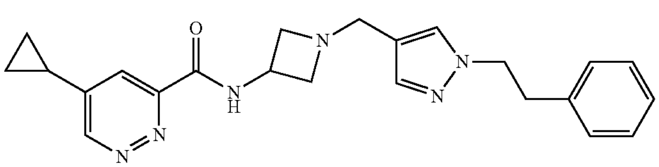 | None |
| 808 | 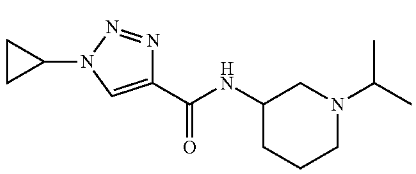 [SMILES: CC(C)N1CCCC(NC(=O)c2cn(C3CC3)nn2)C1] | None |

TABLE 4-continued

| Cpd. No. | Structure | Salt Form |
|---|---|---|
| 809 | 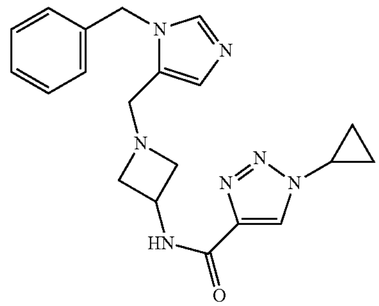 [SMILES: O=C(NC1CN(Cc2cncn2Cc2ccccc2)C1)c1cn(C2CC2)nn1] | None |
| 810 | 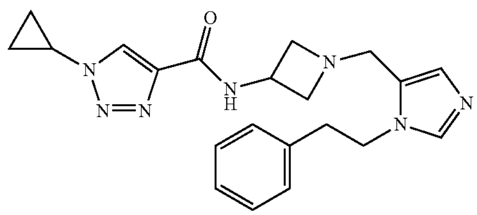 [SMILES: O=C(NC1CN(Cc2cncn2CCc2ccccc2)C1)c1cn(C2CC2)nn1] | None |
| 811 | 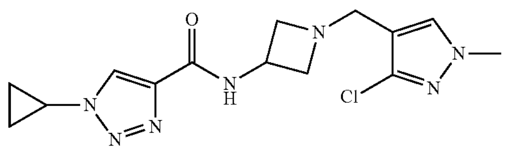 [SMILES: Cn1cc(CN2CC(NC(=O)c3cn(C4CC4)nn3)C2)c(Cl)n1] | None |
| 812 | 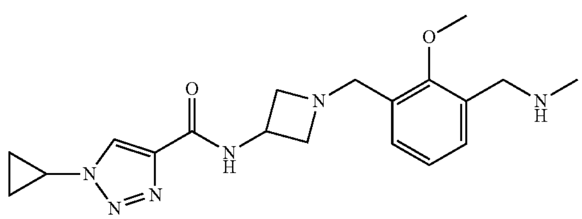 [SMILES: CNCc1cccc(CN2CC(NC(=O)c3cn(C4CC4)nn3)C2)c1OC] | None |
| 813 | 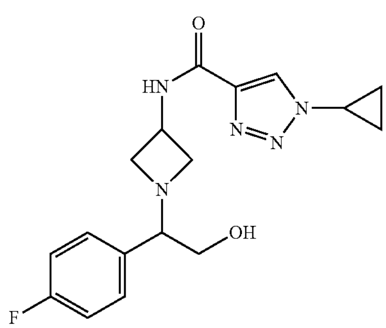 [SMILES: O=C(NC1CN(C(CO)c2ccc(F)cc2)C1)c1cn(C2CC2)nn1] | None |
| 814 | 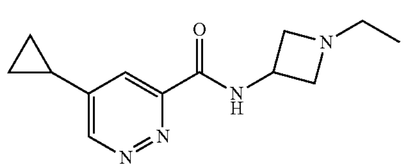 [SMILES: CCN1CC(NC(=O)c2cc(C3CC3)cnn2)C1] | None |
| 815 | 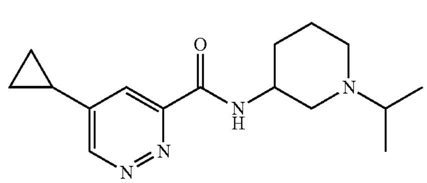 [SMILES: CC(C)N1CCCC(NC(=O)c2cc(C3CC3)cnn2)C1] | None |

TABLE 4-continued

| Cpd. No. | Structure | Salt Form |
|---|---|---|
| 816 | 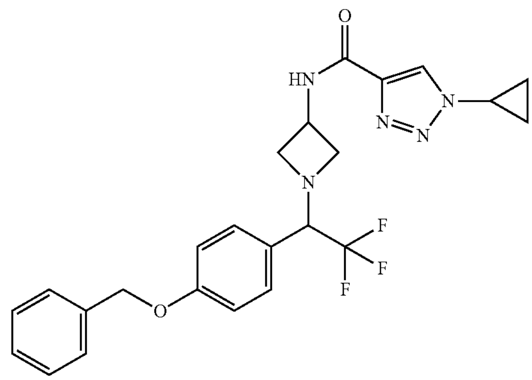 [SMILES: O=C(NC1CN(C(c2ccc(OCc3ccccc3)cc2)C(F)(F)F)C1)c1cn(C2CC2)nn1] | None |
| 817 | 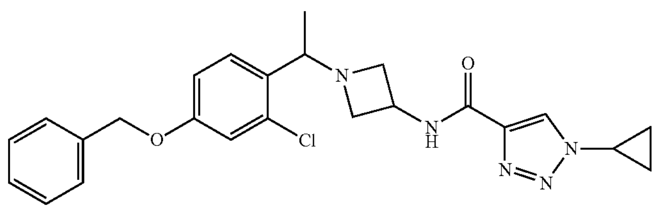 [SMILES: CC(c1ccc(OCc2ccccc2)cc1Cl)N1CC(NC(=O)c2cn(C3CC3)nn2)C1] | None |
| 818 | 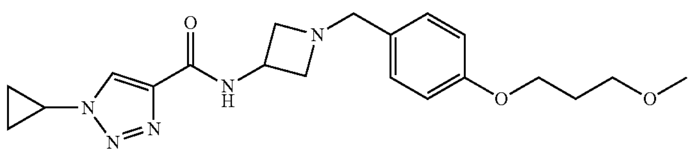 [SMILES: COCCCOc1ccc(CN2CC(NC(=O)c3cn(C4CC4)nn3)C2)cc1] | None |
| 819 | 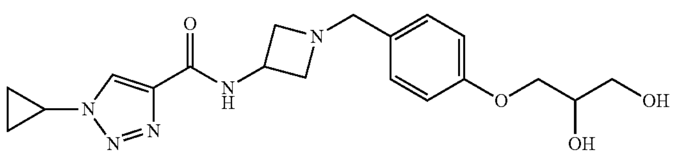 [SMILES: O=C(NC1CN(Cc2ccc(OCC(O)CO)cc2)C1)c1cn(C2CC2)nn1] | None |
| 820 | 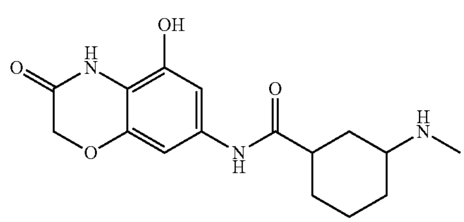 [SMILES: CNC1CCCC(C(=O)Nc2cc(O)c3c(c2)OCC(=O)N3)C1] | None |
| 821 | 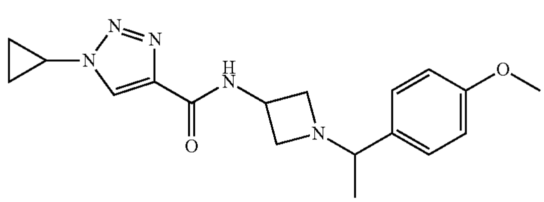 [SMILES: COc1ccc(C(C)N2CC(NC(=O)c3cn(C4CC4)nn3)C2)cc1] | None |
| 822 | 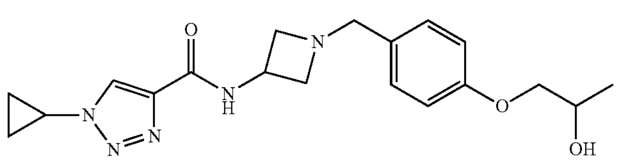 [SMILES: CC(O)COc1ccc(CN2CC(NC(=O)c3cn(C4CC4)nn3)C2)cc1] | None |

TABLE 4-continued

| Cpd. No. | Structure | Salt Form |
|---|---|---|
| 823 | 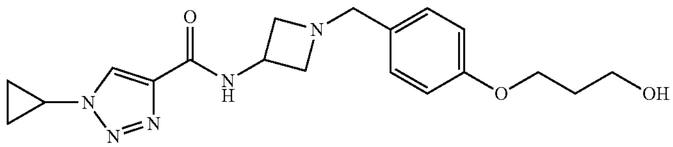 [SMILES: O=C(NC1CN(Cc2ccc(OCCCO)cc2)C1)c1cn(C2CC2)nn1] | None |
| 824 | 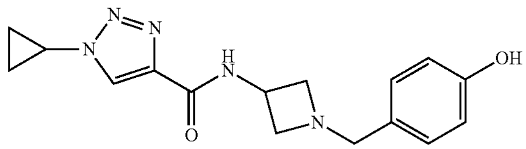 [SMILES: O=C(NC1CN(Cc2ccc(O)cc2)C1)c1cn(C2CC2)nn1] | None |
| 825 | 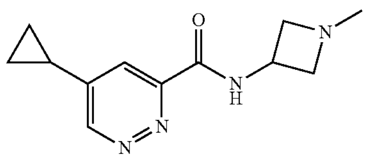 [SMILES: CN1CC(NC(=O)c2cc(C3CC3)cnn2)C1] | None |
| 826 | 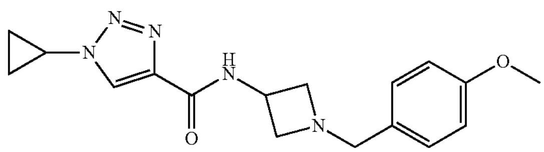 [SMILES: COc1ccc(CN2CC(NC(=O)c3cn(C4CC4)nn3)C2)cc1] | None |
| 827 | 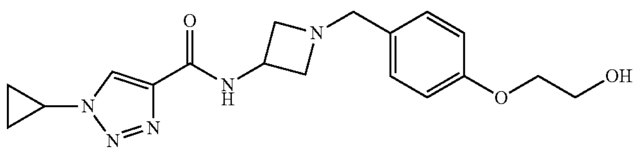 [SMILES: O=C(NC1CN(Cc2ccc(OCCO)cc2)C1)c1cn(C2CC2)nn1] | None |
| 828 | 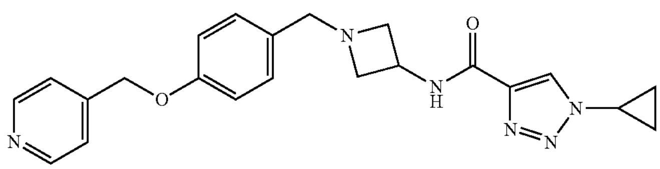 | None |
| 829 | 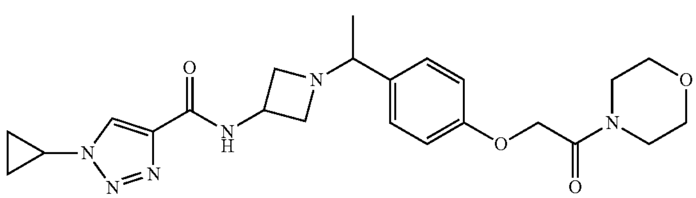 [SMILES: CC(c1ccc(OCC(=O)N2CCOCC2)cc1)N1CC(NC(=O)c2cn(C3CC3)nn2)C1] | None |
| 830 | 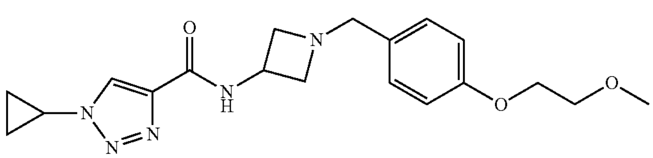 [SMILES: COCCOc1ccc(CN2CC(NC(=O)c3cn(C4CC4)nn3)C2)cc1] | None |
| 831 | 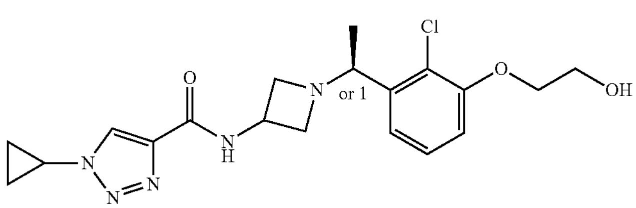 [SMILES: C[C@@H](c1cccc(OCCO)c1Cl)N1CC(NC(=O)c2cn(C3CC3)nn2)C1] | None |

TABLE 4-continued

| Cpd. No. | Structure | Salt Form |
|---|---|---|
| 832 | 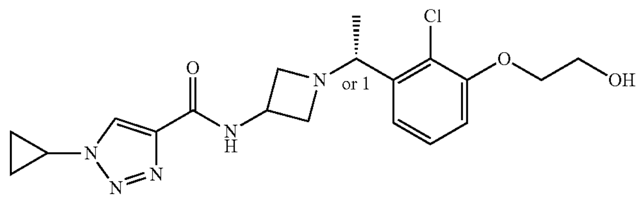 [SMILES: C[C@H](c1cccc(OCCO)c1Cl)N1CC(NC(=O)c2cn(C3CC3)nn2)C1] | None |
| 833 | 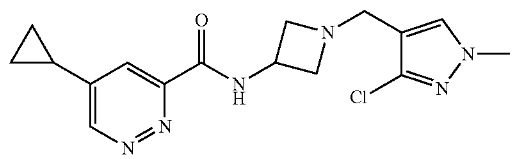 [SMILES: Cn1cc(CN2CC(NC(=O)c3cc(C4CC4)cnn3)C2)c(Cl)n1] | None |
| 834 | 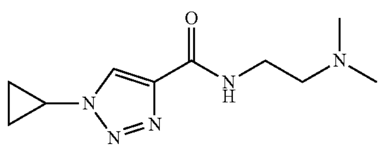 [SMILES: CN(C)CCNC(=O)c1cn(C2CC2)nn1] | None |
| 835 | 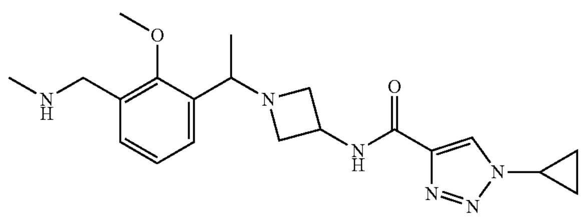 [SMILES: CNCc1cccc(C(C)N2CC(NC(=O)c3cn(C4CC4)nn3)C2)c1OC] | None |
| 836 | 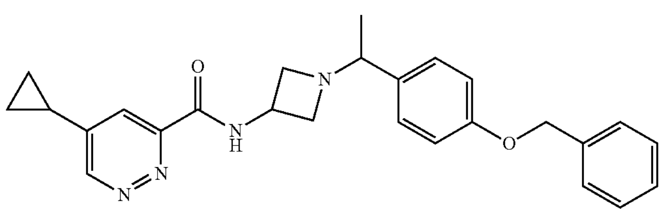 [SMILES: CC(c1ccc(OCc2ccccc2)cc1)N1CC(NC(=O)c2cc(C3CC3)cnn2)C1] | None |
| 837 | 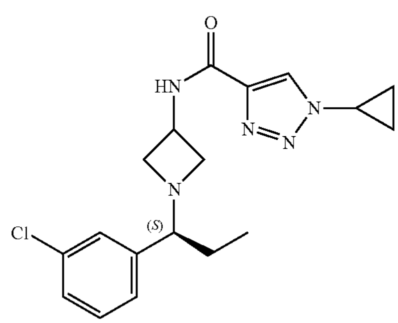 | None |
| 838 | 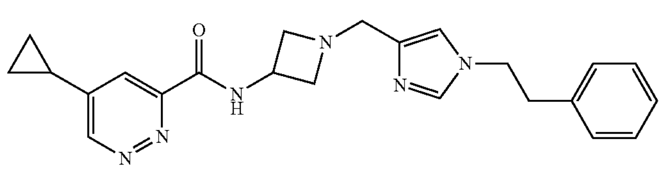 [SMILES: O=C(NC1CN(Cc2cn(CCc3ccccc3)cn2)C1)c1cc(C2CC2)cnn1] | None |

TABLE 4-continued

| Cpd. No. | Structure | Salt Form |
|---|---|---|
| 839 | 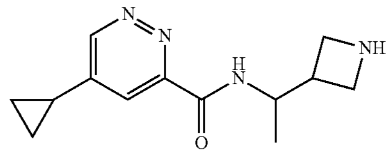 [SMILES: CC(NC(=O)c1cc(C2CC2)cnn1)C1CNC1] | None |
| 840 | 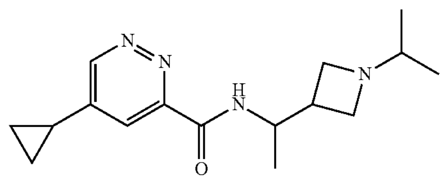 [SMILES: CC(NC(=O)c1cc(C2CC2)cnn1)C1CN(C(C)C)C1] | None |
| 841 | 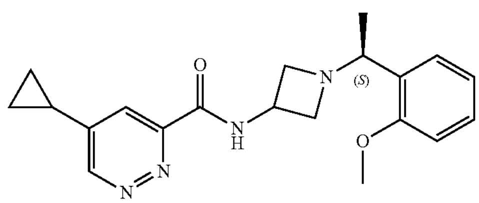 | None |
| 842 | 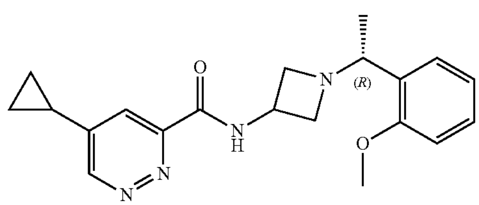 | None |
| 843 | 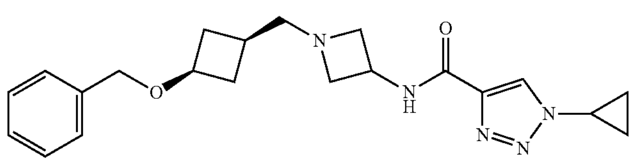 [SMILES: O=C(NC1CN(C[C@H]2C[C@@H](OCc3ccccc3)C2)C1)c1cn(C2CC2)nn1] | None |
| 844 | 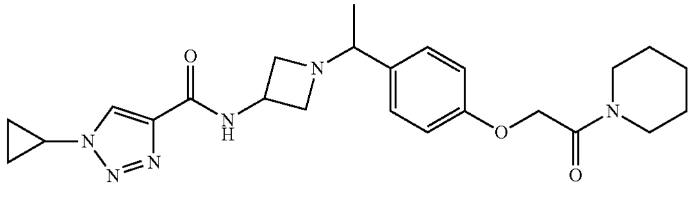 [SMILES: CC(c1ccc(OCC(=O)N2CCCCC2)cc1)N1CC(NC(=O)c2cn(C3CC3)nn2)C1] | None |
| 845 | 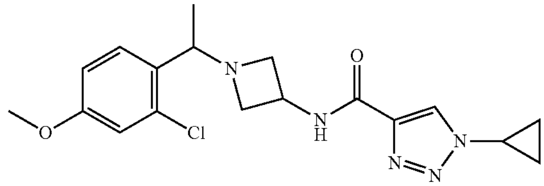 [SMILES: COc1ccc(C(C)N2CC(NC(=O)c3cn(C4CC4)nn3)C2)c(Cl)c1] | None |
| 846 | 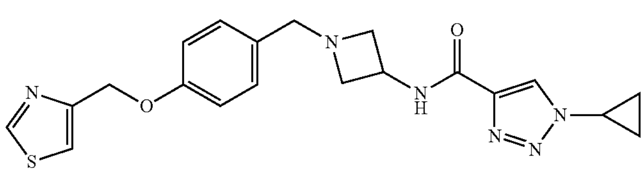 [SMILES: O=C(NC1CN(Cc2ccc(OCc3cscn3)cc2)C1)c1cn(C2CC2)nn1] | None |

TABLE 4-continued

| Cpd. No. | Structure | Salt Form |
|---|---|---|
| 847 | 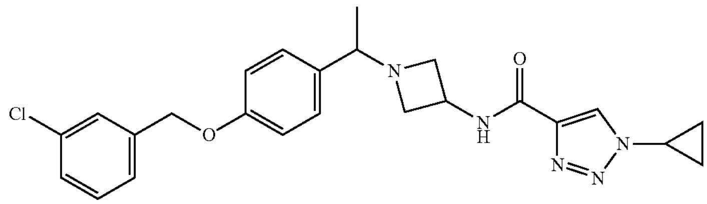 [SMILES: CC(c1ccc(OCc2cccc(Cl)c2)cc1)N1CC(NC(=O)c2cn(C3CC3)nn2)C1] | None |
| 848 | 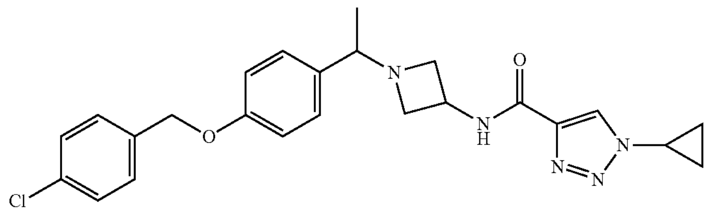 [SMILES: CC(c1ccc(OCc2ccc(Cl)cc2)cc1)N1CC(NC(=O)c2cn(C3CC3)nn2)C1] | None |
| 849 | 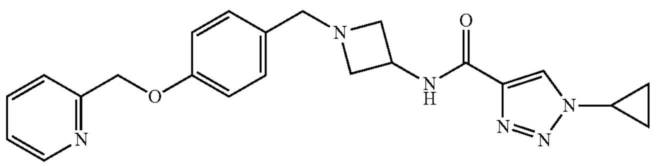 | None |
| 850 | 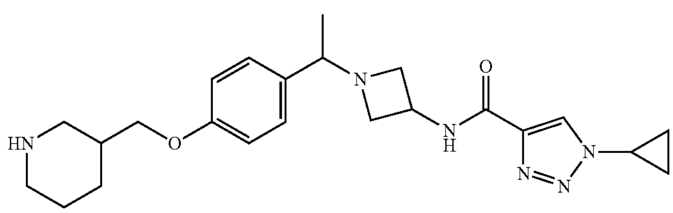 [SMILES: CC(c1ccc(OCC2CCCNC2)cc1)N1CC(NC(=O)c2cn(C3CC3)nn2)C1] | None |
| 851 | 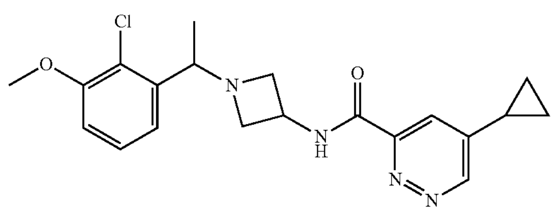 [SMILES: COc1cccc(C(C)N2CC(NC(=O)c3cc(C4CC4)cnn3)C2)c1Cl] | None |
| 852 | 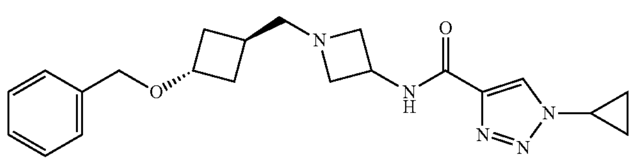 [SMILES: O=C(NC1CN(C[C@H]2C[C@H](OCc3ccccc3)C2)C1)c1cn(C2CC2)nn1] | None |
| 853 | 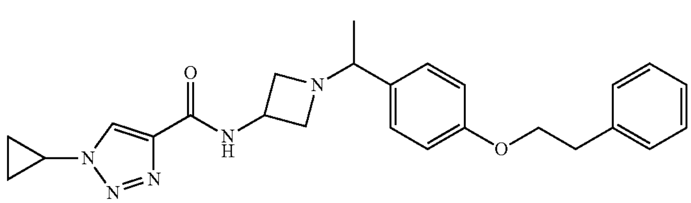 [SMILES: CC(c1ccc(OCCc2ccccc2)cc1)N1CC(NC(=O)c2cn(C3CC3)nn2)C1] | None |

TABLE 4-continued

| Cpd. No. | Structure | Salt Form |
|---|---|---|
| 854 | 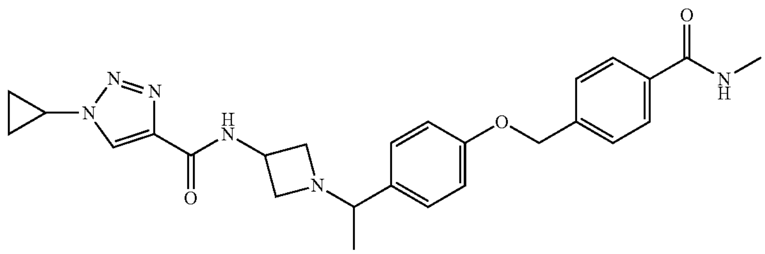 [SMILES: CNC(=O)c1ccc(COc2ccc(C(C)N3CC(NC(=O)c4cn(C5CC5)nn4)C3)cc2)cc1] | None |
| 855 | 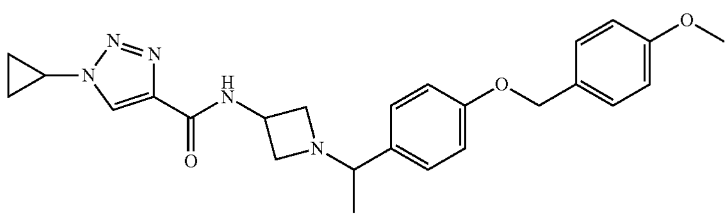 [SMILES: COc1ccc(COc2ccc(C(C)N3CC(NC(=O)c4cn(C5CC5)nn4)C3)cc2)cc1] | None |
| 856 | 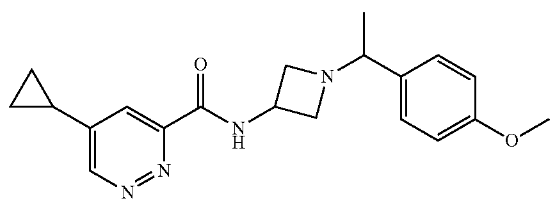 [SMILES: COc1ccc(C(C)N2CC(NC(=O)c3cc(C4CC4)cnn3)C2)cc1] | None |
| 857 | 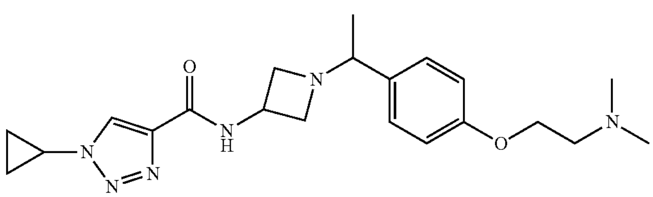 [SMILES: CC(c1ccc(OCCN(C)C)cc1)N1CC(NC(=O)c2cn(C3CC3)nn2)C1] | None |
| 858 | 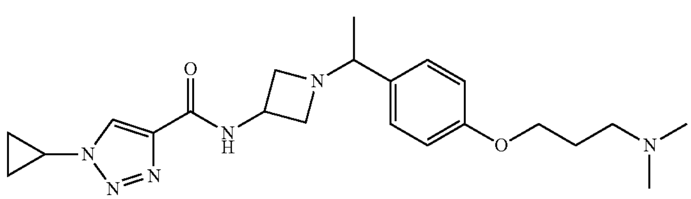 [SMILES: CC(c1ccc(OCCCN(C)C)cc1)N1CC(NC(=O)c2cn(C3CC3)nn2)C1] | None |
| 859 | 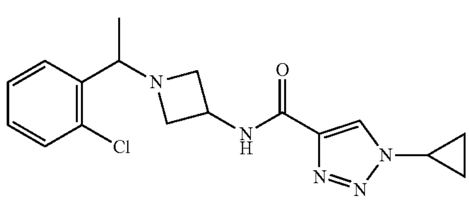 [SMILES: CC(c1ccccc1Cl)N1CC(NC(=O)c2cn(C3CC3)nn2)C1] | None |
| 860 | 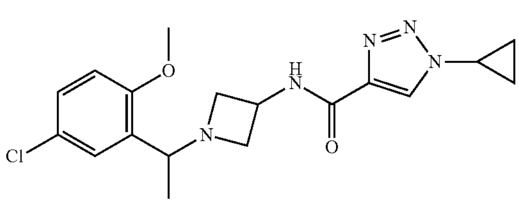 [SMILES: COc1ccc(Cl)cc1C(C)N1CC(NC(=O)c2cn(C3CC3)nn2)C1] | None |

TABLE 4-continued

| Cpd. No. | Structure | Salt Form |
|---|---|---|
| 861 | 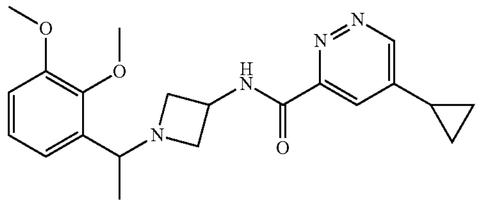 [SMILES: COc1cccc(C(C)N2CC(NC(=O)c3cc(C4CC4)cnn3)C2)c1OC] | None |
| 862 | 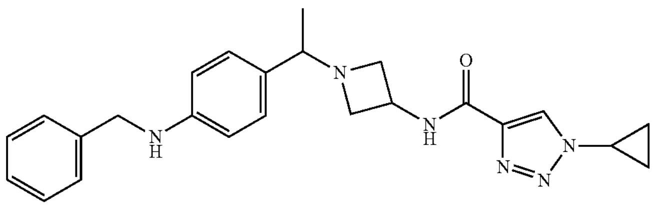 [SMILES: CC(c1ccc(NCc2ccccc2)cc1)N1CC(NC(=O)c2cn(C3CC3)nn2)C1] | None |
| 863 | 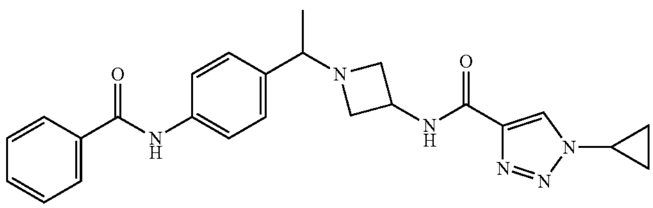 [SMILES: CC(c1ccc(NC(=O)c2ccccc2)cc1)N1CC(NC(=O)c2cn(C3CC3)nn2)C1] | None |
| 864 | 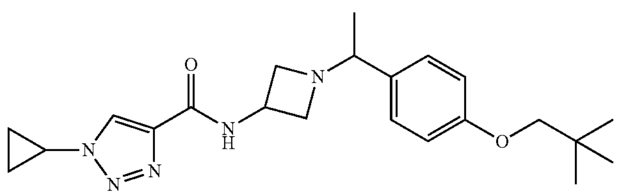 [SMILES: CC(c1ccc(OCC(C)(C)C)cc1)N1CC(NC(=O)c2cn(C3CC3)nn2)C1] | None |
| 865 | 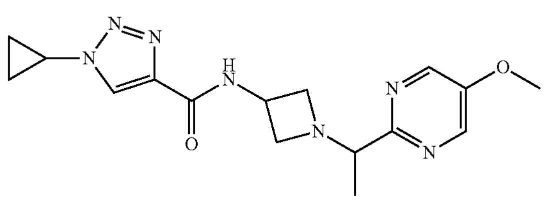 [SMILES: COc1cnc(C(C)N2CC(NC(=O)c3cn(C4CC4)nn3)C2)nc1] | None |
| 866 | 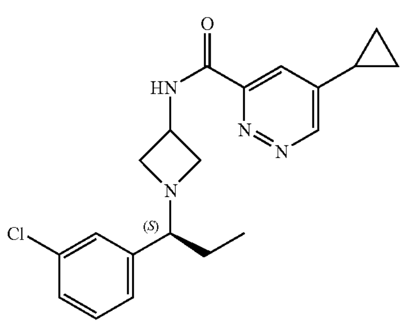 | None |
| 867 | 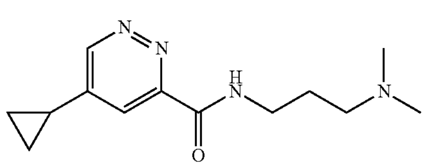 [SMILES: CN(C)CCCNC(=O)c1cc(C2CC2)cnn1] | None |

TABLE 4-continued

| Cpd. No. | Structure | Salt Form |
|---|---|---|
| 868 | 1-cyclopropyl-N-(1-(1-(4-(benzyloxy)-3-chlorophenyl)ethyl)azetidin-3-yl)-1H-1,2,3-triazole-4-carboxamide | None |
| 869 | 5-cyclopropyl-N-(2-(dimethylamino)ethyl)pyridazine-3-carboxamide | None |
| 913 | 5-cyclopropyl-N-(1-isopropylazetidin-3-yl)-1H-imidazole-2-carboxamide | None |
| 914 | (S)-N-(1-(1-phenylethyl)azetidin-3-yl)-5-cyclopropyl-1H-imidazole-2-carboxamide | None |
| 915 | (R)-N-(1-(1-phenylethyl)azetidin-3-yl)-5-cyclopropyl-1H-imidazole-2-carboxamide | None |
| 916 | 5-cyclopropyl-N-(1-isopropylpiperidin-4-yl)pyridazine-3-carboxamide | None |
| 917 | 5-cyclopropyl-N-(1-methylpiperidin-4-yl)pyridazine-3-carboxamide | None |
| 918 | 5-cyclopropyl-N-(1-methylpiperidin-3-yl)pyridazine-3-carboxamide | None |

TABLE 5

| Cpd. No. | Structure | Chemical Name |
|---|---|---|
| 870 | 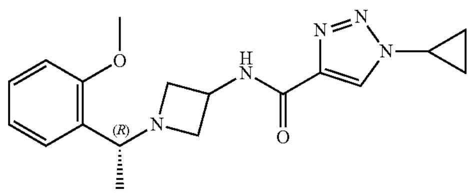 | (R)-1-cyclopropyl-N-(1-(1-(2-methoxyphenyl)ethyl)azetidin-3-yl)-1H-1,2,3-triazole-4-carboxamide |
| 871 | 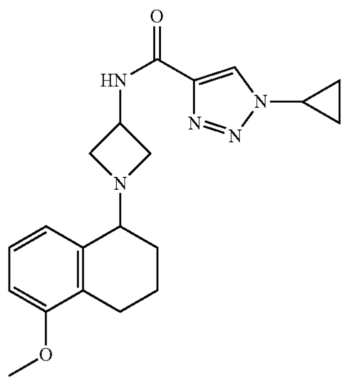 [SMILES: COc1cccc2c1CCCC2N1CC(NC(=O)c2cn(C3CC3)nn2)C1] | 1-cyclopropyl-N-(1-(5-methoxy-1,2,3,4-tetrahydronaphthalen-1-yl)azetidin-3-yl)-1H-1,2,3-triazole-4-carboxamide |
| 872 | 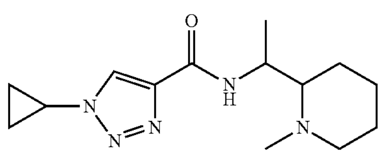 [SMILES: CC(NC(=O)c1cn(C2CC2)nn1)C1CCCCN1C] | 1-cyclopropyl-N-(1-(1-methylpiperidin-2-yl)ethyl)-1H-1,2,3-triazole-4-carboxamide |
| 873 | 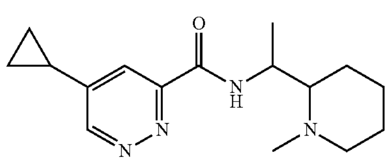 [SMILES: CC(NC(=O)c1cc(C2CC2)cnn1)C1CCCCN1C] | 5-cyclopropyl-N-(1-(1-methylpiperidin-2-yl)ethyl)pyridazine-3-carboxamide |
| 874 | 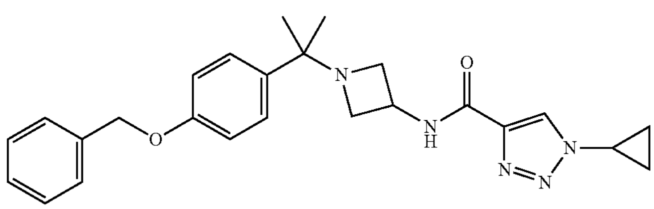 [SMILES: CC(C)(c1ccc(OCc2ccccc2)cc1)N1CC(NC(=O)c2cn(C3CC3)nn2)C1] | N-(1-(2-(4-(benzyloxy)phenyl)propan-2-yl)azetidin-3-yl)-1-cyclopropyl-1H-1,2,3-triazole-4-carboxamide |
| 875 | 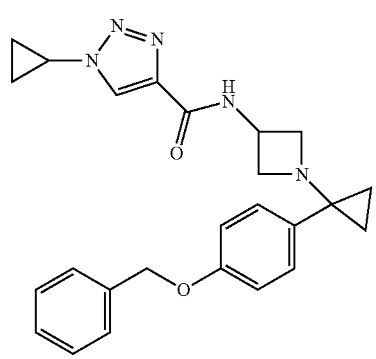 [SMILES: O=C(NC1CN(C2(c3ccc(OCc4ccccc4)cc3)CC2)C1)c1cn(C2CC2)nn1] | N-(1-(1-(4-(benzyloxy)phenyl)cyclopropyl)azetidin-3-yl)-1-cyclopropyl-1H-1,2,3-triazole-4-carboxamide |

TABLE 5-continued

| Cpd. No. | Structure | Chemical Name |
|---|---|---|
| 876 | 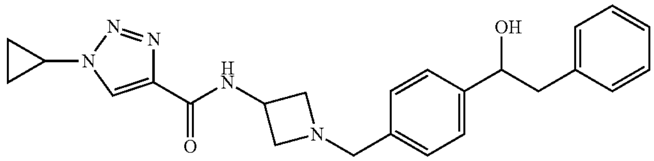 [SMILES: O=C(NC1CN(Cc2ccc(C(O)Cc3ccccc3)cc2)C1)c1cn(C2CC2)nn1] | 1-cyclopropyl-N-(1-(4-(1-hydroxy-2-phenylethyl)benzyl(azetidin-3-yl)-1H-1,2,3-triazole-4-carboxamide |
| 877 | 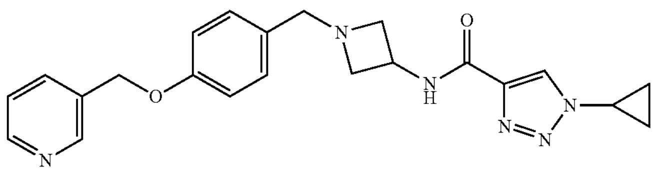 [SMILES: O=C(NC1CN(Cc2ccc(OCc3cccnc3)cc2)C1)c1cn(C2CC2)nn1] | 1-cyclopropyl-N-(1-(4-(pyridin-3-ylmethoxy)benzyl)azetidin-3-yl)-1H-1,2,3-triazole-4-carboxamide |
| 878 | 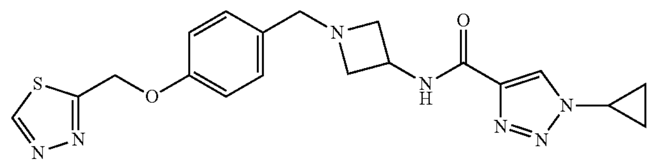 [SMILES: O=C(NC1CN(Cc2ccc(OCc3nncs3)cc2)C1)c1cn(C2CC2)nn1] | N-(1-(4-((1,3,4-thiadiazol-2-yl)methoxy)benzyl)azetidin-3-yl)-1-cyclopropyl-1H-1,2,3-triazole-4-carboxamide |
| 879 | 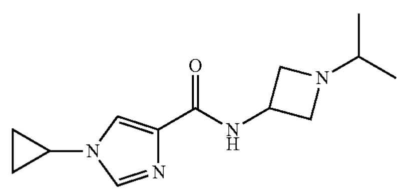 [SMILES: CC(C)N1CC(NC(=O)c2cn(C3CC3)cn2)C1] | 1-cyclopropyl-N-(1-isopropylazetidin-3-yl)-1H-imidazole-4-carboxamide |
| 880 | 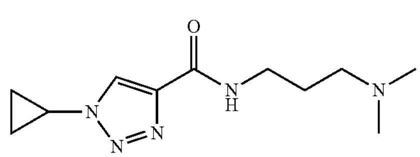 [SMILES: CN(C)CCCNC(=O)c1cn(C2CC2)nn1] | 1-cyclopropyl-N-(3-(dimethylamino)propyl)-1H-1,2,3-triazole-4-carboxamide |
| 881 | 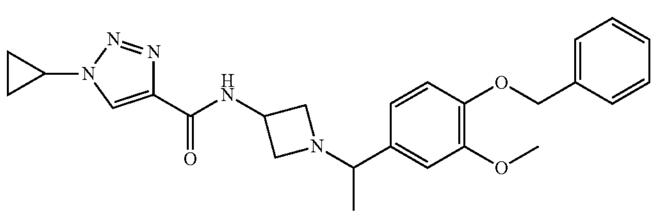 [SMILES: COc1cc(C(C)N2CC(NC(=O)c3cn(C4CC4)nn3)C2)ccc1OCc1ccccc1] | N-(1-(1-(4-(benzyloxy)-3-methoxyphenyl)ethyl)azetidin-3-yl)-1-cyclopropyl-1H-1,2,3-triazole-4-carboxamide |
| 882 | 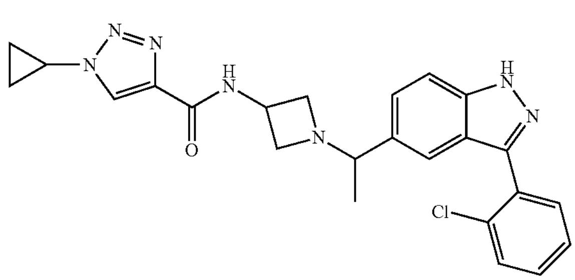 [SMILES: CC(c1ccc2[nH]nc(-c3ccccc3Cl)c2c1)N1CC(NC(=O)c2cn(C3CC3)nn2)C1] | N-(1-1-(3-(2-chlorophenyl)-1H-indazol-5-yl)ethyl)azetidin-3-yl)-1-cyclopropyl-1H-1,2,3-triazole-4-carboxamide |
| 883 | 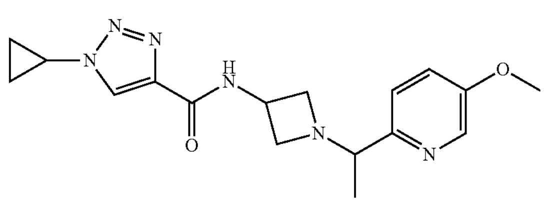 [SMILES: COc1ccc(C(C)N2CC(NC(=O)c3cn(C4CC4)nn3)C2)nc1] | 1-cyclopropyl-N-(1-(1-(5-methoxypyridin-2-yl)ethyl)azetidin-3-yl)-1H-1,2,3-triazole-4-carboxamide |

TABLE 5-continued

| Cpd. No. | Structure | Chemical Name |
|---|---|---|
| 884 | 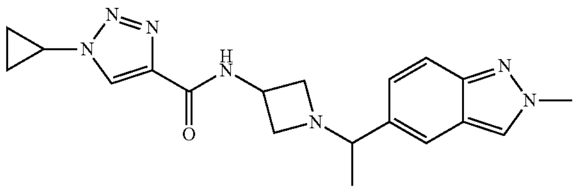 [SMILES: CC(c1ccc2nn(C)cc2c1)N1CC(NC(=O)c2cn(C3CC3)nn2)C1] | 1-cyclopropyl-N-(1-(1-(2-methyl-2H-indazol-5-yl)ethyl)azetidin-3-yl)-1H-1,2,3-triazole-4-carboxamide |
| 885 | 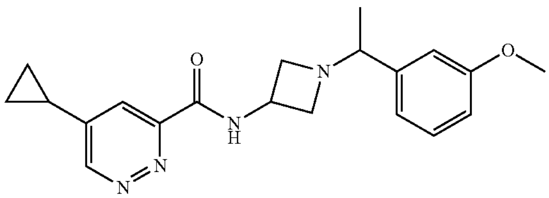 [SMILES: COc1cccc(C(C)N2CC(NC(=O)c3cc(C4CC4)cnn3)C2)c1] | 5-cyclopropyl-N-(1-(1-(3-methoxyphenyl)ethyl)azetidin-3-yl)pyridazine-3-carboxamide |
| 886 | 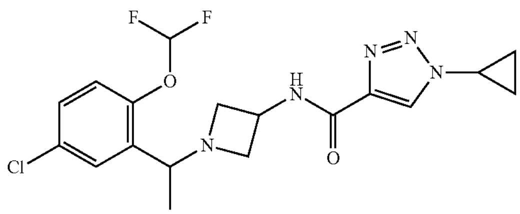 [SMILES: CC(c1cc(Cl)ccc1OC(F)F)N1CC(NC(=O)c2cn(C3CC3)nn2)C1] | N-(1-(1-(5-chloro-2-(difluoromethoxy)phenyl)ethyl)azetidin-3-yl)-1-cyclopropyl-1H-1,2,3-triazole-4-carboxamide |
| 887 | 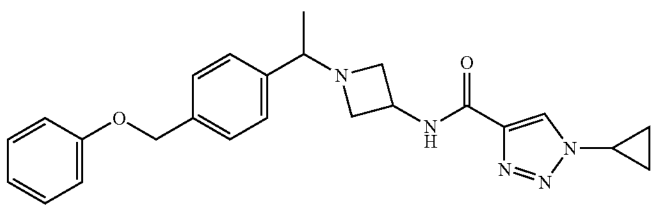 [SMILES: CC(c1ccc(COc2ccccc2)cc1)N1CC(NC(=O)c2cn(C3CC3)nn2)C1] | 1-cyclopropyl-N-(1-(1-(4-(phenoxymethyl)phenyl)ethyl)azetidin-3-yl)-1H-1,2,3-triazole-4-carboxamide |
| 888 | 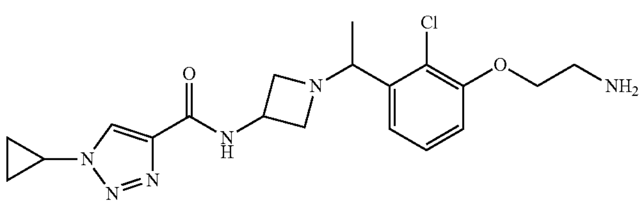 [SMILES: CC(c1cccc(OCCN)c1Cl)N1CC(NC(=O)c2cn(C3CC3)nn2)C1] | N-(1-(1-(3-(2-aminoethoxy)-2-chlorophenyl)ethyl)azetidin-3-yl)-1-cyclopropyl-1H-1,2,3-triazole-4-carboxamide |
| 889 | 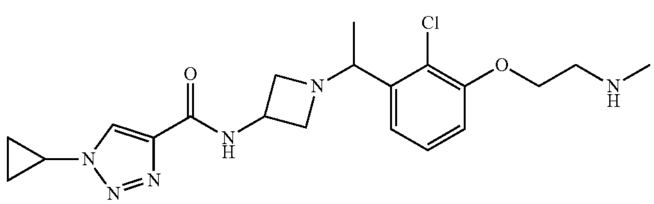 [SMILES: CNCCOc1cccc(C(C)N2CC(NC(=O)c3cn(C4CC4)nn3)C2)c1Cl] | N-(1-(1-(2-chloro-3-(2-(methylamino)ethoxy)phenyl)ethyl)azetidin-3-yl)-1-cyclopropyl-1H-1,2,3-triazole-4-carboxamide |
| 890 | 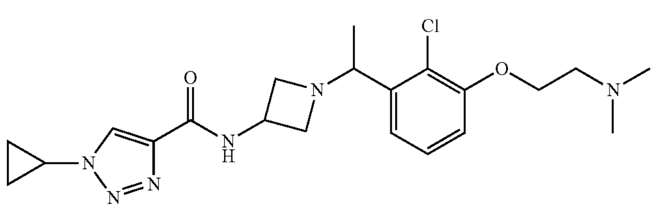 [SMILES: CC(c1cccc(OCCN(C)C)c1Cl)N1CC(NC(=O)c2cn(C3CC3)nn2)C1] | N-(1-(1-(2-chloro-3-(2-(dimethylamino)ethoxy)phenyl)ethyl)azetidin-3-yl)-1-cyclopropyl-1H-1,2,3-triazole-4-carboxamide |

TABLE 5-continued

| Cpd. No. | Structure | Chemical Name |
|---|---|---|
| 891 | 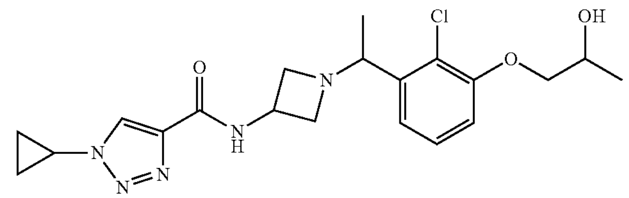 [SMILES: CC(O)COc1cccc(C(C)N2CC(NC(=O)c3cn(C4CC4)nn3)C2)c1Cl] | N-(1-(1-(2-chloro-3-(2-hydroxypropoxy)phenyl)ethyl)azetidin-3-yl)-1-cyclopropyl-1H-1,2,3-triazole-4-carboxamide |
| 892 | 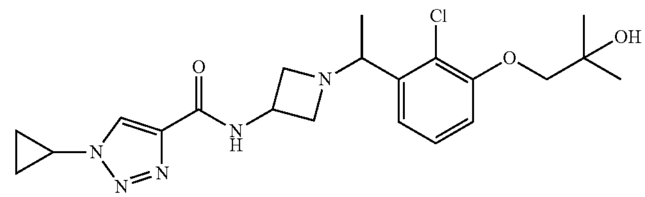 [SMILES: CC(c1cccc(OCC(C)(C)O)c1Cl)N1CC(NC(=O)c2cn(C3CC3)nn2)C1] | N-(1-(1-(2-chloro-3-(2-hydroxy-2-methylpropoxy)phenyl)ethyl)azetidin-3-yl)-1-cyclopropyl-1H-1,2,3-triazole-4-carboxamide |
| 893 | 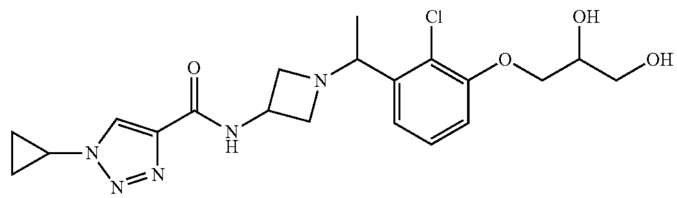 [SMILES: CC(c1cccc(OCC(O)CO)c1Cl)N1CC(NC(=O)c2cn(C3CC3)nn2)C1] | N-(1-(1-(2-chloro-3-(2,3-dihydroxypropoxy)phenyl)ethyl)azetidin-3-yl)-1-cyclopropyl-1H-1,2,3-triazole-4-carboxamide |
| 894 | 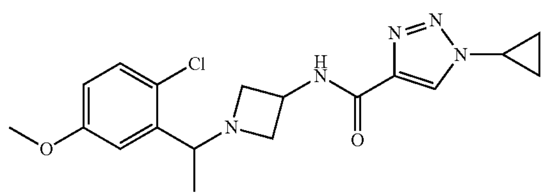 [SMILES: COc1ccc(Cl)c(C(C)N2CC(NC(=O)c3cn(C4CC4)nn3)C2)c1] | N-(1-(1-(2-chloro-5-methoxyphenyl)ethyl)azetidin-3-yl)-1-cyclopropyl-1H-1,2,3-triazole-4-carboxamide |
| 895 | 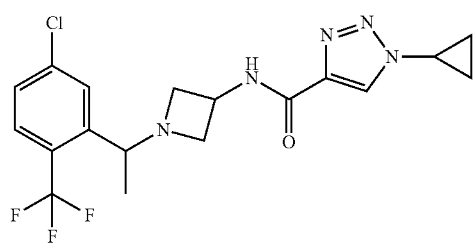 [SMILES: CC(c1cc(Cl)ccc1C(F)(F)F)N1CC(NC(=O)c2cn(C3CC3)nn2)C1] | N-(1-(1-(5-chloro-2-(trifluoromethyl)phenyl)ethyl)azetidin-3-yl)-1-cyclopropyl-1H-1,2,3-triazole-4-carboxamide |
| 896 | 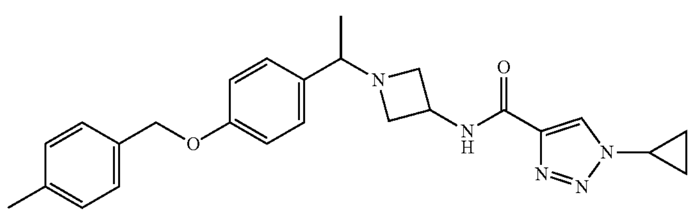 [SMILES: Cc1ccc(COc2ccc(C(C)N3CC(NC(=O)c4cn(C5CC5)nn4)C3)cc2)cc1] | 1-cyclopropyl-N-(1-(1-(4-((4-methylbenzyl)oxy)phenyl)ethyl)azetidin-3-yl)-1H-1,2,3-triazole-4-carboxamide |
| 897 | 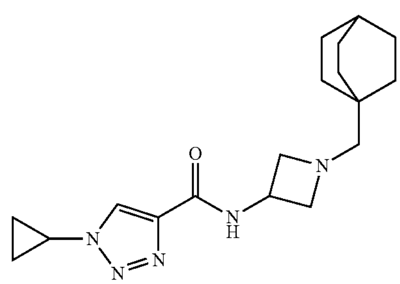 [SMILES: O=C(NC1CN(CC23CCC(CC2)CC3)C1)c1cn(C2CC2)nn1] | N-(1-(bicyclo[2.2.2]octan-1-ylmethyl)azetidin-3-yl)-1-cyclopropyl-1H-1,2,3-triazole-4-carboxamide |

TABLE 5-continued

| Cpd. No. | Structure | Chemical Name |
|---|---|---|
| 898 | 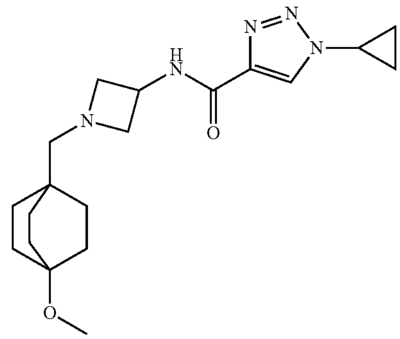 [SMILES: COC12CCC(CN3CC(NC(=O)c4cn(C5CC5)nn4)C3)(CC1)CC2] | 1-cyclopropyl-N-(1-((4-methoxybicyclo[2.2.2]octan-1-yl)methyl)azetidin-3-yl)-1H-1,2,3-triazole-4-carboxamide |
| 899 | 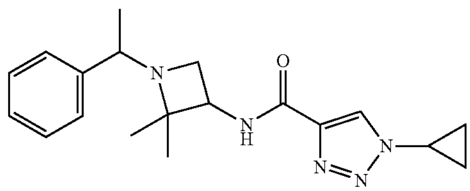 [SMILES: CC(c1ccccc1)N1CC(NC(=O)c2cn(C3CC3)nn2)C1(C)C] | 1-cyclopropyl-N-(2,2-dimethyl-1-(1-phenylethyl)azetidin-3-yl)-1H-1,2,3-triazole-4-carboxamide |
| 900 | 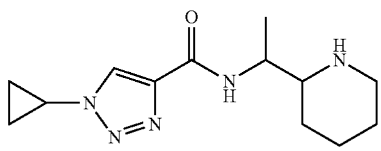 [SMILES: CC(NC(=O)c1cn(C2CC2)nn1)C1CCCCN1] | 1-cyclopropyl-N-(1-(piperidin-2-yl)ethyl)-1H-1,2,3-triazole-4-carboxamide |
| 901 | 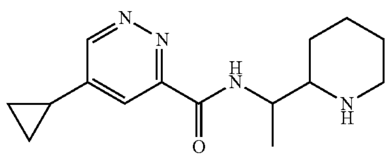 [SMILES: CC(NC(=O)c1cc(C2CC2)cnn1)C1CCCCN1] | 5-cyclopropyl-N-(1-(piperidin-2-yl)ethyl)pyridazine-3-carboxamide |
| 902 | 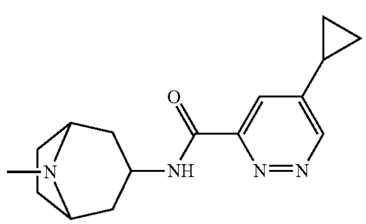 [SMILES: CN1C2CCC1CC(NC(=O)c1cc(C3CC3)cnn1)C2] | 5-cyclopropyl-N-(8-methyl-8-azabicyclo[3.2.1]octan-3-yl)pyridazine-3-carboxamide |
| 903 | 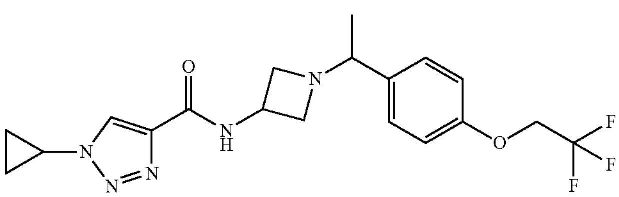 [SMILES: CC(c1ccc(OCC(F)(F)F)cc1)N1CC(NC(=O)c2cn(C3CC3)nn2)C1] | 1-cyclopropyl-N-(1-(1-(4-(2,2,2-trifluoroethoxy)phenyl)ethyl)azetidin-3-yl)-1H-1,2,3-triazole-4-carboxamide |
| 904 | 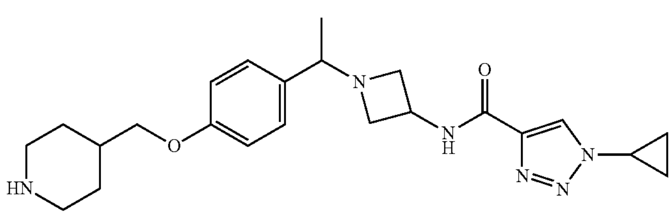 [SMILES: CC(c1ccc(OCC2CCNCC2)cc1)N1CC(NC(=O)c2cn(C3CC3)nn2)C1] | 1-cyclopropyl-N-(1-(1-(4-(piperidin-4-ylmethoxy)phenyl)ethyl)azetidin-3-yl)-1H-1,2,3-triazole-4-carboxamide |

TABLE 5-continued

| Cpd. No. | Structure | Chemical Name |
|---|---|---|
| 905 | 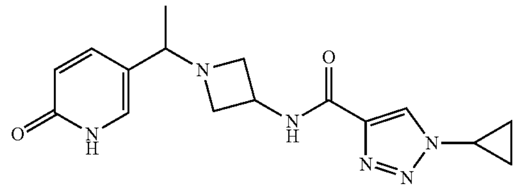 [SMILES: CC(c1ccc(=O)[nH]c1)N1CC(NC(=O)c2cn(C3CC3)nn2)C1] | 1-cyclopropyl-N-(1-(1-(6-oxo-1,6-dihydropyridin-3-yl)ethyl)azetidin-3-yl)-1H-1,2,3-triazole-4-carboxamide |
| 906 | 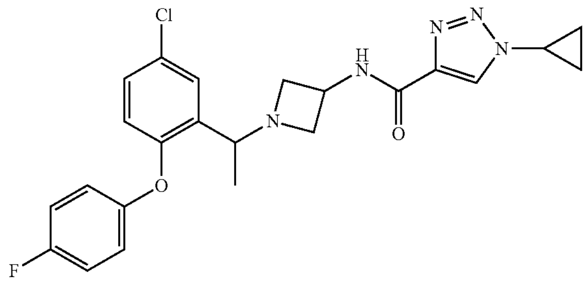 [SMILES: CC(c1cc(Cl)ccc1Oc1ccc(F)cc1)N1CC(NC(=O)c2cn(C3CC3)nn2)C1] | N-(1-(1-(5-chloro-2-(4-fluorophenoxy)phenyl)ethyl)azetidin-3-yl)-1-cyclopropyl-1H-1,2,3-triazole-4-carboxamide |
| 907 | 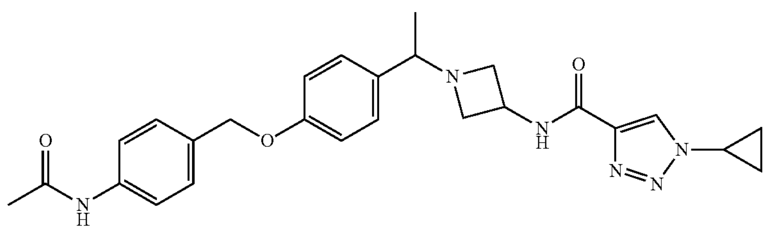 [SMILES: CC(=O)Nc1ccc(COc2ccc(C(C)N3CC(NC(=O)c4cn(C5CC5)nn4)C3)cc2)cc1] | N-(1-(1-(4-((4-acetamidobenzyl)oxy)phenyl)ethyl)azetidin-3-yl)-1-cyclopropyl-1H-1,2,3-triazole-4-carboxamide |
| 908 | 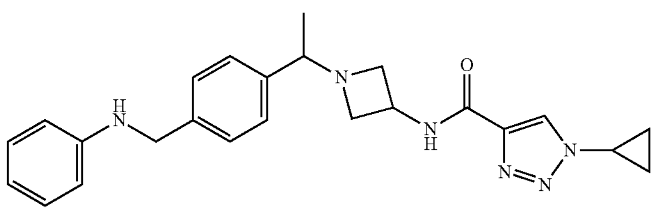 [SMILES: CC(c1ccc(CNc2ccccc2)cc1)N1CC(NC(=O)c2cn(C3CC3)nn2)C1] | 1-cyclopropyl-N-(1-(1-(4-((phenylamino)methyl)phenyl)ethyl)azetidin-3-yl)-1H-1,2,3-triazole-4-carboxamide |
| 909 | 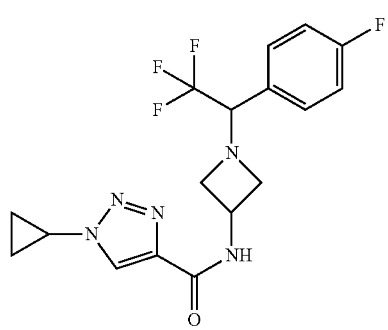 [SMILES: O=C(NC1CN(C(c2ccc(F)cc2)C(F)(F)F)C1)c1cn(C2CC2)nn1] | 1-cyclopropyl-N-(1-(2,2,2-trifluoro-1-(4-fluorophenyl)ethyl)azetidin-3-yl)-1H-1,2,3-triazole-4-carboxamide |
| 910 | 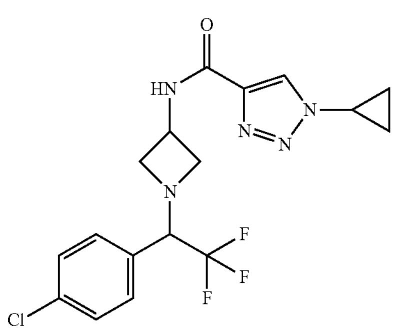 [SMILES: O=C(NC1CN(C(c2ccc(Cl)cc2)C(F)(F)F)C1)c1cn(C2CC2)nn1] | N-(1-(1-(4-chlorophenyl)-2,2,2-trifluoroethyl)azetidin-3-yl)-1-cyclopropyl-1H-1,2,3-triazole-4-carboxamide |

TABLE 5-continued
| Cpd. No. | Structure | Chemical Name |
|---|---|---|
| 911 | 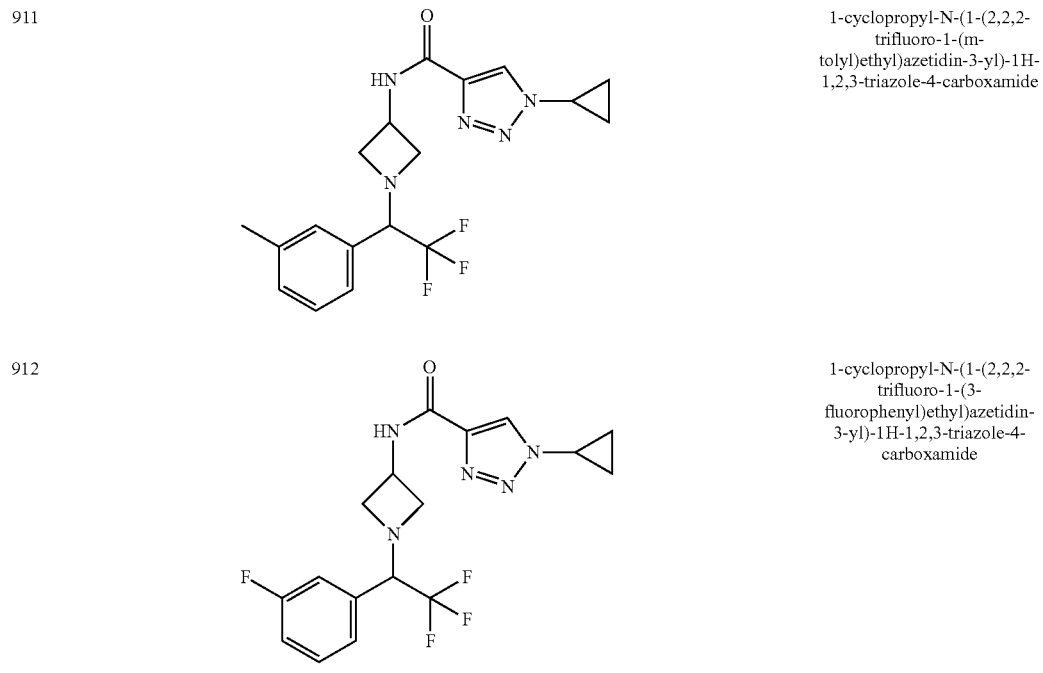 | 1-cyclopropyl-N-(1-(2,2,2-trifluoro-1-(m-tolyl)ethyl)azetidin-3-yl)-1H-1,2,3-triazole-4-carboxamide |
| 912 | 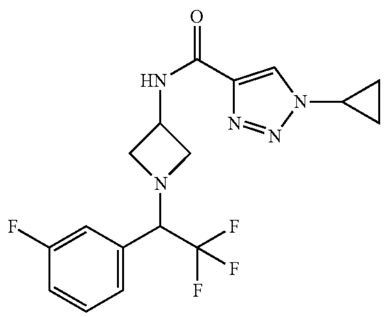 [SMILES: O=C(NC1CN(C(c2cccc(F)c2)C(F)(F)F)C1)c1cn(C2CC2)nn1] | 1-cyclopropyl-N-(1-(2,2,2-trifluoro-1-(3-fluorophenyl)ethyl)azetidin-3-yl)-1H-1,2,3-triazole-4-carboxamide |
TABLE 6
| Cpd. No. | Structure | Salt Form |
|---|---|---|
| 919 | 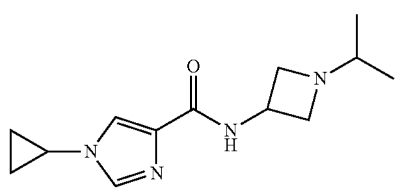 [SMILES: CC(C)N1CC(NC(=O)c2cn(C3CC3)cn2)C1] | none |
| 920 | 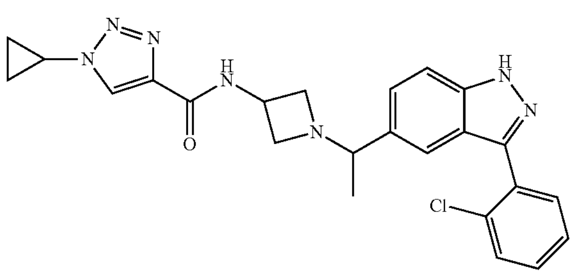 [SMILES: CC(c1ccc2[nH]nc(-c3ccccc3Cl)c2c1)N1CC(NC(=O)c2cn(C3CC3)nn2)C1] | none |
| 921 | 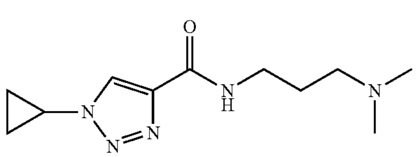 [SMILES: CN(C)CCCNC(=O)c1cn(C2CC2)nn1] | none |

TABLE 6-continued

| Cpd. No. | Structure | Salt Form |
|---|---|---|
| 922 | 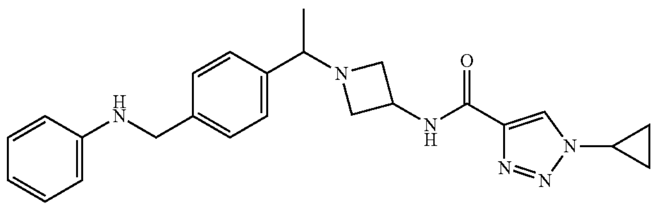 [SMILES: CC(c1ccc(CNc2ccccc2)cc1)N1CC(NC(=O)c2cn(C3CC3)nn2)C1] | none |
| 923 | 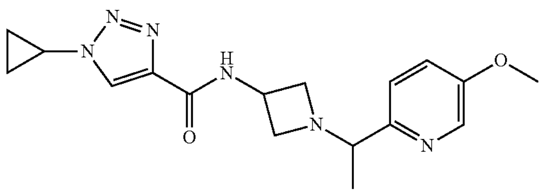 [SMILES: COc1ccc(C(C)N2CC(NC(=O)c3cn(C4CC4)nn3)C2)nc1] | none |
| 924 | 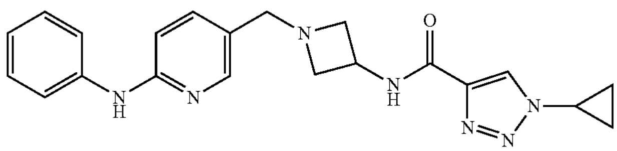 [SMILES: O=C(NC1CN(Cc2ccc(Nc3ccccc3)nc2)C1)c1cn(C2CC2)nn1] | none |
| 925 | 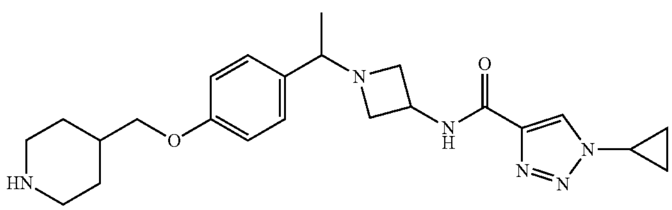 [SMILES: CC(c1ccc(OCC2CCNCC2)cc1)N1CC(NC(=O)c2cn(C3CC3)nn2)C1] | none |
| 926 | 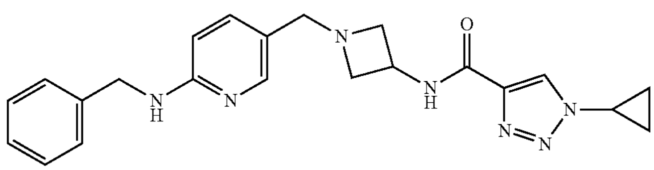 [SMILES: O=C(NC1CN(Cc2ccc(NCc3ccccc3)nc2)C1)c1cn(C2CC2)nn1] | none |
| 927 | 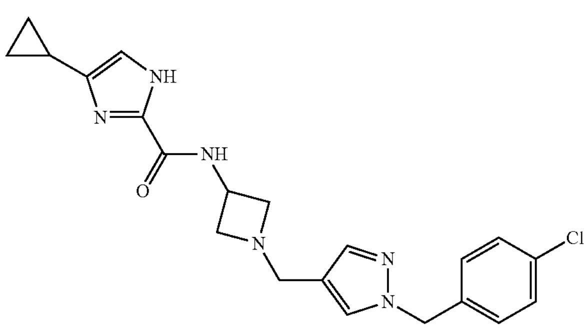 [SMILES: O=C(NC1CN(Cc2cnn(Cc3ccc(Cl)cc3)c2)C1)c1nc(C2CC2)c[nH]1] | none |
| 928 | 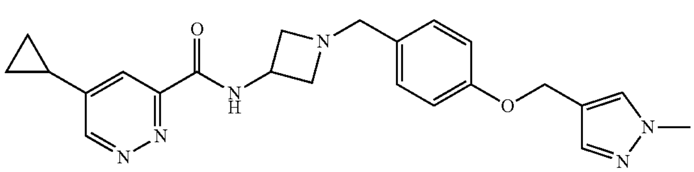 [SMILES: Cn1cc(COc2ccc(CN3CC(NC(=O)c4cc(C5CC5)cnn4)C3)cc2)cn1] | none |

TABLE 6-continued

| Cpd. No. | Structure | Salt Form |
|---|---|---|
| 929 | 5-cyclopropyl-N-(1-((1-(4-chlorobenzyl)-1H-pyrazol-4-yl)methyl)azetidin-3-yl)pyridazine-3-carboxamide | none |
| 930 | 4-cyclopropyl-N-(1-((1-(4-chlorobenzyl)-1H-pyrazol-4-yl)methyl)azetidin-3-yl)picolinamide | none |
| 931 | 1-benzyl-N-(1-((1-cyclopropyl-1H-1,2,3-triazol-4-yl)methyl... | none |
| 932 | 1-cyclopropyl-N-(1-((1-(4-methoxybenzyl)-1H-pyrazol-4-yl)methyl)azetidin-3-yl)-1H-1,2,3-triazole-4-carboxamide | none |
| 933 | 5-cyclopropyl-N-(1-((1-benzyl-1H-pyrazol-4-yl)methyl)azetidin-3-yl)pyridazine-3-carboxamide | none |
| 934 | 5-cyclopropyl-N-(1-(1-(3-methoxyphenyl)ethyl)azetidin-3-yl)pyridazine-3-carboxamide | none |

TABLE 6-continued

| Cpd. No. | Structure | Salt Form |
|---|---|---|
| 935 | 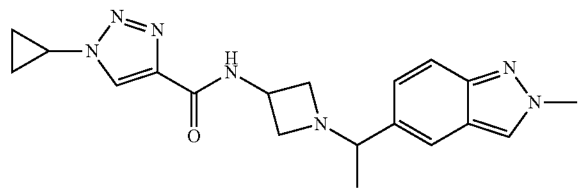 [SMILES: CC(c1ccc2nn(C)cc2c1)N1CC(NC(=O)c2cn(C3CC3)nn2)C1] | none |
| 936 | 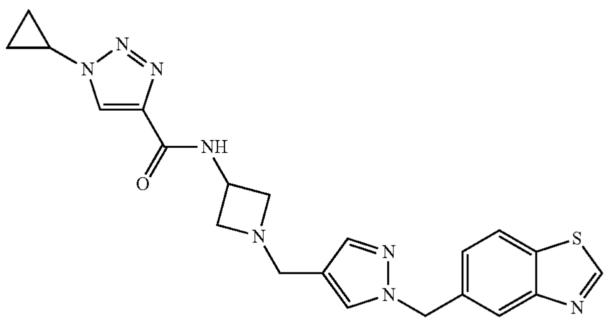 [SMILES: O=C(NC1CN(Cc2cnn(Cc3ccc4scnc4c3)c2)C1)c1cn(C2CC2)nn1] | none |
| 937 | 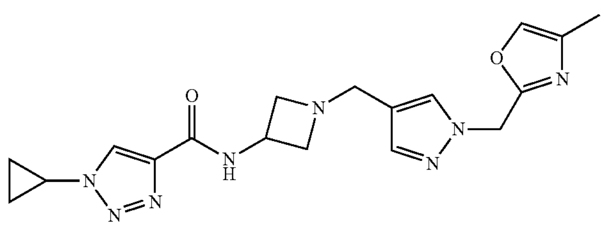 [SMILES: Cc1coc(Cn2cc(CN3CC(NC(=O)c4cn(C5CC5)nn4)C3)cn2)n1] | none |
| 938 | 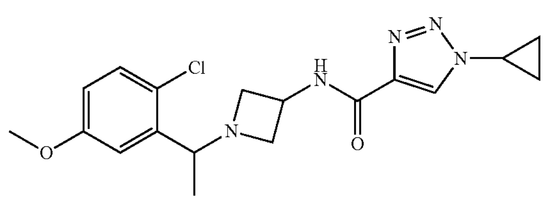 [SMILES: COc1ccc(Cl)c(C(C)N2CC(NC(=O)c3cn(C4CC4)nn3)C2)c1] | none |
| 939 | 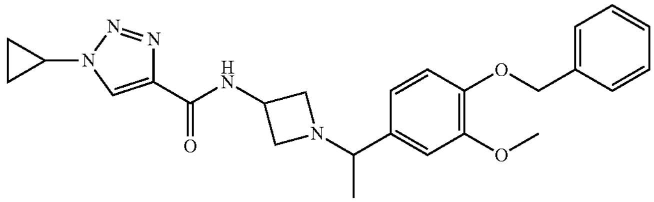 | none |
| 940 | 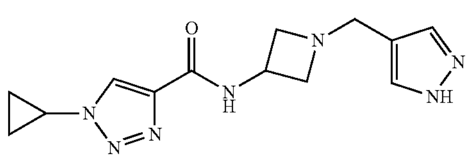 [SMILES: O=C(NC1CN(Cc2cn[nH]c2)C1)c1cn(C2CC2)nn1] | none |

TABLE 6-continued

| Cpd. No. | Structure | Salt Form |
|---|---|---|
| 941 | 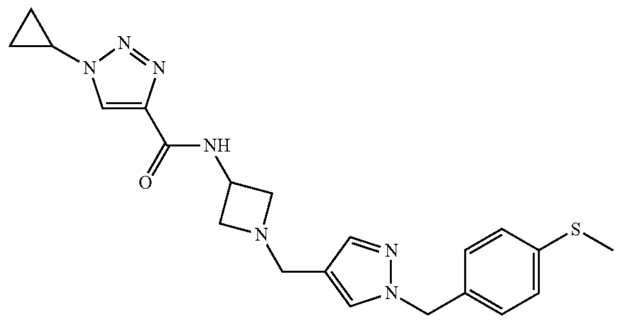 [SMILES: CSc1ccc(Cn2cc(CN3CC(NC(=O)c4cn(C5CC5)nn4)C3)cn2)cc1] | none |
| 942 | 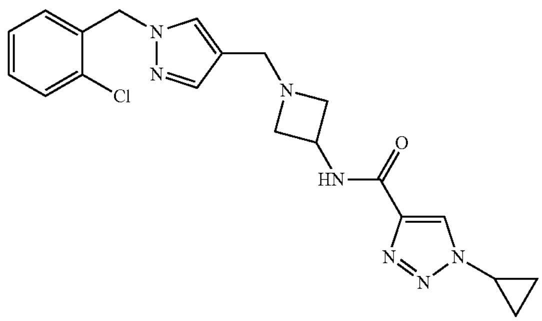 [SMILES: O=C(NC1CN(Cc2cnn(Cc3ccccc3Cl)c2)C1)c1cn(C2CC2)nn1] | none |
| 943 | 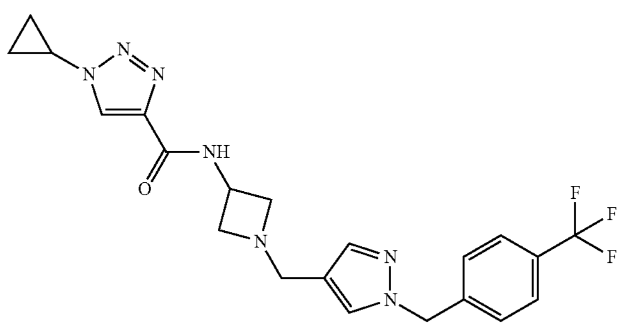 [SMILES: O=C(NC1CN(Cc2cnn(Cc3ccc(C(F)(F)F)cc3)c2)C1)c1cn(C2CC2)nn1] | none |
| 944 | 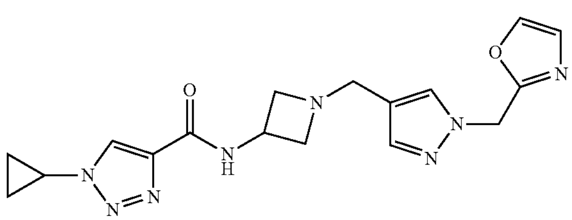 [SMILES: O=C(NC1CN(Cc2cnn(Cc3ncco3)c2)C1)c1cn(C2CC2)nn1] | none |
| 945 | 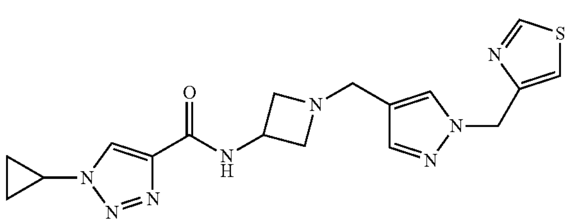 [SMILES: O=C(NC1CN(Cc2cnn(Cc3cscn3)c2)C1)c1cn(C2CC2)nn1] | none |
| 946 | 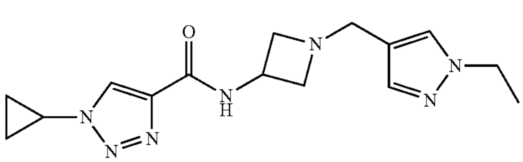 [SMILES: CCn1cc(CN2CC(NC(=O)c3cn(C4CC4)nn3)C2)cn1] | none |

TABLE 6-continued

| Cpd. No. | Structure | Salt Form |
|---|---|---|
| 947 | 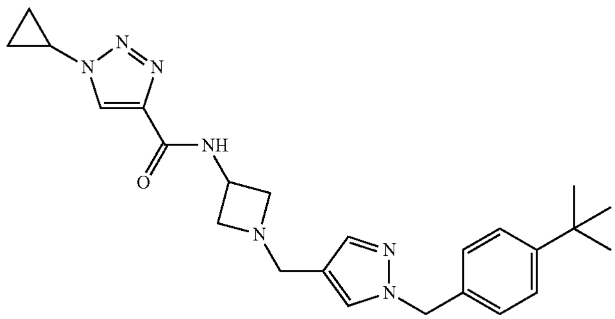 [SMILES: CC(C)(C)c1ccc(Cn2cc(CN3CC(NC(=O)c4cn(C5CC5)nn4)C3)cn2)cc1] | none |
| 948 | 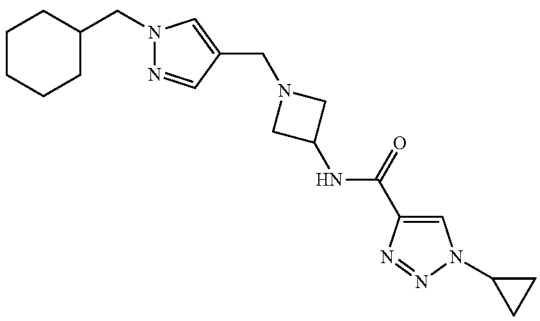 [SMILES: O=C(NC1CN(Cc2cnn(CC3CCCCC3)c2)C1)c1cn(C2CC2)nn1] | none |
| 949 | 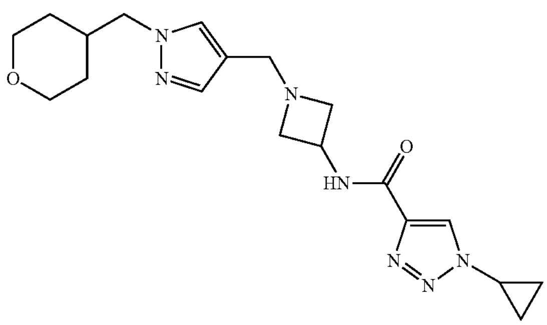 [SMILES: O=C(NC1CN(Cc2cnn(CC3CCOCC3)c2)C1)c1cn(C2CC2)nn1] | none |
| 950 | 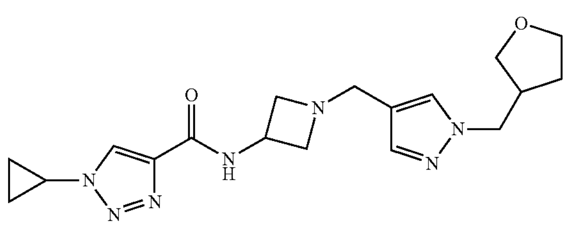 [SMILES: O=C(NC1CN(Cc2cnn(CC3CCOC3)c2)C1)c1cn(C2CC2)nn1] | none |
| 951 | 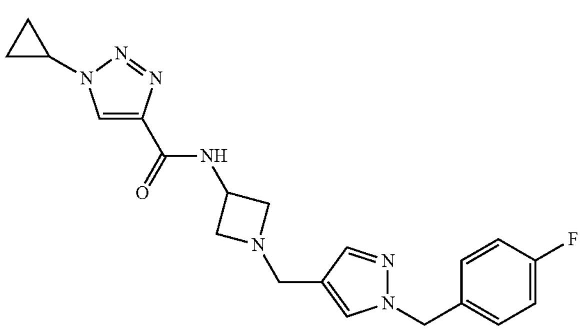 [SMILES: O=C(NC1CN(Cc2cnn(Cc3ccc(F)cc3)c2)C1)c1cn(C2CC2)nn1] | none |

TABLE 6-continued

| Cpd. No. | Structure | Salt Form |
|---|---|---|
| 952 | 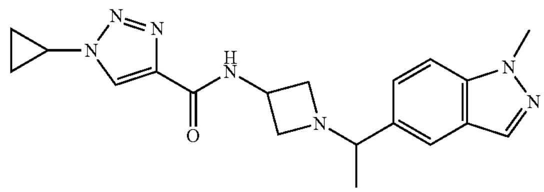 [SMILES: CC(c1ccc2c(cnn2C)c1)N1CC(NC(=O)c2cn(C3CC3)nn2)C1] | none |
| 953 | 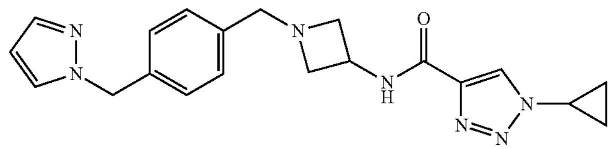 [SMILES: O=C(NC1CN(Cc2ccc(Cn3cccn3)cc2)C1)c1cn(C2CC2)nn1] | none |
| 954 | 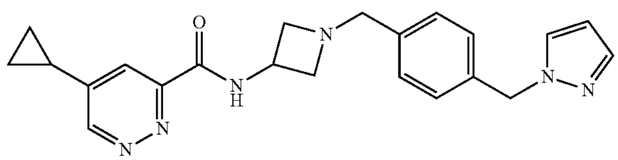 [SMILES: O=C(NC1CN(Cc2ccc(Cn3cccn3)cc2)C1)c1cc(C2CC2)cnn1] | none |
| 955 | 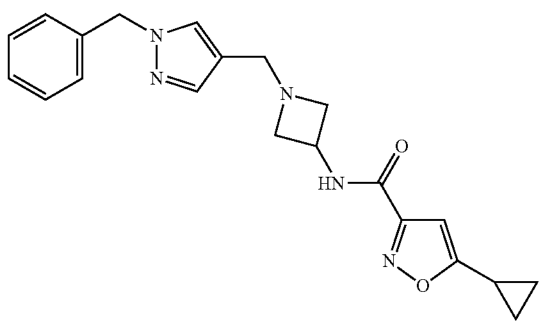 [SMILES: O=C(NC1CN(Cc2cnn(Cc3ccccc3)c2)C1)c1cc(C2CC2)on1] | none |
| 956 | 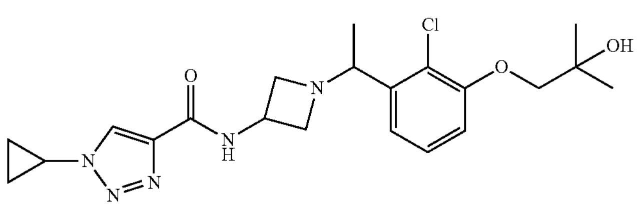 [SMILES: CC(c1cccc(OCC(C)(C)O)c1Cl)N1CC(NC(=O)c2cn(C3CC3)nn2)C1] | none |
| 957 | 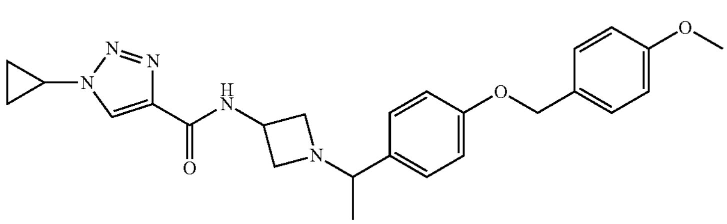 [SMILES: COc1ccc(COc2ccc(C(C)N3CC(NC(=O)c4cn(C5CC5)nn4)C3)cc2)cc1] | none |
| 958 | 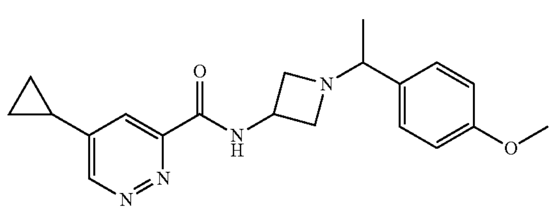 [SMILES: COc1ccc(C(C)N2CC(NC(=O)c3cc(C4CC4)cnn3)C2)cc1] | none |

TABLE 6-continued

| Cpd. No. | Structure | Salt Form |
|---|---|---|
| 959 | 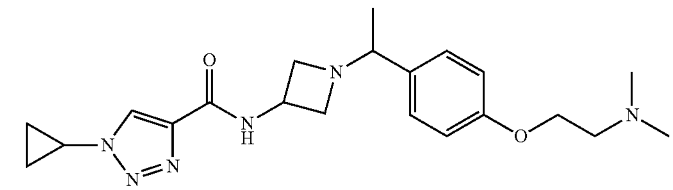 [SMILES: CC(c1ccc(OCCN(C)C)cc1)N1CC(NC(=O)c2cn(C3CC3)nn2)C1] | none |
| 960 | 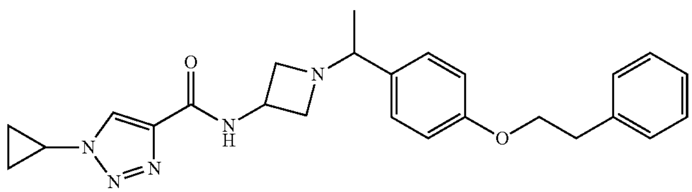 [SMILES: CC(c1ccc(OCCc2ccccc2)cc1)N1CC(NC(=O)c2cn(C3CC3)nn2)C1] | none |
| 961 | 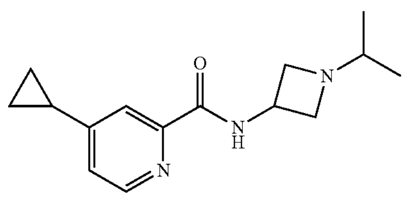 [SMILES: CC(C)N1CC(NC(=O)c2cc(C3CC3)ccn2)C1] | none |
| 962 | 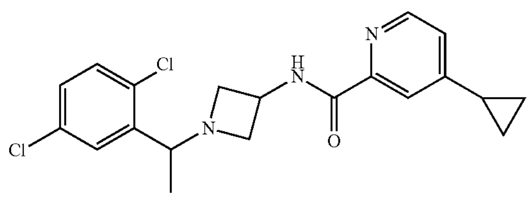 [SMILES: CC(c1cc(Cl)ccc1Cl)N1CC(NC(=O)c2cc(C3CC3)ccn2)C1] | none |
| 963 | 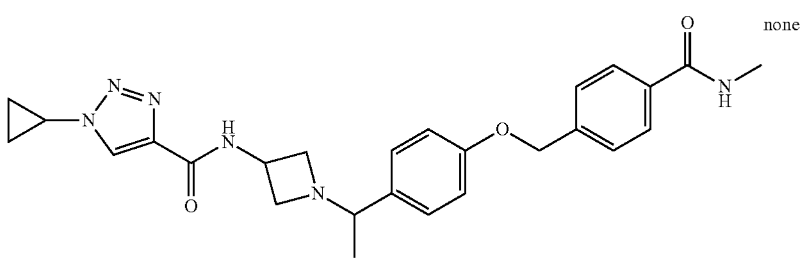 | none |
| 964 | 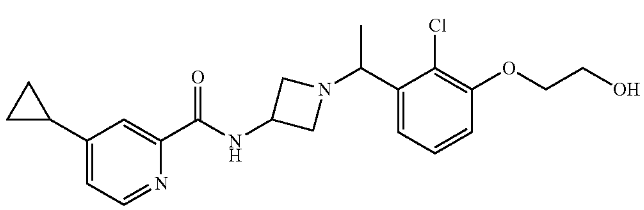 [SMILES: CC(c1cccc(OCCO)c1Cl)N1CC(NC(=O)c2cc(C3CC3)ccn2)C1] | none |
| 965 | 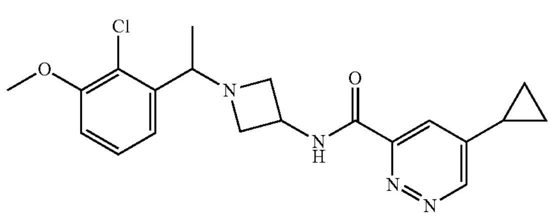 [SMILES: COc1cccc(C(C)N2CC(NC(=O)c3cc(C4CC4)cnn3)C2)c1Cl] | none |

TABLE 6-continued

| Cpd. No. | Structure | Salt Form |
|---|---|---|
| 966 | 4-cyclopropyl-N-(1-((1-benzyl-1H-pyrazol-4-yl)methyl)azetidin-3-yl)picolinamide | none |
| 967 | 4-cyclopropyl-N-(1-(4-(benzyloxy)benzyl)azetidin-3-yl)picolinamide | none |
| 968 | 1-cyclopropyl-N-(1-(1-(4-(2,2,2-trifluoroethoxy)phenyl)ethyl)azetidin-3-yl)-1H-1,2,3-triazole-4-carboxamide | none |
| 969 | 1-cyclopropyl-N-(1-((trans-3-(benzyloxy)cyclobutyl)methyl)azetidin-3-yl)-1H-1,2,3-triazole-4-carboxamide | none |
| 970 | N-(1-(5-chloro-2-(difluoromethoxy)phenyl)ethyl)azetidin-3-yl)-1-cyclopropyl-1H-1,2,3-triazole-4-carboxamide | none |
| 971 | 1-cyclopropyl-N-(1-(1-(4-((4-methylbenzyl)oxy)phenyl)ethyl)azetidin-3-yl)-1H-1,2,3-triazole-4-carboxamide | none |
| 972 | 1-cyclopropyl-N-(1-(4-(pyridin-3-ylmethoxy)benzyl)azetidin-3-yl)-1H-1,2,3-triazole-4-carboxamide | none |
| 973 | N-(1-(1-(2-chloro-3-(2,3-dihydroxypropoxy)phenyl)ethyl)azetidin-3-yl)-1-cyclopropyl-1H-1,2,3-triazole-4-carboxamide | none |

TABLE 6-continued

| Cpd. No. | Structure | Salt Form |
|---|---|---|
| 974 | 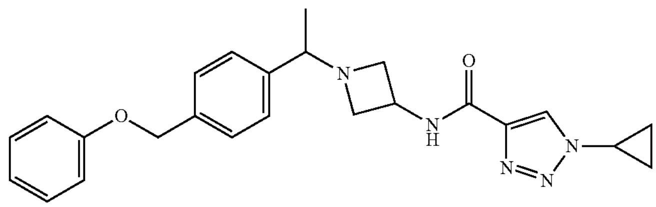 [SMILES: CC(c1ccc(COc2ccccc2)cc1)N1CC(NC(=O)c2cn(C3CC3)nn2)C1] | none |
| 975 | 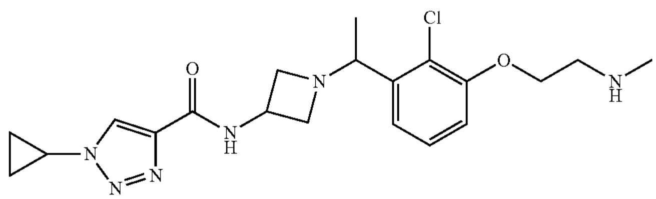 [SMILES: CNCCOc1cccc(C(C)N2CC(NC(=O)c3cn(C4CC4)nn3)C2)c1Cl] | none |
| 976 | 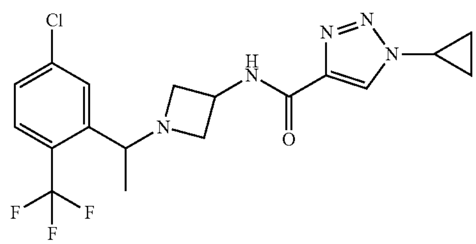 [SMILES: CC(c1cc(Cl)ccc1C(F)(F)F)N1CC(NC(=O)c2cn(C3CC3)nn2)C1] | none |
| 977 | 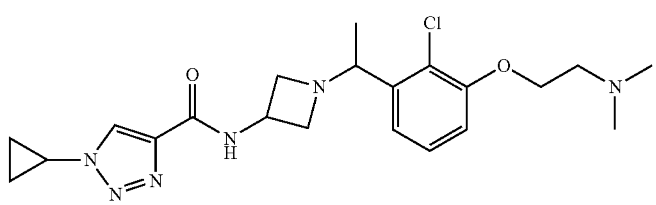 [SMILES: CC(c1cccc(OCCN(C)C)c1Cl)N1CC(NC(=O)c2cn(C3CC3)nn2)C1] | none |
| 978 | 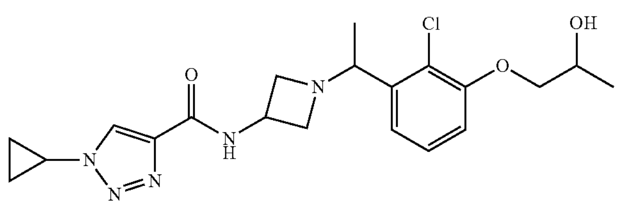 [SMILES: CC(O)COc1cccc(C(C)N2CC(NC(=O)c3cn(C4CC4)nn3)C2)c1Cl] | none |
| 979 | 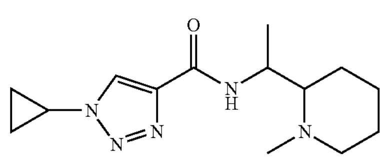 [SMILES: CC(NC(=O)c1cn(C2CC2)nn1)C1CCCCN1C] | none |
| 980 | 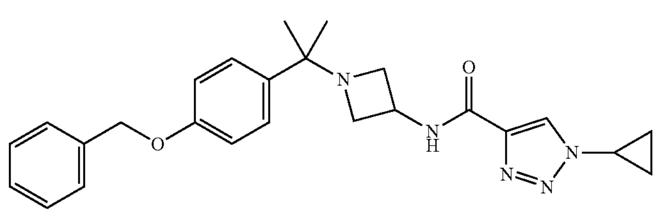 [SMILES: CC(C)(c1ccc(OCc2ccccc2)cc1)N1CC(NC(=O)c2cn(C3CC3)nn2)C1] | none |

TABLE 6-continued

| Cpd. No. | Structure | Salt Form |
|---|---|---|
| 981 | 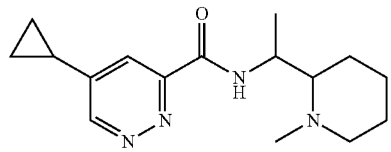 [SMILES: CC(NC(=O)c1cc(C2CC2)cnn1)C1CCCCN1C] | none |
| 982 | 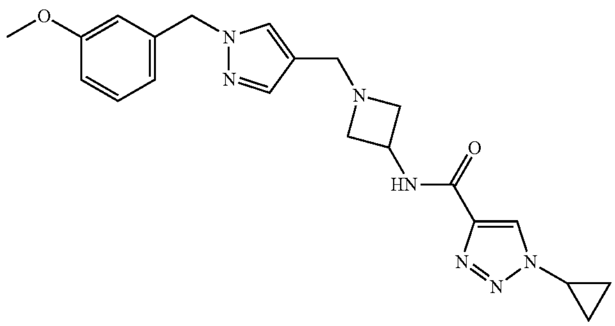 [SMILES: COc1cccc(Cn2cc(CN3CC(NC(=O)c4cn(C5CC5)nn4)C3)cn2)c1] | none |
| 983 | 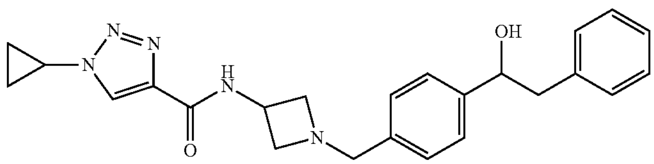 [SMILES: O=C(NC1CN(Cc2ccc(C(O)Cc3ccccc3)cc2)C1)c1cn(C2CC2)nn1] | none |
| 984 | 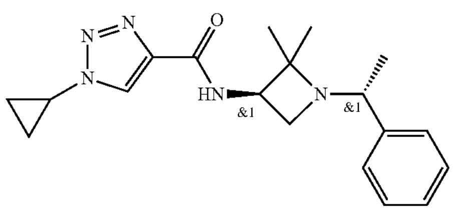 [SMILES: C[C@H](c1ccccc1)N1C[C@@H](NC(=O)c2cn(C3CC3)nn2)C1(C)C] | none |
| 985 | 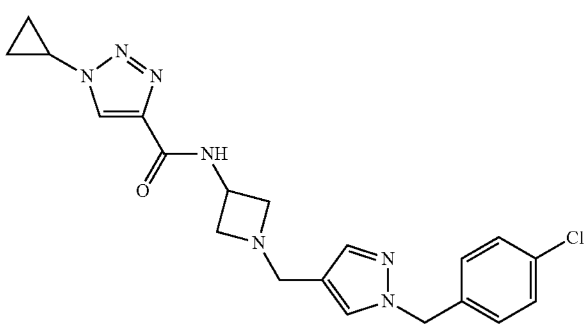 [SMILES: O=C(NC1CN(Cc2cnn(Cc3ccc(Cl)cc3)c2)C1)c1cn(C2CC2)nn1] | none |
| 986 | 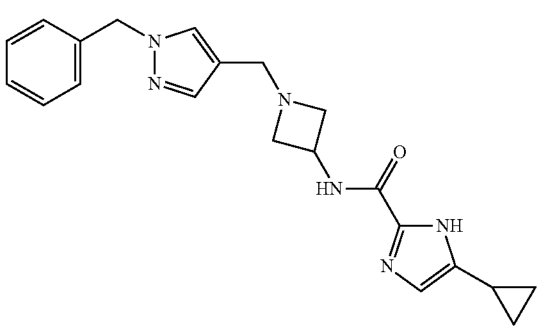 [SMILES: O=C(NC1CN(Cc2cnn(Cc3ccccc3)c2)C1)c1ncc(C2CC2)[nH]1] | none |

TABLE 6-continued
| Cpd. No. | Structure | Salt Form |
|---|---|---|
| 987 | 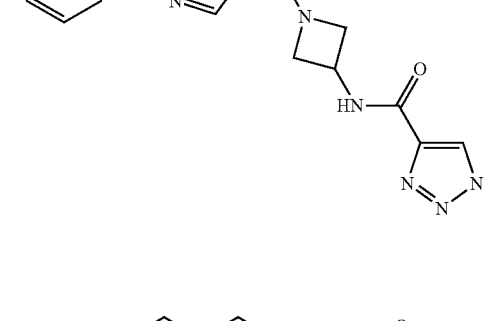 | none |
| 988 | 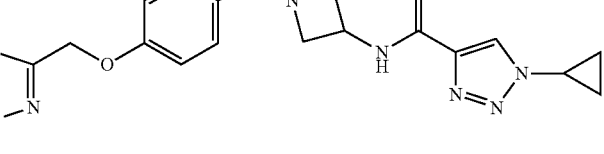 | none |
| 989 | 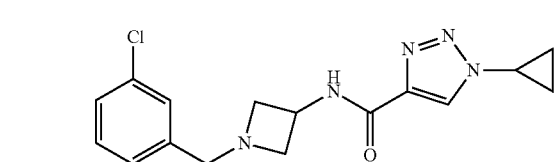 | none |
| 990 | 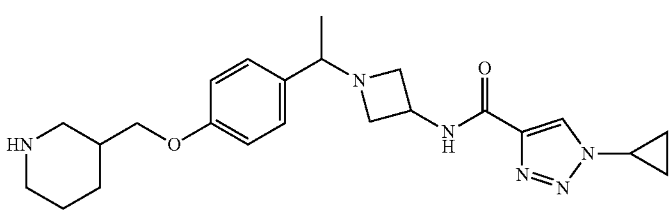 [SMILES: CC(c1ccc(OCC2CCCNC2)cc1)N1CC(NC(=O)c2cn(C3CC3)nn2)C1] | none |
| 991 | 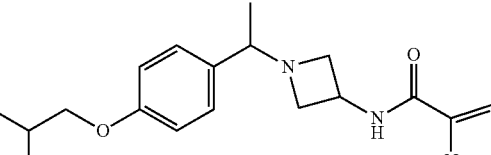 | none |
| 992 | 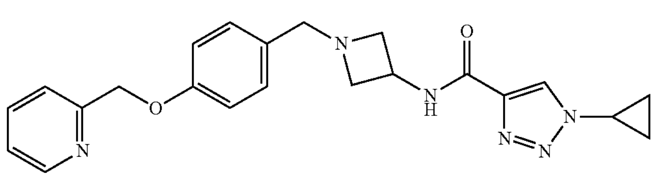 [SMILES: O=C(NC1CN(Cc2ccc(OCc3ccccn3)cc2)C1)c1cn(C2CC2)nn1] | none |

TABLE 6-continued

| Cpd. No. | Structure | Salt Form |
|---|---|---|
| 993 | 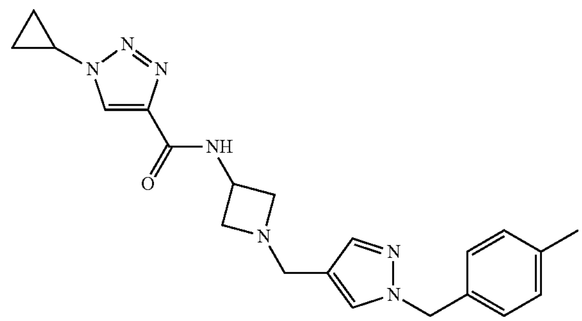 [SMILES: Cc1ccc(Cn2cc(CN3CC(NC(=O)c4cn(C5CC5)nn4)C3)cn2)cc1] | none |
| 994 | 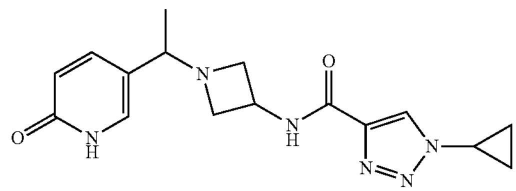 [SMILES: CC(c1ccc(=O)[nH]c1)N1CC(NC(=O)c2cn(C3CC3)nn2)C1] | none |
| 995 | 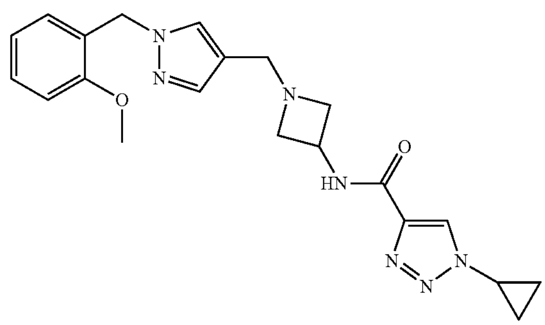 [SMILES: COc1ccccc1Cn1cc(CN2CC(NC(=O)c3cn(C4CC4)nn3)C2)cn1] | none |
| 996 | 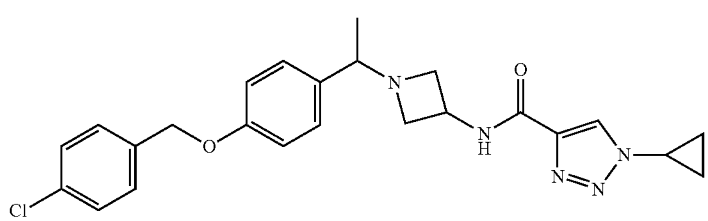 [SMILES: CC(c1ccc(OCc2ccc(Cl)cc2)cc1)N1CC(NC(=O)c2cn(C3CC3)nn2)C1] | none |
| 997 | 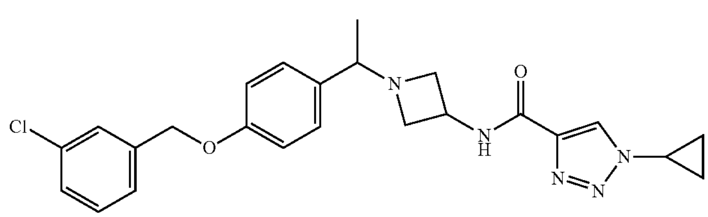 [SMILES: CC(c1ccc(OCc2cccc(Cl)c2)cc1)N1CC(NC(=O)c2cn(C3CC3)nn2)C1] | none |
| 998 | 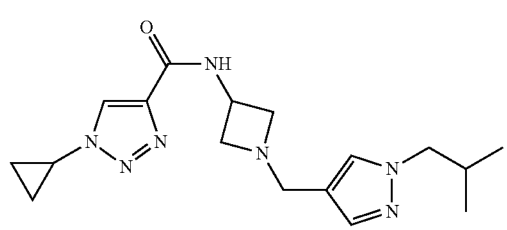 [SMILES: CC(C)Cn1cc(CN2CC(NC(=O)c3cn(C4CC4)nn3)C2)cn1] | none |

TABLE 6-continued

| Cpd. No. | Structure | Salt Form |
|---|---|---|
| 999 | 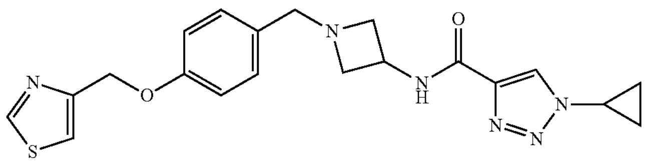 [SMILES: O=C(NC1CN(Cc2ccc(OCc3cscn3)cc2)C1)c1cn(C2CC2)nn1] | none |
| 1000 | 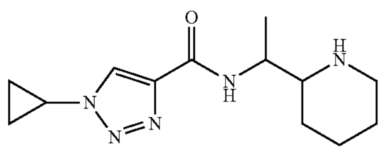 [SMILES: CC(NC(=O)c1cn(C2CC2)nn1)C1CCCCN1] | none |
| 1001 | 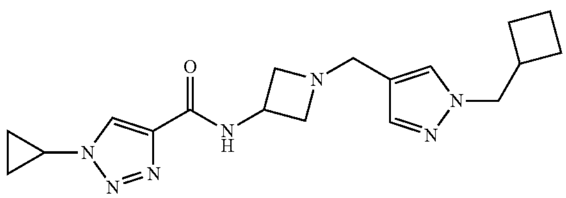 [SMILES: O=C(NC1CN(Cc2cnn(CC3CCC3)c2)C1)c1cn(C2CC2)nn1] | none |
| 1002 | 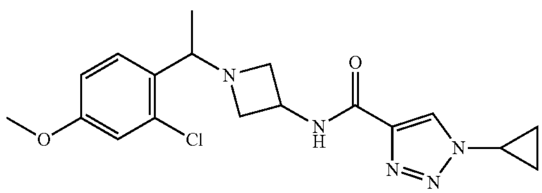 [SMILES: COc1ccc(C(C)N2CC(NC(=O)c3cn(C4CC4)nn3)C2)c(Cl)c1] | none |
| 1003 | 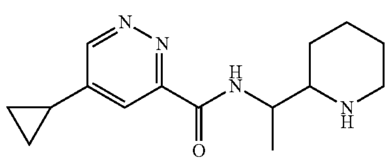 [SMILES: CC(NC(=O)c1cc(C2CC2)cnn1)C1CCCCN1] | none |
| 1004 | 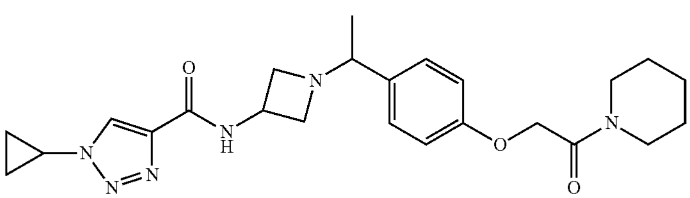 [SMILES: CC(c1ccc(OCC(=O)N2CCCCC2)cc1)N1CC(NC(=O)c2cn(C3CC3)nn2)C1] | none |
| 1005 | 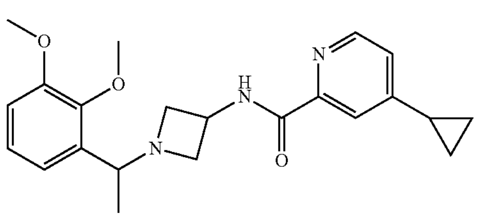 [SMILES: COc1cccc(C(C)N2CC(NC(=O)c3cc(C4CC4)ccn3)C2)c1OC] | none |
| 1006 | 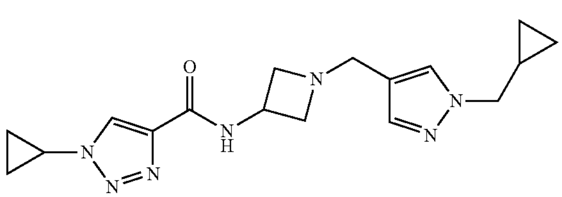 [SMILES: O=C(NC1CN(Cc2cnn(CC3CC3)c2)C1)c1cn(C2CC2)nn1] | none |

TABLE 6-continued

| Cpd. No. | Structure | Salt Form |
|---|---|---|
| 1007 | 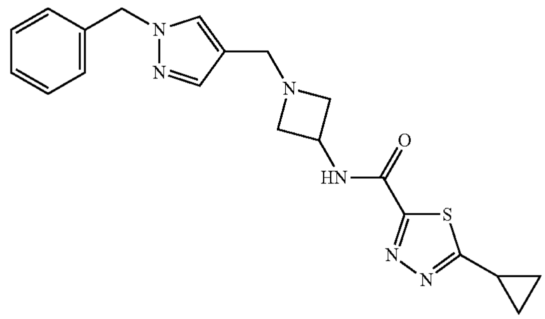 [SMILES: O=C(NC1CN(Cc2cnn(Cc3ccccc3)c2)C1)c1nnc(C2CC2)s1] | none |
| 1008 | 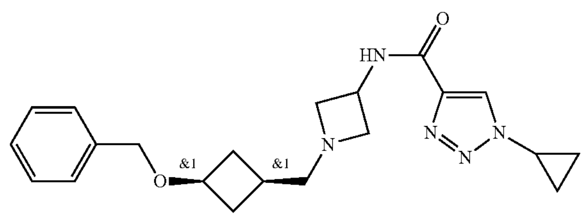 [SMILES: O=C(NC1CN(C[C@H]2C[C@@H](OCc3ccccc3)C2)C1)c1cn(C2CC2)nn1] | none |
| 1009 | 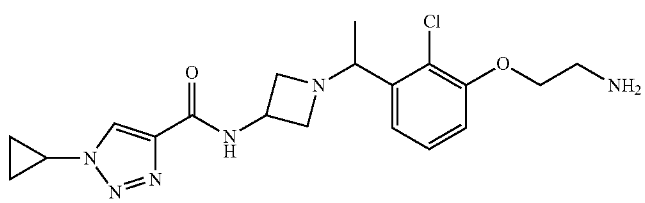 [SMILES: CC(c1cccc(OCCN)c1Cl)N1CC(NC(=O)c2cn(C3CC3)nn2)C1] | none |
| 1012 | 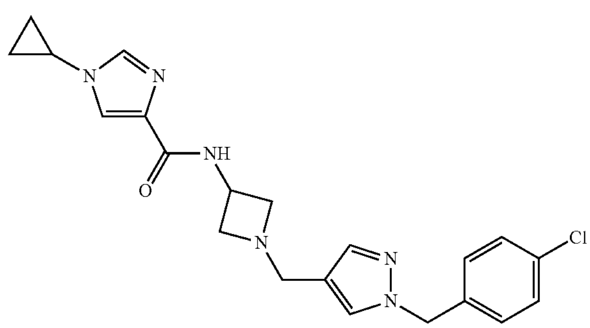 [SMILES: O=C(NC1CN(Cc2cnn(Cc3ccc(Cl)cc3)c2)C1)c1cn(C2CC2)cn1] | none |
| 1017 | 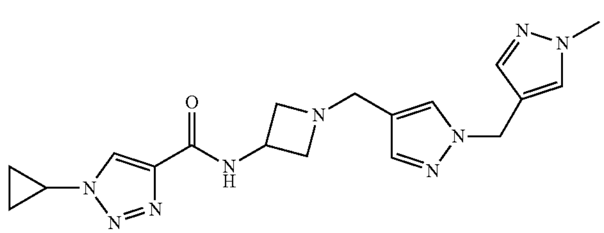 [SMILES: Cn1cc(Cn2cc(CN3CC(NC(=O)c4cn(C5CC5)nn4)C3)cn2)cn1] | none |
| 1020 | 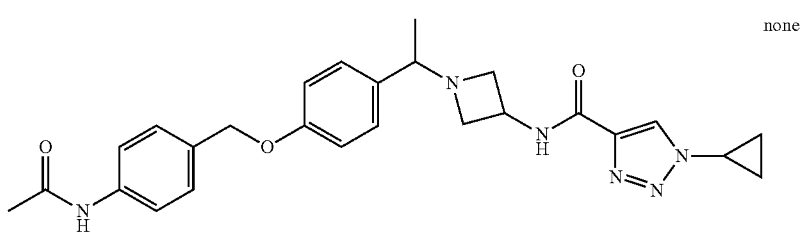 | none |

TABLE 6-continued

| Cpd. No. | Structure | Salt Form |
|---|---|---|
| 1021 | 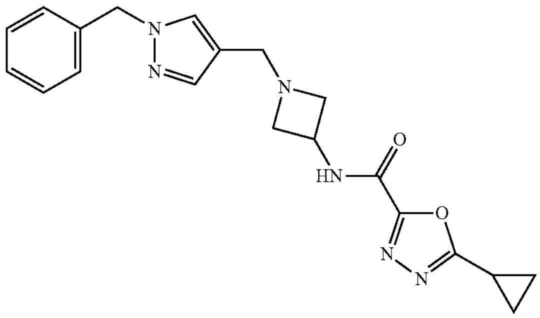 | none |
| 1022 | 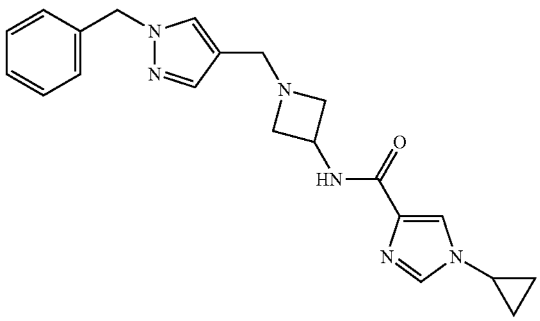 [SMILES: O=C(NC1CN(Cc2cnn(Cc3ccccc3)c2)C1)c1cn(C2CC2)cn1] | none |
| 1023 | 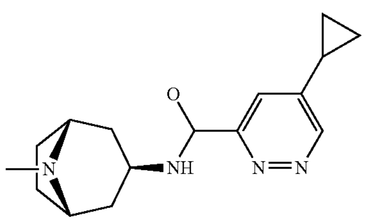 [SMILES: CN1[C@@H]2CC[C@H]1C[C@H](NC(O)c1cc(C3CC3)cnn1)C2] | none |
| 1024 | 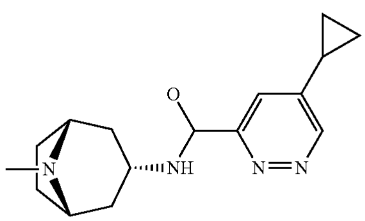 [SMILES: CN1[C@@H]2CC[C@H]1C[C@@H](NC(O)c1cc(C3CC3)cnn1)C2] | none |
| 1025 | 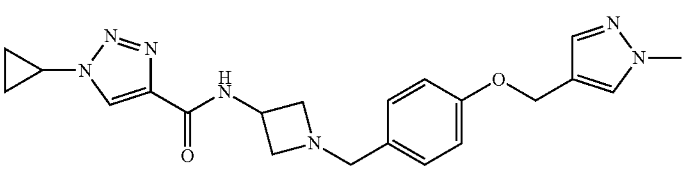 [SMILES: Cn1cc(COc2ccc(CN3CC(NC(=O)c4cn(C5CC5)nn4)C3)cc2)cn1] | none |
| 1026 | 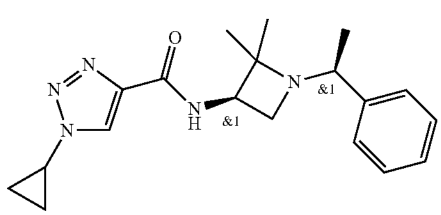 [SMILES: C[C@@H](c1ccccc1)N1C[C@@H](NC(=O)c2cn(C3CC3)nn2)C1(C)C] | none |

TABLE 6-continued

| Cpd. No. | Structure | Salt Form |
|---|---|---|
| 1028 | 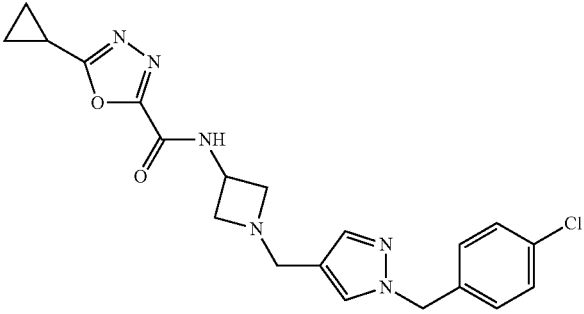 [SMILES: O=C(NC1CN(Cc2cnn(Cc3ccc(Cl)cc3)c2)C1)c1nnc(C2CC2)o1] | none |

TABLE 1A

| Cpd. No. | Chemical Name | LCMS M + H | SMYD3 Biochem IC$_{50}$ (μM)* | SMYD3 Cell IC$_{50}$ (μM)* |
|---|---|---|---|---|
| 3 | N-(1-((4-acetamidophenyl)sulfonyl)piperidin-4-yl)nicotinamide | 403.2 | >100 | |
| 4 | N-(1-((4-acetamidophenyl)sulfonyl)piperidin-4-yl)isonicotinamide | 403.2 | >100 | |
| 5 | N-(1-((4-acetamidophenyl)sulfonyl)piperidin-4-yl)pyrazine-2-carboxamide | 404.2 | >100 | |
| 6 | N-(1-((4-acetamidophenyl)sulfonyl)piperidin-4-yl)-1H-pyrazole-3-carboxamide | 392.3 | >100 | |
| 7 | N-(1-((4-acetamidophenyl)sulfonyl)piperidin-4-yl)-1-methyl-1H-pyrazole-5-carboxamide | 406.3 | >100 | |
| 8 | N-(1-((4-acetamidophenyl)sulfonyl)piperidin-4-yl)-1-methyl-1H-pyrazole-4-carboxamide | 406.3 | >100 | |
| 9 | N-(1-((4-acetamidophenyl)sulfonyl)piperidin-4-yl)-1-methyl-1H-imidazole-4-carboxamide | 406.3 | 60.5 | |
| 10 | N-(1-((4-acetamidophenyl)sulfonyl)piperidin-4-yl)-1-cyclopropyl-1H-1,2,3-triazole-4-carboxamide | 433.2 | 16.98 | |
| 11 | N-((1r,4r)-4-aminocyclohexyl)-1-cyclopropyl-1H-1,2,3-triazole-4-carboxamide | 250 | 15.37 | |
| 12 | N-(1-((4-acetamidophenyl)sulfonyl)piperidin-4-yl)-1-(cyclopropylmethyl)piperidine-4-carboxamide | 463 | 45.94 | |
| 13 | N-((1r,4r)-4-aminocyclohexyl)-1-ethyl-1H-pyrazole-3-carboxamide | 237.1 | 112.37 | |
| 14 | N-((1r,4r)-4-aminocyclohexyl)-3-ethylisoxazole-5-carboxamide | 238.15 | 104.43 | |
| 15 | N-((1r,4r)-4-aminocyclohexyl)-1-ethyl-1H-imidazole-4-carboxamide | 237.1 | 56.59 | |
| 16 | N-((1r,4r)-4-aminocyclohexyl)-2-ethyloxazole-4-carboxamide | NA | 128.43 | |
| 17 | N-((1r,4r)-4-aminocyclohexyl)-5-ethylisothiazole-3-carboxamide | 254.1 | 13.52 | |
| 18 | N-((1r,4r)-4-aminocyclohexyl)-4-ethylbenzamide | 247.1 | 125.3 | |
| 19 | N-((1r,4r)-4-aminocyclohexyl)-3-oxo-3,4-dihydro-2H-benzo[b][1,4]oxazine-7-carboxamide | 289.9 | 102.25 | |
| 20 | N-((1r,4r)-4-aminocyclohexyl)-3-oxo-3,4-dihydro-2H-benzo[b][1,4]oxazine-6-carboxamide | 289.8 | 16.03 | |
| 21 | N-((1r,4r)-4-aminocyclohexyl)-3-ethylbenzamide | 247.3 | 57.46 | |
| 22 | N-((1r,4r)-4-aminocyclohexyl)-5-ethylnicotinamide | 247.9 | 31.29 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 23 | 3-acetyl-N-((1r,4r)-4-aminocyclohexyl)benzamide | 261.2 | 91.55 | |
| 24 | 3-acetamido-N-((1r,4r)-4-aminocyclohexyl)benzamide | 276.2 | 80.28 | |
| 25 | N-((1r,4r)-4-aminocyclohexyl)-3-propionamidobenzamide | 290.2 | 84.27 | |
| 26 | N-((1r,4r)-4-aminocyclohexyl)-3-(hydroxymethyl)benzamide | 248.9 | 86.01 | |
| 27 | N-((1r,4r)-4-aminocyclohexyl)-1-ethyl-3-methyl-1H-pyrazole-5-carboxamide | 251.2 | 101.58 | |
| 28 | N-((1r,4r)-4-aminocyclohexyl)-3-methyl-1-phenyl-1H-pyrazole-5-carboxamide | 299.25 | 110.89 | |
| 29 | N-((1r,4r)-4-aminocyclohexyl)-1-benzyl-3-methyl-1H-pyrazole-5-carboxamide | 313.2 | 13.99 | |
| 30 | 1-ethyl-3-methyl-N-(phenyl(piperidin-4-yl)methyl)-1H-pyrazole-5-carboxamide | 327.15 | 69.19 | |
| 31 | 3-methyl-1-phenyl-N-(phenyl(piperidin-4-yl)methyl)-1H-pyrazole-5-carboxamide | 375.2 | 56.66 | |
| 32 | 1-benzyl-3-methyl-N-(phenyl(piperidin-4-yl)methyl)-1H-pyrazole-5-carboxamide | 389.25 | 91.27 | |
| 33 | N-(4-(aminomethyl)phenyl)-6-hydroxypyridazine-3-carboxamide | 228.05 (−NH$_2$) | 130.63 | |
| 34 | N-(4-(aminomethyl)phenyl)-1-methyl-3-(trifluoromethyl)-1H-pyrazole-5-carboxamide | 282.1 (−NH$_2$) | 153.36 | |
| 35 | N-(4-(aminomethyl)phenyl)-1-ethyl-3-methyl-1H-pyrazole-5-carboxamide | 242.05 (−NH$_2$) | 124.89 | |
| 36 | N-(4-(aminomethyl)phenyl)-3-methyl-1-phenyl-1H-pyrazole-5-carboxamide | 290.15 (−NH$_2$) | 123.93 | |
| 37 | N-((1r,4r)-4-aminocyclohexyl)-3-ethyl-1-methyl-1H-pyrazole-5-carboxamide | 251.34 | 59.91 | |
| 38 | N-((1r,4r)-4-aminocyclohexyl)-4-ethylpicolinamide | 248 | 20.5 | |
| 39 | 2-oxo-N-(piperidin-4-yl)-1,2,3,4-tetrahydroquinoxaline-6-carboxamide | 274.9 | 23.86 | |
| 40 | N-((1r,4r)-4-aminocyclohexyl)-2-oxoindoline-5-carboxamide | 274.1 | 2.84 | |
| 42 | N-((1r,4r)-4-aminocyclohexyl)-2-oxoindoline-5-carboxamide | 274.2 | 3.31 | |
| 43 | N-((1r,4r)-4-aminocyclohexyl)-2-hydroxyquinoxaline-6-carboxamide | 287 | 60.36 | |
| 44 | 2-oxo-N-(phenyl(piperidin-4-yl)methyl)indoline-5-carboxamide | 350.25 | 14.08 | |
| 45 | 5-amino-N-(phenyl(piperidin-4-yl)methyl)-1H-pyrazole-3-carboxamide | 300.25 | 137.24 | |
| 46 | 3-oxo-N-(piperidin-4-yl)-3,4-dihydroquinoxaline-6-carboxamide | 272.9 | 63.74 | |
| 47 | N-((1r,4r)-4-aminocyclohexyl)-2-oxo-2,3-dihydro-1H-pyrrolo[2,3-b]pyridine-5-carboxamide | 274.8 | 11.94 | |
| 48 | 3-amino-N-((1r,4r)-4-aminocyclohexyl)-1-methyl-1H-pyrazole-5-carboxamide | 237.9 | 117.12 | |
| 49 | N-(1-(L-tyrosyl)piperidin-4-yl)-2-oxoindoline-5-carboxamide | 423.3 | 0.86 | |
| 50 | 2-oxo-N-(piperidin-4-yl)indoline-5-carboxamide | 260.2 | 12.15 | |
| 51 | N-(1-(L-tryptophyl)piperidin-4-yl)-2-oxoindoline-5-carboxamide | 446.4 | 0.69 | |
| 52 | N-(4-(aminomethyl)phenyl)-4-propionyl-1H-pyrrole-2-carboxamide | 272.2 | 107.67 | |
| 53 | N-((1r,4r)-4-aminocyclohexyl)-2-butylcyclopropane-1-carboxamide | 239.3 | 121.58 | |
| 54 | N-((1r,4r)-4-aminocyclohexyl)-5-ethylthiophene-2-carboxamide | 253.4 | 49.88 | |
| 55 | 5-ethyl-N-(phenyl(piperidin-4-yl)methyl)thiophene-2-carboxamide | 329.2 | 116.27 | |
| 56 | N-(4-(aminomethyl)phenyl)-5-ethylthiophene-2-carboxamide | 261.1 | 138.14 | |
| 57 | N-((1r,4r)-4-aminocyclohexyl)-2-methyl-4H-furo[3,2-b]pyrrole-5-carboxamide | 261.7 | 134.08 | |
| 58 | 2-methyl-N-(piperidin-4-yl)-4H-furo[3,2-b]pyrrole-5-carboxamide | 248.1 | 76.14 | |
| 59 | N-((1r,4r)-4-aminocyclohexyl)-2-ethylthiazole-5-carboxamide | 254.5 | 184.11 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 60 | 2-ethyl-N-(phenyl(piperidin-4-yl)methyl)thiazole-5-carboxamide | 330.3 | 149.92 | |
| 61 | N-(4-(aminomethyl)phenyl)-2-ethylthiazole-5-carboxamide | 261.9 | 113.72 | |
| 62 | N-((1r,4r)-4-aminocyclohexyl)-3-cyclopropylbutanamide | 225.6 | 155.29 | |
| 63 | 3-cyclopropyl-N-(phenyl(piperidin-4-yl)methyl)butanamide | 301.3 | 131.22 | |
| 64 | 4-acetyl-N-((1r,4r)-4-aminocyclohexyl)-1H-pyrrole-2-carboxamide | 250.2 | 134.14 | |
| 65 | 4-acetyl-N-(piperidin-4-yl)-1H-pyrrole-2-carboxamide | 236 | 45.83 | |
| 66 | 4-acetyl-N-(4-(aminomethyl)phenyl)-1H-pyrrole-2-carboxamide | 258.2 | 60.87 | |
| 67 | N-((1r,4r)-4-ammocyclohexyl)-3-hydroxy-1-methyl-1H-pyrazole-5-carboxamide | 238.8 | 129.1 | |
| 68 | 2-oxo-N-(piperidin-4-yl)-2,3-dihydro-1H-pyrrolo[2,3-b]pyridine-5-carboxamide | 261 | 86.06 | |
| 69 | 3-hydroxy-1-methyl-N-(piperidin-4-yl)-1H-pyrazole-5-carboxamide | 225 | 19.72 | |
| 70 | N-((1r,4r)-4-aminocyclohexyl)-3-oxo-1,2,3,4-tetrahydroquinoxaline-6-carboxamide | 289 | 77.47 | |
| 71 | N-((1r,4r)-4-aminocyclohexyl)-2-oxoindoline-6-carboxamide | 274.2 | 89.26 | |
| 72 | N-(1-(L-tyrosyl)piperidin-4-yl)-2-oxoindoline-6-carboxamide | 423.5 | 35.48 | |
| 73 | N-((1r,4r)-4-aminocyclohexyl)-2-oxo-2,3-dihydro-1H-benzo[d]imidazole-5-carboxamide | 275.1 | 13.7 | |
| 74 | N-((1r,4r)-4-aminocyclohexyl)-2-oxo-1,2,3,4-tetrahydroquinoline-6-carboxamide | NA | 65.8 | |
| 75 | 6-amino-N-((1r,4r)-4-aminocyclohexyl)-2-naphthamide | 284.15 | 62.5 | |
| 76 | N-((1r,4r)-4-aminocyclohexyl)-2-hydroxyquinoline-6-carboxamide | 286.2 | 115.32 | |
| 77 | N-(phenyl(piperidin-4-yl)methyl)-4-propionyl-1H-pyrrole-2-carboxamide | 340.2 | 10.04 | |
| 78 | N-((1r,4r)-4-aminocyclohexyl)-2-(ethylsulfonyl)propanamide | 263.4 | 35.19 | |
| 79 | N-((1r,4r)-4-aminocyclohexyl)-5-((dimethylamino)methyl)furan-2-carboxamide | 266 | 38.86 | |
| 80 | 2-amino-N-(phenyl(piperidin-4-yl)methyl)oxazole-4-carboxamide | 301.4 | 97.11 | |
| 81 | N-(4-(aminomethyl)phenyl)-2-methyl-4H-furo[3,2-b]pyrrole-5-carboxamide | 270.4 | 25.9 | |
| 82 | N-(1-(L-tyrosyl)piperidin-4-yl)-1-methyl-2-oxoindoline-5-carboxamide | 437.3 | 8.7 | |
| 83 | N-(1-(L-tryptophyl)piperidin-4-yl)-1-methyl-2-oxoindoline-5-carboxamide | 460.3 | 12.94 | |
| 84 | N-((1r,4r)-4-aminocyclohexyl)-1-methyl-2-oxoindoline-5-carboxamide | 288.2 | 16.66 | |
| 85 | N-((1r,4r)-4-aminocyclohexyl)-8-methoxy-3-oxo-3,4-dihydro-2H-benzo[b][1,4]oxazine-6-carboxamide | NA | 184.09 | |
| 86 | N-(1-(1-(1-alanyl)piperidin-4-yl)ethyl)-2-oxoindoline-5-carboxamide | 359.25 | 1.43 | |
| 87 | N-(1-(1-(D-alanyl)piperidin-4-yl)ethyl)-2-oxoindoline-5-carboxamide | 359.2 | 9.37 | |
| 88 | N-(1-(L-tyrosyl)piperidin-4-yl)-1-methyl-2-oxoindoline-6-carboxamide | | 193.28 | |
| 89 | N-((1r,4r)-4-aminocyclohexyl)-2-oxo-2,3-dihydrobenzo[d]oxazole-5-carboxamide | 258.89 (−NH$_2$) | 140.17 | |
| 90 | N-((1r,4r)-4-aminocyclohexyl)-2-oxo-2,3-dihydrobenzo[d]oxazole-6-carboxamide | 276.15 | 9.76 | |
| 91 | N-((1r,4r)-4-aminocyclohexyl)-2-oxo-1,2,3,4-tetrahydroquinoline-7-carboxamide | 288.15 | 89.47 | |
| 92 | N-(1-(1-(L-alanyl)piperidin-4-yl)ethyl)-2-oxo-1,2,3,4-tetrahydroquinoline-7-carboxamide | 373.2 | 49.95 | |
| 93 | N-(1-(1-(L-alanyl)piperidin-4-yl)ethyl)-2-oxo-2,3-dihydro-1H-benzo[d]imidazole-5-carboxamide | 360.25 | 6.76 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 94 | N-(1-(1-(L-alanyl)piperidin-4-yl)ethyl)-2-oxo-2,3-dihydrobenzo[d]oxazole-6-carboxamide | 361.25 | 3.94 | |
| 95 | N-(1-(1-(L-alanyl)piperidin-4-yl)ethyl)-2-oxo-2H-chromene-6-carboxamide | 372.3 | 149.61 | |
| 96 | N-(1-(1-(L-alanyl)piperidin-4-yl)ethyl)-2-oxo-1,2,3,4-tetrahydroquinoline-6-carboxamide | 373.3 | 192.59 | |
| 97 | N-(1-(1-(L-alanyl)piperidin-4-yl)ethyl)-6-amino-2-naphthamide | 369.3 | 145.77 | |
| 98 | N-(1-(1-(L-alanyl)piperidin-4-yl)ethyl)-8-methoxy-3-oxo-3,4-dihydro-2H-benzo[b][1,4]oxazine-6-carboxamide | 405.25 | 150.97 | |
| 99 | N-(1-(1-(L-alanyl)piperidin-4-yl)ethyl)-3-hydroxyquinoxaline-6-carboxamide | 372.3 | 35.73 | |
| 100 | 2-oxo-N-(piperidin-4-ylmethyl)indoline-5-carboxamide | 274.1 | 20.04 | |
| 101 | (S)-2-oxo-N-(pyrrolidin-3-ylmethyl)indoline-5-carboxamide | 260.1 | 25.36 | |
| 102 | N-((1-(L-tyrosyl)piperidin-4-yl)methyl)-2-oxoindoline-5-carboxamide | 437.45 | 1.86 | |
| 103 | N-((1-(L-tryptophyl)piperidin-4-yl)methyl)-2-oxoindoline-5-carboxamide | 460.25 | 2.74 | |
| 104 | ethyl 2-(1-(L-alanyl)piperidin-4-yl)-2-(2-oxoindoline-5-carboxamido)acetate | 417.3 | 1.51 | |
| 105 | N-((4-hydroxypiperidin-4-yl)methyl)-2-oxoindoline-5-carboxamide | 290.2 | 40.39 | |
| 106 | N-(4-aminobutyl)-2-oxoindoline-5-carboxamide | 248.2 | 13.42 | |
| 107 | (S)-N-(4-(2-aminopropanamido)butyl)-2-oxoindoline-5-carboxamide | 319.3 | 13.95 | |
| 108 | ethyl 5-(((1r,4r)-4-aminocyclohexyl)amino)-5-oxopentanoate | 257.3 | 92.19 | |
| 109 | 2-methyl-N-(phenyl(piperidin-4-yl)methyl)-3-(pyrrolidin-1-yl)propanamide | 330.5 | 79.04 | |
| 110 | 2-methyl-N-(phenyl(piperidin-4-yl)methyl)-4H-furo[3,2-b]pyrrole-5-carboxamide | 338.7 | 82.75 | |
| 111 | N-((1r,4r)-4-aminocyclohexyl)-2-ethylpyrrolidine-2-carboxamide | 240.1 | 149.59 | |
| 112 | N-((1-(L-alanyl)-4-hydroxypiperidin-4-yl)methyl)-2-oxoindoline-5-carboxamide | 361.15 | 3.04 | |
| 113 | N-((1-(L-alanyl)-4-fluoropiperidin-4-yl)methyl)-2-oxoindoline-5-carboxamide | 363.25 | 3.86 | |
| 114 | (R)-N-(4-(2-aminopropanamido)butyl)-2-oxoindoline-5-carboxamide | 319.15 | 22.28 | |
| 115 | N-((1r,4r)-4-aminocyclohexyl)-3-oxo-3,4-dihydro-2H-benzo[b][1,4]oxazine-8-carboxamide | 290 | 61.18 | |
| 116 | N-((1r,4r)-4-aminocyclohexyl)-5-bromonicotinamide | 296.13/298.13 | 51 | |
| 117 | N-((1r,4r)-4-aminocyclohexyl)-5-chloronicotinamide | 254.2 | 86.99 | |
| 118 | N-((1r,4r)-4-aminocyclohexyl)benzo[d]thiazole-6-carboxamide | 276.2 | 139.34 | |
| 119 | N-((1r,4r)-4-aminocyclohexyl)-2-hydroxyquinoline-7-carboxamide | | 115.79 | |
| 120 | N-(1-(1-(L-alanyl)piperidin-4-yl)ethyl)-2-hydroxyquinoline-7-carboxamide | 371.2 | 86.89 | |
| 121 | N-((4-methylpiperidin-4-yl)methyl)-2-oxoindoline-5-carboxamide | 288.15 | 65.69 | |
| 122 | ethyl 2-(2-oxoindoline-5-carboxamido)-2-(piperidin-4-yl)acetate | 346.3 | 42.26 | |
| 123 | 6-amino-N-((1r,4r)-4-aminocyclohexyl)nicotinamide | 235 | 107.83 | |
| 125 | N-((1r,4r)-4-aminocyclohexyl)-7-fluoro-2-hydroxyquinoline-4-carboxamide | 304.7 | 91.68 | |
| 126 | N-((1r,4r)-4-aminocyclohexyl)-2-chloro-5-(4H-1,2,4-triazol-4-yl)benzamide | 320.1 | 31.99 | |
| 127 | N-((1r,4r)-4-aminocyclohexyl)-4H-1,2,4-triazole-3-carboxamide | 210.1 | 16.44 | |
| 129 | N-((1r,4r)-4-aminocyclohexyl)-2-(pyridin-3-yl)acetamide | 234.1 | >100 | |
| 130 | N-(4-(3-aminopropanamido)cyclohexyl)-2-oxoindoline-5-carboxamide | 345.1 | 0.29 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 131 | ethyl 4-((2-oxoindoline-5-carboxamido)methyl)piperidine-4-carboxylate | 346.2 | 56.28 | |
| 132 | ethyl 1-(L-alanyl)-4-((2-oxoindoline-5-carboxamido)methyl)piperidine-4-carboxylate | 417.2 | 0.94 | |
| 133 | N-(((S)-1-(D-alanyl)pyrrolidin-3-yl)methyl)-2-oxoindoline-5-carboxamide | 331.15 | 10.67 | |
| 134 | N-(((S)-1-(L-alanyl)pyrrolidin-3-yl)methyl)-2-oxoindoline-5-carboxamide | 331.15 | 10.2 | |
| 135 | N-(((R)-1-(L-alanyl)pyrrolidin-3-yl)methyl)-2-oxoindoline-5-carboxamide | 331.1 | 13.62 | |
| 136 | N-((1r,4r)-4-(3-aminopropanamido)cyclohexyl)-4-(5-methyl-1,2,4-oxadiazol-3-yl)benzamide | 372.2 | >100 | |
| 137 | N-((1r,4r)-4-aminocyclohexyl)-4-(5-methyl-1,2,4-oxadiazol-3-yl)benzamide | 301.1 | 46.61 | |
| 138 | N-(1-(1-(L-alanyl)piperidin-4-yl)ethyl)isonicotinamide | 305.2 | >100 | |
| 139 | N-((1r,4r)-4-(3-aminopropanamido)cyclohexyl)isonicotinamide | 291.2 | >100 | |
| 140 | N-((1r,4r)-4-aminocyclohexyl)isonicotinamide | 220.2 | >100 | |
| 141 | N-(1-(1-(L-alanyl)piperidin-4-yl)ethyl)nicotinamide | 305.2 | >100 | |
| 142 | N-((1r,4r)-4-(3-aminopropanamido)cyclohexyl)nicotinamide | 291.2 | >100 | |
| 143 | N-((1r,4r)-4-aminocyclohexyl)nicotinamide | 220.2 | >100 | |
| 144 | N-(1-(1-(L-alanyl)piperidin-4-yl)ethyl)pyrimidine-2-carboxamide | 306.2 | >100 | |
| 145 | N-((1r,4r)-4-(3-aminopropanamido)cyclohexyl)pyrimidine-2-carboxamide | 292.2 | >100 | |
| 146 | N-(1-(1-(L-alanyl)piperidin-4-yl)ethyl)benzo[d][1,3]dioxole-5-carboxamide | 348.2 | >100 | |
| 147 | N-((1r,4r)-4-(3-aminopropanamido)cyclohexyl)benzo[d][1,3]dioxole-5-carboxamide | 334.2 | 98.15 | |
| 148 | N-((1r,4r)-4-aminocyclohexyl)benzo[d][1,3]dioxole-5-carboxamide | 263.1 | >100 | |
| 149 | N-(1-(1-(L-alanyl)piperidin-4-yl)ethyl)-3-(methylsulfonyl)benzamide | 382.2 | >100 | |
| 150 | N-((1r,4r)-4-(3-aminopropanamido)cyclohexyl)-3-(methylsulfonyl)benzamide | 368.2 | >100 | |
| 151 | N-((1r,4r)-4-aminocyclohexyl)-3-(methylsulfonyl)benzamide | 297.1 | >100 | |
| 152 | 3-amino-N-((1r,4r)-4-(3-aminopropanamido)cyclohexyl)pyrazine-2-carboxamide | 307.2 | >100 | |
| 153 | 3-amino-N-((1r,4r)-4-aminocyclohexyl)pyrazine-2-carboxamide | 236.2 | >100 | |
| 154 | N-((1r,4r)-4-(3-aminopropanamido)cyclohexyl)-[1,1'-biphenyl]-4-carboxamide | 366.1 | 37.31 | |
| 155 | N-((1r,4r)-4-aminocyclohexyl)-[1,1'-biphenyl]-4-carboxamide | 295.1 | 79.21 | |
| 156 | N-((1r,4r)-4-(3-aminopropanamido)cyclohexyl)-4-sulfamoylbenzamide | 369.2 | >100 | |
| 157 | N-(1-(1-(L-alanyl)piperidin-4-yl)ethyl)-5-fluoronicotinamide | 323.2 | >100 | |
| 158 | N-((1r,4r)-4-(3-aminopropanamido)cyclohexyl)-5-fluoronicotinamide | 309.2 | >100 | |
| 159 | N-((1r,4r)-4-aminocyclohexyl)-5-fluoronicotinamide | 238.2 | >100 | |
| 160 | N-((1r,4r)-4-aminocyclohexyl)-1H-indole-6-carboxamide | 258.2 | >100 | |
| 161 | N-((1r,4r)-4-aminocyclohexyl)-1H-benzo[d]imidazole-6-carboxamide | 259.2 | >100 | |
| 162 | N-(1-(1-(L-alanyl)piperidin-4-yl)ethyl)quinoline-2-carboxamide | 355.2 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 163 | N-((1r,4r)-4-(3-aminopropanamido)cyclohexyl)quinoline-2-carboxamide | 341.2 | >100 | |
| 164 | N-((1r,4r)-4-aminocyclohexyl)quinoline-2-carboxamide | 270.2 | >100 | |
| 165 | N-((1r,4r)-4-(3-aminopropanamido)cyclohexyl)isoquinoline-6-carboxamide | 341.2 | 15.52 | |
| 166 | N-((1r,4r)-4-aminocyclohexyl)isoquinoline-6-carboxamide | 270.2 | 20.7 | |
| 167 | N-(1-(1-(L-alanyl)piperidin-4-yl)ethyl)-2-(1H-indol-3-yl)acetamide | 357.3 | >100 | |
| 168 | N-((1r,4r)-4-aminocyclohexy l)-2-(1H-indol-3-yl)acetamide | 272.2 | >100 | |
| 169 | 3-amino-N-((1r,4r)-4-(2-(6-methoxynaphthalen-2-yl)propanamido)cyclohexyl)propanamide | 398.3 | >100 | |
| 170 | N-((1r,4r)-4-aminocyclohexyl)-2-(6-methoxynaphthalen-2-yl)propanamide | 327.3 | 76.38 | |
| 171 | N-(1-(1-(L-alanyl)piperidin-4-yl)ethyl)isoquinoline-1-carboxamide | 355.3 | >100 | |
| 172 | N-((1r,4r)-4-aminocyclohexyl)-1H-indazole-3-carboxamide | 259 | >100 | |
| 173 | N-((1r,4r)-4-(3-aminobutanamido)cyclohexyl)-2-oxoindoline-5-carboxamide | 259.3 | 0.11 | |
| 174 | N-((1r,4r)-4-(2-aminoacetamido)cyclohexyl)-2-oxoindoline-5-carboxamide | 331.2 | 0.63 | |
| 175 | N-((1r,4r)-4-(2-aminopropanamido)cyclohexyl)-2-oxoindoline-5-carboxamide | 345.3 | 0.42 | |
| 176 | N-((1-(L-alanyl)-4-methylpiperidin-4-yl)methyl)-2-oxoindoline-5-carboxamide | 359.1 | 3.52 | |
| 177 | N-(((R)-1-(D-alanyl)pyrrolidin-3-yl)methyl)-2-oxoindoline-5-carboxamide | 331.15 | 19.78 | |
| 178 | N-(4-(3-amino-N-methylpropanamido)cyclohexyl)-2-oxoindoline-5-carboxamide | 359.3 | 3.4 | |
| 179 | N-(1-(1-(L-alanyl)piperidin-4-yl)ethyl)-4-(5-methyl-1,2,4-oxadiazol-3-yl)benzamide | 386.2 | >100 | |
| 180 | N-(1-(1-(L-alanyl)piperidin-4-yl)ethyl)-3,5-dimethyl-1H-pyrazole-4-carboxamide | 322.3 | >100 | |
| 181 | N-((1r,4r)-4-(3-aminopropanamido)cyclohexyl)-3,5-dimethyl-1H-pyrazole-4-carboxamide | 308.2 | >100 | |
| 182 | N-((1r,4r)-4-aminocyclohexyl)-3,5-dimethyl-1H-pyrazole-4-carboxamide | 237.1 | >100 | |
| 183 | N-(1-(1-(L-alanyl)piperidin-4-yl)ethyl)-2-methylpyrimidine-5-carboxamide | 320.2 | >100 | |
| 184 | N-((1r,4r)-4-(3-aminopropanamido)cyclohexyl)-2-methylpyrimidine-5-carboxamide | 306.3 | 35.78 | |
| 185 | N-(1-(1-(L-alanyl)piperidin-4-yl)ethyl)-5-methylpyrazine-2-carboxamide | 320.3 | >100 | |
| 186 | N-((1r,4r)-4-aminocyclohexyl)-5-methylpyrazine-2-carboxamide | 235.2 | >100 | |
| 187 | N-(1-(1-(L-alanyl)piperidin-4-yl)ethyl)-2-aminoisonicotinamide | 320.3 | >100 | |
| 188 | N-(1-(1-(L-alanyl)piperidin-4-yl)ethyl)-3-aminopyrazine-2-carboxamide | 321.2 | >100 | |
| 189 | N-(1-(1-(L-alanyl)piperidin-4-yl)ethyl)-[1,1'-biphenyl]-4-carboxamide | 380.3 | >100 | |
| 190 | N-((1r,4r)-4-aminocyclohexyl)-4-sulfamoylbenzamide | 298.2 | >100 | |
| 191 | N-(1-(1-(L-alanyl)piperidin-4-yl)ethyl)-6-hydroxypyridazine-3-carboxamide | 322.2 | >100 | |
| 192 | N-((1r,4r)-4-aminocyclohexyl)-1H-indole-5-carboxamide | 258.2 | >100 | |
| 193 | N-(1-(1-(L-alanyl)piperidin-4-yl)ethyl)-1H-benzo[d]imidazole-6-carboxamide | 344.3 | >100 | |
| 194 | N-(1-(1-(L-alanyl)piperidin-4-yl)ethyl)isoquinoline-6-carboxamide | 355.2 | >100 | |
| 195 | N-((1r,4r)-4-(2-(1H-indol-3-yl)acetamido)cyclohexyl)-3-aminopropanamide | 343.2 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 196 | N-((1r,4r)-4-(3-aminopropanamido)cyclohexyl)isoquinoline-1-carboxamide | 341.2 | >100 | |
| 197 | N-((1r,4r)-4-aminocyclohexyl)isoquinoline-1-carboxamide | 270.2 | >100 | |
| 198 | N-(1-(1-(L-alanyl)piperidin-4-yl)ethyl)-5-fluoro-1H-indole-2-carboxamide | 361.2 | 41.66 | |
| 199 | N-(1-(1-(L-alanyl)piperidin-4-yl)ethyl)-2-hydroxyquinoline-4-carboxamide | 371.3 | >100 | |
| 200 | N-((1r,4r)-4-(3-aminopropanamido)cyclohexyl)-2-hydroxyquinoline-4-carboxamide | 357.2 | 23.31 | |
| 201 | N-((1r,4r)-4-aminocyclohexyl)-2-hydroxyquinoline-4-carboxamide | 286.2 | >100 | |
| 202 | N-(1-(1-(L-alanyl)piperidin-4-yl)ethyl)-5,6,7,8-tetrahydronaphthalene-2-carboxamide | 358.3 | 59 | |
| 203 | N-((1r,4r)-4-(3-aminopropanamido)cyclohexyl)-5,6,7,8-tetrahydronaphthalene-2-carboxamide | 344.2 | 11.21 | |
| 204 | N-((1r,4r)-4-aminocyclohexyl)-5,6,7,8-tetrahydronaphthalene-2-carboxamide | 273.2 | 47.43 | |
| 205 | N-(1-(1-(L-alanyl)piperidin-4-yl)ethyl)pyrazine-2-carboxamide | 306.3 | >100 | |
| 206 | N-(1-(1-(L-alanyl)piperidin-4-yl)ethyl)-2-(4-fluorophenyl)acetamide | 336.2 | >100 | |
| 207 | 3-amino-N-((1r,4r)-4-(2-(4-fluorophenyl)acetamido)cyclohexyl)propanamide | 322.2 | >100 | |
| 208 | N-((1r,4r)-4-aminocyclohexyl)-2-(4-fluorophenyl)acetamide | 251.2 | >100 | |
| 209 | 4-((1-(1-(L-alanyl)piperidin-4-yl)ethyl)carbamoyl)pyridine 1-oxide | 321.2 | >100 | |
| 210 | 4-(((1r,4r)-4-aminocyclohexyl)carbamoyl)pyridine 1-oxide | 236.2 | >100 | |
| 211 | 4-amino-N-((1r,4r)-4-aminocyclohexyl)quinoline-6-carboxamide | 285.15 | 43.73 | |
| 212 | N-(1-(1-(L-alanyl)piperidin-4-yl)ethyl)-4-aminoquinoline-6-carboxamide | 370.3 | 15.16 | |
| 213 | (R)-2-oxo-N-(pyrrolidin-3-ylmethyl)indoline-5-carboxamide | 260.15 | 17.95 | |
| 214 | N-(4-(2-amino-N-methylacetamido)cyclohexyl)-2-oxoindoline-5-carboxamide | 345.3 | 1.25 | |
| 215 | N-((1r,4r)-4-(3-aminopropanamido)cyclohexyl)-5-methylpyrazine-2-carboxamide | 306.1 | >100 | |
| 216 | N-(1-(1-(L-alanyl)piperidin-4-yl)ethyl)-2-(4-bromo-3,5-dimethyl-1H-pyrazol-1-yl)propanamide | 428.2 | >100 | |
| 217 | N-(1-(1-(L-alanyl)piperidin-4-yl)ethyl)-5-methyl-1-phenyl-1H-1,2,3-triazole-4-carboxamide | 385.3 | >100 | |
| 218 | N-(1-(1-(L-alanyl)piperidin-4-yl)ethyl)-4-(3-methyl-5-oxo-4,5-dihydro-1H-pyrazol-1-yl)benzamide | 400.3 | 76.96 | |
| 219 | N-(1-(1-(L-alanyl)piperidin-4-yl)ethyl)-1-methyl-1H-indazole-6-carboxamide | 358.2 | >100 | |
| 220 | N-(1-(1-(L-alanyl)piperidin-4-yl)ethyl)-6-methoxy-2-naphthamide | 384.2 | >100 | |
| 221 | N-(1-(1-(L-alanyl)piperidin-4-yl)ethyl)-2-methoxyquinoline-4-carboxamide | 385.1 | >100 | |
| 222 | N-((1r,4r)-4-(3-aminopropanamido)cyclohexyl)-2-methoxyquinoline-4-carboxamide | 371 | >100 | |
| 223 | N-((1r,4r)-4-aminocyclohexyl)-2-methoxyquinoline-4-carboxamide | 300 | >100 | |
| 224 | N-(1-(1-(L-alanyl)piperidin-4-yl)ethyl)-4-oxo-4H-chromene-2-carboxamide | 372.2 | >100 | |
| 225 | N-(1-(1-(L-alanyl)piperidin-4-yl)ethyl)-4-hydroxyquinoline-2-carboxamide | 371.2 | >100 | |
| 226 | N-(1-(1-(L-alanyl)piperidin-4-yl)ethyl)-4-(4H-1,2,4-triazol-4-yl)benzamide | 371.2 | >100 | |
| 227 | N-(1-(1-(L-alanyl)piperidin-4-yl)ethyl)-4-(pyrrolidin-1-yl)benzamide | 373.3 | 29.17 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 228 | N-(1-(1-(L-alanyl)piperidin-4-yl)ethyl)benzo[d]thiazole-6-carboxamide | 361.2 | >100 | |
| 229 | N-(1-(1-(L-alanyl)piperidin-4-yl)ethyl)-5-chloro-1H-indole-2-carboxamide | 377.2 | 77.9 | |
| 230 | N-((1r,4r)-4-(3-aminopropanamido)cyclohexyl)-5-chloro-1H-indole-2-carboxamide | 363.1 | 37.47 | |
| 231 | N-((1r,4r)-4-aminocyclohexyl)-5-chloro-1H-indole-2-carboxamide | 292.1 | 91.53 | |
| 232 | N-(1-(1-(L-alanyl)piperidin-4-yl)ethyl)-1H-indole-2-carboxamide | 343.3 | >100 | |
| 233 | N-((1r,4r)-4-(3-aminopropanamido)cyclohexyl)-1H-indole-2-carboxamide | 329.3 | >100 | |
| 234 | N-((1r,4r)-4-aminocyclohexyl)-1H-indole-2-carboxamide | 258.2 | >100 | |
| 235 | N-((1r,4r)-4-(3-aminopropanamido)cyclohexyl)-1H-indole-5-carboxamide | 329.2 | 13.44 | |
| 236 | 5-((1-(1-(L-alanyl)piperidin-4-yl)ethyl)carbamoyl)benzo[c][1,2,5]oxadiazole 1-oxide | 362.2 | >100 | |
| 237 | N-(1-(1-(L-alanyl)piperidin-4-yl)ethyl)benzo[c][1,2,5]oxadiazole-5-carboxamide | 346.2 | >100 | |
| 238 | N-(1-(1-(L-alanyl)piperidin-4-yl)ethyl)quinoxaline-2-carboxamide | 356.3 | >100 | |
| 239 | N-(1-(1-(L-alanyl)piperidin-4-yl)ethyl)imidazo[2,1-b]thiazole-6-carboxamide | 350.2 | >100 | |
| 241 | N-(1-(1-(L-alanyl)piperidin-4-yl)ethyl)-4-(1H-imidazol-1-yl)butanamide | 336.3 | 82.88 | |
| 242 | N-((1r,4r)-4-aminocyclohexyl)-5-fluoro-1H-indole-2-carboxamide | 276 | >100 | |
| 243 | N-(1-(1-(L-alanyl)piperidin-4-yl)ethyl)-1H-benzo[d]imidazole-2-carboxamide | 344.2 | 72.93 | |
| 244 | N-(1-(1-(L-alanyl)piperidin-4-yl)ethyl)-1-methyl-1H-indole-2-carboxamide | 357.2 | >100 | |
| 245 | N-((1r,4r)-4-(3-aminopropanamido)cyclohexyl)-1-methyl-1H-indole-2-carboxamide | 343.3 | >100 | |
| 246 | N-((1r,4r)-4-aminocyclohexyl)-1-methyl-1H-indole-2-carboxamide | 272.2 | >100 | |
| 247 | N-(1-(1-(L-alanyl)piperidin-4-yl)ethyl)-4-aminonicotinamide | 320.2 | >100 | |
| 248 | N-(1-(1-(L-alanyl)piperidin-4-yl)ethyl)-1H-indole-4-carboxamide | 343.3 | >100 | |
| 249 | N-(1-(1-(L-alanyl)piperidin-4-yl)ethyl)-2-hydroxyisonicotinamide | 321.2 | 65.86 | |
| 250 | N-(1-(1-(L-alanyl)piperidin-4-yl)ethyl)-2-hydroxyisonicotinamide | 321.2 | >100 | |
| 251 | N-((1r,4r)-4-aminocyclohexyl)picolinamide | 220.1 | >100 | |
| 252 | N-((1r,4r)-4-(3-aminopropanamido)cyclohexyl)pyrazine-2-carboxamide | 292.1 | 37.36 | |
| 253 | N-(1-(1-(L-alanyl)piperidin-4-yl)ethyl)-1-methyl-1H-imidazole-2-carboxamide | 308.2 | 64.91 | |
| 254 | N-(1-(1-(L-alanyl)piperidin-4-yl)ethyl)-3-methylisonicotinamide | 319.3 | >100 | |
| 255 | N-(1-(1-(L-alanyl)piperidin-4-yl)ethyl)-4-methylnicotinamide | 319.3 | 73.38 | |
| 256 | N-(1-(1-(L-alanyl)piperidin-4-yl)ethyl)-5-methylnicotinamide | 319.3 | 61.59 | |
| 257 | N-(1-(1-(L-alanyl)piperidin-4-yl)ethyl)-6-methylnicotinamide | 319.3 | >100 | |
| 258 | N-(1-(1-(L-alanyl)piperidin-4-yl)ethyl)-3-methylisothiazole-4-carboxamide | 325.3 | >100 | |
| 259 | N-(1-(1-(L-alanyl)piperidin-4-yl)ethyl)-1-methyl-1H-pyrazole-3-carboxamide | 308.3 | >100 | |
| 260 | N-(1-(1-(L-alanyl)piperidin-4-yl)ethyl)-3-(tert-butyl)-1-methyl-1H-pyrazole-5-carboxamide | 364.3 | >100 | |
| 261 | N-(1-(1-(L-alanyl)piperidin-4-yl)ethyl)-6-methoxypyrazine-2-carboxamide | 336.2 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 262 | (1r,4S)-N-(1-(1-(L-alanyl)piperidin-4-yl)ethyl)-4-aminocyclohexane-1-carboxamide | 325.2 | >100 | |
| 263 | N-(1-(1-(L-alanyl)piperidin-4-yl)ethyl)-4-chloro-2-(trifluoromethyl)benzamide | 406.2 | >100 | |
| 264 | 4-(((1r,4r)-4-(3-aminopropanamido)cyclohexyl)carbamoyl)pyridine 1-oxide | 307.2 | >100 | |
| 265 | N-(1-(1-(L-alanyl)piperidin-4-yl)ethyl)-6-fluoropicolinamide | 323.2 | >100 | |
| 266 | N-(1-(1-(L-alanyl)piperidin-4-yl)ethyl)-2,2-difluorobenzo[d][1,3]dioxole-4-carboxamide | 384.3 | >100 | |
| 267 | N-(1-(1-(L-alanyl)piperidin-4-yl)ethyl)-3-fluoroisonicotinamide | 323.2 | >100 | |
| 268 | N-(1-(1-(L-alanyl)piperidin-4-yl)ethyl)-1H-indole-3-carboxamide | 343.3 | >100 | |
| 269 | N-((1r,4r)-4-aminocyclohexyl)pyrimidine-2-carboxamide | 221.1 | >100 | |
| 270 | N-((1r,4r)-4-(3-aminopropanamido)cyclohexyl)-6-hydroxypyridazine-3-carboxamide | 308.2 | >100 | |
| 271 | N-((1r,4r)-4-aminocyclohexyl)-6-hydroxypyridazine-3-carboxamide | 237.2 | >100 | |
| 272 | N-((1r,4r)-4-(3-aminopropanamido)cyclohexyl)-1H-indole-6-carboxamide | 329.2 | 37.25 | |
| 273 | N-((1r,4r)-4-aminocyclohexyl)-5-methyl-1-phenyl-1H-1,2,3-triazole-4-carboxamide | 300.1 | >100 | |
| 274 | N-(1-(1-(L-alanyl)piperidin-4-yl)ethyl)-4,6-dimethyl-2-oxo-1,2-dihydropyridine-3-carboxamide | 349.3 | >100 | |
| 275 | N-((1r,4r)-4-aminocyclohexyl)-1-methyl-1H-indazole-6-carboxamide | 273 | >100 | |
| 276 | N-((1r,4r)-4-aminocyclohexyl)-6-methoxy-2-naphthamide | 299.1 | >100 | |
| 277 | N-((1r,4r)-4-aminocyclohexyl)-4-oxo-4H-chromene-2-carboxamide | 287 | >100 | |
| 278 | N-((1r,4r)-4-aminocyclohexyl)-4-(4H-1,2,4-triazol-4-yl)benzamide | 286 | >100 | |
| 279 | N-((1r,4r)-4-(3-aminopropanamido)cyclohexyl)-4-(pyrrolidin-1-yl)benzamide | 359.1 | 43.65 | |
| 280 | N-((1r,4r)-4-aminocyclohexyl)-4-(pyrrolidin-1-yl)benzamide | 288.1 | 48.03 | |
| 281 | N-((1r,4r)-4-(3-aminopropanamido)cyclohexyl)benzo[d]thiazole-6-carboxamide | 347 | 28.96 | |
| 283 | N-(1-(1-(L-alanyl)piperidin-4-yl)ethyl)-1H-indole-5-carboxamide | 343.2 | >100 | |
| 284 | N-(1-(1-(L-alanyl)piperidin-4-yl)ethyl)-2,2-difluorobenzo[d][1,3]dioxole-5-carboxamide | 384.2 | >100 | |
| 285 | N-((1r,4r)-4-aminocyclohexyl)-2,2-difluorobenzo[d][1,3]dioxole-5-carboxamide | 299.2 | 69.12 | |
| 286 | 5-(((1r,4r)-4-aminocyclohexylcarbamoyl)benzo[c][1,2,5]oxadiazole 1-oxide | 277.1 | >100 | |
| 287 | N-((1r,4r)-4-aminocyclohexyl)benzo[c][1,2,5]oxadiazole-5-carboxamide | 261 | >100 | |
| 288 | 4-amino-N-((1r,4r)-4-(3-aminopropanamido)cyclohexyl)nicotinamide | 306.1 | >100 | |
| 289 | 4-amino-N-((1r,4r)-4-aminocyclohexyl)nicotinamide | 235.2 | >100 | |
| 290 | N-((1r,4r)-4-(3-aminopropanamido)cyclohexyl)-1H-indole-4-carboxamide | 329.2 | >100 | |
| 291 | N-((1r,4r)-4-aminocyclohexyl)-1H-indole-4-carboxamide | 258.2 | >100 | |
| 292 | N-((1r,4r)-4-aminocyclohexyl)-2-hydroxyisonicotinamide | 236.2 | >100 | |
| 293 | N-((1r,4r)-4-aminocyclohexyl)-2-hydroxyisonicotinamide | 236.1 | >100 | |
| 294 | N-((1r,4r)-4-(3-aminopropanamido)cyclohexyl)-6-hydroxynicotinamide | 307.2 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 295 | N-((1r,4r)-4-aminocyclohexyl)-6-hydroxynicotinamide | 236.2 | >100 | |
| 296 | N-(1-(1-(L-alanyl)piperidin-4-yl)ethyl)picolinamide | 305.2 | >100 | |
| 297 | N-(4-(3-aminopropanamido)cyclohexyl)picolinamide | 291.2 | 44.24 | |
| 298 | N-((1r,4r)-4-aminocyclohexyl)pyrazine-2-carboxamide | 221.2 | >100 | |
| 299 | N-(1-(1-(L-alanyl)piperidin-4-yl)ethyl)-3-(tert-butyl)-1-(3-methylbenzyl)-1H-pyrazole-5-carboxamide | 454.3 | >100 | |
| 300 | N-(1-(1-(L-alanyl)piperidin-4-yl)ethyl)-7-methyl-1H-indole-2-carboxamide | 357.2 | >100 | |
| 301 | N-(1-(1-(L-alanyl)piperidin-4-yl)ethyl)-6-methoxypicolinamide | 335.2 | >100 | |
| 302 | N-(1-(1-(L-alanyl)piperidin-4-yl)ethyl)-5-methoxypyrazine-2-carboxamide | 336.2 | >100 | |
| 303 | (1r,4r)-4-amino-N-((1r,4r)-4-(3-aminopropanamido)cyclohexyl)cyclohexane-1-carboxamide | 311.2 | >100 | |
| 304 | (1r,4r)-4-amino-N-((1r,4r)-4-aminocyclohexyl)cyclohexane-1-carboxamide | 240.1 | >100 | |
| 305 | (2S,4S)-N-(1-(1-(L-alanyl)piperidin-4-yl)ethyl)-4-fluoropyrrolidine-2-carboxamide | 315.2 | 55.92 | |
| 306 | (3R)-N-(1-(1-(L-alanyl)piperidin-4-yl)ethyl)-1,2,3,4-tetrahydroisoquinoline-3-carboxamide | 359.3 | 48.06 | |
| 307 | N-((1r,4r)-4-aminocyclohexyl)-2,2-difluorobenzo[d][1,3]dioxole-4-carboxamide | 299 | >100 | |
| 308 | N-((1r,4r)-4-aminocyclohexyl)-3-fluoroisonicotinamide | 238.2 | >100 | |
| 309 | N-(1-(1-(L-alanyl)piperidin-4-yl)ethyl)thiazole-5-carboxamide | 311.2 | >100 | |
| 310 | N-(1-(1-(L-alanyl)piperidin-4-yl)ethyl)-5-hydroxypicolinamide | 321.2 | >100 | |
| 311 | N-(1-(1-(L-alanyl)piperidin-4-yl)ethyl)-6-oxo-1,4,5,6-tetrahydropyridazine-3-carboxamide | 324.2 | >100 | |
| 312 | N-(1-(1-(L-alanyl)piperidin-4-yl)ethyl)-1H-indazole-3-carboxamide | 344.2 | >100 | |
| 313 | N-(1-(1-(L-alanyl)piperidin-4-yl)ethyl)-2-(3,5-difluorophenyl)acetamide | 354.2 | 70.71 | |
| 314 | N-(1-(1-(L-alanyl)piperidin-4-yl)ethyl)-2-(pyridin-3-yl)acetamide | 319.2 | >100 | |
| 315 | N-(1-(1-(L-alanyl)piperidin-4-yl)ethyl)-2-(pyrimidin-5-yl)acetamide | 320.3 | >100 | |
| 316 | N-(1-(1-(L-alanyl)piperidin-4-yl)ethyl)-2-(1H-imidazol-1-yl)acetamide | 308.2 | >100 | |
| 317 | N-((1r,4r)-4-(3-aminopropanamido)cyclohexyl)imidazo[2,1-b]thiazole-6-carboxamide | 336 | >100 | |
| 318 | N-((1r,4r)-4-aminocyclohexyl)imidazo[2,1-b]thiazole-6-carboxamide | 265 | >100 | |
| 319 | N-((1r,4r)-4-aminocyclohexyl)imidazo[2,1-b]thiazole-6-carboxamide | 265.2 | >100 | |
| 320 | N-((1r,4r)-4-aminocyclohexyl)-2-methylpyrimidine-5-carboxamide | 235.1 | >100 | |
| 321 | 2-amino-N-((1r,4r)-4-(3-aminopropanamido)cyclohexyl)isonicotinamide | 306.2 | 16.59 | |
| 322 | 2-amino-N-((1r,4r)-4-aminocyclohexyl)isonicotinamide | 235.1 | >100 | |
| 323 | N-(1-(1-(L-alanyl)piperidin-4-yl)ethyl)-4-sulfamoylbenzamide | 383 | >100 | |
| 324 | N-((1r,4r)-4-aminocyclohexyl)-4,6-dimethyl-2-oxo-1,2-dihydropyridine-3-carboxamide | 264.1 | >100 | |
| 325 | N-((1r,4r)-4-(3-aminopropanamido)cyclohexyl)-1-methyl-1H-indazole-6-carboxamide | 344.3 | >100 | |
| 326 | N-((1r,4r)-4-(3-aminopropanamido)cyclohexyl)-6-methoxy-2-naphthamide | 370.3 | 28 | |
| 327 | N-((1r,4r)-4-(3-aminopropanamido)cyclohexyl)-4-oxo-4H-chromene-2-carboxamide | 358.2 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 328 | N-((1r,4r)-4-aminocyclohexyl)-4-hydroxyquinoline-2-carboxamide | 286.2 | >100 | |
| 329 | N-((1r,4r)-4-(3-aminopropanamido)cyclohexyl)-4-(4H-1,2,4-triazol-4-yl)benzamide | 357.3 | >100 | |
| 330 | N-((1r,4r)-4-(3-aminopropanamido)cyclohexyl)-2,2-difluorobenzo[d][1,3]dioxole-5-carboxamide | 370.2 | 7.49 | |
| 331 | 5-(((1r,4r)-4-(3-aminopropanamido)cyclohexyl)carbamoyl)benzo[c][1,2,5]oxadiazole 1-oxide | 348.2 | 85.12 | |
| 332 | N-((1r,4r)-4-(3-aminopropanamido)cyclohexyl)benzo[c][1,2,5]oxadiazole-5-carboxamide | 332.2 | >100 | |
| 333 | N-((1r,4r)-4-aminocyclohexyl)-4-(1H-imidazol-1-yl)butanamide | 251.1 | >100 | |
| 334 | N-(1-(1-(L-alanyl)piperidin-4-yl)ethyl)-2-(6-methoxynaphthalen-2-yl)propanamide | 412.3 | 34.86 | |
| 335 | N-((1r,4r)-4-(3-aminopropanamido)cyclohexyl)-5-fluoro-1H-indole-2-carboxamide | 347.2 | >100 | |
| 336 | N-((1r,4r)-4-aminocyclohexyl)-1H-benzo[d]imidazole-2-carboxamide | 259.1 | >100 | |
| 337 | N-((1r,4r)-4-aminocyclohexyl)-1-methyl-1H-imidazole-2-carboxamide | 223.1 | >100 | |
| 338 | (1r,4r)-N-(1-(1-(L-alanyl)piperidin-4-yl)ethyl)bicyclo[2.2.1]hept-5-ene-2-carboxamide | 320.3 | >100 | |
| 339 | N-((1r,4r)-4-aminocyclohexyl)-4-methylnicotinamide | 234.1 | >100 | |
| 340 | N-((1r,4r)-4-(3-aminopropanamido)cyclohexyl)-3-(tert-butyl)-1-(3-methylbenzyl)-1H-pyrazole-5-carboxamide | 440.3 | >100 | |
| 341 | N-((1r,4r)-4-aminocyclohexyl)-3-(tert-butyl)-1-(3-methylbenzyl)-1H-pyrazole-5-carboxamide | 369.1 | >100 | |
| 342 | N-((1r,4r)-4-(3-aminopropanamido)cyclohexyl)-7-methyl-1H-indole-2-carboxamide | 343.2 | 37.68 | |
| 343 | N-((1r,4r)-4-aminocyclohexyl)-7-methyl-1H-indole-2-carboxamide | 272.2 | 68.49 | |
| 344 | N-((1r,4r)-4-(3-aminopropanamido)cyclohexyl)-5-methylnicotinamide | 305.1 | 36.4 | |
| 345 | N-((1r,4r)-4-aminocyclohexyl)-5-methylnicotinamide | 234.2 | 50.67 | |
| 346 | N-((1r,4r)-4-aminocyclohexyl)-6-methylnicotinamide | 234.1 | >100 | |
| 347 | N-((1r,4r)-4-(3-aminopropanamido)cyclohexyl)-3-methylisothiazole-4-carboxamide | 311.2 | >100 | |
| 348 | N-((1r,4r)-4-aminocyclohexyl)-3-methylisothiazole-4-carboxamide | 240.2 | >100 | |
| 349 | N-((1r,4r)-4-(3-aminopropanamido)cyclohexyl)-1-methyl-1H-pyrazole-3-carboxamide | 294.2 | >100 | |
| 350 | N-((1r,4r)-4-aminocyclohexyl)-1-methyl-1H-pyrazole-3-carboxamide | 223.2 | >100 | |
| 351 | N-((1r,4r)-4-(3-aminopropanamido)cyclohexyl)-3-(tert-butyl)-1-methyl-1H-pyrazole-5-carboxamide | 350.3 | >100 | |
| 352 | N-((1r,4r)-4-aminocyclohexyl)-3-(tert-butyl)-1-methyl-1H-pyrazole-5-carboxamide | 279.3 | >100 | |
| 353 | N-((1r,4r)-4-(3-aminopropanamido)cyclohexyl)-6-methoxypicolinamide | 321.2 | >100 | |
| 354 | N-((1r,4r)-4-aminocyclohexyl)-6-methoxypicolinamide | 250.2 | >100 | |
| 355 | N-((1r,4r)-4-(3-aminopropanamido)cyclohexyl)-6-methoxypyrazine-2-carboxamide | 322 | >100 | |
| 356 | N-((1r,4r)-4-aminocyclohexyl)-6-methoxypyrazine-2-carboxamide | 251.2 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 357 | N-(1-(1-(L-alanyl)piperidin-4-yl)ethyl)-5-aminopicolinamide | 320.2 | >100 | |
| 358 | N-((1r,4r)-4-aminocyclohexyl)-4-chloro-2-(trifluoromethyl)benzamide | 320.9 | >100 | |
| 359 | N-((1r,4r)-4-aminocyclohexyl)thiazole-5-carboxamide | 226.1 | >100 | |
| 360 | N-((1r,4r)-4-aminocyclohexyl)-1H-indole-3-carboxamide | 258.1 | >100 | |
| 361 | N-((1r,4r)-4-(3-aminopropanamido)cyclohexyl)-5-hydroxypicolinamide | 307.1 | >100 | |
| 362 | N-((1r,4r)-4-aminocyclohexyl)-2-(3,5-difluorophenyl)acetamide | 269.2 | >100 | |
| 363 | 3-amino-N-((1r,4r)-4-(2-(pyridin-3-yl)acetamido)cyclohexyl)propanamide | 305.1 | >100 | |
| 364 | 3-amino-N-((1r,4r)-4-(2-(pyrimidin-5-yl)acetamido)cyclohexyl)propanamide | 306.2 | >100 | |
| 365 | N-((1r,4r)-4-aminocyclohexyl)-2-(pyrimidin-5-yl)acetamide | 235.2 | >100 | |
| 366 | N-((1r,4r)-4-(2-(1H-imidazol-1-yl)acetamido)cyclohexyl)-3-aminopropanamide | 294.1 | >100 | |
| 367 | N-((1r,4r)-4-aminocyclohexyl)benzo[d]thiazole-2-carboxamide | 276.1 | >100 | |
| 368 | N-(1-(1-(L-alanyl)piperidin-4-yl)ethyl)-1H-indole-6-carboxamide | 343.3 | 12.33 | |
| 369 | N-((1r,4r)-4-(3-aminopropanamido)cyclohexyl)-1H-benzo[d]imidazole-5-carboxamide | 330.1 | 65.22 | |
| 370 | N-(1-(1-(L-alanyl)piperidin-4-yl)ethyl)-4-methoxy-1H-indole-3-carboxamide | 373.2 | >100 | |
| 371 | N-((1r,4r)-4-(3-aminopropanamido)cyclohexyl)-4-methoxy-1H-indole-3-carboxamide | 359.2 | >100 | |
| 372 | N-((1r,4r)-4-aminocyclohexyl)-4-methoxy-1H-indole-3-carboxamide | 288.1 | >100 | |
| 373 | N-((1r,4r)-4-(3-aminopropanamido)cyclohexyl)quinoxaline-2-carboxamide | 342.1 | >100 | |
| 374 | N-((1r,4r)-4-(3-aminopropanamido)cyclohexyl)-1H-benzo[d]imidazole-2-carboxamide | 330.3 | 86.56 | |
| 375 | N-((1r,4r)-4-(3-aminopropanamido)cyclohexyl)-4-(1H-imidazol-1-yl)butanamide | 322.2 | >100 | |
| 376 | N-((1r,4r)-4-(3-aminopropanamido)cyclohexyl)-2-hydroxyisonicotinamide | 307.2 | >100 | |
| 378 | N-(1-(1-(L-alanyl)piperidin-4-yl)ethyl)-6-hydroxynicotinamide | 321.1 | >100 | |
| 379 | N-((1r,4r)-4-(3-aminopropanamido)cyclohexyl)-3-methylisonicotinamide | 305.1 | >100 | |
| 380 | N-((1r,4r)-4-aminocyclohexyl)-3-methylisonicotinamide | 234.1 | >100 | |
| 381 | N-((1r,4r)-4-(3-aminopropanamido)cyclohexyl)-4-methylnicotinamide | 305.1 | >100 | |
| 382 | N-((1r,4r)-4-(3-aminopropanamido)cyclohexyl)-6-methylnicotinamide | 305.2 | >100 | |
| 383 | N-((1r,4r)-4-(3-aminopropanamido)cyclohexyl)-5-methoxypyrazine-2-carboxamide | 322.1 | >100 | |
| 384 | N-((1r,4r)-4-aminocyclohexyl)-5-methoxypyrazine-2-carboxamide | 251 | >100 | |
| 385 | 6-amino-N-((1r,4r)-4-(3-aminopropanamido)cyclohexyl)picolinamide | 306.2 | >100 | |
| 386 | 6-amino-N-((1r,4r)-4-aminocyclohexyl)picolinamide | 235.1 | >100 | |
| 387 | N-(1-(1-(L-alanyl)piperidin-4-yl)ethyl)-6-aminonicotinamide | 320.2 | >100 | |
| 388 | 6-amino-N-((1r,4r)-4-(3-aminopropanamido)cyclohexyl)nicotinamide | 306.2 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 389 | N-((1r,4r)-4-aminocyclohexyl)-6-fluoropicolinamide | 238.2 | >100 | |
| 390 | N-((1r,4r)-4-(3-aminopropanamido)cyclohexyl)-3-fluoroisonicotinamide | 309.2 | >100 | |
| 391 | N-((1r,4r)-4-(3-aminopropanamido)cyclohexyl)-1H-indole-3-carboxamide | 329.1 | >100 | |
| 392 | N-(1-(1-(L-alanyl)piperidin-4-yl)ethyl)-2-methylisonicotinamide | 319.2 | >100 | |
| 393 | N-((1r,4r)-4-(3-aminopropanamido)cyclohexyl)-2-methylisonicotinamide | 305.2 | >100 | |
| 394 | N-((1r,4r)-4-aminocyclohexyl)-2-methylisonicotinamide | 234.1 | >100 | |
| 395 | N-(1-(1-(L-alanyl)piperidin-4-yl)ethyl)benzo[d]thiazole-2-carboxamide | 361.2 | >100 | |
| 396 | N-(1-(1-(L-alanyl)piperidin-4-yl)ethyl)-5-methylthiazole-2-carboxamide | 325 | 10.61 | |
| 397 | N-((1r,4r)-4-(3-aminopropanamido)cyclohexyl)-5-methylthiazole-2-carboxamide | 311 | 27.42 | |
| 398 | N-((1r,4r)-4-aminocyclohexyl)-5-methylthiazole-2-carboxamide | 240.1 | >100 | |
| 399 | N-(1-(1-(L-alanyl)piperidin-4-yl)ethyl)-2-oxoindoline-4-carboxamide | 359.2 | >100 | |
| 400 | N-((1r,4r)-4-aminocyclohexyl)-2-oxoindoline-4-carboxamide | 274.2 | >100 | |
| 401 | N-((1r,4r)-4-(3-aminopropanamido)cyclohexyl)-5-methyl-1-phenyl-1H-1,2,3-triazole-4-carboxamide | 371.1 | >100 | |
| 402 | N-((1r,4r)-4-(3-aminopropanamido)cyclohexyl)-4,6-dimethyl-2-oxo-1,2-dihydropyridine-3-carboxamide | 335.2 | >100 | |
| 403 | N-((1r,4r)-4-aminocyclohexyl)-4-(3-methyl-5-oxo-4,5-dihydro-1H-pyrazol-1-yl)benzamide | 315.1 | >100 | |
| 404 | N-((1r,4r)-4-(3-aminopropanamido)cyclohexyl)-4-hydroxyquinoline-2-carboxamide | 357.2 | >100 | |
| 405 | N-((1r,4r)-4-aminocyclohexyl)quinoxaline-2-carboxamide | 271.2 | >100 | |
| 406 | N-(1-(1-(L-alanyl)piperidin-4-yl)ethyl)-2-(1H-pyrrolo[3,2-b]pyridin-3-yl)acetamide | 358.2 | >100 | |
| 407 | N-((1r,4r)-4-(2-(1H-pyrrolo[3,2-b]pyridin-3-yl)acetamido)cyclohexyl)-3-aminopropanamide | 344.2 | >100 | |
| 408 | N-((1r,4r)-4-aminocyclohexyl)-2-(1H-pyrrolo[3,2-b]pyridin-3-yl)acetamide | 273.2 | >100 | |
| 409 | N-(1-(1-(L-alanyl)piperidin-4-yl)ethyl)-2-hydroxynicotinamide | 321.2 | 70.41 | |
| 410 | N-((1r,4r)-4-(3-aminopropanamido)cyclohexyl)-2-hydroxynicotinamide | 307.3 | 44.48 | |
| 411 | N-((1r,4r)-4-aminocyclohexyl)-2-hydroxynicotinamide | 236.2 | >100 | |
| 412 | N-((1r,4r)-4-(3-aminopropanamido)cyclohexyl)-1-methyl-1H-imidazole-2-carboxamide | 294.1 | >100 | |
| 413 | N-(l-(1-(L-alanyl)piperidin-4-yl)ethyl)-1-methyl-1H-pyrazole-5-carboxamide | 308.1 | >100 | |
| 414 | N-((1r,4r)-4-(3-aminopropanamido)cyclohexyl)-1-methyl-1H-pyrazole-5-carboxamide | 294.1 | >100 | |
| 415 | N-((1r,4r)-4-aminocyclohexyl)-1-methyl-1H-pyrazole-5-carboxamide | 223.1 | >100 | |
| 416 | (1R,4R)-N-((1r,4R)-4-(3-aminopropanamido)cyclohexyl)bicyclo[2.2.1]hept-5-ene-2-carboxamide | 306.1 | >100 | |
| 417 | (1r,4r)-N-((1R,4R)-4-aminocyclohexyl)bicyclo[2.2.1]hept-5-ene-2-carboxamide | 235.1 | >100 | |
| 418 | N-(1-(1-(L-alanyl)piperidin-4-yl)ethyl)-6-aminopicolinamide | 320.3 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 419 | N-(1-(1-(L-alanyl)piperidin-4-yl)ethyl)-4-aminopyrimidine-5-carboxamide | 321.2 | >100 | |
| 420 | 4-amino-N-((1r,4r)-4-(3-aminopropanamido)cyclohexyl)pyrimidine-5-carboxamide | 307.2 | >100 | |
| 421 | 4-amino-N-((1r,4r)-4-aminocyclohexyl)pyrimidine-5-carboxamide | 236.1 | >100 | |
| 422 | N-((1r,4r)-4-(3-aminopropanamido)cyclohexyl)-6-fluoropicolinamide | 309.2 | >100 | |
| 423 | N-((1r,4r)-4-aminocyclohexyl)-5-hydroxypicolinamide | 236.2 | >100 | |
| 424 | N-((1r,4r)-4-aminocyclohexyl)-6-oxo-1,4,5,6-tetrahydropyridazine-3-carboxamide | 239.1 | >100 | |
| 425 | N-((1r,4r)-4-(3-aminopropanamido)cyclohexyl)-1H-indazole-3-carboxamide | 330.1 | 37.49 | |
| 426 | N-((1r,4r)-4-aminocyclohexyl)-2-(1H-imidazol-1-yl)acetamide | 223.1 | >100 | |
| 427 | N-((1r,4r)-4-(3-aminopropanamido)cyclohexyl)benzo[d]thiazole-2-carboxamide | 347.2 | >100 | |
| 428 | (1r,4r)-4-amino-N-(2-oxoindolin-5-yl)cyclohexane-1-carboxamide | 274.1 | 30.6 | |
| 429 | N-((1r,4r)-4-aminocyclohexyl)-2-oxoindoline-5-sulfonamide | 310 | 14.5 | |
| 430 | N-((1r,4r)-4-(3-aminopropanamido)cyclohexyl)-2-oxoindoline-4-carboxamide | 345.2 | >100 | |
| 431 | 3-amino-N-((1r,4r)-4-(2-(4-bromo-3,5-dimethyl-1H-pyrazol-1-yl)propanamido)cyclohexyl)propanamide | | >100 | |
| 432 | N-((1r,4r)-4-(3-aminopropanamido)cyclohexyl)-4-(3-methyl-5-oxo-4,5-dihydro-1H-pyrazol-1-yl)benzamide | 386.3 | 36.97 | |
| 433 | (2R,4S)-N-(1-(1-(L-alanyl)piperidin-4-yl)ethyl)-4-hydroxypyrrolidine-2-carboxamide | 313.2 | 45.65 | |
| 434 | (2R,4S)-N-((1r,4r)-4-(3-aminopropanamido)cyclohexyl)-4-hydroxypyrrolidine-2-carboxamide | 299.2 | >100 | |
| 435 | (2R,4S)-N-((1r,4r)-4-aminocyclohexyl)-4-hydroxypyrrolidine-2-carboxamide | 228.1 | >100 | |
| 436 | (R)-N-((1r,4r)-4-aminocyclohexyl)-1,2,3,4-tetrahydroquinoline-2-carboxamide | 274.1 | 12.51 | |
| 437 | 5-amino-N-((1r,4r)-4-(3-aminopropanamido)cyclohexyl)picolinamide | 306.2 | >100 | |
| 438 | 5-amino-N-((1r,4r)-4-aminocyclohexyl)picolinamide | 235.2 | >100 | |
| 439 | N-((1r,4r)-4-(3-aminopropanamido)cyclohexyl)-4-chloro-2-(trifluoromethyl)benzamide | 392.2 | >100 | |
| 440 | N-((1r,4r)-4-(3-aminopropanamido)cyclohexyl)-2,2-difluorobenzo[d][1,3]dioxole-4-carboxamide | 370.2 | >100 | |
| 441 | N-(1-(1-(L-alanyl)piperidin-4-yl)ethyl)-3,5-dihydroxy-2-naphthamide | 386.1 | 37.45 | |
| 442 | N-((1r,4r)-4-(3-aminopropanamido)cyclohexyl)thiazole-5-carboxamide | 297.2 | >100 | |
| 443 | 3-amino-N-((1r,4r)-4-(2-(3,5-difluorophenyl)acetamido)cyclohexyl)propanamide | 340.2 | >100 | |
| 444 | 5-acetamido-N-((1r,4r)-4-aminocyclohexyl)picolinamide | 277 | >100 | |
| 445 | N-(1-(1-(L-alanyl)piperidin-4-yl)ethyl)imidazo[1,2-b]pyridazine-2-carboxamide | 345 | >100 | |
| 446 | N-((1r,4r)-4-(3-aminopropanamido)cyclohexyl)imidazo[1,2-b]pyridazine-2-carboxamide | 331.1 | >100 | |
| 447 | N-((1r,4r)-4-aminocyclohexyl)imidazo[1,2-b]pyridazine-2-carboxamide | 260 | >100 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 448 | N-((1r,4r)-4-aminocyclohexyl)-2-(2-oxoindolin-5-yl)acetamide | 288.2 | >100 | |
| 449 | 3-amino-N-((1r,4r)-4-((2-oxoindoline)-5-sulfonamido)cyclohexyl)propanamide | 381.1 | >100 | |
| 450 | N-(1-(1-(L-alanyl)piperidin-4-yl)ethyl)-2-methyl-3-oxo-3,4-dihydro-2H-benzo[b][1,4]oxazine-6-carboxamide | 389.2 | 25.37 | |
| 451 | N-((1r,4r)-4-(3-aminopropanamido)cyclohexyl)-2-methyl-3-oxo-3,4-dihydro-2H-benzo[b][1,4]oxazine-6-carboxamide | 375.2 | 9.9 | |
| 452 | N-((1r,4r)-4-aminocyclohexyl)-2-methyl-3-oxo-3,4-dihydro-2H-benzo[b][1,4]oxazine-6-carboxamide | 304.2 | 39.15 | |
| 453 | N-((1r,4r)-4-((R)-3-aminobutanamido)cyclohexyl)-2-oxoindoline-5-carboxamide | 359.2 | 0.26 | >40 |
| 454 | N-((1r,4r)-4-aminocyclohexyl)-2-(4-bromo-3,5-dimethyl-1H-pyrazol-1-yl)propanamide | 342.9 | >100 | |
| 455 | N-((1r,4r)-4-aminocyclohexyl)-4-(1H-1,2,4-triazol-1-yl)benzamide | 286.2 | >100 | |
| 456 | N-((1r,4r)-4-(3-aminopropanamido)cyclohexyl)-2-hydroxyquinoline-3-carboxamide | 357.2 | 21.97 | |
| 457 | N-((1r,4r)-4-aminocyclohexyl)-2-(3-(trifluoromethyl)phenyl)acetamide | 301 | >100 | |
| 458 | 3-amino-N-((1r,4r)-4-aminocyclohexyl)-2-methylquinoline-4-carboxamide | 299.1 | >100 | |
| 459 | (3R)-N-(4-aminocyclohexyl)-1,2,3,4-tetrahydroisoquinoline-3-carboxamide | 274.1 | >100 | |
| 460 | N-((1r,4r)-4-aminocyclohexyl)-3,5-dihydroxy-2-naphthamide | 301 | 20.71 | |
| 461 | 5-(2-(piperidin-4-yl)acetyl)octahydro-2H-pyrrolo[3,2-c]pyridin-2-one | 266.1 | >100 | |
| 462 | N-(1-(1-(L-alanyl)piperidin-4-yl)ethyl)-5-acetamidopicolinamide | 362.1 | >100 | |
| 463 | 5-acetamido-N-((1r,4r)-4-(3-aminopropanamido)cyclohexyl)picolinamide | 348 | >100 | |
| 464 | N-(1-(1-(L-alanyl)piperidin-4-yl)ethyl)-5-cyclopropyl-1,2,4-oxadiazole-3-carboxamide | 336.2 | 32.68 | |
| 465 | 3-amino-N-((1r,4r)-4-(2-(2-oxoindolin-5-yl)acetamido)cyclohexyl)propanamide | 359.2 | 38.81 | |
| 466 | N-(1-(1-(L-alanyl)piperidin-4-yl)ethyl)-2-(2-oxoindolin-5-yl)acetamide | 373.2 | 60 | |
| 467 | (1r,4r)-4-(3-aminopropanamido)-N-(2-oxoindolin-5-yl)cyclohexane-1-carboxamide | 345 | 4.46 | |
| 468 | 3-amino-N-(2,2-dimethyl-3-((2-oxoindoline)-5-sulfonamido)propyl)propanamide | 369.2 | 18.32 | |
| 469 | N-(1-(1-(L-alanyl)piperidin-4-yl)ethyl)-1-oxoisoindoline-5-carboxamide | 359.2 | >100 | |
| 470 | N-((1r,4r)-4-aminocyclohexyl)-2,3-dioxoindoline-5-carboxamide | 288 | 7.46 | |
| 471 | N-((1r,4r)-4-(3-aminopropanamido)cyclohexyl)-2-oxoindoline-5-carboxamide | 345.2 | 0.61 | |
| 472 | N-(1-(1-(L-alanyl)piperidin-4-yl)ethyl)-4-(1H-1,2,4-triazol-1-yl)benzamide | 371.3 | >100 | |
| 473 | N-((1r,4r)-4-(3-aminopropanamido)cyclohexyl)-4-(1H-1,2,4-triazol-1-yl)benzamide | 357.2 | 53.11 | |
| 474 | N-(1-(1-(L-alanyl)piperidin-4-yl)ethyl)-2-hydroxyquinoline-3-carboxamide | 371.2 | 22.09 | |
| 475 | N-((1r,4r)-4-aminocyclohexyl)-2-hydroxyquinoline-3-carboxamide | 286.2 | 22.16 | |
| 476 | N-(1-(1-(L-alanyl)piperidin-4-yl)ethyl)-2-(3-(trifluoromethyl)phenyl)acetamide | 386.1 | 51.13 | |
| 477 | 3-amino-N-((1r,4r)-4-(2-(3-(trifluoromethyl)phenyl)acetamido)cyclohexyl)propanamide | 372 | 22.78 | |
| 478 | 3-amino-N-((1r,4r)-4-(3-aminopropanamido)cyclohexyl)-2-methylquinoline-4-carboxamide | 370.2 | 31.62 | |
| 479 | N-((1r,4r)-4-(3-aminopropanamido)cyclohexyl)-3,5-dihydroxy-2-naphthamide | 372 | 5.02 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 480 | N-((1r,4r)-4-aminocyclohexyl)-3-hydroxypicolinamide | 236.2 | >100 | |
| 481 | N-((1r,4r)-4-(3-aminopropanamido)cyclohexyl)-6-oxo-1,4,5,6-tetrahydropyridazine-3-carboxamide | 310.2 | 15.1 | |
| 482 | (E)-N-((1r,4r)-4-(3-aminopropanamido)cyclohexyl)-3-(1H-imidazol-4-yl)acrylamide | 306.1 | 71.06 | |
| 483 | 5-(2-(1-(3-aminopropanoyl)piperidin-4-yl)acetyl)octahydro-2H-pyrrolo[3,2-c]pyridin-2-one | 337.2 | 10.25 | |
| 484 | N-((1r,4r)-4-aminocyclohexyl)-5-cyclopropyl-1,2,4-oxadiazole-3-carboxamide | 251.1 | 85.66 | |
| 485 | N-((1r,4r)-4-(3-aminopropanamido)cyclohexyl)-5-cyclopropyl-1,2,4-oxadiazole-3-carboxamide | 322.1 | 12.92 | |
| 486 | 2-amino-N-(2,2-dimethyl-3-((2-oxoindoline)-5-sulfonamido)propyl)acetamide | 355 | 18.82 | |
| 487 | N-((1r,4r)-4-aminocyclohexyl)-1-oxoisoindoline-5-carboxamide | 274.1 | 37.89 | |
| 488 | N-(1-(1-(L-alanyl)piperidin-4-yl)ethyl)-2,3-dioxoindoline-5-carboxamide | 373.1 | 14.08 | |
| 489 | N-(1-(1-(L-alanyl)piperidin-4-yl)ethyl)-3-amino-2-methylquinoline-4-carboxamide | 384.3 | 31.62 | |
| 490 | N-(1-(1-(L-alanyl)piperidin-4-yl)ethyl)-6-chloro-2-oxoindoline-5-carboxamide | 393.2 | 0.43 | >40 |
| 491 | N-((1r,4r)-4-(3-aminopropanamido)cyclohexyl)-6-chloro-2-oxoindoline-5-carboxamide | 379.2 | 0.15 | >40 |
| 492 | N-((1r,4r)-4-aminocyclohexyl)-6-chloro-2-oxoindoline-5-carboxamide | 308.1 | 1.59 | |
| 493 | N-((1r,4r)-4-aminocyclohexyl)-4-hydroxypyrimidine-5-carboxamide | 237.1 | >50 | |
| 494 | (E)-N-(1-(1-(L-alanyl)piperidin-4-yl)ethyl)-3-(1H-imidazol-4-yl)acrylamide | 320.2 | >100 | |
| 495 | (E)-N-((1r,4r)-4-aminocyclohexyl)-3-(1H-imidazol-4-yl)acrylamide | 235.1 | >100 | |
| 496 | N-(1-(1-(L-alanyl)piperidin-4-yl)ethyl)-1H-pyrazolo[3,4-c]pyridine-5-carboxamide | 345.2 | 6.57 | |
| 497 | N-((1r,4r)-4-aminocyclohexyl)-1H-pyrazolo[3,4-c]pyridine-5-carboxamide | 260 | 35.73 | |
| 498 | N-(1-(1-(L-alanyl)piperidin-4-yl)ethyl)-6-fluorobenzo[d]thiazole-2-carboxamide | 379 | 51 | |
| 499 | N-((1r,4r)-4-(3-aminopropanamido)cyclohexyl)-6-fluorobenzo[d]thiazole-2-carboxamide | 365.2 | 86.27 | |
| 500 | N-((1r,4r)-4-aminocyclohexyl)-6-fluorobenzo[d]thiazole-2-carboxamide | 294.1 | >100 | |
| 501 | 1-(2-amino-2-oxoethyl)-N-((1r,4r)-4-aminocyclohexyl)-1H-1,2,3-triazole-4-carboxamide | 267.2 | 50 | |
| 502 | N-((1r,4r)-4-aminocyclohexyl)-1H-imidazole-2-carboxamide | 209.1 | >100 | |
| 503 | N-((1r,4r)-4-(3-aminopropanamido)cyclohexyl)-1-oxoisoindoline-5-carboxamide | 345.2 | >100 | |
| 504 | N-((1r,4r)-4-(3-aminopropanamido)cyclohexyl)-2,3-dioxoindoline-5-carboxamide | 359 | 5.38 | |
| 505 | N-((1r,4r)-4-(3-aminopropanamido)cyclohexyl)-2-oxoindoline-7-carboxamide | 345.2 | 16.1 | |
| 506 | N-(4-aminocyclohexyl)-2-oxoindoline-7-carboxamide | 274.2 | 42.25 | |
| 507 | N-((1r,4r)-4-aminocyclohexyl)-1-methyl-1H-1,2,4-triazole-5-carboxamide | 224.2 | >100 | |
| 508 | 3-amino-N-((1r,4r)-4-aminocyclohexyl)-1H-1,2,4-triazole-5-carboxamide | 225 | >50 | |
| 509 | N-(1-(1-(L-alanyl)piperidin-4-yl)ethyl)-4-hydroxypyrimidine-5-carboxamide | 322.1 | >50 | |
| 510 | N-((1r,4r)-4-(3-aminopropanamido)cyclohexyl)-4-hydroxypyrimidine-5-carboxamide | 308.1 | >50 | |
| 511 | N-(1-(1-(L-alanyl)piperidin-4-yl)ethyl)-3-hydroxypicolinamide | 321.1 | >50 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 512 | N-((1r,4r)-4-(3-aminopropanamido)cyclohexyl)-3-hydroxypicolinamide | 307 | >50 | |
| 513 | N-(1-(1-(L-alanyl)piperidin-4-yl)ethyl)-5-hydroxynicotinamide | 321.2 | >50 | |
| 514 | N-((1r,4r)-4-(3-aminopropanamido)cyclohexyl)-5-hydroxynicotinamide | 307.1 | >50 | |
| 515 | N-((1r,4r)-4-aminocyclohexyl)-5-hydroxynicotinamide | 236.1 | >50 | |
| 516 | 1-(2-amino-2-oxoethyl)-N-((1r,4r)-4-(3-aminopropanamido)cyclohexyl)-1H-1,2,3-triazole-4-carboxamide | 338.2 | >50 | |
| 517 | N-(4-aminocyclohexyl)-1H-imidazole-4-carboxamide | 209.2 | >50 | |
| 518 | N-(4-(3-aminopropanamido)cyclohexyl)-1H-imidazole-2-carboxamide | 280.2 | >50 | |
| 519 | N-((1r,4r)-4-(3-aminopropanamido)cyclohexyl)-2-methyl-1H-indole-5-carboxamide | 343.2 | >50 | |
| 520 | N-((1r,4r)-4-aminocyclohexyl)-2-methyl-1H-indole-5-carboxamide | 272.2 | >50 | |
| 521 | N-((1r,4r)-4-aminocyclohexyl)-1H-imidazole-4-carboxamide | 209.2 | >50 | |
| 522 | N-((1r,4r)-4-aminocyclohexyl)-2-methyl-1H-imidazole-5-carboxamide | 223.2 | >50 | |
| 523 | N-(1-(1-(L-alanyl)piperidin-4-yl)ethyl)-4H-1,2,4-triazole-3-carboxamide | 295.1 | >50 | |
| 525 | N-((1r,4r)-4-(3-aminopropanamido)cyclohexyl)-4H-1,2,4-triazole-3-carboxamide | 281.1 | >50 | |
| 527 | N-(1-(1-(L-alanyl)piperidin-4-yl)ethyl)-5-chloro-1H-pyrazole-3-carboxamide | 328 | >50 | |
| 528 | N-((1r,4r)-4-(3-aminopropanamido)cyclohexyl)-5-chloro-1H-pyrazole-3-carboxamide | 314 | >50 | |
| 529 | N-((1r,4r)-4-(3-aminopropanamido)cyclohexyl)-1H-pyrazolo[3,4-c]pyridine-5-carboxamide | 331.2 | 4.45 | |
| 530 | N-((1r,4r)-4-(3-aminopropanamido)cyclohexyl)-5-oxo-4,5-dihydro-1H-1,2,4-triazole-3-carboxamide | 297.1 | >50 | |
| 531 | N-((1r,4r)-4-aminocyclohexyl)-5-oxo-4,5-dihydro-1H-1,2,4-triazole-3-carboxamide | 226.1 | >50 | |
| 532 | N-((1r,4r)-4-(3-aminopropanamido)cyclohexyl)thiazolo[5,4-c]pyridine-2-carboxamide | 348.1 | >50 | |
| 533 | N-((1r,4r)-4-aminocyclohexyl)thiazolo[5,4-c]pyridine-2-carboxamide | 277.1 | >50 | |
| 534 | N-(1-(1-(L-alanyl)piperidin-4-yl)ethyl)-1-(2-amino-2-oxoethyl)-1H-1,2,3-triazole-4-carboxamide | 352.2 | >50 | |
| 535 | N-((1r,4r)-4-aminocyclohexyl)-5-ethyl-1H-1,2,4-triazole-3-carboxamide | 238.1 | >50 | |
| 536 | N-((1r,4r)-4-(3-aminopropanamido)cyclohexyl)-5-ethyl-4H-1,2,4-triazole-3-carboxamide | 309.2 | >50 | |
| 537 | N-((1r,4r)-4-(3-aminopropanamido)cyclohexyl)-1H-imidazole-4-carboxamide | 280.2 | >50 | |
| 538 | N-(1-(1-(L-alanyl)piperidin-4-yl)ethyl)-2-methyl-1H-indole-5-carboxamide | 357.2 | >50 | |
| 539 | N-((1R,4r)-4-((1r,4R)-4-aminocyclohexane-1-carboxamido)cyclohexyl)-1H-1,2,4-triazole-5-carboxamide | 335.2 | >50 | |
| 540 | N-((1r,4r)-4-(4-aminobutanamido)cyclohexyl)-4H-1,2,4-triazole-3-carboxamide | 295.1 | >50 | |
| 541 | N-((1r,4r)-4-aminocyclohexyl)-5-chloro-1H-1,2,4-triazole-3-carboxamide | 244.1 | >50 | |
| 542 | N-((1r,4r)-4-aminocyclohexyl)-5-methyl-1H-imidazole-4-carboxamide | 223.1 | >50 | |
| 543 | N-((1r,4r)-4-(3-aminopropanamido)cyclohexyl)-5-methyl-4H-1,2,4-triazole-3-carboxamide | 295.1 | >50 | |

TABLE 1A-continued

| Cpd. No. | Chemical Name | LCMS M + H | SMYD3 Biochem IC$_{50}$ (μM)* | SMYD3 Cell IC$_{50}$ (μM)* |
|---|---|---|---|---|
| 544 | N-((1r,4r)-4-aminocyclohexyl)-1-methyl-1H-1,2,4-triazole-3-carboxamide | 224.2 | >50 | |
| 545 | N-((1r,4r)-4-aminocyclohexyl)-5-chloro-1H-pyrazole-3-carboxamide | 243.1 | >50 | |
| 546 | N-(1-(1-(L-alanyl)piperidin-4-yl)ethyl)-5-oxo-4,5-dihydro-1H-1,2,4-triazole-3-carboxamide | 311.1 | 9.76 | |
| 547 | N-(1-(2-(piperidin-4-yl)acetyl)piperidin-4-yl)-4H-1,2,4-triazole-3-carboxamide | 321.2 | >50 | |
| 548 | N-((1r,4r)-4-aminocyclohexyl)-3-iodo-1H-1,2,4-triazole-5-carboxamide | 335.9 | >50 | |
| 549 | N-(1-(1-(L-alanyl)piperidin-4-yl)ethyl)-3-methyl-1H-1,2,4-triazole-5-carboxamide | 309.2 | >50 | |
| 550 | N-((1r,4r)-4-aminocyclohexyl)-5-methyl-1H-1,2,4-triazole-3-carboxamide | 224.1 | 14.71 | |
| 551 | N-(1-(1-(L-alanyl)piperidin-4-yl)ethyl)thiazolo[5,4-c]pyridine-2-carboxamide | 362.2 | >50 | |
| 552 | N-(1-(1-(L-alanyl)piperidin-4-yl)ethyl)-5-ethylthiazole-2-carboxamide | 339.2 | 6.44 | |
| 553 | N-((1r,4r)-4-(3-aminopropanamido)cyclohexyl)-5-ethylthiazole-2-carboxamide | 325.2 | 25.61 | |
| 554 | N-((1r,4r)-4-aminocyclohexyl)-5-ethylthiazole-2-carboxamide | 254.1 | >50 | |
| 555 | N-(1-((1r,4r)-4-aminocyclohexane-1-carbonyl)piperidin-4-yl)-4H-1,2,4-triazole-3-carboxamide | 321.1 | >50 | |
| 556 | N-(1-(3-aminopropanoyl)piperidin-4-yl)-4H-1,2,4-triazole-3-carboxamide | 267.2 | >50 | |
| 557 | (±)-trans-N-(1-(4-aminocyclohexane-1-carbonyl)-2-methylpiperidin-4-yl)benzamide | 344.1 | >10 | |
| 558 | (±)-cis-N-(1-(4-aminocyclohexane-1-carbonyl)-2-methylpiperidin-4-yl)benzamide | 358.1 (+Na) | >10 | |
| 559 | N-((1r,4r)-4-aminocyclohexyl)-2-oxo-2,3-dihydro-1H-pyrrolo[2,3-c]pyridine-5-carboxamide | 275.1 | 3.49 | |
| 560 | N-(1-(4-aminobutanoyl)piperidin-4-yl)-4H-1,2,4-triazole-3-carboxamide | 281.1 | >10 | |
| 561 | N-((1r,4r)-4-aminocyclohexyl)-N-methyl-1H-1,2,4-triazole-5-carboxamide | 224.1 | >10 | |
| 562 | N-((1r,4r)-4-aminocyclohexyl)-4-methyl-1H-imidazole-2-carboxamide | 223.2 | >10 | |
| 563 | (±)-trans-N-(1-((3-aminopropyl)sulfonyl)-2-methylpiperidin-4-yl)benzamide | 340.05 | >10 | |
| 564 | (±)-cis-N-(1-((3-aminopropyl)sulfonyl)-2-methylpiperidin-4-yl)benzamide | 340.05 | >10 | |
| 565 | N-((1r,4r)-4-aminocyclohexyl)-6-bromo-2-hydroxyquinoline-3-carboxamide | 364 | >10 | |
| 566 | N-((1r,4r)-4-(3-aminopropanamido)cyclohexyl)-6-bromo-2-hydroxyquinoline-3-carboxamide | | >10 | |
| 567 | (±)-cis-N-(1-(4-aminocyclohexane-1-carbonyl)-2-methylpiperidin-4-yl)benzamide | 366.3 (+Na) | >10 | |
| 568 | (±)-cis-N-(1-((3-aminopropyl)sulfonyl)-2-methylpiperidin-4-yl)-[1,1'-biphenyl]-4-carboxamide | 438.15 (+Na) | >10 | |
| 569 | (±)-cis-N-(1-((3-aminopropyl)sulfonyl)-2-methylpiperidin-4-yl)-3-ethylbenzamide | 368.1 | 8.02 | |
| 570 | (±)-cis-N-(1-((3-aminopropyl)sulfonyl)-2-methylpiperidin-4-yl)benzamide | 340.1 | >10 | |
| 571 | (±)-trans-N-(1-(4-aminocyclohexane-1-carbonyl)-2-methylpiperidin-4-yl)benzamide | 344.1 | >10 | |
| 572 | 2-amino-N-((1r,4r)-4-aminocyclohexyl)-1H-imidazole-4-carboxamide | 224.1 | >10 | |
| 573 | (±)-trans-N-(1-((3-aminopropyl)sulfonyl)-2-methylpiperidin-4-yl)-3-ethylbenzamide | 368.2 | >10 | |
| 574 | N-((1r,4r)-4-aminocyclohexyl)imidazo[1,2-a]pyrimidine-3-carboxamide | 260.1 | >10 | |

*IC$_{50}$ values are an average of n = 1 to n = 50

TABLE 3A

| Cpd. No. | Chemical Name | LCMS M + H or (M + Na) or ((M − NH$_2$)) | SMYD3 Biochem IC$_{50}$ (μM)* | SMYD3 cell IC$_{50}$ (μM)* |
|---|---|---|---|---|
| 575 | N-((1R,3R,5S)-8-(((1r,4R)-4-aminocyclohexyl)sulfonyl)-8-azabicyclo[3.2.1]octan-3-yl)-2-oxoindoline-5-carboxamide | 447 | 0.00044 | 2.17352 |
| 576 | N-((1R,3r,5S)-8-((4-aminopiperidin-1-yl)sulfonyl)-8-azabicyclo[3.2.1]octan-3-yl)-6-fluoro-2-oxoindoline-5-carboxamide | 466 | 0.00049 | 0.52547 |
| 577 | N-((1R,3r,5S)-8-(((1-methylpiperidin-4-yl)methyl)sulfonyl)-8-azabicyclo[3.2.1]octan-3-yl)-2-oxoindoline-5-carboxamide | 461 | 0.00067 | 0.4806 |
| 578 | N-((1R,3r,5S)-8-((4-aminopiperidin-1-yl)sulfonyl)-8-azabicyclo[3.2.1]octan-3-yl)-2-oxoindoline-5-carboxamide | 448 | 0.00068 | 0.85408 |
| 579 | N-((1R,3r,5S)-8-((4-aminopiperidin-1-yl)sulfonyl)-8-azabicyclo[3.2.1]octan-3-yl)-6-chloro-2-oxoindoline-5-carboxamide | 482 | 0.00081 | 1.12914 |
| 580 | N-((2S,4S)-1-((4-aminopiperidin-1-yl)sulfonyl)-2-methylpiperidin-4-yl)-2-oxoindoline-5-carboxamide | 436 | 0.0009 | 1.63568 |
| 581 | N-((1R,3r,5S)-8-(((1-(3-hydroxypropyl)piperidin-4-yl)methyl)sulfonyl)-8-azabicyclo[3.2.1]octan-3-yl)-2-oxoindoline-5-carboxamide | 505 | 0.00095 | 1.67455 |
| 582 | N-((2S,4S)-1-((4-aminopiperidin-1-yl)sulfonyl)-2-methylpiperidin-4-yl)-6-chloro-2-oxoindoline-5-carboxamide | 470 | 0.00098 | 0.81381 |
| 583 | N-((1R,3R,5S)-8-(((1r,4R)-4-aminocyclohexyl)sulfonyl)-8-azabicyclo[3.2.1]octan-3-yl)-6-chloro-2-oxoindoline-5-carboxamide | 481 | 0.0011 | 1.50735 |
| 584 | N-((2S)-1-((4-(2-aminopropan-2-yl)phenyl)sulfonyl)-2-methylpiperidin-4-yl)-2-oxoindoline-5-carboxamide | 471 | 0.00147 | 0.65295 |
| 585 | 6-chloro-N-((1R,3r,5S)-8-(((1-(3-hydroxypropyl)piperidin-4-yl)methyl)sulfonyl)-8-azabicyclo[3.2.1]octan-3-yl)-2-oxoindoline-5-carboxamide | 539 | 0.00173 | 0.76375 |
| 586 | 6-chloro-N-((1R,3r,5S)-8-((4-(methylamino)piperidin-1-yl)sulfonyl)-8-azabicyclo[3.2.1]octan-3-yl)-2-oxoindoline-5-carboxamide | 496 | 0.00189 | 0.42454 |
| 587 | N-((1R,3r,5S)-8-((4-(benzylamino)piperidin-1-yl)sulfonyl)-8-azabicyclo[3.2.1]octan-3-yl)-2-oxoindoline-5-carboxamide | 538 | 0.00198 | 0.07099 |
| 588 | N-((2S,4S)-1-((4-(2-aminopropan-2-yl)phenyl)sulfonyl)-2-methylpiperidin-4-yl)-6-chloro-2-oxoindoline-5-carboxamide | 505 | 0.00198 | 0.35648 |
| 589 | N-((1R,3r,5S)-8-((4-(methylamino)piperidin-1-yl)sulfonyl)-8-azabicyclo[3.2.1]octan-3-yl)-2-oxoindoline-5-carboxamide | 462 | 0.00213 | 0.98725 |
| 590 | 2-oxo-N-((1R,3r,5S)-8-((piperidin-3-ylmethyl)sulfonyl)-8-azabicyclo[3.2.1]octan-3-yl)indoline-5-carboxamide | 447 | 0.00214 | 0.76757 |
| 591 | N-((1R,3R,5S)-8-(((1s,4S)-4-aminocyclohexyl)sulfonyl)-8-azabicyclo[3.2.1]octan-3-yl)-2-oxoindoline-5-carboxamide | 447 | 0.00233 | 2.31394 |

TABLE 3A-continued

| Cpd. No. | Chemical Name | LCMS M + H or (M + Na) or ((M − NH$_2$)) | SMYD3 Biochem IC$_{50}$ (μM)* | SMYD3 cell IC$_{50}$ (μM)* |
|---|---|---|---|---|
| 592 | N-((1R,3r,5S)-8-((4-(benzylamino)piperidin-1-yl)sulfonyl)-8-azabicyclo[3.2.1]octan-3-yl)-6-chloro-2-oxoindoline-5-carboxamide | 572 | 0.00258 | 0.05357 |
| 593 | N-((1R,3r,5S)-8-((4-(dimethylamino)piperidin-1-yl)sulfonyl)-8-azabicyclo[3.2.1]octan-3-yl)-2-oxoindoline-5-carboxamide | 476 | 0.00289 | 0.50002 |
| 594 | 6-chloro-N-((1R,3r,5S)-8-((4-(dimethylamino)piperidin-1-yl)sulfonyl)-8-azabicyclo[3.2.1]octan-3-yl)-2-oxoindoline-5-carboxamide | 510 | 0.00346 | 0.30139 |
| 595 | 6-chloro-2-oxo-N-((1R,3r,5S)-8-(((1-(4,4,4-trifluorobutyl)piperidin-4-yl)methyl)sulfonyl)-8-azabicyclo[3.2.1]octan-3-yl)indoline-5-carboxamide | 591 | 0.00354 | 0.03609 |
| 596 | 6-chloro-2-oxo-N-((1R,3r,5S)-8-((piperidin-4-ylmethyl)sulfonyl)-8-azabicyclo[3.2.1]octan-3-yl)indoline-5-carboxamide | 481 | 0.0036 | 2.66255 |
| 597 | 2-oxo-N-((1R,3r,5S)-8-((piperidin-4-ylmethyl)sulfonyl)-8-azabicyclo[3.2.1]octan-3-yl)indoline-5-carboxamide | 447 | 0.00398 | 3.43731 |
| 598 | 6-chloro-2-oxo-N-((1R,3S,5S)-8-((((S)-piperidin-3-yl)methyl)sulfonyl)-8-azabicyclo[3.2.1]octan-3-yl)indoline-5-carboxamide | 481 | 0.00412 | 1.26702 |
| 599 | N-((2S,4S)-2-methyl-1-((piperidin-4-ylmethyl)sulfonyl)piperidin-4-yl)-2-oxoindoline-5-carboxamide | 435 | 0.00442 | 9.48804 |
| 600 | 6-chloro-2-oxo-N-((1R,3R,5S)-8-((((R)-piperidin-3-yl)methyl)sulfonyl)-8-azabicyclo[3.2.1]octan-3-yl)indoline-5-carboxamide | 481 | 0.00499 | 0.72841 |
| 601 | 2-oxo-N-((1R,3r,5S)-8-((piperidin-4-ylmethyl)sulfonyl)-8-azabicyclo[3.2.1]octan-3-yl)-2,3-dihydrobenzo[d]oxazole-6-carboxamide | 449 | 0.00521 | 4.54161 |
| 602 | N-((1R,3r,5S)-8-((4-aminopiperidin-1-yl)sulfonyl)-8-azabicyclo[3.2.1]octan-3-yl)-6-bromo-2-oxoindoline-5-carboxamide | 528 | 0.00712 | 3.72505 |
| 603 | N-((3S)-1-((4-aminopiperidin-1-yl)sulfonyl)-3-methylpiperidin-4-yl)-6-chloro-2-oxoindoline-5-carboxamide | 470 | 0.00853 | 2.67708 |
| 604 | N-((1R,3r,5S)-8-((4-aminopiperidin-1-yl)sulfonyl)-8-azabicyclo[3.2.1]octan-3-yl)-6-chloro-1-methyl-2-oxoindoline-5-carboxamide | 496 | 0.01347 | 0.20704 |
| 605 | N-((2S,4S)-1-((4-aminopiperidin-1-yl)sulfonyl)-2-methylpiperidin-4-yl)-5-ethylisothiazole-3-carboxamide | 416 | 0.01544 | 0.20068 |
| 606 | N-((1R,3r,5S)-8-((4-aminopiperidin-1-yl)sulfonyl)-8-azabicyclo[3.2.1]octan-3-yl)-6-methyl-2-oxoindoline-5-carboxamide | 462 | 0.01561 | 1.79073 |
| 607 | N-((2S,4S)-1-((4-aminopiperidin-1-yl)sulfonyl)-2-methylpiperidin-4-yl)-5-cyclopropyl-1,3,4-thiadiazole-2-carboxamide | (451) | 0.01813 | 0.20535 |

TABLE 3A-continued

| Cpd. No. | Chemical Name | LCMS M + H or (M + Na) or ((M − NH$_2$)) | SMYD3 Biochem IC$_{50}$ (μM)* | SMYD3 cell IC$_{50}$ (μM)* |
|---|---|---|---|---|
| 608 | N-((3R,4R)-1-((4-aminopiperidin-1-yl)sulfonyl)-3-methylpiperidin-4-yl)-6-chloro-2-oxoindoline-5-carboxamide | 470 | 0.02137 | 6.23686 |
| 609 | N-((1R,3r,5S)-8-((4-aminopiperidin-1-yl)sulfonyl)-8-azabicyclo[3.2.1]octan-3-yl)-3-oxo-3,4-dihydro-2H-benzo[b][1,4]oxazine-6-carboxamide | 464 | 0.02365 | 3.70034 |
| 610 | N-((1R,3r,5S)-8-((4-aminopiperidin-1-yl)sulfonyl)-8-azabicyclo[3.2.1]octan-3-yl)-5-ethylisothiazole-3-carboxamide | 428 | 0.02378 | 0.21618 |
| 611 | 1-methyl-2-oxo-N-((1R,3r,5S)-8-((piperidin-4-ylmethyl)sulfonyl)-8-azabicyclo[3.2.1]octan-3-yl)indoline-5-carboxamide | 461 | 0.02593 | 3.91552 |
| 612 | N-((1R,3r,5S)-8-((4-(2-aminopropan-2-yl)phenyl)sulfonyl)-8-azabicyclo[3.2.1]octan-3-yl)-2-oxoindoline-5-carboxamide | 483 | 0.03068 | 2.53133 |
| 613 | N-((1R,3r,5S)-8-((4-(2-aminopropan-2-yl)phenyl)sulfonyl)-8-azabicyclo[3.2.1]octan-3-yl)-6-chloro-2-oxoindoline-5-carboxamide | 517 | 0.03712 | 1.77071 |
| 614 | 6-chloro-2-oxo-N-((1R,3r,5S)-8-((2-(pyrrolidin-1-yl)ethyl)sulfonyl)-8-azabicyclo[3.2.1]octan-3-yl)indoline-5-carboxamide | 481 | 0.04599 | 0.37965 |
| 615 | 2-oxo-N-((1R,3r,5S)-8-((2-(pyrrolidin-1-yl)ethyl)sulfonyl)-8-azabicyclo[3.2.1]octan-3-yl)indoline-5-carboxamide | 447 | 0.04974 | 0.76121 |
| 616 | N-((1R,3r,5S)-8-((4-aminopiperidin-1-yl)sulfonyl)-8-azabicyclo[3.2.1]octan-3-yl)-5-ethylpyridazine-3-carboxamide | 423 | 0.0499 | 0.53953 |
| 617 | 6-chloro-1-methyl-2-oxo-N-((1R,3r,5S)-8-((piperidin-4-ylmethyl)sulfonyl)-8-azabicyclo[3.2.1]octan-3-yl)indoline-5-carboxamide | 495 | 0.05233 | 2.95866 |
| 618 | N-((1R,3r,5S)-8-((4-aminopiperidin-1-yl)sulfonyl)-8-azabicyclo[3.2.1]octan-3-yl)-5-cyclopropyl-1,3,4-thiadiazole-2-carboxamide | 441 | 0.05583 | 0.3477 |
| 619 | N-((2S,4S)-1-((4-aminopiperidin-1-yl)sulfonyl)-2-methylpiperidin-4-yl)-5-ethylpyridazine-3-carboxamide | 411 | 0.05959 | 0.46793 |
| 620 | 2-oxo-N-(1-((piperidin-4-ylmethyl)sulfonyl)piperidin-4-yl)indoline-5-carboxamide | 421 | 0.06816 | 10 |
| 621 | N-(1-((3-aminopropyl)sulfonyl)piperidin-4-yl)-6-chloro-2-oxoindoline-5-carboxamide | 415 | 0.07749 | 6.83658 |
| 622 | N-((1R,3r,5S)-8-((4-aminocyclohexyl)sulfonyl)-8-azabicyclo[3.2.1]octan-3-yl)-2,2-difluorobenzo[d][1,3]dioxole-5-carboxamide | 472 | 0.13055 | 1.07968 |
| 623 | N-((1R,3R,5S)-8-(((1r,4R)-4-aminocyclohexyl)sulfonyl)-8-azabicyclo[3.2.1]octan-3-yl)-2,2-difluorobenzo[d][1,3]dioxole-5-carboxamide | 472 | 0.1358 | 0.89555 |
| 624 | N-(1-((3-aminopropyl)sulfonyl)piperidin-4-yl)-2-oxoindoline-5-carboxamide | 381 | 0.15882 | 10 |

TABLE 3A-continued

| Cpd. No. | Chemical Name | LCMS M + H or (M + Na) or ((M − NH$_2$)) | SMYD3 Biochem IC$_{50}$ (μM)* | SMYD3 cell IC$_{50}$ (μM)* |
|---|---|---|---|---|
| 625 | (R)-2-methyl-3-oxo-N-((1R,3r,5S)-8-((piperidin-4-ylmethyl)sulfonyl)-8-azabicyclo[3.2.1]octan-3-yl)-3,4-dihydro-2H-benzo[b][1,4]oxazine-6-carboxamide | 477 | 0.18459 | 10 |
| 626 | N-((1R,3r,5S)-8-((4-aminopiperidin-1-yl)sulfonyl)-8-azabicyclo[3.2.1]octan-3-yl)-2,2-difluorobenzo[d][1,3]dioxole-5-carboxamide | 473 | 0.22228 | 2.96871 |
| 627 | N-((1R,3R,5S)-8-(((1r,4R)-4-(benzylamino)cyclohexyl)sulfonyl)-8-azabicyclo[3.2.1]octan-3-yl)-2,2-difluorobenzo[d][1,3]dioxole-5-carboxamide | 562 | 0.22495 | 1.54162 |
| 628 | 2,2-difluoro-N-((1R,3r,5S)-8-((piperidin-4-ylmethyl)sulfonyl)-8-azabicyclo[3.2.1]octan-3-yl)benzo[d][1,3]dioxole-5-carboxamide | 472 | 0.23189 | 3.62035 |
| 629 | N-((2S,4R)-1-((4-aminopiperidin-1-yl)sulfonyl)-2-methylpiperidin-4-yl)-5-ethylisothiazole-3-carboxamide | (438) | 0.32589 | 2.08253 |
| 630 | 2,2-difluoro-N-((1R,3r,5S)-8-(((1-methylpiperidin-4-yl)methyl)sulfonyl)-8-azabicyclo[3.2.1]octan-3-yl)benzo[d][1,3]dioxole-5-carboxamide | 486 | 0.3614 | 6.55362 |
| 631 | N-((2S,4R)-1-((4-aminopiperidin-1-yl)sulfonyl)-2-methylpiperidin-4-yl)-5-cyclopropyl-1,3,4-thiadiazole-2-carboxamide | (451) | 0.4699 | 4.89772 |
| 632 | N-((2S,4S)-1-((4-acetamidophenyl)sulfonyl)-2-methylpiperidin-4-yl)-2-oxoindoline-5-carboxamide | 471 | 0.52572 | 10 |
| 633 | N-((1R,3r,5S)-8-((4-aminopiperidin-1-yl)sulfonyl)-8-azabicyclo[3.2.1]octan-3-yl)-5-cyclopropyl-1H-pyrazole-3-carboxamide | 423 | 0.52917 | 10 |
| 634 | N-((3R,4S)-1-((4-aminopiperidin-1-yl)sulfonyl)-3-methylpiperidin-4-yl)-6-chloro-2-oxoindoline-5-carboxamide | 470 | 0.52937 | 0.97208 |
| 635 | 3-ethyl-N-((1R,3r,5S)-8-((piperidin-4-ylmethyl)sulfonyl)-8-azabicyclo[3.2.1]octan-3-yl)benzamide | 420 | 0.62038 | 10 |
| 636 | N-((1R,3r,5S)-8-((4-aminopiperidin-1-yl)sulfonyl)-8-azabicyclo[3.2.1]octan-3-yl)-3-oxo-3,4-dihydro-2H-benzo[b][1,4]oxazine-7-carboxamide | 464 | 0.81894 | 10 |
| 637 | N-((1R,3r,5S)-8-((4-aminopiperidin-1-yl)sulfonyl)-8-azabicyclo[3.2.1]octan-3-yl)-1-cyclopropyl-1H-pyrazole-4-carboxamide | 423 | 0.8386 | 10 |
| 638 | N-((1R,3R,5S)-8-((1r,4R)-4-aminocyclohexane-1-carbonyl)-8-azabicyclo[3.2.1]octan-3-yl)-2-oxoindoline-5-carboxamide | 411 | 0.96185 | 10 |
| 639 | N-((2S,4S)-1-((4-aminopiperidin-1-yl)sulfonyl)-2-methylpiperidin-4-yl)-1-cyclopropyl-1H-pyrazole-4-carboxamide | 411 | 1.00072 | 10 |
| 640 | N-((2S)-1-((1r,4S)-4-aminocyclohexane-1-carbonyl)-2-methylpiperidin-4-yl)-6-chloro-2-oxoindoline-5-carboxamide | ((416)) | 2.04146 | 10 |

TABLE 3A-continued

| Cpd. No. | Chemical Name | LCMS M + H or (M + Na) or ((M − NH$_2$)) | SMYD3 Biochem IC$_{50}$ (μM)* | SMYD3 cell IC$_{50}$ (μM)* |
|---|---|---|---|---|
| 641 | N-(1-((4-acetamidophenyl)sulfonyl)piperidin-4-yl)-6-chloro-2-oxoindoline-5-carboxamide | 491 | 5.93159 | 10 |
| 642 | N-((2S,4S)-1-((1r,4S)-4-aminocyclohexane-1-carbonyl)-2-methylpiperidin-4-yl)-2-oxoindoline-5-carboxamide | ((382)) | 6.81095 | 10 |
| 643 | N-(1-((4-acetamidophenyl)sulfonyl)piperidin-4-yl)-2-oxoindoline-5-carboxamide | 457 | 16.85335 | 10 |
| 644 | N-((1R,3r,5S)-8-((4-aminopiperidin-1-yl)sulfonyl)-8-azabicyclo[3.2.1]octan-3-yl)-3-cyclopropylisoxazole-5-carboxamide | 424.00 | 0.0185 | 0.25715 |

*IC$_{50}$ values are an average of n = 1 to n = 50

TABLE 4A

| Cpd. No. | Chemical Name | LCMS M + H | SMYD2 Biochem IC$_{50}$ (μM)* |
|---|---|---|---|
| 645 | 5-cyclopropyl-N-[1-(propan-2-yl)azetidin-3-yl]pyridazine-3-carboxamide | 261.2 | 0.74472 |
| 646 | 5-cyclopropyl-N-{1-[(1S)-1-phenylethyl]azetidin-3-yl}pyridazine-3-carboxamide | 323.2 | 0.51586 |
| 647 | 5-cyclopropyl-N-{1-[(1R)-1-phenylethyl]azetidin-3-yl}pyridazine-3-carboxamide | 323.2 | 7.80106 |
| 648 | N-{1-[(5-chloro-1-methyl-1H-imidazol-4-yl)methyl]azetidin-3-yl}-5-cyclopropylpyridazine-3-carboxamide | 347.2 | 7.32825 |
| 649 | 5-cyclopropyl-N-{1-[1-(2,5-dichlorophenyl)ethyl]azetidin-3-yl}pyridazine-3-carboxamide | 391.1 | 0.14034 |
| 650 | 5-cyclopropyl-N-(1-{1-[3-(2-hydroxyethoxy)-2-methoxyphenyl]ethyl}azetidin-3-yl)pyridazine-3-carboxamide | 413.2 | 0.31235 |
| 651 | N-(1-benzylazetidin-3-yl)-5-cyclopropylpyridazine-3-carboxamide | 309.2 | 0.54112 |
| 652 | N-(1-{1-[2-chloro-3-(2-hydroxyethoxy)phenyl]ethyl}azetidin-3-yl)-5-cyclopropylpyridazine-3-carboxamide | 417.2 | 0.04156 |
| 657 | N-(azetidin-3-yl)-1-cyclopropyl-1H-1,2,3-triazole-4-carboxamide | 208.1 | 10.38816 |
| 659 | 1-cyclopropyl-N-(1-methylazetidin-3-yl)-1H-1,2,3-triazole-4-carboxamide | 222.1 | 2.8375 |
| 660 | 1-cyclopropyl-N-(1-propylazetidin-3-yl)-1H-1,2,3-triazole-4-carboxamide | 250.1 | 1.16661 |
| 661 | 1-cyclopropyl-N-(1-ethylazetidin-3-yl)-1H-1,2,3-triazole-4-carboxamide | 236.2 | 1.57571 |
| 662 | 1-cyclopropyl-N-[1-(propan-2-yl)azetidin-3-yl]-1H-1,2,3-triazole-4-carboxamide | 250.2 | 0.84606 |
| 663 | 1-cyclopropyl-N-[1-(propan-2-yl)azetidin-3-yl]-1H-1,2,3-triazole-4-carboxamide | 250.2 | 0.58519 |
| 664 | 1-cyclopropyl-N-(1-cyclopropylazetidin-3-yl)-1H-1,2,3-triazole-4-carboxamide | 248.1 | 1.48071 |
| 665 | 1-cyclopropyl-N-[1-(cyclopropylmethyl)azetidin-3-yl]-1H-1,2,3-triazole-4-carboxamide | 262.2 | 1.99933 |
| 666 | 1-cyclopropyl-N-[1-(oxetan-3-ylmethyl)azetidin-3-yl]-1H-1,2,3-triazole-4-carboxamide | 278.2 | 6.06091 |
| 667 | 1-cyclopropyl-N-[1-(2-methoxyethyl)azetidin-3-yl]-1H-1,2,3-triazole-4-carboxamide | 266.2 | 2.45794 |
| 668 | 1-cyclopropyl-N-[1-(2-methylpropyl)azetidin-3-yl]-1H-1,2,3-triazole-4-carboxamide | 264.2 | 2.74698 |
| 669 | N-[1-(cyclobutylmethyl)azetidin-3-yl]-1-cyclopropyl-1H-1,2,3-triazole-4-carboxamide | 276.2 | 1.61707 |
| 670 | 1-cyclopropyl-N-[1-(2-hydroxyethyl)azetidin-3-yl]-1H-1,2,3-triazole-4-carboxamide | 252.1 | 4.53271 |

TABLE 4A-continued

| Cpd. No. | Chemical Name | LCMS M + H | SMYD2 Biochem IC$_{50}$ (μM)* |
|---|---|---|---|
| 671 | N-(1-benzylazetidin-3-yl)-1-cyclopropyl-1H-1,2,3-triazole-4-carboxamide | 298.1 | 4.20527 |
| 672 | N-(1-benzylazetidin-3-yl)-1-cyclopropyl-1H-1,2,3-triazole-4-carboxamide | 298.2 | 1.55139 |
| 673 | 1-cyclopropyl-N-[1-(2-phenylethyl)azetidin-3-yl]-1H-1,2,3-triazole-4-carboxamide | 312.2 | 1.55399 |
| 674 | 1-cyclopropyl-N-[1-(2-hydroxy-1-phenylethyl)azetidin-3-yl]-1H-1,2,3-triazole-4-carboxamide | 328.2 | 4.27205 |
| 675 | 1-cyclopropyl-N-[1-(1-phenylpropyl)azetidin-3-yl]-1H-1,2,3-triazole-4-carboxamide | 326.2 | 0.49364 |
| 676 | N-{1-[1-(4-chlorophenyl)ethyl]azetidin-3-yl}-1-cyclopropyl-1H-1,2,3-triazole-4-carboxamide | 346.2 | 2.18182 |
| 677 | 1-cyclopropyl-N-{1-[1-(2,4-difluorophenyl)ethyl]azetidin-3-yl}-1H-1,2,3-triazole-4-carboxamide | 348.2 | 2.86259 |
| 678 | 1-cyclopropyl-N-{1-[1-(2-fluorophenyl)ethyl]azetidin-3-yl}-1H-1,2,3-triazole-4-carboxamide | 330.2 | 0.90683 |
| 679 | 1-cyclopropyl-N-{1-[1-(3-methoxyphenyl)ethyl]azetidin-3-yl}-1H-1,2,3-triazole-4-carboxamide | 342.2 | 1.45146 |
| 680 | 1-cyclopropyl-N-(1-{1-[4-(trifluoromethyl)phenyl]ethyl}azetidin-3-yl)-1H-1,2,3-triazole-4-carboxamide | 380.2 | >50.0 |
| 681 | N-{1-[1-(4-butoxyphenyl)ethyl]azetidin-3-yl}-1-cyclopropyl-1H-1,2,3-triazole-4-carboxamide | 384.2 | 1.29111 |
| 682 | 1-cyclopropyl-N-{1-[1-(2-methoxyphenyl)ethyl]azetidin-3-yl}-1H-1,2,3-triazole-4-carboxamide | 342.3 | 0.66494 |
| 683 | 1-cyclopropyl-N-{1-[1-(2-methoxyphenyl)ethyl]azetidin-3-yl}-1H-1,2,3-triazole-4-carboxamide | 342.3 | 0.79678 |
| 684 | 1-cyclopropyl-N-(1-{1-[2-(trifluoromethoxy)phenyl]ethyl}azetidin-3-yl)-1H-1,2,3-triazole-4-carboxamide | 396.2 | 2.13234 |
| 685 | 1-cyclopropyl-N-{1-[1-(pyridin-2-yl)ethyl]azetidin-3-yl}-1H-1,2,3-triazole-4-carboxamide | 313.1 | 3.56033 |
| 686 | 1-cyclopropyl-N-[1-(3-methoxypropyl)azetidin-3-yl]-1H-1,2,3-triazole-4-carboxamide | 280.1 | 3.76161 |
| 687 | 1-cyclopropyl-N-{1-[1-(3,4-difluorophenyl)ethyl]azetidin-3-yl}-1H-1,2,3-triazole-4-carboxamide | 348.2 | 2.89677 |
| 688 | 1-cyclopropyl-N-{1-[1-(3,4-dimethoxyphenyl)propan-2-yl]azetidin-3-yl}-1H-1,2,3-triazole-4-carboxamide | 386.2 | 5.09675 |
| 689 | 1-cyclopropyl-N-{1-[1-(4-fluoro-2-methoxyphenyl)ethyl]azetidin-3-yl}-1H-1,2,3-triazole-4-carboxamide | 360.2 | 1.88646 |
| 690 | 1-cyclopropyl-N-(1-{1-[2-methoxy-5-(trifluoromethyl)phenyl]ethyl}azetidin-3-yl)-1H-1,2,3-triazole-4-carboxamide | 410.2 | 7.98548 |
| 691 | N-{1-[1-(2H-1,3-benzodioxol-5-yl)ethyl]azetidin-3-yl}-1-cyclopropyl-1H-1,2,3-triazole-4-carboxamide | 356.2 | 0.80698 |
| 692 | N-(1-{1-[4-(benzyloxy)phenyl]ethyl}azetidin-3-yl)-1-cyclopropyl-1H-1,2,3-triazole-4-carboxamide | 418.2 | 0.17228 |
| 693 | N-(1-{1-[4-(benzyloxy)phenyl]ethyl}azetidin-3-yl)-1-cyclopropyl-1H-1,2,3-triazole-4-carboxamide | 418.3 | 0.17574 |
| 694 | 1-cyclopropyl-N-{1-[1-(4-fluorophenyl)propyl]azetidin-3-yl}-1H-1,2,3-triazole-4-carboxamide | 344.2 | 0.78735 |
| 695 | N-{1-[1-(3-chlorophenyl)ethyl]azetidin-3-yl}-1-cyclopropyl-1H-1,2,3-triazole-4-carboxamide | 346.1 | 1.00761 |
| 696 | 1-cyclopropyl-N-{1-[1-(2,5-dichlorophenyl)ethyl]azetidin-3-yl}-1H-1,2,3-triazole-4-carboxamide | 380.1 | 0.18717 |
| 697 | 1-cyclopropyl-N-{1-[1-(2,5-dichlorophenyl)ethyl]azetidin-3-yl}-1H-1,2,3-triazole-4-carboxamide | 380.1 | 0.18937 |
| 698 | 1-cyclopropyl-N-{1-[1-(3,4-dimethoxyphenyl)ethyl]azetidin-3-yl}-1H-1,2,3-triazole-4-carboxamide | 372.2 | 3.69446 |
| 699 | 1-cyclopropyl-N-{1-[1-(pyrimidin-5-yl)ethyl]azetidin-3-yl}-1H-1,2,3-triazole-4-carboxamide | 314.2 | 9.54128 |

TABLE 4A-continued

| Cpd. No. | Chemical Name | LCMS M + H | SMYD2 Biochem IC$_{50}$ (μM)* |
|---|---|---|---|
| 700 | 1-cyclopropyl-N-(1-{1-[4-(trifluoromethyl)phenyl]propyl}azetidin-3-yl)-1H-1,2,3-triazole-4-carboxamide | 394.2 | 2.66609 |
| 701 | 1-cyclopropyl-N-(1-{[3-(2-methoxyethoxy)phenyl]methyl}azetidin-3-yl)-1H-1,2,3-triazole-4-carboxamide | 372.2 | 8.02678 |
| 702 | 1-cyclopropyl-N-(1-{1-[3-(2-methoxyethoxy)phenyl]ethyl}azetidin-3-yl)-1H-1,2,3-triazole-4-carboxamide | 386.1 | 3.57947 |
| 703 | 1-(2-hydroxyethyl)-N-[1-(propan-2-yl)azetidin-3-yl]-1H-1,2,3-triazole-4-carboxamide | 254.2 | >50.0 |
| 704 | 1-cyclopropyl-N-(1-{1-[3-(2-hydroxyethoxy)phenyl]ethyl}azetidin-3-yl)-1H-1,2,3-triazole-4-carboxamide | 372.2 | 0.64045 |
| 705 | 1-cyclopropyl-N-[1-(1-{3-[2-(methylamino)ethoxy]phenyl}ethyl)azetidin-3-yl]-1H-1,2,3-triazole-4-carboxamide | 385.2 | 2.04485 |
| 706 | 1-cyclopropyl-N-[1-(1-{3-[2-(dimethylamino)ethoxy]phenyl}ethyl)azetidin-3-yl]-1H-1,2,3-triazole-4-carboxamide | 399.2 | 2.1244 |
| 707 | 1-cyclopropyl-N-[1-(3-hydroxypropyl)azetidin-3-yl]-1H-1,2,3-triazole-4-carboxamide | 266.1 | 1.91172 |
| 708 | 1-cyclopropyl-N-{1-[3-(dimethylamino)propyl]azetidin-3-yl}-1H-1,2,3-triazole-4-carboxamide | 293.2 | >50.0 |
| 709 | 1-cyclopropyl-N-{1-[(1S)-1-phenylethyl]azetidin-3-yl}-1H-1,2,3-triazole-4-carboxamide | 312.2 | 0.37665 |
| 710 | N-{1-[1-(2-chloro-4-fluorophenyl)ethyl]azetidin-3-yl}-1-cyclopropyl-1H-1,2,3-triazole-4-carboxamide | 364.1 | 0.34116 |
| 711 | 1-cyclopropyl-N-{1-[1-(3-fluorophenyl)propyl]azetidin-3-yl}-1H-1,2,3-triazole-4-carboxamide | 344.2 | 1.00729 |
| 712 | N-(1-{1-[4-chloro-3-(trifluoromethyl)phenyl]ethyl}azetidin-3-yl)-1-cyclopropyl-1H-1,2,3-triazole-4-carboxamide | 414.2 | 7.35557 |
| 713 | N-[1-(4-chloro-5-methoxy-2,3-dihydro-1H-inden-1-yl)azetidin-3-yl]-1-cyclopropyl-1H-1,2,3-triazole-4-carboxamide | 388.1 | 12.88746 |
| 714 | N-{1-[1-(3-chloro-5-fluorophenyl)ethyl]azetidin-3-yl}-1-cyclopropyl-1H-1,2,3-triazole-4-carboxamide | 364.1 | 2.12503 |
| 715 | 1-cyclopropyl-N-{1-[1-(pyrimidin-2-yl)ethyl]azetidin-3-yl}-1H-1,2,3-triazole-4-carboxamide | 314.2 | 1.9389 |
| 716 | 1-cyclopropyl-N-{1-[1-(1,3-thiazol-2-yl)ethyl]azetidin-3-yl}-1H-1,2,3-triazole-4-carboxamide | 319.1 | 30.73955 |
| 717 | 1-cyclopropyl-N-(1-{[1-(2-methoxyethyl)-1H-pyrazol-4-yl]methyl}azetidin-3-yl)-1H-1,2,3-triazole-4-carboxamide | 346.3 | 3.05744 |
| 718 | 1-cyclopropyl-N-{1-[1-(dimethyl-1,3-thiazol-5-yl)ethyl]azetidin-3-yl}-1H-1,2,3-triazole-4-carboxamide | 347.2 | 2.95156 |
| 719 | N-[1-(5-chloro-2,3-dihydro-1H-inden-1-yl)azetidin-3-yl]-1-cyclopropyl-1H-1,2,3-triazole-4-carboxamide | 358.2 | 4.40844 |
| 720 | 1-cyclopropyl-N-{1-[(1R)-1-phenylethyl]azetidin-3-yl}-1H-1,2,3-triazole-4-carboxamide | 312.2 | 23.25339 |
| 721 | 1-cyclopropyl-N-{1-[(1R)-1-phenylpropyl]azetidin-3-yl}-1H-1,2,3-triazole-4-carboxamide | 326.2 | 4.80835 |
| 722 | 1-cyclopropyl-N-{1-[(1S)-1-phenylpropyl]azetidin-3-yl}-1H-1,2,3-triazole-4-carboxamide | 326.3 | 0.19827 |
| 723 | 1-(2-aminoethyl)-N-[1-(propan-2-yl)azetidin-3-yl]-1H-1,2,3-triazole-4-carboxamide | 253.2 | >50.0 |
| 724 | 1-cyclopropyl-N-{1-[1-(4-methoxypyridin-2-yl)ethyl]azetidin-3-yl}-1H-1,2,3-triazole-4-carboxamide | 343.2 | 1.27222 |
| 725 | 1-cyclopropyl-N-{1-[1-(3-methoxypyridin-2-yl)ethyl]azetidin-3-yl}-1H-1,2,3-triazole-4-carboxamide | 343.2 | 1.02479 |
| 726 | 1-cyclopropyl-N-(1-{[3-(methylcarbamoyl)phenyl]methyl}azetidin-3-yl)-1H-1,2,3-triazole-4-carboxamide | 355.2 | 10.70724 |
| 727 | N-{1-[(3-carbamoylphenyl)methyl]azetidin-3-yl}-1-cyclopropyl-1H-1,2,3-triazole-4-carboxamide | 341.1 | 7.29596 |

TABLE 4A-continued

| Cpd. No. | Chemical Name | LCMS M + H | SMYD2 Biochem IC$_{50}$ (μM)* |
|---|---|---|---|
| 728 | 1-cyclopropyl-N-(1-{1-[4-(morpholin-4-yl)phenyl]ethyl}azetidin-3-yl)-1H-1,2,3-triazole-4-carboxamide | 397.2 | 0.75494 |
| 729 | 1-cyclopropyl-N-{1-[2,2,2-trifluoro-1-(3-methoxyphenyl)ethyl]azetidin-3-yl}-1H-1,2,3-triazole-4-carboxamide | 396.2 | >50.0 |
| 730 | 1-cyclopropyl-N-{1-[1-(3-phenoxyphenyl)ethyl]azetidin-3-yl}-1H-1,2,3-triazole-4-carboxamide | 404.2 | 3.04417 |
| 731 | N-{1-[cyclobutyl(phenyl)methyl]azetidin-3-yl}-1-cyclopropyl-1H-1,2,3-triazole-4-carboxamide | 352.2 | 1.51599 |
| 732 | 1-cyclopropyl-N-{1-[1-(4-fluoro-3-methoxyphenyl)ethyl]azetidin-3-yl}-1H-1,2,3-triazole-4-carboxamide | 360.2 | 2.58965 |
| 733 | 1-cyclopropyl-N-{1-[(1-methyl-1H-imidazol-4-yl)methyl]azetidin-3-yl}-1H-1,2,3-triazole-4-carboxamide | 302.2 | 6.80081 |
| 734 | 1-cyclopropyl-N-(1-{[3-(2-hydroxyethoxy)phenyl]methyl}azetidin-3-yl)-1H-1,2,3-triazole-4-carboxamide | 358.2 | 2.30886 |
| 735 | 1-cyclopropyl-N-[1-({3-[2-(methylamino)ethoxy]phenyl}methyl)azetidin-3-yl]-1H-1,2,3-triazole-4-carboxamide | 371.2 | 2.33404 |
| 736 | 1-cyclopropyl-N-[1-({3-[2-(dimethylamino)ethoxy]phenyl}methyl)azetidin-3-yl]-1H-1,2,3-triazole-4-carboxamide | 385.2 | 2.80792 |
| 737 | N-(1-{1-[3-(benzyloxy)phenyl]ethyl}azetidin-3-yl)-1-cyclopropyl-1H-1,2,3-triazole-4-carboxamide | 418.3 | 0.71843 |
| 738 | 1-cyclopropyl-N-[1-(5-methoxy-1,2,3,4-tetrahydronaphthalen-1-yl)azetidin-3-yl]-1H-1,2,3-triazole-4-carboxamide | 368.3 | 5.82879 |
| 739 | 1-cyclopropyl-N-{1-[1-(4-phenoxyphenyl)ethyl]azetidin-3-yl}-1H-1,2,3-triazole-4-carboxamide | 404.2 | 1.07309 |
| 740 | 1-cyclopropyl-N-[1-(5-fluoro-2,3-dihydro-1H-inden-1-yl)azetidin-3-yl]-1H-1,2,3-triazole-4-carboxamide | 342.2 | 6.96336 |
| 741 | 1-cyclopropyl-N-(1-{1-[2-(trifluoromethyl)phenyl]ethyl}azetidin-3-yl)-1H-1,2,3-triazole-4-carboxamide | 380.2 | 1.00727 |
| 742 | 1-cyclopropyl-N-{1-[1-(2,6-difluorophenyl)ethyl]azetidin-3-yl}-1H-1,2,3-triazole-4-carboxamide | 348.2 | 2.84963 |
| 743 | 1-cyclopropyl-N-{1-[1-(2,3-dichlorophenyl)ethyl]azetidin-3-yl}-1H-1,2,3-triazole-4-carboxamide | 380.2 | 0.48846 |
| 744 | 1-cyclopropyl-N-[1-(4,5-dimethoxy-2,3-dihydro-1H-inden-1-yl)azetidin-3-yl]-1H-1,2,3-triazole-4-carboxamide | 384.2 | 23.71632 |
| 745 | 1-cyclopropyl-N-{1-[1-(pyrazin-2-yl)ethyl]azetidin-3-yl}-1H-1,2,3-triazole-4-carboxamide | 314.1 | 7.44095 |
| 746 | 1-cyclopropyl-N-{1-[1-(2,5-difluorophenyl)ethyl]azetidin-3-yl}-1H-1,2,3-triazole-4-carboxamide | 348.2 | 7.77636 |
| 747 | 1-cyclopropyl-N-{1-[1-(4-fluorophenyl)ethyl]azetidin-3-yl}-1H-1,2,3-triazole-4-carboxamide | 330.2 | 1.92161 |
| 748 | 1-cyclopropyl-N-(1-{1-[3-(trifluoromethyl)phenyl]ethyl}azetidin-3-yl)-1H-1,2,3-triazole-4-carboxamide | 380.2 | 2.80977 |
| 749 | 1-cyclopropyl-N-{1-[2,2,2-trifluoro-1-(4-methoxyphenyl)ethyl]azetidin-3-yl}-1H-1,2,3-triazole-4-carboxamide | 396.1 | 0.56478 |
| 750 | 1-cyclopropyl-N-{1-[1-(2-hydroxy-6-methoxyphenyl)ethyl]azetidin-3-yl}-1H-1,2,3-triazole-4-carboxamide | 358.2 | 1.27817 |
| 751 | 1-cyclopropyl-N-{1-[1-(1,3-thiazol-2-yl)propyl]azetidin-3-yl}-1H-1,2,3-triazole-4-carboxamide | 333.2 | 20.98439 |
| 752 | 1-cyclopropyl-N-[1-(2-methoxy-1-phenylethyl)azetidin-3-yl]-1H-1,2,3-triazole-4-carboxamide | 342.2 | 6.09419 |
| 753 | 1-cyclopropyl-N-[1-({3-[(methylamino)methyl]phenyl}methyl)azetidin-3-yl]-1H-1,2,3-triazole-4-carboxamide | 341.3 | 15.98565 |

TABLE 4A-continued

| Cpd. No. | Chemical Name | LCMS M + H | SMYD2 Biochem IC$_{50}$ (μM)* |
|---|---|---|---|
| 754 | N-(1-{[3-(aminomethyl)phenyl]methyl}azetidin-3-yl)-1-cyclopropyl-1H-1,2,3-triazole-4-carboxamide | 327.2 | 7.33653 |
| 755 | 1-cyclopropyl-N-[1-(1-phenylcyclopropyl)azetidin-3-yl]-1H-1,2,3-triazole-4-carboxamide | 324.2 | 30.45617 |
| 756 | 1-cyclopropyl-N-[1-({1-[2-(methylamino)ethyl]-2-oxopyrrolidin-3-yl}methyl)azetidin-3-yl]-1H-1,2,3-triazole-4-carboxamide | 362.3 | 17.04064 |
| 757 | 1-cyclopropyl-N-[1-(2-phenylpropan-2-yl)azetidin-3-yl]-1H-1,2,3-triazole-4-carboxamide | 326.2 | 3.8847 |
| 758 | 1-cyclopropyl-N-(1-{[4-(methylamino)oxan-2-yl]methyl}azetidin-3-yl)-1H-1,2,3-triazole-4-carboxamide | 335.3 | >50.0 |
| 759 | 1-cyclopropyl-N-[1-(1-phenylpropan-2-yl)azetidin-3-yl]-1H-1,2,3-triazole-4-carboxamide | 326.2 | 1.39034 |
| 760 | 1-cyclopropyl-N-{1-[1-(4-fluorophenyl)-2-methylpropyl]azetidin-3-yl}-1H-1,2,3-triazole-4-carboxamide | 358.2 | 3.27451 |
| 761 | 1-cyclopropyl-N-{1-[1-(1H-indazol-3-yl)ethyl]azetidin-3-yl}-1H-1,2,3-triazole-4-carboxamide | 352.2 | 3.21089 |
| 762 | 1-cyclopropyl-N-[1-(7-methoxy-2,3-dihydro-1H-inden-1-yl)azetidin-3-yl]-1H-1,2,3-triazole-4-carboxamide | 354.3 | 7.97221 |
| 763 | 1-cyclopropyl-N-{1-[1-(2,3-dimethoxyphenyl)ethyl]azetidin-3-yl}-1H-1,2,3-triazole-4-carboxamide | 372.2 | 0.08855 |
| 764 | 1-cyclopropyl-N-{1-[1-(2,3-dimethoxyphenyl)ethyl]azetidin-3-yl}-1H-1,2,3-triazole-4-carboxamide | 372.2 | 0.09346 |
| 765 | 1-cyclopropyl-N-{1-[(3-oxo-2,3-dihydro-1H-isoindol-5-yl)methyl]azetidin-3-yl}-1H-1,2,3-triazole-4-carboxamide | 353.1 | 10.21303 |
| 766 | 1-cyclopropyl-N-[1-(2,2,2-trifluoro-1-phenylethyl)azetidin-3-yl]-1H-1,2,3-triazole-4-carboxamide | 366.2 | >50.0 |
| 767 | 1-cyclopropyl-N-{1-[1-(2,3-dihydro-1,4-benzodioxin-6-yl)ethyl]azetidin-3-yl}-1H-1,2,3-triazole-4-carboxamide | 370.1 | 0.57587 |
| 768 | 1-cyclopropyl-N-{1-[1-(2,6-dimethoxyphenyl)ethyl]azetidin-3-yl}-1H-1,2,3-triazole-4-carboxamide | 372.3 | 1.68248 |
| 769 | 1-cyclopropyl-N-{1-[1-(2,6-dichlorophenyl)ethyl]azetidin-3-yl}-1H-1,2,3-triazole-4-carboxamide | 380.1 | 1.19872 |
| 770 | 1-(2,2-difluorocyclopropyl)-N-[1-(propan-2-yl)azetidin-3-yl]-1H-1,2,3-triazole-4-carboxamide | 286.2 | 4.19117 |
| 771 | 1-cyclopropyl-N-[1-(1-{3-[(methylamino)methyl]phenyl}ethyl)azetidin-3-yl]-1H-1,2,3-triazole-4-carboxamide | 355.2 | 4.98252 |
| 772 | 1-cyclopropyl-N-(1-{[3-(hydroxymethyl)-2-methoxyphenyl]methyl}azetidin-3-yl)-1H-1,2,3-triazole-4-carboxamide | 358.2 | 10.81324 |
| 773 | 1-cyclopropyl-N-[1-(2-methanesulfonyl-1-phenylethyl)azetidin-3-yl]-1H-1,2,3-triazole-4-carboxamide | 390.1 | >50.0 |
| 774 | 1-cyclopropyl-N-{1-[1-(3-oxo-3,4-dihydro-2H-1,4-benzoxazin-6-yl)ethyl]azetidin-3-yl}-1H-1,2,3-triazole-4-carboxamide | 383.2 | 1.61549 |
| 775 | N-(1-{1-[2-chloro-3-(2-hydroxyethoxy)phenyl]ethyl}azetidin-3-yl)-1-cyclopropyl-1H-1,2,3-triazole-4-carboxamide | 406.2 | 0.04944 |
| 776 | 1-cyclopropyl-N-(1-{1-[3-(2-hydroxyethoxy)-2-methoxyphenyl]ethyl}azetidin-3-yl)-1H-1,2,3-triazole-4-carboxamide | 402.2 | 0.34533 |
| 777 | 1-cyclopropyl-N-{1-[(3-methoxy-1-methyl-1H-pyrazol-4-yl)methyl]azetidin-3-yl}-1H-1,2,3-triazole-4-carboxamide | 332.2 | 5.61969 |
| 778 | rel-N-{1-[(1R)-1-[4-(benzyloxy)phenyl]ethyl]azetidin-3-yl}-1-cyclopropyl-1H-1,2,3-triazole-4-carboxamide | 418.2 | 0.08453 |
| 779 | rel-1-cyclopropyl-N-{1-[(1R)-1-(2,5-dichlorophenyl)ethyl]azetidin-3-yl}-1H-1,2,3-triazole-4-carboxamide | 380.1 | 0.10953 |

TABLE 4A-continued

| Cpd. No. | Chemical Name | LCMS M + H | SMYD2 Biochem IC$_{50}$ (μM)* |
|---|---|---|---|
| 780 | rel-1-cyclopropyl-N-{1-[(1R)-1-(2-methoxyphenyl)ethyl]azetidin-3-yl}-1H-1,2,3-triazole-4-carboxamide | 342.3 | 0.3468 |
| 781 | 1-cyclopropyl-N-[1-(3-phenyloxetan-3-yl)azetidin-3-yl]-1H-1,2,3-triazole-4-carboxamide | 340.2 | >50.0 |
| 782 | 1-cyclopropyl-N-(1-{[1-(2-phenylethyl)-1H-imidazol-4-yl]methyl}azetidin-3-yl)-1H-1,2,3-triazole-4-carboxamide | 392.4 | 2.61584 |
| 783 | 1-cyclopropyl-N-{1-[1-(3-acetamidophenyl)ethyl]azetidin-3-yl}-1H-1,2,3-triazole-4-carboxamide | 369.1 | 3.13518 |
| 784 | N-{1-[(5-chloro-1-methyl-1H-imidazol-4-yl)methyl]azetidin-3-yl}-1-cyclopropyl-1H-1,2,3-triazole-4-carboxamide | 336.2 | 21.02524 |
| 785 | 1-cyclopropyl-N-{1-[1-(1H-imidazol-4-yl)ethyl]azetidin-3-yl}-1H-1,2,3-triazole-4-carboxamide | 302.2 | 2.594 |
| 786 | 1-cyclopropyl-N-{1-[cyclopropyl(4-fluorophenyl)methyl]azetidin-3-yl}-1H-1,2,3-triazole-4-carboxamide | 356.1 | 1.70115 |
| 787 | 1-cyclopropyl-N-{1-[(2-methyl-1-phenylpropyl)azetidin-3-yl]-1H-1,2,3-triazole-4-carboxamide | 340.3 | 1.42952 |
| 788 | rel-N-{1-[(1R)-1-[4-(benzyloxy)phenyl]ethyl]azetidin-3-yl}-1-cyclopropyl-1H-1,2,3-triazole-4-carboxamide | | 0.4137 |
| 789 | rel-1-cyclopropyl-N-{1-[(1R)-1-(2,5-dichlorophenyl)ethyl]azetidin-3-yl}-1H-1,2,3-triazole-4-carboxamide | | 31.57011 |
| 790 | rel-1-cyclopropyl-N-{1-[(1R)-1-(2-methoxyphenyl)ethyl]azetidin-3-yl}-1H-1,2,3-triazole-4-carboxamide | | 28.78884 |
| 791 | 1-cyclopropyl-N-{1-[1-(pyridin-2-yl)propyl]azetidin-3-yl}-1H-1,2,3-triazole-4-carboxamide | 327.1 | 2.47462 |
| 792 | N-{1-[(1-benzyl-1H-pyrazol-4-yl)methyl]azetidin-3-yl}-1-cyclopropyl-1H-1,2,3-triazole-4-carboxamide | 378.2 | 0.01635 |
| 793 | 1-cyclopropyl-N-[1-(6-methoxy-1,2,3,4-tetrahydronaphthalen-1-yl)azetidin-3-yl]-1H-1,2,3-triazole-4-carboxamide | 368.2 | 9.91987 |
| 794 | N-(1-{[3-(aminomethyl)-2-methoxyphenyl]methyl}azetidin-3-yl)-1-cyclopropyl-1H-1,2,3-triazole-4-carboxamide | 357.3 | 32.30456 |
| 795 | N-{1-[(1-benzyl-1H-imidazol-4-yl)methyl]azetidin-3-yl}-1-cyclopropyl-1H-1,2,3-triazole-4-carboxamide | 378.3 | 7.14819 |
| 796 | N-(1-{1-[2-(benzyloxy)phenyl]ethyl}azetidin-3-yl)-1-cyclopropyl-1H-1,2,3-triazole-4-carboxamide | 418.2 | 0.4215 |
| 797 | 1-cyclopropyl-N-(1-{1-[4-(1H-imidazol-1-yl)phenyl]ethyl}azetidin-3-yl)-1H-1,2,3-triazole-4-carboxamide | 378.1 | 1.56764 |
| 798 | 1-cyclopropyl-N-{1-[1-(2-fluorophenyl)propyl]azetidin-3-yl}-1H-1,2,3-triazole-4-carboxamide | 344.2 | 0.42506 |
| 799 | 1-cyclopropyl-N-[2,2-dimethyl-1-(propan-2-yl)azetidin-3-yl]-1H-1,2,3-triazole-4-carboxamide | 278.2 | 9.59545 |
| 800 | N-(1-{1-[4-(benzyloxy)-2-methoxyphenyl]ethyl}azetidin-3-yl)-1-cyclopropyl-1H-1,2,3-triazole-4-carboxamide | 448.3 | 0.96532 |
| 801 | 1-cyclopropyl-N-{1-[1-(2,4-dimethoxyphenyl)ethyl]azetidin-3-yl}-1H-1,2,3-triazole-4-carboxamide | 372.3 | 1.05608 |
| 802 | N-(1-{[4-(benzyloxy)phenyl]methyl}azetidin-3-yl)-1-cyclopropyl-1H-1,2,3-triazole-4-carboxamide | 404.2 | 0.08341 |
| 803 | N-{1-[1-(2-chloro-3-methoxyphenyl)ethyl]azetidin-3-yl}-1-cyclopropyl-1H-1,2,3-triazole-4-carboxamide | 376.2 | 0.06945 |
| 804 | rel-1-cyclopropyl-N-{1-[(1R)-1-(2,3-dimethoxyphenyl)ethyl]azetidin-3-yl}-1H-1,2,3-triazole-4-carboxamide | 372.2 | 0.04426 |
| 805 | rel-1-cyclopropyl-N-{1-[(1S)-1-(2,3-dimethoxyphenyl)ethyl]azetidin-3-yl}-1H-1,2,3-triazole-4-carboxamide | | 42.35178 |

TABLE 4A-continued

| Cpd. No. | Chemical Name | LCMS M + H | SMYD2 Biochem IC$_{50}$ (μM)* |
|---|---|---|---|
| 806 | 1-cyclopropyl-N-(1-{[1-(2-phenylethyl)-1H-pyrazol-4-yl]methyl}azetidin-3-yl)-1H-1,2,3-triazole-4-carboxamide | 392.2 | 0.97043 |
| 807 | 5-cyclopropyl-N-(1-{[1-(2-phenylethyl)-1H-pyrazol-4-yl]methyl}azetidin-3-yl)pyridazine-3-carboxamide | 403.2 | 0.52752 |
| 808 | 1-cyclopropyl-N-[1-(propan-2-yl)piperidin-3-yl]-1H-1,2,3-triazole-4-carboxamide | 278.2 | 19.78446 |
| 809 | N-{1-[(1-benzyl-1H-imidazol-5-yl)methyl]azetidin-3-yl}-1-cyclopropyl-1H-1,2,3-triazole-4-carboxamide | 378.3 | >50.0 |
| 810 | 1-cyclopropyl-N-(1-{[1-(2-phenylethyl)-1H-imidazol-5-yl]methyl}azetidin-3-yl)-1H-1,2,3-triazole-4-carboxamide | 392.3 | 9.28801 |
| 811 | N-{1-[(3-chloro-1-methyl-1H-pyrazol-4-yl)methyl]azetidin-3-yl}-1-cyclopropyl-1H-1,2,3-triazole-4-carboxamide | 336.1 | 1.2247 |
| 812 | 1-cyclopropyl-N-[1-({2-methoxy-3-[(methylamino)methyl]phenyl}methyl)azetidin-3-yl]-1H-1,2,3-triazole-4-carboxamide | 371.2 | 41.20464 |
| 813 | 1-cyclopropyl-N-{1-[1-(4-fluorophenyl)-2-hydroxyethyl]azetidin-3-yl}-1H-1,2,3-triazole-4-carboxamide | 346.2 | 15.19205 |
| 814 | 5-cyclopropyl-N-(1-ethylazetidin-3-yl)pyridazine-3-carboxamide | 247.2 | 0.59765 |
| 815 | 5-cyclopropyl-N-[1-(propan-2-yl)piperidin-3-yl]pyridazine-3-carboxamide | 289.2 | 18.67277 |
| 816 | N-(1-{1-[4-(benzyloxy)phenyl]-2,2,2-trifluoroethyl}azetidin-3-yl)-1-cyclopropyl-1H-1,2,3-triazole-4-carboxamide | 472.3 | >50.0 |
| 817 | N-(1-{1-[4-(benzyloxy)-2-chlorophenyl]ethyl}azetidin-3-yl)-1-cyclopropyl-1H-1,2,3-triazole-4-carboxamide | 452.2 | 0.10155 |
| 818 | 1-cyclopropyl-N-(1-{[4-(3-methoxypropoxy)phenyl]methyl}azetidin-3-yl)-1H-1,2,3-triazole-4-carboxamide | 386.3 | 3.00034 |
| 819 | 1-cyclopropyl-N-(1-{[4-(2,3-dihydroxypropoxy)phenyl]methyl}azetidin-3-yl)-1H-1,2,3-triazole-4-carboxamide | 388.2 | 1.99348 |
| 820 | N-(5-hydroxy-3-oxo-3,4-dihydro-2H-1,4-benzoxazin-7-yl)-3-(methylamino)cyclohexane-1-carboxamide | 320 | >50.0 |
| 821 | 1-cyclopropyl-N-{1-[1-(4-methoxyphenyl)ethyl]azetidin-3-yl}-1H-1,2,3-triazole-4-carboxamide | 342.3 | 0.78452 |
| 822 | 1-cyclopropyl-N-(1-{[4-(2-hydroxypropoxy)phenyl]methyl}azetidin-3-yl)-1H-1,2,3-triazole-4-carboxamide | 372.3 | 1.96551 |
| 823 | 1-cyclopropyl-N-(1-{[4-(3-hydroxypropoxy)phenyl]methyl}azetidin-3-yl)-1H-1,2,3-triazole-4-carboxamide | 372.2 | 3.21621 |
| 824 | 1-cyclopropyl-N-{1-[(4-hydroxyphenyl)methyl]azetidin-3-yl}-1H-1,2,3-triazole-4-carboxamide | 314.1 | 0.88212 |
| 825 | 5-cyclopropyl-N-(1-methylazetidin-3-yl)pyridazine-3-carboxamide | 233.2 | 0.39067 |
| 826 | 1-cyclopropyl-N-{1-[(4-methoxyphenyl)methyl]azetidin-3-yl}-1H-1,2,3-triazole-4-carboxamide | 328.2 | 1.83875 |
| 827 | 1-cyclopropyl-N-(1-{[4-(2-hydroxyethoxy)phenyl]methyl}azetidin-3-yl)-1H-1,2,3-triazole-4-carboxamide | 358.3 | 1.37605 |
| 828 | 1-cyclopropyl-N-(1-{[4-(pyridin-4-ylmethoxy)phenyl]methyl}azetidin-3-yl)-1H-1,2,3-triazole-4-carboxamide | 405.2 | 1.03298 |
| 829 | 1-cyclopropyl-N-[1-(1-(4-[2-(morpholin-4-yl)-2-oxoethoxy]phenyl}ethyl)azetidin-3-yl]-1H-1,2,3-triazole-4-carboxamide | 455.3 | 0.71252 |
| 830 | 1-cyclopropyl-N-(1-{[4-(2-methoxyethoxy)phenyl]methyl}azetidin-3-yl)-1H-1,2,3-triazole-4-carboxamide | 372.3 | 2.06713 |
| 831 | rel-N-{1-[(1S)-1-[2-chloro-3-(2-hydroxyethoxy)phenyl]ethyl]azetidin-3-yl}-1-cyclopropyl-1H-1,2,3-triazole-4-carboxamide | 406.2 | 0.05775 |

TABLE 4A-continued

| Cpd. No. | Chemical Name | LCMS M + H | SMYD2 Biochem IC$_{50}$ (μM)* |
|---|---|---|---|
| 832 | rel-N-{1-[(1R)-1-[2-chloro-3-(2-hydroxyethoxy)phenyl]ethyl]azetidin-3-yl}-1-cyclopropyl-1H-1,2,3-triazole-4-carboxamide | 406.2 | 14.28102 |
| 833 | N-{1-[(3-chloro-1-methyl-1H-pyrazol-4-yl)methyl]azetidin-3-yl}-5-cyclopropylpyridazine-3-carboxamide | 347.1 | 0.94017 |
| 834 | 1-cyclopropyl-N-[2-(dimethylamino)ethyl]-1H-1,2,3-triazole-4-carboxamide | 224.3 | >50.0 |
| 835 | 1-cyclopropyl-N-[1-(1-(2-methoxy-3-[(methylamino)methyl]phenyl}ethyl)azetidin-3-yl]-1H-1,2,3-triazole-4-carboxamide | 385.3 | 0.77956 |
| 836 | N-(1-{1-[4-(benzyloxy)phenyl]ethyl}azetidin-3-yl)-5-cyclopropylpyridazine-3-carboxamide | 429.3 | 0.02651 |
| 837 | N-{1-[(1S)-1-(3-chlorophenyl)propyl]azetidin-3-yl}-1-cyclopropyl-1H-1,2,3-triazole-4-carboxamide | 360.3 | 0.33977 |
| 838 | 5-cyclopropyl-N-(1-{[1-(2-phenylethyl)-1H-imidazol-4-yl]methyl}azetidin-3-yl)pyridazine-3-carboxamide | 403.3 | 0.49607 |
| 839 | N-[1-(azetidin-3-yl)ethyl]-5-cyclopropylpyridazine-3-carboxamide | 247.2 | 18.24266 |
| 840 | 5-cyclopropyl-N-{1-[1-(propan-2-yl)azetidin-3-yl]ethyl}pyridazine-3-carboxamide | 289.2 | 36.83929 |
| 841 | 5-cyclopropyl-N-{1-[(1S)-1-(2-methoxyphenyl)ethyl]azetidin-3-yl}pyridazine-3-carboxamide | 353.3 | 5.00737 |
| 842 | 5-cyclopropyl-N-{1-[(1R)-1-(2-methoxyphenyl)ethyl]azetidin-3-yl}pyridazine-3-carboxamide | 353.3 | 0.18913 |
| 843 | (±)-cis-N-(1-{[3-(benzyloxy)cyclobutyl]methyl}azetidin-3-yl)-1-cyclopropyl-1H-1,2,3-triazole-4-carboxamide | 382.2 | 1.15555 |
| 844 | 1-cyclopropyl-N-[1-(1-{4-[2-oxo-2-(piperidin-1-yl)ethoxy]phenyl}ethyl)azetidin-3-yl]-1H-1,2,3-triazole-4-carboxamide | 453.3 | 1.54771 |
| 845 | N-{1-[1-(2-chloro-4-methoxyphenyl)ethyl]azetidin-3-yl}-1-cyclopropyl-1H-1,2,3-triazole-4-carboxamide | 376.2 | 0.08798 |
| 846 | 1-cyclopropyl-N-(1-{[4-(1,3-thiazol-4-ylmethoxy)phenyl]methyl}azetidin-3-yl)-1H-1,2,3-triazole-4-carboxamide | 411.2 | 1.08508 |
| 847 | N-[1-(1-{4-[(3-chlorophenyl)methoxy]phenyl}ethyl)azetidin-3-yl]-1-cyclopropyl-1H-1,2,3-triazole-4-carboxamide | 452.2 | 0.27389 |
| 848 | N-[1-(1-{4-[(4-chlorophenyl)methoxy]phenyl}ethyl)azetidin-3-yl]-1-cyclopropyl-1H-1,2,3-triazole-4-carboxamide | 452.2 | 0.06933 |
| 849 | 1-cyclopropyl-N-(1-{[4-(pyridin-2-ylmethoxy)phenyl]methyl}azetidin-3-yl)-1H-1,2,3-triazole-4-carboxamide | 405.1 | 2.66119 |
| 850 | 1-cyclopropyl-N-(1-{1-[4-(piperidin-3-ylmethoxy)phenyl]ethyl}azetidin-3-yl)-1H-1,2,3-triazole-4-carboxamide | 425.2 | 3.32842 |
| 851 | N-{1-[1-(2-chloro-3-methoxyphenyl)ethyl]azetidin-3-yl}-5-cyclopropylpyridazine-3-carboxamide | 387.2 | 0.07206 |
| 852 | (±)-trans-N-(1-{[3-(benzyloxy)cyclobutyl]methyl}azetidin-3-yl)-1-cyclopropyl-1H-1,2,3-triazole-4-carboxamide | 382.3 | 0.98162 |
| 853 | 1-cyclopropyl-N-(1-{1-[4-(2-phenylethoxy)phenyl]ethyl}azetidin-3-yl)-1H-1,2,3-triazole-4-carboxamide | 432.3 | 0.77613 |
| 854 | 1-cyclopropyl-N-{1-[1-(4-{[4-(methylcarbamoyl)phenyl]methoxy}phenyl)ethyl]azetidin-3-yl}-1H-1,2,3-triazole-4-carboxamide | 475.3 | 0.96536 |
| 855 | 1-cyclopropyl-N-[1-(1-{4-[(4-methoxyphenyl)methoxy]phenyl}ethyl)azetidin-3-yl]-1H-1,2,3-triazole-4-carboxamide | 448.3 | 0.15904 |
| 856 | 5-cyclopropyl-N-{1-[1-(4-methoxyphenyl)ethyl]azetidin-3-yl}pyridazine-3-carboxamide | 353.2 | 0.60267 |
| 857 | 1-cyclopropyl-N-[1-(1-{4-[2-(dimethylamino)ethoxy]phenyl}ethyl)azetidin-3-yl]-1H-1,2,3-triazole-4-carboxamide | 399.2 | 1.97865 |
| 858 | 1-cyclopropyl-N-[1-(1-{4-[3-(dimethylamino)propoxy]phenyl}ethyl)azetidin-3-yl]-1H-1,2,3-triazole-4-carboxamide | 413.2 | 4.79409 |

TABLE 4A-continued

| Cpd. No. | Chemical Name | LCMS M + H | SMYD2 Biochem IC$_{50}$ (μM)* |
|---|---|---|---|
| 859 | N-{1-[1-(2-chlorophenyl)ethyl]azetidin-3-yl}-1-cyclopropyl-1H-1,2,3-triazole-4-carboxamide | 346.2 | 0.16007 |
| 860 | N-{1-[1-(5-chloro-2-methoxyphenyl)ethyl]azetidin-3-yl}-1-cyclopropyl-1H-1,2,3-triazole-4-carboxamide | 376.2 | 2.79163 |
| 861 | 5-cyclopropyl-N-{1-[1-(2,3-dimethoxyphenyl)ethyl]azetidin-3-yl}pyridazine-3-carboxamide | 383.2 | 0.12148 |
| 862 | N-(1-{1-[4-(benzylamino)phenyl]ethyl}azetidin-3-yl)-1-cyclopropyl-1H-1,2,3-triazole-4-carboxamide | 417.3 | 0.334 |
| 863 | N-{1-[1-(4-benzamidophenyl)ethyl]azetidin-3-yl}-1-cyclopropyl-1H-1,2,3-triazole-4-carboxamide | 431.3 | 1.73815 |
| 864 | 1-cyclopropyl-N-(1-{1-[4-(2,2-dimethylpropoxy)phenyl]ethyl}azetidin-3-yl)-1H-1,2,3-triazole-4-carboxamide | 398.3 | 3.14078 |
| 865 | 1-cyclopropyl-N-{1-[1-(5-methoxypyrimidin-2-yl)ethyl]azetidin-3-yl}-1H-1,2,3-triazole-4-carboxamide | 344.2 | 1.6379 |
| 866 | N-{1-[(1S)-1-(3-chlorophenyl)propyl]azetidin-3-yl}-5-cyclopropylpyridazine-3-carboxamide | 371.2 | 0.35518 |
| 867 | 5-cyclopropyl-N-[3-(dimethylamino)propyl]pyridazine-3-carboxamide | 249.2 | >50.0 |
| 868 | N-(1-{1-[4-(benzyloxy)-3-chlorophenyl]ethyl}azetidin-3-yl)-1-cyclopropyl-1H-1,2,3-triazole-4-carboxamide | 452.2 | 0.92507 |
| 869 | 5-cyclopropyl-N-[2-(dimethylamino)ethyl]pyridazine-3-carboxamide | 235.2 | 21.10972 |
| 913 | 5-cyclopropyl-N-[1-(propan-2-yl)azetidin-3-yl]-1H-imidazole-2-carboxamide | 249.2 | 1.69797 |
| 914 | 5-cyclopropyl-N-{1-[(1S)-1-phenylethyl]azetidin-3-yl}-1H-imidazole-2-carboxamide | 311.2 | 0.72872 |
| 915 | 5-cyclopropyl-N-{1-[(1R)-1-phenylethyl]azetidin-3-yl}-1H-imidazole-2-carboxamide | 311.2 | >50.0 |
| 916 | 5-cyclopropyl-N-[1-(propan-2-yl)piperidin-4-yl]pyridazine-3-carboxamide | 289.3 | 29.10492 |
| 917 | 5-cyclopropyl-N-(1-methylpiperidin-4-yl)pyridazine-3-carboxamide | 261.2 | >50.0 |
| 918 | 5-cyclopropyl-N-(1-methylpiperidin-3-yl)pyridazine-3-carboxamide | 261.3 | >50.0 |

*IC$_{50}$ values are an average of n = 1 to n = 50

TABLE 6A

| Cpd. No. | Chemical Name | LCMS M + H | SMYD2 Biochem IC$_{50}$ (μM)* |
|---|---|---|---|
| 919 | 1-cyclopropyl-N-(1-isopropylazetidin-3-yl)-1H-imidazole-4-carboxamide | 249.2 | 4.6 |
| 920 | N-(1-(1-(3-(2-chlorophenyl)-1H-indazol-5-yl)ethyl)azetidin-3-yl)-1-cyclopropyl-1H-1,2,3-triazole-4-carboxamide | 462.2 | >50 |
| 921 | 1-cyclopropyl-N-(3-(dimethylamino)propyl)-1H-1,2,3-triazole-4-carboxamide | 238.3 | 5.4 |
| 922 | 1-cyclopropyl-N-(1-(1-(4-((phenylamino)methyl)phenyl)ethyl)azetidin-3-yl)-1H-1,2,3-triazole-4-carboxamide | 417.2 | 0.65 |
| 923 | 1-cyclopropyl-N-(1-(1-(5-methoxypyridin-2-yl)ethyl)azetidin-3-yl)-1H-1,2,3-triazole-4-carboxamide | 343.3 | 2.7 |
| 924 | 1-cyclopropyl-N-(1-((6-(phenylamino)pyridin-3-yl)methyl)azetidin-3-yl)-1H-1,2,3-triazole-4-carboxamide | 390.2 | |
| 925 | 1-cyclopropyl-N-(1-(1-(4-(piperidin-4-ylmethoxy)phenyl)ethyl)azetidin-3-yl)-1H-1,2,3-triazole-4-carboxamide | 425.3 | 4.3 |
| 926 | N-(1-((6-(benzylamino)pyridin-3-yl)methyl)azetidin-3-yl)-1-cyclopropyl-1H-1,2,3-triazole-4-carboxamide | 404.2 | |
| 927 | N-(1-((1-(4-chlorobenzyl)-1H-pyrazol-4-yl)methyl)azetidin-3-yl)-4-cyclopropyl-1H-imidazole-2-carboxamide | 411.2 | 0.011 |

TABLE 6A-continued

| Cpd. No. | Chemical Name | LCMS M + H | SMYD2 Biochem IC$_{50}$ (μM)* |
|---|---|---|---|
| 928 | 5-cyclopropyl-N-(1-(4-((1-methyl-1H-pyrazol-4-yl)methoxy)benzyl)azetidin-3-yl)pyridazine-3-carboxamide | 419.3 | 0.61 |
| 929 | N-(1-((1-(4-chlorobenzyl)-1H-pyrazol-4-yl)methyl)azetidin-3-yl)-5-cyclopropylpyridazine-3-carboxamide | 423.2 | 0.0012 |
| 930 | N-(1-((1-(4-chlorobenzyl)-1H-pyrazol-4-yl)methyl)azetidin-3-yl)-4-cyclopropylpicolinamide | 422.7 | 0.0033 |
| 931 | N-(1-((1-benzyl-1H-1,2,3-triazol-4-yl)methyl)azetidin-3-yl)-1-cyclopropyl-1H-1,2,3-triazole-4-carboxamide | 379.3 | 11.1 |
| 932 | 1-cyclopropyl-N-(1-(((1-(4-methoxybenzyl)-1H-pyrazol-4-yl)methyl)azetidin-3-yl)-1H-1,2,3-triazole-4-carboxamide | 408.2 | 0.028 |
| 933 | N-(1-((1-benzyl-1H-pyrazol-4-yl)methyl)azetidin-3-yl)-5-cyclopropylpyridazine-3-carboxamide | 389.2 | 0.0078 |
| 934 | 5-cyclopropyl-N-(1-(1-(3-methoxyphenyl)ethyl)azetidin-3-yl)pyridazine-3-carboxamide | 353.2 | 0.69 |
| 935 | 1-cyclopropyl-N-(1-(1-(2-methyl-2H-indazol-5-yl)ethyl)azetidin-3-yl)-1H-1,2,3-triazole-4-carboxamide | 366.2 | 1.6 |
| 936 | N-(1-(((1-(benzo[d]thiazol-5-ylmethyl)-1H-pyrazol-4-yl)methyl)azetidin-3-yl)-1-cyclopropyl-1H-1,2,3-triazole-4-carboxamide | 435.2 | 0.080 |
| 937 | 1-cyclopropyl-N-(1-(((1-((4-methyloxazol-2-yl)methyl)-1H-pyrazol-4-yl)methyl)azetidin-3-yl)-1H-1,2,3-triazole-4-carboxamide | 383.2 | 0.12 |
| 938 | N-(1-(1-(2-chloro-5-methoxyphenyl)ethyl)azetidin-3-yl)-1-cyclopropyl-1H-1,2,3-triazole-4-carboxamide | 376.2 | 0.13 |
| 939 | N-(1-(1-(4-(benzyloxy)-3-methoxyphenyl)ethyl)azetidin-3-yl)-1-cyclopropyl-1H-1,2,3-triazole-4-carboxamide | 448.3 | 3.6 |
| 940 | N-(1-((1H-pyrazol-4-yl)methyl)azetidin-3-yl)-1-cyclopropyl-1H-1,2,3-triazole-4-carboxamide | 288.2 | 7.7 |
| 941 | 1-cyclopropyl-N-(1-(((1-(4-(methylthio)benzyl)-1H-pyrazol-4-yl)methyl)azetidin-3-yl)-1H-1,2,3-triazole-4-carboxamide | 424.2 | 0.028 |
| 942 | N-(1-(((1-(2-chlorobenzyl)-1H-pyrazol-4-yl)methyl)azetidin-3-yl)-1-cyclopropyl-1H-1,2,3-triazole-4-carboxamide | 412.1 | 0.11 |
| 943 | 1-cyclopropyl-N-(1-(((1-(4-(trifluoromethyl)benzyl)-1H-pyrazol-4-yl)methyl)azetidin-3-yl)-1H-1,2,3-triazole-4-carboxamide | 446.2 | 0.014 |
| 944 | 1-cyclopropyl-N-(1-(((1-(oxazol-2-ylmethyl)-1H-pyrazol-4-yl)methyl)azetidin-3-yl)-1H-1,2,3-triazole-4-carboxamide | 369.2 | 0.92 |
| 945 | 1-cyclopropyl-N-(1-(((1-(thiazol-4-ylmethyl)-1H-pyrazol-4-yl)methyl)azetidin-3-yl)-1H-1,2,3-triazole-4-carboxamide | 385.2 | 1.2 |
| 946 | 1-cyclopropyl-N-(1-(((1-ethyl-1H-pyrazol-4-yl)methyl)azetidin-3-yl)-1H-1,2,3-triazole-4-carboxamide | 316.2 | 2.0 |
| 947 | N-(1-(((1-(4-(tert-butyl)benzyl)-1H-pyrazol-4-yl)methyl)azetidin-3-yl)-1-cyclopropyl-1H-1,2,3-triazole-4-carboxamide | 434.3 | 0.056 |
| 948 | N-(1-(((1-(cyclohexylmethyl)-1H-pyrazol-4-yl)methyl)azetidin-3-yl)-1-cyclopropyl-1H-1,2,3-triazole-4-carboxamide | 384.3 | 0.36 |
| 949 | 1-cyclopropyl-N-(1-(((1-((tetrahydro-2H-pyran-4-yl)methyl)-1H-pyrazol-4-yl)methyl)azetidin-3-yl)-1H-1,2,3-triazole-4-carboxamide | 386.2 | 2.4 |
| 950 | 1-cyclopropyl-N-(1-(((1-((tetrahydrofuran-3-yl)methyl)-1H-pyrazol-4-yl)methyl)azetidin-3-yl)-1H-1,2,3-triazole-4-carboxamide | 372.3 | 2.0 |
| 951 | 1-cyclopropyl-N-(1-(((1-(4-fluorobenzyl)-1H-pyrazol-4-yl)methyl)azetidin-3-yl)-1H-1,2,3-triazole-4-carboxamide | 396.2 | 0.022 |
| 952 | 1-cyclopropyl-N-(1-(1-(1-methyl-1H-indazol-5-yl)ethyl)azetidin-3-yl)-1H-1,2,3-triazole-4-carboxamide | 366.2 | 1.63 |
| 953 | N-(1-(4-((1H-pyrazol-1-yl)methyl)benzyl)azetidin-3-yl)-1-cyclopropyl-1H-1,2,3-triazole-4-carboxamide | 378.3 | 5.6 |
| 954 | N-(1-(4-((1H-pyrazol-1-yl)methyl)benzyl)azetidin-3-yl)-5-cyclopropylpyridazine-3-carboxamide | 389.3 | 2.4 |

TABLE 6A-continued

| Cpd. No. | Chemical Name | LCMS M + H | SMYD2 Biochem IC$_{50}$ (μM)* |
|---|---|---|---|
| 955 | N-(1-((1-benzyl-1H-pyrazol-4-yl)methyl)azetidin-3-yl)-5-cyclopropylisoxazole-3-carboxamide | 378.2 | 0.073 |
| 956 | N-(1-(1-(2-chloro-3-(2-hydroxy-2-methylpropoxy)phenyl)ethyl)azetidin-3-yl)-1-cyclopropyl-1H-1,2,3-triazole-4-carboxamide | 434.2 | 2.6 |
| 957 | 1-cyclopropyl-N-(1-(1-(4-((4-methoxybenzyl)oxy)phenyl)ethyl)azetidin-3-yl)-1H-1,2,3-triazole-4-carboxamide | 448.3 | 0.16 |
| 958 | 5-cyclopropyl-N-(1-(1-(4-methoxyphenyl)ethyl)azetidin-3-yl)pyridazine-3-carboxamide | 353.2 | 0.60 |
| 959 | 1-cyclopropyl-N-(1-(1-(4-(2-(dimethylamino)ethoxy)phenyl)ethyl)azetidin-3-yl)-1H-1,2,3-triazole-4-carboxamide | 399.2 | 2.0 |
| 960 | 1-cyclopropyl-N-(1-(1-(4-phenethoxyphenyl)ethyl)azetidin-3-yl)-1H-1,2,3-triazole-4-carboxamide | 432.3 | 0.78 |
| 961 | 4-cyclopropyl-N-(1-isopropylazetidin-3-yl)picolinamide | 260.2 | 1.3 |
| 962 | 4-cyclopropyl-N-(1-(1-(2,5-dichlorophenyl)ethyl)azetidin-3-yl)picolinamide | 390.1 | 0.48 |
| 963 | 1-cyclopropyl-N-(1-(1-(4-((4-(methylcarbamoyl)benzyl)oxy)phenyl)ethyl)azetidin-3-yl)-1H-1,2,3-triazole-4-carboxamide | 475.3 | 0.97 |
| 964 | N-(1-(1-(2-chloro-3-(2-hydroxyemoxy)phenyl)ethyl)azetidin-3-yl)-4-cyclopropylpicolinamide | 416.2 | 10.5 |
| 965 | N-(1-(1-(2-chloro-3-memoxyphenyl)ethyl)azetidin-3-yl)-5-cyclopropylpyridazine-3-carboxamide | 387.2 | 0.072\ |
| 966 | N-(1-((1-benzyl-1H-pyrazol-4-yl)methyl)azetidin-3-yl)-4-cyclopropylpicolinamide | 388.3 | 0.013 |
| 967 | N-(1-(4-(benzyloxy)benzyl)azetidin-3-yl)-4-cyclopropylpicolinamide | 414.2 | 0.15 |
| 968 | 1-cyclopropyl-N-(1-(1-(4-(2,2,2-trifluoroethoxy)phenyl)ethyl)azetidin-3-yl)-1H-1,2,3-triazole-4-carboxamide | 410.2 | 1.7 |
| 969 | rac-N-(1-(((1r,3r)-3-(benzyloxy)cyclobutyl)methyl)azetidin-3-yl)-1-cyclopropyl-1H-1,2,3-triazole-4-carboxamide | 382.3 | 0.98 |
| 970 | N-(1-(1-(5-chloro-2-(difluoromethoxy)phenyl)ethyl)azetidin-3-yl)-1-cyclopropyl-1H-1,2,3-triazole-4-carboxamide | 412.2 | 5.1 |
| 971 | 1-cyclopropyl-N-(1-(1-(4-((4-methylbenzyl)oxy)phenyl)ethyl)azetidin-3-yl)-1H-1,2,3-triazole-4-carboxamide | 432.3 | 0.088 |
| 972 | 1-cyclopropyl-N-(1-(4-(pyridin-3-ylmemoxy)benzyl)azetidin-3-yl)-1H-1,2,3-triazole-4-carboxamide | 405.3 | 1.3 |
| 973 | N-(1-(1-(2-chloro-3-(2,3-dihydroxypropoxy)phenyl)ethyl)azetidin-3-yl)-1-cyclopropyl-1H-1,2,3-triazole-4-carboxamide | 436.2 | >50 |
| 974 | 1-cyclopropyl-N-(1-(1-(4-(phenoxymethyl)phenyl)ethyl)azetidin-3-yl)-1H-1,2,3-triazole-4-carboxamide | 418.3 | 0.87 |
| 975 | N-(1-(1-(2-chloro-3-(2-(methylamino)ethoxy)phenyl)ethyl)azetidin-3-yl)-1-cyclopropyl-1H-1,2,3-triazole-4-carboxamide | 419.3 | 5.4 |
| 976 | N-(1-(1-(5-chloro-2-(trifluoromethyl)phenyl)ethyl)azetidin-3-yl)-1-cyclopropyl-1H-1,2,3-triazole-4-carboxamide | 414.2 | 1.8 |
| 977 | N-(1-(1-(2-chloro-3-(2-(dimethylamino)ethoxy)phenyl)ethyl)azetidin-3-yl)-1-cyclopropyl-1H-1,2,3-triazole-4-carboxamide | 433.2 | 7.5 |
| 978 | N-(1-(1-(2-chloro-3-(2-hydroxypropoxy)phenyl)ethyl)azetidin-3-yl)-1-cyclopropyl-1H-1,2,3-triazole-4-carboxamide | 420.2 | 1.1 |
| 979 | 1-cyclopropyl-N-(1-(1-methylpiperidin-2-yl)ethyl)-1H-1,2,3-triazole-4-carboxamide | 278.2 | >50 |
| 980 | N-(1-(2-(4-(benzyloxy)phenyl)propan-2-yl)azetidin-3-yl)-1-cyclopropyl-1H-1,2,3-triazole-4-carboxamide | 432.3 | 0.99 |
| 981 | 5-cyclopropyl-N-(1-(1-methylpiperidin-2-yl)ethyl)pyridazine-3-carboxamide | 289.2 | >50 |
| 982 | 1-cyclopropyl-N-(1-((1-(3-methoxybenzyl)-1H-pyrazol-4-yl)methyl)azetidin-3-yl)-1H-1,2,3-triazole-4-carboxamide | 408.3 | 0.169 |

TABLE 6A-continued

| Cpd. No. | Chemical Name | LCMS M + H | SMYD2 Biochem IC$_{50}$ (μM)* |
|---|---|---|---|
| 983 | 1-cyclopropyl-N-(1-(4-(1-hydroxy-2-phenylethyl)benzyl)azetidin-3-yl)-1H-1,2,3-triazole-4-carboxamide | 418.2 | 1.39 |
| 984 | rac-1-cyclopropyl-N-((R)-2,2-dimethyl-1-((R)-1-phenylethyl)azetidin-3-yl)-1H-1,2,3-triazole-4-carboxamide | 340.2 | 18.9 |
| 985 | N-(1-((1-(4-chlorobenzyl)-1H-pyrazol-4-yl)methyl)azetidin-3-yl)-1-cyclopropyl-1H-1,2,3-triazole-4-carboxamide | 412.2 | 0.0039 |
| 986 | N-(1-((1-benzyl-1H-pyrazol-4-yl)methyl)azetidin-3-yl)-5-cyclopropyl-1H-imidazole-2-carboxamide | 377.3 | >50 |
| 987 | N-(1-((1-(3-chlorobenzyl)-1H-pyrazol-4-yl)methyl)azetidin-3-yl)-1-cyclopropyl-1H-1,2,3-triazole-4-carboxamide | 412.2 | 0.024 |
| 988 | N-(1-(4-((1,3,4-thiadiazol-2-yl)methoxy)benzyl)azetidin-3-yl)-1-cyclopropyl-1H-1,2,3-triazole-4-carboxamide | 412.2 | 1.9 |
| 989 | N-(1-(1-(5-chloro-2-(4-fluorophenoxy)phenyl)ethyl)azetidin-3-yl)-1-cyclopropyl-1H-1,2,3-triazole-4-carboxamide | 456.2 | >50.0 |
| 990 | 1-cyclopropyl-N-(1-(1-(4-(piperidin-3-ylmethoxy)phenyl)ethyl)azetidin-3-yl)-1H-1,2,3-triazole-4-carboxamide | 425.2 | 3.3 |
| 991 | 1-cyclopropyl-N-(1-((1-(thiazol-2-ylmethyl)-1H-pyrazol-4-yl)methyl)azetidin-3-yl)-1H-1,2,3-triazole-4-carboxamide | 385.2 | 0.76 |
| 992 | 1-cyclopropyl-N-(1-(4-(pyridin-2-ylmethoxy)benzyl)azetidin-3-yl)-1H-1,2,3-triazole-4-carboxamide | 405.1 | 2.7 |
| 993 | 1-cyclopropyl-N-(1-((1-(4-methylbenzyl)-1H-pyrazol-4-yl)methyl)azetidin-3-yl)-1H-1,2,3-triazole-4-carboxamide | 392.3 | 0.016 |
| 994 | 1-cyclopropyl-N-(1-(1-(6-oxo-1,6-dihydropyridin-3-yl)ethyl)azetidin-3-yl)-1H-1,2,3-triazole-4-carboxamide | 329.2 | 5.4 |
| 995 | 1-cyclopropyl-N-(1-((1-(2-methoxybenzyl)-1H-pyrazol-4-yl)methyl)azetidin-3-yl)-1H-1,2,3-triazole-4-carboxamide | 408.2 | 1.3 |
| 996 | N-(1-(1-(4-((4-chlorobenzyl)oxy)phenyl)ethyl)azetidin-3-yl)-1-cyclopropyl-1H-1,2,3-triazole-4-carboxamide | 452.2 | 0.069 |
| 997 | N-(1-(1-(4-((3-chlorobenzyl)oxy)phenyl)ethyl)azetidin-3-yl)-1-cyclopropyl-1H-1,2,3-triazole-4-carboxamide | 452.2 | 0.27 |
| 998 | 1-cyclopropyl-N-(1-((1-isobutyl-1H-pyrazol-4-yl)methyl)azetidin-3-yl)-1H-1,2,3-triazole-4-carboxamide | 343.4 | 2.4 |
| 999 | 1-cyclopropyl-N-(1-(4-(thiazol-4-ylmethoxy)benzyl)azetidin-3-yl)-1H-1,2,3-triazole-4-carboxamide | 411.2 | 1.1 |
| 1000 | 1-cyclopropyl-N-(1-(piperidin-2-yl)ethyl)-1H-1,2,3-triazole-4-carboxamide | 264.1 | >50 |
| 1001 | N-(1-((1-(cyclobutylmethyl)-1H-pyrazol-4-yl)methyl)azetidin-3-yl)-1-cyclopropyl-1H-1,2,3-triazole-4-carboxamide | 356.2 | 1.4 |
| 1002 | N-(1-(1-(2-chloro-4-methoxyphenyl)ethyl)azetidin-3-yl)-1-cyclopropyl-1H-1,2,3-triazole-4-carboxamide | 376.2 | 0.088 |
| 1003 | 5-cyclopropyl-N-(1-(piperidin-2-yl)ethyl)pyridazine-3-carboxamide | 275.2 | 19.0 |
| 1004 | 1-cyclopropyl-N-(1-(1-(4-(2-oxo-2-(piperidin-1-yl)ethoxy)phenyl)ethyl)azetidin-3-yl)-1H-1,2,3-triazole-4-carboxamide | 453.3 | 1.5 |
| 1005 | 4-cyclopropyl-N-(1-(1-(2,3-dimethoxyphenyl)ethyl)azetidin-3-yl)picolinamide | 381.9 | 0.13 |
| 1006 | 1-cyclopropyl-N-(1-((1-(cyclopropylmethyl)-1H-pyrazol-4-yl)methyl)azetidin-3-yl)-1H-1,2,3-triazole-4-carboxamide | 342.2 | 1.7 |
| 1007 | N-(1-((1-benzyl-1H-pyrazol-4-yl)methyl)azetidin-3-yl)-5-cyclopropyl-1,3,4-thiadiazole-2-carboxamide | 395.1 | 0.072 |
| 1008 | rac-N-(1-(((1s,3s)-3-(benzyloxy)cyclobutyl)methyl)azetidin-3-yl)-1-cyclopropyl-1H-1,2,3-triazole-4-carboxamide | 382.2 | 1.2 |
| 1009 | N-(1-(3-(2-aminoethoxy)-2-chlorophenyl)ethyl)azetidin-3-yl)-1-cyclopropyl-1H-1,2,3-triazole-4-carboxamide | 405.3 | 5.7 |

TABLE 6A-continued

| Cpd. No. | Chemical Name | LCMS M + H | SMYD2 Biochem IC$_{50}$ (μM)* |
|---|---|---|---|
| 1012 | N-(1-((1-(4-chlorobenzyl)-1H-pyrazol-4-yl)methyl)azetidin-3-yl)-1-cyclopropyl-1H-imidazole-4-carboxamide | 411.1 | |
| 1017 | 1-cyclopropyl-N-(1-((1-((1-methyl-1H-pyrazol-4-yl)methyl)-1H-pyrazol-4-yl)methyl)azetidin-3-yl)-1H-1,2,3-triazole-4-carboxamide | 382.2 | |
| 1020 | N-(1-(1-(4-((4-acetamidobenzyl)oxy)phenyl)ethyl)azetidin-3-yl)-1-cyclopropyl-1H-1,2,3-triazole-4-carboxamide | 475.3 | 0.95 |
| 1021 | N-(1-((1-benzyl-1H-pyrazol-4-yl)methyl)azetidin-3-yl)-5-cyclopropyl-1,3,4-oxadiazole-2-carboxamide | 379.2 | 0.065 |
| 1022 | N-(1-((1-benzyl-1H-pyrazol-4-yl)methyl)azetidin-3-yl)-1-cyclopropyl-1H-imidazole-4-carboxamide | 377.2 | 0.073 |
| 1023 | 5-cyclopropyl-N-((1R,3s,5S)-8-methyl-8-azabicyclo[3.2.1]octan-3-yl)pyridazine-3-carboxamide | 287.2 | 6.3 |
| 1024 | 5-cyclopropyl-N-((1R,3r,5S)-8-methyl-8-azabicyclo[3.2.1]octan-3-yl)pyridazine-3-carboxamide | 287.2 | >50 |
| 1025 | 1-cyclopropyl-N-(1-(4-((1-methyl-1H-pyrazol-4-yl)methoxy)benzyl)azetidin-3-yl)-1H-1,2,3-triazole-4-carboxamide | 408.3 | 1.2 |
| 1026 | rac-1-cyclopropyl-N-((R)-2,2-dimethyl-1-((S)-1-phenylethyl)azetidin-3-yl)-1H-1,2,3-triazole-4-carboxamide | 340.3 | 0.91 |
| 1028 | N-(1-((1-(4-chlorobenzyl)-1H-pyrazol-4-yl)methyl)azetidin-3-yl)-5-cyclopropyl-1,3,4-oxadiazole-2-carboxamide | 413.2 | |

*IC$_{50}$ values are an average of n = 1 to n = 50

In another embodiment, a Compound of the Disclosure is a compound having Formulae I-XVIII, provided that the compound is not N-(1-((4-acetamidophenyl)sulfonyl)piperidin-4-yl)benzamide:

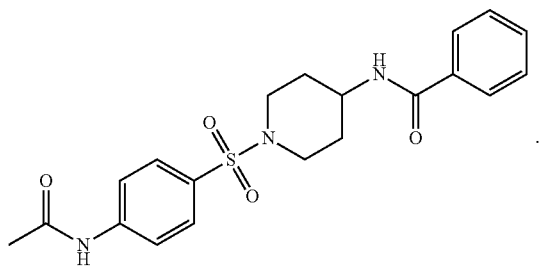 [SMILES: CC(=O)Nc1ccc(S(=O)(=O)N2CCC(NC(=O)c3ccccc3)CC2)cc1]

In some embodiments, the disclosure relates to pharmaceutical compositions comprising N-(1-((4-acetamidophenyl)sulfonyl)piperidin-4-yl)benzamide and a pharmaceutically acceptable carrier.

In some embodiments, the disclosure relates to a method of inhibiting SMYD proteins, such as SMYD3 or SMYD2, or both, in a subject, comprising administering to a subject in need thereof an effective amount of N-(1-((4-acetamidophenyl) sulfonyl)piperidin-4-yl)benzamide.

Definitions

For the purpose of the present disclosure, the terms used in connection with A or A$^1$ have the chemical structures set forth in Table 2, each of which may be optionally substituted with one or more substituents, e.g., 1, 2, 3, 4, or 5 substituents, depending on the nature of the group and the number of available positions. For example, when A or A$^1$ is 2-furanyl there are three carbon atoms for available for substitution. When A or A$^1$ is 2-naphthalenyl there are seven carbon atoms available for substitution. Substitution may occur at any available carbon or nitrogen atom. Optional substituents include, but are not limited to, halo, hydroxy, alkoxy, amino, alkylamino, dialkylamino, (amino)alkyl, (alkylamino)alkyl, (dialkylamino)alkyl, C$_{1-6}$ alkyl, haloalkyl, hydroxyalkyl, (carboxamido)alkyl, (cycloalkyl)alkyl, optionally substituted C$_{3-12}$ cycloalkyl, optionally substituted C$_{6-14}$ aryl, optionally substituted 5- to 14-membered heteroaryl, optionally substituted 4- to 14-membered heterocyclo, or aralkyl.

TABLE 2

| A or A$^1$ | Chemical structure |
|---|---|
| 1,2,3-triazolyl | 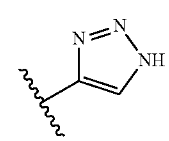 [SMILES: *c1c[nH]nn1] |
| 1,2,4-triazolyl | 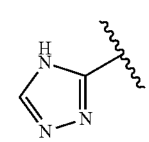 [SMILES: *c1nnc[nH]1] |
| 1-imidazolyl | 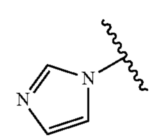 [SMILES: *n1ccnc1] |

TABLE 2-continued

| A or A¹ | Chemical structure |
| --- | --- |
| 1-isoquinolinyl | 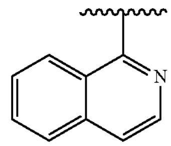 [SMILES: *c1nccc2ccccc12] |
| 1-pyrazolyl | 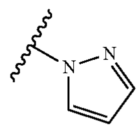 [SMILES: *n1cccn1] |
| 2-(1,2,3,4-tetrahydroquinolinyl) | 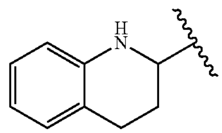 [SMILES: *C1CCc2ccccc2N1] |
| 2-benzo[d]imidazolyl | 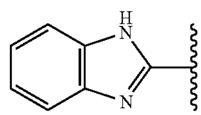 [SMILES: *c1nc2ccccc2[nH]1] |
| 2-benzo[d]thiazolyl | 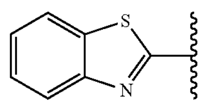 [SMILES: *c1nc2ccccc2s1] |
| 2-chromenyl-4-one | 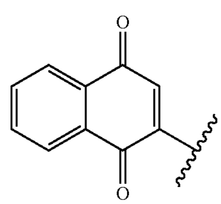 [SMILES: *C1=CC(=O)c2ccccc2C1=O] |
| 2-furanyl | 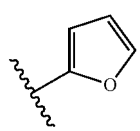 [SMILES: *c1ccco1] |
| 2-imidazo[1,2-b]pyridazinyl | 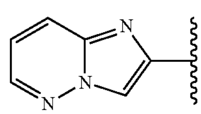 [SMILES: *c1cn2ncccc2n1] |
| 2-imidazolyl | 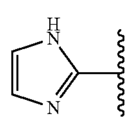 [SMILES: *c1ncc[nH]1] |
| 2-indolyl | 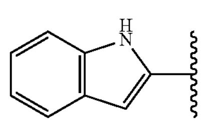 [SMILES: *c1cc2ccccc2[nH]1] |
| 2-naphthalenyl | 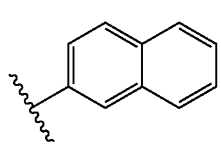 [SMILES: *c1ccc2ccccc2c1] |

TABLE 2-continued

| A or A¹ | Chemical structure |
| --- | --- |
| 2-pyrazinyl | 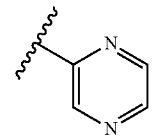 [SMILES: *c1cnccn1] |
| 2-pyridyl | 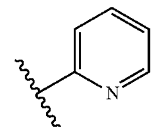 [SMILES: *c1ccccn1] |
| 2-pyrimidinyl | 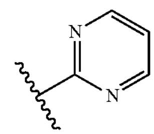 [SMILES: *c1ncccn1] |
| 2-pyrrolidinyl | 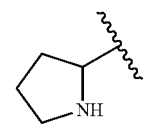 [SMILES: *C1CCCN1] |
| 2-pyrrolyl | 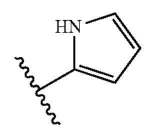 [SMILES: *c1ccc[nH]1] |
| 2-quinolinyl | 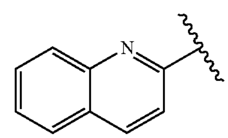 [SMILES: *c1ccc2ccccc2n1] |
| 2-quinoxalinyl | 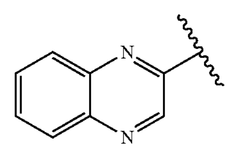 [SMILES: *c1cnc2ccccc2n1] |
| 2-thiazolo[5,4-c]pyridinyl | 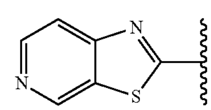 [SMILES: *c1nc2ccncc2s1] |
| 2-thiazolyl | 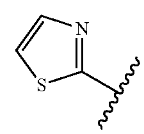 [SMILES: *c1nccs1] |
| 2-thiophenyl | 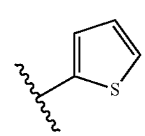 [SMILES: *c1cccs1] |
| 3-(1,2,3,4-tetrahydroisoquinoline) | 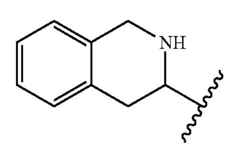 [SMILES: *C1Cc2ccccc2CN1] |

TABLE 2-continued
| A or A¹ | Chemical structure |
|---|---|
| 3-(1,2,4-oxadiazolyl) | 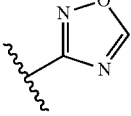 |
| 3-imidazo[1,2-a]pyrimidinyl | 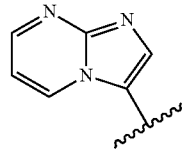 [SMILES: *c1cnc2ncccn12] |
| 3-indazolyl | 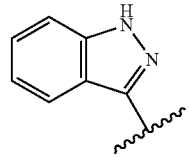 [SMILES: *c1n[nH]c2ccccc12] |
| 3-indolyl | 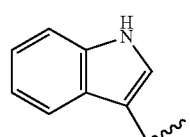 |
| 3-isothiazolyl | 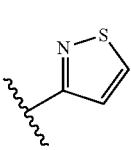 [SMILES: *c1ccsn1] |
| 3-pyrazolyl | 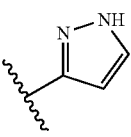 [SMILES: *c1cc[nH]n1] |
| 3-pyridazinyl | 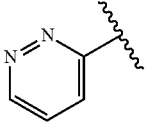 |
| 3-pyridinyl-2-one | 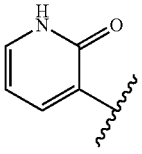 [SMILES: *c1ccc[nH]c1=O] |
| 3-pyridyl | 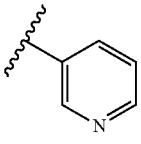 [SMILES: *c1cccnc1] |
| 3-pyrrolo[3,2-b]pyridinyl | 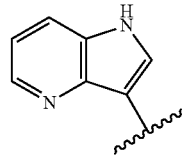 [SMILES: *c1c[nH]c2cccnc12] |
| 3-quinolinyl | 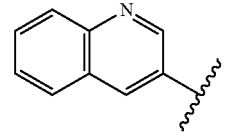 [SMILES: *c1cnc2ccccc2c1] |
| 4-(2,2-difluorobenzo[d][1,3]dioxolyl) | 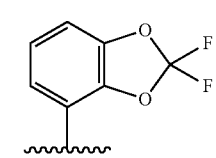 [SMILES: *c1cccc2c1OC(F)(F)O2] |
| 4-cyclohexanyl-1-amine | 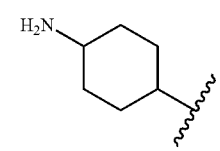 [SMILES: *C1CCC(N)CC1] |
| 4-imidazolyl | 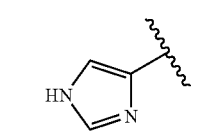 |
| 4-indolinyl-2-one | 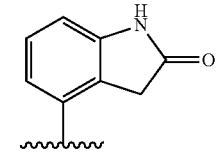 [SMILES: *c1cccc2c1CC(=O)N2] |
| 4-indolyl | 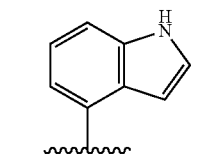 [SMILES: *c1cccc2[nH]ccc12] |
| 4-isothiazolyl | 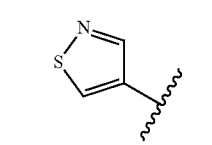 [SMILES: *c1cnsc1] |
| 4-oxazolyl | 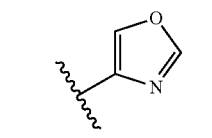 [SMILES: *c1cocn1] |
| 4-piperidinyl | 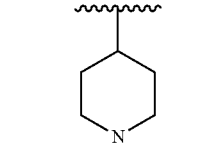 |
| 4-pyrazolyl | 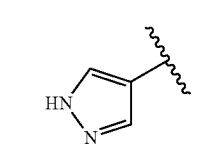 [SMILES: *c1cn[nH]c1] |

TABLE 2-continued

| A or A¹ | Chemical structure |
|---|---|
| 4-pyridyl | 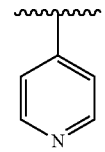 |
| 4-quinolinyl | 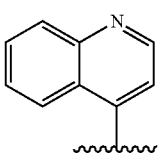 [SMILES: *c1ccnc2ccccc12] |
| 5-(1,3-dihydro-2H-benzo[d]imidazolyl-2-one) | 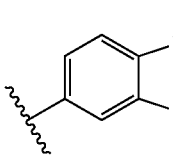 |
| 5-(1,3-dihydro-2H-pyrrolo[2,3-b]pyridinyl-2-one) | 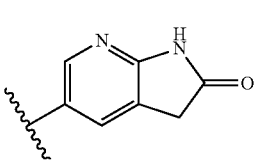 [SMILES: *c1cnc2c(c1)CC(=O)N2] |
| 5-(1,3-dihydro-2H-pyrrolo[2,3-c]pyridinyl-2-one) | 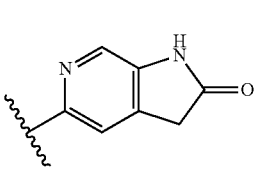 [SMILES: *c1cc2c(cn1)NC(=O)C2] |
| 5-(2,2-difluorobenzo[d][1,3]dioxolyl) | 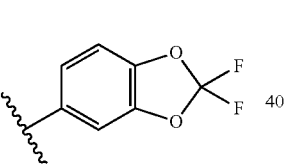 |
| 5-(2,4-dihydro-3H-1,2,4-triazolyl-3-one) | 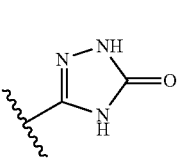 |
| 5-4H-furo[3,2-b]pyrrolyl | 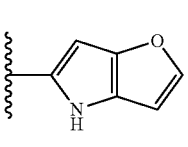 [SMILES: *c1cc2occc2[nH]1] |
| 5-benzo[c][1,2,5]oxadiazolyl | 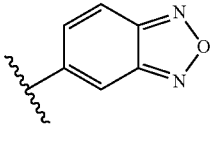 [SMILES: *c1ccc2nonc2c1] |
| 5-benzo[d][1,3]dioxolyl | 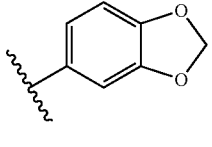 [SMILES: *c1ccc2c(c1)OCO2] |
| 5-benzo[d]oxazolyl-2(3H)-one |  |
| 5-bicyclo[2.2.1]heptyl-2-ene | 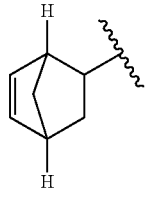 [SMILES: *C1CC2C=CC1C2] |
| 5-indolinyl-2,3-dione | 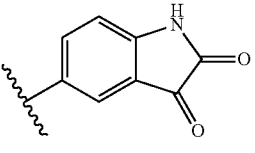 [SMILES: *c1ccc2c(c1)C(=O)C(=O)N2] |
| 5-indolinyl-2-one | 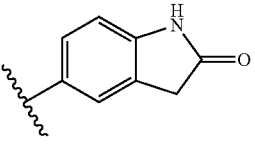 [SMILES: *c1ccc2c(c1)CC(=O)N2] |
| 5-indolyl | 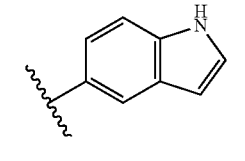 [SMILES: *c1ccc2[nH]ccc2c1] |
| 5-isoindolinyl-1-one | 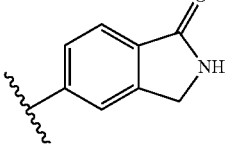 |
| 5-isoxazolyl | 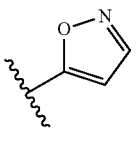 [SMILES: *c1ccno1] |
| 5-pyrazolo[3,4-c]pyridinyl | 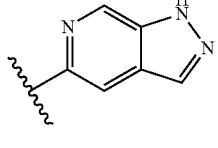 |
| 5-pyrazolyl | 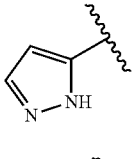 |
| 5-pyrimidinyl | 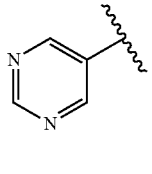 [SMILES: *c1cncnc1] |

TABLE 2-continued

| A or A¹ | Chemical structure |
|---|---|
| 5-thiazolyl | 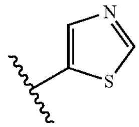 [SMILES: *c1cncs1] |
| 6-(1,2,3,4-tetrahydronaphthalenyl) | 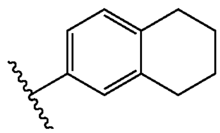 [SMILES: *c1ccc2c(c1)CCCC2] |
| 6-(3,4-dihydroquinolinyl-2(1H)-one) | 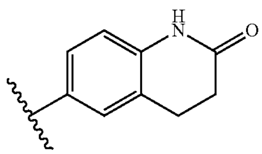 [SMILES: *c1ccc2c(c1)CCC(=O)N2] |
| 6-(3,4-dihydroquinoxalinyl-2(1H)-one) | 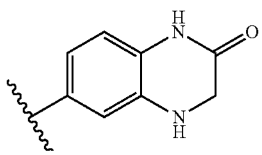 [SMILES: *c1ccc2c(c1)NCC(=O)N2] |
| 6-(4,5-dihydropyridazinyl-3(2H)-one) | 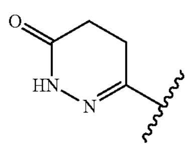 [SMILES: *C1=NNC(=O)CC1] |
| 6-benzo[b][1,4]oxazinyl-3-one | 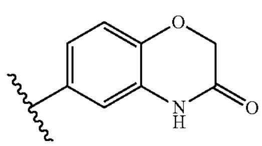 [SMILES: *c1ccc2c(c1)NC(=O)CO2] |
| 6-benzo[d]imidazolyl | 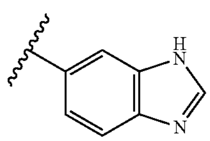 [SMILES: *c1ccc2nc[nH]c2c1] |
| 6-benzo[d]oxazolyl-2(3H)-one | 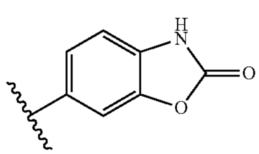 [SMILES: *c1ccc2[nH]c(=O)oc2c1] |
| 6-benzo[d]thiazolyl | 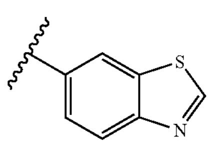 [SMILES: *c1ccc2ncsc2c1] |
| 6-chromenyl-2-one | 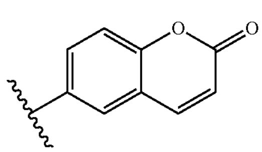 [SMILES: *c1ccc2oc(=O)ccc2c1] |
| 6-imidazo[2,1-b]thiazole | 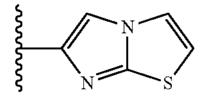 [SMILES: *c1cn2ccsc2n1] |
| 6-indazolyl | 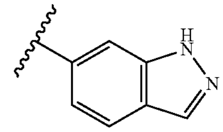 [SMILES: *c1ccc2cn[nH]c2c1] |
| 6-indolinyl-2-one | 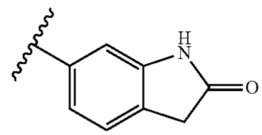 [SMILES: *c1ccc2c(c1)NC(=O)C2] |
| 6-indolyl | 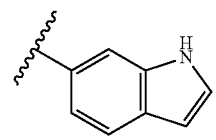 [SMILES: *c1ccc2cc[nH]c2c1] |
| 6-isoquinolinyl | 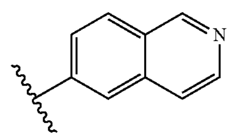 [SMILES: *c1ccc2cnccc2c1] |
| 6-quinolinyl | 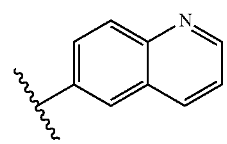 [SMILES: *c1ccc2ncccc2c1] |
| 6-quinoxalinyl | 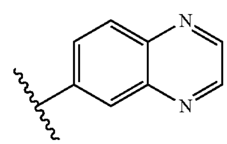 [SMILES: *c1ccc2nccnc2c1] |
| 6-quinoxalinyl-2(1H)-one | 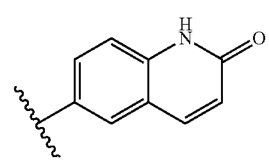 [SMILES: *c1ccc2[nH]c(=O)ccc2c1] |
| 7-(3,4-dihydroquinolinyl-2(1H)-one) | 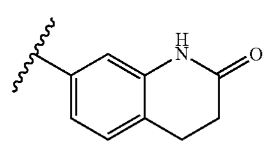 [SMILES: *c1ccc2c(c1)NC(=O)CC2] |
| 7-(3,4-dihydroquinoxalin-2(1H)-one) | 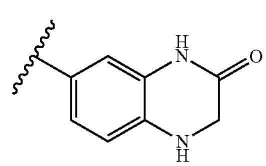 [SMILES: *c1ccc2c(c1)NC(=O)CN2] |

TABLE 2-continued

| A or A¹ | Chemical structure |
|---|---|
| 7-benzo[b][1,4]oxazinyl-3-one | 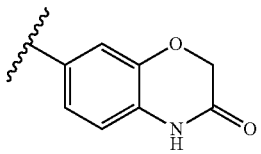 [SMILES: *c1ccc2c(c1)OCC(=O)N2] |
| 7-indolinyl-2-one | 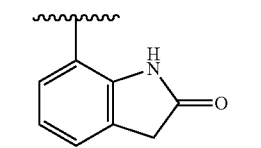 [SMILES: *c1cccc2c1NC(=O)C2] |
| 7-quinolinyl | 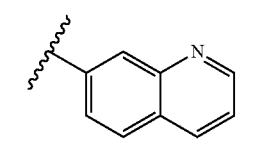 [SMILES: *c1ccc2cccnc2c1] |
| 8-benzo[b][1,4]oxazinyl-3-one | 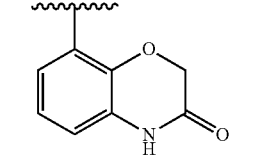 [SMILES: *c1cccc2c1OCC(=O)N2] |
| cyclopropanyl | 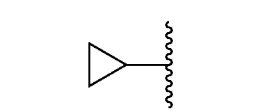 [SMILES: *C1CC1] |
| phenyl | 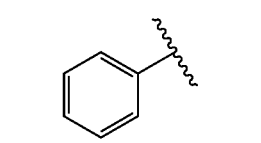 [SMILES: *c1ccccc1] |
| 4-(prop-1-en-1-yl)-imidazole | 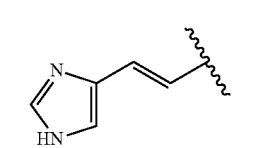 [SMILES: */C=C/c1c[nH]cn1] |
| 1-butanyl-imidazole | 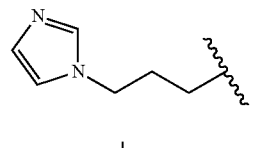 |
| sec-butylcyclopropane | 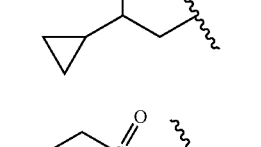 |
| 2-(ethylsulfonyl)propanyl | 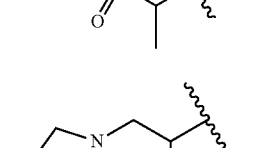 |
| 1-isobutylpyrrolidine | 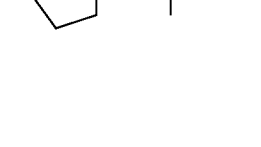 |
| 4-pyridyl 1-oxide | 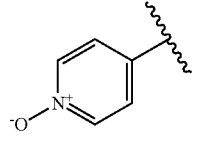 |
| 5-benzo[c][1,2,5]oxadiazolyl 1-oxide | 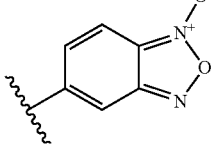 |

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-10}$ alkyl groups include methyl (including —$CD_3$), ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, alkoxycarbonyl, and carboxyalkyl. In one embodiment, the alkyl is a $C_{1-6}$ alkyl. In another embodiment, the alkyl is a $C_{1-4}$ alkyl. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, and —$CH_2C_6H_{11}$.

For the purpose of the present disclosure, the term "alkylenyl" as used herein by itself or part of another group refers to a divalent form of an alkyl group as defined above. In one embodiment, the alkylenyl is a divalent form of a $C_{1-6}$ alkyl. In one embodiment, the alkylenyl is a divalent form of a $C_{1-4}$ alkyl. Non-limiting exemplary alkylenyl groups include —$CH_2CH_2$—, —$CH_2CH_2CH_2$—, —$CH_2CH(CH_3)CH_2$—, and —$CH_2C(CH_3)_2CH_2$—.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, spiro[3.3]heptane, and bicyclo[3.3.1]nonane.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, cycloalkylamino, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted cycloalkyl is substituted with two substituents. In another embodiment, the optionally substituted cycloalkyl is substituted with one substituent. In one embodiment, the optionally substituted cycloalkyl is an (amino)cyclo alkyl. For the purpose of the present disclosure, the term "(amino)cycloalkyl" as used by itself or as part of another group means that the optionally substituted cycloalkyl as defined above is substituted with one amino or alkylamino group, and optionally one or two additional substituents. In one embodiment, the optionally substituted cycloalkyl is an (amino)cyclohexyl. For the purpose of the present disclosure, the term "(amino)cyclohexyl" as used by itself or as part of another group means that the optionally substituted cycloalkyl as defined above is a cyclohexyl group substituted with one amino or alkylamino group, and optionally one or two additional substituents. Non-limiting exemplary optionally substituted cycloalkyl groups include:

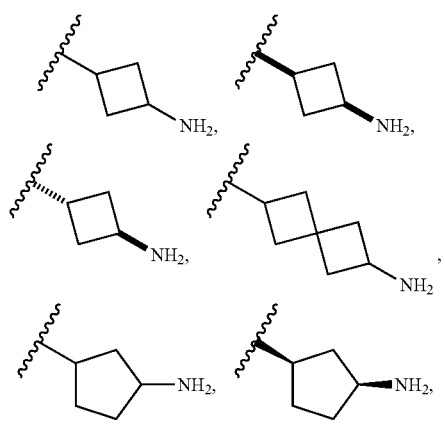

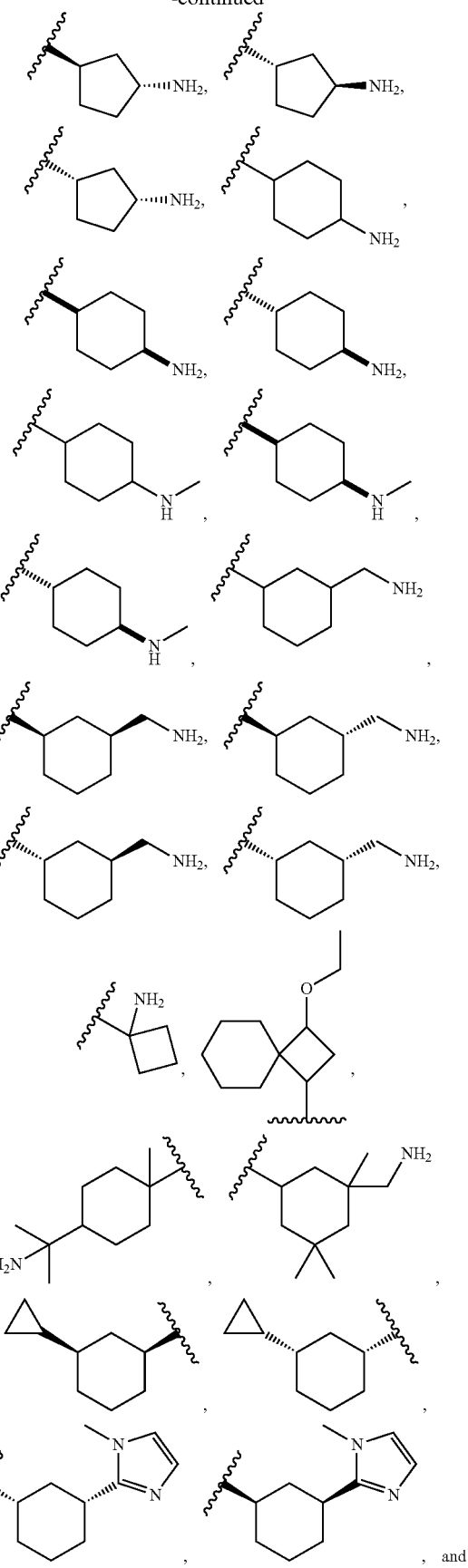

-continued

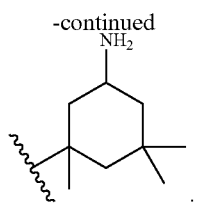

Non-limiting exemplary (amino)cycloalkyl groups include:

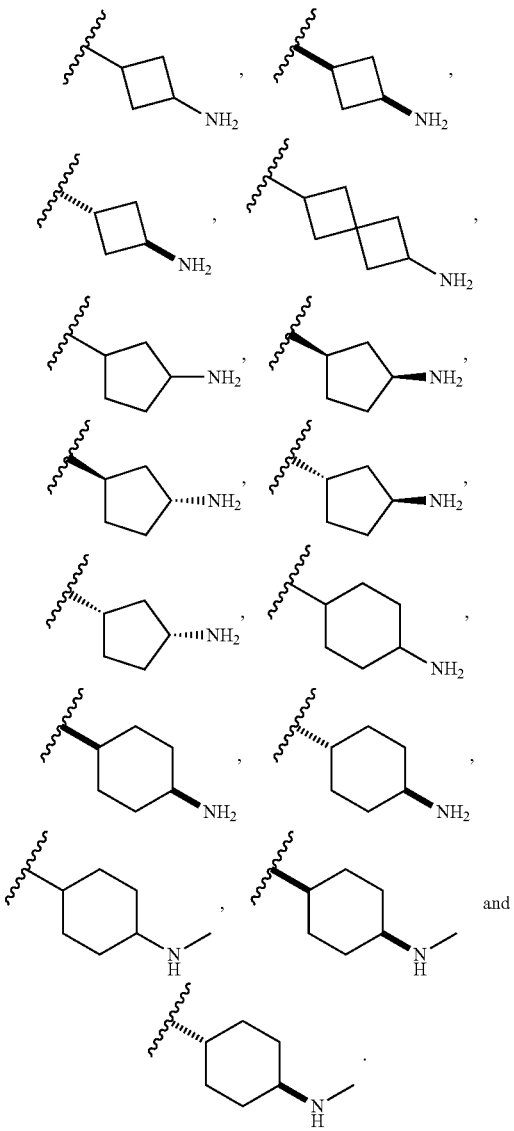

Non-Limiting Exemplary (Amino)Cyclohexyl Groups Include:

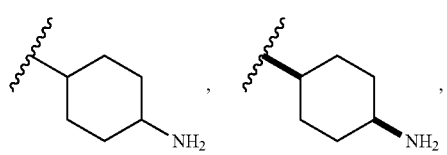

-continued

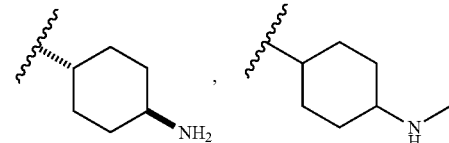

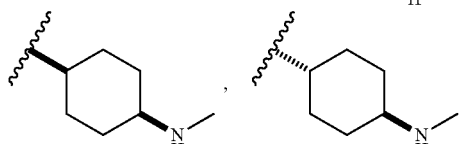

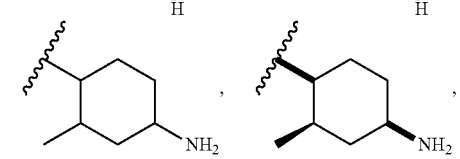

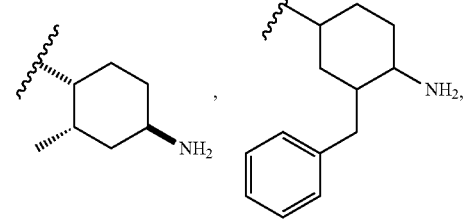

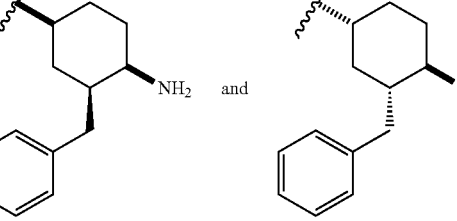

For the purpose of the present disclosure, the term "optionally substituted cyclohexyl" as used by itself or as part of another group means that the optionally substituted cycloalkyl as defined above is an optionally substituted cyclohexyl group.

For the purpose of the present disclosure, the term "cycloalkylenyl" as used herein by itself or part of another group refers to a divalent form of an optionally substituted cycloalkyl group as defined above. In one embodiment, the cycloalkylenyl is a "cyclohexylenyl." The term "cyclohexylenyl" as used herein by itself or part of another group refers to a divalent form of an optionally substituted cyclohexyl group. Non-limiting exemplary cycloalkylenyl groups include:

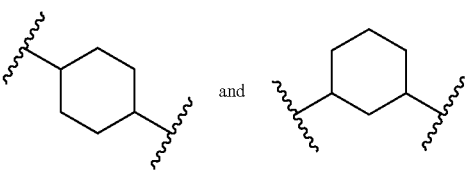

For the purpose of the present disclosure, the term "1,4-cyclohexylenyl" as used herein by itself or part of another group refers to a cyclohexylenyl as defined above wherein the 1- and 4-positions of the cyclohexyl ring are substituted. Non-limiting exemplary 1,4-cyclohexylenyl groups include:

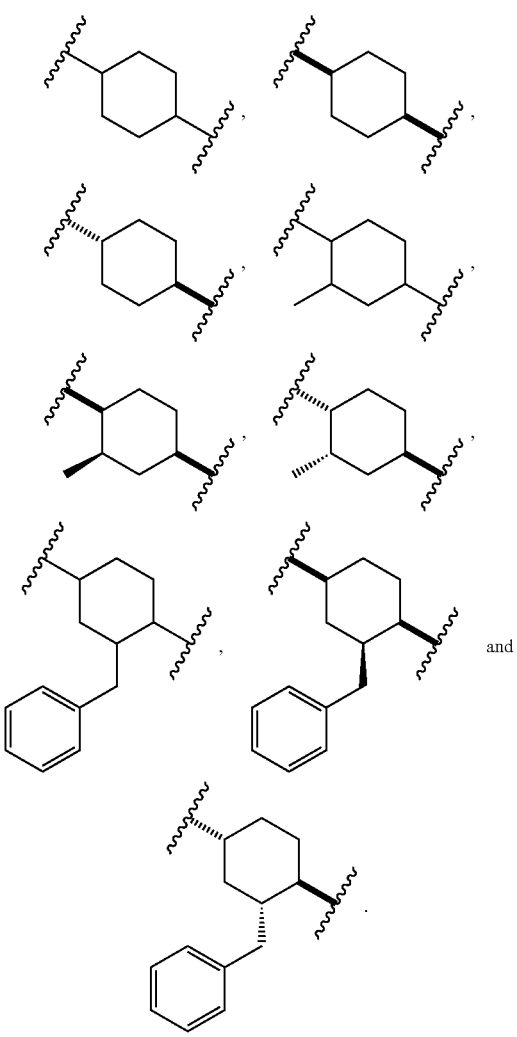

For the purpose of the present disclosure, the term "(cycloalkylenyl)alkyl" as used herein by itself or part of another group refers to an alkyl group substituted with a divalent form of an optionally substituted cycloalkyl group. In one embodiment, the cycloalkylenyl is a divalent for of optionally substituted cyclohexyl. In one embodiment, the alkyl is $C_{1-4}$ alkyl. Non-limiting exemplary (cycloalkylenyl)alkyl groups include:

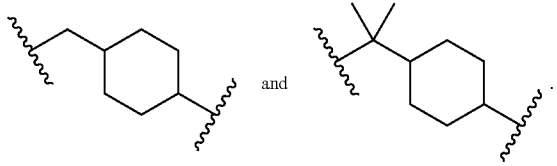 [SMILES: *CC1CCC(*)CC1 ; *C1CCC(C(*)(C)C)CC1]

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl and cyclohexenyl.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, or optionally substituted heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1, 1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "fluoroalkyl" as used by itself or as part of another group refers to an alkyl group substituted by one or more fluorine atoms. In one embodiment, the alkyl group is substituted by one, two, or three fluorine atoms. In another embodiment, the fluoroalkyl group is chosen from a $C_{1-4}$ fluoroalkyl group. Non-limiting exemplary fluoroalkyl groups include fluoromethyl, difluoromethyl, trifluoromethyl, pentafluoroethyl, 1, 1-difluoroethyl, 2,2-difluoroethyl, 2,2,2-trifluoroethyl, 3,3,3-trifluoropropyl, and 4,4,4-trifluorobutyl.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, tert-butoxy, —OCH$_2$C≡CH, —OCH$_2$C≡CCH$_3$, and —OCH$_2$CH$_2$CH$_2$C≡CH.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —SCH$_3$, and —SCH$_2$CH$_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, pentyloxymethyl, —CH$_2$OCH$_2$C≡CH and —CH$_2$OCH$_2$CH$_2$CH$_2$C≡CH.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. In one embodiment, the heteroalkyl contains one oxygen and one nitrogen atom, e.g., a (hydroxyalkylamino)alkyl group, e.g., —CH$_2$N(CH$_3$)CH$_2$CH$_2$CH$_2$OH. In one embodiment, the heteroalkyl contains two nitrogen atoms. Non-limiting exemplary heteroalkyl groups include —CH$_2$OCH$_2$CH$_2$OCH$_3$, —OCH$_2$CH$_2$OCH$_2$CH$_2$OCH$_3$, —CH$_2$NHCH$_2$CH$_2$OCH$_2$, —OCH$_2$CH$_2$NH$_2$, —NHCH$_2$CH$_2$N(H)CH$_3$, —NHCH$_2$CH$_2$OCH$_3$, —CH$_2$OCH$_2$CH$_2$NH$_2$, —CH$_2$OCH$_2$CH$_2$N(H)CH$_2$CH$_3$, and —OCH$_2$CH$_2$OCH$_3$.

For the purpose of the present disclosure, the term "aryl" as used by itself or as part of another group refers to a monocyclic or bicyclic aromatic ring system having from six to fourteen carbon atoms (i.e., $C_{6-14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl. In one embodiment, the aryl group is phenyl.

For the purpose of the present disclosure, the term "optionally substituted aryl" as used herein by itself or as part of another group means that the aryl as defined above is either unsubstituted or substituted with one to five substituents independently selected from the group consisting of halo, nitro, cyano, hydroxy, amino, alkylamino, dialkylamino, aralkylamino, haloalkyl, hydroxyalkyl, alkoxy, haloalkoxy, aryloxy, heteroaryloxy, aralkyl, aralkyloxy, (aralkyloxy)alkyl, alkylthio, carboxamido, sulfonamido, alkylcarbonyl, arylcarbonyl, alkylsulfonyl, arylsulfonyl, ureido, guanidino, carboxy, carboxyalkyl, heteroalkyl, optionally substituted alkyl, optionally substituted cycloalkyl, alkenyl, alkynyl, optionally substituted aryl, optionally substituted heteroaryl, optionally substituted heterocyclo, ($C_{1-4}$ haloalkoxy)alkyl, alkoxyalkyl, (amino)alkyl, hydroxyalkylamino, (alkylamino)alkyl, (dialkylamino)alkyl, (cyano)alkyl, (carboxamido)alkyl, (carboxamido)alkyl-O—, mercapto alkyl, (heterocyclo)alkyl, (heterocyclo)alkyl-O—, (cycloalkylamino)alkyl, (hydroxyalkylamino)alkyl, (amino)(heteroaryl)alkyl, (heterocycloamino)alkyl (amino)(hydroxy)alkyl, (heteroaryl)alkyl, (hetero aryl)alkyl-O—, —N(R$^{43}$)(R$^{44}$), —CH$_2$N(R$^{43}$)(R$^{44}$), —CH$_2$N(H)C(=O)—R$^{45}$, and —N(H)C(=O)—R$^{45}$, wherein R$^{43}$ is hydrogen, $C_{1-4}$ alkyl, optionally substituted aryl, or optionally substituted heteroaryl; R$^{44}$ is alkoxyalkyl, (heterocyclo)alkyl, (amino)alkyl, (alkylamino)alkyl, aralkyl, or (dialkylamino)alkyl; and R$^{45}$ is alkyl, alkoxyalkyl, (heterocyclo)alkyl, (amino)alkyl, (alkylamino)alkyl, (dialkylamino)alkyl, optionally substituted aryl, optionally substituted heteroaryl, aralkyl, or (heteroaryl)alkyl. In another embodiment, the optionally substituted aryl is substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, heteroaryloxy, aralkyl, aralkyloxy, (aralkyloxy)alkyl, alkylthio, carboxamido, sulfonamido, alkylcarbonyl, arylcarbonyl, alkylsulfonyl, arylsulfonyl, ureido, guanidino, carboxy, carboxyalkyl, heteroalkyl, optionally substituted alkyl, optionally substituted cycloalkyl, alkenyl, alkynyl, optionally substituted aryl, optionally substituted heteroaryl, optionally substituted heterocyclo, ($C_{1-4}$ haloalkoxy)alkyl, alkoxyalkyl, (amino)alkyl, hydroxyalkylamino, (alkylamino)alkyl, (dialkylamino)alkyl, (cyano)alkyl, (carboxamido)alkyl, mercapto alkyl, (heterocyclo)alkyl, (cycloalkylamino)alkyl, (hydroxyalkylamino)alkyl, (amino)(heteroaryl)alkyl, (heterocycloamino)alkyl (amino)(hydroxy)alkyl, (heteroaryl)alkyl, —N($R^{43}$)($R^{44}$), —$CH_2$N(H)C(=O)—$R^{45}$, and —N(H)C(=O)—$R^{45}$.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. In another embodiment, the optionally substituted phenyl has at least one amino, alkylamino, dialkylamino, (amino)alkyl, (alkylamino)alkyl, (dialkylamino)alkyl, (amino)(heteroaryl)alkyl, or (amino)(hydroxy)alkyl substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-methoxyphenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl is meant to include aryl groups having fused optionally substituted cycloalkyl and fused optionally substituted heterocyclo rings. Examples include:

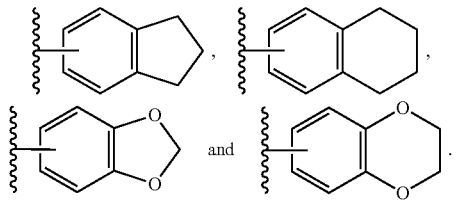

For the purpose of the present disclosure, the term "arylenyl" as used herein by itself or part of another group refers to a divalent form of an optionally substituted aryl group as defined above. In one embodiment, the arylenyl is a divalent form of an optionally substituted phenyl. In one embodiment, the arylenyl is a divalent form of phenyl. Non-limiting exemplary alkylenyl groups include:

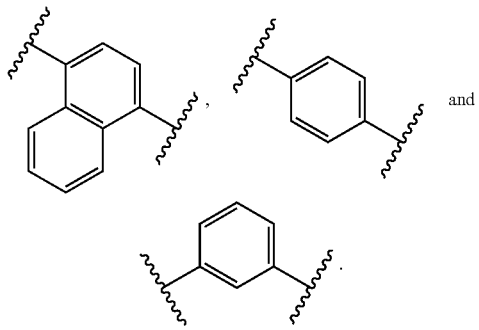

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "heteroaryloxy" as used by itself or as part of another group refers to an optionally substituted heteroaryl attached to a terminal oxygen atom.

For the purpose of the present disclosure, the term "aralkyloxy" or "arylalkyloxy" as used by itself or as part of another group refers to an aralkyl group attached to a terminal oxygen atom. A non-limiting exemplary aralkyloxy group is $PhCH_2O$—.

For the purpose of the present disclosure, the term "(aralkyloxy)alkyl" as used by itself or as part of another group refers to an alkyl group substituted with an aralkyloxy group. In one embodiment, the alkyl is a $C_{1-4}$ alkyl. Non-limiting exemplary "(aralkyloxy)alkyl" groups include —$CH_2OCH_2$(3-F-Ph) and —$CH_2OCH_2CH_2CH_2$(2-OMe-Ph).

For the purpose of the present disclosure, the term "heteroaryl" or "heteroaromatic" refers to monocyclic and bicyclic aromatic ring systems having 5 to 14 ring atoms (i.e., a 5- to 14-membered heteroaryl) and 1, 2, 3, or 4 heteroatoms independently chosen from oxygen, nitrogen, or sulfur. In one embodiment, the heteroaryl has three heteroatoms. In another embodiment, the heteroaryl has two heteroatoms. In another embodiment, the heteroaryl has one heteroatom. In one embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aralkyl, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)

alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, —N(R$^{43}$)(R$^{44}$), or —N(H)C(=O)—R$^{45}$, wherein R$^{43}$ is hydrogen or C$_{1-4}$ alkyl; R$^{44}$ is alkoxyalkyl, (heterocyclo)alkyl, (amino)alkyl, (alkylamino)alkyl, or (dialkylamino)alkyl; and R$^{45}$ is alkyl, optionally substituted aryl, or optionally substituted heteroaryl. In one embodiment, the optionally substituted heteroaryl has one substituent. In one embodiment, the substituent is amino, alkylamino, dialkylamino, (amino)alkyl, hydroxyalkylamino, (alkylamino)alkyl, (dialkylamino)alkyl, (heterocyclo)alkyl, —N(R$^{43}$)(R$^{44}$), or —N(H)C(=O)—R$^{45}$. In another embodiment, the substituent is aralkyl or (heteroaryl)alkyl. Examples include:

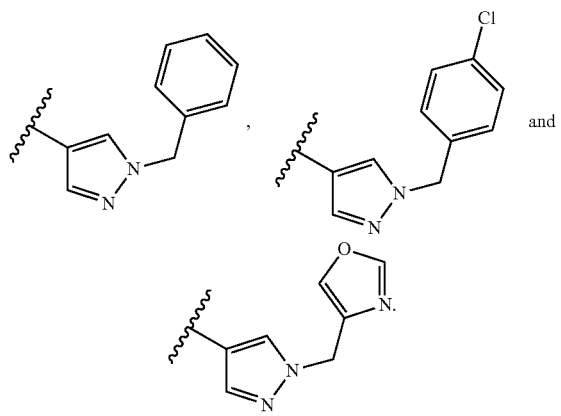

In one embodiment, the optionally substituted is an optionally substituted pyridyl, i.e., 2-, 3-, or 4-pyridyl. Any available carbon or nitrogen atom can be substituted. The term optionally substituted heteroaryl is meant to include heteroaryl groups having fused optionally substituted cycloalkyl and fused optionally substituted heterocyclo rings. Examples include:

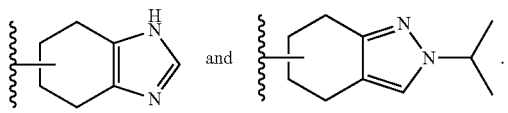

For the purpose of the present disclosure, the term "heteroarylenyl" as used herein by itself or part of another group refers to a divalent form of an optionally substituted heteroaryl group as defined above. In one embodiment, the heteroarylenyl is a divalent form of an optionally substituted pyridyl. Non-limiting exemplary heteroarylenyl groups include:

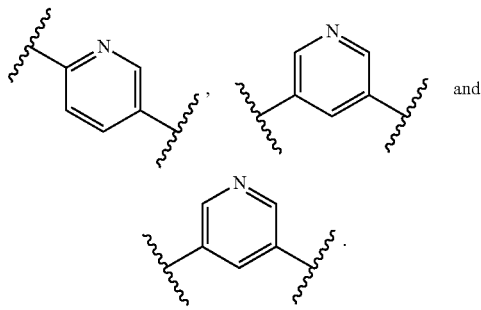

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as imidazolidinyl-2-one, cyclic amide groups such as β-lactam, γ-lactam, δ-lactam and 8-lactam, and cyclic carbamate groups such as oxazolidinyl-2-one. The term "heterocyclo" is also meant to include groups having fused optionally substituted aryl groups, e.g., indolinyl, indolinyl-2-one, benzo[d]oxazolyl-2 (3H)-one. In one embodiment, the heterocyclo group is chosen from a 4-, 5-, 6-, 7- or 8-membered cyclic group containing one ring and one or two oxygen and/or nitrogen atoms. In one embodiment, the heterocyclo group is chosen from a 5- or 6-membered cyclic group containing one ring and one or two nitrogen atoms. In one embodiment, the heterocyclo group is chosen from a 8-, 9-, 10-, 11-, or 12-membered cyclic group containing two rings and one or two nitrogen atoms. The heterocyclo can be optionally linked to the rest of the molecule through a carbon or nitrogen atom. Non-limiting exemplary heterocyclo groups include 2-oxopyrrolidin-3-yl, 2-imidazolidinone, piperidinyl, morpholinyl, piperazinyl, pyrrolidinyl, 8-azabicyclo[3.2.1]octane (nortropane), 6-azaspiro[2.5]octane, 6-azaspiro[3.4]octane, indolinyl, indolinyl-2-one, 1,3-dihydro-2H-benzo[d]imidazol-2-one For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, aralkylamino, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. Substitution may occur on any available carbon or nitrogen atom, and may form a spirocycle. In another embodiment, the optionally substituted heterocyclo is substituted with one to four substituents independently selected from halo, nitro, cyano, hydroxy, amino, alkylamino, dialkylamino, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heterocyclo is substituted with at least one amino, alkylamino, or dialkylamino group. Non-limiting exemplary optionally substituted heterocyclo groups include:

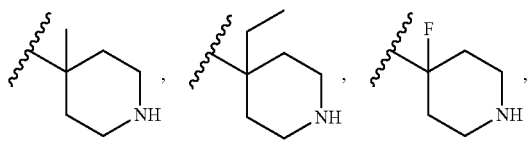

-continued

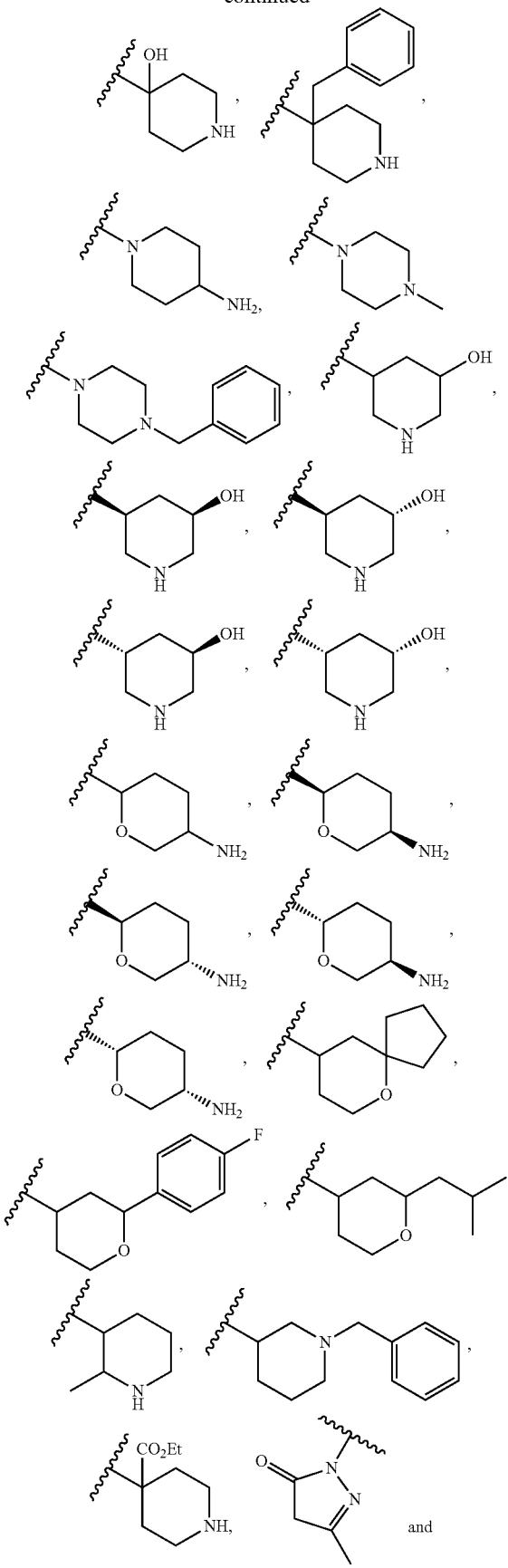

-continued

For the purpose of the present disclosure, the term "heterocyclenyl" as used herein by itself or part of another group refers to a divalent form of an optionally substituted heterocyclo group as defined above. In one embodiment, the heterocyclenyl is a divalent form of an optionally substituted azetidine. In one embodiment, the heterocyclenyl is a divalent form of an optionally substituted piperidinyl. Non-limiting exemplary heterocyclenyl groups include:

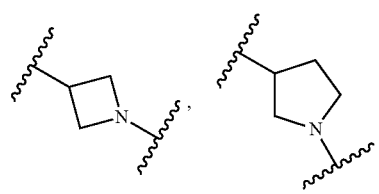

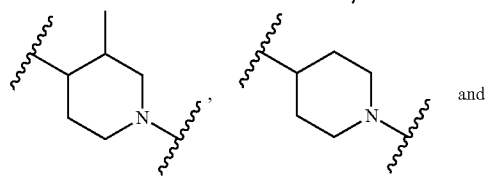

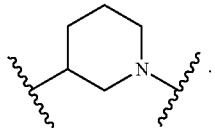

For the purpose of the present disclosure, the term "optionally substituted pyrrolidinyl" as used by itself or as part of another group means that the optionally substituted heterocyclo as defined above is an optionally substituted pyrrolidinyl group.

For the purpose of the present disclosure, the term "optionally substituted pyrrolidinenyl" as used herein by itself or part of another group refers to a divalent form of an optionally substituted pyrrolidinyl group as defined above. Non-limiting exemplary optionally substituted pyrrolidinenyl groups include:

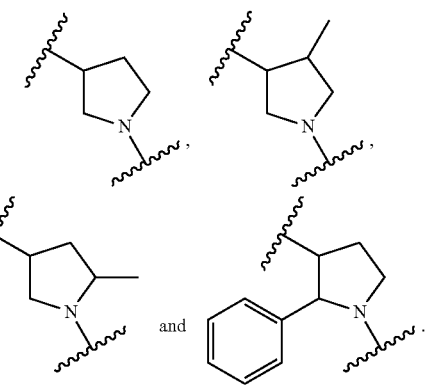

For the purpose of the present disclosure, the term "amino" as used by itself or as part of another group refers to —NH$_2$.

For the purpose of the present disclosure, the term "alkylamino" as used by itself or as part of another group refers to —NHR$^{22}$, wherein R$^{22}$ is C$_{1-6}$ alkyl. In one embodiment, R$^{22}$ is C$_{1-4}$ alkyl. Non-limiting exemplary alkylamino groups include —N(H)CH$_3$ and —N(H)CH$_2$CH$_3$.

For the purpose of the present disclosure, the term "dialkylamino" as used by itself or as part of another group refers to —NR$^{23a}$R$^{23b}$, wherein R$^{23a}$ and R$^{23b}$ are each independently C$_{1-6}$ alkyl. In one embodiment, R$^{23a}$ and R$^{23b}$ are each independently C$_{1-4}$ alkyl. Non-limiting exemplary dialkylamino groups include —N(CH$_3$)$_2$ and —N(CH$_3$)CH$_2$CH(CH$_3$)$_2$.

For the purpose of the present disclosure, the term "hydroxyalkylamino" as used by itself or as part of another group refers to —NR$^{24a}$R$^{24b}$, wherein R$^{24a}$ is hydrogen or C$_{1-4}$ alkyl, and R$^{24b}$ is hydroxyalkyl. Non-limiting exemplary hydroxyalkylamino groups include —N(H)CH$_2$CH$_2$OH, —N(H)CH$_2$CH$_2$CH$_2$OH, —N(CH$_3$)CH$_2$CH$_2$OH, and —N(CH$_3$)CH$_2$CH$_2$CH$_2$OH.

For the purpose of the present disclosure, the term "(hydroxyalkylamino)alkyl" as used by itself or as part of another group refers to an alkyl group substituted with an hydroxyalkylamino group. In one embodiment, the alkyl is a C$_{1-4}$ alkyl. A non-limiting exemplary (hydroxyalkylamino)alkyl group is —CH$_2$N(CH$_3$)CH$_2$CH$_2$CH$_2$OH.

For the purpose of the present disclosure, the term "cycloalkylamino" as used by itself or as part of another group refers to —NR$^{25a}$R$^{25b}$, wherein R$^{25a}$ is optionally substituted cycloalkyl and R$^{25b}$ is hydrogen or C$_{1-4}$ alkyl.

For the purpose of the present disclosure, the term "heterocycloamino" as used by itself or as part of another group refers to —NR$^{25c}$R$^{25d}$, wherein R$^{25c}$ is optionally substituted heterocyclo and R$^{25d}$ is hydrogen or C$_{1-4}$ alkyl. Non-limiting exemplary heterocycloamino groups include:

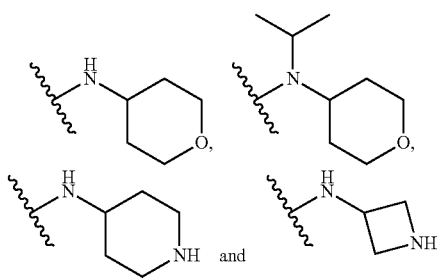

For the purpose of the present disclosure, the term "(heterocycloamino)alkyl" as used by itself or as part of another group refers to an alkyl group substituted with an heterocycloamino group. In one embodiment, the alkyl is a C$_{1-4}$ alkyl.

For the purpose of the present disclosure, the term "aralkylamino" as used by itself or as part of another group refers to —NR$^{26a}$R$^{26b}$, wherein R$^{26a}$ is aralkyl and R$^{26b}$ is hydrogen or C$_{1-4}$ alkyl. Non-limiting exemplary aralkylamino groups include —N(H)CH$_2$Ph and —N(CH$_3$)CH$_2$Ph.

For the purpose of the present disclosure, the term "(amino)alkyl" as used by itself or as part of another group refers to an alkyl group substituted with an amino group. In one embodiment, the alkyl is a C$_{1-4}$ alkyl. Non-limiting exemplary (amino)alkyl groups include —CH$_2$NH$_2$, —C(NH$_2$)(H)CH$_3$, —CH$_2$CH$_2$NH$_2$, —CH$_2$C(NH$_2$)(H)CH$_3$, —CH$_2$CH$_2$CH$_2$NH$_2$, —CH$_2$CH$_2$CH$_2$CH$_2$NH$_2$, and —CH$_2$C(CH$_3$)$_2$CH$_2$NH$_2$ For the purpose of the present disclosure, the term "(alkylamino)alkyl" as used by itself or as part of another group refers to an alkyl group substituted with an alkylamino group. In one embodiment, the alkyl is a C$_{1-4}$ alkyl. A non-limiting exemplary (alkylamino)alkyl group is —CH$_2$CH$_2$N(H)CH$_3$.

For the purpose of the present disclosure, the term "(dialkylamino)alkyl" as used by itself or as part of another group refers to an alkyl group substituted by a dialkylamino group. In one embodiment, the alkyl is a C$_{1-4}$ alkyl. Non-limiting exemplary (dialkylamino)alkyl groups are —CH$_2$CH$_2$N(CH$_3$)$_2$.

For the purpose of the present disclosure, the term "(cycloalkylamino)alkyl" as used by itself or as part of another group refers to an alkyl group substituted by a cycloalkylamino group. In one embodiment, the alkyl is a C$_{1-4}$ alkyl. Non-limiting exemplary (cycloalkylamino)alkyl groups include —CH$_2$N(H)cyclopropyl, —CH$_2$N(H)cyclobutyl, and —CH$_2$N(H)cyclohexyl.

For the purpose of the present disclosure, the term "(aralkylamino)alkyl" as used by itself or as part of another group refers to an alkyl group substituted with an aralkylamino group. In one embodiment, the alkyl is a C$_{1-4}$ alkyl. A non-limiting exemplary (aralkylamino)alkyl group is —CH$_2$CH$_2$CH$_2$N(H)CH$_2$Ph.

For the purpose of the present disclosure, the term "(hydroxyalkylamino)alkyl" as used by itself or as part of another group refers to an alkyl group substituted with an hydroxyalkylamino group. A non-limiting exemplary (hydroxyalkylamino)alkyl group is —CH$_2$CH$_2$NHCH$_2$CH$_2$OH For the purpose of the present disclosure, the term "(cyano)alkyl" as used by itself or as part of another group refers to an alkyl group substituted with one or more cyano, e.g., —CN, groups. In one embodiment, the alkyl is a C$_{1-4}$ alkyl. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "(amino)(hydroxy)alkyl" as used by itself or as part of another group refers to an alkyl group substituted with one amino, alkylamino, dialkylamino, or heterocyclo group and one hydroxy group. In one embodiment, the alkyl is a C$_{1-6}$ alkyl. In another embodiment, the alkyl is a C$_{1-4}$ alkyl. Non-limiting exemplary (amino)(hydroxy)alkyl groups include:

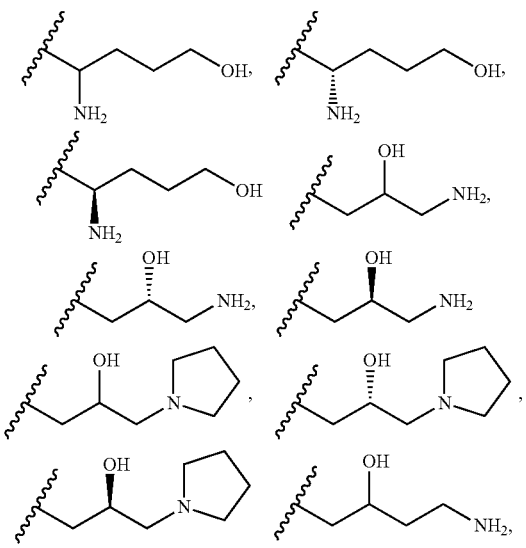

-continued

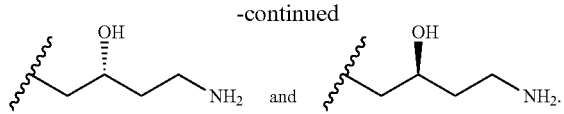

For the purpose of the present disclosure, the term "(amino)(carboxamido)alkyl" as used by itself or as part of another group refers to an alkyl group substituted with one amino, alkylamino, or dialkylamino, and one carboxamido group. In one embodiment, the alkyl is a $C_{1-6}$ alkyl. Non-limiting exemplary (amino)(carboxamido)alkyl groups include:

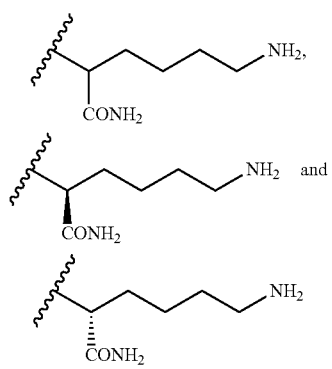

For the purpose of the present disclosure, the term "(amino)(aryl)alkyl" as used by itself or as part of another group refers to an alkyl group substituted with one amino, alkylamino, or dialkylamino group and one optionally substituted aryl group. In one embodiment, the alkyl is a $C_{1-6}$ alkyl. In one embodiment, the optionally substituted aryl group is an optionally substituted phenyl. Non-limiting exemplary (amino)(aryl)alkyl groups include:

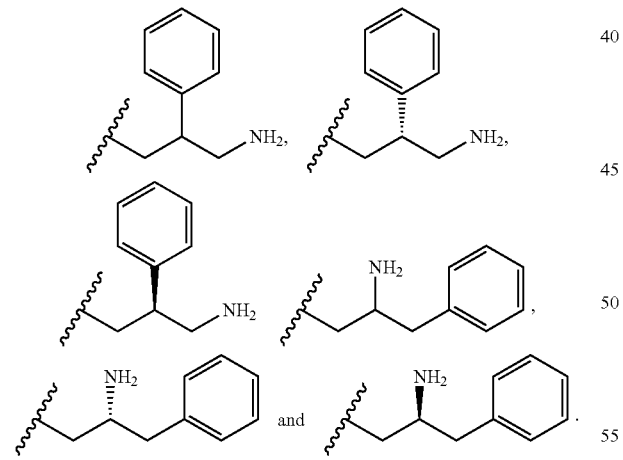

For the purpose of the present disclosure, the term "(amino)(heteroaryl)alkyl" as used by itself or as part of another group refers to an alkyl group substituted with one amino, alkylamino, or dialkylamino group and one optionally substituted heteroaryl group. In one embodiment, the alkyl is a $C_{1-6}$ alkyl. In one embodiment, the alkyl is a $C_{1-4}$ alkyl. In one embodiment, the optionally substituted heteroaryl group is an optionally substituted pyridyl. Non-limiting exemplary (amino)(heteroaryl)alkyl groups include:

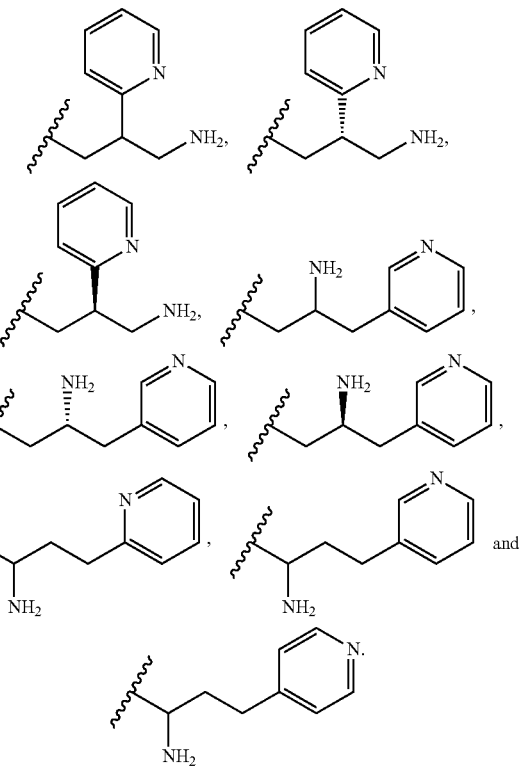

For the purpose of the present disclosure, the term "(cycloalkyl)alkyl" as used by itself or as part of another group refers to an alkyl group substituted with one optionally substituted cycloalkyl group. In one embodiment, the alkyl is a $C_{1-4}$ alkyl. In one embodiment, the cycloalkyl is a $C_{3-6}$ cycloalkyl. In one embodiment, the optionally substituted cycloalkyl group is substituted with an amino or (amino)alkyl group. Non-limiting exemplary (cycloalkyl)alkyl groups include:

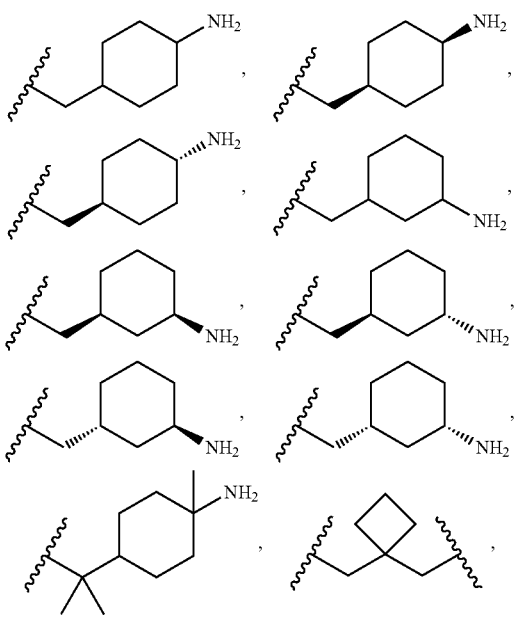

-continued

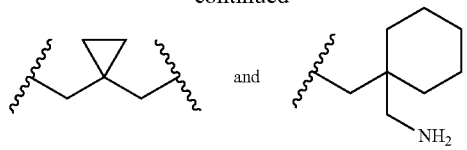

and

For the purpose of the present disclosure, the term "(hydroxy)(aryl)alkyl" as used by itself or as part of another group refers to an alkyl group substituted with one hydroxy group and one optionally substituted aryl group. In one embodiment, the alkyl is a $C_{1-6}$ alkyl. In one embodiment, the optionally substituted aryl group is an optionally substituted phenyl. Non-limiting exemplary (hydroxy)(aryl)alkyl groups include:

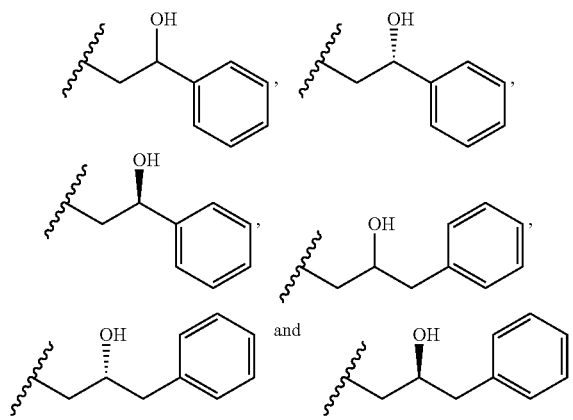

For the purpose of the present disclosure, the term "carboxamido" as used by itself or as part of another group refers to a radical of formula $—C(=O)NR^{26a}R^{26b}$, wherein $R^{26a}$ and $R^{26b}$ are each independently hydrogen, optionally substituted alkyl, optionally substituted aryl, aralkyl, (heteroaryl)alkyl, or optionally substituted heteroaryl, or $R^{26a}$ and $R^{26b}$ taken together with the nitrogen to which they are attached from a 3- to 8-membered heterocyclo group. In one embodiment, $R^{26a}$ and $R^{26b}$ are each independently hydrogen or optionally substituted alkyl. Non-limiting exemplary carboxamido groups include —$CONH_2$, —$CON(H)CH_3$, —$CON(CH_3)_2$, and —$CON(H)Ph$.

For the purpose of the present disclosure, the term "(carboxamido)alkyl" as used by itself or as part of another group refers to an alkyl group substituted with a carboxamido group. Non-limiting exemplary (carboxamido)alkyl groups include —$CH_2CONH_2$, —$C(H)CH_3$—$CONH_2$, and —$CH_2CON(H)CH_3$.

For the purpose of the present disclosure, the term "sulfonamido" as used by itself or as part of another group refers to a radical of the formula —$SO_2NR^{27a}R^{27b}$, wherein $R^{27a}$ and $R^{27b}$ are each independently hydrogen, optionally substituted alkyl, or optionally substituted aryl, or $R^{27a}$ and $R^{27b}$ taken together with the nitrogen to which they are attached from a 3- to 8-membered heterocyclo group. Non-limiting exemplary sulfonamido groups include —$SO_2NH_2$, —$SO_2N(H)CH_3$, and —$SO_2N(H)Ph$.

For the purpose of the present disclosure, the term "alkylcarbonyl" as used by itself or as part of another group refers to a carbonyl group, i.e., —$C(=O)$—, substituted by an alkyl group. A non-limiting exemplary alkylcarbonyl group is —$COCH_3$.

For the purpose of the present disclosure, the term "arylcarbonyl" as used by itself or as part of another group refers to a carbonyl group, i.e., —$C(=O)$—, substituted by an optionally substituted aryl group. A non-limiting exemplary arylcarbonyl group is —$COPh$.

For the purpose of the present disclosure, the term "alkylsulfonyl" as used by itself or as part of another group refers to a sulfonyl group, i.e., —$SO_2$—, substituted by any of the above-mentioned optionally substituted alkyl groups. A non-limiting exemplary alkylsulfonyl group is —$SO_2CH_3$.

For the purpose of the present disclosure, the term "arylsulfonyl" as used by itself or as part of another group refers to a sulfonyl group, i.e., —$SO_2$—, substituted by any of the above-mentioned optionally substituted aryl groups. A non-limiting exemplary arylsulfonyl group is —$SO_2Ph$.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —$CH_2CO_2H$.

For the purpose of the present disclosure, the term "alkoxycarbonyl" as used by itself or as part of another group refers to a carbonyl group, i.e., —$C(=O)$—, substituted by an alkoxy group. Non-limiting exemplary alkoxycarbonyl groups are —$CO_2Me$ and —$CO_2Et$.

For the purpose of the present disclosure, the term "aralkyl" or "arylalkyl" as used by itself or as part of another group refers to an alkyl group substituted with one, two, or three optionally substituted aryl groups. In one embodiment, the aralkyl group is a $C_{1-4}$ alkyl substituted with one optionally substituted aryl group. In another embodiment, the aralkyl group is a $C_1$ or $C_2$ alkyl substituted with one optionally substituted phenyl group. In another embodiment, the aralkyl group is a $C_1$ alkyl substituted with one optionally substituted phenyl group, i.e., a benzyl group wherein the phenyl is optionally substituted. Non-limiting exemplary aralkyl groups include benzyl, phenethyl, —$CHPh_2$, —$CH_2$(4-OH-Ph), and —$CH(4-F-Ph)_2$.

For the purpose of the present disclosure, the term "ureido" as used by itself or as part of another group refers to a radical of the formula —$NR^{30a}$—$C(=O)$—$NR^{30b}R^{30c}$, wherein $R^{22a}$ is hydrogen, alkyl, or optionally substituted aryl, and $R^{30b}$ and $R^{30c}$ are each independently hydrogen, alkyl, or optionally substituted aryl, or $R^{30b}$ and $R^{30c}$ taken together with the nitrogen to which they are attached form a 4- to 8-membered heterocyclo group. Non-limiting exemplary ureido groups include —NH—C(C=O)—$NH_2$ and —NH—C(C=O)—$NHCH_3$.

For the purpose of the present disclosure, the term "guanidino" as used by itself or as part of another group refers to a radical of the formula —$NR^{28a}$—$C(=NR^{29})$—$NR^{28b}R^{28c}$, wherein $R^{28a}$, $R^{28b}$, and $R^{28c}$ are each independently hydrogen, alkyl, or optionally substituted aryl, and $R^{29}$ is hydrogen, alkyl, cyano, alkylsulfonyl, alkylcarbonyl, carboxamido, or sulfonamido. Non-limiting exemplary guanidino groups include —NH—C(C=NH)—$NH_2$, —NH—C(C=NCN)—$NH_2$, and —NH—C(C=NH)—$NHCH_3$.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a $C_{1-4}$ alkyl substituted with one optionally substituted heterocyclo group. The heterocyclo can be linked to the alkyl group through a carbon or nitrogen atom. Non-limiting exemplary (heterocyclo)alkyl groups include:

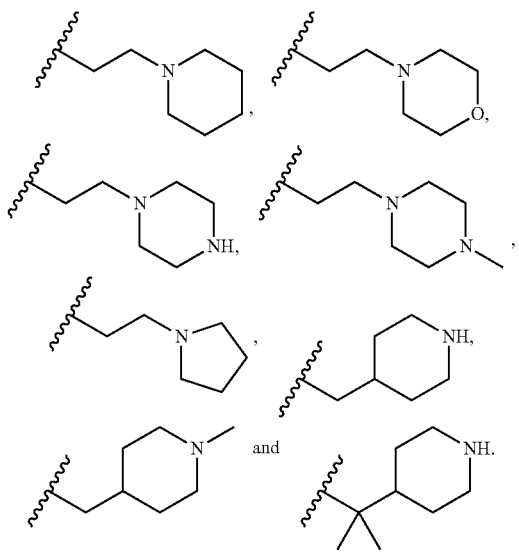

For the purpose of the present disclosure, the term "(heteroaryl)alkyl" or "heteroaralkyl" as used by itself or as part of another group refers to an alkyl group substituted with one, two, or three optionally substituted heteroaryl groups. In one embodiment, the (heteroaryl)alkyl group is a $C_{1-4}$ alkyl substituted with one optionally substituted heteroaryl group. Non-limiting exemplary (heteroaryl)alkyl groups include:

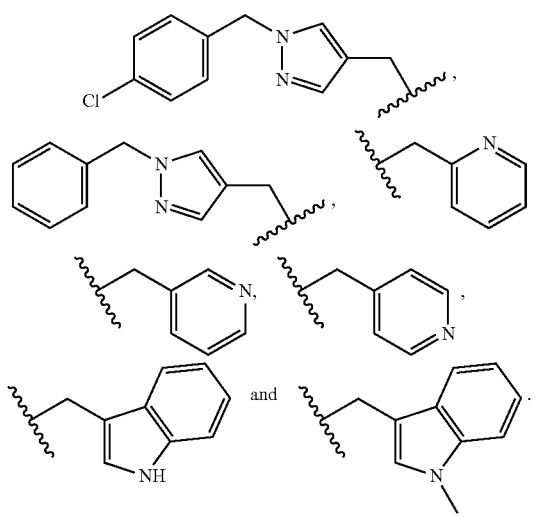

For the purpose of the present disclosure, the term "alkylcarbonylamino" as used by itself or as part of another group refers to an alkylcarbonyl group attached to an amino. A non-limiting exemplary alkylcarbonylamino group is —NHCOCH$_3$.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, $^{11}$C, and $^{14}$C. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number." Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in Pure & Appl. Chem 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The terms "a" and "an" refer to one or more.

The term "about," as used herein, includes the recited number ±10%. Thus, "about 10" means 9 to 11.

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparaginate, glutamate and the like. The term "pharmaceutically acceptable salt" as used herein, refers to any salt, e.g., obtained by reaction with an acid or a base, of a Compound of the Disclosure that is physiologically tolerated in the target patient (e.g., a mammal, e.g., a human).

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since Compounds of the Disclosure are inhibitors of SMYD proteins, such as SMYD3 and SMYD2, a number of diseases, conditions, or disorders mediated by SMYD proteins, such as SMYD3 and SMYD2, can be treated by employing these compounds. The present disclosure is thus directed generally to a method for treating a disease, condition, or disorder responsive to the inhibition of SMYD proteins, such as SMYD3 and SMYD2, in an animal suffering from, or at risk of suffering from, the disorder, the method comprising administering to the animal an effective amount of one or more Compounds of the Disclosure.

The present disclosure is further directed to a method of inhibiting SMYD proteins in an animal in need thereof, the method comprising administering to the animal a therapeutically effective amount of at least one Compound of the Disclosure.

The present disclosure is further directed to a method of inhibiting SMYD3 in an animal in need thereof, the method comprising administering to the animal a therapeutically effective amount of at least one Compound of the Disclosure.

The present disclosure is further directed to a method of inhibiting SMYD2 in an animal in need thereof, the method comprising administering to the animal a therapeutically effective amount of at least one Compound of the Disclosure.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; modulate protein methylation in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The term "disease" or "condition" or "disorder" denotes disturbances and/or anomalies that as a rule are regarded as being pathological conditions or functions, and that can manifest themselves in the form of particular signs, symptoms, and/or malfunctions. As demonstrated below, Compounds of the Disclosure inhibit SMYD proteins, such as SMYD3 and SMYD2 and can be used in treating diseases and conditions such as proliferative diseases, wherein inhibition of SMYD proteins, such as SMYD3 and SMYD2 provides a benefit.

In some embodiments, the Compounds of the Disclosure can be used to treat a "SMYD protein mediated disorder" (e.g., a SMYD3-mediated disorder or a SMYD2-mediated disorder). A SMYD protein mediated disorder is any pathological condition in which a SMYD protein is know to play a role. In some embodiments, a SMYD-mediated disorder is a proliferative disease.

In some embodiments inhibiting SMYD proteins, such as SMYD3 and SMYD2, is the inhibition of the activity of one or more activities of SMYD proteins such as SMYD3 and SMYD2. In some embodiments, the activity of the SMYD proteins such as SMYD3 and SMYD2 is the ability of the SMYD protein such as SMYD3 or SMYD2 to transfer a methyl group to a target protein (e.g., histone). It should be appreciated that the activity of the one or more SMYD proteins such as SMYD3 and SMYD2 may be inhibited in vitro or in vivo. Exemplary levels of inhibition of the activity one or more SMYD proteins such as SMYD3 and SMYD2 include at least 10% inhibition, at least 20% inhibition, at least 30% inhibition, at least 40% inhibition, at least 50% inhibition, at least 60% inhibition, at least 70% inhibition, at least 80% inhibition, at least 90% inhibition, and up to 100% inhibition.

The SMYD (SET and MYND domain) family of lysine methyltransferases (KMTs) plays pivotal roles in various cellular processes, including gene expression regulation and DNA damage response. The family of human SMYD proteins consists of SMYD1, SMYD2, SMYD3, SMYD4 and SMYD5. SMYD1, SMYD2, and SMYD3 share a high degree of sequence homology and, with the exception of SMYD5, human SMYD proteins harbor at least one C-terminal tetratrico peptide repeat (TPR) domain. (See e.g., Abu-Farha et al. *J Mol Cell Biol* (2011) 3 (5) 301-308). The SMYD proteins have been found to be linked to various cancers (See e.g., Hamamoto et al. *Nat Cell. Biol.* 2004, 6: 731-740), Hu et al. Cancer Research 2009, 4067-4072, and Komatsu et al. *Carcinogenesis* 2009, 301139-1146.)

SMYD3 is a protein methyltransferase found to be expressed at high levels in a number of different cancers (Hamamoto, R., et al., *Nat. Cell Biol.*, 6(8):731-40 (2004)). SMYD3 likely plays a role in the regulation of gene transcription and signal transduction pathways critical for survival of breast, liver, prostate and lung cancer cell lines (Hamamoto, R., et al., *Nat. Cell Biol.*, 6(8):731-40 (2004); Hamamoto, R., et al., *Cancer Sci.*, 97(2):113-8 (2006); Van Aller, G. S., et al., *Epigenetics*, 7(4):340-3 (2012); Liu, C., et al., *J. Natl. Cancer Inst.*, 105(22):1719-28 (2013); Mazur, P. K., et al., *Nature*, 510(7504):283-7 (2014)).

Genetic knockdown of SMYD3 leads to a decrease in proliferation of a variety of cancer cell lines (Hamamoto, R., et al., *Nat. Cell Biol.*, 6(8):731-40 (2004); Hamamoto, R., et al., *Cancer Sci.*, 97(2):113-8 (2006); Van Aller, G. S., et al., *Epigenetics*, 7(4):340-3 (2012); Liu, C., et al., *J. Natl. Cancer Inst.*, 105(22):1719-28 (2013); Mazur, P. K., et al., *Nature*, 510(7504):283-7 (2014)). Several studies employing RNAi-based technologies have shown that ablation of SMYD3 in hepatocellular carcinoma cell lines greatly reduces cell viability and that its pro-survival role is dependent on its catalytic activity (Hamamoto, R., et al., *Nat. Cell Biol.*, 6(8):731-40 (2004); Van Aller, G. S., et al., *Epigenetics*, 7(4):340-3 (2012)). Moreover, SMYD3 has also been shown to be a critical mediator of transformation resulting from gain of function mutations in the oncogene, KRAS for both pancreatic and lung adenocarcinoma in mouse models. The dependence of KRAS on SMYD3 was also shown to be dependent on its catalytic activity (Mazur, P. K., et al., *Nature*, 510(7504):283-7 (2014)). SMYD3 function has also been implicated in colerectal cancers and RNAi mediated knockdown of SMYD3 has been shown to impair colerectal cell proliferation. (Peserico et al., *Cell Physiol.* 2015 Feb. 28. doi: 10.1002/jcp.24975. [Epub ahead of print]).

Furthermore, SMYD3 function has also been shown to play a role in immunology and development. For instance, de Almeida reported that SMYD3 plays a role in generation of inducible regulatory T cells (iTreg) cells. In a mouse model of respiratory syncytial virus (RSV) infection, a model in which iTreg cells have a critical role in regulating lung pathogenesis, SMYD3−/− mice demonstrated exacerbation of RSV-induced disease related to enhanced proinflammatory responses and worsened pathogenesis within the lung (de Almeida et al. *Mucosal Immunol.* 2015 Feb. 11. doi: 10.1038/mi.2015.4. [Epub ahead of print]). In addition, as to development, Proserpio et al. have shown the importance of SMYD3 in the regulation of skeletal muscle atrophy (Proserpio et al. Genes Dev. 2013 Jun. 1; 27(11):1299-312), while Fujii et al. have elucidated the role of SMYD3 in cardiac and skeletal muscle development (Fujii et al. *PLoS One.* 2011; 6(8):e23491).

SMYD2 (SET and MYND domain-containing protein 2) was first characterized as protein that is a member of a sub-family of SET domain containing proteins which catalyze the site-specific transfer of methyl groups onto substrate proteins. SMYD2 was initially shown to have methyltransferase activity towards lysine 36 on histone H3 (H3K36) but has subsequently been shown to have both histone and non-histone methyltransferase activity.

SMYD2 has been implicated in the pathogenesis of multiple cancers. It has been shown to be over-expressed, compared to matched normal samples, in tumors of the breast, cervix, colon, kidney, liver, head and neck, skin, pancreas, ovary, esophagus and prostate, as well as hematologic malignancies such as AML, B- and T-ALL, CLL and MCL, suggesting a role for SMYD2 in the biology of these cancers. More specifically, studies using genetic knockdown of SMYD2 have demonstrated anti-proliferative effects in esophageal squamous cell carcinoma (ESCC), bladder carcinoma and cervical carcinoma cell lines. (See e.g., Komatsu et al., *Carcinogenesis* 2009, 30, 1139, and Cho et al., *Neoplasia.* 2012 June; 14(6):476-86). Moreover, high expression of SMYD2 has been shown to be a poor prognostic factor in both ESCC and pediatric ALL. (See e.g., Komatsu et al. *Br J Cancer.* 2015 Jan. 20; 112(2):357-64, and Sakamoto et al., *Leuk Res.* 2014 April; 38(4):496-502). Recently, Nguyen et al., have shown that a small molecule inhibitor of SMYD2 (LLY-507) inhibited the proliferation of several esophageal, liver and breast cancer cell lines in a dose-dependent manner. (Nguyen et al. *J Biol Chem.* 2015 Mar. 30. pii: jbc.M114.626861. [Epub ahead of print]).

SMYD2 has also been implicated in immunology. For instance, Xu et al. have shown that SMYD2 is a negative regulator of macrophage activation by suppressing Interleukin-6 and TNF-alpha production. (Xu et al., J Biol Chem. 2015 Feb. 27; 290(9):5414-23).

In one aspect, the present disclosure provides a method of treating cancer in a patient comprising administering a therapeutically effective amount of a Compound of the Disclosure. While not being limited to a specific mechanism, in some embodiments, Compounds of the Disclosure can treat cancer by inhibiting SMYD proteins, such as SMYD3 and SMYD2. Examples of treatable cancers include, but are not limited to, adrenal cancer, acidic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the cancer is breast, cervix, colon, kidney, liver, head and neck, skin, pancreas, ovary, esophagus, or prostate cancer.

In another embodiment, the cancer is a hematologic malignancy such as acute myeloid leukemia (AML), B- and T-acute lymphoblastic leukemia (ALL), chronic lymphocytic leukemia (CLL), or mantle cell lymphoma (MCL).

In another embodiment, the cancer is esophageal squamous cell carcinoma (ESCC), bladder carcinoma, or cervical carcinoma.

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a therapeutic method of modulating protein methylation, gene expression, cell proliferation, cell differentiation and/or apoptosis in vivo in the cancers mentioned above by administering a therapeutically effective amount of a Compound of the Disclosure to a subject in need of such therapy.

Compounds of the Disclosure can be administered to a mammal in the form of a raw chemical without any other components present. Compounds of the Disclosure can also be administered to a mammal as part of a pharmaceutical composition containing the compound combined with a suitable pharmaceutically acceptable carrier. Such a carrier can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose. While individual needs may vary, a determination of optimal ranges of effective amounts of each compound is within the skill of the art. Typically, a Compound of the Disclosure can be administered to a mammal, e.g., a human, orally at a dose of from about 0.0025 to about 1500 mg per kg body weight of the mammal, or an equivalent amount of a pharmaceutically acceptable salt or solvate thereof, per day to treat the particular disorder. A useful oral dose of a Compound of the Disclosure administered to a mammal is from about 0.0025 to about 50 mg per kg body weight of the mammal, or an equivalent amount of the pharmaceutically acceptable salt or solvate thereof. For intramuscular injection, the dose is typically about one-half of the oral dose.

A unit oral dose may comprise from about 0.01 mg to about 1 g of the Compound of the Disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A pharmaceutical composition of the present disclosure can be administered to any patient that may experience the beneficial effects of a Compound of the Disclosure. Foremost among such patients are mammals, e.g., humans and companion animals, although the disclosure is not intended to be so limited. In one embodiment, the patient is a human.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present disclosure can be administered orally. In another embodiment, a pharmaceutical composition of the present disclosure can be administered orally and is formulated into tablets, dragees, capsules, or an oral liquid preparation. In one embodiment, the oral formulation comprises extruded multiparticulates comprising the Compound of the Disclosure.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation or by intranasal or transmucosal administration.

Alternatively, a pharmaceutical composition of the present disclosure can be administered by the intravaginal route.

A pharmaceutical composition of the present disclosure can contain from about 0.01 to 99 percent by weight, e.g., from about 0.25 to 75 percent by weight, of a Compound of the Disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of a Compound of the Disclosure.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

General Synthesis of Compounds

Compounds of the Disclosure are prepared using methods known to those skilled in the art in view of this disclosure, or by the illustrative methods shown in the General Schemes below. In the General Schemes, A, Y, $R^{12a}$, $R^{12b}$, $R^{13a}$, $R^{13b}$, and Z of Formulae A-D are as defined in connection with Formula VI, unless otherwise indicated. In any of the General Schemes, suitable protecting can be employed in the synthesis, for example, when Z is (amino)alkyl or any other group that may group that may require protection. (See, Wuts, P. G. M.; Greene, T. W., "Greene's Protective Groups in Organic Synthesis", 4th Ed., J. Wiley & Sons, N Y, 2007).

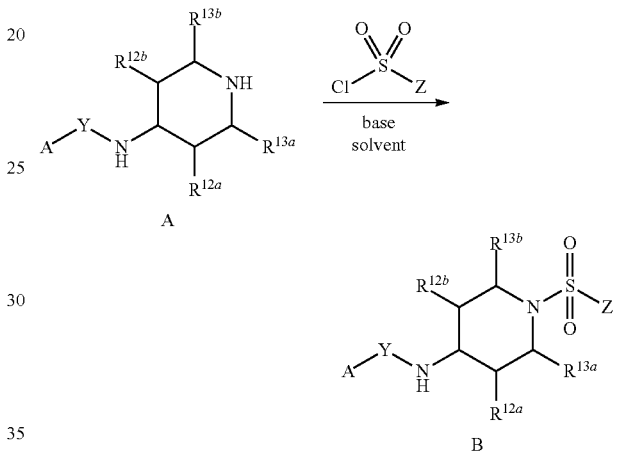

Compound A is converted to compound B (i.e, a compound having Formula VI, wherein X is —S(=O)$_2$—) by coupling with a suitable sulfonyl chloride (Z—SO$_2$Cl) in the presence of a suitable base such as TEA or DIPEA in a suitable solvent such as dichloromethane, acetonitrile, or DMF.

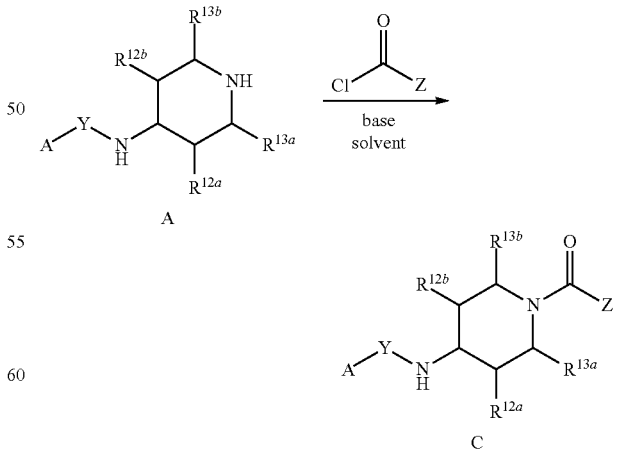

Compound A is converted to compound C (i.e, a compound having Formula VI, wherein X is —C(=O)—) by coupling with a suitable acid chloride (Z—COCl) in the presence of a suitable base such as TEA or DIPEA in a suitable solvent such as dichloromethane, acetonitrile, or DMF, or by coupling with a suitable carboxylic acid (Z—CO$_2$H) in the presence of a suitable coupling reagent such as HATU and a suitable base such as TEA or DIPEA in a suitable solvent such as dichloromethane, acetonitrile, or DMF.

General Scheme 3

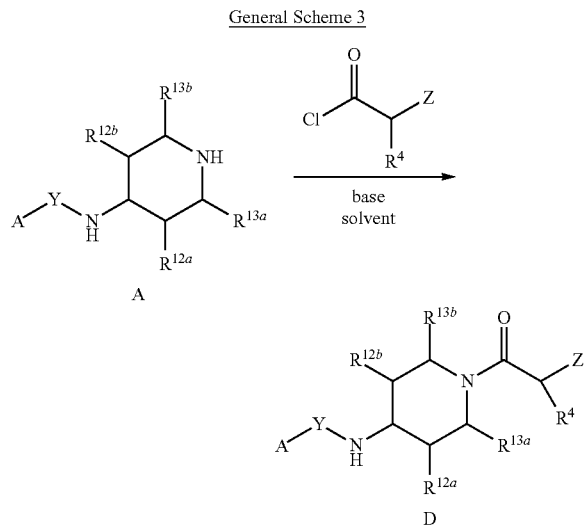

Compound A is converted to compound D (i.e, a compound having Formula VI, wherein X is —C(=O)C(R$^4$)(H)—) by coupling with a suitable carboxylic acid (Z—C(H)R$^4$CO$_2$H) in the presence of a suitable coupling reagent such as HATU and a suitable base such as TEA or DIPEA in a suitable solvent such as dichloromethane, acetonitrile, or DMF.

EXAMPLES

General Synthetic Methods

General methods and experimental procedures for preparing and characterizing Compounds of the Disclosure are set forth in the general schemes above and the examples below. Wherever needed, reactions were heated using conventional hotplate apparatus or heating mantle or microwave irradiation equipment. Reactions were conducted with or without stirring, under atmospheric or elevated pressure in either open or closed vessels. Reaction progress was monitored using conventional techniques such as TLC, HPLC, UPLC, or LCMS using instrumentation and methods described below. Reactions were quenched and crude compounds isolated using conventional methods as described in the specific examples provided. Solvent removal was carried out with or without heating, under atmospheric or reduced pressure, using either a rotary or centrifugal evaporator.

Compound purification was carried out as needed using a variety of traditional methods including, but not limited to, preparative chromatography under acidic, neutral, or basic conditions using either normal phase or reverse phase HPLC or flash columns or Prep-TLC plates. Compound purity and mass confirmations were conducted using standard HPLC and/or UPLC and/or MS spectrometers and/or LCMS and/or GC equipment (i.e., including, but not limited to the following instrumentation: Waters Alliance 2695 with 2996 PDA detector connected with ZQ detector and ESI source; Shimadzu LDMS-2020; Waters Acquity H Class with PDA detector connected with SQ detector and ESI source; Agilent 1100 Series with PDA detector; Waters Alliance 2695 with 2998 PDA detector; AB SCIEX API 2000 with ESI source; Agilent 7890 GC). Exemplified compounds were dissolved in either MeOH or MeCN to a concentration of approximately 1 mg/mL and analyzed by injection of 0.5-10 μL into an appropriate LCMS system using the methods provided in the following table. In each case the flow rate is 1 ml/min.

| Method | Column | Mobile Phase A | Mobile Phase B | Gradient Profile | MS Heat Block Temp (° C.) | MS Detector Voltage (kV) |
|---|---|---|---|---|---|---|
| A | Shim-pack XR-ODS 2.2 μm 3.0 × 50 mm | Water/ 0.05% TFA | ACN/ 0.05% TFA | 5% to 100% B in 2.0 minutes, 100% B for 1.1 minutes, 100% to 5% B in 0.2 minutes, then stop | 250 | 1.5 |
| B | Gemini-NX 3 μm C18 110A | Water/ 0.04% Ammonia | ACN | 5% to 100% B in 2.0 minutes, 100% B for 1.1 minutes, 100% to 5% B in 0.1 minutes, then stop | 200 | 0.75 |
| C | Shim-pack XR-ODS 1.6 μm 2.0 × 50 mm | Water/ 0.05% TFA | ACN/ 0.05% TFA | 5% to 100% B in 2.0 minutes, 100% B for 1.1 minutes, 100% to 5% B in 0.1 minutes, then stop | 250 | 0.85 |
| D | Shim-pack XR-ODS 2.2 μm 3.0 × 50 mm | Water/ 0.05% TFA | ACN/ 0.05% TFA | 5% to 100% B in 2.0 minutes, 100% B for 1.1 minutes, 100% to 5% B in 0.1 minutes, then stop | 250 | 0.95 |

Compound structure confirmations were carried out using standard 300 or 400 MHz NMR spectrometers with nOe's conducted whenever necessary.

The following abbreviations are used herein:

| Abbreviation | Meaning |
| --- | --- |
| ACN | acetonitrile |
| atm. | atmosphere |
| DCM | dichloromethane |
| DHP | dihydropyran |
| DIBAL | diisobutyl aluminum hydride |
| DIEA | diisopropyl ethylamine |
| DMF | dimethyl formamide |
| DMF-DMA | dimethyl formamide dimethyl acetal |
| DMSO | dimethyl sulfoxide |
| Dppf | 1,1'-bis(diphenylphosphino)ferrocene |
| EA | ethyl acetate |
| ESI | electrospray ionization |
| EtOH | Ethanol |
| FA | formic acid |
| GC | gas chromatography |
| H | hour |
| Hex | hexanes |
| HMDS | hexamethyl disilazide |
| HPLC | high performance liquid chromatography |
| IPA | Isopropanol |
| LCMS | liquid chromatography/mass spectrometry |
| MeOH | Methanol |
| Min | Minutes |
| NBS | N-bromo succinimide |
| NCS | N-chloro succinimide |
| NIS | N-iodo succinimide |
| NMR | nuclear magnetic resonance |
| nOe | nuclear Overhauser effect |
| Prep. | Preparative |
| PTSA | para-toluene sulfonic acid |
| Rf | retardation factor |
| rt | room temperature |
| RT | retention time |
| sat. | Saturated |
| SGC | silica gel chromatography |
| TBAF | tetrabutyl ammonium fluoride |
| TEA | Triethylamine |
| TFA | trifluoroacetic acid |
| THF | Tetrahydrofuran |
| TLC | thin layer chromatography |
| UPLC | ultra performance liquid chromatography |

Example 1

Synthesis of tert-butyl ((2S)-1-(4-(1-aminoethyl) piperidin-1-yl)-1-oxopropan-2-yl)carbamate

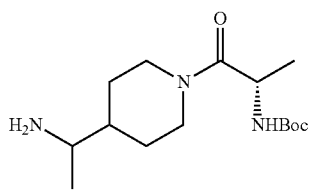 [SMILES: CC(N)C1CCN(C(=O)[C@H](C)NC(=O)OC(C)(C)C)CC1]

Step 1: Synthesis of tert-butyl 4-(methoxy(methyl) carbamoyl)piperidine-1-carboxylate

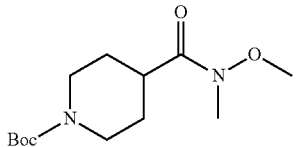

To a solution of 1-(tert-butoxycarbonyl)piperidine-4-carboxylic acid (20.0 g, 87.23 mmol) in DCM (200 mL) was added HATU (36.46 g, 95.95 mmol), TEA (17.62 g, 174.46 mmol) and N,O-dimethylhydroxylamine (8.93 g, 91.59 mmol). The mixture was stirred at 25° C. for 16 h. The mixture was washed with H$_2$O and the DCM layer was evaporated and the residue purified by silica column (PE/EA=1:1) to give the tert-butyl 4-(methoxy(methyl)carbamoyl)piperidine-1-carboxylate (21.0 g, yield: 88.5%). $^1$H NMR (400 MHz, CDCl$_3$): δ=4.27-4.01 (m, 2H), 3.71 (s, 3H), 3.19 (s, 3H), 2.85-2.70 (m, 3H), 1.75-1.62 (m, 4H), 1.46 (s, 9H).

Step 2: Synthesis of tert-butyl 4-acetylpiperidine-1-carboxylate

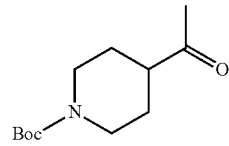

To a solution of tert-butyl 4-(methoxy(methyl)carbamoyl) piperidine-1-carboxylate (10.0 g, 36.76 mmol) in THF (150 mL) was added MeMgBr (24.5 mL, 73.52 mmol) at −78° C. The mixture was stirred at 25° C. for 16 h. TLC showed the reaction worked well. The mixture was quenched with aq. NH$_4$Cl and H$_2$O (100 mL) was added. The mixture was extracted with DCM (100 mL×3). The DCM layer was dried and evaporated to give the tert-butyl 4-acetylpiperidine-1-carboxylate (7.9 g, yield: 94.7%). $^1$H NMR (400 MHz, CDCl$_3$): δ=4.10 (br. s., 2H), 2.88-2.70 (m, 2H), 2.46 (tt, J=3.6, 11.5 Hz, 1H), 2.17 (s, 3H), 1.84 (d, J=11.5 Hz, 2H), 1.58-1.48 (m, 2H), 1.48-1.41 (m, 9H).

Step 3: Synthesis of tert-butyl 4-(1-aminoethyl)piperidine-1-carboxylate

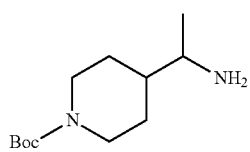 [SMILES: CC(N)C1CCN(C(=O)OC(C)(C)C)CC1]

To a solution of tert-butyl 4-acetylpiperidine-1-carboxylate (7.9 g, 34.8 mmol) in MeOH (100 mL) was added NH$_4$OAc (10.72 g, 139.2 mmol) and AcOH (1 mL). The mixture was stirred at 25° C. for 2 h, then was added NaBH$_3$CN (2.63 g, 41.76 mmol). The mixture was stirred at 25° C. for 16 h. The mixture was evaporated and 2N NaOH (50 mL) was added to the residue. The solution was extracted with DCM (100 mL×3). The DCM layer was washed with H$_2$O and brine dried and evaporated to give the tert-butyl 4-(1-aminoethyl)piperidine-1-carboxylate (7.93 g, yield: 100%). $^1$H NMR (400 MHz, CDCl$_3$): δ=4.15 (br. s., 2H), 2.77-2.57 (m, 3H), 1.76-1.59 (m, 2H), 1.46 (s, 9H), 1.33-10 (m, 5H), 1.06 (d, J=6.5 Hz, 3H).

Step 4: Synthesis of tert-butyl 4-(1-(((benzyloxy) carbonyl)amino)ethyl)piperidine-1-carboxylate

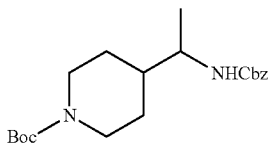

To a solution of tert-butyl 4-(1-aminoethyl)piperidine-1-carboxylate (7.93 g, 34.8 mmol) in THF (80 mL) was added K$_2$CO$_3$ (9.6 g, 69.6 mmol) and Cbz-Cl (7.1 g, 41.76 mmol). The mixture was stirred at 25° C. for 16 h. The mixture diluted with H$_2$O and extracted with EA (50 mL×3) and the EA layer evaporated to give tert-butyl 4-(1-(((benzyloxy) carbonyl)amino)ethyl)piperidine-1-carboxylate (10.1 g, yield: 80.2%). $^1$H NMR (400 MHz, DMSO-d$_6$): δ=7.42-7.23 (m, 5H), 7.16 (d, J=8.8 Hz, 1H), 5.00 (s, 2H), 3.94 (d, J=11.8 Hz, 2H), 3.45-3.34 (m, 1H), 2.71-2.55 (m, 2H), 1.67-1.42 (m, 3H), 1.38 (s, 9H), 1.13-0.89 (m, 5H).

Step 5: Synthesis of benzyl (1-(piperidin-4-yl)ethyl)carbamate

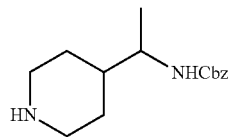 [SMILES: CC(NC(=O)OCc1ccccc1)C1CCNCC1]

To a solution of tert-butyl 4-(1-(((benzyloxy)carbonyl) amino)ethyl)piperidine-1-carboxylate (10.1 g, 27.87 mmol) in EA (50 mL) was added HCl/EA (50 mL). The mixture was stirred at 25° C. for 16 h. Solvents were then evaporated to give the benzyl (1-(piperidin-4-yl)ethyl)carbamate as a white solid. (8.3 g, yield: 100%). $^1$H NMR (400 MHz, DMSO-d$_6$): δ=8.88 (br. s., 1H), 8.50 (d, J=9.5 Hz, 1H), 7.42-7.30 (m, 5H), 7.26 (d, J=8.8 Hz, 1H), 5.04-4.98 (m, 2H), 3.46-3.41 (m, 1H), 3.24 (d, J=11.8 Hz, 2H), 2.84-2.71 (m, 2H), 1.74 (d, J=13.6 Hz, 2H), 1.53 (d, J=3.8 Hz, 1H), 1.40-1.28 (m, 2H), 1.05-0.99 (m, 3H).

Step 6: Synthesis of tert-butyl N-[(1S)-2-[4-[1-(benzyloxycarbonylamino)ethyl]-1-piperidyl]-1-methyl-2-oxo-ethyl]carbamate

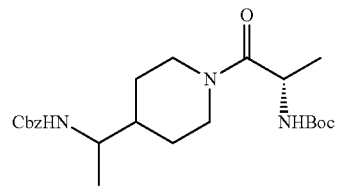 [SMILES: CC(NC(=O)OCc1ccccc1)C1CCN(C(=O)[C@H](C)NC(=O)OC(C)(C)C)CC1]

To a solution of benzyl (1-(piperidin-4-yl)ethyl)carbamate (7.0 g, 23.43 mmol) in DCM (100 mL) was added HATU (8.9 g, 23.43 mmol), TEA (4.73 g, 46.86 mmol) and (S)-2-((tert-butoxycarbonyl)amino)propanoic acid (4.43 g, 23.43 mmol). The mixture was stirred at 25° C. for 5 h. The mixture was washed with H$_2$O and the DCM layer evaporated. The residue was purified by silica column (PE/EA=1:1) to give the tert-butyl N-[(1S)-2-[4-[1-(benzyloxycarbonylamino)ethyl]-1-piperidyl]-1-methyl-2-oxo-ethyl] carbamate (8.9 g, yield: 87.7%). $^1$H NMR (400 MHz, CDCl$_3$): δ=7.37 (s, 5H), 5.58 (br. s., 1H), 5.15-5.03 (m, 2H), 4.60 (dd, J=7.4, 14.7 Hz, 3H), 3.96-3.86 (m, 1H), 3.68 (br. s., 1H), 2.99 (br. s., 1H), 2.54 (d, J=11.0 Hz, 1H), 1.91-1.63 (m, 3H), 1.44 (br. s., 9H), 1.28 (d, J=6.8 Hz, 4H), 1.21-1.07 (m, 4H).

Step 7: Synthesis of tert-butyl ((2S)-1-(4-(1-aminoethyl)piperidin-1-yl)-1-oxopropan-2-yl)carbamate

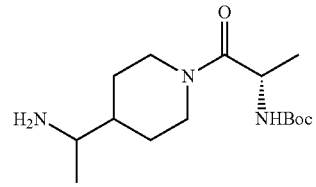 [SMILES: CC(N)C1CCN(C(=O)[C@H](C)NC(=O)OC(C)(C)C)CC1]

To a solution of tert-butyl N-[(1S)-2-[4-[1-(benzyloxycarbonylamino)ethyl]-1-piperidyl]-1-methyl-2-oxo-ethyl]carbamate (8.9 g, 20.55 mmol) in MeOH (100 mL) was added Pd/C (900 mg). The mixture was stirred at 25° C. for 16 hours under H$_2$ (50 psi). The reaction mixture was filtered and the filtrate was evaporated to give the tert-butyl ((2S)-1-(4-(1-aminoethyl)piperidin-1-yl)-1-oxopropan-2-yl)carbamate. (5.6 g, yield: 91.2%). $^1$H NMR (400 MHz, MeOD-d$_4$): δ=5.61 (t, J=7.2 Hz, 1H), 4.71-4.56 (m, 2H), 3.91 (br. s., 1H), 3.06-2.96 (m, 1H), 2.77-2.71 (m, 1H), 2.59-2.50 (m, 1H), 1.85-1.68 (m, 2H), 1.44 (d, J=3.0 Hz, 9H), 1.35-1.22 (m, 4H), 1.19-1.04 (m, 4H); LCMS (m/z): 300.2 [M+H]$^+$.

Example 2

Synthesis of tert-butyl (3-(((1r,4r)-4-aminocyclohexyl)amino)-3-oxopropyl)carbamate

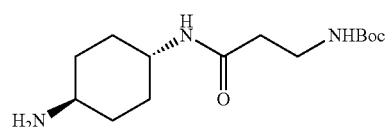

Step 1: Synthesis of tert-butyl N-[3-[[4-(benzyloxycarbonylamino)cyclohexyl]amino]-3-oxo-propyl] carbamate

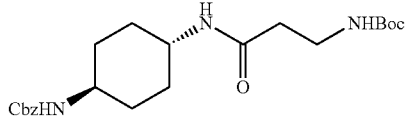 [SMILES: CC(C)(C)OC(=O)NCCC(=O)N[C@H]1CC[C@H](NC(=O)OCc2ccccc2)CC1]

To a solution of 3-((tert-butoxycarbonyl)amino)propanoic acid (8.38 g, 44.30 mmol, 1.10 Eq) and TEA (8.2 g, 80 mmol, 2.0 Eq) in DCM (500 mL) was added HATU (15.31 g, 40.27 mmol, 1.00 Eq) in one portion at 20° C. The mixture was stirred at 20° C. for 30 minutes. Then benzyl N-(4-aminocyclohexyl)carbamate (10.00 g, 40.27 mmol, 1.00 Eq) was added in one portion at 20° C. The mixture was stirred at 20° C. for 12 hr at which point LCMS analysis showed the reaction was complete. The mixture was washed with water (400 mL×3) and extracted with DCM (600 mL×3). The combined organic layer was concentrated in vacuum. The residue was purified by recrystallization (from minimum MeOH) to afford tert-butyl N-[3-[[4-(benzyloxycarbonylamino)cyclohexyl]amino]-3-oxo-propyl]carbamate (14.60 g, 34.80 mmol, 86.42% yield) as white solid. 1H NMR (400 MHz, DMSO-d$_6$) δ 7.74 (d, J=7.78 Hz, 1H), 7.31-7.40 (m, 5H), 7.20 (d, J=7.78 Hz, 1H), 6.73 (t, J=5.40 Hz, 1H), 5.00 (s, 2H), 3.44 (d, J=6.78 Hz, 1H), 3.23 (dd, J=7.40, 3.14 Hz, 1H), 3.10 (q, J=6.61 Hz, 2H), 2.18 (t, J=7.40 Hz, 2H), 1.78 (br. s., 4H), 1.37 (s, 9H), 1.16-1.27 (m, 4H); LCMS (m/z): 320.2 [M+H−100]$^+$.

Step 2: Synthesis of tert-butyl (3-(((1r,4r)-4-aminocyclohexyl)amino)-3-oxopropyl)carbamate To a solution of tert-butyl N-[3-[[4-(benzyloxycarbonylamino)cyclohexyl]amino]-3-oxo-propyl]carbamate (14.60 g, 34.80 mmol, 1.00 Eq) in MeOH (500 mL) was added Pd/C (5 g) under N$_2$. The suspension was degassed under vacuum and purged with H$_2$ several times. The mixture was stirred under H$_2$ (50 psi) at 50° C. for 12 hours. LCMS showed the starting material was consumed completely. The reaction mixture was filtered and concentrated to give tert-butyl N-[3-[(4-aminocyclohexyl) amino]-3-oxopropyl]carbamate (9.80 g, 34.34 mmol, 98.67% yield) as yellow solid. $^1$H NMR (400 MHz, DMSO-d$_6$) δ 7.74 (d, J=7.53 Hz, 1H), 6.63-6.84 (m, 1H), 3.43 (br. s., 1H), 3.09 (q, J=6.78 Hz, 2H), 2.60 (br. s., 1H), 2.18 (t, J=7.28 Hz, 2H), 1.70-1.82 (m, 4H), 1.37 (s, 9H), 1.08-1.20 (m, 4H); LCMS (m/z): 230.2 [M+H−56]$^+$.

Example 3

Synthesis of N-(1-(1-((S)-2-aminopropanoyl)piperidin-4-yl)ethyl)-6-chloro-2-oxoindoline-5-carboxamide (Cpd. No. 490)

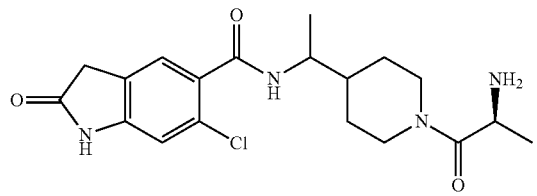 [SMILES: CC(NC(=O)c1cc2c(cc1Cl)NC(=O)C2)C1CCN(C(=O)[C@H](C)N)CC1]

Step 1: Synthesis of ((2S)-1-(4-(1-(6-chloro-2-oxoindoline-5-carboxamido) ethyl)piperidin-1-yl)-1-oxopropan-2-yl)carbamate

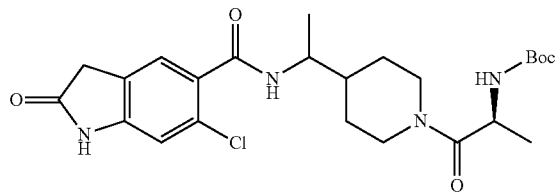 [SMILES: CC(NC(=O)c1cc2c(cc1Cl)NC(=O)C2)C1CCN(C(=O)[C@H](C)NC(=O)OC(C)(C)C)CC1]

To a mixture of 6-chloro-2-oxoindoline-5-carboxylic acid (100.00 mg, 472.59 umol, 1.00 Eq), HATU (179.69 mg, 472.59 umol, 1.00 Eq) and TEA (47.82 mg, 472.59 umol, 1.00 Eq) in DCM (10 mL) was added tert-butyl ((2S)-1-(4-(1-amino ethyl)piperidin-1-yl)-1-oxopropan-2-yl)carbamate (141.50 mg, 472.59 umol, 1.00 Eq). The mixture was stirred at 20° C. for 3 hours. LCMS showed the reaction was complete. Water (5 mL) was added to the reaction and the aqueous phase was extracted with DCM (10 mL×3). The combined organic phase was dried over anhydrous Na$_2$SO$_4$, filtered and concentrated in vacuum to afford tert-butyl ((2S)-1-(4-(1-(6-chloro-2-oxoindoline-5-carboxamido) ethyl)piperidin-1-yl)-1-oxopropan-2-yl)carbamate (100.00 mg, crude). LCMS (m/z): 493.2 [M+H]$^+$.

Step 2: Synthesis of N-(1-(1-((S)-2-aminopropanoyl)piperidin-4-yl)ethyl)-6-chloro-2-oxoindoline-5-carboxamide

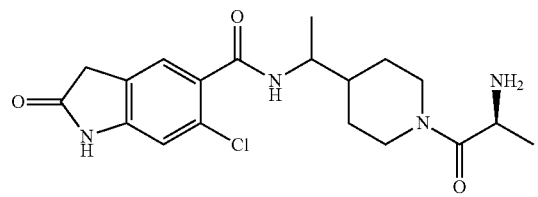 [SMILES: CC(NC(=O)c1cc2c(cc1Cl)NC(=O)C2)C1CCN(C(=O)[C@H](C)N)CC1]

To a solution of tert-butyl ((2S)-1-(4-(1-(6-chloro-2-oxoindoline-5-carboxamido)ethyl)piperidin-1-yl)-1-oxopropan-2-yl)carbamate (100.00 mg, 202.84 umol, 1.00 Eq) in DCM (10 mL) was added dropwise TFA (3 mL) at 0° C. The resulting solution was then stirred for 3 hours at 25° C. TLC showed the reaction was complete. The mixture was evaporated and purified by prep-HPLC to afford N-(1-(1-((S)-2-aminopropanoyl)piperidin-4-yl)ethyl)-6-chloro-2-oxoindoline-5-carboxamide (38.50 mg, yield: 48.31%). $^1$H NMR (400 MHz, MeOD-d$_4$): =7.29 (s, 1H), 6.95 (s, 1H), 4.56 (d, J=12.5 Hz, 1H), 4.45-4.38 (m, 1H), 3.91 (d, J=12.3 Hz, 2H), 3.54 (s, 2H), 3.15 (br. s., 2H), 2.72-2.63 (m, 1H), 2.01-1.85 (m, 2H), 1.75 (br. s., 1H), 1.46 (dd, J=6.9, 11.7 Hz, 3H), 1.29-1.18 (m, 4H). LCMS (m/z): 393.2 [M+H]$^+$.

Example 4

Synthesis of N-(1-(1-((S)-2-aminopropanoyl)piperidin-4-yl)ethyl)-2-oxoindoline-5-carboxamide Hydrochloride (Cpd. No. 86)

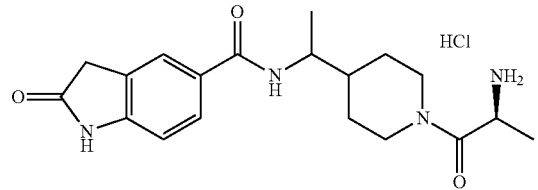 [SMILES: CC(NC(=O)c1ccc2c(c1)CC(=O)N2)C1CCN(C(=O)[C@H](C)N)CC1 ; Cl]

Step 1: Synthesis of tert-butyl ((2S)-1-oxo-1-(4-(1-(2-oxoindoline-5-carboxamido)ethyl)piperidin-1-yl)propan-2-yl)carbamate

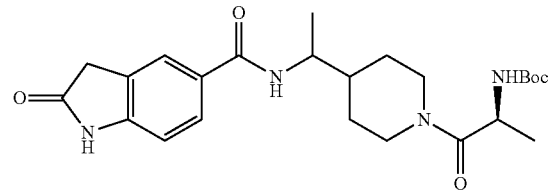 [SMILES: CC(NC(=O)c1ccc2c(c1)CC(=O)N2)C1CCN(C(=O)[C@H](C)NC(=O)OC(C)(C)C)CC1]

To a stirred solution of 2-oxoindoline-5-carboxylic acid (0.177 g, 1.00 mmol) in DMF (2 mL), were added EDCI·HCl (0.24 g, 1.25 mmol), HOBt (0.168 g, 1.25 mmol) and triethylamine (0.35 mL, 2.5 mmol). The solution was stirred for 10 min at 0° C. tert-Butyl ((2S)-1-(4-(1-aminoethyl)piperidin-1-yl)-1-oxopropan-2-yl)carbamate (0.25 g, 0.83 mmol) was added and the reaction stirred at rt for 6 h. The progress of the reaction was monitored by TLC. After complete consumption of starting material, the reaction was quenched with water and extracted with ethyl acetate. The organic layer was separated, washed with brine, dried over anhydrous $Na_2SO_4$ and concentrated under reduced pressure to obtain a crude residue which was purified by column chromatography to afford tert-butyl ((2S)-1-oxo-1-(4-(1-(2-oxoindoline-5-carboxamido)ethyl)piperidin-1-yl)propan-2-yl)carbamate (0.11 g, 28%). LCMS: 359.25 (M-Boc)$^+$.

Step 2: Synthesis of N-(1-(1-((S)-2-aminopropanoyl)piperidin-4-yl)ethyl)-2-oxoindoline-5-carboxamide Hydrochloride

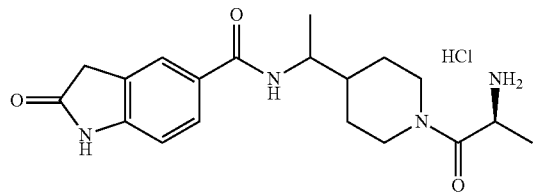 [SMILES: CC(NC(=O)c1ccc2c(c1)CC(=O)N2)C1CCN(C(=O)[C@H](C)N)CC1 ; Cl]

To a stirred solution of tert-butyl ((2S)-1-oxo-1-(4-(1-(2-oxoindoline-5-carboxamido)ethyl)piperidin-1-yl)propan-2-yl)carbamate (0.1 g, 0.47 mmol) in dioxane (2 mL) was added 4 M dioxane:HCl solution (4 mL) at 0° C. and the reaction mixture stirred at rt for 5 h. The progress of the reaction was monitored by TLC. After complete consumption of tert-butyl ((2S)-1-oxo-1-(4-(1-(2-oxoindoline-5-carboxamido)ethyl) piperidin-1-yl)propan-2-yl)carbamate, the solvent was removed under reduced pressure to obtain a crude residue which was purified by repeated washing with ether and pentane to obtain N-(1-(1-((S)-2-aminopropanoyl)piperidin-4-yl)ethyl)-2-oxoindoline-5-carboxamide hydrochloride (0.08 g, 93%). $^1$H NMR (400 MHz, DMSO-d6): δ 10.63 (s, 1H), 8.06 (q, J=11.0, 8.4 Hz, 4H), 7.77-7.70 (m, 2H), 6.85 (d, J=8.5 Hz, 1H), 4.38-4.35 (m, 2H), 3.85 (d, J=13.9 Hz, 2H), 3.53 (s, 2H), 3.09-2.90 (m, 1H), 2.57 (dd, J=25.3, 12.8 Hz, 1H), 1.75 (dd, J=26.2, 12.6 Hz, 3H), 1.3-1.28 (m, 3H), 1.12 (d, J=6.8 Hz, 4H), 1.02 (d, J=12.5 Hz, 1H); LCMS: 359.25 (M+1)$^+$.

Example 5

Synthesis of N-(1-(1-((S)-2-aminopropanoyl)piperidin-4-yl)ethyl)-2-oxo-2,3-dihydrobenzo[d]oxazole-6-carboxamide Hydrochloride (Cpd. No. 94)

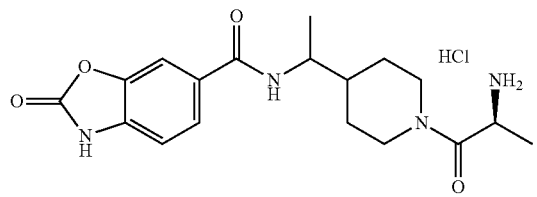 [SMILES: CC(NC(=O)c1ccc2[nH]c(=O)oc2c1)C1CCN(C(=O)[C@H](C)N)CC1 ; Cl]

Step 1: Synthesis of tert-butyl ((2S)-1-oxo-1-(4-(1-(2-oxo-2,3-dihydrobenzo[d]oxazole-6-carboxamido)ethyl)piperidin-1-yl)propan-2-yl)carbamate

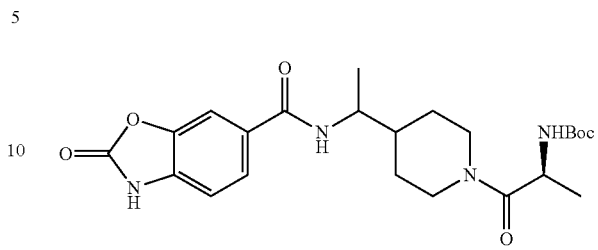

To a stirred solution of 2-oxo-2,3-dihydrobenzo[d]oxazole-6-carboxylic acid (0.2 g, 0.66 mmol) in DMF (1.5 mL) was added EDCI.HCl (0.191 g, 1.00 mmol), HOBt (0.091 g, 0.66 mmol) and diisopropylethylamine (0.34 mL, 2.00 mmol). The solution was stirred for 10 min at 0° C. After that, tert-butyl ((2S)-1-(4-(1-aminoethyl)piperidin-1-yl)-1-oxopropan-2-yl)carbamate (0.142 g, 0.80 mmol) was added and the reaction stirred at rt for 12 h. The progress of the reaction was monitored by TLC. After complete consumption of starting material, the reaction was quenched with water and extracted with ethyl acetate. The organic layer was separated, washed with brine, dried over anhydrous $Na_2SO_4$ and concentrated under reduced pressure to obtain a crude residue which was purified by column chromatography to afford tert-butyl ((2S)-1-oxo-1-(4-(1-(2-oxo-2,3-dihydrobenzo[d]oxazole-6-carboxamido)ethyl)piperidin-1-yl)propan-2-yl)carbamate (0.104 g, 33%). LCMS: 361.05 (M-Boc)$^+$.

Step 2: Synthesis of N-(1-(1-((S)-2-aminopropanoyl)piperidin-4-yl)ethyl)-2-oxo-2,3-dihydrobenzo[d]oxazole-6-carboxamide Hydrochloride

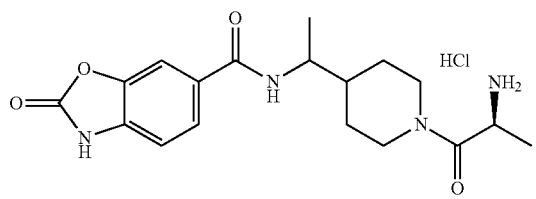 [SMILES: CC(NC(=O)c1ccc2[nH]c(=O)oc2c1)C1CCN(C(=O)[C@H](C)N)CC1 ; Cl]

To a stirred solution of ((2S)-1-oxo-1-(4-(1-(2-oxo-2,3-dihydrobenzo[d]oxazole-6-carboxamido)ethyl)piperidin-1-yl)propan-2-yl)carbamate (0.03 g, 0.08 mmol) in dioxane (1 mL) at 0° C. was added 4M dioxane:HCl solution (1 mL). The reaction mixture was stirred at rt for 3 h. The progress of the reaction was monitored by TLC. After complete consumption of starting material, the solvent was removed under reduced pressure to obtain a crude residue which was purified by repeated washing with ether and hexane to obtain N-(1-(1-((S)-2-aminopropanoyl)piperidin-4-yl)ethyl)-2-oxo-2,3-dihydrobenzo[d]oxazole-6-carboxamide hydrochloride (0.008 g, 36%). $^1$H NMR (400 MHz, DMSO-d$_6$): δ 10.66 (s, 1H), 8.72 (d, J=12.3 Hz, 1H), 8.42 (q, J=8.1, 7.1 Hz, 2H), 7.74 (d, J=8.0 Hz, 2H), 6.86 (d, J=8.1 Hz, 1H), 3.54 (s, 2H), 3.25 (d, J=12.4 Hz, 2H), 3.16 (t, J=6.1 Hz, 2H), 2.82 (q, J=11.8 Hz, 2H), 2.62 (s, 1H), 1.79 (d, J=13.4 Hz, 2H), 1.35-1.32 (m, 2H); LCMS: 274.15 (M+H)$^+$

Example 6

Synthesis of N-(1-(1-(((S)-2-aminopropanoyl)piperidin-4-yl)ethyl)-2-oxo-2,3-dihydro-1H-benzo[d]imidazole-5-carboxamide (Cpd. No. 93)

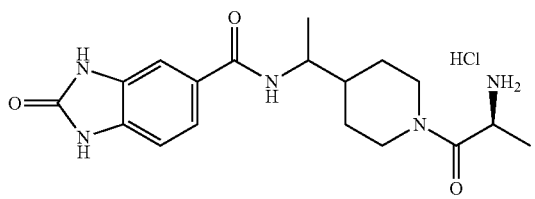 [SMILES: CC(NC(=O)c1ccc2[nH]c(=O)[nH]c2c1)C1CCN(C(=O)[C@H](C)N)CC1 ; Cl]

Step 1: Synthesis of N-(1-(1-((S)-2-aminopropanoyl)piperidin-4-yl)ethyl)-2-oxo-2,3-dihydro-1H-benzo[d]imidazole-5-carboxamide Hydrochloride

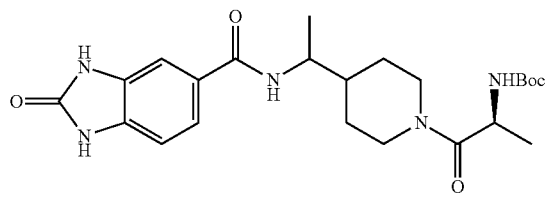 [SMILES: CC(NC(=O)c1ccc2[nH]c(=O)[nH]c2c1)C1CCN(C(=O)[C@H](C)NC(=O)OC(C)(C)C)CC1]

To a stirred solution of 2-oxo-2,3-dihydro-1H-benzo[d]imidazole-5-carboxylic acid (0.2 g, 0.66 mmol) in DMF (1.5 mL) was added EDCI.HCl (0.191 g, 1.00 mmol), HOBt (0.091 g, 0.66 mmol) and diisopropylethylamine (0.34 mL, 2.00 mmol). The solution was stirred for 10 min at 0° C. After that tert-butyl ((2S)-1-(4-(1-aminoethyl)piperidin-1-yl)-1-oxopropan-2-yl)carbamate (0.142 g, 0.80 mmol) was added and the reaction stirred at rt for 12 h. The progress of the reaction was monitored by TLC. After complete consumption of starting material, the reaction was quenched with water and extracted with ethyl acetate. The organic layer was washed with brine, dried over anhydrous $Na_2SO_4$ and concentrated under reduced pressure to obtain a crude residue which was purified by column chromatography to afford tert-butyl ((2S)-1-oxo-1-(4-(1-(2-oxo-2,3-dihydro-1H-benzo[d]imidazole-5-carboxamido)ethyl)piperidin-1-yl)propan-2-yl)carbamate (0.140 g, 45%). LCMS: 360.2 (M-Boc)$^+$.

Step 2: Synthesis of N-(1-(1-((S)-2-aminopropanoyl)piperidin-4-yl)ethyl)-2-oxo-2,3-dihydro-1H-benzo[d]imidazole-5-carboxamide Hydrochloride

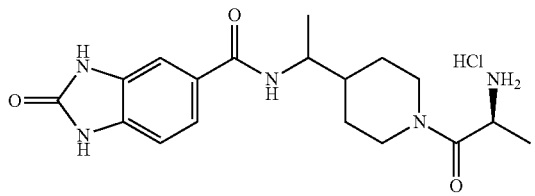 [SMILES: CC(NC(=O)c1ccc2[nH]c(=O)[nH]c2c1)C1CCN(C(=O)[C@H](C)N)CC1 ; Cl]

To a stirred solution of tert-butyl ((2S)-1-oxo-1-(4-(1-(2-oxo-2,3-dihydro-1H-benzo[d]imidazole-5-carboxamido)ethyl)piperidin-1-yl)propan-2-yl)carbamate (0.1 g, 0.21 mmol) in dioxane (2 mL) at 0° C. was added 4M dioxane: HCl solution (1 mL). The reaction mixture was stirred at rt for 3 h. The progress of the reaction was monitored by TLC. After complete consumption of the starting material, the solvent was removed under reduced pressure to obtain a crude residue which was purified by repeated washing with ether and hexane to obtain N-(1-(1-((S)-2-aminopropanoyl)piperidin-4-yl)ethyl)-2-oxo-2,3-dihydro-1H-benzo[d]imidazole-5-carboxamide hydrochloride (0.060 g, 69%). $^1$H NMR (400 MHz, DMSO-$d_6$): δ 10.85 (d, J=16.4 Hz, 2H), 8.10 (p, J=8.9, 7.6 Hz, 4H), 7.55-7.52 (m, 1H), 7.44 (q, J=2.0 Hz, 1H), 6.95 (d, J=8.1 Hz, 1H), 4.44-4.24 (m, 2H), 3.88-3.86 (m, 2H), 3.09-2.91 (m, 1H), 2.6-2.57 (m, 1H), 1.83-1.64 (m, 3H), 1.33-0.99 (m, 8H); LCMS: 360.25 (M+1)$^+$.

Example 7

N-(1-(4-aminobutanoyl)piperidin-4-yl)-1H-1,2,4-triazole-5-carboxamide (Cpd. No. 560)

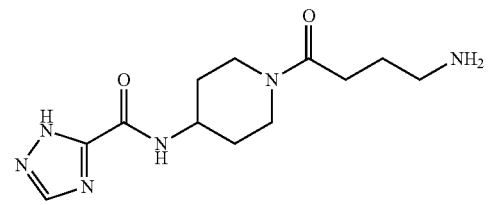 [SMILES: NCCCC(=O)N1CCC(NC(=O)c2ncn[nH]2)CC1]

Step 1: Synthesis of tert-butyl 4-(1H-1,2,4-triazole-5-carbonylamino)piperidine-1-carboxylate

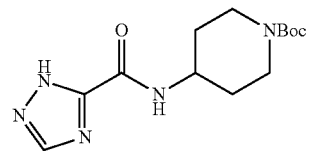 [SMILES: CC(C)(C)OC(=O)N1CCC(NC(=O)c2ncn[nH]2)CC1]

To a solution of 1H-1,2,4-triazole-5-carboxylic acid (2.00 g, 17.69 mmol, 1.00 Eq) in DMF (100 mL) was added TEA (2.68 g, 26.53 mmol, 1.50 Eq), BOP—Cl (4.95 g, 19.46 mmol, 1.10 Eq), and tert-butyl 4-aminopiperidine-1-carboxylate (3.90 g, 19.46 mmol, 1.10 Eq). The reaction mixture was stirred at 20° C. for 12 hr. The reaction mixture was concentrated and dissolved in MeOH, filtered, the organic layer was concentrated and purified by silica gel column chromatography to give tert-butyl 4-(1H-1,2,4-triazole-5-carbonylamino)piperidine-1-carboxylate (3.13 g, 10.60 mmol, 59.9% yield) as a yellow solid. LCMS (m/z): 240.1 [M+H−56]$^+$.

Step 2: Synthesis of N-(4-piperidyl)-1H-1,2,4-triazole-5-carboxamide

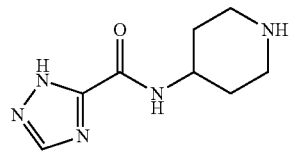 [SMILES: O=C(NC1CCNCC1)c1ncn[nH]1]

To a solution of tert-butyl 4-(1H-1,2,4-triazole-5-carbonylamino)piperidine-1-carboxylate (3.13 g, 10.60 mmol, 1.00 Eq) in DCM (50 mL) was added TFA (10 mL). The reaction mixture was stirred at 20° C. for 5 hr. The reaction mixture was concentrated and lyophilized to afford N-(4-piperidyl)-1H-1,2,4-triazole-5-carboxamide (6.00 g, 19.40 mmol, 91.51% yield) as a light yellow solid. LCMS (m/z): 196.2 [M+H]$^+$ Step 3: Synthesis of tert-butyl (4-(4-(1H-1,2,4-triazole-5-carboxamido)piperidin-1-yl)-4-oxobutyl)carbamate

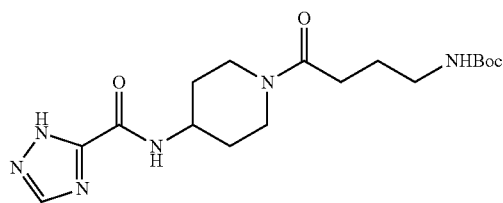 [SMILES: CC(C)(C)OC(=O)NCCCC(=O)N1CCC(NC(=O)c2ncn[nH]2)CC1]

To a mixture of 4-((tert-butoxycarbonyl)amino)butanoic acid (203.00 mg, 998.87 umol, 1.00 q) and HATU (379.80 mg, 998.87 umol, 1.00 Eq) in DCM (10 mL) was added Et$_3$N (202.15 mg, 2.00 mmol, 2.00 Eq) in one portion at 20° C. The mixture was stirred at 20° C. for 30 min. Then N-(piperidin-4-yl)-1H-1,2,4-triazole-5-carboxamide (195.00 mg, 998.87 umol, 1.00 Eq) was added in one portion at 20° C. The mixture was stirred at 20° C. for 12 h. LCMS showed the reaction was complete. The reaction mixture was washed with water (40 mL×3) and extracted with DCM (50 mL×3). The combined organic layer was concentrated under vacuum. The residue was purified by prep-HPLC to afford tert-butyl (4-(4-(1H-1,2,4-triazole-5-carboxamido)piperidin-1-yl)-4-oxobutyl)carbamate (200.00 mg, 525.71 umol, 52.63% yield) as white solid. $^1$H NMR (400 MHz, MeOD-d$_4$) δ 8.45 (s, 1H) 4.54 (d, J=13.30 Hz, 1H) 4.13-4.21 (m, 1H) 4.01 (d, J=13.80 Hz, 1H) 3.23-3.30 (m, 1H) 3.11 (t, J=6.78 Hz, 2H) 2.85 (t, J=11.67 Hz, 1H) 2.46 (t, J=7.53 Hz, 2H) 1.97-2.07 (m, 2H) 1.78 (quip, J=7.15 Hz, 2H) 1.53-1.65 (m, 2H) 1.38-1.53 (m, 9H); LCMS (m/z): 381.2 [M+H]$^+$.

Step 4: Synthesis of N-(1-(4-aminobutanoyl)piperidin-4-yl)-1H-1,2,4-triazole-5-carboxamide

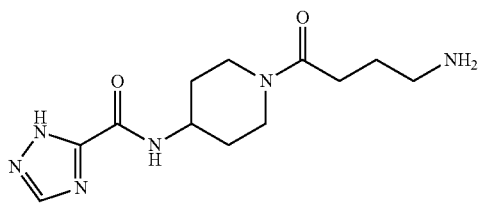 [SMILES: NCCCC(=O)N1CCC(NC(=O)c2ncn[nH]2)CC1]

To a mixture of tert-butyl (4-(4-(1H-1,2,4-triazole-5-carboxamido)piperidin-1-yl)-4-oxobutyl)carbamate (200.00 mg, 525.71 umol, 1.00 Eq) in DCM (20 mL) was added TFA (5 mL) dropwise at 0° C. The mixture was stirred at 0° C. for 30 min. The reaction then warmed slowly to 20° C. and stirred at this temperature for another 12 h. LCMS showed the reaction complete. The mixture was concentrated under reduced pressure at ° C. The residue was purified by prep-HPLC to afford N-(1-(4-aminobutanoyl)piperidin-4-yl)-1H-1,2,4-triazole-5-carboxamide (104.20 mg, 50.26% yield) as colorless oil (TFA salt). $^1$H NMR (400 MHz, MeOD-d4) δ 8.49 (s, 1H) 4.54 (d, J=13.55 Hz, 1H) 4.12-4.21 (m, 1H) 4.00 (d, J=13.80 Hz, 1H) 3.25 (t, J=11.80 Hz, 1H) 3.02 (t, J=7.28 Hz, 2H) 2.86 (t, J=11.67 Hz, 1H) 2.60 (t, J=6.90 Hz, 2H) 1.92-2.08 (m, 4H) 1.46-1.73 (m, 2H); LCMS (m/z): 281.1 [M+H]$^+$ Example 8

Synthesis of N-((1r,4r)-4-aminocyclohexyl)-1-benzyl-3-methyl-1H-pyrazole-5-carboxamide Hydrochloride (Cpd. No. 29)

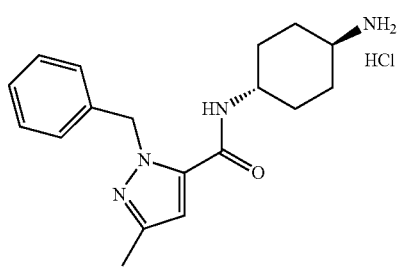 [SMILES: Cc1cc(C(=O)N[C@H]2CC[C@H](N)CC2)n(Cc2ccccc2)n1 ; Cl]

Step 1: Synthesis of tert-butyl ((1r,4r)-4-(1-benzyl-3-methyl-1H-pyrazole-5-carboxamido)cyclohexyl)carbamate

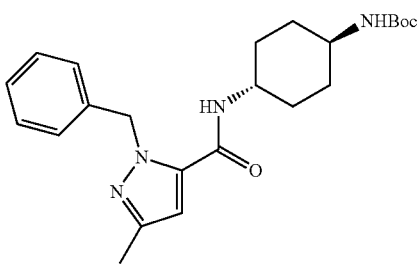 [SMILES: Cc1cc(C(=O)N[C@H]2CC[C@H](NC(=O)OC(C)(C)C)CC2)n(Cc2ccccc2)n1]

To a stirred solution of 1-benzyl-3-methyl-1H-pyrazole-5-carboxylic acid (0.150 g, 0.69 mmol) in DMF (5 mL) was added HATU (0.393 g, 1.0 mmol) and diisopropylethylamine (0.24 mL, 1.4 mmol). The solution was stirred for 10 min at 0° C. tert-Butyl ((1r,4r)-4-aminocyclohexyl)carbamate (0.147 g, 0.69 mmol) was added and the reaction stirred at rt for 2 h. The progress of the reaction was monitored by TLC. After complete consumption of starting material, the reaction was quenched with water and extracted with ethyl acetate. The organic layer was separated, washed with brine, dried over anhydrous Na$_2$SO$_4$ and concentrated under reduced pressure to obtain a crude residue which was purified by column chromatography to afford tert-butyl ((1r,4r)-4-(1-benzyl-3-methyl-1H-pyrazole-5-carboxamido)cyclohexyl)carbamate (0.08 g, 25%). LCMS: 313.1 (M−100)$^+$.

Step 2: Synthesis of N-((1r,4r)-4-aminocyclohexyl)-1-benzyl-3-methyl-1H-pyrazole-5-carboxamide Hydrochloride

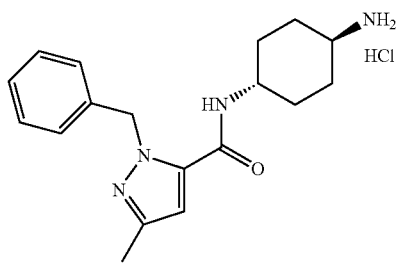 [SMILES: Cc1cc(C(=O)N[C@H]2CC[C@H](N)CC2)n(Cc2ccccc2)n1 ; Cl]

To a stirred solution of tert-butyl ((1r,4r)-4-(1-benzyl-3-methyl-1H-pyrazole-5-carboxamido)cyclohexyl)carbamate (0.05 g, 0.121 mmol) in dioxane (1 mL) at 0° C. was added 4 M dioxane:HCl (1.5 mL). The reaction mixture was stirred at rt for 1 h. The progress of the reaction was monitored by TLC. After complete consumption of the starting material, the solvent was removed under reduced pressure to obtain a crude residue. The material was purified by repeated washing with ether and pentane to obtain N-((1r,4r)-4-aminocyclohexyl)-1-benzyl-3-methyl-1H-pyrazole-5-carboxamide hydrochloride (0.03 g, 51%). $^1$H NMR (400 MHz, DMSO-d6): δ 8.26 (d, J=7.8 Hz, 1H), 7.94 (d, J=5.3 Hz, 3H), 7.33-7.10 (m, 5H), 6.66 (s, 1H), 5.60 (s, 2H), 2.96 (d, J=10.9 Hz, 1H), 2.16 (s, 3H), 1.96 (d, J=10.4 Hz, 2H), 1.83 (d, J=11.1 Hz, 2H), 1.47-1.26 (m, 4H); LCMS: 313.2 (M+H)$^+$.

Example 9

Synthesis of N-((1r,4r)-4-aminocyclohexyl)-1-cyclopropyl-1H-1,2,3-triazole-4-carboxamide Hydrochloride

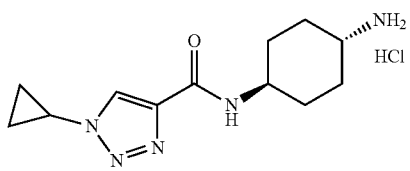 [SMILES: N[C@H]1CC[C@H](NC(=O)c2cn(C3CC3)nn2)CC1 ; Cl]

Step 1: Synthesis of tert-butyl ((1r,4r)-4-(1-cyclopropyl-1H-1,2,3-triazole-4-carboxamido)cyclohexyl)carbamate

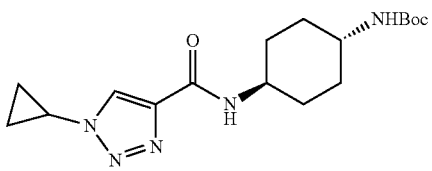 [SMILES: CC(C)(C)OC(=O)N[C@H]1CC[C@H](NC(=O)c2cn(C3CC3)nn2)CC1]

To a stirred solution of tert-butyl ((1r,4r)-4-aminocyclohexyl)carbamate (0.090 g, 0.420 mmol) in DMF (2 mL) was added EDCI (0.096 g, 0.504 mmol), HOBT (0.068 g, 0.504 mmol) and DIPEA (0.3 mL) and the solution stirred for 10 min at 0° C. 1-cyclopropyl-1H-1,2,3-triazole-4-carboxylic acid (0.064 g, 0.420 mmol) was then added and the reaction mixture stirred at rt for 2 hr. The progress of the reaction was monitored by TLC. After complete consumption of starting material, the reaction was quenched with water and extracted with ethyl acetate. The organic layer was separated, washed with brine, dried using Na$_2$SO$_4$ and concentrated under reduced pressure to obtain a residue which was purified by column chromatography to afford tert-butyl ((1r,4r)-4-(1-cyclopropyl-1H-1,2,3-triazole-4-carboxamido)cyclohexyl)carbamate (0.035 g, 24%). LCMS: 250.1 (M−100)$^+$ observed.

Step 2: Synthesis of N-((1r,4r)-4-aminocyclohexyl)-1-cyclopropyl-1H-1,2,3-triazole-4-carboxamide Hydrochloride

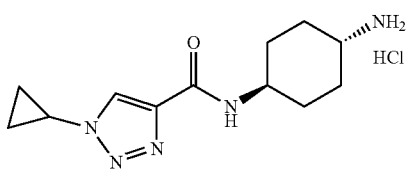 [SMILES: N[C@H]1CC[C@H](NC(=O)c2cn(C3CC3)nn2)CC1 ; Cl]

To a stirred solution of tert-butyl ((1r,4r)-4-(1-cyclopropyl-1H-1,2,3-triazole-4-carboxamido)cyclohexyl)carbamate (0.035 g, 0.10 mmol) in methanol (3 mL) was added 4M methanol:HCl (3 mL) at 0° C. and the reaction stirred at rt for 16 hr. The progress of the reaction was monitored by TLC. After complete consumption of starting material, the solvent was removed under reduced pressure and the residue was purified by washings with diethyl ether and DCM to obtain N-((1r,4r)-4-aminocyclohexyl)-1-cyclopropyl-1H-1,2,3-triazole-4-carboxamide hydrochloride (0.013 g, 49%). $^1$H NMR (400 MHz, DMSO-d6) δ 8.58 (s, 1H), 8.31 (d, J=8.3 Hz, 1H), 7.97 (s, 2H), 4.1-4.05 (m, J=7.5, 3.9 Hz, 1H), 3.75-3.66 (m, 1H), 3.01-2.88 (m, 1H), 1.97 (d, J=10.5 Hz, 2H), 1.83 (d, J=9.5 Hz, 2H), 1.55-1.34 (m, 4H), 1.25-1.07 (m, 4H); LCMS: 250.05 (M+H)$^+$.

Example 10

Synthesis of 2-oxo-N-(piperidin-4-ylmethyl)indoline-5-carboxamide Hydrochloride (Cpd. No. 100)

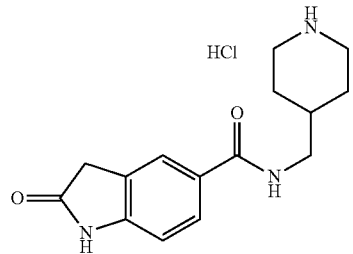 [SMILES: O=C1Cc2cc(C(=O)NCC3CCNCC3)ccc2N1 ; Cl]

Step 1: Synthesis of tert-butyl 4-((2-oxoindoline-5-carboxamido)methyl)piperidine-1-carboxylate

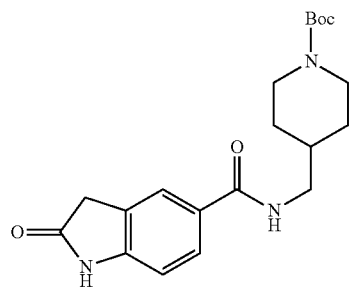 [SMILES: CC(C)(C)OC(=O)N1CCC(CNC(=O)c2ccc3c(c2)CC(=O)N3)CC1]

To a stirred solution of 2-oxoindoline-5-carboxylic acid (0.7 g, 3.95 mmol) in DMF (5 mL) was added EDCI.HCl (1.13 g, 5.92 mmol), HOBt (0.8 g, 5.92 mmol) and triethylamine (1.7 mL, 11.8 mmol). The solution was stirred for 10 min at 0° C. After that tert-butyl 4-(aminomethyl)piperidine-1-carboxylate (0.93 g, 4.34 mmol) was added and the reaction stirred at rt for 16 h. The progress of the reaction was monitored by TLC. After complete consumption of starting material, the reaction was quenched with water and extracted with ethyl acetate. The organic layer was washed with brine, dried over anhydrous $Na_2SO_4$ and concentrated under reduced pressure to obtain a crude residue which was purified by preparative HPLC to afford tert-butyl 4-((2-oxoindoline-5-carboxamido)methyl)piperidine-1-carboxylate (0.130 g, 8%) LCMS: 274.1 (M-Boc)$^+$.

Step 2: Synthesis of 2-oxo-N-(piperidin-4-ylmethyl) indoline-5-carboxamide Hydrochloride

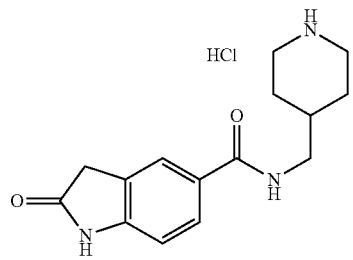 [SMILES: O=C1Cc2cc(C(=O)NCC3CCNCC3)ccc2N1 ; Cl]

To a stirred solution of tert-butyl 4-((2-oxoindoline-5-carboxamido)methyl)piperidine-1-carboxylate (0.03 g, 0.08 mmol) in dioxane (1 mL) at 0° C. was added 4M dioxane: HCl solution (1 mL). The reaction mixture was stirred at rt for 3 h. The progress of the reaction was monitored by TLC. After complete consumption of starting material, the solvent was removed under reduced pressure to obtain a crude residue which was purified by repeated washing with ether and hexane to obtain 2-oxo-N-(piperidin-4-ylmethyl)indoline-5-carboxamide hydrochloride (0.008 g, 36%). $^1$H NMR (400 MHz, DMSO-d$_6$): δ 10.66 (s, 1H), 8.72 (d, J=12.3 Hz, 1H), 8.42 (q, J=8.1, 7.1 Hz, 2H), 7.74 (d, J=8.0 Hz, 2H), 6.86 (d, J=8.1 Hz, 1H), 3.54 (s, 2H), 3.25 (d, J=12.4 Hz, 2H), 3.16 (t, J=6.1 Hz, 2H), 2.82 (q, J=11.8 Hz, 2H), 2.62 (s, 1H), 1.79 (d, J=13.4 Hz, 2H), 1.35-1.32 (m, 2H); LCMS: 274.15 (M+H)$^+$.

Example 11

Synthesis of 2-oxo-N-((1R,3r,5SR)-8-(piperidin-4-ylmethylsulfonyl)-8-aza-bicyclo[3.2.1]octan-3-yl)-2,3-dihydrobenzo[d]oxazole-6-carboxamide Hydrochloride (Cpd. No. 601)

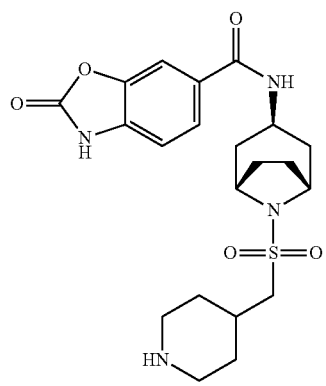 [SMILES: O=C(N[C@H]1C[C@H]2CC[C@@H](C1)N2S(=O)(=O)CC1CCNCC1)c1ccc2[nH]c(=O)oc2c1]

Step 1: Synthesis of benzyl4-(((1R,3r,5S)-3-(2,2,2-trichloroethoxy)carbonylamino)-8-aza-bicyclo[3.2.1]octan-8-ylsulfonyl)methyl)piperidine-1-carboxylate

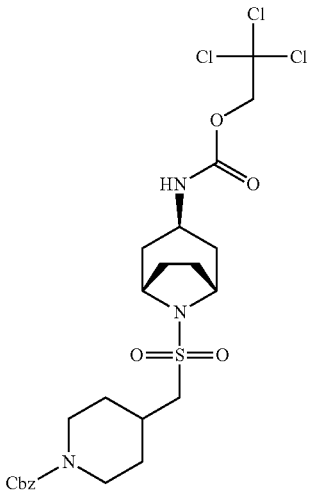 [SMILES: O=C(N[C@H]1C[C@H]2CC[C@@H](C1)N2S(=O)(=O)CC1CCN(C(=O)OCc2ccccc2)CC1)OCC(Cl)(Cl)Cl]

Into a 100-mL round-bottom flask was placed 2,2,2-trichloroethyl N-[(1R,3S,5S)-8-azabicyclo[3.2.1]octan-3-yl]carbamate (780 mg, 2.59 mmol, 1.00 equiv), dichloromethane (10 mL), TEA (0.93 g) added dropwise at 0° C. Then benzyl 4-[(chlorosulfonyl)methyl]piperidine-1-carboxylate (1 g, 3.01 mmol, 1.17 equiv) was added in several portions. The resulting solution was stirred overnight at room temperature. The resulting mixture was concentrated under vacuum. The residue was chromatographed on a silica gel column with dichloromethane/methanol (20:1-10:1). This resulted in 1.3 g (84%) of benzyl 4-[[(1R,3r,5S)-3-[[(2,2,2-trichloro ethoxy)carbonyl]amino]-8-azabicyclo[3.2.1]octane-8-sulfonyl]methyl]piperidine-1-carboxylate as a white solid. $^1$H NMR (400 MHz, CDCl$_3$) δ: 7.41-7.32 (m, 5H), 5.32-5.10 (m, 2H), 4.48 (s, 2H), 4.27-4.12 (m, 4H), 4.00-3.96 (m, 1H), 2.93-2.80 (m, 4H), 2.30-2.07 (m, 5H), 1.98-1.91 (m, 6H), 1.30-1.26 (m, 3H) ppm. LCMS (method A, ESI): RT=1.32 min, m/z=620.2 [M+Na]$^+$.

Step 2: Synthesis of benzyl 4-(((1R,3r,5S)-3-amino-8-aza-bicyclo[3.2.1]octan-8-ylsulfonyl)methyl)piperidine-1-carboxylate

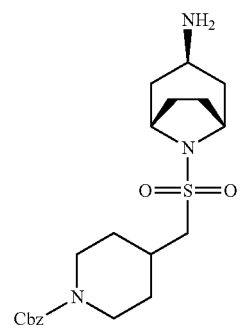 [SMILES: N[C@H]1C[C@H]2CC[C@@H](C1)N2S(=O)(=O)CC1CCN(C(=O)OCc2ccccc2)CC1]

Into a 100-mL round-bottom flask was placed benzyl 4-[[(1R,3r,5S)-3-[[(2,2,2-trichloroethoxy)carbonyl]amino]-8-azabicyclo[3.2.1]octane-8-sulfonyl]methyl]piperidine-1-carboxylate (1 g, 1.68 mmol, 1.00 equiv), acetic acid (15 mL), water (1 mL), and zinc (1.63 g, 24.92 mmol, 14.88 equiv). The resulting mixture was stirred for 2 h at room temperature and then diluted with 30 mL of H₂O. The solids were filtered out. The pH value of the filtrate was adjusted to 9 with NaOH (40%, aq.). The resulting solution was extracted with 3×30 mL of dichloromethane and the organic layers combined, dried over anhydrous sodium sulfate and concentrated under vacuum. This resulted in 0.7 g (99%) of benzyl 4-[[(1R,3r,5S)-3-amino-8-azabicyclo[3.2.1]octane-8-sulfonyl]methyl]piperidine-1-carboxylate as a white solid. LCMS (method D, ESI): RT=0.85 min, m/z=422.3 [M+H]⁺.

Step 3: Synthesis of benzyl 4-(((1R,3r,5S)-3-(2-oxo-2,3-dihydrobenzo[d]oxazole-6-carboxamido)-8-aza-bicyclo[3.2.1]octan-8-ylsulfonyl)methyl)piperidine-1-carboxylate

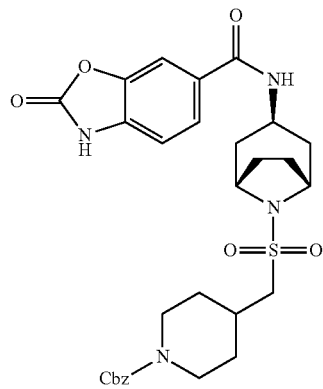 [SMILES: O=C(N[C@H]1C[C@H]2CC[C@@H](C1)N2S(=O)(=O)CC1CCN(C(=O)OCc2ccccc2)CC1)c1ccc2[nH]c(=O)oc2c1]

Into a 25-mL round-bottom flask was placed 2-oxo-2,3-dihydro-1,3-benzoxazole-6-carboxylic acid (100 mg, 0.56 mmol, 2.35 equiv), N,N-dimethylformamide (10 mL), HOBT (135 mg, 2.00 equiv) and EDCI (191 mg, 2.00 equiv). Then benzyl 4-[[(1R,3r,5S)-3-amino-8-azabicyclo[3.2.1]octane-8-sulfonyl]methyl]piperidine-1-carboxylate (100 mg, 0.24 mmol, 1.00 equiv) was added in several portions. After complete addition, TEA (250 mg, 5.00 equiv) was added dropwise. The resulting solution was stirred for 1 h at room temperature. The mixture was concentrated under vacuum and the residue diluted with 10 mL of H₂O. This mixture was extracted with 3×10 ml of ethyl acetate and the organic layers combined. The combined extracts were washed with 2×30 mL of brine, dried, and concentrated. The residue was chromatographed on a silica gel column with dichloromethane/methanol (10/1). This resulted in 100 mg (72%) of benzyl 4-[[(1R,3r,5S)-3-(2-oxo-2,3-dihydro-1,3-benzoxazole-6-amido)-8-azabicyclo[3.2.1]octane-8-sulfonyl]methyl]piperidine-1-carboxylate as yellow oil. LCMS (method D, ESI): RT=1.38 min, m/z=583.0 [M+H]⁺.

Step 4: Synthesis of 2-oxo-N-((1R,3r,5S)-8-(piperidin-4-ylmethylsulfonyl)-8-aza-bicyclo[3.2.1]octan-3-yl)-2,3-dihydrobenzo[d]oxazole-6-carboxamide

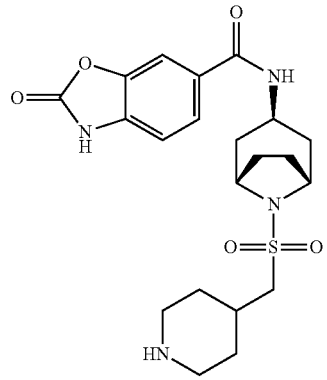

Into a 25-mL round-bottom flask was placed benzyl 4-[[(1R,3r,5S)-3-(2-oxo-2,3-dihydro-1,3-benzoxazole-6-amido)-8-azabicyclo[3.2.1]octane-8-sulfonyl]methyl]piperidine-1-carboxylate (100 mg, 0.17 mmol, 1.00 equiv) and hydrochloric acid (12N, 10 mL). The resulting solution was stirred for 4 h at room temperature and then concentrated under vacuum. The residue was applied onto Pre-HPLC with the following conditions: Column: X Bridge C18, 19*150 mm, 5 um; Mobile Phase A: Water/0.05% TFA, Mobile Phase B: ACN; Flow rate: 20 mL/min; Gradient: 30% B to 70% B in 10 min; 254 nm. The product was dissolved again into hydrochloric acid (5 mL, 12 N) and concentrated under vacuum. This resulted in 7.3 mg (9%) of 2-oxo-N-[(1R,3r,5S)-8-[(piperidin-4-ylmethane)sulfonyl]-8-azabicyclo[3.2.1]octan-3-yl]-2,3-dihydro-1,3-benzoxazole-6-carboxamide as a white solid. ¹H NMR (300 MHz, D₂O) δ: 7.52-7.49 (m, 2H), 7.18-7.16 (m, 1H), 4.21 (s, 2H), 4.08-4.03 (m, 1H), 3.38-3.34 (m, 2H), 3.20-3.18 (m, 2H), 3.02-2.93 (m, 2H), 2.24-1.94 (m, 11H), 1.54-1.51 (m, 2H) ppm. LCMS (method D, ESI): RT=1.65 min, m/z=449.2 [M−HCl+H]⁺.

Example 12

Synthesis of (2R)-2-methyl-3-oxo-N-[(1R,3r,5S)-8-[(piperidin-4-ylmethane)sulfonyl]-8-azabicyclo[3.2.1]octan-3-yl]-3,4-dihydro-2H-1,4-benzoxazine-6-carboxamide Hydrochloride (Cpd. No. 625)

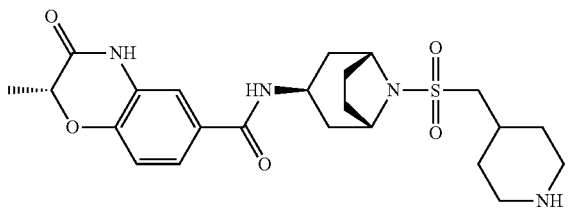 [SMILES: C[C@H]1Oc2ccc(C(=O)N[C@H]3C[C@H]4CC[C@@H](C3)N4S(=O)(=O)CC3CCNCC3)cc2NC1=O]

Step 1: Synthesis of methyl 3-(2-bromopropanamido)-4-hydroxybenzoate

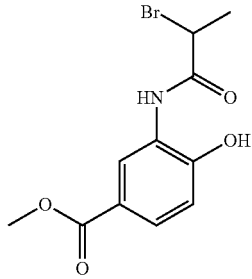 [SMILES: COC(=O)c1ccc(O)c(NC(=O)C(C)Br)c1]

Into a 100-mL round-bottom flask was placed ethyl acetate (10 mL), water (10 mL), methyl 3-amino-4-hydroxybenzoate (1 g, 5.98 mmol, 1.00 equiv), and sodium bicarbonate (553 mg, 1.10 equiv). This was followed by the addition 2-bromopropanoyl bromide (1.3 g, 6.02 mmol, 1.00 equiv) which was added dropwise with stirring at 0° C. The resulting solution was stirred for 30 min at room temperature. The mixture was then washed with 2×30 mL of $H_2O$ and 1×30 mL of brine. The mixture was dried over anhydrous sodium sulfate, filtered and concentrated under vacuum. This resulted in 1.5 g (83%) of methyl 3-(2-bromopropanamido)-4-hydroxybenzoate as a brown solid. $^1$H NMR (300 MHz, $CDCl_3$) δ: 8.89 (s, 1H), 8.43 (s, 1H), 7.89-7.82 (m, 2H), 7.04 (d, J=8.4 Hz, 1H), 4.65 (q, J=14.1 Hz, 1H), 3.07 (s, 3H), 2.01 (d, J=7.2 Hz, 3H) ppm. LCMS (method D, ESI): RT=1.30 min, m/z=302.0 $[M+H]^+$.

Step 2: Synthesis of methyl 2-methyl-3-oxo-3,4-dihydro-2H-benzo[b][1,4]oxazine-6-carboxylate

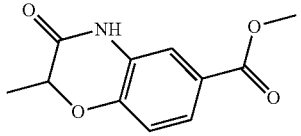

Into a 100-mL round-bottom flask was placed N,N-dimethylformamide (10 mL), methyl 3-(2-bromopropanamido)-4-hydroxybenzoate (1.5 g, 4.96 mmol, 1.00 equiv), and potassium carbonate (880 mg, 1.30 equiv). The resulting mixture was stirred for 15 h at room temperature. The mixture was then diluted with 30 mL of $H_2O$. The solids were collected by filtration. This resulted in 1 g (91%) of methyl 2-methyl-3-oxo-3,4-dihydro-2H-benzo[b][1,4]oxazine-6-carboxylate as a brown solid. $^1$H NMR (400 MHz, $CDCl_3$) δ : 8.29 (s, 1H), 7.72 (q, J=8.4 Hz, 1H), 7.56 (d, J=2 Hz, 1H), 7.03 (d, J=8.4 Hz, 1H), 4.77 (q, J=14 Hz, 1H), 3.93 (s, 3H), 1.64 (d, J=7.2 Hz, 3H) ppm. LCMS (method C, ESI): RT=0.96 min, m/z=222.0 $[M+H]^+$.

Step 3: Synthesis of 2-methyl-3-oxo-3,4-dihydro-2H-benzo[b]1,4]oxazine-6-carboxylic Acid

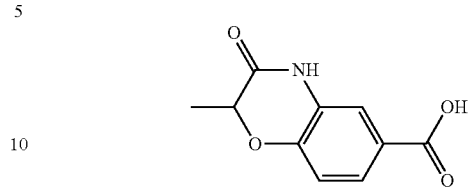

Into a 100-mL round-bottom flask was placed tetrahydrofuran (15 mL), methanol (15 mL), water (10 mL), and methyl 2-methyl-3-oxo-3,4-dihydro-2H-1,4-benzo[b][1,4]oxazine-6-carboxylate (1 g, 4.52 mmol, 1.00 equiv). This was followed by the addition of a solution of sodium hydroxide (362 mg, 2.00 equiv) in 5 ml $H_2O$ which was added dropwise with stirring at 0° C. The resulting solution was stirred for 10 min at 0° C. in an ice/salt bath. The resulting solution was allowed to react, with stirring, for an additional 15 h at room temperature. The reaction mixture was concentrated under vacuum. The residue was diluted with 30 mL of $H_2O$ and the pH adjusted to 3-4 with hydrochloric acid (1 N). The solids were collected by filtration. This resulted in 900 mg (96%) of 2-methyl-3-oxo-3,4-dihydro-2H-benzo[b][1,4]oxazine-6-carboxylic acid as a white solid. $^1$H NMR (400 MHz, $CD_3OD$) δ: 7.68 (q, J=8.4 Hz, 1H), 7.59 (d, J=2 Hz, 1H), 4.47 (s, 1H), 7.03 (d, J=8.4 Hz, 1H), 4.75 (q, J=13.6 Hz, 1H), 1.55 (d, J=6.8 Hz, 3H) ppm. LCMS (method A, ESI): RT=1.08 min, m/z=208.0 $[M+H]^+$.

Step 4: Synthesis of tert-butyl (1R,3r,5S)-3-(2-methyl-3-oxo-3,4-dihydro-2H-benzo[b][1,4]oxazine-6-carboxamido)-8-azabicyclo[3.2.1]octane-8-carboxylate

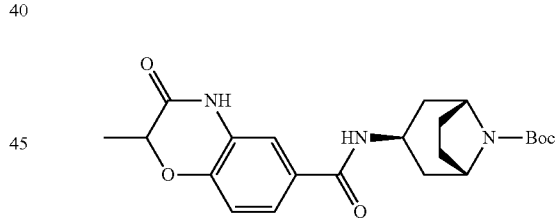

Into a 100-mL round-bottom flask was placed N,N-dimethylformamide (50 mL), 2-methyl-3-oxo-3,4-dihydro-2H-benzo[b][1,4]oxazine-6-carboxylic acid (500 mg, 2.41 mmol, 1.00 equiv), EDCI (923 mg, 2.00 equiv), HOBT (652 mg, 2.00 equiv), and tert-butyl (1R,3r,5S)-3-amino-8-azabicyclo[3.2.1]octane-8-carboxylate (710 mg, 3.14 mmol, 1.30 equiv). This was followed by the addition of TEA (1232 mg, 5.0 equiv) which was added dropwise with stirring at 0° C. The resulting solution was stirred for 14 h at room temperature. The reaction mixture was then diluted with 50 mL of EA. The resulting mixture was washed with 3×30 mL of $H_2O$ and 1×30 mL of brine. The mixture was dried over anhydrous sodium sulfate, filtered and concentrated. The residue was chromatographed on a silica gel column with ethyl acetate/petroleum ether (4:1). This resulted in 800 mg (80%) of tert-butyl (1R,3r,5S)-3-(2-methyl-3-oxo-3,4-dihydro-2H-benzo[b][1,4]oxazine-6-carboxamido)-8-azabicyclo[3.2.1]octane-8-carboxylate as a white solid. $^1$H NMR (400 MHz, CDCl$_3$) δ: 8.66 (s, 1H), 7.52 (d, J=1.6 Hz, 1H), 7.22 (q, J=8.4 Hz, 1H), 7.02 (d, J=8.4 Hz, 1H), 6.51 (d, J=6.8 Hz, 1H), 4.72 (q, J=13.6 Hz, 1H), 4.39-4.20 (m, 3H), 2.45-2.25 (m, 2H), 2.20-2.10 (m, 2H), 1.95-1.75 (m, 4H), 1.60 (d, J=7.2 Hz, 3H), 1.50 (s, 9H) ppm. LCMS (method C, ESI): RT=1.08 min, m/z=416.0 [M+H]$^+$.

Step 5: Synthesis of N-[(1R,3r,5S)-8-azabicyclo[3.2.1]octan-3-yl]-2-methyl-3-oxo-3,4-dihydro-2H-benzo[b][1,4]oxazine-6-carboxamide

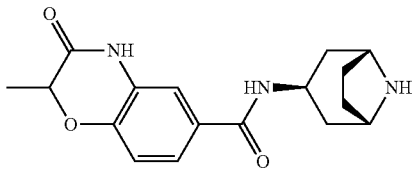 [SMILES: CC1Oc2ccc(C(=O)N[C@H]3C[C@H]4CC[C@@H](C3)N4)cc2NC1=O]

Into a 100-mL round-bottom flask was placed dichloromethane (20 mL) and tert-butyl (1R,3r,5S)-3-(2-methyl-3-oxo-3,4-dihydro-2H-benzo[b][1,4]oxazine-6-carboxamido)-8-azabicyclo[3.2.1]octane-8-carboxylate (800 mg, 1.93 mmol, 1.00 equiv). To the above, hydrogen chloride (gas) was introduced. The resulting solution was stirred for 4 h at room temperature and then was concentrated under vacuum. The residue was diluted with 40 mL of H$_2$O. The pH was adjusted to 8 with saturated aqueous sodium carbonate and the resulting mixture extracted with 3×40 mL of DCM. The organic layers were combined and washed with 2×40 mL of brine. The extract was concentrated under vacuum. This resulted in 500 mg (82%) of N-[(1R,3r,5S)-8-azabicyclo[3.2.1]octan-3-yl]-2-methyl-3-oxo-3,4-dihydro-2H-benzo[b][1,4]oxazine-6-carboxamide as a light yellow solid. $^1$H NMR (400 MHz, CDCl$_3$) δ: 7.42 (q, J=8.4 Hz, 1H), 7.37 (d, J=2 Hz, 1H), 7.04 (d, J=8.4 Hz, 1H), 4.72 (q, J=13.6 Hz, 1H), 4.12 (t, J=6.4 Hz, 1H), 3.69 (s, 2H), 2.22-2.15 (m, 4H), 2.10-1.95 (m, 4H), 1.54 (d, J=6.8 Hz, 3H) ppm. LCMS (method A, ESI): RT=0.93 min, m/z=364.0 [M+H]$^+$.

Step 6: Synthesis of benzyl 4-[[(1R,3r,5S)-3-(2-methyl-3-oxo-3,4-dihydro-2H-benzo[b][1,4]oxazine-6-carboxamido)-8-azabicyclo[3.2.1]octane-8-sulfonyl]methyl]piperidine-1-carboxylate

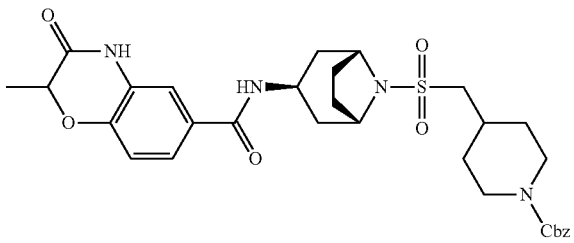 [SMILES: CC1Oc2ccc(C(=O)N[C@H]3C[C@H]4CC[C@@H](C3)N4S(=O)(=O)CC3CCN(C(=O)OCc4ccccc4)CC3)cc2NC1=O]

Into a 100-mL 3-necked round-bottom flask was placed N,N-dimethylformamide (10 mL), N-[(1R,3r,5S)-8-azabicyclo[3.2.1]octan-3-yl]-2-methyl-3-oxo-3,4-dihydro-2H-benzo[b][1,4]oxazine-6-carboxamide (250 mg, 0.79 mmol, 1.00 equiv), and TEA (231 mg, 3.00 equiv). This was followed by the addition of a solution of benzyl 4-[(chlorosulfonyl)methyl]piperidine-1-carboxylate (657 mg, 1.98 mmol, 2.50 equiv) in 2 ml N,N-dimethylformamide which was added dropwise with stirring at −20° C. The resulting solution was stirred for 30 min at −20° C. The mixture was allowed to react, with stirring, for an additional 15 h at room temperature. The mixture was diluted with 50 mL of EA and washed with 2×20 mL of water and 2×20 mL of brine. The organic phase was dried over anhydrous sodium sulfate and filtered. The residue was chromatographed on a silica gel column with dichloromethane/methanol (20:1). This resulted in 60 mg (12%) of benzyl 4-[[(1R,3r,5S)-3-(2-methyl-3-oxo-3,4-dihydro-2H-benzo[b][1,4]oxazine-6-carboxamido)-8-azabicyclo[3.2.1]octane-8-sulfonyl]methyl]piperidine-1-carboxylate as a white solid. LCMS (method B, ESI): RT=1.43 min, m/z=611.0 [M+H]$^+$.

Step 7: Synthesis of benzyl 4-[[(1R,3r,5S)-3-[(2R)-2-methyl-3-oxo-3,4-dihydro-2H-benzo[b][1,4]oxazine-6-amido]-8-azabicyclo[3.2.1]octane-8-sulfonyl]methyl]piperidine-1-carboxylate

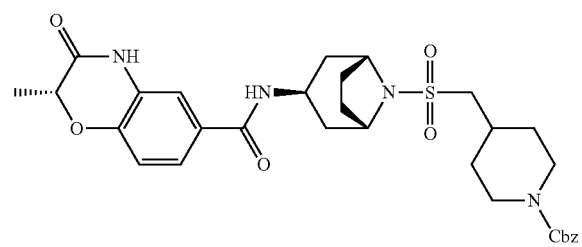 [SMILES: C[C@H]1Oc2ccc(C(=O)N[C@H]3C[C@H]4CC[C@@H](C3)N4S(=O)(=O)CC3CCN(C(=O)OCc4ccccc4)CC3)cc2NC1=O]

Benzyl 4-[[(1R,3r,5S)-3-(2-methyl-3-oxo-3,4-dihydro-2H-benzo[b][1,4]oxazine-6-carboxamido)-8-azabicyclo[3.2.1]octane-8-sulfonyl]methyl]piperidine-1-carboxylate (60 mg) was purified by Chiral-Prep-HPLC with the following conditions (Chiral HPLC): Column, CHIRALPAK IA; mobile phase, MTBE:EtOH=50:50; Detector, 254 nm. This resulted in 28 mg (47%) of benzyl 4-[[(1R,3r,5S)-3-[(2R)-2-methyl-3-oxo-3,4-dihydro-2H-benzo[b][1,4]oxazine-6-carboxamido]-8-azabicyclo[3.2.1]octane-8-sulfonyl]methyl]piperidine-1-carboxylate as a white solid. ee value: 100%

Step 8: Synthesis of (2R)-2-methyl-3-oxo-N-[(1R,3r,5S)-8-[(piperidin-4-ylmethane)sulfonyl]-8-azabicyclo[3.2.1]octan-3-yl]-3,4-dihydro-2H-benzo[b][1,4]oxazine-6-carboxamide Hydrochloride

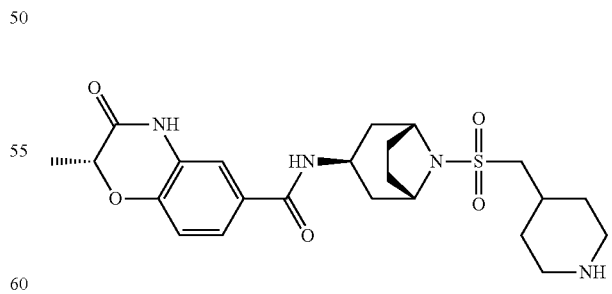

Into a 50-mL round-bottom flask was placed benzyl 4-[[(1R,3r,5S)-3-[(2R)-2-methyl-3-oxo-3,4-dihydro-2H-benzo[b][1,4]oxazine-6-carboxamido]-8-azabicyclo[3.2.1]octane-8-sulfonyl]methyl]piperidine-1-carboxylate (28 mg, 0.05 mmol, 1.00 equiv) and hydrochloric acid (12N, 10 mL). The resulting solution was stirred for 4 h at room temperature. The resulting mixture was washed with 2×10 mL of DCM and the aqueous layer concentrated under vacuum. The crude product was purified by Prep-HPLC with the following conditions (Prep_HPLC_MC5): Column, X Select C18, 19*250 mm, 5 um; mobile phase, Water/0.05% TFA, Mobile Phase B: ACN; Flow rate: 30 mL/min; Gradient: 23% B to 42% B in 11.5 min; Detector, 254 nm. The resulting fractions were concentrated under vacuum. The solids were dissolved in 2 ml hydrochloric acid (12 N) and again concentrated under vacuum. This resulted in 4.9 mg (21%) of (2R)-2-methyl-3-oxo-N-[(1R,3r,5S)-8-[(piperidin-4-ylmethane)sulfonyl]-8-azabicyclo[3.2.1]octan-3-yl]-3,4-dihydro-2H-benzo[b][1,4]oxazine-6-carboxamide hydrochloride as a white solid. $^1$HNMR (400 MHz, D$_2$O) δ: 7.32 (d, J=8 Hz, 1H), 7.21 (s, 1H), 7.01 (d, J=8.4 Hz, 1H), 4.79-4.72 (m, 1H), 4.21 (s, 2H), 4.04 (s, 1H), 3.37 (d, J=12.8 Hz, 2H), 3.20 (d, J=6.4 Hz, 2H), 2.95 (t, J=10.4 Hz, 2H), 2.25-2.15 (m, 3H), 2.14-2.00 (m, 6H), 1.95 (d, J=14.8 Hz, 2H), 1.65-1.40 (m, 5H) ppm. LCMS (method A, ESI): RT=1.49 min, m/z=477.3[M−HCl+H]$^+$.

Example 13

Synthesis of N-[(1R,3r,5S)-8-[4-(benzylamino)piperidine-1-sulfonyl]-8-azabicyclo[3.2.1]octan-3-yl]-2-oxo-2,3-dihydro-1H-indole-5-carboxamide (Cpd. No. 587)

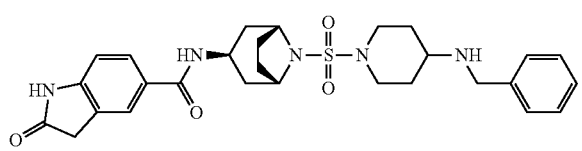 [SMILES: O=C1Cc2cc(C(=O)N[C@H]3C[C@H]4CC[C@@H](C3)N4S(=O)(=O)N3CCC(NCc4ccccc4)CC3)ccc2N1]

Step 1: Synthesis of tert-butyl (1R,3r,5S)-3-[[(2,2,2-trichloroethoxy)carbonyl]amino]-8-azabicyclo[3.2.1]octane-8-carboxylate

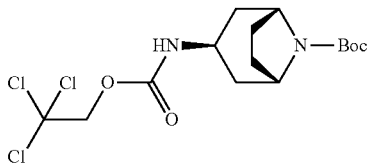 [SMILES: CC(C)(C)OC(=O)N1[C@@H]2CC[C@H]1C[C@@H](NC(=O)OCC(Cl)(Cl)Cl)C2]

Into a 250-mL 3-necked round-bottom flask was placed tert-butyl (1R,3r,5S)-3-amino-8-azabicyclo[3.2.1]octane-8-carboxylate (5 g, 22.09 mmol, 1.00 equiv), water (100 mL), and NaHCO$_3$ (4.83 g, 149.50 mmol, 2.60 equiv). The solution was cooled to 0° C. and 2,2,2-trichloroethyl chloroformate (5.63 g, 26.57 mmol, 1.20 equiv) added dropwise over 10 mins. The resulting solution was stirred at room temperature overnight. The reaction mixture was extracted with 3×100 mL of dichloromethane and the organic layers combined. The combined extracts were washed with 3×100 mL of brine, dried over anhydrous sodium sulfate, filtered and concentrated under vacuum. The resulting residue was washed with 3×100 mL of hexane. This resulted in 8.32 g (94%) of tert-butyl (1R,3r,5S)-3-[[(2,2,2-trichloroethoxy)carbonyl]amino]-8-azabicyclo[3.2.1]octane-8-carboxylate as a white solid. $^1$H NMR (300 MHz, CDCl$_3$) δ: 5.30 (brs, 1H), 4.73 (s, 2H), 4.23 (brs, 2H), 4.00-3.89 (m, 1H), 2.30-2.17 (m, 2H), 2.12-2.03 (m, 2H), 1.90-1.80 (m, 2H), 1.78-1.69 (m, 2H), 1.46 (s, 9H) ppm. LCMS (method C, ESI): RT=1.27 min, m/z=386.0 [M+H−15]$^+$.

Step 2: Synthesis of 2,2,2-trichloroethyl N-[(1R,3r,5S)-8-azabicyclo[3.2.1]octan-3-yl]carbamate

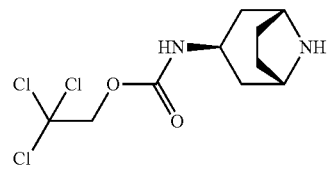 [SMILES: O=C(N[C@H]1C[C@H]2CC[C@@H](C1)N2)OCC(Cl)(Cl)Cl]

Into a 250-mL round-bottom flask was placed tert-butyl (1R,3r,5S)-3-[[(2,2,2-trichloroethoxy)carbonyl]amino]-8-azabicyclo[3.2.1]octane-8-carboxylate (4 g, 9.96 mmol, 1.00 equiv) and dichloromethane (40 mL). To this hydrogen chloride (gas) was introduced. The resulting solution was stirred for 1 h at room temperature. The mixture was then concentrated under vacuum. This resulted in 3.3 g (98%) of 2,2,2-trichloroethyl N-[(1R,3r,5S)-8-azabicyclo[3.2.1]octan-3-yl]carbamate hydrochloride as a white solid. $^1$H NMR (300 MHz, D$_2$O) δ: 4.72 (s, 2H), 4.09 (brs, 2H), 3.83-3.75 (m, 1H), 2.28-1.95 (m, 8H) ppm.

Step 3: Synthesis of 2,2,2-trichloroethyl N-[(1R,3r,5S)-8-(4-[[(tert-butoxy)carbonyl]amino]piperidine-1-sulfonyl)-8-azabicyclo[3.2.1]octan-3-yl]carbamate

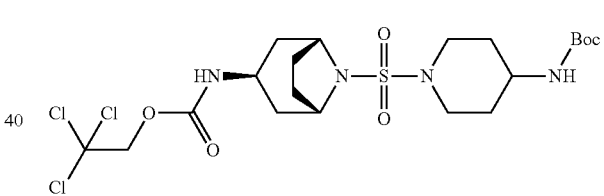

Into a 25-mL round-bottom flask was placed 2,2,2-trichloroethyl N-[(1R,3r,5S)-8-azabicyclo[3.2.1]octan-3-yl]carbamate hydrochloride (1.0 g, 2.96 mmol, 1.00 equiv) and dichloromethane (15 mL). This was followed by the addition of TEA (1.5 g, 14.82 mmol, 5.01 equiv) dropwise with stirring at 0° C. To this was then added tert-butyl N-[1-(chlorosulfonyl)piperidin-4-yl]carbamate (1.8 g, 6.02 mmol, 2.04 equiv) in several batches at 0° C. The resulting solution was stirred for 14 h at 20° C. The reaction mixture was diluted with 35 mL of dichloromethane and washed with 3×10 mL of brine. The organic layer was dried over anhydrous sodium sulfate and concentrated under vacuum. The residue was chromatographed on a silica gel column with ethyl acetate/petroleum ether (1:2). This resulted in 1.5 g (90%) of 2,2,2-trichloroethyl N-[(1R,3r,5S)-8-(4-[[(tert-butoxy)carbonyl]amino]piperidine-1-sulfonyl)-8-azabicyclo[3.2.1]octan-3-yl]carbamate as a white solid. $^1$H NMR (400 MHz, CDCl$_3$) δ: 5.22 (brs, 1H), 4.75 (s, 2H), 4.46 (brs, 1H), 4.13 (brs, 2H), 4.01-3.95 (m, 1H), 3.70 (d, J=12.0 Hz, 2H), 3.58 (brs, 1H), 2.84 (t, J=11.2 Hz, 2H), 2.33-2.14 (m, 4H), 2.10-1.98 (m, 2H), 1.96-1.84 (m, 3H), 1.65-1.50 (m, 3H), 1.47 (s, 9H) ppm. LCMS (method D, ESI): RT=1.58 min, m/z=507.0 [M+H−56]$^+$.

Step 4: Synthesis of tert-butyl N-[1-[(1R,3r,5S)-3-amino-8-azabicyclo[3.2.1]octane-8-sulfonyl]piperidin-4-yl]carbamate

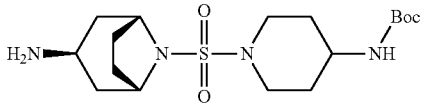

Into a 100-mL round-bottom flask was placed 2,2,2-trichloroethyl N-[(1R,3r,5S)-8-(4-[[(tert-butoxy)carbonyl]amino]piperidine-1-sulfonyl)-8-azabicyclo[3.2.1]octan-3-yl]carbamate (1.0 g, 1.77 mmol, 1.00 equiv), AcOH (15 mL), zinc (1.73 g, 26.45 mmol, 14.92 equiv) and water (1 mL). The resulting mixture was stirred for 1 h at 25° C. The mixture was then diluted with 30 mL of H₂O and the solids were filtered out. The pH was adjusted to 9 with sodium carbonate (aq. sat.). The resulting solution was extracted with 5×30 mL of dichloromethane and the organic layers combined. After concentration this resulted in 500 mg (73%) of tert-butyl N-[1-[(1R,3r,5S)-3-amino-8-azabicyclo[3.2.1]octane-8-sulfonyl]piperidin-4-yl]carbamate as a white solid. LCMS (method A, ESI): RT=1.08 min, m/z=333.0 [M+H−56]⁺.

Step 5: Synthesis of tert-butyl N-[1-[(1R,3r,5S)-3-(2-oxo-2,3-dihydro-1H-indole-5-carboxamido)-8-azabicyclo[3.2.1]octane-8-sulfonyl]piperidin-4-yl]carbamate

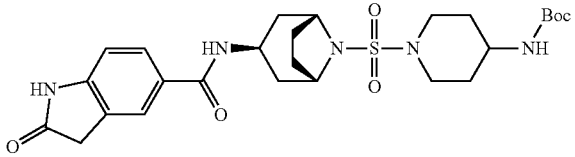 [SMILES: CC(C)(C)OC(=O)NC1CCN(S(=O)(=O)N2[C@@H]3CC[C@H]2C[C@@H](NC(=O)c2ccc4c(c2)CC(=O)N4)C3)CC1]

Into a 25-mL round-bottom flask was placed tert-butyl N-[1-[(1R,3r,5S)-3-amino-8-azabicyclo[3.2.1]octane-8-sulfonyl]piperidin-4-yl]carbamate (200 mg, 0.51 mmol, 1.00 equiv), dichloromethane (5 mL), 2-oxo-2,3-dihydro-1H-indole-5-carboxylic acid (109 mg, 0.62 mmol, 1.20 equiv), EDCI (118 mg, 0.62 mmol, 1.20 equiv), and HOBT (104 mg, 0.77 mmol, 1.50 equiv). This was followed by the addition of TEA (260 mg, 2.57 mmol, 4.99 equiv) dropwise with stirring at 0° C. The resulting solution was stirred for 14 h at 20° C. The reaction mixture was then diluted with 10 mL of dichloromethane and was washed with 2×5 mL of brine. The organic layer was dried over anhydrous sodium sulfate and concentrated under vacuum. The residue was chromatographed on a silica gel column with ethyl acetate/petroleum ether (1:1). This resulted in 243 mg (86%) of tert-butyl N-[1-[(1R,3r,5S)-3-(2-oxo-2,3-dihydro-1H-indole-5-carboxamido)-8-azabicyclo[3.2.1]octane-8-sulfonyl]piperidin-4-yl]carbamate as a off-white solid. LCMS (method A, ESI): RT=1.27 min, m/z=448.0 [M+H−100]⁺.

Step 6: Synthesis of N-[(1R,3r,5S)-8-(4-aminopiperidine-1-sulfonyl)-8-azabicyclo[3.2.1]octan-3-yl]-2-oxo-2,3-dihydro-1H-indole-5-carboxamide

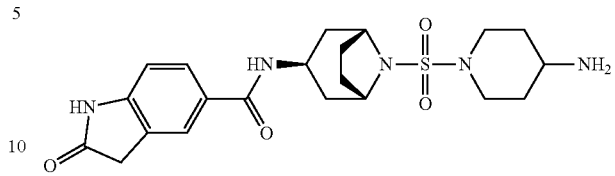

Into a 25-mL round-bottom flask was placed tert-butyl N-[1-[(1R,3r,5S)-3-(2-oxo-2,3-dihydro-1H-indole-5-carboxamido)-8-azabicyclo[3.2.1]octane-8-sulfonyl]piperidin-4-yl]carbamate (241 mg, 0.44 mmol, 1.00 equiv) and dichloromethane (5 mL). To this hydrogen chloride (gas) was introduced. The resulting solution was stirred for 2 h at 15° C. The mixture was then concentrated under vacuum. This resulted in 200 mg (94%) of N-[(1R,3r,5S)-8-(4-aminopiperidine-1-sulfonyl)-8-azabicyclo[3.2.1]octan-3-yl]-2-oxo-2,3-dihydro-1H-indole-5-carboxamide hydrochloride as a yellow solid. ¹H NMR (400 MHz, CD₃OD): 7.70 (d, J=8.0 Hz, 2H), 6.97 (d, J=8.0 Hz, 1H), 4.14 (s, 3H), 3.86 (d, J=13.2 Hz, 2H), 3.61 (s, 2H), 3.31-3.25 (m, 1H), 2.91 (t, J=12.4 Hz, 2H), 2.37-2.25 (m, 2H), 2.21-1.98 (m, 8H), 1.76-1.63 (m, 2H) ppm. LCMS (method A, ESI): RT=1.07 min, m/z=448.3 [M+H]⁺.

Step 7: Synthesis of N-[(1R,3r,5S)-8-[4-(benzylamino)piperidine-1-sulfonyl]-8-azabicyclo[3.2.1]octan-3-yl]-2-oxo-2,3-dihydro-1H-indole-5-carboxamide

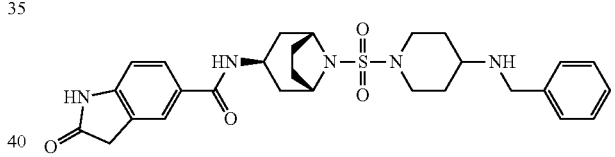

Into a 25-mL round-bottom flask was placed N-[(1R,3r,5S)-8-(4-aminopiperidine-1-sulfonyl)-8-azabicyclo[3.2.1]octan-3-yl]-2-oxo-2,3-dihydro-1H-indole-5-carboxamide hydrochloride (60 mg, 0.12 mmol, 1.00 equiv), methanol (5 mL), and benzaldehyde (13 mg, 0.12 mmol, 0.99 equiv). The mixture was stirred for 0.5 h at 20° C. To this NaBH₃CN (7.8 mg, 0.12 mmol, 1.00 equiv) was added in batches. The resulting solution was stirred for 2 h at 70° C. The reaction mixture was concentrated under vacuum. The residue was diluted with 5 mL of H₂O and extracted with 2×5 mL of dichloromethane. The organic layers combined and concentrated. The crude product was purified by Prep-HPLC with the following conditions: Column, X Bridge C18, 19*150 mm, 5 um; Mobile Phase A: Water/0.05% TFA, Mobile Phase B: ACN; Flow rate: 20 mL/min; Gradient: 30% B to 70% B in 10 min; Detector, 254 nm. This resulted in 14.8 mg (18%) of N-[(1R,3r,5S)-8-[4-(b enzylamino)piperidine-1-sulfonyl]-8-azabicyclo[3.2.1]octan-3-yl]-2-oxo-2,3-dihydro-1H-indole-5-carboxamide trifluoroacetic acid as a white solid. ¹H NMR (300 MHz, CD₃OD): 7.70 (d, J=7.8 Hz, 2H), 7.69-7.48 (m, 5H), 6.97 (d, J=8.4 Hz, 1H), 4.28 (s, 2H), 4.14 (s, 3H), 3.92 (d, J=12.6 Hz, 2H), 3.60 (s, 2H), 3.54-3.35 (m, 1H), 2.90 (t, J=13.2 Hz, 2H), 2.35-2.22 (m, 4H), 2.21-2.10 (m, 4H), 2.09-1.98 (m, 2H), 1.85-1.68 (m, 2H) ppm. LCMS (method A, ESI): RT=2.26 min, m/z=538.4 [M+H]⁺.

Example 14

Synthesis of N-[(1R,3r,5S)-8-[4-(benzylamino)piperidine-1-sulfonyl]-8-azabicyclo[3.2.1]octan-3-yl]-6-chloro-2-oxo-2,3-dihydro-1H-indole-5-carboxamide Trifluoroacetate (Cpd. No. 592)

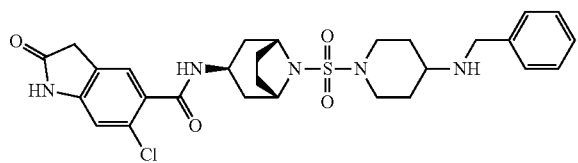 [SMILES: O=C1Cc2cc(C(=O)N[C@H]3C[C@H]4CC[C@@H](C3)N4S(=O)(=O)N3CCC(NCc4ccccc4)CC3)c(Cl)cc2N1]

Step 1: Synthesis of tert-butyl N-[1-[(1R,3r,5S)-3-(6-chloro-2-oxo-2,3-dihydro-1H-indole-5-carboxamido)-8-azabicyclo[3.2.1]octane-8-sulfonyl]piperidin-4-yl]carbamate

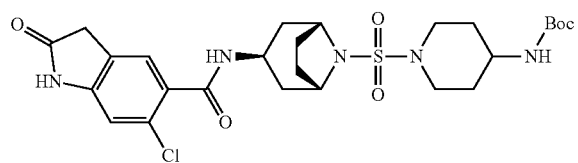 [SMILES: CC(C)(C)OC(=O)NC1CCN(S(=O)(=O)N2[C@@H]3CC[C@H]2C[C@@H](NC(=O)c2cc4c(cc2Cl)NC(=O)C4)C3)CC1]

Into a 25-mL round-bottom flask was placed 6-chloro-2-oxo-2,3-dihydro-1H-indole-5-carboxylic acid (170 mg, 0.80 mmol, 1.00 equiv), dichloromethane (10 mL), HOBT (216 mg, 1.60 mmol, 2.00 equiv), EDCI (306 mg, 1.60 mmol, 2.00 equiv), and tert-butyl N-1-[(1R,3r,5S)-3-amino-8-azabicyclo[3.2.1]octane-8-sulfonyl]piperidin-4-ylcarbamate (375 mg, 0.97 mmol, 1.20 equiv). This was followed by the addition of TEA (400 mg, 3.95 mmol, 5.00 equiv) dropwise with stirring at 0° C. The resulting solution was stirred for 2 h at room temperature. The reaction mixture was diluted with 10 mL of dichloromethane and washed with 2×5 mL of brine. The organic layer was dried over anhydrous sodium sulfate and concentrated under vacuum. The residue was chromatographed on a silica gel column with ethyl acetate/petroleum ether (3:1). This resulted in 300 mg (64%) of tert-butyl N-[1-[(1R,3r,5S)-3-(6-chloro-2-oxo-2,3-dihydro-1H-indole-5-carboxamido)-8-azabicyclo[3.2.1]octane-8-sulfonyl]piperidin-4-yl]carbamate as a red solid. LCMS (method C, ESI): RT=0.88 min, m/z=582.0 [M+H]$^+$.

Step 2: Synthesis of N-[(1R,3r,5S)-8-(4-aminopiperidine-1-sulfonyl)-8-azabicyclo[3.2.1]octan-3-yl]-6-chloro-2-oxo-2,3-dihydro-1H-indole-5-carboxamide Hydrochloride

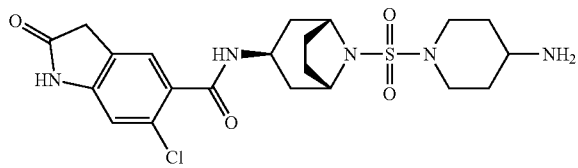 [SMILES: NC1CCN(S(=O)(=O)N2[C@@H]3CC[C@H]2C[C@@H](NC(=O)c2cc4c(cc2Cl)NC(=O)C4)C3)CC1]

Into a 25-mL round-bottom flask was placed tert-butyl N-[1-[(1R,3r,5S)-3-(6-chloro-2-oxo-2,3-dihydro-1H-indole-5-carboxamido)-8-azabicyclo[3.2.1]octane-8-sulfonyl]piperidin-4-yl]carbamate (300 mg, 0.52 mmol, 1.00 equiv) and hydrogen chloride/dioxane (10 mL, saturated, this solution was made by introducing hydrogen chloride gas into 1,4-dioxane under 0° C. for 6 hours). The resulting solution was stirred for 4 h at room temperature. The mixture was then concentrated under vacuum. This resulted in 170 mg (64%) of N-[(1R,3r,5S)-8-(4-aminopiperidine-1-sulfonyl)-8-azabicyclo[3.2.1]octan-3-yl]-6-chloro-2-oxo-2,3-dihydro-1H-indole-5-carboxamide hydrochloride as a red solid. LCMS (method A, ESI): RT=0.96 min, m/z=482.0 [M+H]$^+$.

Step 3: Synthesis of N-[(1R,3r,5S)-8-[4-(b enzylamino)piperidine-1-sulfonyl]-8-azabicyclo[3.2.1] octan-3-yl]-6-chloro-2-oxo-2,3-dihydro-1H-indole-5-carboxamide; trifluoroacetic Acid

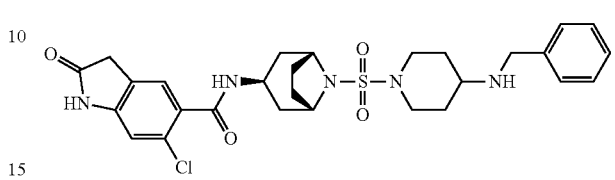

Into a 25-mL round-bottom flask was placed N-[(1R,3r,5S)-8-(4-aminopiperidine-1-sulfonyl)-8-azabicyclo[3.2.1]octan-3-yl]-6-chloro-2-oxo-2,3-dihydro-1H-indole-5-carboxamide hydrochloride (50 mg, 0.10 mmol, 1.00 equiv), methanol (5 mL), and benzaldehyde (12.3 mg, 0.12 mmol, 1.20 equiv). The mixture was stirred for 0.5 h at 20° C. To the above NaBH$_3$CN (7.3 mg, 0.12 mmol, 1.20 equiv) was added in batches. The resulting solution was stirred for 1 h at 70° C. The reaction mixture was then concentrated under vacuum and the crude product purified by Prep-HPLC with the following conditions: Column: X Select C18, 19*250 mm, 5 um; Mobile Phase A: Water/0.05% TFA, Mobile Phase B: ACN; Flow rate: 30 mL/min; Gradient: 5% B to 36% B in 12.5 min; Detector: 254 nm. This resulted in 28 mg (42%) of N-[(1R,3r,5S)-8-[4-(b enzylamino)piperidine-1-sulfonyl]-8-azabicyclo[3.2.1]octan-3-yl]-6-chloro-2-oxo-2,3-dihydro-1H-indole-5-carboxamide trifluoroacetate as a white solid. $^1$H NMR (400 MHz, CD$_3$OD): 7.53-7.49 (m, 5H), 7.33 (s, 1H), 6.97 (s, 1H), 4.29 (s, 2H), 4.16 (s, 3H), 3.91 (d, J=12.8 Hz, 2H), 3.57 (s, 2H), 3.41-3.37 (m, 1H), 2.89 (t, J=10.8 Hz, 2H), 2.37-2.21 (m, 4H), 2.20-2.08 (m, 4H), 2.05-1.96 (m, 2H), 1.80-1.70 (m, 2H) ppm. LCMS (method A, ESI): RT=1.31 min, m/z=572.2 [M+H]$^+$.

Example 15

Synthesis of 6-chloro-2-oxo-N-((1S,3r,5R)-8-((1-(4,4,4-trifluorobutyl)piperidin-4-yl)methylsulfonyl)-8-aza-bicyclo[3.2.1]octan-3-yl)indoline-5-carboxamide (Cpd. No. 595)

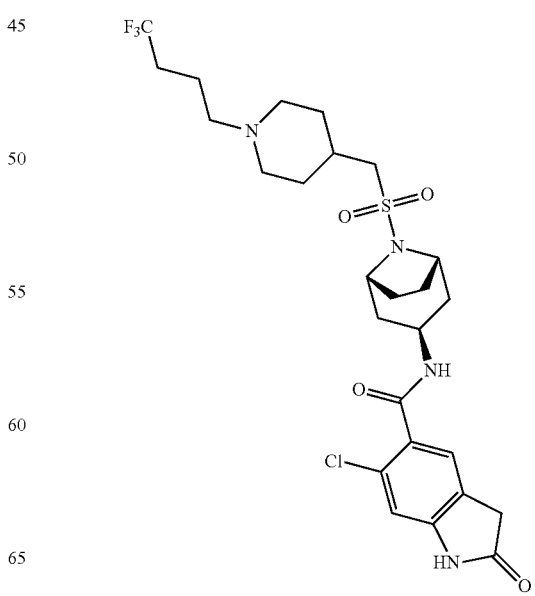

Step 1: Synthesis of tert-butyl (1R,3S,5S)-3-[[(2,2,2-trichloroethoxy)carbonyl]amino]-8-azabicyclo[3.2.1]octane-8-carboxylate

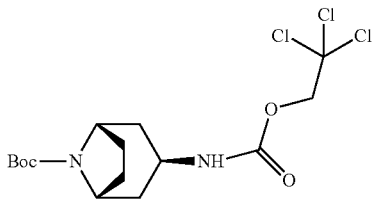 [SMILES: CC(C)(C)OC(=O)N1[C@@H]2CC[C@H]1C[C@@H](NC(=O)OCC(Cl)(Cl)Cl)C2]

Into a 250-mL round-bottom flask, was placed water (120 mL). This was followed by the addition of tert-butyl (1R,5S)-3-amino-8-azabicyclo[3.2.1]octane-8-carboxylate (2 g, 8.84 mmol, 1.00 equiv), sodium bicarbonate (1.92 g, 22.85 mmol, 2.59 equiv). To the mixture was added 2,2,2-trichloroethyl chloroformate (2.28 g, 10.76 mmol, 1.22 equiv) dropwise with stirring at 0° C. The resulting solution was stirred for 18 h at 20° C. The resulting solution was extracted with 3×150 mL of ethyl acetate and the organic layers combined and dried over anhydrous sodium sulfate and concentrated under vacuum. This resulted in 4.16 g (crude) of tert-butyl (1R,5S)-3-[[(2,2,2-trichloroethoxy)carbonyl]amino]-8-azabicyclo[3.2.1]octane-8-carboxylate as a white solid. $^1$H NMR (300 MHz, CDCl$_3$): δ 4.75 (s, 2H), 4.25 (s, 2H), 4.00-3.90 (m, 1H), 2.29-2.00 (m, 4H), 2.89-2.71 (m, 4H), 1.45 (s, 9H) ppm.

Step 2: Synthesis of 2,2,2-trichloroethyl (1S,3r,5R)-8-aza-bicyclo[3.2.1]octan-3-ylcarbamate

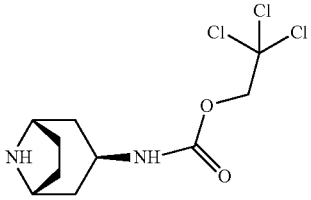 [SMILES: O=C(N[C@H]1C[C@H]2CC[C@@H](C1)N2)OCC(Cl)(Cl)Cl]

Into a 100-mL round-bottom flask, was placed dichloromethane (20 mL), tert-butyl (1R,3S,5S)-3-[[(2,2,2-trichloroethoxy)carbonyl]amino]-8-azabicyclo[3.2.1]octane-8-carboxylate (2 g, 4.98 mmol, 1.00 equiv). Then hydrogen chloride gas was introduced into mixture. The resulting solution was stirred for 12 h at 80° C. The resulting mixture was concentrated under vacuum. This resulted in 1.7 g (crude) of 2,2,2-trichloroethyl N-[(1R,3S,5S)-8-azabicyclo[3.2.1]octan-3-yl]carbamate as a yellow solid. LCMS (method D, ESI): RT=0.86 min, m/z=303.2 [M+H]$^+$.

Step 3: Synthesis of benzyl 4-(((1S,3r,5R)-3-(2,2,2-trichloroethoxy)carbonylamino)-8-aza-bicyclo[3.2.1]octan-8-ylsulfonyl)methyl)piperidine-1-carboxylate

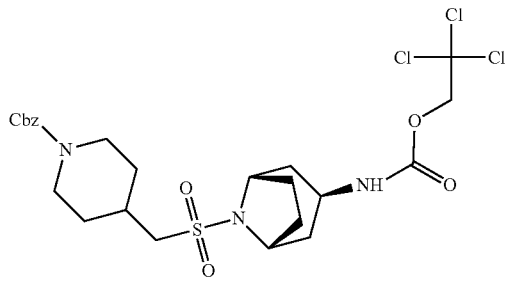 [SMILES: O=C(N[C@H]1C[C@H]2CC[C@@H](C1)N2S(=O)(=O)CC1CCN(C(=O)OCc2ccccc2)CC1)OCC(Cl)(Cl)Cl]

Into a 100-mL round-bottom flask, was placed dichloromethane (30 mL), 2,2,2-trichloroethyl N-[(1R,3S,5S)-8-azabicyclo[3.2.1]octan-3-yl]carbamate (2.4 g, 7.96 mmol, 1.00 equiv), TEA (3.2 g, 31.62 mmol, 3.97 equiv). Then benzyl 4-[(chlorosulfonyl)methyl]piperidine-1-carboxylate (4 g, 12.05 mmol, 1.51 equiv) was added by dropwise at 0° C. The resulting solution was stirred for 12 h at 10° C. The resulting mixture was washed with 3×30 mL of water and 1×30 mL of brine. The mixture was dried over anhydrous sodium sulfate and concentrated under vacuum. The residue was applied onto a silica gel column with dichloromethane/methanol (20:1). This resulted in 2.8 g (59%) of benzyl 4-[[[(1R,3S,5S)-3-[[(2,2,2-trichloroethoxy)carbonyl]amino]-8-azabicyclo[3.2.1]octane-8-sulfonyl]methyl]piperidine-1-carboxylate as a yellow solid. $^1$H NMR (300 MHz, CDCl$_3$): δ 7.41-7.30 (m, 5H), 5.15 (s, 2H), 4.75 (s, 2H), 4.30-4.15 (m, 4H), 4.05-3.90 (m, 1H), 2.95-2.76 (m, 4H), 2.35-2.10 (m, 4H), 2.10-1.90 (m, 5H), 1.57 (s, 1H), 1.40-1.20 (m, 3H) ppm. LCMS (method D, ESI): RT=1.15 min, m/z=596.1 [M+H]$^+$.

Step 4 2,2,2-trichloro ethyl (1S,3r,5R)-8-(piperidin-4-ylmethylsulfonyl)-8-aza-bicyclo[3.2.1]octan-3-ylcarbamate Hydrochloride Salts

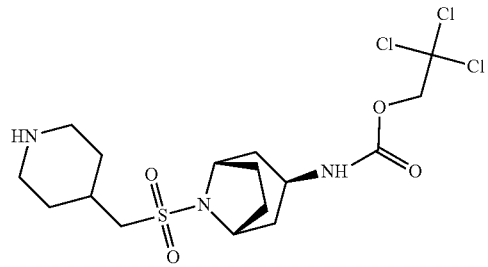 [SMILES: O=C(N[C@H]1C[C@H]2CC[C@@H](C1)N2S(=O)(=O)CC1CCNCC1)OCC(Cl)(Cl)Cl]

Into a 250-mL round-bottom flask, was placed benzyl 4-[[[(1R,5S)-3-[[(2,2,2-trichloroethoxy)carbonyl]amino]-8-azabicyclo[3.2.1]octane-8-sulfonyl]methyl]piperidine-1-carboxylate (1.5 g, 2.51 mmol, 1.00 equiv). This was followed by the addition of hydrochloric acid (12 N, 140 mL) at 10° C. The resulting solution was stirred for 12 h at 50° C. The resulting mixture was concentrated under vacuum. This resulted in 1.1 g (88%) of 2,2,2-trichloroethyl N-[(1R,5S)-8-[(piperidin-4-ylmethane)sulfonyl]-8-azabicyclo[3.2.1]octan-3-yl]carbamate hydrochloride as a yellow solid. LCMS (method D, ESI): RT=0.67 min, m/z=464.0 [M+H]$^+$.

Step 5: Synthesis of 2,2,2-trichloro ethyl (1S,3r,5R)-8-((1-(4,4,4-trifluorobutyl)piperidin-4-yl)methylsulfonyl)-8-aza-bicyclo[3.2.1]octan-3-ylcarbamate

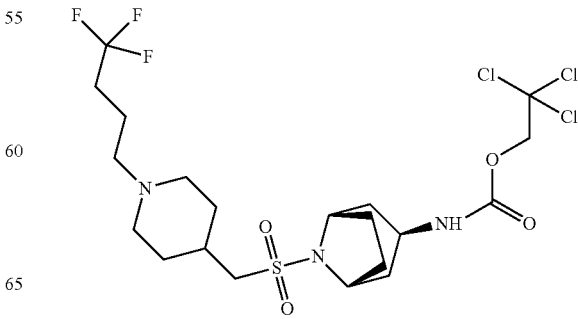

Into a 100-mL round-bottom flask, was placed dichloromethane (40 mL). This was followed by the addition of methanol (20 mL), 2,2,2-trichloroethyl N-[(1R,5S)-8-[(piperidin-4-ylmethane)sulfonyl]-8-azabicyclo[3.2.1]octan-3-yl]carbamate hydrochloride (300 mg, 0.60 mmol, 1.00 equiv), 4,4,4-trifluorobutanol (227 mg, 1.80 mmol, 3.00 equiv). Then NaBH₃CN (303 mg, 4.81 mmol, 8.00 equiv) was added into by batchwise. To the mixture was added acetic acid (1 mL). The resulting solution was stirred for 6 h at 10° C. The resulting mixture was concentrated under vacuum. The resulting solution was extracted with 3×100 mL of dichloromethane and the organic layers combined. The resulting mixture was washed with 1×50 mL of brine. The mixture was dried over anhydrous sodium sulfate and concentrated under vacuum. The residue was purified by flash chromatography with eluent (PE/EtOAc=2/1 to 100% EtOAc). This resulted in 295 mg (86%) of 2,2,2-trichloroethylN-[(1R,5S)-8-([[1-(4,4,4-trifluorobutyl)piperidin-4-yl]methane]sulfonyl)-8-azabicyclo[3.2.1]octan-3-yl]carbamate as yellow oil. ¹H NMR (300 MHz, CDCl₃): δ 4.75 (s, 2H), 4.30 (s, 2H), 4.02-3.95 (m, 1H), 3.10-3.02 (m, 2H), 3.00-2.95 (m, 2H), 2.58-2.50 (m, 2H), 2.32-1.78 (m, 17H), 1.60-1.48 (m, 2H) ppm. LCMS (method D, ESI): RT=0.97 min, m/z=572.0 [M+H]⁺.

Step 6: Synthesis of (1S,3r,5R)-8-((1-(4,4,4-trifluorobutyl)piperidin-4-yl)methylsulfonyl)-8-aza-bicyclo[3.2.1]octan-3-amine

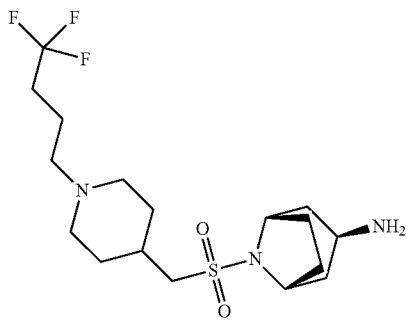 [SMILES: N[C@H]1C[C@H]2CC[C@@H](C1)N2S(=O)(=O)CC1CCN(CCCC(F)(F)F)CC1]

Into a 100-mL round-bottom flask, was placed 2,2,2-trichloroethyl N-[(1R,3S,5S)-8-([[1-(4,4,4-trifluorobutyl)piperidin-4-yl]methane]sulfonyl)-8-azabicyclo[3.2.1]octan-3-yl]carbamate (50 mg, 0.09 mmol, 1.00 equiv). This was followed by the addition of acetic acid (15 mL), water (1 mL) and Zn (90 mg). The resulting solution was stirred for 12 h at 10° C. The solids were filtered out. The pH value of the solution was adjusted to 8 with sodium carbonate (sat. aq.). The resulting solution was extracted with 3×50 mL of ethyl acetate and the organic layers combined and concentrated under vacuum. This resulted in 25 mg (72%) of (1R,3S,5S)-8-([[1-(4,4,4-trifluorobutyl)piperidin-4-yl]methane]sulfonyl)-8-azabicyclo[3.2.1]octan-3-amine as a yellow solid. LCMS (method B, ESI): RT=1.24 min, m/z=398.0 [M+H]⁺.

Step 7: Synthesis of 6-chloro-2-oxo-N-((1S,3r,5R)-8-((1-(4,4,4-trifluorobutyl)piperidin-4-yl)methylsulfonyl)-8-aza-bicyclo[3.2.1]octan-3-yl)indoline-5-carboxamide

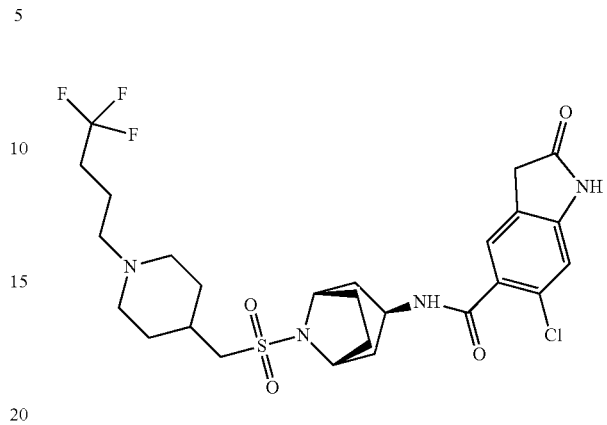

Into a 100-mL round-bottom flask, was placed N,N-dimethylformamide (10 mL), (1R,3S,5S)-8-([[1-(4,4,4-trifluorobutyl)piperidin-4-yl]methane]sulfonyl)-8-azabicyclo[3.2.1]octan-3-amine (50 mg, 0.13 mmol, 1.00 equiv), 6-chloro-2-oxo-2,3-dihydro-1H-indole-5-carboxylic acid (46 mg, 0.22 mmol, 1.73 equiv), 1H-1,2,3-benzotriazol-1-ol (35 mg, 0.26 mmol, 2.06 equiv), EDCI (50 mg, 0.26 mmol, 2.07 equiv), TEA (0.3 mL). The resulting solution was stirred for 12 h at 10° C. The solids were filtered out. The resulting mixture was diluted with 10 mL of water. The resulting solution was extracted with of 2×10 mL dichloromethane and the organic layers combined. The organic phase was dried over anhydrous sodium sulfate and concentrated under vacuum. The crude reside was purified by Prep-HPLC with the following conditions (2#-Waters 2767-2(HPLC-08)): Column, Xbridge Prep Phenyl, 5 um, 19×150 mm; mobile phase, Water with 50 mmol ammonium bicarbonate and acetonitrile (10.0% acetonitrile up to 33.0% in 2 min, up to 53.0% in 8 min, up to 100.0% in 1 min, down to 10.0% in 1 min); Detector, UV 254 nm. This resulted in 5.7 mg (8%) of 6-chloro-2-oxo-N-[(1R,3S,5S)-8-([[1-(4,4,4-trifluorobutyl)piperidin-4-yl]methane]sulfonyl)-8-azabicyclo[3.2.1]octan-3-yl]-2,3-dihydro-1H-indole-5-carboxamide as a light pink solid. ¹HNMR (300 MHz, CD₃OD): δ 7.32 (s, 1H), 6.95 (s, 1H), 4.30-4.10 (m, 3H), 3.35 (s, 2H), 3.10-2.90 (m, 4H), 2.50-2.40 (m, 2H), 2.40-1.90 (m, 15H), 1.85-1.70 (m, 2H), 1.51-1.35 (m, 2H) ppm. LCMS (method B, ESI): RT=1.67 min, m/z=591.1 [M+H]⁺.

Example 16

Synthesis of N-((1R,3r,5S)-8-(4-aminocyclohexylsulfonyl)-8-aza-bicyclo[3.2.1]octan-3-yl)-2,2-difluorobenzo[d][1,3]dioxole-5-carboxamide Trifluoroacetate (Cpd. No. 622)

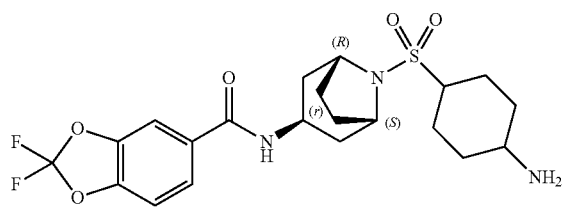

Step 1: Synthesis of tert-butyl (1R,3r,5S)-3-(2,2-difluoro-2H-1,3-benzo[d][1,3]dioxole-5-carboxamido)-8-azabicyclo[3.2.1]octane-8-carboxylate

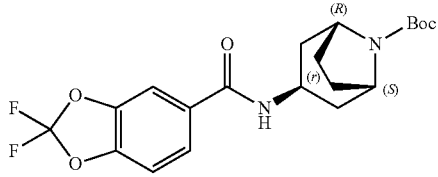

Into a 100-mL round-bottom flask was placed dichloromethane (50 mL), 2,2-difluoro-2H-1,3-benzo[d][1,3]dioxole-5-carboxylic acid (1.5 g, 7.42 mmol, 1.00 equiv), tert-butyl (1R,5 S,7S)-7-amino-3-azabicyclo[3.3.2]decane-3-carboxylate (2.0 g, 7.86 mmol, 1.06 equiv), HATU (5.65 g), and TEA (2.25 g, 22.24 mmol, 3.00 equiv). The resulting solution was stirred for 12 h at 25° C. The resulting mixture was washed with 3×50 ml, of $H_2O$. The organic layer was dried over anhydrous sodium sulfate and concentrated. The residue was chromatographed on a silica gel column with PE:EA (1:1). This resulted in 3.0 g (92%) of tert-butyl(1R,5r,7S)-7-(2,2-difluoro-2H-1,3-benzo[d][1,3]dioxole-5-carboxamido)-3-azabicyclo[3.3.2]decane-3-carboxylate as a white solid. $^1$HNMR (300 MHz, DMSO): δ 8.20-8.15 (m, 1H), 7.77 (s, 1H), 7.68 (d, J=8.7 Hz, 1H), 7.52 (d, J=8.4 Hz, 1H), 4.08-3.90 (m, 1H), 3.50-3.10 (m, 2H), 2.15-1.80 (m, 8H), 1.50-1.30 (m, 9H) ppm. LCMS (method C, ESI): RT=1.25 min, m/z=411.2 [M+H]$^+$.

Step 2: Synthesis of N-((1R,3r,5S)-8-aza-bicyclo[3.2.1]octan-3-yl)-2,2-difluorobenzo[d][1,3]dioxole-5-carboxamide

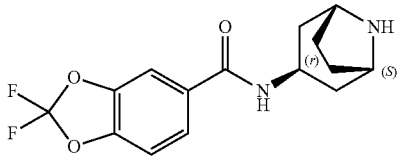

Into a 100-mL round-bottom flask was placed a solution of tert-butyl (1R,3r,5S)-3-(2,2-difluoro-2H-1,3-benzo[d][1,3]dioxole-5-carboxamido)-8-azabicyclo[3.2.1]octane-8-carboxylate (1.5 g, 3.65 mmol, 1.00 equiv) in methanol (30 mL). Hydrogen chloride gas was introduced into the solution at 0° C. for 1 h. The resulting solution was stirred for another 1 h at 20° C. The mixture was then concentrated under vacuum. This resulted in 1.3 g (crude) of N-[(1R,3r,5S)-8-azabicyclo[3.2.1]octan-3-yl]-2,2-difluoro-2H-1,3-benzo[d][1,3]dioxole-5-carboxamide as a white solid. LCMS (method A, ESI): RT=0.80 min, m/z=311.2 [M+H]$^+$.

Step 3: Synthesis of 2,2-difluoro-N-((1R,3r,5S)-8-(4-oxocyclohexylsulfonyl)-8-aza-bicyclo[3.2.1]octan-3-yl)benzo[d][1,3]dioxole-5-carboxamide

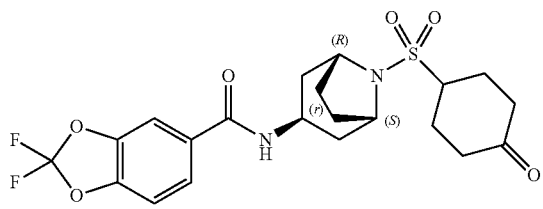

Into a 250-mL 3-necked round-bottom flask purged and maintained with an inert atmosphere of nitrogen was placed a solution of N-[(1R,3r,5S)-8-azabicyclo[3.2.1]octan-3-yl]-2,2-difluoro-2H-1,3-benzo[d][1,3]dioxole-5-carboxamide (900 mg, 2.90 mmol, 1.00 equiv) in THF (150 mL). This was followed by the addition of LiHMDS (1M in THF, 10 mL) dropwise with stirring at −60° C. To this was added 4-oxocyclohexane-1-sulfonyl chloride (700 mg, 3.56 mmol, 1.23 equiv) in portions at −60° C. The resulting solution was allowed to warm to room temperature and stirred for another 12 hours at 25° C. The resulting mixture was concentrated under vacuum. The residue was extracted with 3×60 mL of dichloromethane and the organic layers combined, dried over anhydrous sodium sulfate and concentrated. The residue was chromatographed on a C18 gel column with $H_2O$/$CH_3CN$=3:5. This resulted in 260 mg (19%) of 2,2-difluoro-N-[(1R,3rS,5S)-8-[(4-oxocyclohexane)sulfonyl]-8-azabicyclo[3.2.1]octan-3-yl]-2H-1,3-benzo[d][1,3]dioxole-5-carboxamide as a white solid. LCMS (method B, ESI): RT=1.08 min, m/z=471.0 [M+H]$^+$.

Step 4: Synthesis of N-((1R,3r,5S)-8-(4-aminocyclohexylsulfonyl)-8-aza-bicyclo[3.2.1]octan-3-yl)-2,2-difluorobenzo[d][1,3]dioxole-5-carboxamide Trifluoroacetate

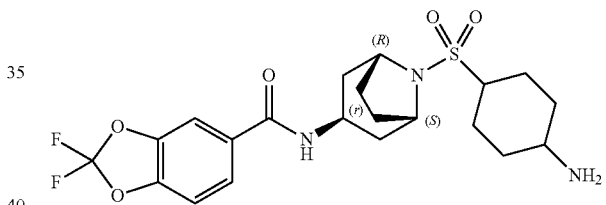

Into a 250-mL round-bottom flask was placed methanol (130 mL), 2,2-difluoro-N-[(1R,3r,5S)-8-[(4-oxocyclohexane)sulfonyl]-8-azabicyclo[3.2.1]octan-3-yl]-2H-1,3-benzo[d][1,3]dioxole-5-carboxamide (200 mg, 0.43 mmol, 1.00 equiv), $HCOONH_4$ (1080 mg, 17.13 mmol, 40.29 equiv), and acetic acid (24 mg, 0.40 mmol, 0.94 equiv). Then $NaBH_3CN$ (50 mg, 0.79 mmol, 1.87 equiv) was added batchwise. The resulting solution was stirred for 2 h at 20° C. The mixture was then concentrated under vacuum. The residue was slurried with 150 mL of EtOAc and then filtrated. The filtrate was concentrated under vacuum. The crude product was purified by Prep-HPLC with the following conditions: Column, X Bridge C18, 19*150 mm, 5 um; mobile phase, Mobile Phase A: Water/0.05% TFA, Mobile Phase B: ACN; Flow rate: 20 mL/min; Detector, 254 nm. This resulted in 15.2 mg (6%) of N-[(1R,3r,5S)-8-[(4-aminocyclohexane)sulfonyl]-8-azabicyclo[3.2.1]octan-3-yl]-2,2-difluoro-2H-1,3-benzo[d][1,3]dioxole-5-carboxamide trifluoroacetic acid as a white solid. $^1$H NMR (300 MHz, $D_2O$): δ 7.46-7.44 (m, 2H), 7.19 (d, J=6 Hz, 1H), 4.18 (s, 2H), 4.05 (t, J=6.0 Hz, 1H), 3.48-3.10 (m, 2H), 2.30-1.80 (m, 13H), 1.65-1.38 (m, 3H) ppm. LCMS (method D, ESI): RT=1.55 min, m/z=472.0 [M+H]$^+$.

Example 17

Synthesis of N-[(1R,3r,5S)-8-(4-aminopiperidine-1-sulfonyl)-8-azabicyclo[3.2.1]octan-3-yl]-5-ethyl-1,2-thiazole-3-carboxamide Hydrochloride (Cpd. No. 610)

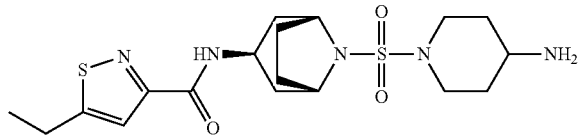 [SMILES: CCc1cc(C(=O)N[C@H]2C[C@H]3CC[C@@H](C2)N3S(=O)(=O)N2CCC(N)CC2)ns1]

Step 1: Synthesis of tert-butyl N-[1-[(1R,3r,5S)-3-(5-ethyl-1,2-thiazole-3-carboxamido)-8-azabicyclo[3.2.1]octane-8-sulfonyl]piperidin-4-yl]carbamate

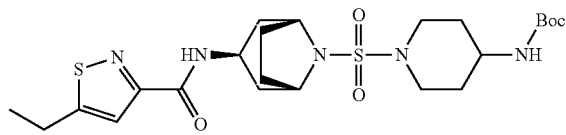 [SMILES: CCc1cc(C(=O)N[C@H]2C[C@H]3CC[C@@H](C2)N3S(=O)(=O)N2CCC(NC(=O)OC(C)(C)C)CC2)ns1]

Into a 50-mL round-bottom flask purged and maintained with an inert atmosphere of nitrogen was placed dichloromethane (10 mL), 5-ethyl-1,2-thiazole-3-carboxylic acid (44 mg, 0.28 mmol, 1.00 equiv), tert-butyl N-[1-[(1R,3r,5S)-3-amino-8-azabicyclo[3.2.1]octane-8-sulfonyl]piperidin-4-yl]carbamate (100 mg, 0.34 mmol, 1.21 equiv), HOBT (52 mg, 0.38 mmol, 1.36 equiv)), and EDCI (150 mg, 0.79 mmol, 2.80 equiv). This was followed by the addition of a solution of triethylamine (80 mg, 0.79 mmol, 2.80 equiv) in dichloromethane (1 ml) which was added dropwise with stirring at 0° C. The resulting solution was stirred for 15 hours at 20° C. The reaction was quenched by the addition of 50 mL of water and extracted with 2×100 mL of dichloromethane. The organic layers were combined and washed with 1×50 mL of brine. The organic layer was dried over anhydrous sodium sulfate and concentrated under vacuum. The residue was chromatographed on a silica gel column with ethyl acetate/petroleum ether (1:2). This resulted in 120 mg (81%) of tert-butyl N-[1-[(1R,3r,5S)-3-(5-ethyl-1,2-thiazole-3-carboxamido)-8-azabicyclo[3.2.1]octane-8-sulfonyl]piperidin-4-yl]carbamate as a solid. LCMS (method A, ESI): RT=1.61 min, m/z=528.0[M+H]$^+$.

Step 2: Synthesis of N-[(1R,3r,5S)-8-(4-aminopiperidine-1-sulfonyl)-8-azabicyclo[3.2.1]octan-3-yl]-5-ethyl-1,2-thiazole-3-carboxamide Hydrochloride

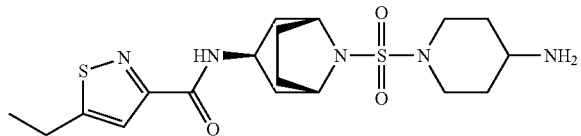 [SMILES: CCc1cc(C(=O)N[C@H]2C[C@H]3CC[C@@H](C2)N3S(=O)(=O)N2CCC(N)CC2)ns1]

Into a 50-mL round-bottom flask was placed tert-butyl N-[1-[(1R,3r,5S)-3-(5-ethyl-1,2-thiazole-3-carboxamido)-8-azabicyclo[3.2.1]octane-8-sulfonyl]piperidin-4-yl]carbamate (120 mg, 0.23 mmol, 1.00 equiv) and hydrogen chloride/dioxane (10 mL, saturated, this solution was made by introducing hydrogen chloride gas into 1,4-dioxane under 0° C. for 6 hours). The resulting solution was stirred for 3 hours at 20° C. The mixture was then concentrated under vacuum. This resulted in 57.8 mg (55%) of N-[(1R,3r,5S)-8-(4-aminopiperidine-1-sulfonyl)-8-azabicyclo[3.2.1]octan-3-yl]-5-ethyl-1,2-thiazole-3-carboxamide hydrochloride as a solid. $^1$H NMR (300 MHz, D$_2$O) δ: 7.45 (s, 1H), 4.15-4.02 (m, 3H), 3.80-3.78 (m, 2H), 3.38-3.22 (m, 1H), 2.98-2.82 (m, 4H), 2.30-2.18 (m, 2H), 2.11-1.87 (m, 8H), 1.71-1.52 (m, 2H), 1.30-1.20 (m, 3H) ppm. LCMS (method A, ESI): RT=1.81 min, m/z=428.2 [M−HCl+H]$^+$.

Example 18

Synthesis of N-((1R,3r,5S)-8-(4-aminopiperidin-1-ylsulfonyl)-8-aza-bicyclo[3.2.1]octan-3-yl)-3-oxo-3,4-dihydro-2H-benzo[b][1,4]oxazine-6-carboxamide Hydrochloride (Cpd, No. 609)

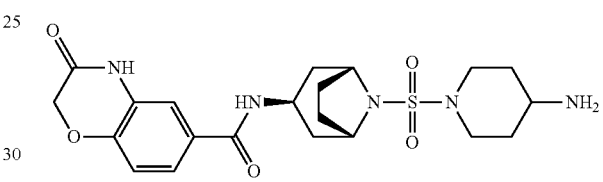

Step 1: Synthesis of 3-oxo-3,4-dihydro-2H-1,4-benzo[b][1,4]oxazine-6-carboxylic Acid

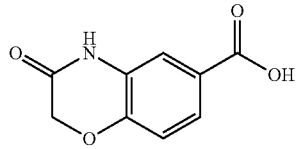 [SMILES: O=C1COc2ccc(C(=O)O)cc2N1]

Into a 100-mL round-bottom flask was placed methyl 3-oxo-3,4-dihydro-2H-1,4-benzo[b][1,4]oxazine-6-carboxylate (1 g, 4.83 mmol, 1.00 equiv), methanol (15 mL), tetrahydrofuran (15 mL), and water (15 mL). This was followed by the addition of a solution of sodium hydroxide (386 mg, 9.65 mmol, 2.00 equiv) in 5 ml H$_2$O which was added dropwise with stirring at 0° C. The solution was stirred for 20 min at 0° C. in an ice/salt bath. The resulting solution was allowed to react, with stirring, for an additional 18 h at room temperature. The reaction mixture was then concentrated under vacuum. The residue was diluted with 50 mL of H$_2$O and The pH adjusted to 3-4 with hydrochloric acid (1 N). The resulting mixture was extracted with 3×50 mL of ethyl acetate. The organic layers were combined and washed with 2×30 mL of water and 1×30 mL of brine. The organic layer was dried over anhydrous sodium sulfate, filtered, and the filtrate concentrated under vacuum. This resulted in 850 mg (91%) of 3-oxo-3,4-dihydro-2H-1,4-benzo[b][1,4]oxazine-6-carboxylic acid as a brown solid. $^1$H NMR (300 MHz, CD$_3$OD) δ: 7.68 (q, J=8.4 Hz, 1H), 7.61 (d, J=1.8 Hz, 1H), 7.02 (d, J=8.4 Hz, 1H), 4.68 (s, 2H) ppm. LCMS (method A, ESI): RT=1.01 min, m/z=194.0 [M+H]$^+$.

Step 2: Synthesis of 2,2,2-trichloroethyl N-[(1R,3r,5S)-8-(4-[[(tert-butoxy)carbonyl]amino]piperidine-1-sulfonyl)-8-azabicyclo[3.2.1]octan-3-yl]carbamate

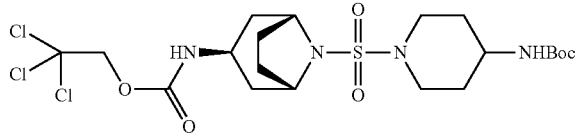 [SMILES: CC(C)(C)OC(=O)NC1CCN(S(=O)(=O)N2[C@@H]3CC[C@H]2C[C@@H](NC(=O)OCC(Cl)(Cl)Cl)C3)CC1]

Into a 100-mL round-bottom flask was placed dichloromethane (30 mL), 2,2,2-trichloro ethyl N-[(1R,3r,5S)-8-azabicyclo[3.2.1]octan-3-yl]carbamate hydrochloride (900 mg, 2.66 mmol, 1.00 equiv), and TEA (1.37 g, 13.54 mmol, 5.00 equiv). This was followed by the addition of a solution of tert-butyl N-[1-(chlorosulfonyl)piperidin-4-yl]carbamate (1.6 g, 5.35 mmol, 2.00 equiv) in 2 ml dichloromethane which was added dropwise with stirring at 0° C. The resulting solution was stirred for 14 h at 10° C. The mixture was then washed with 3×30 mL of brine. The organic layer was dried over anhydrous sodium sulfate, filtered, and the filtrate concentrated under vacuum. The residue was chromatographed on a silica gel column with ethyl acetate/petroleum ether (1:1). This resulted in 1.1 g (73%) of 2,2,2-trichloroethyl N-[(1R,3r,5S)-8-(4-[[(tert-butoxy)carbonyl]amino]piperidine-1-sulfonyl)-8-azabicyclo[3.2.1]octan-3-yl]carbamate as a white solid. $^1$H NMR (400 MHz, CDCl$_3$) δ: 5.22 (s, 1H), 4.75 (s, 2H), 4.47 (s, 1H), 4.14 (s, 2H), 3.98 (d, J=6 Hz, 1H), 3.70 (d, J=12 Hz, 2H), 3.58 (s, 1H), 2.84 (t, J=11.2 Hz, 2H), 2.27-2.25 (m, 4H), 2.03 (d, J=10.8 Hz, 2H), 1.95-1.87 (m, 4H), 1.58 (s, 2H), 1.55-1.40 (m, 9H) ppm. LCMS (method C, ESI): RT=1.24 min, m/z=563.0 [M+H]$^+$.

Step 3: Synthesis of tert-butyl N-[1-[(1R,3r,5S)-3-amino-8-azabicyclo[3.2.1]octane-8-sulfonyl]piperidin-4-yl]carbamate

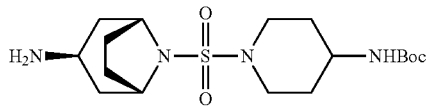 [SMILES: CC(C)(C)OC(=O)NC1CCN(S(=O)(=O)N2[C@@H]3CC[C@H]2C[C@@H](N)C3)CC1]

Into a 100-mL round-bottom flask was placed 2,2,2-trichloroethyl N-[(1R,3r,5S)-8-(4-[[(tert-butoxy)carbonyl]amino]piperidine-1-sulfonyl)-8-azabicyclo[3.2.1]octan-3-yl]carbamate (1.1 g, 1.95 mmol, 1.00 equiv), Zn (1.9 g, 15.00 equiv), AcOH (15 mL), and water (1 mL). The resulting mixture was stirred for 3 h at 10° C. The solids were filtered out. The pH was adjusted to 8 with sodium carbonate (aq. sat.). The resulting solution was extracted with 4×50 mL of ethyl acetate. The organic layers were combined, dried over anhydrous sodium sulfate, filtered, and concentrated under vacuum. This resulted in 750 mg (crude) of tert-butyl N-[1-[(1R,3r,5S)-3-amino-8-azabicyclo[3.2.1]octane-8-sulfonyl]piperidin-4-yl]carbamate as a light yellow crude solid. LCMS (method C, ESI): RT=0.61 min, m/z=389.0 [M+H]$^+$.

Step 4: Synthesis of tert-butyl (1-(((1R,3r,5S)-3-(3-oxo-3,4-dihydro-2H-benzo[b][1,4]oxazine-6-carboxamido)-8-azabicyclo[3.2.1]octan-8-yl)sulfonyl)piperidin-4-yl)carbamate

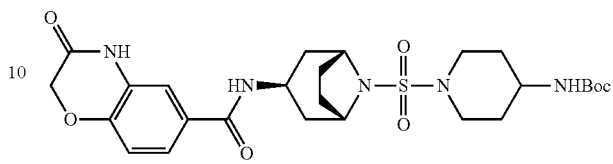

Into a 100-mL round-bottom flask was placed N,N-dimethylformamide (10 mL), 3-oxo-3,4-dihydro-2H-1,4-benzo[b][1,4]oxazine-6-carboxylic acid (55 mg, 0.28 mmol, 1.10 equiv), EDCI (98 mg, 0.51 mmol, 2.00 equiv), HOBT (70 mg, 0.52 mmol, 2.00 equiv), and tert-butyl N-1-[(1R,3r,5S)-3-amino-8-azabicyclo[3.2.1]octane-8-sulfonyl]piperidin-4-ylcarbamate (100 mg, 0.26 mmol, 1.00 equiv). This was followed by the addition of TEA (131 mg, 1.29 mmol, 5.00 equiv) which was added dropwise with stirring at 0° C. The resulting solution was stirred for 15 h at 10° C. The reaction mixture was diluted with 10 mL of H$_2$O and extracted with 3×10 mL of ethyl acetate. The organic layers were combined, dried over anhydrous sodium sulfate, filtered, and concentrated under vacuum. The residue was chromatographed on a silica gel column with dichloromethane/methanol (10:1). This resulted in 100 mg (69%) of tert-butyl N-[1-[(1R,3r,5S)-3-(3-oxo-3,4-dihydro-2H-1,4-benzo[b][1,4]oxazine-6-carboxamido)-8-azabicyclo[3.2.1]octane-8-sulfonyl]piperidin-4-yl]carbamate as a white solid. LCMS (method A, ESI): RT=1.32 min, m/z=586.0 [M+Na]$^+$.

Step 5: Synthesis of N-((1R,3r,5S)-8-(4-aminopiperidin-1-ylsulfonyl)-8-aza-bicyclo[3.2.1]octan-3-yl)-3-oxo-3,4-dihydro-2H-benzo[b][1,4]oxazine-6-carboxamide Hydrochloride

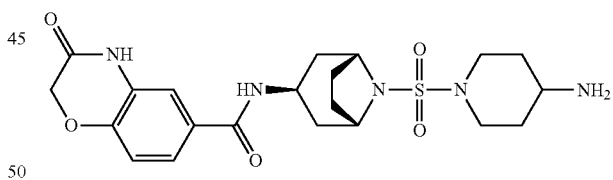

Into a 50-mL round-bottom flask was placed dichloromethane (10 mL) and tert-butyl N-[1-[(1R,3r,5S)-3-(3-oxo-3,4-dihydro-2H-1,4-benzo[1])[1,4]oxazine-6-carboxamido)-8-azabicyclo[3.2.1]octane-8-sulfonyl]piperidin-4-yl]carbamate (100 mg, 0.18 mmol, 1.00 equiv). To the above hydrogen chloride (gas) was introduced. The resulting solution was stirred for 3 h at 10° C. The reaction mixture was then concentrated under vacuum. The crude product (80 mg) was purified by Prep-HPLC with the following conditions (Prep_HPLC_MC5): Column, X Select C18, 19*250 mm, 5 um; mobile phase, A: Water/0.05% TFA, Mobile Phase B: ACN; Flow rate: 30 mL/min; Gradient: 5% B to 36% B in 12.5 min; Detector, 254 nm. The isolated purified product was dissolved in 2 ml concentrated hydrochloric acid and this solution concentrated under vacuum. This resulted in 45.7 mg (52%) of N-[(1R,3r,5S)-8-(4-aminopiperidine-1- sulfonyl)-8-azabicyclo[3.2.1]octan-3-yl]-3-oxo-3,4-dihydro-2H-1,4-benzo[b][1,4]oxazine-6-carboxamide hydrochloride as a white solid. ¹H NMR (400 MHz, D₂O) δ: 7.28 (q, J=8.4 Hz, 1H), 7.18 (s, 1H), 6.98 (d, J=8.4 Hz, 1H), 4.60 (s, 2H), 4.10-3.95 (m, 3H), 3.74 (d, J=13.2 Hz, 2H), 3.35-3.25 (m, 1H), 2.88 (t, J=12 Hz, 2H), 2.25-2.18 (m, 2H), 2.10-1.98 (m, 6H), 1.91 (d, J=14.8 Hz, 2H), 1.67-1.52 (m, 2H) ppm. LCMS (method A, ESi): RT=1.40 min, m/z=464.0 [M−HCl+H]⁺.

Example 19

Synthesis of N-((2S,4S)-1-(4-aminopiperidin-1-ylsulfonyl)-2-methylpiperidin-4-yl)-5-ethyl-1,2-thiazole-3-carboxamide Hydrochloride (Cpd. No. 605)

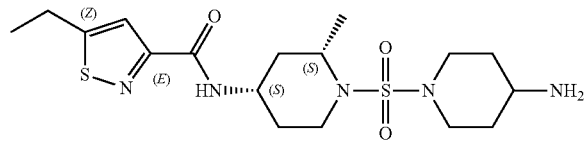

Step 1: Synthesis of ethyl 2-amino-4-oxohex-2-enoate

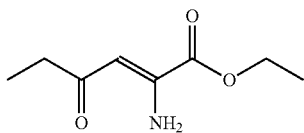

Into a 250-mL round-bottom flask was placed ethyl 2,4-dioxohexanoate (10 g, 58.08 mmol, 1.00 equiv), benzene (100 mL), CH₃COONH₄ (13.4 g, 173.84 mmol, 2.99 equiv), and acetic acid (10 mL). The resulting solution was stirred at 80° C. overnight. The reaction mixture was cooled and concentrated under vacuum. The residue was diluted with 200 mL of ice-water and the pH adjusted to 8 with Na₂CO₃ (aq. Sat.). The resulting mixture was extracted with 3×100 mL of ethyl acetate and the organic layers combined, dried over anhydrous sodium sulfate and concentrated under vacuum. The residue was chromatographed on a silica gel column with ethyl acetate/petroleum ether (1:10-1:5). This resulted in 7 g (70%) of ethyl 2-amino-4-oxohex-2-enoate as yellow oil. ¹H NMR (400 MHz, CDCl₃) δ: 5.92 (s, 1H), 4.36-4.30 (m, 2H), 2.49-2.44 (m, 2H), 1.28-1.24 (m, 3H), 1.14-1.11 (m, 3H) ppm.

Step 2: Synthesis of ethyl 5-ethyl-1,2-thiazole-3-carboxylate

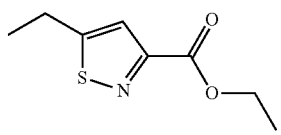

Into a 250-mL round-bottom flask was placed ethyl 2-amino-4-oxohex-2-enoate (4 g, 23.37 mmol, 1.00 equiv), tetrahydrofuran (50 mL), and P₂S₅ (2.6 g, 11.70 mmol, 0.50 equiv). The mixture was stirred overnight at room temperature. Then the mixture was concentrated and the residue was dissolved in ethyl acetate (20 mL). This solution was cooled to 0° C. and H₂O₂ (30%, 10 mL) was added dropwise. The resulting mixture was stirred for 10 min at room temperature. To the mixture was added activated charcoal. After filtration, the filtrate was diluted with H₂O (20 mL). This was extracted with EA (20 mL×3). The organic layers were combined, dried over anhydrous sodium sulfate and concentrated under vacuum. This resulted in 2.44 g (56%) of ethyl 5-ethyl-1,2-thiazole-3-carboxylate as brown oil. LCMS (method A, ESI): RT=1.36 min, m/z=186.1 [M+H]⁺.

Step 3: Synthesis of 5-ethyl-1,2-thiazole-3-carboxylic Acid

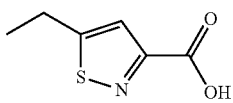

Into a 100-mL round-bottom flask was placed ethyl 5-ethyl-1,2-thiazole-3-carboxylate (2.44 g, 13.17 mmol, 1.00 equiv), methanol (10 mL), water (10 mL), tetrahydrofuran (10 mL) and LiOH.H₂O (1.66 g, 39.56 mmol, 3.00 equiv). The resulting solution was stirred for 1 h at room temperature. The reaction mixture was then concentrated under vacuum. The residue was diluted with 30 mL of H₂O and extracted with 5×30 mL of dichloromethane. The organic layers were combined, dried over anhydrous sodium sulfate and concentrated under vacuum. This resulted in 1.44 g (70%) of 5-ethyl-1,2-thiazole-3-carboxylic acid as a brown solid. ¹H NMR (400 MHz, CDCl₃) δ : 7.63 (s, 1H), 3.04-2.96 (m, 2H), 1.42-1.19 (m, 3H) ppm. LCMS (method D, ESI): RT=1.09 min, m/z=158.2 [M+H]⁺.

Step 4: Synthesis of (2S)-tert-butyl 4-(5-ethyl-1,2-thiazole-3-carboxamido)-2-methylpiperidine-1-carboxylate

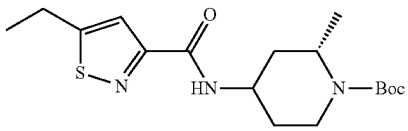 [SMILES: CCc1cc(C(=O)NC2CCN(C(=O)OC(C)(C)C)[C@@H](C)C2)ns1]

Into a 250-mL round-bottom flask was placed 5-ethyl-1,2-thiazole-3-carboxylic acid (1.5 g, 9.54 mmol, 1.00 equiv), EDCI (2.92 g, 15.23 mmol, 1.60 equiv), 1H-1,2,3-benzotriazol-1-ol (2.1 g, 15.54 mmol, 1.63 equiv), dichloromethane (20 mL), and (2S)-tert-butyl 4-amino-2-methylpiperidine-1-carboxylate (2.45 g, 11.43 mmol, 1.20 equiv). Then TEA (2.89 g, 28.56 mmol, 2.99 equiv) was added dropwise. The resulting solution was stirred overnight at room temperature. The reaction mixture was diluted with 30 mL of H₂O and extracted with 3×30 mL of dichloromethane. The organic layers were combined, dried over anhydrous sodium sulfate and concentrated under vacuum. The residue was chromatographed on a combi-flash with eluent (EA:PE=1/1). This resulted in 1.5 g of (2S)-tert-butyl 4-(5-ethyl-1,2-thiazole- 3-carboxamido)-2-methylpiperidine-1-carboxylate as a brown oil. LCMS (method D, ESI): RT=1.60 min, m/z=376.1 [M+Na]+.

Step 5: Synthesis of (2S,4S)-tert-butyl 4-(5-ethyl-1,2-thiazole-3-carboxamido)-2-methylpiperidine-1-carboxylate

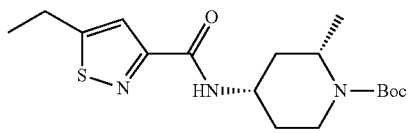 [SMILES: CCc1cc(C(=O)N[C@H]2CCN(C(=O)OC(C)(C)C)[C@@H](C)C2)ns1]

tert-Butyl (2S)-4-(5-ethyl-1,2-thiazole-3-carboxamido)-2-methylpiperidine-1-carboxylate (470 mg, 1.33 mmol, 1.00 equiv was purified by Chiral-Prep-HPLC with the following conditions: Column, CHIRALCEL OJ-3, mobile phase, Hex (0.2% IPA):EtOH=70:30; Detector, 254 nm. This resulted in 200 mg (43%) of tert-butyl (2S,4S)-4-(5-ethyl-1,2-thiazole-3-carboxamido)-2-methylpiperidine-1-carboxylate as a yellow solid. ee value: 100%

Step 6: Synthesis of 5-ethyl-N-((2S,4S)-2-methylpiperidin-4-yl)-1,2-thiazole-3-carboxamide

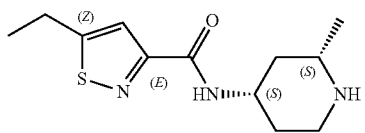

Into a 25-mL round-bottom flask was placed tert-butyl (2S,4S)-4-(5-ethyl-1,2-thiazole-3-carboxamido)-2-methylpiperidine-1-carboxylate (200 mg, 0.57 mmol, 1.00 equiv), dichloromethane (10 mL). To the above hydrogen chloride (gas) was introduced. The resulting solution was stirred for 1 h at room temperature. The resulting mixture was then concentrated under vacuum. This resulted in 150 mg (91%) of 5-ethyl-N-[(2S,4S)-2-methylpiperidin-4-yl]-1,2-thiazole-3-carboxamide hydrochloride as a white solid. LCMS (method C, ESI): RT=0.49 min, m/z=254.4 [M−HCl+H]+.

Step 7: Synthesis of tert-butyl 1-((2S,4S)-4-(5-ethyl-1,2-thiazole-3-carboxamido)-2-methylpiperidin-1-ylsulfonyl)piperidin-4-ylcarbamate

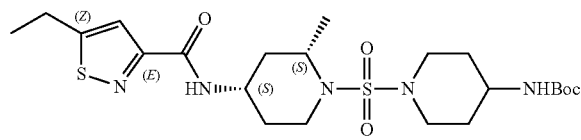

Into a 25-mL round-bottom flask was placed 5-ethyl-N-[(2S,4S)-2-methylpiperidin-4-yl]-1,2-thiazole-3-carboxamide hydrochloride (150 mg, 0.52 mmol, 1.00 equiv) and dichloromethane (10 mL). Then TEA (260 mg, 5.00 equiv) added dropwise followed by tert-butyl N-[1-(chlorosulfonyl)piperidin-4-yl]carbamate (750 mg, 2.51 mmol, 4.85 equiv) which was added in several portions. The resulting mixture was stirred for 2 h at room temperature. The mixture was concentrated under vacuum and the. residue was chromatographed on a silica gel column with ethyl acetate/petroleum ether (1/1). This resulted in 150 mg (56%) of tert-butyl N-[1-[(2S,4S)-4-(5-ethyl-1,2-thiazole-3-amido)-2-methylpiperidine-1-sulfonyl]piperidin-4-yl]carbamate as a yellow solid. LCMS (method C, ESI): RT=1.57 min, m/z=516.2 [M+H]+.

Step 8: Synthesis of N-((2S,4S)-1-(4-aminopiperidin-1-ylsulfonyl)-2-methylpiperidin-4-yl)-5-ethyl-1,2-thiazole-3-carboxamide Hydrochloride

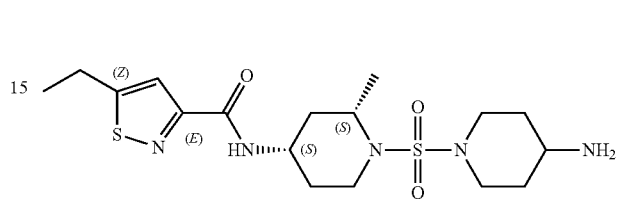

Into a 25-mL round-bottom flask was placed tert-butyl N-[1-[(2S,4S)-4-(5-ethyl-1,2-thiazole-3-carboxamido)-2-methylpiperidine-1-sulfonyl]piperidin-4-yl]carbamate (150 mg, 0.29 mmol, 1.00 equiv) and dichloromethane (10 mL). To the above hydrogen chloride (gas) was introduced. The resulting solution was stirred for 1 h at room temperature. The mixture was then concentrated under vacuum. This resulted in 90 mg (68%) of N-[(2S,4S)-1-(4-aminopiperidine-1-sulfonyl)-2-methylpiperidin-4-yl]-5-ethyl-1,2-thiazole-3-carboxamide hydrochloride as a white solid. $^1$H NMR (300 MHz, D$_2$O) δ: 7.46 (s, 1H), 4.06-4.01 (m, 1H), 3.71-3.55 (m, 4H), 3.33-3.20 (m, 2H), 2.95-2.82 (m, 4H), 2.04-1.97 (m, 4H), 1.80-1.57 (m, 4H), 1.30-1.22 (m, 6H) ppm. LCMS (method A, ESI): RT=1.74 min, m/z=416.2 [M−HCl+H]+.

Example 20

Synthesis of N-((2S,4R)-1-(4-aminopiperidin-1-ylsulfonyl)-2-methylpiperidin-4-yl)-5-ethyl-1,2-thiazole-3-carboxamide (Cpd. No. 629)

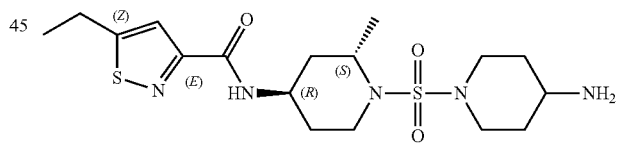

Step 1: Synthesis of (2S,4R)-tert-butyl 4-(5-ethyl-1,2-thiazole-3-carboxamido)-2-methylpiperidine-1-carboxylate

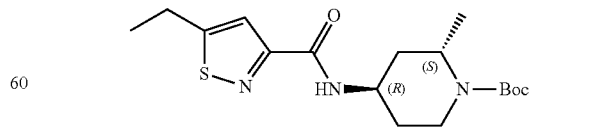

tert-Butyl (2S)-4-(5-ethyl-1,2-thiazole-3-carboxamido)-2-methylpiperidine-1-carboxylate (470 mg, 1.33 mmol, 1.00 equiv) was purified by Chiral-Prep-HPLC with the following conditions: Column: CHIRALCEL OJ-3-; mobile phase, Hex (0.2% IPA): EtOH=70:30; Detector, 254 nm. This resulted in 100 mg (21%) of tert-butyl (2S,4R)-4-(5-ethyl-1,2-thiazole-3-amido)-2-methylpiperidine-1-carboxylate as a yellow solid. ee value: 100%.

Step 2: Synthesis of 5-ethyl-N-((2S,4R)-2-methylpiperidin-4-yl)-1,2-thiazole-3-carboxamide

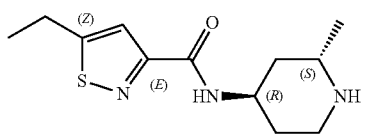

Into a 25-mL round-bottom flask was placed tert-butyl (2S,4R)-4-(5-ethyl-1,2-thiazole-3-carboxamido)-2-methylpiperidine-1-carboxylate (100 mg, 0.28 mmol, 1.00 equiv) and dichloromethane (10 mL). To the above hydrogen chloride (gas) was introduced. The resulting solution was stirred for 1 h at room temperature. The mixture was concentrated under vacuum. This resulted in 70 mg (85%) of 5-ethyl-N-[(2S,4R)-2-methylpiperidin-4-yl]-1,2-thiazole-3-carboxamide hydrochloride as a white solid. LCMS (method C, ESI): RT=0.49 min, m/z=254.2 [M−HCl+H]$^+$.

Step 3: Synthesis of tert-butyl 1-((2S,4R)-4-(5-ethyl-1,2-thiazole-3-carboxamido)-2-methylpiperidin-1-ylsulfonyl)piperidin-4-ylcarbamate

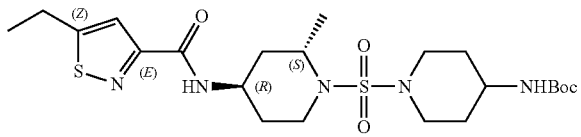

Into a 25-mL round-bottom flask was placed 5-ethyl-N-[(2S,4R)-2-methylpiperidin-4-yl]-1,2-thiazole-3-carboxamide hydrochloride (70 mg, 0.24 mmol, 1.00 equiv) and dichloromethane (10 mL). TEA (120 mg) was added dropwise at 0° C. tert-Butyl N-[1-(chlorosulfonyl)piperidin-4-yl]carbamate (350 mg, 1.17 mmol, 4.85 equiv) was then added in several portions. The resulting solution was stirred for 2 h at room temperature. The mixture was then concentrated under vacuum. The residue was chromatographed on a silica gel column with ethyl acetate/petroleum ether (1/1). This resulted in 70 mg (56%) of tert-butyl N-[1-[(2S,4R)-4-(5-ethyl-1,2-thiazole-3-carboxamido)-2-methylpiperidine-1-sulfonyl]piperidin-4-yl]carbamate as a yellow solid. LCMS (method C, ESI): RT=1.54 min, m/z=538.2 [M+Na]$^+$.

Step 4: Synthesis of N-((2S,4S)-1-(4-aminopiperidin-1-ylsulfonyl)-2-methylpiperidin-4-yl)-5-ethyl-1,2-thiazole-3-carboxamide

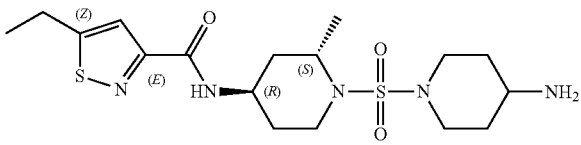

Into a 25-mL round-bottom flask was placed tert-butyl N-[1-[(2S,4R)-4-(5-ethyl-1,2-thiazole-3-carboxamido)-2-methylpiperidine-1-sulfonyl]piperidin-4-yl]carbamate (70 mg, 0.14 mmol, 1.00 equiv) and dichloromethane (10 mL). To the above hydrogen chloride (gas) was introduced. The resulting solution was stirred for 1 h at room temperature. The mixture was then concentrated under vacuum. The crude product was purified by Prep-HPLC with the following conditions: Column: X Bridge RP, 19*150 mm, 5 um; Mobile Phase A: Water/0.05% NH$_4$HCO$_3$, Mobile Phase B: ACN; Flow rate: 30 mL/min; Gradient: 25% B to 45% B in 8 min; 254 nm. This resulted in 13.8 mg (24%) of N-[(2 S,4R)-1-(4-aminopiperidine-1-sulfonyl)-2-methylpiperidin-4-yl]-5-ethyl-1,2-thiazole-3-carboxamide as a white solid. $^1$H NMR (400 MHz, CD$_3$OD) δ: 7.57 (s, 1H) 4.40-4.25 (m, 1H), 4.25-4.15 (m, 1H), 3.67-3.62 (m, 3H), 3.30-3.15 (m, 1H), 3.06-3.00 (m, 2H), 2.89-2.79 (m, 3H), 1.98-1.85 (m, 5H), 1.80-1.58 (m, 2H), 1.51-1.40 (m, 1H), 1.40-1.36 (m, 6H) ppm. LCMS (method A, ESI): RT=1.68 min, m/z=438.1 [M+Na]$^+$.

Example 21

Synthesis of N-((2S,4S)-1-(4-acetamidophenylsulfonyl)-2-methylpiperidin-4-yl)-2-oxoindoline-5-carboxamide (Cpd. No. 632)

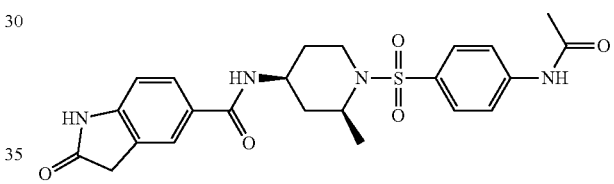

Step 1: Synthesis of (2S)-tert-butyl 4-amino-2-methylpiperidine-1-carboxylate

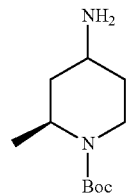

Into a 1-L round-bottom flask was placed methanol (600 mL), HCOONH$_4$ (32 g, 507.45 mmol, 36.08 equiv) and tert-butyl (2S)-2-methyl-4-oxopiperidine-1-carboxylate (3 g, 14.07 mmol, 1.00 equiv). NaCNBH$_3$ (1.7 g, 27.05 mmol, 1.92 equiv) was added batchwise slowly at 0-5° C. The resulting solution was stirred for 16 hours at 25° C. The reaction mixture was then diluted with 250 mL of ethyl acetate and washed with 3×250 mL of brine. The organic layer was dried over anhydrous sodium sulfate and concentrated under vacuum. This resulted in 2.5 g (83%) of tert-butyl (2S)-4-amino-2-methylpiperidine-1-carboxylate as colorless oil. $^1$H-NMR (400 MHz, CDCl$_3$) δ: 4.13-4.11 (m, 1H), 3.98-3.97 (m, 1H), 3.49-3.28 (m, 2H), 2.24-2.10 (m, 2H), 1.76-1.75 (m, 2H), 1.45 (s, 9H), 1.27 (d, J=6.0 Hz, 3H) ppm. LCMS (method D, ESI): RT=1.04 min, m/z=215.0 [M+H]$^+$.

Step 2: Synthesis of (2S)-tert-butyl 4-(benzyloxycarbonylamino)-2-methylpiperidine-1-carboxylate

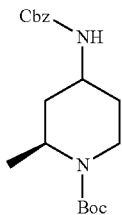

Into a 250-mL round-bottom flask was placed water (50 mL), tetrahydrofuran (50 mL), sodium carbonate (3.7 g, 34.91 mmol, 2.99 equiv), and tert-butyl (2S)-4-amino-2-methylpiperidine-1-carboxylate (2.5 g, 11.67 mmol, 1.00 equiv). Then benzyl chloroformate (4 g, 23.45 mmol, 2.01 equiv) was added dropwise at 0-5° C. The resulting solution was stirred for 16 hours at 25° C. The resulting mixture was concentrated under vacuum. The residue was diluted with 100 mL of ethyl acetate and washed with 3×100 mL of brine. The organic layer was dried over anhydrous sodium sulfate and concentrated under vacuum. The residue was chromatographed on a silica gel column with ethyl acetate/petroleum ether (1/1). This resulted in 2 g (49%) of tert-butyl (2S)-4-[[(benzyloxy)carbonyl]amino]-2-methylpiperidine-1-carboxylate as colorless oil. $^1$H-NMR (300 MHz, CD$_3$OD) δ: 7.36-7.30 (m, 5H), 5.09 (s, 2H), 4.10-4.08 (m, 1H), 3.76-3.70 (m, 2H), 3.27-3.17 (m, 1H), 1.97-1.78 (m, 3H), 1.62-1.55 (m, 1H), 1.41 (s, 9H), 1.25 (d, J=8.0 Hz, 3H) ppm. LCMS (method D, ESI): RT=1.57 min, m/z=349.3 [M+H]$^+$.

Step 3: Synthesis of Benzyl (2S)-2-methylpiperidin-4-ylcarbamate

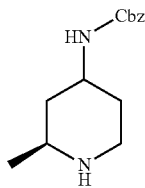

Into a 25-mL round-bottom flask was placed tert-butyl (2S)-4-[[(benzyloxy)carbonyl]amino]-2-methylpiperidine-1-carboxylate (400 mg, 1.15 mmol, 1.00 equiv) and dichloromethane (6 mL). Trifluoroacetic acid (3 mL) was then added dropwise at 0-5° C. The resulting solution was stirred for 30 min at 25° C. The mixture was concentrated under vacuum which resulted in 300 mg (crude) of benzyl N-[(2S)-2-methylpiperidin-4-yl]carbamate as a yellow liquid. LCMS (method A, ESI): RT=1.07 min, m/z=249.1 [M+H]$^+$.

Step 4: Synthesis of benzyl (2S)-1-(4-acetamidophenylsulfonyl)-2-methylpiperidin-4-ylcarbamate

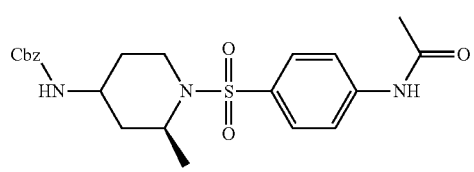

Into a 50-mL round-bottom flask was placed benzyl N-[(2S)-2-methylpiperidin-4-yl]carbamate (300 mg, 1.21 mmol, 1.00 equiv) and triethylamine (600 mg, 5.93 mmol, 4.00 equiv) in dichloromethane (30 mL). This was followed by the addition of 4-acetamidobenzene-1-sulfonyl chloride (720 mg, 3.08 mmol, 2.00 equiv) dropwise with stirring at 0° C. The resulting solution was stirred for 16 hours at 25° C. The mixture was then concentrated under vacuum. The residue was chromatographed on a silica gel column with ethyl acetate/petroleum ether (2/1). This resulted in 300 mg (56%) of benzyl N-[(2S)-1-[(4-acetamidobenzene)sulfonyl]-2-methylpiperidin-4-yl]carbamate as a yellow solid. LCMS (method D, ESI): RT=1.40 min, m/z=446.2 [M+H]$^+$.

Step 5: Synthesis of N-(4-((2S)-4-amino-2-methylpiperidin-1-ylsulfonyl) phenyl)acetamide

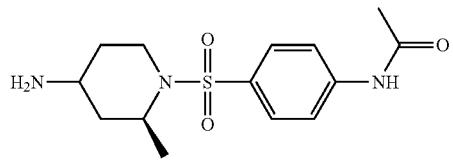 [SMILES: CC(=O)Nc1ccc(S(=O)(=O)N2CCC(N)C[C@@H]2C)cc1]

Into a 50-mL round-bottom flask was placed benzyl N-[(2S)-1-[(4-acetamidobenzene)sulfonyl]-2-methylpiperidin-4-yl]carbamate (300 mg, 0.67 mmol, 1.00 equiv) and trifluoroacetic acid (10 mL). The resulting solution was stirred for 1 hour at 60° C. in an oil bath. The mixture was then concentrated under vacuum. This resulted in 280 mg (crude) of N-[4-[(2S)-4-amino-2-methylpiperidine-1-sulfonyl]phenyl]acetamide as yellow oil. LCMS (method D, ESI): RT=0.96 min, m/z=312.2 [M+H]$^+$.

Step 6: Synthesis of N-(4-((2S,4S)-4-amino-2-methylpiperidin-1-ylsulfonyl)phenyl)acetamide and N-(4-(((2S,4R)-4-amino-2-methylpiperidin-1-yl)sulfonyl)phenyl)acetamide

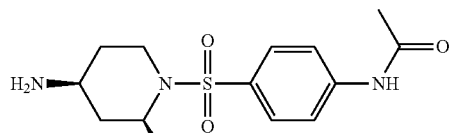

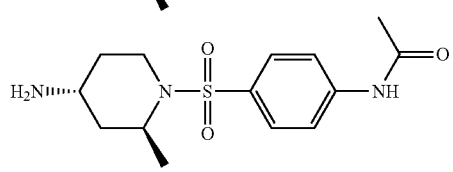

N-[4-[(2S)-4-amino-2-methylpiperidine-1-sulfonyl]phenyl]acetamide (200 mg, 0.64 mmol, 1.00 equiv) was separated by Prep-SFC with the following conditions: Column, Lux 5u Cellulose-44.6*150 mm, 5 um Chiral-A (LUX-4); mobile phase, 25% IPA with MeOH; Detector, UV 254/220 nm. This resulted in 100 mg (100%) of N-[4-[(2S,4S)-4-amino-2-methylpiperidine-1-sulfonyl]phenyl]acetamide as a yellow solid and 40 mg (98%) of N-[4-[(2 S,4R)-4-amino-2-methylpiperidine-1-sulfonyl]phenyl]acetamide as a yellow solid. ee value: 100%.

Step 7: Synthesis of N-((2S,4S)-1-(4-acetamidophenylsulfonyl)-2-methylpiperidin-4-yl)-2-oxoindoline-5-carboxamide

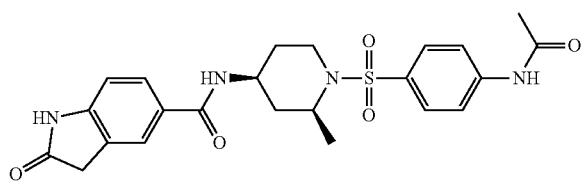 [SMILES: CC(=O)Nc1ccc(S(=O)(=O)N2CC[C@H](NC(=O)c3ccc4c(c3)CC(=O)N4)C[C@@H]2C)cc1]

Into a 10-mL round-bottom flask was placed 2-oxo-2,3-dihydro-1H-indole-5-carboxylic acid (48 mg, 0.27 mmol, 2.00 equiv), 1-hydroxybenzotrizole (40 mg, 1.26 mmol, 2.00 equiv), triethylamine (50 mg, 0.49 mmol, 4.00 equiv), N-[4-[(2S,4S)-4-amino-2-methylpiperidine-1-sulfonyl]phenyl]acetamide (40 mg, 0.13 mmol, 1.00 equiv), and dichloromethane (4 mL). N-(3-dimethylaminopropyl)-N'-ethylcarbodiimide hydrochloride (56 mg, 0.29 mmol, 2.00 equiv) was added batchwise at 0-5° C. The resulting solution was stirred for 16 hours at 25° C. The mixture was then washed with 3×5 mL of brine and the organic layer concentrated under vacuum. The crude product was purified by Prep-HPLC with the following conditions (2#-Waters 2767-2 (HPLC-08)): Column, Xbridge Shield RP 18, 5 um, 19*150 mm; mobile phase, water with 50 mmol $NH_4HCO_3$ and $CH_3CN$ (10.0% $CH_3CN$ up to 28.0% in 2 min, up to 46.0% in 10 min, up to 100.0% in 1 min, down to 10.0% in 1 min); Detector, UV 254 nm. This resulted in 2.6 mg (4%) of N-[(2S,4S)-1-[(4-acetamidobenzene)sulfonyl]-2-methylpiperidin-4-yl]-2-oxo-2,3-dihydro-1H-indole-5-carboxamide as a white solid. $^1$H-NMR (400 MHz, $CD_3OD$) δ: 7.84-7.78 (m, 4H), 7.74-7.71 (m, 2H), 6.95 (d, J=8.0 Hz, 1H), 3.95-3.90 (m, 2H), 3.62-3.51 (m, 1H), 3.33-3.32 (m, 2H), 3.15-3.04 (m, 1H), 2.19 (s, 3H), 2.06-1.98 (m, 1H), 1.93-1.88 (m, 1H), 1.73-1.68 (m, 2H), 1.40 (d, J=8.0 Hz, 3H) ppm. LCMS (method D, ESI): RT=2.62 min, m/z=471.2 [M+H]$^+$.

Example 22

Synthesis of N-[(1R,3r,5S)-8-(4-aminopiperidine-1-sulfonyl)-8-azabicyclo[3.2.1]octan-3-yl]-5-ethyl-pyridazine-3-carboxamide Trifluoroacetate (Cpd. No. 616)

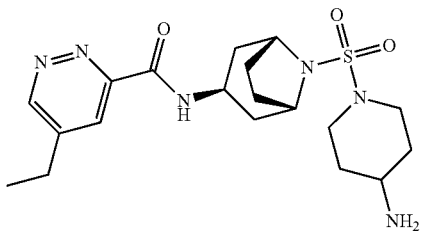 [SMILES: CCc1cnnc(C(=O)N[C@H]2C[C@H]3CC[C@@H](C2)N3S(=O)(=O)N2CCC(N)CC2)c1]

Step 1: Synthesis of 3-chloro-5-ethylpyridazine

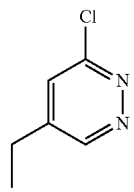

Into a 50-mL round-bottom flask was placed 5-ethyl-2,3-dihydropyridazin-3-one (100 mg, 0.81 mmol, 1.00 equiv) and $POCl_3$ (5 mL). The resulting solution was stirred for 2 hours at 80° C. in an oil bath. The mixture was then concentrated under vacuum. The residue was extracted with 1×100 mL of dichloromethane and the organic layer washed with 50 mL of sodium bicarbonate (aq. sat.) and brine. The organic layer was dried over anhydrous sodium sulfate and concentrated under vacuum. The residue was chromatographed on a silica gel column with ethyl acetate/petroleum ether (30:100). This resulted in 80 mg (69%) of 3-chloro-54-ethylpyridazine as yellow oil. TLC, Rf=0.2 (PE:EA=10:1).

Step 2: Synthesis of methyl 5-ethylpyridazine-3-carboxylate

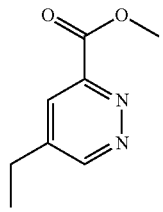

Into a 30-mL pressure tank reactor (100 mL) was placed 3-chloro-5-ethylpyridazine (80 mg, 0.55 mmol, 1.00 equiv), methanol (10 mL), triethylamine (112 mg, 1.11 mmol, 2.02 equiv), and Pd(dppf)Cl2 (148 mg). To the above CO (gas) was introduced and maintained at 30 atm. The resulting solution was stirred for 15 h at 80° C. The solids were filtered out. The filtrate was extracted with 2×100 mL of ethyl acetate and the organic layers combined, washed with 50 mL of brine, dried over anhydrous sodium sulfate and concentrated under vacuum. The residue was chromatographed on a silica gel column with ethyl acetate/petroleum ether (30:100). This resulted in 80 mg (86%) of methyl 5-ethylpyridazine-3-carboxylate as yellow oil. LCMS (method C, ESI): RT=0.78 min, m/z=167.0 [M+H]$^+$.

Step 3: Synthesis of 5-ethylpyridazine-3-carboxylic Acid

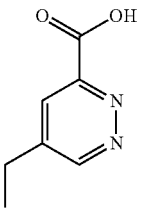

Into a 10-mL round-bottom flask was placed methyl 5-ethylpyridazine-3-carboxylate 80 mg, 0.48 mmol, 1.00 equiv) and $C_2H_5OH$ (5 mL). This was followed by the addition of a solution of LiOH.$H_2O$ (100 mg, 2.4 mmol, 5.00 equiv) in water (1 mL) which was added dropwise with stirring at 0° C. The resulting solution was stirred for 3 hour at 20° C. The reaction was then quenched by the addition of 50 mL of water. The pH was adjusted to 5 with hydrochloric acid (6N). The mixture was extracted with 2×100 mL of dichloromethane and the combined organic layers dried over anhydrous sodium sulfate and concentrated under vacuum. This resulted in 60 mg (34.7%) of 5-ethylpyridazine-3-carboxylic acid as black oil. LCMS (method D, ESI): RT=0.90 min, m/z=153.0 [M+H]$^+$.

Step 4: Synthesis of tert-butyl N-[1-[(1R,3r,5S)-3-(5-ethylpyridazine-3-carboxamido)-8-azabicyclo[3.2.1]octane-8-sulfonyl]piperidin-4-yl]carbamate

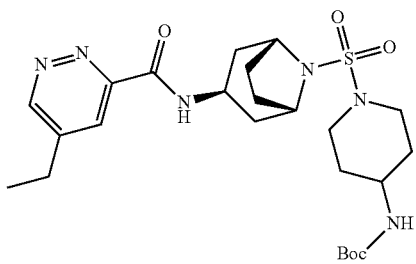 [SMILES: CCc1cnnc(C(=O)N[C@H]2C[C@H]3CC[C@@H](C2)N3S(=O)(=O)N2CCC(NC(=O)OC(C)(C)C)CC2)c1]

Into a 50-mL round-bottom flask purged and maintained with an inert atmosphere of nitrogen was placed dichloromethane 20 mL) and 5-ethylpyridazine-3-carboxylic acid (60 mg, 0.39 mmol, 1.00 equiv). To the above was added tert-butyl N-[1-[(1R,3r,5S)-3-amino-8-azabicyclo[3.2.1]octane-8-sulfonyl]piperidin-4-yl]carbamate (150 mg, 0.39 mmol, 0.98 equiv), HOBT (79 mg, 0.58 mmol, 1.49 equiv)), and EDCI (223 mg, 1.17 mmol, 2.99 equiv). This was followed by the addition of a solution of triethylamine (118 mg, 1.17 mmol, 2.99 equiv) in dichloromethane (2 ml) which was added dropwise with stirring at 0° C. over 3 min. The resulting solution was stirred for 15 hours at 20° C. The mixture was extracted with 2×100 mL of dichloromethane and the organic layers combined, washed with 50 mL of water and 50 mL of brine, and concentrated under vacuum. The residue was chromatographed on a silica gel column with ethyl acetate/petroleum ether (50:100). This resulted in 50 mg (24%) of tert-butyl N-[1-[(1R,3r,5S)-3-(5-ethylpyridazine-3-carboxamido)-8-azabicyclo[3.2.1]octane-8-sulfonyl]piperidin-4-yl]carbamate as yellow oil. LCMS (method D, ESI): RT=1.46 min, m/z=523.0 [M+H]$^+$.

Step 5: Synthesis of N-[(1R,3r,5S)-8-(4-aminopiperidine-1-sulfonyl)-8-azabicyclo[3.2.1]octan-3-yl]-5-ethylpyridazine-3-carboxamide Trifluoroacetate

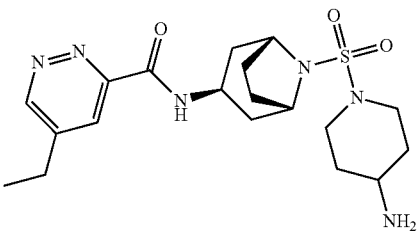 [SMILES: CCc1cnnc(C(=O)N[C@H]2C[C@H]3CC[C@@H](C2)N3S(=O)(=O)N2CCC(N)CC2)c1]

Into a 25-mL round-bottom flask was placed tert-butyl N-[1-[(1R,3r,5S)-3-(5-ethylpyridazine-3-carboxamido)-8-azabicyclo[3.2.1]octane-8-sulfonyl]piperidin-4-yl]carbamate (50 mg, 0.10 mmol, 1.00 equiv) and hydrogen chloride/dioxane (10 mL, saturated, this solution was made by introducing hydrogen chloride gas into 1,4-dioxane under 0° C. for 6 hours). The resulting solution was stirred for 4 h at 20° C. The mixture was then concentrated under vacuum. The crude product was purified by Prep-HPLC with the following conditions: Column: X Select C18, 19*250 mm, 5 um; Mobile Phase A: Water/0.05% TFA, Mobile Phase B: ACN; Flow rate: 30 mL/min; Gradient: 12% B to 52% B in 11.5 min; 254 nm. This resulted in 17.9 mg (35%) of N-[(1R,3r,5S)-8-(4-aminopiperidine-1-sulfonyl)-8-azabicyclo[3.2.1]octan-3-yl]-5-ethylpyridazine-3-carboxamide trifluoroacetate as a yellow solid. $^1$H NMR (300 MHz, CD$_3$OD) δ: 9.29 (s, 1H), 8.19 (s, 1H), 4.37-4.28 (m, 1H), 4.21-4.11 (s, 2H), 3.86 (d, J=15.0 Hz, 2H), 3.30-3.20 (m, 1H), 2.99-2.80 (m, 4H), 2.45-2.30 (m, 2H), 2.18-2.00 (m, 8H), 1.79-1.61 (m, 2H), 1.40-1.29 (m, 3H) ppm. LCMS (method D, ESI): RT=1.27 min, m/z=423.2 [M+H]$^1$.

Example 23

Synthesis of 2-oxo-N-[1-[(piperidin-4-ylmethane)sulfonyl]piperidin-4-yl]-2,3-dihydro-1H-indole-5-carboxamide Trifluoroacetate (Cpd. No. 620)

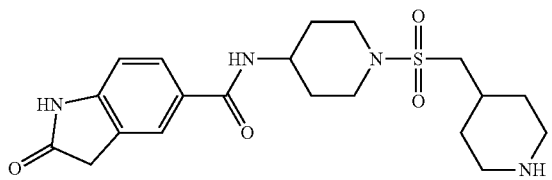 [SMILES: O=C1Cc2cc(C(=O)NC3CCN(S(=O)(=O)CC4CCNCC4)CC3)ccc2N1]

Step 1: Synthesis of 2-oxo-2,3-dihydro-1H-indole-5-carboxylic Acid

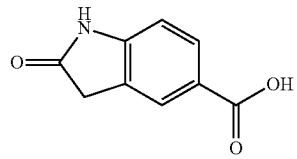 [SMILES: O=C1Cc2cc(C(=O)O)ccc2N1]

Into a 50-mL round-bottom flask was placed methyl 2-oxo-2,3-dihydro-1H-indole-5-carboxylate (800 mg, 4.18 mmol, 1.00 equiv) and methanol (10 mL). This was followed by the addition of a solution of NaOH (670 mg, 16.75 mmol, 4.00 equiv) in water (10 mL) dropwise with stirring at 0° C. The resulting solution was stirred for 14 h at 20° C. The mixture was then concentrated under vacuum and the residue taken up in 20 mL of H$_2$O. This was washed with 2×5 mL of dichloromethane. The pH was adjusted to 4 with hydrochloric acid (1 N) and extracted with 5×50 mL of ethyl acetate and the organic layers combined. Concentration resulted in 592 mg (80%) of 2-oxo-2,3-dihydro-1H-indole-5-carboxylic acid as a yellow solid. $^1$H NMR (400 MHz, DMSO) δ: 12.5 (brs, 1H), 10.7 (s, 1H), 7.82 (d, J=8.4 Hz, 1H), 7.76 (s, 1H), 6.88 (d, J=8.0 Hz, 1H), 3.54 (s, 2H) ppm. LCMS (method A, ESI): RT=0.97 min, m/z=178.0 [M+H]$^+$.

Step 2: Synthesis of tert-butyl 4-(2-oxo-2,3-dihydro-1H-indole-5-carboxamido)piperidine-1-carboxylate

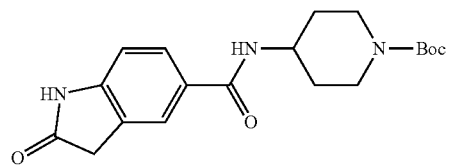 [SMILES: CC(C)(C)OC(=O)N1CCC(NC(=O)c2ccc3c(c2)CC(=O)N3)CC1]

Into a 25-mL round-bottom flask was placed tert-butyl 4-aminopiperidine-1-carboxylate (300 mg, 1.50 mmol, 1.00 equiv), dichloromethane (10 mL), 2-oxo-2,3-dihydro-1H-indole-5-carboxylic acid (319 mg, 1.80 mmol, 1.20 equiv), EDCI (344 mg, 1.79 mmol, 1.20 equiv), and HOBT (304 mg, 2.25 mmol, 1.50 equiv). This was followed by the addition of TEA (454 mg, 4.49 mmol, 3.00 equiv) dropwise with stirring at 0° C. The resulting solution was stirred for 14 h at 20° C. The solids were collected by filtration. This resulted in 393 mg (73%) of tert-butyl 4-(2-oxo-2,3-dihydro-1H-indole-5-amido)piperidine-1-carboxylate as a yellow solid. LCMS (method C, ESI): RT=0.78 min, m/z=304.0 [M+H−56]+.

Step 3: Synthesis of 2-oxo-N-(piperidin-4-yl)-2,3-dihydro-1H-indole-5-carboxamide Hydrochloride

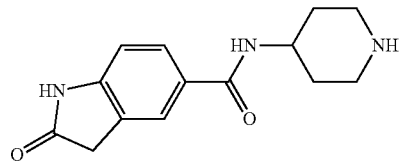 [SMILES: O=C1Cc2cc(C(=O)NC3CCNCC3)ccc2N1]

Into a 25-mL round-bottom flask was placed tert-butyl 4-(2-oxo-2,3-dihydro-1H-indole-5-carboxamido)piperidine-1-carboxylate (250 mg, 0.70 mmol, 1.00 equiv) and hydrogen chloride/dioxane (3 mL, saturated, this solution was made by introducing hydrogen chloride gas into 1,4-dioxane under 0° C. for 6 hours). The resulting solution was stirred for 2 h at 20° C. The mixture was then concentrated under vacuum. This resulted in 200 mg (97%) of 2-oxo-N-(piperidin-4-yl)-2,3-dihydro-1H-indole-5-carboxamide hydrochloride as a light yellow solid. $^1$H NMR (400 MHz, D$_2$O) δ: 7.65 (s, 2H), 6.95 (s, 1H), 4.04 (t, J=10.4 Hz, 1H), 3.54 (s, 2H), 3.42 (d, J=13.2 Hz, 2H), 3.12-3.01 (m, 2H), 2.13 (d, J=14.0 Hz, 2H), 1.81-1.65 (m, 2H) ppm. LCMS (method A, ESI): RT=0.89 min, m/z=260.0 [M+H]$^1$.

Step 4: Synthesis of benzyl 4-[[4-(2-oxo-2,3-dihydro-1H-indole-5-carboxamido)piperidine-1-sulfonyl]methyl]piperidine-1-carboxylate

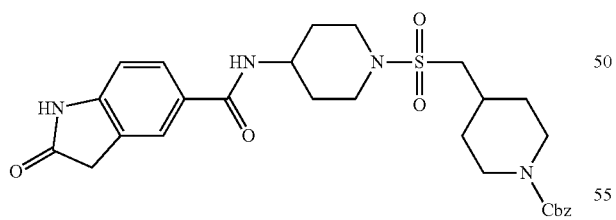

Into a 50-mL round-bottom flask was placed 2-oxo-N-(piperidin-4-yl)-2,3-dihydro-1H-indole-5-carboxamide hydrochloride (80 mg, 0.27 mmol, 1.00 equiv) and NMP (16 mL). This was followed by the addition of TEA (82 mg, 0.81 mmol, 3.00 equiv) dropwise with stirring at 0° C. To this was then added benzyl 4-[(chlorosulfonyl)methyl]piperidine-1-carboxylate (135 mg, 0.41 mmol, 1.50 equiv) in several batches at 0° C. The resulting solution was stirred for 2 h at 20° C. The mixture was concentrated under vacuum. The residue was chromatographed on a silica gel column with dichloromethane/methanol (50:1-20:1). The collected fractions were combined and concentrated under vacuum. This resulted in 100 mg (67%) of benzyl 4-[[4-(2-oxo-2,3-dihydro-1H-indole-5-carboxamido)piperidine-1-sulfonyl]methyl]piperidine-1-carboxylate as a yellow solid. LCMS (method C, ESI): RT=1.04 min, m/z=555.0 [M+H]$^1$.

Step 5: Synthesis of 2-oxo-N-[1-[(piperidin-4-yl-methane)sulfonyl]piperidin-4-yl]-2,3-dihydro-1H-indole-5-carboxamide Trifluoroacetate

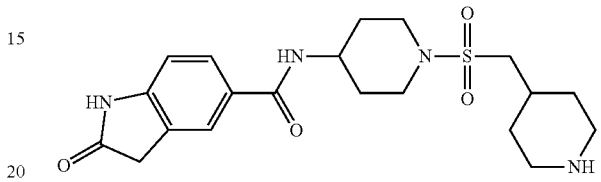

Into a 25-mL round-bottom flask was placed benzyl 4-[[4-(2-oxo-2,3-dihydro-1H-indole-5-carboxamido)piperidine-1-sulfonyl]methyl]piperidine-1-carboxylate (80 mg, 0.14 mmol, 1.00 equiv) and hydrochloric acid (12 N, 5 mL). The resulting solution was stirred for 2 h at 20° C. The mixture was then concentrated under vacuum. The crude product was purified by Prep-HPLC with the following conditions: Column: X Bridge C18, 19*150 mm, 5 um; Mobile Phase A: Water/0.05% TFA, Mobile Phase B: ACN; Flow rate: 30 mL/min; Gradient: 15% B to 43% B in 10 min; Detector: 254 nm. This resulted in 13.2 mg (17%) of 2-oxo-N-[1-[(piperidin-4-ylmethane)sulfonyl]piperidin-4-yl]-2,3-dihydro-1H-indole-5-carboxamide trifluoroacetate as a white solid. $^1$H NMR (400 MHz, D$_2$O) δ: 7.61 (s, 2H), 7.00 (d, J=4.4 Hz, 1H), 4.00-3.90 (m, 1H), 3.75-3.66 (m, 2H), 3.60 (s, 2H), 3.43-3.37 (m, 2H), 3.15 (d, J=6.4 Hz, 2H), 3.05-2.92 (m, 4H), 2.31-2.18 (m, 1H), 2.15-1.97 (m, 4H), 1.69-1.50 (m, 4H) ppm. LCMS (method A, ESI): RT=1.03 min, m/z=421.1 [M+H]$^+$.

Example 24

Synthesis of N-(azetidin-3-yl)-1-cyclopropyl-1H-1,2,3-triazole-4-carboxamide

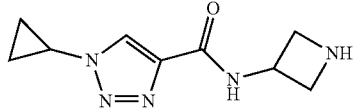 [SMILES: O=C(NC1CNC1)c1cn(C2CC2)nn1]

Step 1: Synthesis of Ethyl 2-diazo-3-oxopropanoate

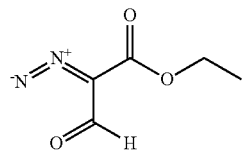

Oxalyl chloride (87.9 g, 693 mmol) was added to a cold solution of N,N-dimethylformamide (42.3 g, 578 mmol) in CHCl₃ (150 mL) and the reaction was stirred at room temperature for 30 min, followed by heating at 40° C. for a further 1 h. After chilling the reaction to −10° C., ethyl 2-diazoacetate (63.0 g, 552 mmol) was added and the mixture was stirred at room temperature for 2 h. The mixture was then concentrated and the residue was diluted with ether (200 mL), the solid was collected by filtration and dissolved in 10% aq. HOAc (200 mL), then stirred for a further 1 h. The resulting mixture was extracted with ethyl acetate (300 mL×3) and the organic was washed with saturated Na₂CO₃ aq. (300 mL) and brine (300 mL), dried over Na₂SO₄, filtered and concentrated to give crude ethyl 2-diazo-3-oxopropanoate (27 g, 32.8%) as red oil, which was used for next step without further purification. ¹H-NMR (400 MHz, CD₃OD) δ ppm: 9.67 (s, 1H), 4.33 (q, J=7.2 Hz, 2H), 1.32 (t, J=7.2, 3H).

Step 2: Synthesis of ethyl 1-cyclopropyl-1H-1,2,3-triazole-4-carboxylate

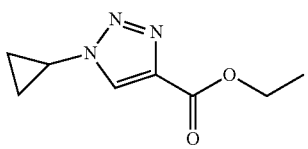

To a solution of ethyl 2-diazo-3-oxopropanoate (27 g, 189 mmol) in EtOH (100 mL) was added acetic acid (28.3 g, 472 mmol). Cyclopropanamine (10.7 g, 189 mmol) was added slowly and the mixture was stirred at room temperature overnight. The solvent was removed and saturated Na₂CO₃ aq. was added to the residue to bring the pH to 8. The mixture was extracted with ethyl acetate (200 mL×3), washed with brine (100 mL), dried over Na₂SO₄, filtered and concentrated. The resulting residue was purified by flash chromatography (PE:EA=2:1) to give crude ethyl 1-cyclopropyl-1H-1,2,3-triazole-4-carboxylate (18.5 g, 54.0%) as yellow oil. ESI-LCMS (m/z): 182.2 [M+H]⁺.

Step 3: Synthesis of 1-cyclopropyl-1H-1,2,3-triazole-4-carboxylic Acid

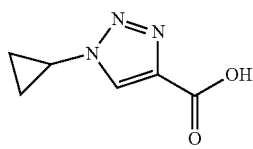 [SMILES: O=C(O)c1cn(C2CC2)nn1]

To a solution of ethyl 1-cyclopropyl-1H-1,2,3-triazole-4-carboxylate (18.5 g, 102 mmol) in THF (80 mL)/H₂O (40 mL) was added lithium hydroxide hydrate (4.5 g, 107 mmol), the resulting mixture was stirred at room temperature for 3 hr. The solvent was removed and the residue was dissolved in H₂O (50 mL), extracted with EA (100 mL). The organic phase was discarded and the water phase was acidified with 2N HCl until the pH=5, The aqueous solution was extracted with DCM:MeOH=10:1 (1.5 L). The organic layer was dried and concentrated to afford 6.3 g of 1-cyclopropyl-1H-1,2,3-triazole-4-carboxylic acid as white solid. The aqueous layer was concentrated to afford another 11.4 g crude product, which was used for next step without further purification. ESI-LCMS (m/z): 154.1[M+H]⁺.

Step 4: Synthesis of tert-butyl 3-(1-cyclopropyl-1H-1, 2, 3-triazole-4-carboxamido)azetidine-1-carboxylate

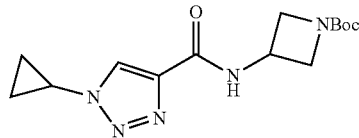 [SMILES: CC(C)(C)OC(=O)N1CC(NC(=O)c2cn(C3CC3)nn2)C1]

A solution of 1-cyclopropyl-1H-1,2,3-triazole-4-carboxylic acid (2 g, 13.0 mmol) in thionyl chloride (10 mL) was stirred at 65° C. for 2 h. The reaction mixture was concentrated under reduced pressure. Then the reaction residue was diluted with DMF (5 mL) and added dropwise to the solution of tert-butyl 3-aminoazetidine-1-carboxylate (2.23 g, 13.0 mmol) and DIPEA (4.19 g, 32.5 mmol) in DCM (15 mL) under 0° C. The resulting mixture was stirred at room temperature overnight. The solvent was removed and the residue was diluted with ethyl acetate (200 mL), washed with water (10 mL×3) and brine (50 mL), dried over Na₂SO₄, filtered and concentrated. The resulting residue was purified by Flash chromatography (DCM:NH₃ in MeOH (7N)=100:050:1) to give tert-butyl 3-(1-cyclopropyl-1H-1,2,3-triazole-4-carboxamido)azetidine-1-carboxylate (3 g, 75.1%) as a yellow solid. ESI-LCMS (m/z): 252.2 [M−55]⁺.

Step 5: Synthesis of N-(Azetidin-3-yl)-1-cyclopropyl-1H-1,2,3-triazole-4-carboxamide

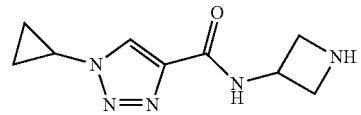 [SMILES: O=C(NC1CNC1)c1cn(C2CC2)nn1]

A solution of tert-butyl 3-(1-cyclopropyl-1H-1, 2,3-triazole-4-carboxamido)azetidine-1-carboxylate (3.0 g, 9.8 mmol) in HCl/MeOH (20 mL) was stirred at 50° C. for 2 h. After completion, the solvent was removed in vacuo. The residue was dissolved in NH₃/MeOH (7 mol/L, 20 mL) and stirred for 30 min. The solvent was removed and the residue was purified by Flash chromatography (DCM:NH₃ in MeOH (7N)=100:0~30:1~15:1) to give N-(azetidin-3-yl)-1-cyclopropyl-1H-1,2,3-triazole-4-carboxamide (1.6 g, 80%) as a white solid. ESI-LCMS (m/z): 208.1 [M+H]⁺. ¹H-NMR (400 MHz, CD₃OD) δ ppm: 8.38 (s, 1H), 4.92-4.86 (m, 1H), 3.98-3.97 (m, 1H), 3.82-3.72 (m, 4H), 1.26-1.20 (m, 4H).

Example 25

Synthesis of 5-cyclopropylpyridazine-3-carboxylic Acid

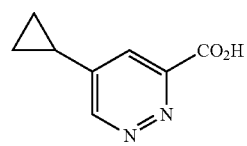 [SMILES: O=C(O)c1cc(C2CC2)cnn1]

Step 1: Synthesis of 5-cyclopropylpyridazin-3-ol

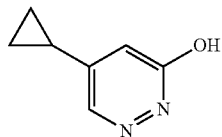

To a solution of 5-chloropyridazin-3-ol (1.0 g, 7.7 mmol) in toluene/H₂O (100:5, 50 mL) was added sequentially cyclopropylboronic acid (987 mg, 11.5 mmol), K₃PO₄ (4.51 g, 23.0 mmol), diacetoxypalladium (86.2 mg, 384 μmol) and tricyclohexylphosphine (107 mg, 384 μmol). The reaction mixture was stirred at 100° C. under N₂ atmosphere for 20 h. then concentrated in vacuum to remove the solvent Water (20 mL) was added and the solution was acidified with hydrochloric acid (4 M) to pH=3. The solution was extracted with EtOAc (200 mL×3) and the combined organic layer were washed with saturated NaCl solution, dried over Na₂SO₄, concentrated to give a brown residue then purified by silica-gel chromatography (PE:EA=1:1) to afford the desired product (350 mg, 34% yield) as white solid. ESI-LCMS (m/z): 137.1 [M+1]⁺.

Step 2: Synthesis of 3-chloro-5-cyclopropylpyridazine

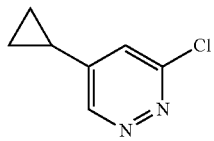

A solution of 5-cyclopropylpyridazin-3-ol (350 mg, 2.6 mmol) in phosphorous oxychloride (10 mL) was stirred at 80° C. for 2 h. The remaining POCl₃ was removed under vacuum then the residue was cooled and added to 20 g of ice. The reaction mixture was neutralized with saturated NaHCO₃ solution and extracted with EtOAc (40 mL×3), the combined organic extract is washed with brine (100 mL×2), dried over Na₂SO₄ and the solvent is removed under vacuum. the resulting residue was purified by silica-gel chromatography (PE:EA=2:1) to afford the product 3-chloro-5-cyclopropylpyridazine as a colorless oil (200 mg, 50% yield). ESI-LCMS (m/z): 155.2 [M+1]⁺.

Step 3: Synthesis of ethyl 5-cyclopropylpyridazine-3-carboxylate

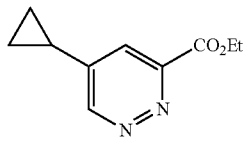 [SMILES: CCOC(=O)c1cc(C2CC2)cnn1]

Potassium acetate (284 mg, 2.9 mmol) was added to a solution of 3-chloro-5-cyclopropylpyridazine (150 mg, 1.0 mmol) in ethanol (10 mL). The mixture was degassed, then Pd(dppf)Cl₂ (35.4 mg, 0.05 mmol) was added. The resulting mixture was heated under an atmosphere of CO at 70° C. for 20 hr. The reaction mixture was filtrated and the filtrate was concentrated under reduced pressure. The residue was purified by column chromatography (PE:EA=1:1) to obtain the desired product ethyl 5-cyclopropylpyridazine-3-carboxylate (100 mg, 54% yield, colorless oil). ESI-LCMS (m/z): 193.1 [M+H]⁺; ¹HNMR (400 MHz, CD₃OD) δ ppm: 9.06 (d, J=2.4 Hz, 1H), 7.81 (d, J=2.4 Hz, 1H), 7.39 (q, J=6.8 Hz, 2H), 2.11-1.92 (m, 1H), 1.34 (t, J=6.8 Hz, 3H), 0.96-0.93 (m, 2H).

Step 4: Synthesis of 5-cyclopropylpyridazine-3-carboxylic Acid

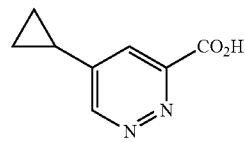 [SMILES: O=C(O)c1cc(C2CC2)cnn1]

To a solution of methyl 5-cyclopropylpyridazine-3-carboxylate (185 mg, 1.03 mmol) in THF/H₂O (8 mL/2 mL) was added lithium hydroxide hydrate (64.6 mg, 1.54 mmol). The reaction mixture was stirred at room temperature for 3 h. Progress of the reaction was monitored by TLC and LCMS. After completion, the mixture was adjusted to pH=5 with 1N HCl, then concentrated directly to 5-cyclopropylpyridazine-3-carboxylic acid (170 mg, 94.6%) as yellow solid and used in next step directly. ESI-LCMS (m/z): 165 [M+1]⁺.

Example 26

Synthesis of 2-(3-(1-(3-Aminoazetidin-1-yl)ethyl)-2-chlorophenoxy)ethan-1-ol

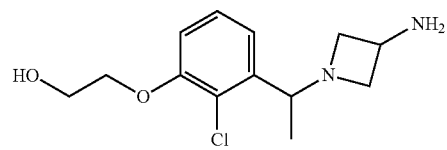 [SMILES: CC(c1cccc(OCCO)c1Cl)N1CC(N)C1]

Step 1: Synthesis of 1-(2-chloro-3-methoxyphenyl)ethanol

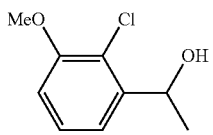

A mixture of 2-chloro-3-methoxybenzaldehyde (2.38 g, 14 mmol) in THF (50 mL) was stirred at 0° C., and a solution of methylmagnesium bromide (5.6 mL, 16.7 mmol, 3M) in ether was added. The resulting mixture was stirred overnight. The reaction mixture was diluted with 1 N HCl (50 mL) and extracted with ethyl acetate (50 mL×3), the combined organic phase was washed with brine, dried over sodium sulfate and concentrated to afford 1-(2-chloro-3-methoxyphenyl)ethanol (2.60 g, 99.6%) as a yellow oil. ¹HNMR (400 MHz, CD₃OD) δ ppm: 7.49 (d, J=8.4 Hz, 1H), 6.90-6.85 (m, 2H), 5.25 (q, J=6.4, 12.8 Hz, 1H), 3.81 (s, 3H), 1.48 (d, J=6.4 Hz, 3H).

Step 2: Synthesis of 1-(2-chloro-3-methoxyphenyl)ethanone

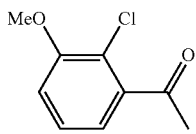

A mixture of 1-(2-chloro-3-methoxyphenyl)ethanol (2.0 g, 10.7 mmol) and manganese(IV) oxide (4.65 g, 53.5 mmol) in DCM (50 mL) was heated to 40° C. and stirred overnight. The reaction mixture was filtered through Celite and the filtrate was concentrated to afford 1-(2-chloro-3-methoxyphenyl)ethanone (1.83 g, 89.8%) as a yellow oil. ESI-LCMS (m/z): 185.0 [M+1]⁺.

Step 3: Synthesis of 1-(2-chloro-3-hydroxyphenyl)ethanone

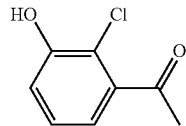

A mixture of 1-(2-chloro-3-methoxyphenyl)ethanone (540 mmol, 2.92 mmol) and aluminum trichloride (972 mg, 7.29 mmol) in monochlorobenzene (10 mL) was stirred at 120° C. for 2 hrs. After cooling to rt, the reaction mixture was added dropwise into 1N HCl in a water bath and the mixture was extracted with ethyl acetate (20 mL×3). The combined organic phase was washed with brine, dried over sodium sulfate and concentrated. The residue was purified by chromatography (PE:EA=5:1) to afford 1-(2-chloro-3-hydroxyphenyl)ethanone (400 mg, 80.3%) as a yellow solid ESI-LCMS (m/z): 171.0[M+H]⁺.

Step 4: Synthesis of 1-(2-chloro-3-(2-hydroxyethoxy)phenyl)ethanone

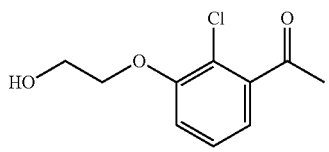

A mixture of 1-(2-chloro-3-hydroxyphenyl)ethanone (330 mg, 1.93 mmol), 2-bromoethanol (482 mg, 3.86 mmol) and K₂CO₃ (800 mg, 5.79 mmol) in DMF (10 mL) was heated to 80° C. overnight. Water was added and the mixture was extracted with ethyl acetate (30 mL×3), the combined organic phase was washed with brine, dried over sodium sulfate and concentrated. The residue was purified by chro-matography (DCM:MeOH=50:1) to afford 1-(2-chloro-3-(2-hydroxyethoxy) phenyl)ethanone (400 mg, 79.2%) as a yellow oil. ESI-LCMS (m/z): 251.1 [M+H]⁺.

Step 5: Synthesis of tert-butyl 1-(1-(2-chloro-3-(2-hydroxyethoxy)phenyl)ethyl)azetidin-3-ylcarbamate

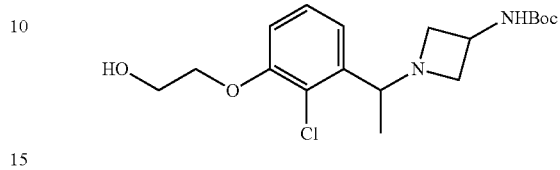

A mixture of 1-(2-chloro-3-(2-hydroxyethoxy)phenyl)ethanone (214 mg, 1 mmol), tert-butyl azetidin-3-ylcarbamate (206 mg, 1.20 mmol), acetic acid (120 mg, 2.00 mmol) and NaBH₃CN (125 mg, 2.00 mmol) in MeOH (10 ml) was stirred at 70° C. overnight. The reaction mixture was concentrated and adjusted pH=8-9 with a saturated solution of Na₂CO₃. The resulting mixture was extracted with DCM (30 mL×3) and the combined organic phase was washed with brine, dried over sodium sulfate and concentrated. The residue was purified by prep-TLC (DCM:MeOH=20:1) to afford tert-butyl (1-(1-(2-chloro-3-(2-hydroxyethoxy)phenyl)ethyl)azetidin-3-yl) carbamate (220 mg, 52.7%) as a yellow oil. ESI-LCMS (m/z): 371.2 [M+l]⁺.

Step 6: Synthesis of 2-(3-(1-(3-Amino azetidin-1-yl)ethyl)-2-chlorophenoxy)ethanol

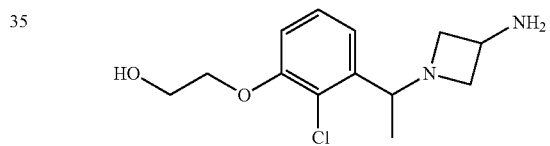

A mixture of tert-butyl (1-(1-(2-chloro-3-(2-hydroxy-ethoxy)phenyl)ethyl and azetidin-3-yl)carbamate (200 mg, 539 µmol) in a solution of HCl/MeOH (10 mL, 3N) was stirred at rt for 3 hrs. The reaction mixture was concentrated under reduced pressure to afford 2-(3-(1-(3-amino azetidin-1-yl)ethyl)-2-chlorophenoxy)ethanol (120 mg, 68.9%) as a yellow oil. ESI-LCMS (m/z): 271.2 [M+l]⁺.

Example 27

Synthesis of (S)—N-(1-(1-(2-chloro-3-(2-hydroxy-ethoxy)phenyl)ethyl)azetidin-3-yl)-1-cyclopropyl-1H-1,2,3-triazole-4-carboxamide (Cpd. No. 831)

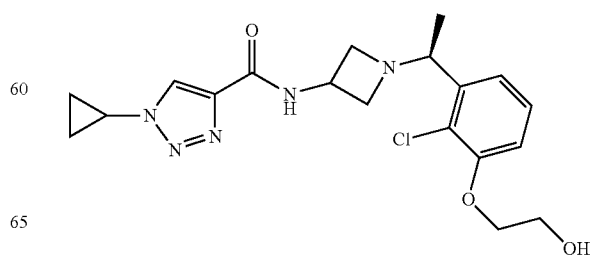

Step 1: Synthesis of N-(1-(1-(2-Chloro-3-(2-hydroxyethoxy)phenyl)ethyl)azetidin-3-yl)-1-cyclopropyl-1H-1,2,3-triazole-4-carboxamide

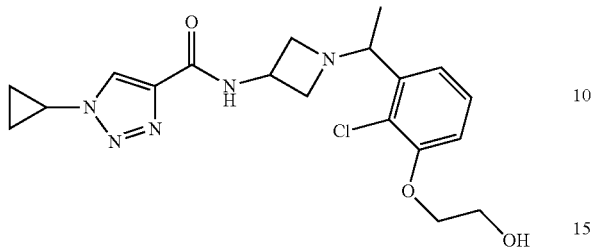

A mixture of 1-cyclopropyl-1H-1,2,3-triazole-4-carboxylic acid (22.9 mg, 150 µmol), 2 (3-(1-(3-aminoazetidin-1-yl)ethyl)-2-chlorophenoxy)ethanol (40.6 mg, 0.15 mmol), HATU (85.4 mg, 225 µmol) and DIPEA (38.6 mg, 300 µmol) in DMF (2 mL) was stirred at rt for 2 h. water was added and the mixture was extracted with ethyl acetate (10 mL×3), the combined organic phase was washed with brine, dried over sodium sulfate and concentrated. The residue was purified by Pre-TLC (DCM:MEOH=20:1) to afford N-(1-(1-(2-chloro-3-(2-hydroxyethoxy)phenyl)ethyl)azetidin-3-yl)-1-cyclopropyl-1H-1,2,3-triazole-4-carboxamide (15 mg, 24.6%) as a white solid. ESI-LCMS (m/z): 406.1 [M+23]$^+$. $^1$HNMR (400 MHz, CD$_3$OD) δ ppm: 8.38 (s, 1H), 7.43 (d, J=8.4 Hz, 1H), 7.00-6.93 (m, 2H), 4.66-4.59 (m, 1H), 4.06-3.95 (m, 4H), 3.89-3.86 (m, 2H), 3.83-3.79 (m, 1H), 3.53-3.50 (m, 1H), 3.22 (t, J=7.2 Hz, 1H), 3.04 (t, J=7.2 Hz, 1H), 1.30-1.19 (m, 7H).

Step 2: Synthesis of (S)—N-(1-(1-(2-chloro-3-(2-hydroxyethoxy)phenyl)ethyl)azetidin-3-yl)-1-cyclopropyl-1H-1,2,3-triazole-4-carboxamide

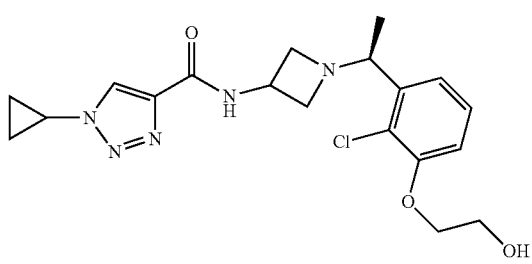 [SMILES: C[C@@H](c1cccc(OCCO)c1Cl)N1CC(NC(=O)c2cn(C3CC3)nn2)C1]

N-(1-(1-(2-chloro-3-(2-hydroxyethoxy)phenyl)ethyl)azetidin-3-yl)-1-cyclopropyl-1H-1,2,3-triazole-4-carboxamide (350 mg, 862 µmol) was separated by chiral HPLC to obtain two single enantiomers, (isomer 1:160 mg, white solid, Ret time 5.02 min; isomer 2:170 mg, Ret time 6.51 min), absolute stereochemistry is undefined, the isomer (Ret time: 5.02 min) was assumed to be S configuration, (S)—N-(1-(1-(2-chloro-3-(2-hydroxyethoxy)phenyl)ethyl)azetidin-3-yl)-1-cyclopropyl-1H-1,2,3-triazole-4-carboxamide (160 mg, 45.8%) as a white solid. ESI-LCMS (m/z): 406.2 [M+1]$^+$. $^1$HNMR (400 MHz, CD$_3$OD) δ ppm: 8.38 (s, 1H), 7.44 (d, J=8.4 Hz, 1H), 6.99-6.94 (m, 2H), 4.63 (t, J=7.2 Hz, 1H), 4.06-3.98 (m, 4H), 3.89-3.86 (m, 2H), 3.82 (t, J=7.2 Hz, 1H), 3.52 (t, J=7.2 Hz, 1H), 3.22 (t, J=7.2 Hz, 1H), 3.05 (t, J=7.2 Hz, 1H), 1.27-1.21 (m, 7H). SFC conditions: Instrument: SFC-80 (Thar, Waters) t; Column: REGISCELL 20*250 mm, 5 um (Dacel); Column temperature: 35° C.; Mobile phase: CO$_2$/MEOH (0.2% methanol amina)=60/40: Flow rate: 80 g/min: Back pressure: 100 bar; Detection wavelength: 214 nm; Cycle time: 8.8 min; Sample solution: 350 mg dissolved in 15 ml Methanol; Injection volume: 3 mL.

Example 28

Synthesis of N-(1-((1-(4-Chlorobenzyl)-1H-pyrazol-4-yl)methyl)azetidin-3-yl)-1-cyclopropyl-1H-1,2,3-triazole-4-carboxamide (Cpd. No. 985)

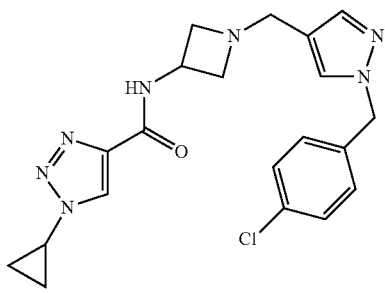 [SMILES: O=C(NC1CN(Cc2cnn(Cc3ccc(Cl)cc3)c2)C1)c1cn(C2CC2)nn1]

Step 1: Synthesis of 1-(4-Chlorobenzyl)-1H-pyrazole-4-carbaldehyde

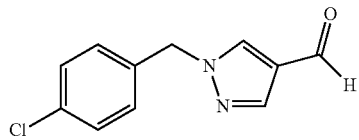 [SMILES: O=Cc1cnn(Cc2ccc(Cl)cc2)c1]

To a solution of 1H-pyrazole-4-carbaldehyde (70 mg, 728 µmol) in MeCN (5 mL) was added 1-(bromomethyl)-4-chlorobenzene (149 mg, 728 µmol) and cesium carbonate (472 mg, 1.45 mmol). The mixture was stirred at r.t. for 2 h. The mixture was concentrated, diluted with EA and water. The organic phase was washed with brine (10 mL×2), dried over Na$_2$SO$_4$ and concentrated to give 1-(4-chlorobenzyl)-1H-pyrazole-4-carbaldehyde (162 mg, 101%) as a white solid, which was used in the next step without further purification. ESI-LCMS (m/z): 221[M+H]$^+$.

Step 2: Synthesis of N-(1-((1-(4-Chlorobenzyl)-1H-pyrazol-4-yl)methyl)azetidin-3-yl)-1-cyclopropyl-1H-1,2,3-triazole-4-carboxamide

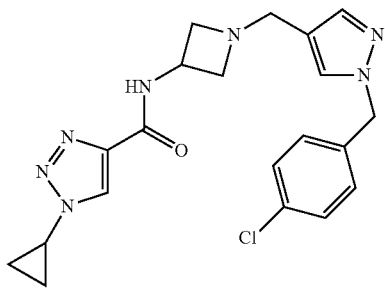 [SMILES: O=C(NC1CN(Cc2cnn(Cc3ccc(Cl)cc3)c2)C1)c1cn(C2CC2)nn1]

A mixture of N-(azetidin-3-yl)-1-cyclopropyl-1H-1,2,3-triazole-4-carboxamide (62 mg, 299 µmol), 1-(4-chlorobenzyl)-1H-pyrazole-4-carbaldehyde (65.9 mg, 299 µmol), and sodium cyanoborohydride (56.3 mg, 897 µmol) in MeOH (10 mL) was stirred at 60° C. for 16 h. The mixture was cooled and concentrated. The residue was diluted with EA, washed with water (10 mL) and brine (10 mL×2), dried over Na$_2$SO$_4$ and concentrated. The residue was purified by prep-HPLC to give N-(1-((1-(4-chlorobenzyl)-1H-pyrazol-4-yl)methyl)azetidin-3-yl)-1-cyclopropyl-1H-1,2,3-triazole-4-carboxamide (70 mg, 56.9%) as a white solid. ESI-LCMS (m/z): 412[M+H]$^+$; $^1$HNMR (400 MHz, CD$_3$OD) δ ppm: 8.38 (s, 1H), 7.67 (s, 1H), 7.50 (s, 1H), 7.35 (d, J=8.0 Hz, 2H), 7.21 (d, J=8.0 Hz, 2H), 5.31 (s, 2H), 4.65-4.61 (m, 1H), 4.00-3.96 (m, 1H), 3.71-3.67 (m, 2H), 3.61 (s, 2H), 3.22 (t, J=8.0 Hz, 2H), 1.30-1.24 (m, 2H), 1.21-1.19 (m, 2H).

Example 29

Synthesis of N-(1-((1-(4-chlorobenzyl)-1H-pyrazol-4-yl)methyl)azetidin-3-yl)-5-cyclopropylpyridazine-3-carboxamide (Cpd No. 929)

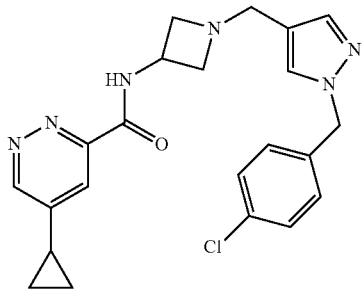 [SMILES: O=C(NC1CN(Cc2cnn(Cc3ccc(Cl)cc3)c2)C1)c1cc(C2CC2)cnn1]

Step 1: Synthesis of tert-butyl (1-((1-(4-chlorobenzyl)-1H-pyrazol-4-yl)methyl)azetidin-3-yl)carbamate

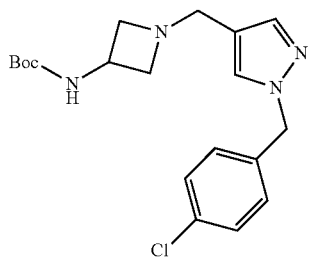 [SMILES: CC(C)(C)OC(=O)NC1CN(Cc2cnn(Cc3ccc(Cl)cc3)c2)C1]

A mixture of 1-(4-chlorobenzyl)-1H-pyrazole-4-carbaldehyde (200 mg, 0.9063 mmol), tert-Butyl (azetidin-3-yl)carbamate hydrochloride (377 mg, 1.81 mmol) and acetic acid (54.4 mg, 0.9063 mmol) were dissolved in MeOH (40 ml). After stirred for 2 h at r.t., sodium cyanoborohydride (142 mg, 2.26 mmol) was added to the solution. The mixture was stirring over night at r.t. Then, the solution was concentrated under reduced pressure and the residue purified by flash column chromatography (eluant: DCM:MeOH=10:1 (600 ml)). To furnish tert-butyl (1-((1-(4-chlorobenzyl)-1H-pyrazol-4-yl)methyl)azetidin-3-yl)carbamate (273 mg, 54.2%) as colorless oil. ESI-LCMS (m/z): 377 [M+H]$^+$.

Step 2: Synthesis of 1-((1-(4-chlorobenzyl)-1H-pyrazol-4-yl)methyl)azetidin-3-amine

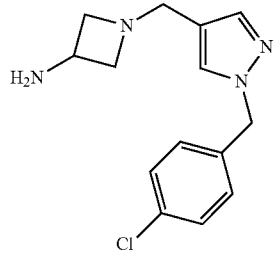 [SMILES: NC1CN(Cc2cnn(Cc3ccc(Cl)cc3)c2)C1]

tert-Butyl (1-((1-(4-chlorobenzyl)-1H-pyrazol-4-yl)methyl)azetidin-3-yl)carbamate (273 mg, 0.4908 mmol) was dissolved in HCl in MeOH (3M) (20 ml). The solution was stirring over night at 50° C. After cooled to r.t., the solution was concentrated to afford 1-((1-(4-chlorobenzyl)-1H-pyrazol-4-yl)methyl)azetidin-3-amine (200 mg, 71.7%) as yellow solid, which was used for next step without purification. ESI-LCMS (m/z): 277[M+H]$^+$.

Step 3: Synthesis of N-(1-((1-(4-chlorobenzyl)-1H-pyrazol-4-yl)methyl)azetidin-3-yl)-5-cyclopropylpyridazine-3-carboxamide

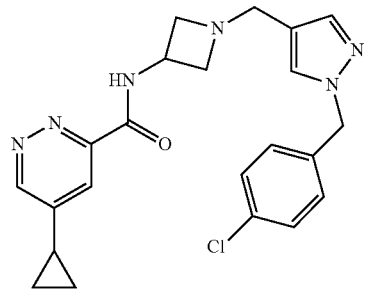 [SMILES: O=C(NC1CN(Cc2cnn(Cc3ccc(Cl)cc3)c2)C1)c1cc(C2CC2)cnn1]

5-cyclopropylpyridazine-3-carboxylic acid (60 mg, 0.3654 mmol) and HATU (250 mg, 0.6577 mmol) were dissolved in DMF (6 ml). After stirred for 1 h at r.t., 1-(1-(4-chlorobenzyl)-1H-pyrazol-4-yl)methyl)azetidin-3-amine (219 mg, 0.3836 mmol) and triethylamine (110 mg, 1.09 mmol) were added to the solution. Then, the mixture was stirring for 4 h at r.t. Then, ethyl acetate (100 ml) was added and the ethyl acetate layer was washed by brine (50 mL×1), dried by Na$_2$SO$_4$, and concentrated. The residue was purified by Prep-HPLC to afford N-(1-((1-(4-chlorobenzyl)-1H-pyrazol-4-yl)methyl)azetidin-3-yl)-5-cyclopropylpyridazine-3-carboxamide (72 mg, 46.7%) as white solid. ESI-LCMS (m/z): 423[M+H]$^+$; $^1$HNMR (400 MHz, CD$_3$OD) δ ppm: 9.15 (s, 1H), 7.86 (s, 1H), 7.69 (s, 1H), 7.51 (s, 1H), 7.36-7.32 (m, 2H), 7.20 (d, J=8.4 Hz, 2H), 5.32 (s, 2H), 4.72-4.68 (m, 1H), 3.74-3.70 (m, 2H), 3.63 (s, 2H), 3.30-3.26 (m, 2H), 2.12-2.08 (m, 1H), 1.33-1.28 (m, 2H), 1.04-1.00 (m, 2H).

Example 30

Synthesis of N-(1-((1-(4-chlorobenzyl)-1H-pyrazol-4-yl)methyl)azetidin-3-yl)-4-cyclopropylpicolinamide (Cpd. No. 930)

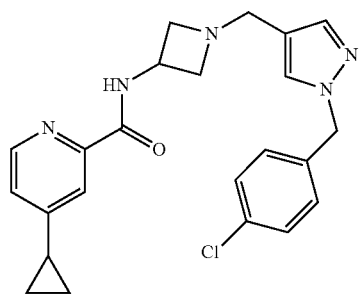 [SMILES: O=C(NC1CN(Cc2cnn(Cc3ccc(Cl)cc3)c2)C1)c1cc(C2CC2)ccn1]

Step 1: Synthesis of tert-butyl 3-(4-bromopicolinamido)azetidine-1-carboxylate

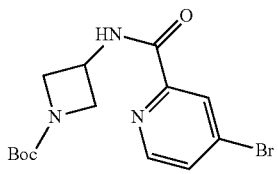 [SMILES: CC(C)(C)OC(=O)N1CC(NC(=O)c2cc(Br)ccn2)C1]

To a solution of 4-bromopicolinic acid (10.0 mmol, 2.02 g), HATU (15.0 mmol, 5.7 g), HOAT (15.0 mmol, 2.04 g) and DIPEA (20.0 mmol, 2.58 g) in DMF (50 ml) was added tert-butyl 3-aminoazetidine-1-carboxylate (10.0 mmol, 1.72 g) and stirred at r.t. overnight. Added ethyl acetate (300 ml), washed with water (150 ml×6), dried over $Na_2SO_4$, concentrated and the residue was crystallized with ethyl acetate:petroleum ether=1:5 to give pale yellow powder (2.63 g, 74%). ESI-LCMS (m/z): 356 [M+H]$^+$.

Step 2: Synthesis of tert-butyl 3-(4-cyclopropylpicolinamido)azetidine-1-carboxylate

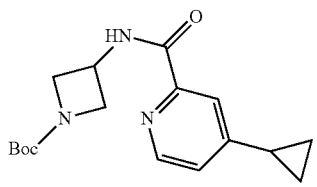 [SMILES: CC(C)(C)OC(=O)N1CC(NC(=O)c2cc(C3CC3)ccn2)C1]

To a solution of tert-butyl 3-(4-bromopicolinamido)azetidine-1-carboxylate (16.2 mmol, 5.8 g), cyclopropylboronic acid (32.4 mmol, 22.8 g), $K_3PO_4$ (48.5 mmol, 10.2 g) in dioxane (50 mL) was added Pd(dppf)Cl2 (1.61 mmol, 1.2 g). The mixture was degassed under reduced pressure while stirring and recharged with argon gas, this procedure was repeated for seven times and then heated to 100° C. overnight. The solvent was removed and the residue was purified by column chromatography (eluant: ethyl acetate:petroleum ether=1:3) to give tert-butyl 3-(4-cyclopropylpicolinamido)azetidine-1-carboxylate as a white solid (2.6 g, 50.5%). ESI-LCMS (m/z): 318 [M+H]$^+$.

Step 3: Synthesis of N-(azetidin-3-yl)-4-cyclopropylpicolinamide

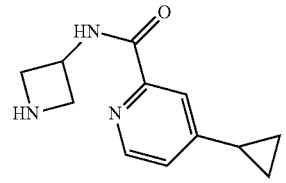 [SMILES: O=C(NC1CNC1)c1cc(C2CC2)ccn1]

tert-Butyl 3-(4-cyclopropylpicolinamido)azetidine-1-carboxylate (1.1 g, 3.46 mmol) in 3N HCl in MeOH (50 ml) was stirred at room temperature for 16 h. LCMS showed the reaction was completed, the solvent was removed under reduced pressure, then $NH_3$ in MeOH (7N, 10 ml) was added and concentrated. The crude product was purified by flash column chromatography (40 g silica gel column, eluted with DCM:$NH_3$ in MeOH (7N)=10:1) to give the desired product N-(azetidin-3-yl)-4-cyclopropylpicolinamide (537 mg, 71.5%) as a white solid.

Step 4: Synthesis of N-(1-((1-(4-chlorobenzyl)-1H-pyrazol-4-yl)methyl)azetidin-3-yl)-4-cyclopropylpicolinamide

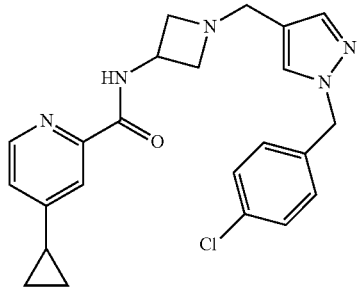 [SMILES: O=C(NC1CN(Cc2cnn(Cc3ccc(Cl)cc3)c2)C1)c1cc(C2CC2)ccn1]

A mixture of N-(azetidin-3-yl)-4-cyclopropylpicolinamide (50 mg, 0.2301 mmol), 1-(4-chlorobenzyl)-1H-pyrazole-4-carbaldehyde (50.7 mg, 0.2301 mmol) and HOAc (34.5 mg, 0.6903 mmol) in MeOH (10 ml) was stirred at r.t. for 16 h. LCMS showed the reaction was completed, the solvent was removed under reduced pressure, $NH_3$ in MeOH (7N, 10 ml) was added and concentrated, the crude product, which was purified by Prep-TLC (eluant: DCM:$NH_3$ in MeOH (7N)=20:1) to give the desired product N-(1-(1-(4-chlorobenzyl)-1H-pyrazol-4-yl)methyl)azetidin-3-yl)-4-cyclopropylpicolinamide (30 mg, 30.9%) as a colorless oil. ESI-LCMS (m/z): 422[M+H]$^+$; $^1$HNMR (400 MHz, CD$_3$OD) δ ppm: 8.44 (d, J=5.2 Hz, 1H), 7.76 (s, 1H), 7.68 (s, 1H), 7.51 (s, 1H), 7.35-7.32 (m, 2H), 7.28-7.26 (m, 1H), 7.20 (d, J=8.4 Hz, 2H), 5.32 (s, 2H), 4.67-4.63 (m, 1H), 3.73-3.69 (m, 2H), 3.62 (s, 2H), 3.26-3.22 (m, 2H), 2.05-2.01 (m, 1H), 1.20-1.15 (m, 2H), 0.91-0.87 (m, 2H).

Example 31

Synthesis of N-(1-((1-(4-chlorobenzyl)-1H-pyrazol-4-yl)methyl)azetidin-3-yl)-4-cyclopropyl-1H-imidazole-2-carboxamide (Cpd. No. 927)

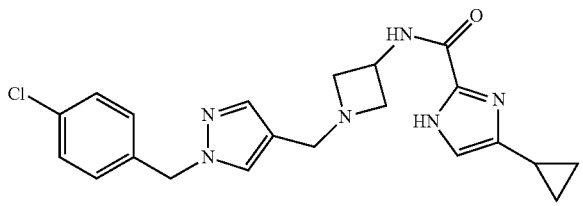 [SMILES: O=C(NC1CN(Cc2cnn(Cc3ccc(Cl)cc3)c2)C1)c1nc(C2CC2)c[nH]1]

Step 1: Synthesis of 4-cyclopropyl-1-((2-(trimethylsilyl)ethoxy)methyl)-1H-imidazole

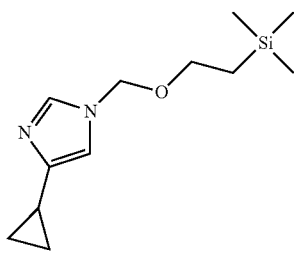 [SMILES: C[Si](C)(C)CCOCn1cnc(C2CC2)c1]

To a solution of 5-cyclopropyl-1H-imidazole (5.16 g, 47.7 mmol) in anhydrous THF (50 mL) was added NaH (2.85 g, 71.5 mmol) portion-wise at 0° C. under nitrogen atmosphere and the mixture was stirred 0° C. for 0.5 h. To the reaction mixture was added SEM-Cl (11.9 g, 71.5 mmol) dropwise at 0° C. under nitrogen atmosphere and the mixture was stirred at 0° C. for 2 h. The mixture was concentrated in vacuo and the residue was purified with column chromatograph on silica gel (petroleum ether:ethyl acetate=2:1) to afford 4-cyclopropyl-1-((2-(trimethylsilyl)ethoxy)methyl)-1H-imidazole (2.10 g, 18.4%) as a yellow liquid. ESI-LCMS (m/z): 239[M+H]$^+$.

Step 2: Synthesis of 4-cyclopropyl-1-((2-(trimethylsilyl)ethoxy)methyl)-1H-imidazole-2-carboxylic Acid

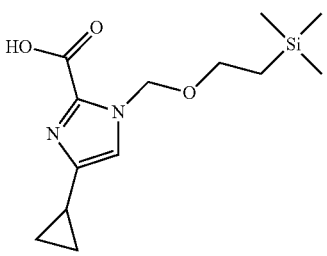 [SMILES: C[Si](C)(C)CCOCn1cc(C2CC2)nc1C(=O)O]

Into the stirred solution of 4-cyclopropyl-1-((2-(trimethylsilyl)ethoxy)methyl)-1H-imidazole (400 mg, 1.7 mmol) in THF (20 mL) was added BuLi (0.7 mL, 2.5 M) at −70° C., the mixture was stirred at −70° C. for 1 h, then solid $CO_2$ was added at −70° C., stirred for the next 1 h, acidified with HCl (1 M). Concentrated in vacuum to obtained desired product (350 mg, yellow oil, Y: 74%). ESI-LCMS (m/z): 283[M+H]$^+$.

Step 3: Synthesis of tert-butyl 3-(4-cyclopropyl-1-((2-(trimethylsilyl)ethoxy)methyl)-1H-imidazole-2-carboxamido)azetidine-1-carboxylate

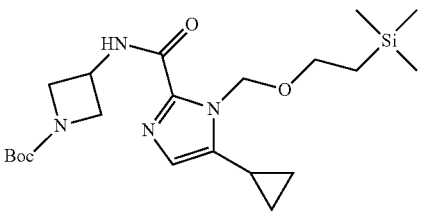 [SMILES: CC(C)(C)OC(=O)N1CC(NC(=O)c2ncc(C3CC3)n2COCC[Si](C)(C)C)C1]

Into the stirred solution of 4-cyclopropyl-1-((2-(trimethylsilyl)ethoxy)methyl)-1H-imidazole-2-carboxylic acid (350 mg, 1.23 mmol), tert-butyl 3-aminoazetidine-1-carboxylate (316 mmol, 1.84 mmol) and HATU (700 mg, 1.84 mmol) in DMF (10 mL) was added DIPEA (478 mg, 3.7 mmol). The mixture was stirred at r.t. for 2 h. Concentrated in vacuum to remove the solvent, the residue was purified by Pre-TLC (petroleum ether:ethyl acetate 1:1) to afford tert-butyl 3-(4-cyclopropyl-1-((2-(trimethylsilyl)ethoxy)methyl)-1H-imidazole-2-carboxamido)azetidine-1-carboxylate as a colorless oil (200 mg, 37%). ESI-LCMS (m/z): 437[M+H]$^+$.

Step 4: Synthesis of N-(azetidin-3-yl)-4-cyclopropyl-1H-imidazole-2-carboxamide

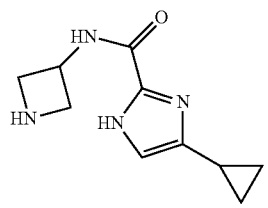 [SMILES: O=C(NC1CNC1)c1nc(C2CC2)c[nH]1]

Into the stirred solution of tert-butyl 3-(4-cyclopropyl-1-((2-(trimethylsilyl)ethoxy)methyl)-1H-imidazole-2-carboxamido)azetidine-1-carboxylate (200 mgn 0.5 mmol) in DCM (10 mL) was added TFA (444 mg, 4.6 mmol). The mixture was stirred at r.t. for 2 h. Concentrated in vacuum to remove the solvent to obtained the residue, basified with saturated $NaHCO_3$, extracted with EtOAc (30 mL×3), combined the organic layer, dried over $Na_2SO_4$, concentrated in vacuum to obtained the crude N-(azetidin-3-yl)-4-cyclopropyl-1H-imidazole-2-carboxamide, which was used without further purification (80 mg, brown oil, Y: 84%). ESI-LCMS (m/z): 207[M+H]$^+$.

Step 5: Synthesis of N-(1-((1-(4-chlorobenzyl)-1H-pyrazol-4-yl)methyl)azetidin-3-yl)-4-cyclopropyl-1H-imidazole-2-carboxamide

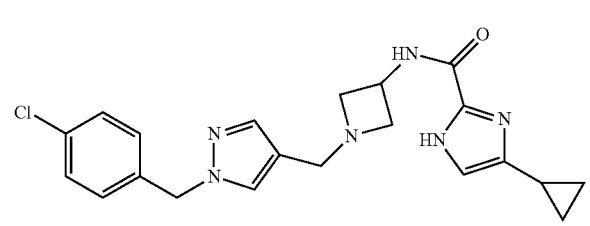 [SMILES: O=C(NC1CN(Cc2cnn(Cc3ccc(Cl)cc3)c2)C1)c1nc(C2CC2)c[nH]1]

Into the stirred solution of N-(azetidin-3-yl)-4-cyclopropyl-1H-imidazole-2-carboxamide (400 mg, 1.9 mmol) and 1-(4-chlorobenzyl)-1H-pyrazole-4-carbaldehyde (425 mg, 1.9 mmol) in MeOH (20 mL) was added NaBH₃CN (600 mg, 9.6 mmol). The mixture was stirred at 60° C. for 20 h. The product was purified by reversed phase prep-HPLC (TFA, CH3CN:H2O 2O=5%-95%) to afford N-(1-(1-(4-chlorobenzyl)-1H-pyrazol-4-yl)methyl)azetidin-3-yl)-4-cyclopropyl-1H-imidazole-2-carboxamide (49 mg, 6%). ESI-LCMS (m/z): 411[M+H]⁺; ¹HNMR (400 MHz, CD₃OD) δ ppm: 7.92 (s, 1H), 7.67 (s, 1H), 7.36-7.34 (m, 2H), 7.24 (d, J=8.8 Hz, 2H), 6.91 (brs, 1H), 5.36 (s, 2H), 4.77-4.74 (m, 1H), 4.31-4.26 (m, 4H), 4.16-4.11 (m, 2H), 1.91-1.87 (m, 1H), 0.93-0.90 (m, 2H), 0.75-0.72 (m, 2H).

Example 32

Synthesis of 1-cyclopropyl-N-(1-((1-(4-methoxybenzyl)-1H-pyrazol-4-yl)methyl)azetidin-3-yl)-1H-1,2,3-triazole-4-carboxamide (Cpd. No. 932)

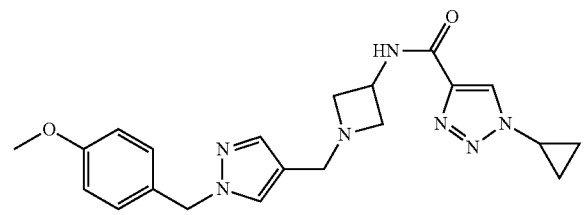 [SMILES: COc1ccc(Cn2cc(CN3CC(NC(=O)c4cn(C5CC5)nn4)C3)cn2)cc1]

Step 1: Synthesis of 1-(4-methoxybenzyl)-1H-pyrazole-4-carbaldehyde

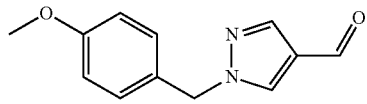 [SMILES: COc1ccc(Cn2cc(C=O)cn2)cc1]

To a mixture of 1H-pyrazole-4-carbaldehyde (100 mg, 1.04 mmol) and 1-(chloromethyl)-4-methoxybenzene (162 mg, 1.04 mmol) in CH₃CN (6 mL) was added potassium carbonate (287 mg, 2.08 mmol), the resulting mixture was stirred at reflux for 1 h. The mixture was poured into water (20 mL) and extracted with EtOAc (3×20 mL). The organic layer was dried over Na₂SO₄ and concentrated to give 1-(4-methoxybenzyl)-1H-pyrazole-4-carbaldehyde (220 mg, 93.3%) as a colorless oil. ESI-LCMS (m/z): 217 [M+H]⁺.

Step 2: Synthesis of 1-cyclopropyl-N-(1-((1-(4-methoxybenzyl)-1H-pyrazol-4-yl)methyl)azetidin-3-yl)-1H-1,2,3-triazole-4-carboxamide

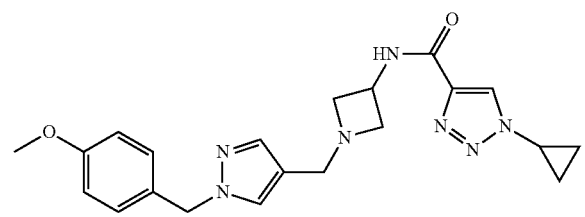 [SMILES: COc1ccc(Cn2cc(CN3CC(NC(=O)c4cn(C5CC5)nn4)C3)cn2)cc1]

To a mixture of N-(azetidin-3-yl)-1-cyclopropyl-1H-1,2,3-triazole-4-carboxamide (50 mg, 0.2412 mmol) and 1-(4-methoxybenzyl)-1H-pyrazole-4-carbaldehyde (62.5 mg, 0.2894 mmol) in methanol (5 mL) was added acetic acid (724 μg, 0.01206 mmol), the mixture was stirred at r.t. for 15 min, then sodium cyanoborohydride (30.3 mg, 0.4824 mmol) was added, the resulting mixture was stirred at 40° C. overnight. The mixture was concentrated under reduced pressure. The residue was dissolved in aqueous solution of Na₂CO₃ and extracted with EtOAc (3×20 mL). The organic layer was dried over Na₂SO₄ and concentrated. The residue was purified by prep-TLC (CH₂Cl₂/NH₃.MeOH=20/1) to give 1-cyclopropyl-N-(1-((1-(4-methoxybenzyl)-1H-pyrazol-4-yl)methyl)azetidin-3-yl)-1H-1,2,3-triazole-4-carboxamide (53 mg, 53.9%) as a white solid. ESI-LCMS (m/z): 408[M+H]⁺; ¹HNMR (400 MHz, CD₃OD) δ ppm: 8.39 (s, 1H), 7.62 (s, 1H), 7.48 (s, 1H), 7.19 (d, J=8.4 Hz, 2H), 6.90 d, J=8.4 Hz, 2H), 5.24 (s, 2H), 4.64-4.62 (m, 1H), 3.99-3.98 (m, 1H), 3.79 (s, 3H), 3.73-3.69 (m, 2H), 3.63 (s, 2H), 3.27-3.23 (m, 2H), 1.28-1.22 (m, 4H).

Example 33

SMYD3 Biochemical Assay

General Materials

S-adenosylmethionine (SAM), S-adenosylhomocysteine (SAH), Tris, Tween20, dimethylsulfoxide (DMSO), bovine skin gelatin (BSG), and Tris(2-carboxyethyl)phosphine hydrochloride solution (TCEP) were purchased from Sigma-Aldrich at the highest level of purity possible. ³H-SAM was purchase from American Radiolabeled Chemicals with a specific activity of 80 Ci/mmol. 384-well opaque white OptiPlates and SPA beads (Perkin Elmer, catalog # RPNQ0013) were purchased from PerkinElmer.

Substrates

N-terminally GST-tagged MEKK2 (MAP3K2) protein corresponding to reference sequence AAF63496.3 was purchased from Life Technologies (catalog # PV4010). This protein was expressed in High Five insect cells and purified to >85% purity. Protein identity was confirmed by MS/MS analysis after proteolytic digestion. The protein sequence used was:

```
                                          (SEQ ID No. 1)
MAPILGYWKIKGLVQPTRLLLEYLEEKYEEHLYERDEGDKWRNK

KFELGLEFPNLPYYIDGDVKLTQSMAIIRYIADKHNMLGGCPKERA

EISMLEGAVLDIRYGVSRIAYSKDFETLKVDFLSKLPEMLKMFEDR

LCHKTYLNGDHVTHPDFMLYDALDVVLYMDPMCLDAFPKLVCF

KKRIEAIPQIDKYLKSSKYIAWPLQGWQATFGGGDHPPKSDLVPRH

NQTSLYKKAGTMDDQQALNSIMQDLAVLHKASRPALSLQETRKA

KSSSPKKQNDVRVKFEHRGEKRILQFPRPVKLEDLRSKAKIAFGQS

MDLHYTNNELVIPLTTQDDLDKALELLDRSIHMKSLKILLVINGST

QATNLEPLPSLEDLDNTVFGAERKKRLSIIGPTSRDRSSPPPGYIPDE

LHQVARNGSFTSINSEGEFIPESMEQMLDPLSLSSPENSGSGSCPSL

DSPLDGESYPKSRMPRAQSYPDNHQEFSDYDNPIFEKFGKGGTYPR

RYHVSYHHQEYNDGRKTFPRARRTQGNQLTSPVSFSPTDHSLSTSS

GSSIFTPEYDDSRIRRRGSDIDNPTLTVMDISPPSRSPRAPTNWRLG
```

-continued
KLLGQGAFGRVYLCYDVDTGRELAVKQVQFDPDSPETSKEVNAL

ECEIQLLKNLLHERIVQYYGCLRDPQEKTLSIFMEYMPGGSIKDQL

KAYGALTENVTRKYTRQILEGVHYLHSNMIVHRDIKGANILRDST

GNVKLGDFGASKRLQTICLSGTGMKSVTGTPYWMSPEVISGQGYG

RKADIWSVACTVVEMLTEKPPWAEFEAMAAIFKIATQPTNPKLPP

HVSDYTRDFLKRIFVEAKLRPSADELLRHMFVHYH..

Molecular Biology

Full-length human SMYD3 isoform 1 (BAB86333) was inserted into a modified pET21b plasmid containing a His6 tag and TEV and SUMO cleavage sites. Because two common variants of SMYD3 exist in the population, site directed mutagenesis was subsequently performed to change amino acid 13 from an asparagine to a lysine, resulting in plasmid pEPZ533. A lysine at position 13 conforms to the more commonly occurring sequence (NP_001161212).

Protein Expression

E. coli (BL21 codonplus RIL strain, Stratagene) were transformed with plasmid pEPZ553 by mixing competent cells and plasmid DNA and incubating on ice for 30 minutes followed by heat shock at 42° C. for 1 minute and cooling on ice for 2 minutes. Transformed cells were grown and selected on LB agar with 100 µg/mL ampicillin and 17 µg/mL chloramphenicol at 37° C. overnight. A single clone was used to inoculate 200 mL of LB medium with 100 µg/mL ampicillin and 17 µg/mL chloramphenicol and incubated at 37° C. on an orbital shaker at 180 rpm. Once in log growth, the culture was diluted 1:100 into 2 L of LB medium and grown until $OD_{600}$ was about 0.3 after which the culture was incubated at 15° C. and 160 rpm. Once $OD_{600}$ reached about 0.4, IPTG was added to a final concentration of 0.1 mM and the cells were grown overnight at 15° C. and 160 rpm. Cells were harvested by centrifugation at 8000 rpm, for 4 minutes at 4° C. and stored at −80° C. for purification.

Protein Purification

Expressed full-length human His-tagged SMYD3 protein was purified from cell paste by Nickel affinity chromatography after equilibration of the resin with Buffer A (25 mM Tris, 200 mM NaCl, 5% glycerol, 5 mM β-mercaptoethanol, pH7.8). The column was washed with Buffer B (Buffer A plus 20 mM imidazole) and His-tagged SMYD3 was eluted with Buffer C (Buffer A plus 300 mM imidazole). The His tag, TEV and SUMO cleavage sites were removed generating native SMYD3 by addition of ULP1 protein at a ratio of 1:200 (ULP1:SMYD3). Imidazole was removed by dialysis overnight in Buffer A. The dialyzed solution was applied to a second Nickel column and the native SMYD3 protein was collected from the column flow-through. The flow-through was dialyzed in Buffer D (25 mM Tris, 5% glycerol, 5 mM β-mercaptoethanol, 50 mM NaCl, pH7.8) and ULP1 was removed using a Q sepharose fast flow column. SMYD3 was eluted in Buffer A and further purified using an S200 size-exclusion column equilibrated with Buffer A. SMYD3 was concentrated to 2 mg/mL with a final purity of 89%.

Predicted Translation:

SMYD3 (Q9H7B4)
(SEQ ID No. 2)
MEPLKVEKFATAKRGNGLRAVTPLRPGELLFRSDPLAYTVCKGSR

GVVCDRCLLGKEKLMRCSQCRVAKYCSAKCQKKAWPDHKRECK

-continued
CLKSCKPRYPPDSVRLLGRVVFKLMDGAPSESEKLYSFYDLESNIN

KLTEDKKEGLRQLVMTFQHFMREEIQDASQLPPAFDLFEAFAKVIC

NSFTICNAEMQEVGVGLYPSISLLNHSCDPNCSIVFNGPHLLLRAV

RDIEVGEELTICYLDMLMTSEERRKQLRDQYCFECDCFRCQTQDK

DADMLTGDEQVWKEVQESLKKIEELKAHWKWEQVLAMCQAIISS

NSERLPDINIYQLKVLDCAMDACINLGLLEEALFYGTRTMEPYRIFF

PGSHPVRGVQVMKVGKLQLHQGMFPQAMKNLRLAFDIMRVTHG

REHSLIEDLILLLEECDANIRAS..

General Procedure for SMYD3 Enzyme Assays on MEKK2 Protein Substrate

The assays were all performed in a buffer consisting of 25 mM Tris-Cl pH 8.0, 1 mM TCEP, 0.005% BSG, and 0.005% Tween 20, prepared on the day of use. Compounds in 100% DMSO (1 ul) were spotted into a 384-well white opaque OptiPlate using a Bravo automated liquid handling platform outfitted with a 384-channel head (Agilent Technologies). DMSO (1 ul) was added to Columns 11, 12, 23, 24, rows A-H for the maximum signal control and 1 ul of SAH, a known product and inhibitor of SMYD3, was added to columns 11, 12, 23, 24, rows I-P for the minimum signal control. A cocktail (40 ul) containing the SMYD3 enzyme was added by Multidrop Combi (Thermo-Fisher). The compounds were allowed to incubate with SMYD3 for 30 min at room temperature, then a cocktail (10 ul) containing SAM and MEKK2 was added to initiate the reaction (final volume=51 ul). The final concentrations of the components were as follows: SMYD3 was 0.4 nM, $^3$H-SAM was 8 nM, MEKK2 was 12 nM, SAH in the minimum signal control wells was 1 mM, and the DMSO concentration was 2%. The assays were stopped by the addition of non-radiolabeled SAM (10 ul) to a final concentration of 100 uM, which dilutes the $^3$H-SAM to a level where its incorporation into MEKK2 is no longer detectable. Radiolabeled MEKK2 was detected using a scintillation proximity assay (SPA). 10 uL of a 10 mg/mL solution of SPA beads in 0.5 M citric acid was added and the plates centrifuged at 600 rpm for 1 min to precipitate the radiolabeled MEKK2 onto the SPA beads. The plates were then read in a PerkinElmer TopCount plate reader to measure the quantity of $^3$H-labeled MEKK2 as disintegrations per minute (dpm) or alternatively, referred to as counts per minute (cpm).

% Inhibition Calculation $$\% \; inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter IC50 Fit $$Y = \text{Bottom} + \frac{(\text{Top} - \text{Bottom})}{\left(1 + \left(\frac{X}{IC_{50}}\right)^{\text{Hill Coefficient}}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

SMYD3 biochemical assay data for representative Compounds of the Disclosure are presented in Tables 1A and 3A in the column titled "SMYD3 Biochem IC$_{50}$ (µM)."

Example 34

SMYD3 Cell Assay

Trimethyl-MEKK2-in-Cell Western Assay

293T/17 adherent cells were purchased from ATCC (American Type Culture Collection), Manassas, Va., USA. MEM/Glutamax medium, Optimem Reduced Serum medium, penicillin-streptomycin, 0.05% trypsin and 1×D-PBS were purchased from Life Technologies, Grand Island, N.Y., USA. PBS-10× was purchased from Ambion, Life Technologies, Grand Island, N.Y., USA. PBS with Tween 20 (PBST (10×)) was purchased from KPL, Gaithersburg, Md., USA. Tet System FBS-approved FBS US Source was purchased from Clontech, Mountain View, Calif., USA. Odyssey blocking buffer, 800CW goat anti-rabbit IgG (H+L) antibody, 680CW Goat anti-mouse IgG (H+L) and Licor Odyssey infrared scanner were purchased from Licor Biosciences, Lincoln, Nebr., USA. Tri-methyl-Lysine [A260]-MEKK2 antibody, MEKK2 and SMYD3 plasmids were made at Epizyme. Anti-flag monoclonal mouse antibody was purchased from Sigma, St. Louis, Mo., USA. Methanol was purchased from VWR, Franklin, Mass., USA. 10% Tween 20 was purchased from KPL, Inc., Gaithersburg, Md., USA. Fugene was purchased from Promega, Madison, Wis., USA. The Biotek ELx405 was purchased from BioTek, Winooski, Vt., USA. The multidrop combi was purchased from Thermo Scientific, Waltham, Mass., USA.

293T/17 adherent cells were maintained in growth medium (MEM/Glutamax medium supplemented with 10% v/v Tet System FBS and cultured at 37° C. under 5% $CO_2$. Cell Treatment, in Cell Western (ICW) for Detection of Trimethyl-Lysine-MEKK2 and MEKK2.

293T/17 cells were seeded in assay medium at a concentration of 33,333 cells per cm$^2$ in 30 mL medium per T150 flask and incubated at 37° C. under 5% $CO_2$. Plasmids were prepared for delivery to cells by first mixing 1350 µL Opti-MEM with Fugene (81 µL) in a sterile Eppendorf and incubated for five minutes at room temperature (RT). MEKK2-flag (13.6 ug/T150) MEKK2 p3×Flag-CMV-14 with C-3×Flag and SMYD3 (0.151 ug/T150) SMYD3 p3×Flag-CMV-14 without C-3×Flag plasmids were aliquotted to a 1.7 mL sterile microfuge tube. The gene ID for MEKK2 and SMYD3 is NM 006609.3 and Q9H7B4, respectively. Entire volume of Opti-MEM/Fugene mixture was then added to a microfuge tube containing DNA plasmid, mixed and then incubated ×15 minutes at RT. The medium on the 293T/17 cells was refreshed, and the DNA/Fugene complex is added aseptically to each flask, rocked gently, and incubated at 37 C for 5 hours. Medium was then removed, and cells were washed once with PBS in the flask. Trypsin 0.05% (3 mL) was added and cells incubated for three minutes. Room temperature MEM+10% Tet system FBS was added and cells were mixed gently, and counted using the Vi-cell. Cells were seeded at 100,000 cells/mL in 50 µL MEM/10% Tet FBS/Pen/Strep to a 384 well black/clear poly-D-lysine coated plate containing test agent diluted in DMSO. The final top concentration of test compound was 40 µM. The total concentration of DMSO did not exceed 0.2% (v/v). Plates were incubated ×30 minutes at RT in low-airflow area, followed by incubation at 37° C. under 5% $CO_2$ for 24 hours. Medium was aspirated from all wells of assay plates prior to fixation and permeabilization with ice cold (−20° C.) methanol (90 µL/well) for ten minutes. Plates were rinsed with PBS three times on BioTek ELx405. PBS was removed with a final aspiration, and Odyssey blocking buffer (50 µL/well) was added to each well and incubated for one hour at RT. Primary antibody solution was prepared (anti-trimethyl-MEKK2 at 1:600 dilution plus mouse anti-flag antibody at 1:10,000 dilution in diluent (Odyssey Blocking buffer+0.1% Tween 20)) and 20 µL per well was dispensed using the Multidrop Combi. Assay plates were then sealed with foil, and incubated overnight at 4° C. Plates were washed five times with PBS-Tween (1×) on Biotek ELx405 and blotted on paper towel to remove excess reagent. Detection antibody solution (IRDye 800 CW goat anti-rabbit IgG diluted 1:400 in diluent (Odyssey Blocking buffer+0.1% Tween 20), plus IRDye 680CW goat anti-mouse IgG at 1:500 in diluent (Odyssey Blocking buffer+0.1% Tween 20) was added (20 µL/well) and incubated in dark for one hour at RT. Plates were then washed four times with PBS-T (1×) on ELx405. A final rinse with water was performed (115 µL/well×three washes on the ELx405). Plates were then centrifuged upside down, on paper towel, at 200×g to remove excess reagent. Plates were left to dry in dark for one hour. The Odyssey Imager was used to measure the integrated intensity of 700 and 800 wavelengths at resolution of 84 µm, medium quality, focus offset 4.0, 700 channel intensity=3.5 to measure the MEKK2-flag signal, 800 channel intensity=5 to measure the Trimethyl-MEKK2 signal of each well.

Calculations:

First, the ratio for each well was determined by:

$$\left( \frac{\text{Trimethyl } MEKK2 \text{ 800 nm value}}{\text{flag tagged } MEKK2 \text{ 700 nm value}} \right)$$

Each plate included fourteen control wells of DMSO only treatment (Minimum Inhibition) as well as fourteen control wells for maximum inhibition (Background). The average of the ratio values for each control type was calculated and used to determine the percent inhibition for each test well in the plate. Reference compound was serially diluted two-fold in DMSO for a total of nine test concentrations, beginning at 40 µM. Percent inhibition was calculated (below).

Percent Inhibition = 100 −

$$\left( \left( \frac{\text{(Individual Test Sample Ratio)} - \text{(Background Avg Ratio)}}{\text{(Minimum Inhibition Ratio)} - \text{(Background Average Ratio)}} \right) * 100 \right)$$

Non-linear regression curves were generated to calculate the IC$_{50}$ and dose-response relationship using triplicate wells per concentration of compound.

SMYD3 cell assay data for representative Compounds of the Disclosure are presented in Tables 1A and 3A in the column titled "SMYD3 Cell IC$_{50}$ (µM)."

Example 35

SMYD2 Biochemical Assay

General Materials

S-adenosylmethionine (SAM), S-adenosylhomocysteine (SAH), bicine, Tween20, dimethylsulfoxide (DMSO), bovine skin gelatin (BSG), and Tris(2-carboxyethyl)phosphine hydrochloride (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates

Peptide was synthesized with a N-terminal linker-affinity tag motif and a C-terminal amide cap by 21$^{st}$ Century Biochemicals. The peptide was high high-performance liquid chromatography (HPLC) purified to greater than 95% purity and confirmed by liquid chromatography mass spectrometry (LC-MS). The sequence was ARTKQTARKSTG-GKAPRKQLATKAARKSA(K-Biot)-amide. (SEQ ID NO: 3)

Production of Recombinant SMYD2 Enzymes for Biochemical Enzyme Activity Assays

Full length SMYD2 (NP_064582.2) was cloned into a pFastbac-Htb-lic vector with an N-terminal His6 tag and FLAG tag, preceded by a TEV protease cleavage site. The protein was expressed in Sf9 insect cells. Cells were resuspended in lysis buffer (25 mM HEPES-NaOH, pH 7.5, 200 mM NaCl, 5% glycerol, and 5 mM (3-ME) and lysed by sonication. The protein was purified by Ni-NTA (Qiagen), followed by TEV cleavage to remove the His6 tag, subtractive Ni-NTA (Qiagen), and gel filtration chromatography using an S200 column (GE Healthcare). Purified protein was stored in 20 mM Tris-HCl, pH 8.0, 100 mM NaCl, and 1 mM TCEP.

General Procedure for SMYD2 Enzyme Assays on Peptide Substrates

The assays were all performed in a buffer consisting of 20 mM Bicine (pH=7.6), 1 mM TCEP, 0.005% Bovine Skin Gelatin, and 0.002% Tween20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of SMYD2, was added to columns 11, 12, 23, 24, rows I-P for the minimum signal control. A cocktail (40 ul) containing the SMYD2 enzyme was added by Multidrop Combi (Thermo-Fisher). The compounds were allowed to incubate with SMYD2 for 30 min at room temperature, then a cocktail (10 ul) containing $^3$H-SAM and peptide was added to initiate the reaction (final volume=51 ul). The final concentrations of the components were as follows: SMYD2 was 1.5 nM, $^3$H-SAM was 10 nM, and peptide was 60 nM, SAH in the minimum signal control wells was 1000 uM, and the DMSO concentration was 2%. The assays were stopped by the addition of non-radioactive SAM (10 ul) to a final concentration of 600 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed three times with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \; inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter IC50 Fit $$\% \; inhibition = Bottom + \frac{Top - Bottom}{(1 + (IC_{50}/[I])^{Hill \; Coefficient})}$$

Where top and bottom are the normally allowed to float, but may be fixed at 100 or 0 respectively in a 3-parameter fit. The Hill Coefficient normally allowed to float but may also be fixed at 1 in a 3-parameter fit. I is the compound concentration.

SMYD2 biochemical assay data for representative Compounds of the Disclosure are presented in Tables 4A and 6A in the column titled "SMYD2 Biochem IC$_{50}$ (µM)."

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having Formula I:

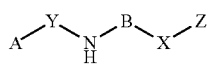

or a pharmaceutically acceptable salt thereof,
wherein:
A is 1,2,3-triazolyl, optionally substituted with one, two, or three substituents independently selected from the group consisting of halo, hydroxy, alkoxy, amino, alkylamino, dialkylamino, (amino)alkyl, (alkylamino)alkyl, (dialkylamino)alkyl, $C_{1-6}$ alkyl, haloalkyl, hydroxyalkyl, (carboxamido)alkyl, (cycloalkyl)alkyl, optionally substituted $C_{3-12}$ cycloalkyl, optionally substituted $C_{6-14}$ aryl, optionally substituted 5- to 14-membered heteroaryl, optionally substituted 4- to 14-membered heterocyclo, aralkyl, —N(H)C(=O)R$^6$, —C(=O)R$^7$, and —S(=O)$_2$R$^8$;

each optionally substituted $C_{3-12}$ cycloalkyl is independently unsubstituted or substituted with one, two, or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyl, aralkyloxy, alkylthio, carboxamido sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl;

each optionally substituted $C_{6-14}$ aryl is independently unsubstituted or substituted with one, two, three, four, or five substituents independently selected from the group consisting of halo, nitro, cyano, hydroxy, amino, alkylamino, dialkylamino, aralkylamino, haloalkyl, hydroxyalkyl, alkoxy, haloalkoxy, aryloxy, heteroaryloxy, aralkyl, aralkyloxy, (aralkyloxy)alkyl, alkylthio, carboxamido, sulfonamido, alkylcarbonyl, arylcarbonyl, alkylsulfonyl, arylsulfonyl, ureido, guanidino, carboxy, carboxyalkyl, heteroalkyl, alkyl, cycloalkyl, alkenyl, alkynyl, aryl, heteroaryl, heterocyclo, ($C_{1-4}$ haloalkoxy)alkyl, alkoxyalkyl, (amino)alkyl, hydroxyalkylamino, (alkylamino)alkyl, (dialkylamino)alkyl, (cyano)alkyl, (carboxamido)alkyl, (carboxamido)alkyl-O—, mercaptoalkyl, (heterocyclo)alkyl, (heterocyclo)alkyl-O—, (cycloalkylamino)alkyl, (hydroxyalkylamino)alkyl, (amino)(heteroaryl)alkyl, (heterocycloamino)alkyl (amino)(hydroxy)alkyl, (heteroaryl)alkyl, (heteroaryl)alkyl-O—, —N(R$^{43}$)(R$^{44}$), —CH$_2$N(R$^{43}$)(R$^{44}$), —CH$_2$N(H)C(=O)—R$^{45}$, and —N(H)C(=O)—R$^{45}$;

each optionally substituted 5- to 14-membered heteroaryl is independently unsubstituted or substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aralkyl aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, —N(R$^{43}$)(R$^{44}$), and —N(H)C(=O)—R$^{45}$, each optionally substituted 4- to 14-membered heterocyclo is independently unsubstituted or substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyl aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl, Y is —C(=O)—;

B is selected from the group consisting of $C_{3-12}$ cycloalkylenyl, optionally substituted with one, two, or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkenyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl; and 4 to 14-membered heterocyclenyl, optionally substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyl aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl, with the proviso that B is not pyrrolidinenyl, optionally substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyl aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl;

X is selected from the group consisting of —N($R^3$)—, —S(=O)$_2$—, —S(=O)$_2$N($R^3$)—, —N($R^3$)S(=O)$_2$—, —S(=O)$_2$C($R^4$)(H)—, —C(=O)—, —C(=O)N($R^3$)—, —N($R^3$)C(=O)—, —C(=O)O—, —OC(=O)—, —C(=O)C($R^4$)(H)N($R^3$)—, —N($R^3$)C(=O)C($R^4$)(H)—, and —C(=O)C($R^4$)(H)—; or X is absent;

Z is (heteroaryl)alkyl, wherein the heteroaryl is optionally substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, —N($R^{43}$)($R^{44}$), and —N(H)C(=O)—$R^{45}$;

$R^3$ is selected from the group consisting of hydrogen and $C_{1-4}$ alkyl;

$R^4$ is selected from the group consisting of hydrogen, $C_{1-4}$ alkyl, hydroxy, amino, alkylamino, dialkylamino, cycloalkylamino, (amino)alkyl, (alkylamino)alkyl, (dialkylamino)alkyl, and hydroxyalkyl;

$R^6$ is $C_{1-4}$ alkyl;

$R^7$ is $C_{1-4}$ alkyl;

$R^8$ is selected from the group consisting of $C_{1-4}$ alkyl, amino, alkylamino, and dialkylamino;

$R^{43}$ is hydrogen or $C_{1-4}$ alkyl;

$R^{44}$ is alkoxyalkyl, (heterocyclo)alkyl, (amino)alkyl, (alkylamino)alkyl, or (dialkylamino)alkyl; and $R^{45}$ is alkyl; unsubstituted $C_{6-14}$ aryl; substituted $C_{6-14}$ aryl with one, two, three, four, or five substituents independently selected from the group consisting of halo, nitro, cyano, hydroxy, amino, alkylamino, dialkylamino, haloalkyl, hydroxyalkyl, alkoxy, and haloalkoxy; unsubstituted $C_{5-14}$ heteroaryl; or substituted $C_{5-14}$ heteroaryl with one, two, three, or four substituents independently selected from the group consisting of halo, nitro, cyano, hydroxy, amino, alkylamino, dialkylamino, haloalkyl, hydroxyalkyl, alkoxy, and haloalkoxy, wherein —X—Z is attached to any available carbon or nitrogen atom of B.

2. The compound of claim 1, or a pharmaceutically acceptable salt thereof, having Formula III, Formula IV, or Formula V:

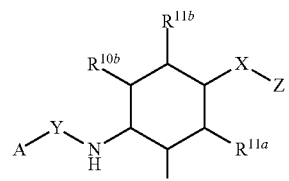

III

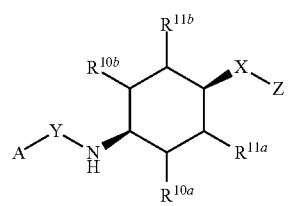

IV

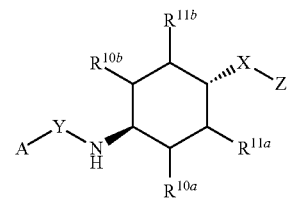

V wherein $R^{10a}$, $R^{10b}$, $R^{11a}$, and $R^{11b}$ are each independently selected from the group consisting of hydrogen and $C_{1-4}$ alkyl.

3. The compound of claim 1, or a pharmaceutically acceptable salt thereof having Formula VI, Formula VII or Formula VIII:

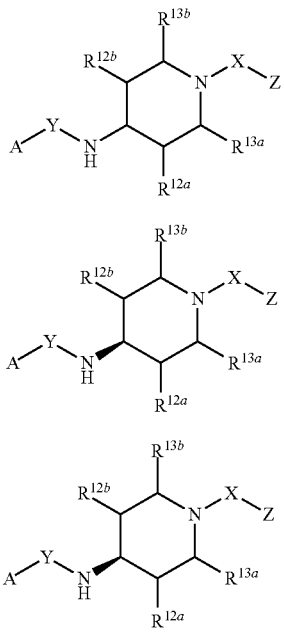

wherein:
  $R^{12a}$, $R^{12b}$, $R^{13a}$, and $R^{13b}$ are each independently selected from the group consisting of hydrogen and $C_{1-4}$ alkyl;
  X is selected from the group consisting of —C(=O)C($R^4$)(H)—, —C(=O)—, and —S(=O)$_2$—; and
  $R^4$ is selected from the group consisting of hydrogen and amino.

4. The compound of claim 1, or a pharmaceutically acceptable salt thereof, having Formula XV:

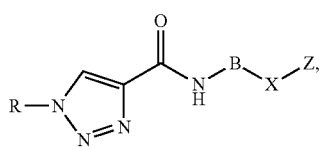

wherein R is selected from the group consisting of $C_{1-6}$ alkyl and $C_{3-12}$ cycloalkyl; and
B is 4- to 14-membered heterocyclenyl, optionally substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyl aralkyloxy, alkylthio, carboxamido, sulfonamido, alkylcarbonyl, arylcarbonyl, alkylsulfonyl, arylsulfonyl, ureido, guanidino, carboxy, carboxyalkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl.

5. The compound of claim 4, or a pharmaceutically acceptable salt thereof, wherein B is:

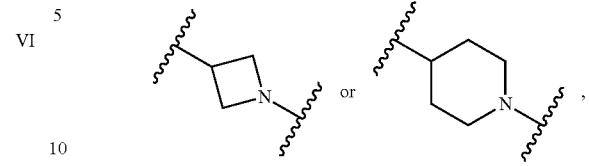

wherein the nitrogen atom is attached to —X—Z.

6. The compound of claim 5, or a pharmaceutically acceptable salt thereof, wherein X is absent.

7. The compound of claim 5, or a pharmaceutically acceptable salt thereof, wherein Z is (heteroaryl)alkyl, wherein the heteroaryl is substituted with one, two, three or four substituents independently selected from the group consisting of aralkyl and (heteroaryl)alkyl.

8. The compound of claim 1, or a pharmaceutically acceptable salt thereof, having Formula XVII:

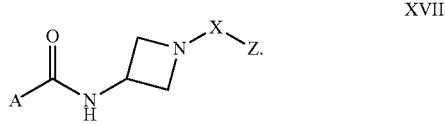

9. The compound of claim 1, or a pharmaceutically acceptable salt thereof, having Formula XVIII:

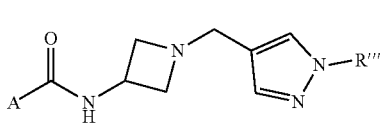

wherein:
  R''' is selected from the group consisting of aralkyl and (heteroaryl)alkyl; and
  A is 1,2,3-triazolyl which is substituted with one substituent selected from the group consisting of $C_{1-6}$ alkyl and $C_{3-6}$ cycloalkyl.

10. The compound of claim 9, or a pharmaceutically acceptable salt thereof, wherein A is

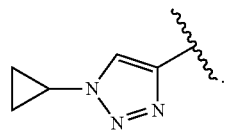 [SMILES: *c1cn(C2CC2)nn1]

11. The compound of claim 1, or a pharmaceutically acceptable salt thereof, wherein B is unsubstituted $C_{3-12}$ cycloalkylenyl.

12. The compound of claim 1, or a pharmaceutically acceptable salt thereof, wherein B is unsubstituted 4- to 14-membered heterocyclenyl.

13. The compound of claim 1, or a pharmaceutically acceptable salt thereof, wherein X is absent.

14. A pharmaceutical composition comprising the compound of claim 1, or a pharmaceutically acceptable salt thereof, and a pharmaceutically acceptable carrier.

15. A kit comprising the compound of claim 1, or a pharmaceutically acceptable salt thereof, and instructions for administering the compound, or a pharmaceutically acceptable salt thereof, to a patient having cancer.

16. The kit of claim 15, wherein the cancer is selected from the group consisting of adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia adult T-cell lymphoma, aggressive natural killer-cell leukemia, acquired immunodeficiency syndrome-relaxed lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hem angioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, Liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, mucosa-associated lymphoid tissue lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

17. A compound selected from the group consisting of:
N-(1-((1-(4-chlorobenzyl)-1H-pyrazol-4-yl)methyl)azetidin-3-yl)-1-cyclopropyl-1H-1,2,3-triazole-4-carboxamide; and
1-cyclopropyl-N-(1-((1-(4-methoxybenzyl)-1H-pyrazol-4-yl)methyl)azetidin-3-yl)-1H-1,2,3-triazole-4-carboxamide;
or a pharmaceutically acceptable salt thereof.

* * * * *